(12) United States Patent
McCauley et al.

(10) Patent No.: US 12,350,270 B2
(45) Date of Patent: Jul. 8, 2025

(54) ANTIMALARIAL AGENTS

(71) Applicants: Merck Sharp & Dohme LLC, Rahway, NJ (US); The Walter and Eliza Hall Institute of Medical Research, Parkville (AU); MSD R&D (China) Co. LTD., Beijing (CN)

(72) Inventors: John A. McCauley, Maple Glen, PA (US); Alan F. Cowman, Melbourne (AU); Manuel de Lera Ruiz, Perkasie, PA (US); Paola Favuzza, Melbourne (AU); Zhuyan Guo, Scotch Plains, NJ (US); Bin Hu, Shanghai (CN); Michael J. Kelly, III, Paoli, PA (US); Zhiyu Lei, Shanghai (CN); David B. Olsen, Lansdale, PA (US); Brad Sleebs, Bundoora (AU); Jennifer K. Thompson, Melbourne (AU); Tony Triglia, Melbourne (AU); Dongmei Zhan, Shanghai (CN); Cailing Zhang, Shanghai (CN); Lianyun Zhao, Shanghai (CN)

(73) Assignees: MSD R&D (China) Co. Ltd., Beijing (CN); The Walter and Eliza Hall Institute of Medical Research, Parkville (AU); Merck Sharp & Dohme LLC, Rahway, NJ (US)

( * ) Notice: Subject to any disclaimer, the term of this patent is extended or adjusted under 35 U.S.C. 154(b) by 734 days.

(21) Appl. No.: 17/633,655

(22) PCT Filed: Jul. 21, 2020

(86) PCT No.: PCT/CN2020/103178
§ 371 (c)(1),
(2) Date: Feb. 8, 2022

(87) PCT Pub. No.: WO2021/027502
PCT Pub. Date: Feb. 18, 2021

(65) Prior Publication Data
US 2022/0331321 A1    Oct. 20, 2022

(30) Foreign Application Priority Data

Aug. 15, 2019    (WO) ................ PCT/CN2019/100781

(51) Int. Cl.
| | | |
|---|---|---|
| *A61K 31/513* | (2006.01) |
| *A61K 45/06* | (2006.01) |
| *A61P 33/06* | (2006.01) |
| *C07D 239/22* | (2006.01) |
| *C07D 405/12* | (2006.01) |
| *C07D 405/14* | (2006.01) |

(Continued)

(52) U.S. Cl.
CPC ............ *A61K 31/513* (2013.01); *A61K 45/06* (2013.01); *A61P 33/06* (2018.01); *C07D 239/22* (2013.01); *C07D 405/12* (2013.01); *C07D 405/14* (2013.01); *C07D 409/04* (2013.01); *C07D 409/14* (2013.01); *C07D 491/052* (2013.01); *C07D 493/10* (2013.01)

(58) Field of Classification Search
CPC .. C07D 239/22; C07D 405/12; C07D 405/14; C07D 409/04; C07D 409/14; C07D 491/052; C07D 493/10; A61K 31/513; A61P 33/06
See application file for complete search history.

(56) References Cited

U.S. PATENT DOCUMENTS

2019/0046507 A1    2/2019 Khan

FOREIGN PATENT DOCUMENTS

| WO | 2005058311 | 6/2005 |
| WO | 2007053506 A1 | 5/2007 |

(Continued)

OTHER PUBLICATIONS

Favuzza, Paola et al., Dual Plasmepsin-Targeting Antimalarial Agents Disrupt Multiple Stages of the Malaria Parasite Life Cycle, Cell Host & Microbe, 2020, 642-658, 27.

(Continued)

*Primary Examiner* — Alicia L Otton
(74) *Attorney, Agent, or Firm* — Sylvia A. Ayler; Catherine Fitch

(57) ABSTRACT

Methods of treating malaria comprising administration of compounds of Formula (I') or a pharmaceutically acceptable salt thereof, to a subject in need thereof, wherein the variables are as defined herein. It also provides uses of the compounds of Formula (I), as defined herein, for inhibiting plasmepsin X, plasmepsin IX or plasmepsin X and IX activity, for treating a *Plasmodium* infection, and for treating malaria. Also provided are methods of treatment further comprising administration of one or more additional antimalarial compounds.

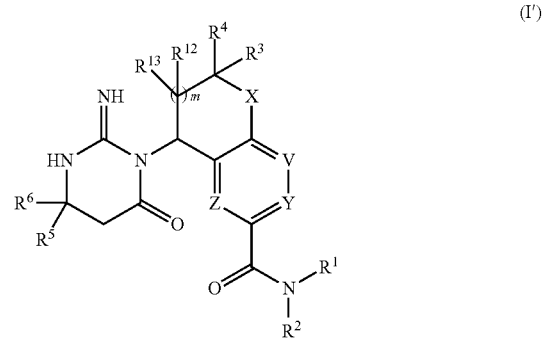

52 Claims, No Drawings

(51) Int. Cl.
*C07D 409/04* (2006.01)
*C07D 409/14* (2006.01)
*C07D 491/052* (2006.01)
*C07D 493/10* (2006.01)

(56) References Cited

FOREIGN PATENT DOCUMENTS

| | | |
|---|---|---|
| WO | 2008103351 A2 | 8/2008 |
| WO | 2011044181 A1 | 4/2011 |
| WO | 2017089453 A1 | 6/2017 |
| WO | 2017142821 A1 | 8/2017 |
| WO | 2017142825 A2 | 8/2017 |
| WO | 2017144517 A1 | 8/2017 |
| WO | 2020229427 A1 | 11/2020 |
| WO | 2021155791 A1 | 8/2021 |

OTHER PUBLICATIONS

Baldi, D. et al., RAPI controls rhoptry targeting of RAP2 in the malaria parasite Plasmodium falciparum, Embo Journal, 2000, 2435-2443, 19.
Berge, S.M., et al.,, "Pharmaceutical Salts", J. Pharm. Sci, 1977, pp. 1-19, vol. 66, No. 1.
Bingham, A.L., et al.,, "Over One Hundred Solvates of sulfathiazole", Chem. Commun., 2001, pp. 603-604.
Caira, M.R., et al.,, "Preparation and Crystal Characterization of a Polymorph,a Monohydrate, and an Ethyl Acetate Solvate of the Antifungal Fluconazole", J. Pharmaceutical Sci., 2004, pp. 601-611, vol. 93, No. 3.
Gould, Salt Selections for Basic Drugs, Intl. J. Pharmaceutics, 1986, pp. 201-217, vol. 33.
Pino, P. et al., A multi-stage antimalarial targets the plasmepsins IX and X essential for invasion and egress, Science, 2017, 522-528, 6362(358).
Powles, Mary Ann et al., MK-4815, a Potential New Oral Agent for Treatment of Malaria, Antimicrobial Agents and Chemotherapy, 2012, 2414-2419, 56(5).
Salmon, B.L. et al., Malaria parasite exit from the host erythrocyte: A two-step process requiring extraerythrocytic proteolysis, Proc Natl Acad Sci USA, 2001, 271-276, 98.
Stahl, P. Heinrich et al., Handbook of Pharmaceutical Salts: Properties, Selection, and Use, Verlag Helvetica Chimica Acta, Zürich, 2002, 1-377, N/A.
Van Tonder, E.C., et al.,, "Preparation and Physicochemical Characterization of 5 Niclosamide Solvates and 1 Hemisolvate", AAPS Pharm Sci Tech, 2004, pp. 1-10, vol. 5, No. 1, Article 12, US.
Lihong, Ping et al., Practical Therapeutic Pharmacology, Jilin Science and Technology Press, 2018, 11-18, 1st Edition.
Lihong, Ping et al., Practical Therapeutic Pharmacology, Jilin Science and Technology Press, 2018, 11-19, 1st Edition.

ANTIMALARIAL AGENTS

CROSS-REFERENCE TO RELATED APPLICATIONS

This application is a U.S. National Phase application under 35 U.S.C. § 371 of PCT Application No. PCT/CN2020/103178, filed Jul. 21, 2020, which published as WO 2021/027502 A1 on Feb. 18, 2021, and claims priority under 35 U.S.C. § 365 (b) from Patent Application No. PCT/CN2019/100781, filed Aug. 15, 2019.

FIELD OF THE INVENTION

The present invention relates to compounds of Formula (I') and (I), or pharmaceutically acceptable salts thereof, useful for the treatment of *Plasmodium* infections. More specifically, the present invention relates to compounds of Formula (I') and (I), or pharmaceutically acceptable salts thereof, useful for the treatment of *Plasmodium* infections, more particularly for the treatment of malaria.

BACKGROUND OF THE INVENTION

Malaria is a major disease in humans with several hundred million infections and over 450,000 deaths each year. The most lethal form of malaria is caused by *Plasmodium falciparum*. This protozoan parasite is responsible for almost all malarial deaths with most occurring in Africa. *P. falciparum* has a complex life cycle starting in the *Anopheles* mosquito vector when sporozoite forms are injected into the human host during a blood feed. These sporozoites migrate to the liver and invade hepatocytes in which they develop to form thousands of liver merozoites that egress into the blood where they invade erythrocytes to commence the asexual cycle of the parasite responsible for the symptoms of malaria. The parasite develops within the protected niche of the red cell to form 16-32 merozoites that, once mature, egress from the host cell to invade new red blood cells. Some of these parasites differentiate to form gametocytes, the sexual form of the parasite. These can be taken up by the mosquito where male and female gametes form, fuse and differentiate into oocysts on the mosquito midgut extracellular matrix. Sporozoites form within the oocyst and upon egress migrate to the salivary gland for delivery to the next host during blood feeding for perpetuation and survival of the parasite.

Other forms of malaria include a relapsing form of malaria caused by *P. vivax* which is responsible for significant morbidity, can cause virulent forms of this disease with some deaths and is mainly a problem outside Africa. *P. knowlesi* is found in South East Asia and is a zoonotic parasite that normally infects long-tailed macaques but has been shown to infect humans in Malaysian Borneo.

Artemisinin combined with partner drugs have become a mainstay in the treatment and control of malaria. However, due to the increasing threat of artemisinin-based combination therapy (ACT) drug resistance, the development of new antimalarials with novel targets that inhibit multiple steps in the parasite life cycle is an urgent priority for the malaria control field. Such novel antimalarials, as monotherapies or ACT partner drugs, could make strides towards malaria elimination as there is a reduced likelihood of parasites with preexisting resistance mutations being present in the parasite population.

Currently, aspartic acid proteases are prime targets for drug development: the HIV aspartic acid protease has been successfully targeted with a drug in clinical use; inhibitors that target human renin, BACE1 and gamma-secretase have been or are in clinical development. In the antimalarial drug space, *P. falciparum* aspartic acid proteases plasmepsin X and IX (PMX and PMIX) have been identified as potential targets since inhibitors block parasite egress and invasion of the host cell and prevent maturation of some rhoptry and micronemal proteins required for this process (Pino P, Caldelari R, Mukherjee B, Vahokoski J, Klages N, Maco B, et al. A multistage antimalarial targets the plasmepsins IX and X essential for invasion and egress. Science. 2017; 358(6362):522-8.)

SUMMARY OF THE INVENTION

The present invention is directed to compounds of Formula (I'):

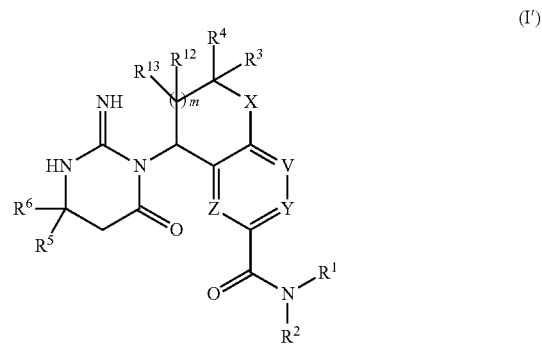

(I')

wherein X, V, Y, Z, $R^1$, $R^2$, $R^3$, $R^4$, $R^5$, $R^6$, $R^{12}$ and $R^{13}$ are described below.

The present invention is directed to compounds of Formula (I):

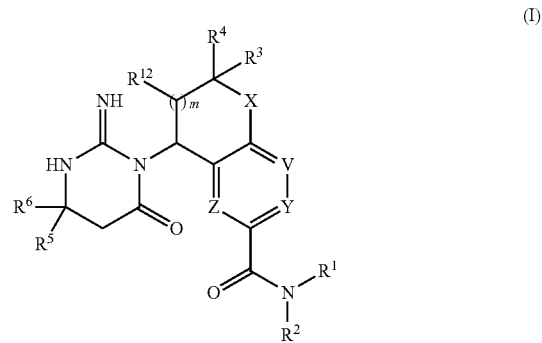

(I)

wherein X, V, Y, Z, $R^1$, $R^2$, $R^3$, $R^4$, $R^5$, $R^6$ and $R^{12}$ are described below.

Also described herein are methods of treatment of *Plasmodium* infections comprising administering to a subject in need thereof a compound of Formula (I') and (I), or a pharmaceutically acceptable salt thereof. Also described herein are methods of treatment of *Plasmodium* infections comprising administering to a subject in need thereof a compound of Formula (I') and (I), or a pharmaceutically acceptable salt thereof, and a pharmaceutically acceptable carrier.

Also described herein are methods of treatment of malaria comprising administering to a subject in need thereof a compound of Formula (I') and (I), or a pharmaceutically acceptable salt thereof.

The present invention further provides the use of compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent, for the treatment of malaria.

Moreover, the present invention provides methods for the use of pharmaceutical compositions comprising one or more of said compounds in the free form or in pharmaceutically acceptable salt form, together with one or more customary pharmaceutical excipient(s), for the treatment of *Plasmodium* infections, the treatment of malaria, the inhibition of plasmepsin X, or the dual inhibition of plasmepsin X and plasmepsin IX. Methods for the use of combinations of the compounds or salts of the invention together with one or more additional pharmaceutically active agents are also provided.

The present invention further provides methods for the inhibition of plasmepsin X, or the dual inhibition of plasmepsin X and plasmepsin IX activity and of treatment, prevention, amelioration and/or delaying onset of diseases or disorders in which the inhibition of plasmepsin X and/or plasmepsin IX has or may have a therapeutic effect, e.g. malaria.

The present invention further provides methods for the inhibition of *P. falciparum* aspartic acid proteases. The present invention further provides methods for blocking *P. falciparum* growth by inhibiting plasmepsin X. The present invention further provides methods for blocking *P. falciparum* growth by inhibiting both PMX and Plasmepsin IX.

The present invention further provides methods for the treatment of malaria by inhibiting plasmepsin X. The present invention further provides methods for the treatment of malaria by inhibiting both PMX and Plasmepsin IX.

These and other embodiments of the invention, which are described in detail below or will become clear to those of ordinary skill in the art, are included within the scope of the invention.

DETAILED DESCRIPTION OF THE INVENTION

Described herein are compounds having the structural Formula (I'):

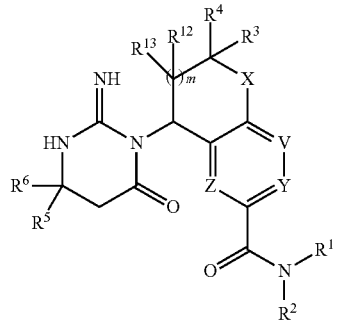

(I')

or a pharmaceutically acceptable salt thereof, wherein:
X is a bond, $C(R^{14})_2$, O, S, SO, $SO_2$ or NH;
Y is $CR^9$ or N, wherein when Y is N, Z is $CR^{11}$ and V is $CR^{10}$;
V is $CR^{10}$ or N, wherein when V is N, Z is $CR^{11}$ and Y is $CR^9$;
Z is $CR^{11}$ or N, wherein when Z is N, V is $CR^{10}$ and Y is $CR^9$;
$R^1$ is a heterocycloalkyl, $C_3$-$C_{12}$cycloalkyl, aryl, $C_1$-$C_6$alkylaryl or when taken with $R^2$, and the nitrogen which they are bonded, forms nitrogen-containing ring, wherein the heterocycloalkyl, $C_3$-$C_{12}$cycloalkyl, aryl, $C_1$-$C_6$alkylaryl or nitrogen-containing ring is unsubstituted or substituted with 1 to 5 substituents independently selected from the group consisting of halogen, CN, OH, $C_1$-$C_6$alkoxy, $C_1$-$C_6$alkylOC$_1$-$C_6$alkyl, $C_1$-$C_6$alkylCOOH, COOH, oxo, COOC$_1$-$C_6$alkyl, $C_1$-$C_6$alkylCOOC$_1$-$C_6$alkyl, $C_3$-$C_6$cycloalkyl, $C_1$-$C_6$alkylC$_3$-$C_6$cycloalkyl, aryl, $C_1$-$C_6$alkyl, $C_1$-$C_6$alkylOhaloC$_1$-$C_6$alkyl, haloC$_1$-$C_6$alkyl, $C_1$-$C_6$alkylOH, $CON(R^7)(R^8)$, $N(R^7)(R^8)$ and $C_1$-$C_6$alkylN($R^7$)($R^8$);
$R^2$ is hydrogen, $C_1$-$C_6$alkylCOOH, COOH, $C_3$-$C_6$cycloalkyl, $C_1$-$C_6$alkyl, haloC$_1$-$C_6$alkyl or $C_1$-$C_6$alkylOH or when taken with $R^1$, and the nitrogen which they are bonded, forms a nitrogen-containing ring, wherein the nitrogen-containing ring is unsubstituted or substituted with 1 to 5 substituents independently selected from the group consisting of halogen, CN, OH, $C_1$-$C_6$alkoxy, $C_1$-$C_6$alkylOC$_1$-$C_6$alkyl, $C_1$-$C_6$alkylCOOH, COOH, oxo, COOC$_1$-$C_6$alkyl, $C_3$-$C_6$cycloalkyl, $C_1$-$C_6$alkyl, haloC$_1$-$C_6$alkyl, $C_1$-$C_6$alkylOH, $CON(R^7)(R^8)$, $N(R^7)(R^8)$ and $C_1$-$C_6$alkylN($R^7$)($R^8$);
$R^3$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, haloC$_1$-$C_6$alkyl, $C_1$-$C_6$alkylOH, $CON(R^7)(R^8)$, $N(R^7)(R^8)$, $C_1$-$C_6$alkylN($R^7$)($R^8$), $C_1$-$C_6$alkyl(OCH$_2$CH$_2$)$_n$N($R^7$)($R^8$) or $C_1$-$C_6$alkylOhaloC$_1$-$C_6$alkyl or when taken with $R^4$ forms a $C_3$-$C_6$cycloalkyl or $C_3$-$C_6$heterocycloalkyl;
$R^4$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, haloC$_1$-$C_6$alkyl, $C_1$-$C_6$alkylOH, $CON(R^7)(R^8)$, $N(R^7)(R^8)$, $C_1$-$C_6$alkylN($R^7$)($R^8$), $C_1$-$C_6$alkyl(OCH$_2$CH$_2$)$_n$N($R^7$)($R^8$) or $C_1$-$C_6$alkylOhaloC$_1$-$C_6$alkyl or when taken with $R^3$ forms a $C_3$-$C_6$cycloalkyl or $C_3$-$C_6$heterocycloalkyl;
$R^5$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, haloC$_1$-$C_6$alkyl, $C_1$-$C_6$alkylOH, $CON(R^7)(R^8)$, $N(R^7)(R^8)$ or $C_1$-$C_6$alkylN($R^7$)($R^8$) or when taken with $R^6$ forms a $C_3$-$C_6$cycloalkyl or $C_3$-$C_6$heterocycloalkyl;
$R^6$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, haloC$_1$-$C_6$alkyl, $C_1$-$C_6$alkylOH, $CON(R^7)(R^8)$, $N(R^7)(R^8)$ or $C_1$-$C_6$alkylN($R^7$)($R^8$) or when taken with $R^5$ forms a $C_3$-$C_6$cycloalkyl or $C_3$-$C_6$heterocycloalkyl;
$R^7$ is hydrogen, $C_1$-$C_6$alkylCOOH, COOH, $C_3$-$C_6$cycloalkyl, $C_1$-$C_6$alkyl, haloC$_1$-$C_6$alkyl, $C_1$-$C_6$alkylOH, COC$_1$-$C_6$alkyl or COOC$_1$-$C_6$alkyl;
$R^8$ is hydrogen, $C_1$-$C_6$alkylCOOH, COOH, $C_3$-$C_6$cycloalkyl, $C_1$-$C_6$alkyl, haloC$_1$-$C_6$alkyl, $C_1$-$C_6$alkylOH, COC$_1$-$C_6$alkyl or COOC$_1$-$C_6$alkyl;

$R^9$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$);

$R^{10}$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$);

$R^{11}$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$);

$R^{12}$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$);

$R^{13}$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$);

each occurrence of $R^{14}$ is independently selected from the group consisting of hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) and $C_1$-$C_6$alkylN($R^7$)($R^8$);

n is 1, 2, 3 or 4; and m is 0, 1 or 2.

Also described herein are compounds having the structural Formula (I):

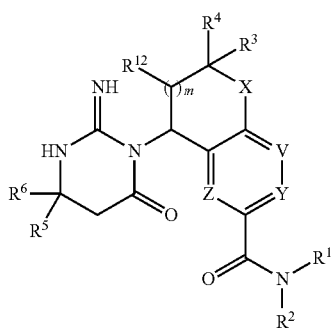

(I)

or a pharmaceutically acceptable salt thereof, wherein:

X is $CH_2$, O, S, SO, $SO_2$ or NH;

Y is $CR^9$ or N, wherein when Y is N, Z is $CR^{11}$ and V is $CR^{10}$;

V is $CR^{10}$ or N, wherein when V is N, Z is $CR^{11}$ and Y is $CR^9$;

Z is $CR^{11}$ or N, wherein when Z is N, V is $CR^{10}$ and Y is $CR^9$;

$R^1$ is a heterocycloalkyl, $C_3$-$C_{12}$cycloalkyl, aryl, $C_1$-$C_6$alkylaryl or when taken with $R^2$, and the nitrogen which they are bonded, forms nitrogen-containing ring, wherein the heterocycloalkyl, $C_3$-$C_{12}$cycloalkyl, aryl, $C_1$-$C_6$alkylaryl or nitrogen-containing ring is unsubstituted or substituted with 1 to 5 substituents independently selected from the group consisting of halogen, CN, OH, $C_1$-$C_6$alkoxy, $C_1$-$C_6$alkylO$C_1$-$C_6$alkyl, $C_1$-$C_6$alkylCOOH, COOH, oxo, COO$C_1$-$C_6$alkyl, $C_1$-$C_6$alkylCOO$C_1$-$C_6$alkyl, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) and $C_1$-$C_6$alkylN($R^7$)($R^8$);

$R^2$ is hydrogen, $C_1$-$C_6$alkylCOOH, COOH, $C_3$-$C_6$cycloalkyl, $C_1$-$C_6$alkyl, halo$C_1$-$C_6$alkyl or $C_1$-$C_6$alkylOH or when taken with $R^1$, and the nitrogen which they are bonded, forms a nitrogen-containing ring, wherein the nitrogen-containing ring is unsubstituted or substituted with 1 to 5 substituents independently selected from the group consisting of halogen, CN, OH, $C_1$-$C_6$alkoxy, $C_1$-$C_6$alkylO$C_1$-$C_6$alkyl, $C_1$-$C_6$alkylCOOH, COOH, oxo, COO$C_1$-$C_6$alkyl, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) and $C_1$-$C_6$alkylN($R^7$)($R^8$);

$R^3$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$) or when taken with $R^4$ forms a $C_3$-$C_6$cycloalkyl or $C_3$-$C_6$heterocycloalkyl;

$R^4$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$) or when taken with $R^3$ forms a $C_3$-$C_6$cycloalkyl or $C_3$-$C_6$heterocycloalkyl;

$R^5$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$) or when taken with $R^6$ forms a $C_3$-$C_6$cycloalkyl or $C_3$-$C_6$heterocycloalkyl;

$R^6$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$) or when taken with $R^5$ forms a $C_3$-$C_6$cycloalkyl or $C_3$-$C_6$heterocycloalkyl;

$R^7$ is hydrogen, $C_1$-$C_6$alkylCOOH, COOH, $C_3$-$C_6$cycloalkyl, $C_1$-$C_6$alkyl, halo$C_1$-$C_6$alkyl or $C_1$-$C_6$alkylOH;

$R^8$ is hydrogen, $C_1$-$C_6$alkylCOOH, COOH, $C_3$-$C_6$cycloalkyl, $C_1$-$C_6$alkyl, halo$C_1$-$C_6$alkyl or $C_1$-$C_6$alkylOH;

$R^9$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$);

$R^{10}$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$);

$R^{11}$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$);

$R^{12}$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$); and m is 0, 1 or 2.

In the embodiments described herein, X is a bond, $C(R^{14})_2$, O, S, SO, $SO_2$ or NH. In certain embodiments described herein X is a bond. In certain embodiments, X is $C(R^{14})_2$, wherein $R^{14}$ is discussed in further detail below. In certain embodiments, X is a bond, $CH_2$, $CH(CH_3)$, $C(CH_3)_2$, O, $CH(OCH_3)$, $SO_2$ or $CF_2$. In other embodiments X is $CH_2$, O, S, SO, $SO_2$ or NH. In certain embodiments, X is $CH_2$. In the embodiments described herein, X is O. In the embodiments described herein, X is S. In the embodiments described herein, X is SO. In the embodiments described herein, X is $SO_2$. In the embodiments described herein, X is NH. In the embodiments described herein, X is O or $SO_2$.

In the embodiments described herein, Y is $CR^9$ or N. In certain embodiments, Y is $CR^9$, wherein $R^9$ is discussed in detail below. In certain embodiments, Y is N. In certain embodiments, Y is CH. In certain embodiments, wherein when Y is N, Z is $CR^{11}$ and V is $CR^{10}$.

In the embodiments described herein, V is $CR^{10}$ or N. In certain embodiments, V is $CR^{10}$, $R^{10}$ are discussed in detail below. In certain embodiments, V is N. In certain embodiments, V is CH. In certain embodiments, wherein when V is N, Z is $CR^{11}$ and Y is $CR^9$.

In the embodiments described herein, Z is $CR^{11}$ or N. In certain embodiments, Z is $CR^{11}$, $R^{11}$ are discussed in detail below. In certain embodiments, Z is CH. In certain embodiments, Z is N. In certain embodiments, wherein when Z is N, V is $CR^{10}$ and Y is $CR^9$.

In certain embodiments, X is O, Y and V are each CH and Z is N. In certain embodiments, X is O, Y and Z are each CH and V is N. In certain embodiments, X is O and V, Y and Z are all simultaneously CH.

These embodiments are represented as Formulas IA-IC:

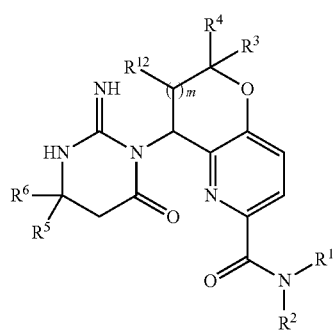

IA

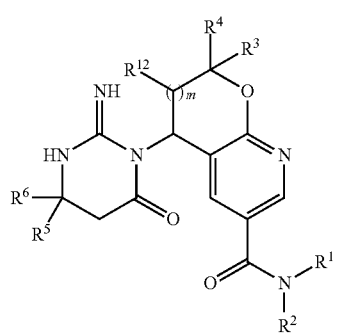

IB

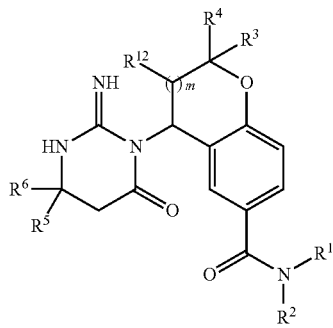

IC

In the embodiments described herein, $R^1$ is a heterocycloalkyl, $C_3$-$C_{12}$cycloalkyl, aryl, $C_1$-$C_6$alkylaryl or when taken with $R^2$, and the nitrogen which they are bonded, forms nitrogen-containing ring, wherein the heterocycloalkyl, $C_3$-$C_{12}$cycloalkyl, aryl, $C_1$-$C_6$alkylaryl or nitrogen-containing ring is unsubstituted or substituted with 1 to 5 substituents independently selected from the group consisting of halogen, CN, OH, $C_1$-$C_6$alkoxy, $C_1$-$C_6$alkylOC$_1$-$C_6$alkyl, $C_1$-$C_6$alkylCOOH, COOH, oxo, COOC$_1$-$C_6$alkyl, $C_1$-$C_6$alkylCOOC$_1$-$C_6$alkyl, $C_3$-$C_6$cycloalkyl, $C_1$-$C_6$alkylC$_3$-$C_6$cycloalkyl, aryl, $C_1$-$C_6$alkyl, $C_1$-$C_6$alkylOhaloC$_1$-$C_6$alkyl, haloC$_1$-$C_6$alkyl, $C_1$-$C_6$alkylOH, CON($R^7$)($R^8$), N($R^7$)($R^8$) and $C_1$-$C_6$alkylN($R^7$)($R^8$).

In the embodiments described herein, $R^1$ is a heterocycloalkyl, $C_3$-$C_{12}$cycloalkyl, aryl, $C_1$-$C_6$alkylaryl or when taken with $R^2$, and the nitrogen which they are bonded, forms nitrogen-containing ring, wherein the heterocycloalkyl, $C_3$-$C_{12}$cycloalkyl, aryl, $C_1$-$C_6$alkylaryl or nitrogen-containing ring is unsubstituted or substituted with 1 to 5 substituents independently selected from the group consisting of halogen, CN, OH, $C_1$-$C_6$alkoxy, $C_1$-$C_6$alkylOC$_1$-$C_6$alkyl, $C_1$-$C_6$alkylCOOH, COOH, oxo, COOC$_1$-$C_6$alkyl, $C_3$-$C_6$cycloalkyl, $C_1$-$C_6$alkyl, haloC$_1$-$C_6$alkyl, $C_1$-$C_6$alkylOH, CON($R^7$)($R^8$), N($R^7$)($R^8$) and $C_1$-$C_6$alkylN($R^7$)($R^8$).

In certain embodiments, $R^1$ is a bicyclic ring. In certain embodiments, $R^1$ is a bicyclic heterocycloalkyl, bicyclic $C_3$-$C_{12}$cycloalkyl, bicyclic aryl or when taken with $R^2$ and the nitrogen to which they are bonded, forms a bicyclic nitrogen-containing ring. In certain embodiments, $R^1$ is a bicyclic heterocycloalkyl, bicyclic $C_3$-$C_{12}$cycloalkyl, bicyclic aryl or when taken with $R^2$ and the nitrogen to which they are bonded, forms a bicyclic nitrogen-containing ring, wherein one of the rings is a benzene ring. In certain embodiments, $R^1$ is a bicyclic heterocycloalkyl, bicyclic $C_3$-$C_{12}$cycloalkyl, $C_1$-$C_6$alkylphenyl or when taken with $R^2$ and the nitrogen to which they are bonded, forms a bicyclic nitrogen-containing ring, wherein one of the rings of the bicyclic heterocycloalkyl, bicyclic $C_3$-$C_{12}$cycloalkyl or when taken with $R^2$ and the nitrogen to which they are bonded, is a benzene ring.

In certain embodiments, $R^1$ is a heterocycloalkyl. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of bicyclic heterocycloalkyl groups include, but are not limited to,

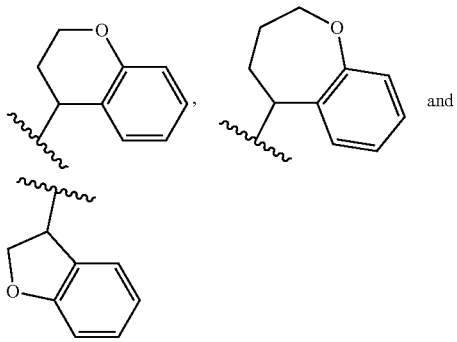

Non-limiting examples of bicyclic heterocycloalkyl groups include, but are not limited to,

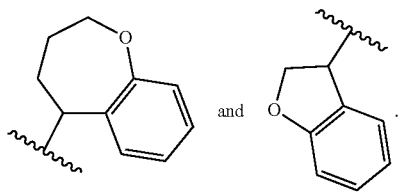 [SMILES: *C1CCCOc2ccccc21 ; *C1COc2ccccc21]

In certain embodiments, $R^1$ is

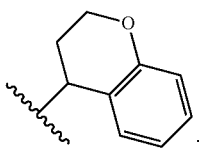 [SMILES: *C1CCOc2ccccc21]

In certain embodiments, $R^1$ is a $C_3$-$C_{12}$cycloalkyl. In certain embodiments, the cycloalkyl is a monocyclic cycloalkyl. Suitable examples of cycloalkyls include, but are not limited to, cyclopropyl, cyclobutyl, cyclopentyl and cyclohexyl. In certain embodiments, the cycloalkyl is a bicyclic cycloalkyl. Suitable examples of cycloalkyls include, but are not limited to:

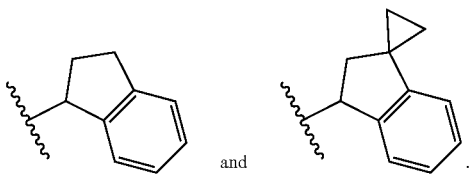 [SMILES: *C1CCc2ccccc21 ; *C1CC2(CC2)c2ccccc21]

Suitable examples of cycloalkyls include, but are not limited to:

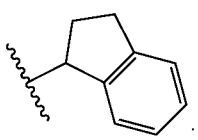 [SMILES: *C1CCc2ccccc21]

In certain embodiments, $R^1$ is an aryl ring. Suitable examples of aryls include, but are not limited to, monocyclic aryl groups such as, phenyl and bicyclic aryl groups such as naphthyl.

In certain embodiments, $R^1$ is a $C_1$-$C_6$alkylaryl ring. Suitable examples of $C_1$-$C_6$alkylaryls include, but are not limited to:

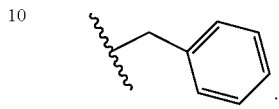

In certain embodiments, $R^1$ is taken with $R^2$ and forms a nitrogen-containing ring. Suitable examples of nitrogen-containing rings include, but are not limited to, aziridinyl, azirinyl, azetidinyl, azete, indoline, pyrrolidinyl, pyrrolyl, piperidinyl and pyridinyl. In certain embodiments, $R^1$ is taken with $R^2$ and forms a nitrogen-containing ring, wherein the nitrogen-containing ring is an indoline. In certain embodiments, $R^1$ is taken with $R^2$ and forms a nitrogen-containing ring, wherein the nitrogen-containing ring is:

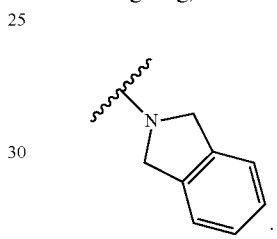

In certain embodiments, $R^1$ is unsubstituted. In other embodiments, $R^1$ is substituted with 1 to 5 substituents independently selected from the group consisting of halogen, CN, OH, $C_1$-$C_6$alkoxy, $C_1$-$C_6$alkylOC$_1$-$C_6$alkyl, $C_1$-$C_6$alkylCOOH, COOH, oxo, COOC$_1$-$C_6$alkyl, $C_1$-$C_6$alkylCOOC$_1$-$C_6$alkyl, $C_3$-$C_6$cycloalkyl, $C_1$-$C_6$alkylC$_3$-$C_6$cycloalkyl, aryl, $C_1$-$C_6$alkyl, $C_1$-$C_6$alkylOhaloC$_1$-$C_6$alkyl, haloC$_1$-$C_6$alkyl, $C_1$-$C_6$alkylOH, CON(R$^7$)(R$^8$), N(R$^7$)(R$^8$) and $C_1$-$C_6$alkylN(R$^7$)(R$^8$). In other embodiments, $R^1$ is substituted with 1 to 5 substituents independently selected from the group consisting of halogen, CN, OH, $C_1$-$C_6$alkoxy, $C_1$-$C_6$alkylOC$_1$-$C_6$alkyl, $C_1$-$C_6$alkylCOOH, COOH, oxo, COOC$_1$-$C_6$alkyl, $C_3$-$C_6$cycloalkyl, $C_1$-$C_6$alkyl, haloC$_1$-$C_6$alkyl, $C_1$-$C_6$alkylOH, CON(R$^7$)(R$^8$), N(R$^7$)(R$^8$) and $C_1$-$C_6$alkylN(R$^7$)(R$^8$).

In certain embodiments, $R^1$ is substituted with 1 substituent. In certain embodiments, $R^1$ is substituted with 2 substituents. In certain embodiments, $R^1$ is substituted with 3 substituents. In certain embodiments, $R^1$ is substituted with 4 substituents. In certain embodiments, $R^1$ is substituted with 5 substituents.

In certain embodiments, $R^1$ is substituted with halogen. Examples of suitable halogens include chlorine, bromine, fluorine and iodine. In certain embodiments, $R^1$ is substituted with CN. In certain embodiments, $R^1$ is substituted with OH. In certain embodiments, $R^1$ is substituted with an oxo group. In certain embodiments, $R^1$ is substituted with $C_1$-$C_6$alkoxy. Suitable alkoxys include, but are not limited to, methoxy, ethoxy, n-propoxy, isopropoxy and n-butoxy. In certain embodiments, $R^1$ is substituted with $C_1$-$C_6$alkylOC$_1$-$C_6$alkyl. In certain embodiments, $R^1$ is substituted with $C_1$-$C_6$alkylCOOH. In certain embodiments, $R^1$ is substituted with COOH. In certain embodiments, $R^1$ is substituted with $C_1$-$C_6$alkylCOOC$_1$-$C_6$alkyl.

In certain embodiments, $R^1$ is substituted with $C_3$-$C_6$cycloalkyl. Suitable examples of cycloalkyls include, but are not limited to, cyclopropyl, cyclobutyl, cyclopentyl and cyclohexyl.

In certain embodiments, $R^1$ is substituted with $C_1$-$C_6$alkylC$_3$-$C_6$cycloalkyl. Suitable examples of cycloalkyls include, but are not limited to

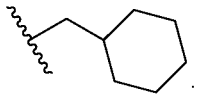 [SMILES: *CC1CCCCC1]

In certain embodiments, $R^1$ is substituted with aryl. Suitable examples of cycloalkyls include, but are not limited to, phenyl.

In certain embodiments, $R^1$ is substituted with $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^1$ is substituted with $C_1$-$C_6$alkylOhaloC$_1$-$C_6$alkyl. Suitable examples of haloalkyls include, but are not limited to,

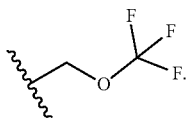

In certain embodiments, $R^1$ is substituted with haloC$_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^1$ is substituted with $C_1$-$C_6$alkylOH. Examples of suitable alcohols include, but are not limited to, methanol, ethanol, propanol, butanol and iso-butanol. In certain embodiments, $R^1$ is substituted with CON($R^7$)($R^8$). In certain embodiments, $R^1$ is substituted with N($R^7$)($R^8$). In certain embodiments, $R^1$ is substituted with $C_1$-$C_6$alkylN($R^7$)($R^8$), wherein $R^7$ and $R^8$ will be described in detail below.

In certain embodiments, $R^1$ is substituted with 1 to 4 substituents selected independently from the group consisting of bromine, fluorine, chlorine, methyl, OH, halogen, CN oxo, methoxymethyl, COOCH$_2$CH$_3$ and trifluoromethyl.

In certain embodiments described herein, $R^2$ is hydrogen, $C_1$-$C_6$alkylCOOH, COOH, $C_3$-$C_6$cycloalkyl, $C_1$-$C_6$alkyl, haloC$_1$-$C_6$alkyl or $C_1$-$C_6$alkylOH or when taken with $R^1$, and the nitrogen which they are bonded, forms a nitrogen-containing ring, wherein the nitrogen-containing ring is unsubstituted or substituted with 1 to 5 substituents independently selected from the group consisting of halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, haloC$_1$-$C_6$alkyl, $C_1$-$C_6$alkylOH, CON($R^7$)($R^8$), N($R^7$)($R^8$) and $C_1$-$C_6$alkylN($R^7$)($R^8$).

In certain embodiments, $R^2$ is hydrogen. In certain embodiments, $R^2$ is $C_1$-$C_6$alkylCOOH. In certain embodiments, $R^2$ is COOH. In certain embodiments, $R^2$ is $C_3$-$C_6$cycloalkyl. Suitable examples of cycloalkyls include, but are not limited to, cyclopropyl, cyclobutyl, cyclopentyl and cyclohexyl. In certain embodiments, $R^2$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl.

In certain embodiments, $R^2$ is haloC$_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^2$ is $C_1$-$C_6$alkylOH. Examples of suitable alcohols include, but are not limited to, methanol, ethanol, propanol, butanol and iso-butanol.

In certain embodiments, $R^2$ is taken with $R^1$ and forms a nitrogen-containing ring. Suitable examples of nitrogen-containing rings include, but are not limited to, aziridinyl, azirinyl, azetidinyl, azete, indoline, pyrrolidinyl, pyrrolyl, piperidinyl and pyridinyl. In certain embodiments, $R^2$ is taken with $R^1$ and forms an indoline.

In certain embodiments, the nitrogen-containing ring is unsubstituted. In other embodiments, the nitrogen-containing ring is substituted with 1 to 5 substituents independently selected from the group consisting of halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, haloC$_1$-$C_6$alkyl, $C_1$-$C_6$alkylOH, CON($R^7$)($R^8$), N($R^7$)($R^8$) and $C_1$-$C_6$alkylN($R^7$)($R^8$). In certain embodiments, the nitrogen-containing ring is substituted with 1 substituent. In certain embodiments, the nitrogen-containing ring is substituted with 2 substituents. In certain embodiments, the nitrogen-containing ring is substituted with 3 substituents. In certain embodiments, the nitrogen-containing ring is substituted with 4 substituents. In certain embodiments, the nitrogen-containing ring is substituted with 5 substituents.

In certain embodiments, the nitrogen-containing ring is substituted with halogen. Examples of suitable halogens include chlorine, bromine, fluorine and iodine. In certain embodiments, the nitrogen-containing ring is substituted with CN. In certain embodiments, the nitrogen-containing ring is substituted with OH. In certain embodiments, the nitrogen-containing ring is substituted with alkoxy. Suitable alkoxys include, but are not limited to, methoxy, ethoxy, n-propoxy, isopropoxy and n-butoxy. In certain embodiments, the nitrogen-containing ring is substituted with $C_1$-$C_6$alkylalkoxy. In certain embodiments, the nitrogen-containing ring is substituted with $C_1$-$C_6$alkylCOOH. In certain embodiments, the nitrogen-containing ring is substituted with COOH.

In certain embodiments, the nitrogen-containing ring is substituted with $C_3$-$C_6$cycloalkyl. Suitable examples of cycloalkyls include, but are not limited to, cyclopropyl, cyclobutyl, cyclopentyl and cyclohexyl. In certain embodiments, the nitrogen-containing ring is substituted with $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^1$ is substituted with haloC$_1$-C$_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^1$ is substituted with C$_1$-C$_6$alkylOH. Examples of suitable alcohols include, but are not limited to, methanol, ethanol, propanol, butanol and iso-butanol. In certain embodiments, the nitrogen-containing ring is substituted with CON(R$^7$)(R$^8$). In certain embodiments, the nitrogen-containing ring is substituted with N(R$^7$)(R$^8$). In certain embodiments, the nitrogen-containing ring is substituted with C$_1$-C$_6$alkylN(R$^7$)(R$^8$), wherein $R^7$ and $R^8$ will be described in detail below.

In certain embodiments, $R^1$ is selected from the group consisting of:

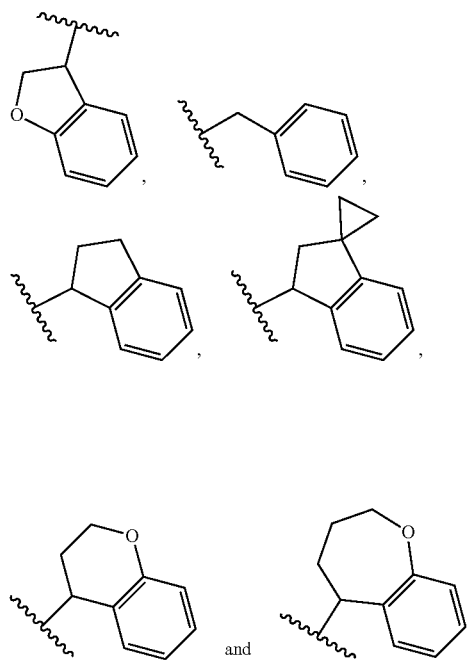

wherein $R^1$ is unsubstituted or substituted with 1 to 5 substituents selected from the group consisting of halogen, CN, OH, C$_1$-C$_6$alkoxy, C$_1$-C$_6$alkylOC$_1$-C$_6$alkyl, C$_1$-C$_6$alkylCOOH, COOH, oxo, COOC$_1$-C$_6$alkyl, C$_3$-C$_6$cycloalkyl, C$_1$-C$_6$alkylC$_3$-C$_6$cycloalkyl, aryl, C$_1$-C$_6$alkyl, haloC$_1$-C$_6$alkyl, C$_1$-C$_6$alkylOhaloC$_1$-C$_6$alkyl, C$_1$-C$_6$alkylOH, CON(R$^7$)(R$^8$), N(R$^7$)(R$^8$) and C$_1$-C$_6$alkylN(R$^7$)(R$^8$);

$R^7$ is hydrogen, C$_1$-C$_6$alkylCOOH, COOH, C$_3$-C$_6$cycloalkyl, C$_1$-C$_6$alkyl, haloC$_1$-C$_6$alkyl or C$_1$-C$_6$alkylOH; and $R^8$ is hydrogen, C$_1$-C$_6$alkylCOOH, COOH, C$_3$-C$_6$cycloalkyl, C$_1$-C$_6$alkyl, haloC$_1$-C$_6$alkyl or C$_1$-C$_6$alkylOH.

In certain embodiments, $R^2$ is hydrogen and $R^1$ is is selected from the group consisting of:

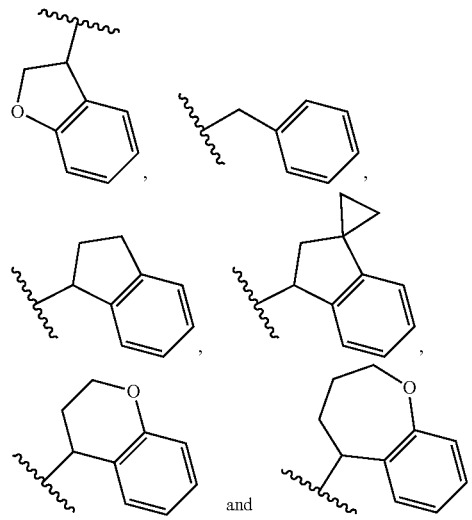

wherein $R^1$ is unsubstituted or substituted with 1 to 5 substituents selected from the group consisting of methyl, OH, NH$_2$, CH$_2$OH, methoxy, fluorine, phenyl, cyclohexyl, chlorine, trifluoromethyl, CH$_2$cyclohexyl, CH$_2$OCHF$_2$ and COOCH$_2$CH$_3$.

With regard to the compounds described herein, $R^3$ is hydrogen, halogen, CN, OH, C$_1$-C$_6$alkoxy, C$_1$-C$_6$alkylOC$_1$-C$_6$alkyl, C$_1$-C$_6$alkylCOOH, COOH, C$_3$-C$_6$cycloalkyl, C$_1$-C$_6$alkyl, haloC$_1$-C$_6$alkyl, C$_1$-C$_6$alkylOH, CON(R$^7$)(R$^8$), N(R$^7$)(R$^8$), C$_1$-C$_6$alkylN(R$^7$)(R$^8$), C$_1$-C$_6$alkyl(OCH$_2$CH$_2$)$_6$N(R$^7$)(R$^8$) or C$_1$-C$_6$alkylOhaloC$_1$-C$_6$alkyl or when taken with $R^4$ forms a C$_3$-C$_6$cycloalkyl or C$_3$-C$_6$heterocycloalkyl. In certain embodiments of the compounds described herein, $R^3$ is hydrogen, halogen, CN, OH, C$_1$-C$_6$alkoxy, C$_1$-C$_6$alkylOC$_1$-C$_6$alkyl, C$_1$-C$_6$alkylCOOH, COOH, C$_3$-C$_6$cycloalkyl, C$_1$-C$_6$alkyl, haloC$_1$-C$_6$alkyl, C$_1$-C$_6$alkylOH, CON(R$^7$)(R$^8$), N(R$^7$)(R$^8$) or C$_1$-C$_6$alkylN(R$^7$)(R$^8$) or when taken with $R^4$ forms a C$_3$-C$_6$cycloalkyl or C$_3$-C$_6$heterocycloalkyl. In certain embodiments, $R^3$ is hydrogen. In certain embodiments, $R^3$ is halogen. Suitable halogens include fluorine, chlorine, bromine, and iodine. In certain embodiments, $R^3$ is CN. In certain embodiments, $R^3$ is OH.

In certain embodiments, $R^3$ is C$_1$-C$_6$alkoxy. Suitable alkoxys include, but are not limited to, methoxy, ethoxy, n-propoxy, isopropoxy and n-butoxy. In certain embodiments, $R^3$ is C$_1$-C$_6$alkylOC$_1$-C$_6$alkyl. In certain embodiments, $R^3$ is COOH. In certain embodiments, $R^3$ is C$_1$-C$_6$alkylCOOH. In certain embodiments, $R^3$ is C$_3$-C$_6$cycloalkyl. Suitable examples of cycloalkyls include, but are not limited to, cyclopropyl, cyclobutyl, cyclopentyl and cyclohexyl. In certain embodiments, $R^3$ is C$_1$-C$_6$alkyl. Examples of C$_1$-C$_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^3$ is haloC$_1$-C$_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^3$ is $C_1$-$C_6$alkylOH. Examples of suitable alcohols include, but are not limited to, methanol, ethanol, propanol, butanol and iso-butanol. In certain embodiments, $R^3$ is $CON(R^7)(R^8)$. Suitable examples of $N(R^7)(R^8)$ include, but are not limited to, $CONH_2$ and $CON(CH_3)_2$. In certain embodiments, $R^3$ is $N(R^7)(R^8)$. Suitable examples of $N(R^7)(R^8)$ include, but are not limited to, $NH_2$ and $N(CH_3)_2$. In certain embodiments, $R^3$ is $C_1$-$C_6$alkylN$(R^7)(R^8)$. Suitable examples of $C_1$-$C_6$alkylN$(R^7)(R^8)$ include, but are not limited to,

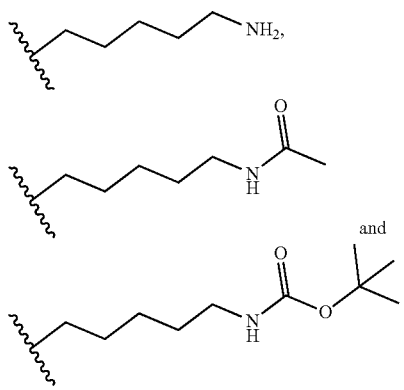

$R^7$ and $R^8$ are discussed in further detail below.

In certain embodiments, $R^3$ is $C_1$-$C_6$alkylOhaloC$_1$-$C_6$alkyl. Suitable examples of haloalkyls include, but are not limited to,

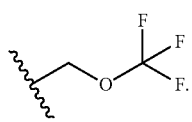 [SMILES: *COC(F)(F)F]

In certain embodiments, $R^3$ is $C_1$-$C_6$alkyl(OCH$_2$CH$_2$)$_n$N$(R^7)(R^8)$. $R^7$, $R^8$ and n are discussed in detail below. Suitable examples of $C_1$-$C_6$alkyl(OCH$_2$CH$_2$)$_n$N$(R^7)(R^8)$ include, but are not limited to,

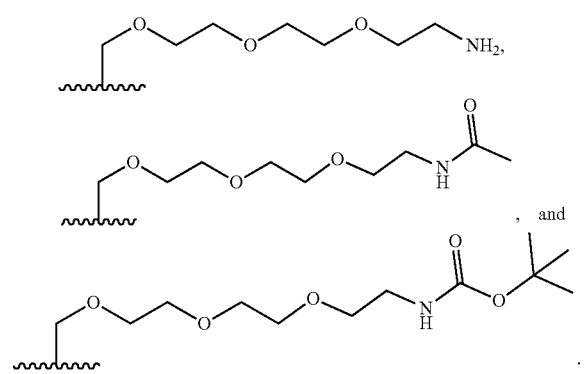

With regard to the compounds described herein, n is 1, 2, 3 or 4. In certain embodiments, n is 1. In certain embodiments, n is 2. In certain embodiments, n is 3. In certain embodiments, n is 4.

In certain embodiments, $R^3$ is taken with $R^4$ and forms a $C_3$-$C_6$cycloalkyl or $C_3$-$C_6$heterocycloalkyl. In certain embodiments, $R^3$ is taken with $R^4$ and forms a $C_3$-$C_6$cycloalkyl. Suitable examples of cycloalkyls include, but are not limited to, cyclopropyl, cyclobutyl, cyclopentyl and cyclohexyl. In certain embodiments, $R^3$ is taken with $R^4$ and forms a $C_3$-$C_6$heterocycloalkyl. Suitable examples of heterocycloalkyls include, but are not limited to, piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof.

In certain embodiments, $R^3$ is hydrogen, fluorine, methyl, ethyl, OH, methoxy,

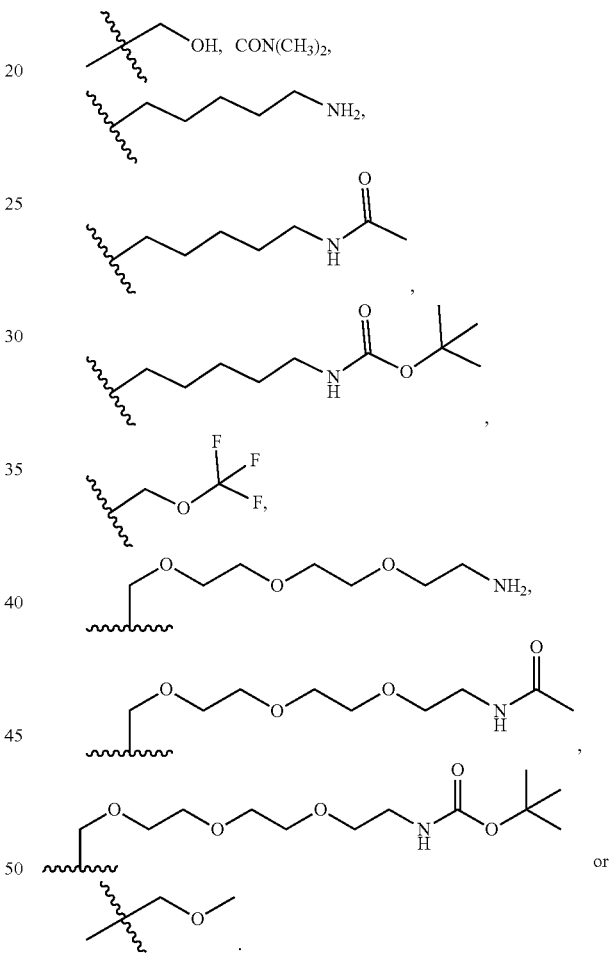

In certain embodiments, $R^3$ is hydrogen, methyl, ethyl or

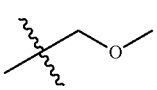

In certain embodiments, $R^3$ is taken with $R^4$ to form oxetanyl.

With regard to the compounds described herein, $R^4$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$), $C_1$-$C_6$alkylN($R^7$)($R^8$), $C_1$-$C_6$alkyl (OCH$_2$CH$_2$)$_n$N($R^7$)($R^8$) or $C_1$-$C_6$alkylOhalo$C_1$-$C_6$alkyl or when taken with $R^3$ forms a $C_3$-$C_6$cycloalkyl or $C_3$-$C_6$heterocycloalkyl. In certain embodiments of the compounds described herein, $R^4$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$) or when taken with $R^3$ forms a $C_3$-$C_6$cycloalkyl or $C_3$-$C_6$heterocycloalkyl. In certain embodiments, $R^4$ is hydrogen. In certain embodiments, $R^4$ is halogen. Suitable halogens include fluorine, chlorine, bromine, or iodine. In certain embodiments, $R^4$ is CN. In certain embodiments, $R^4$ is OH.

In certain embodiments, $R^4$ is $C_1$-$C_6$alkoxy. Suitable alkoxys include, but are not limited to, methoxy, ethoxy, n-propoxy, isopropoxy and n-butoxy. In certain embodiments, $R^4$ is $C_1$-$C_6$alkylO$C_1$-$C_6$alkyl. In certain embodiments, $R^4$ is COOH. In certain embodiments, $R^4$ is $C_1$-$C_6$alkylCOOH. In certain embodiments, $R^4$ is $C_3$-$C_6$cycloalkyl. Suitable examples of cycloalkyls include, but are not limited to, cyclopropyl, cyclobutyl, cyclopentyl and cyclohexyl. In certain embodiments, $R^4$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^4$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^4$ is $C_1$-$C_6$alkylOH. Examples of suitable alcohols include, but are not limited to, methanol, ethanol, propanol, butanol and iso-butanol. In certain embodiments, $R^4$ is CON($R^7$)($R^8$). Suitable examples of N($R^7$)($R^8$) include, but are not limited to, CONH$_2$ and CON(CH$_3$)$_2$. In certain embodiments, $R^4$ is N($R^7$)($R^8$). Suitable examples of N($R^7$)($R^8$) include, but are not limited to, NH$_2$ and N(CH$_3$)$_2$. In certain embodiments, $R^4$ is $C_1$-$C_6$alkylN($R^7$)($R^8$). Suitable examples of $C_1$-$C_6$alkylN($R^7$)($R^8$) include, but are not limited to,

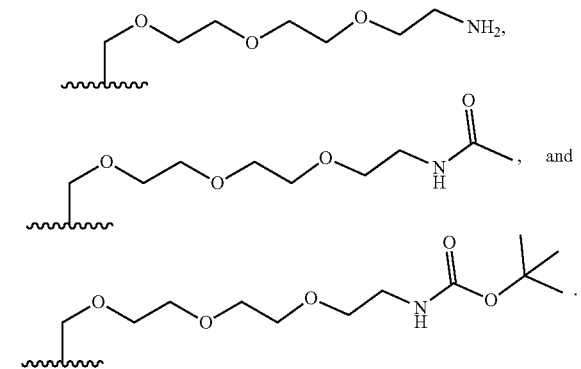

and $R^8$ are discussed in further detail below.

In certain embodiments, $R^4$ is $C_1$-$C_6$alkylOhalo$C_1$-$C_6$alkyl. Suitable examples of haloalkyls include, but are not limited to,

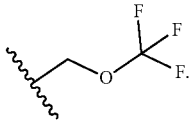 [SMILES: *COC(F)(F)F]

In certain embodiments, $R^4$ is $C_1$-$C_6$alkyl(OCH$_2$CH$_2$)$_n$N($R^7$)($R^8$). $R^7$, $R^8$ are discussed in detail below and n is discussed above. Suitable examples of $C_1$-$C_6$alkyl (OCH$_2$CH$_2$)$_n$N($R^7$)($R^8$) include, but are not limited to, In certain embodiments, $R^4$ is taken with $R^3$ and forms a $C_3$-$C_6$cycloalkyl or $C_3$-$C_6$heterocycloalkyl. In certain embodiments, $R^4$ is taken with $R^3$ and forms a $C_3$-$C_6$cycloalkyl. Suitable examples of cycloalkyls include, but are not limited to, cyclopropyl, cyclobutyl, cyclopentyl and cyclohexyl. In certain embodiments, $R^4$ is taken with $R^3$ and forms a $C_3$-$C_6$heterocycloalkyl. Suitable examples of heterocycloalkyls include, but are not limited to, piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof.

In certain embodiments, $R^4$ is hydrogen or methyl. In certain embodiments, $R^4$ is hydrogen, methyl, ethyl or In certain embodiments, $R^4$ is taken with $R^3$ to form oxetanyl. In certain embodiments, $R^3$ and $R^4$ are both hydrogen, methyl or ethyl.

In certain embodiments, $R^3$ is hydrogen and $R^4$ is hydrogen, methyl, ethyl or With regard to the compounds described herein, $R^5$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$) or when taken with $R^6$ forms a $C_3$-$C_6$cycloalkyl or $C_3$-$C_6$heterocycloalkyl. In certain embodiments, $R^5$ is hydrogen. In certain embodiments, $R^5$ is halogen. Suitable halogens include fluorine, chlorine, bromine, or iodine. In certain embodiments, $R^5$ is CN. In certain embodiments, $R^5$ is OH.

In certain embodiments, $R^5$ is $C_1$-$C_6$alkoxy. Suitable alkoxys include, but are not limited to, methoxy, ethoxy, n-propoxy, isopropoxy and n-butoxy. In certain embodiments, $R^5$ is $C_1$-$C_6$alkylOC$_1$-$C_6$alkyl. In certain embodiments, $R^5$ is COOH. In certain embodiments, $R^5$ is $C_1$-$C_6$alkylCOOH. In certain embodiments, $R^5$ is $C_3$-$C_6$cycloalkyl. Suitable examples of cycloalkyls include, but are not limited to, cyclopropyl, cyclobutyl, cyclopentyl and cyclohexyl. In certain embodiments, $R^5$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^5$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^5$ is $C_1$-$C_6$alkylOH. Examples of suitable alcohols include, but are not limited to, methanol, ethanol, propanol, butanol and iso-butanol. In certain embodiments, $R^5$ is CON($R^7$)($R^8$). In certain embodiments, $R^5$ is N($R^7$)($R^8$). In certain embodiments, $R^5$ is $C_1$-$C_6$alkylN($R^7$)($R^8$). $R^7$ and $R^8$ are discussed in detail below.

In certain embodiments, $R^5$ is taken with $R^6$ and forms a $C_3$-$C_6$cycloalkyl or $C_3$-$C_6$heterocycloalkyl. In certain embodiments, $R^5$ is taken with $R^6$ and forms a $C_3$-$C_6$cycloalkyl. Suitable examples of cycloalkyls include, but are not limited to, cyclopropyl, cyclobutyl, cyclopentyl and cyclohexyl. In certain embodiments, $R^5$ is taken with $R^6$ and forms a $C_3$-$C_6$heterocycloalkyl. Suitable examples of heterocycloalkyls include, but are not limited to, piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof.

In certain embodiments, $R^5$ is methyl, ethyl or t-butyl.

With regard to the compounds described herein, $R^6$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$) or when taken with $R^5$ forms a $C_3$-$C_6$cycloalkyl or $C_3$-$C_6$heterocycloalkyl. In certain embodiments, $R^6$ is hydrogen. In certain embodiments, $R^6$ is halogen. Suitable halogens include fluorine, chlorine, bromine, or iodine. In certain embodiments, $R^6$ is CN. In certain embodiments, $R^6$ is OH.

In certain embodiments, $R^6$ is $C_1$-$C_6$alkoxy. Suitable alkoxys include, but are not limited to, methoxy, ethoxy, n-propoxy, isopropoxy and n-butoxy. In certain embodiments, $R^6$ is $C_1$-$C_6$alkylOC$_1$-$C_6$alkyl. In certain embodiments, $R^6$ is COOH. In certain embodiments, $R^6$ is $C_1$-$C_6$alkylCOOH. In certain embodiments, $R^6$ is $C_3$-$C_6$cycloalkyl. Suitable examples of cycloalkyls include, but are not limited to, cyclopropyl, cyclobutyl, cyclopentyl and cyclohexyl. In certain embodiments, $R^6$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^6$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^6$ is $C_1$-$C_6$alkylOH. Examples of suitable alcohols include, but are not limited to, methanol, ethanol, propanol, butanol and iso-butanol. In certain embodiments, $R^6$ is CON($R^7$)($R^8$). In certain embodiments, $R^6$ is N($R^7$)($R^8$). In certain embodiments, $R^6$ is $C_1$-$C_6$alkylN($R^7$)($R^8$). $R^7$ and $R^8$ are discussed in detail below.

In certain embodiments, $R^6$ is taken with $R^5$ and forms a $C_3$-$C_6$cycloalkyl or $C_3$-$C_6$heterocycloalkyl. In certain embodiments, $R^6$ is taken with $R^5$ and forms a $C_3$-$C_6$cycloalkyl. Suitable examples of cycloalkyls include, but are not limited to, cyclopropyl, cyclobutyl, cyclopentyl and cyclohexyl. In certain embodiments, $R^6$ is taken with $R^5$ and forms a $C_3$-$C_6$heterocycloalkyl. Suitable examples of heterocycloalkyls include, but are not limited to, piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof.

In certain embodiments, $R^6$ is methyl, ethyl or t-butyl.

With regard to the compounds described herein, $R^7$ is hydrogen, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, COC$_1$-$C_6$alkyl or COOC$_1$-$C_6$alkyl. In certain embodiments, $R^7$ is hydrogen, $C_1$-$C_6$alkylCOOH, COOH, $C_3$-$C_6$cycloalkyl, $C_1$-$C_6$alkyl, halo$C_1$-$C_6$alkyl or $C_1$-$C_6$alkylOH.

In certain embodiments, $R^7$ is hydrogen. In certain embodiments, $R^7$ is $C_1$-$C_6$alkylCOOH. In certain embodiments, $R^7$ is COOH. In certain embodiments, $R^7$ is $C_3$-$C_6$cycloalkyl. Suitable examples of cycloalkyls include, but are not limited to, cyclopropyl, cyclobutyl, cyclopentyl and cyclohexyl. In certain embodiments, $R^7$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^7$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^7$ is $C_1$-$C_6$alkylOH. Examples of suitable alcohols include, but are not limited to, methanol, ethanol, propanol, butanol and iso-butanol.

In certain embodiments, $R^7$ is COC$_1$-$C_6$alkyl. Suitable examples include, but are not limited to, COCH$_3$. In certain embodiments, $R^7$ is COOC$_1$-$C_6$alkyl. Suitable examples include, but are not limited to, COOCH$_3$.

With regard to the compounds described herein, $R^8$ is hydrogen, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, COC$_1$-$C_6$alkyl or COOC$_1$-$C_6$alkyl. In certain embodiments, $R^8$ is hydrogen, $C_1$-$C_6$alkylCOOH, COOH, $C_3$-$C_6$cycloalkyl, $C_1$-$C_6$alkyl, halo$C_1$-$C_6$alkyl or $C_1$-$C_6$alkylOH.

In certain embodiments, $R^8$ is hydrogen. In certain embodiments, $R^8$ is $C_1$-$C_6$alkylCOOH. In certain embodiments, $R^8$ is COOH. In certain embodiments, $R^8$ is $C_3$-$C_6$cycloalkyl. Suitable examples of cycloalkyls include, but are not limited to, cyclopropyl, cyclobutyl, cyclopentyl and cyclohexyl. In certain embodiments, $R^8$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^8$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^8$ is $C_1$-$C_6$alkylOH. Examples of suitable alcohols include, but are not limited to, methanol, ethanol, propanol, butanol and iso-butanol.

In certain embodiments, $R^8$ is COC$_1$-$C_6$alkyl. Suitable examples include, but are not limited to, COCH$_3$. In certain embodiments, $R^8$ is COOC$_1$-$C_6$alkyl. Suitable examples include, but are not limited to, COOCH$_3$.

With regard to the compounds described herein, $R^9$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$) and N($R^7$)($R^8$). In certain embodiments, $R^9$ is hydrogen. In certain embodiments, $R^9$ is halogen. Suitable halogens include fluorine, chlorine, bromine, or iodine. In certain embodiments, $R^9$ is CN. In certain embodiments, $R^9$ is OH.

In certain embodiments, $R^9$ is $C_1$-$C_6$alkoxy. Suitable alkoxys include, but are not limited to, methoxy, ethoxy, n-propoxy, isopropoxy and n-butoxy. In certain embodiments, $R^9$ is $C_1$-$C_6$alkylOC$_1$-$C_6$alkyl. In certain embodiments, $R^9$ is COOH. In certain embodiments, $R^9$ is $C_1$-$C_6$alkylCOOH. In certain embodiments, $R^9$ is $C_3$-$C_6$cycloalkyl. Suitable examples of cycloalkyls include, but are not limited to, cyclopropyl, cyclobutyl, cyclopentyl and cyclohexyl. In certain embodiments, $R^9$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^9$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^9$ is $C_1$-$C_6$alkylOH. Examples of suitable alcohols include, but are not limited to, methanol, ethanol, propanol, butanol and iso-butanol. In certain embodiments, $R^9$ is CON($R^7$)($R^8$). In certain embodiments, $R^9$ is N($R^7$)($R^8$). In certain embodiments, $R^9$ is $C_1$-$C_6$alkylN($R^7$)($R^8$).

With regard to the compounds described herein, $R^{10}$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$) and N($R^7$)($R^8$). In certain embodiments, $R^{10}$ is hydrogen. In certain embodiments, $R^{10}$ is halogen. Suitable halogens include fluorine, chlorine, bromine, or iodine. In certain embodiments, $R^{10}$ is CN. In certain embodiments, $R^{10}$ is OH.

In certain embodiments, $R^{10}$ is $C_1$-$C_6$alkoxy. Suitable alkoxys include, but are not limited to, methoxy, ethoxy, n-propoxy, isopropoxy and n-butoxy. In certain embodiments, $R^{10}$ is $C_1$-$C_6$alkylOC$_1$-$C_6$alkyl. In certain embodiments, $R^{10}$ is COOH. In certain embodiments, $R^{10}$ is $C_1$-$C_6$alkylCOOH. In certain embodiments, $R^{10}$ is $C_3$-$C_6$cycloalkyl. Suitable examples of cycloalkyls include, but are not limited to, cyclopropyl, cyclobutyl, cyclopentyl and cyclohexyl. In certain embodiments, $R^{10}$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{10}$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^{10}$ is $C_1$-$C_6$alkylOH. Examples of suitable alcohols include, but are not limited to, methanol, ethanol, propanol, butanol and iso-butanol. In certain embodiments, $R^{10}$ is CON($R^7$)($R^8$). In certain embodiments, $R^{10}$ is N($R^7$)($R^8$). In certain embodiments, $R^{10}$ is $C_1$-$C_6$alkylN($R^7$)($R^8$).

With regard to the compounds described herein, $R^{11}$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$) and N($R^7$)($R^8$). In certain embodiments, $R^{11}$ is hydrogen. In certain embodiments, $R^{11}$ is halogen. Suitable halogens include fluorine, chlorine, bromine, or iodine. In certain embodiments, $R^{11}$ is CN. In certain embodiments, $R^{11}$ is OH. In certain embodiments, $R^{11}$ is $C_1$-$C_6$alkoxy. Suitable alkoxys include, but are not limited to, methoxy, ethoxy, n-propoxy, isopropoxy and n-butoxy. In certain embodiments, $R^{11}$ is $C_1$-$C_6$alkylOC$_1$-$C_6$alkyl. In certain embodiments, $R^{11}$ is COOH. In certain embodiments, $R^{11}$ is $C_1$-$C_6$alkylCOOH. In certain embodiments, $R^{11}$ is $C_3$-$C_6$cycloalkyl. Suitable examples of cycloalkyls include, but are not limited to, cyclopropyl, cyclobutyl, cyclopentyl and cyclohexyl. In certain embodiments, $R^{11}$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{11}$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^{11}$ is $C_1$-$C_6$alkylOH. Examples of suitable alcohols include, but are not limited to, methanol, ethanol, propanol, butanol and iso-butanol. In certain embodiments, $R^{11}$ is CON($R^7$)($R^8$). In certain embodiments, $R^{11}$ is N($R^7$)($R^8$). In certain embodiments, $R^{11}$ is $C_1$-$C_6$alkylN($R^7$)($R^8$).

With regard to the compounds described herein, $R^{12}$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$). In certain embodiments, $R^{12}$ is hydrogen. In certain embodiments, $R^{12}$ is halogen. Suitable halogens include fluorine, chlorine, bromine, or iodine. In certain embodiments, $R^{12}$ is CN. In certain embodiments, $R^{12}$ is OH.

In certain embodiments, $R^{12}$ is $C_1$-$C_6$alkoxy. Suitable alkoxy groups include, but are not limited to, methoxy, ethoxy, n-propoxy, isopropoxy and n-butoxy. In certain embodiments, $R^{12}$ is $C_1$-$C_6$alkylOC$_1$-$C_6$alkyl. In certain embodiments, $R^{12}$ is COOH. In certain embodiments, $R^{12}$ is $C_1$-$C_6$alkylCOOH. In certain embodiments, $R^{12}$ is $C_3$-$C_6$cycloalkyl. Suitable examples of cycloalkyls include, but are not limited to, cyclopropyl, cyclobutyl, cyclopentyl and cyclohexyl. In certain embodiments, $R^{12}$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{12}$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^{12}$ is $C_1$-$C_6$alkylOH. Examples of suitable alcohols include, but are not limited to, methanol, ethanol, propanol, butanol and iso-butanol. In certain embodiments, $R^{12}$ is CON($R^7$)($R^8$). In certain embodiments, $R^{12}$ is N($R^7$)($R^8$). In certain embodiments, $R^{12}$ is $C_1$-$C_6$alkylN($R^7$)($R^8$).

In certain embodiments, $R^{12}$ is hydrogen, methyl, ethyl, methoxy, OH or

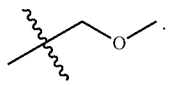

With regard to the compounds described herein, $R^{13}$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$). In certain embodiments, $R^{13}$ is hydrogen. In certain embodiments, $R^{13}$ is halogen. Suitable halogens include fluorine, chlorine, bromine, or iodine. In certain embodiments, $R^{13}$ is CN. In certain embodiments, $R^{13}$ is OH.

In certain embodiments, $R^{13}$ is $C_1$-$C_6$alkoxy. Suitable alkoxy groups include, but are not limited to, methoxy, ethoxy, n-propoxy, isopropoxy and n-butoxy. In certain embodiments, $R^{13}$ is $C_1$-$C_6$alkylOC$_1$-$C_6$alkyl. In certain embodiments, $R^{13}$ is COOH. In certain embodiments, $R^{13}$ is $C_1$-$C_6$alkylCOOH. In certain embodiments, $R^{13}$ is $C_3$-$C_6$cycloalkyl. Suitable examples of cycloalkyls include, but are not limited to, cyclopropyl, cyclobutyl, cyclopentyl and cyclohexyl. In certain embodiments, $R^{13}$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{13}$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^{13}$ is $C_1$-$C_6$alkylOH. Examples of suitable alcohols include, but are not limited to, methanol, ethanol, propanol, butanol and iso-butanol. In certain embodiments, $R^{13}$ is CON($R^7$)($R^8$). In certain embodiments, $R^{13}$ is N($R^7$)($R^8$). In certain embodiments, $R^{13}$ is $C_1$-$C_6$alkylN($R^7$)($R^8$).

In certain embodiments, $R^{13}$ is hydrogen, methyl, ethyl, methoxy, OH or

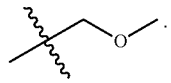

In certain embodiments, wherein m is 1 or 2, $R^{12}$ and $R^{13}$ are independently selected from the group consisting of hydrogen, halogen, OH, $C_1$-$C_6$alkylOH, $C_1$-$C_6$alkylalkoxy and $C_1$-$C_6$alkylOC$_1$-$C_6$alkyl, $C_1$-$C_6$alkyl.

With regard to the compounds described herein, each occurrence of $R^{14}$ is selected from the group consisting of hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$). In certain embodiments, $R^{14}$ is hydrogen. In certain embodiments, $R^{14}$ is halogen. Suitable halogens include fluorine, chlorine, bromine, or iodine. In certain embodiments, $R^{14}$ is CN. In certain embodiments, $R^{14}$ is OH.

In certain embodiments, $R^{14}$ is $C_1$-$C_6$alkoxy. Suitable alkoxy groups include, but are not limited to, methoxy, ethoxy, n-propoxy, isopropoxy and n-butoxy. In certain embodiments, $R^{14}$ is $C_1$-$C_6$alkylOC$_1$-$C_6$alkyl. In certain embodiments, $R^{14}$ is COOH. In certain embodiments, $R^{14}$ is $C_1$-$C_6$alkylCOOH. In certain embodiments, $R^{14}$ is $C_3$-$C_6$cycloalkyl. Suitable examples of cycloalkyls include, but are not limited to, cyclopropyl, cyclobutyl, cyclopentyl and cyclohexyl. In certain embodiments, $R^{14}$ is $C_1$-$C_6$alkyl. Examples of $C_1$-$C_6$alkyl groups can include but are not limited to, methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl and 1-ethyl-1-methylpropyl. In certain embodiments, $R^{14}$ is halo$C_1$-$C_6$alkyl. Suitable examples of haloalkyls include, but are not limited to, fluoromethyl, difluoromethyl, trifluoromethyl, 2-fluoroethyl, 1,2-difluoroethyl and 2,2-difluoroethyl. In certain embodiments, $R^{14}$ is $C_1$-$C_6$alkylOH. Examples of suitable alcohols include, but are not limited to, methanol, ethanol, propanol, butanol and iso-butanol. In certain embodiments, $R^{14}$ is CON($R^7$)($R^8$). In certain embodiments, $R^{14}$ is N($R^7$)($R^8$). In certain embodiments, $R^{14}$ is $C_1$-$C_6$alkylN($R^7$)($R^8$).

In certain embodiments, wherein X is C($R^{14}$)$_2$, $R^{14}$ is independently selected from the group consisting of hydrogen, halogen, OH, $C_1$-$C_6$alkylOH, $C_1$-$C_6$alkylalkoxy, $C_1$-$C_6$alkylOC$_1$-$C_6$alkyl and $C_1$-$C_6$alkyl.

In certain embodiments, $R^{14}$ is hydrogen, methyl, ethyl, methoxy, OH or

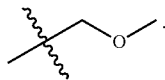 [SMILES: *COC]

With regard to the compounds described herein, m is 0, 1 or 2. In certain embodiments, m is 0. In certain embodiments, m is 1. In certain embodiments, m is 2.

In certain embodiments, m is 1 and X is O.
In certain embodiments, m is 1 and X is $CH_2$.
In certain embodiments, m is 0 and X is O.
In certain embodiments, m is 1 and X is $SO_2$.
In certain embodiments, m is 0 and X is $C(R^{14})_2$, wherein each occurrence of $R^{14}$ is independently selected from the group consisting of hydrogen, halogen, OH, $C_1$-$C_6$alkoxy and $C_1$-$C_6$alkyl.

In certain embodiments, m is 1 and X is $C(R^{14})_2$, wherein each occurrence of $R^{14}$ is independently selected from the group consisting of hydrogen, halogen, OH, $C_1$-$C_6$alkoxy and $C_1$-$C_6$alkyl.

For example, in certain embodiments of Formula (I'), (I), (IA), (IB), and (IC), m is 1. In the following formula (ID), m is 0:

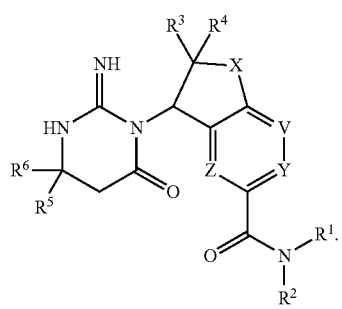

(ID)

For example, in certain embodiments X is a bond and m is 0, as shown in Formula (IE)

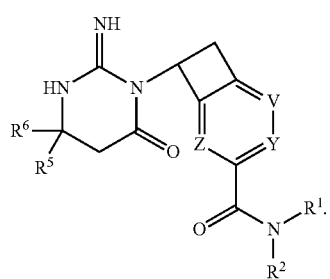

(IE)

In each of the various embodiments of the invention, in the compounds used in the methods herein, each variable (including those in each of Formula (I'), (I), (IA), (IB), (IC), (ID) and (IE), and the various embodiments thereof) it shall be understood that each variable is to be selected independently of the others unless otherwise indicated.

In each of the various embodiments of the invention, the compounds described herein, including those in each of Formula (I'), (I), (IA), (IB), (IC), (ID) and (IE) and the various embodiments thereof, may exit in different forms of the compounds such as, for example, any solvates, hydrates, stereoisomers, and tautomers of said compounds and of any pharmaceutically acceptable salts thereof.

In certain embodiments, compounds described herein include:

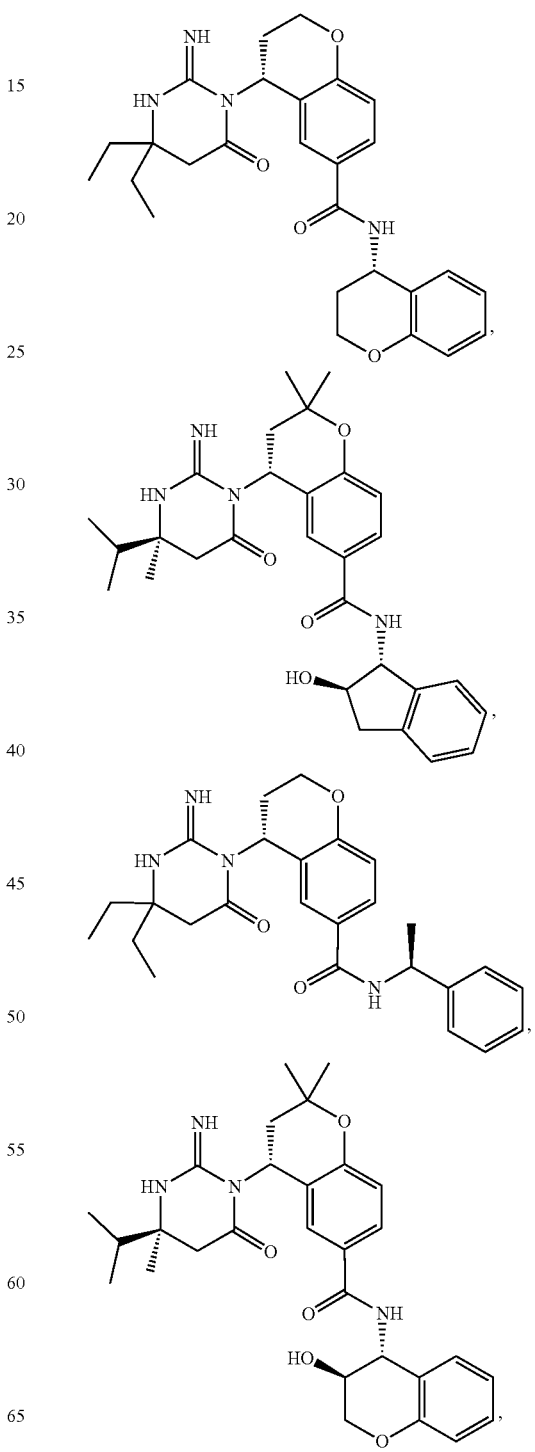

-continued
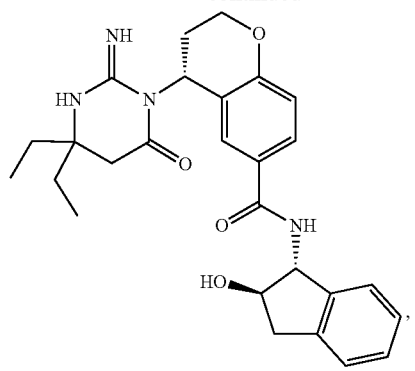
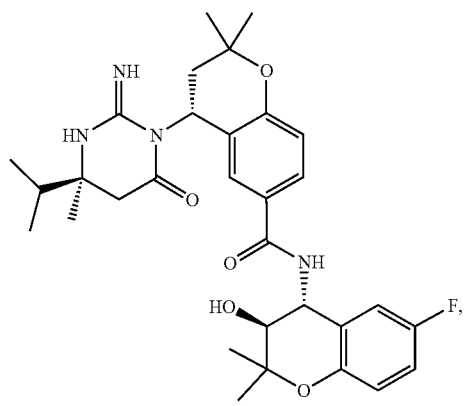
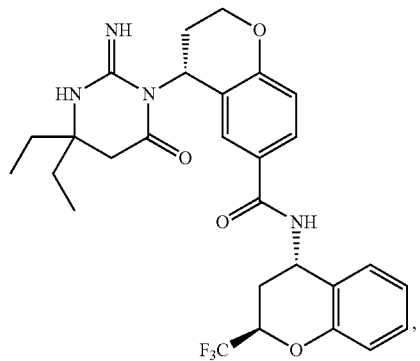
-continued
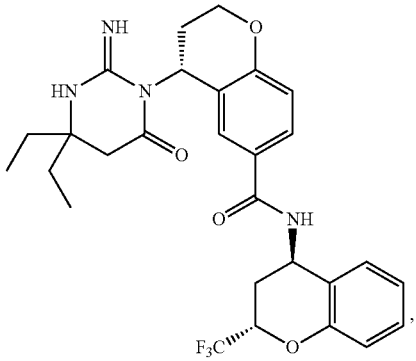
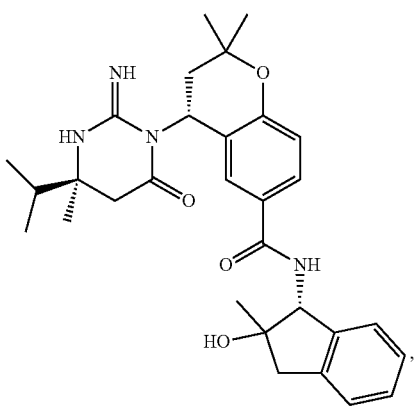
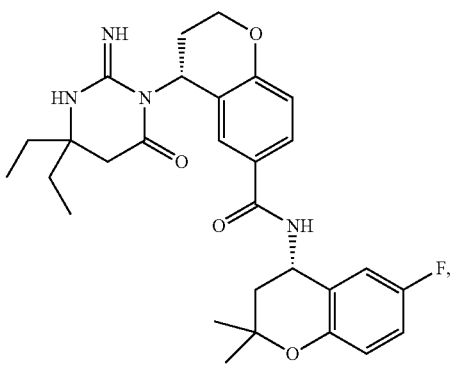
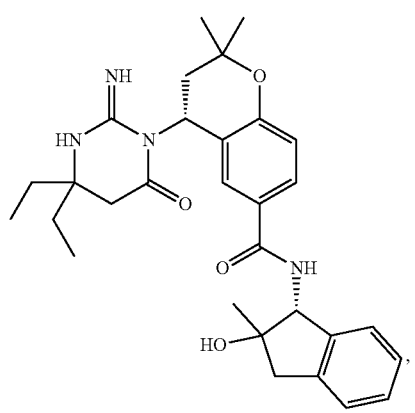
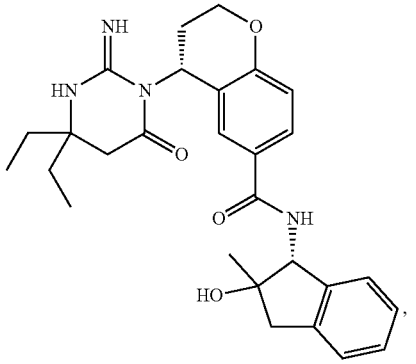

-continued
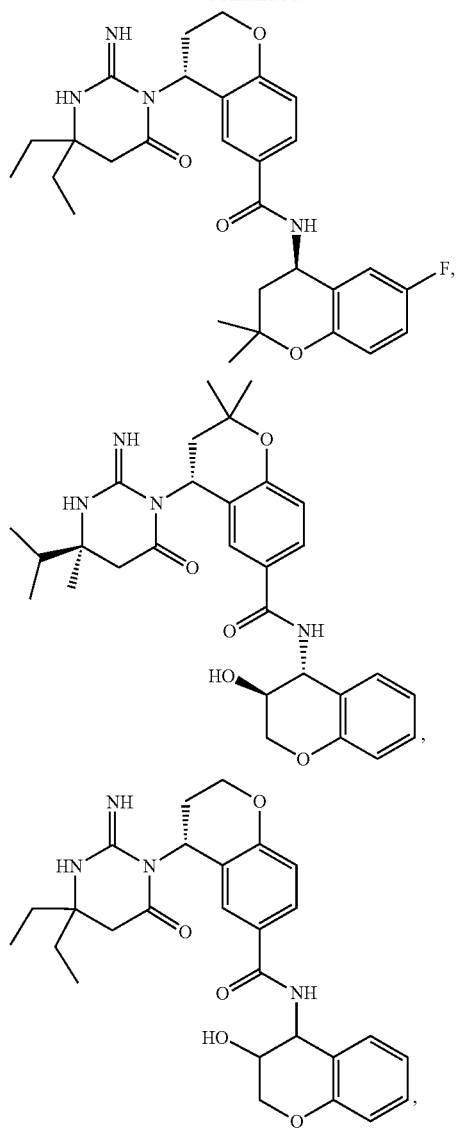
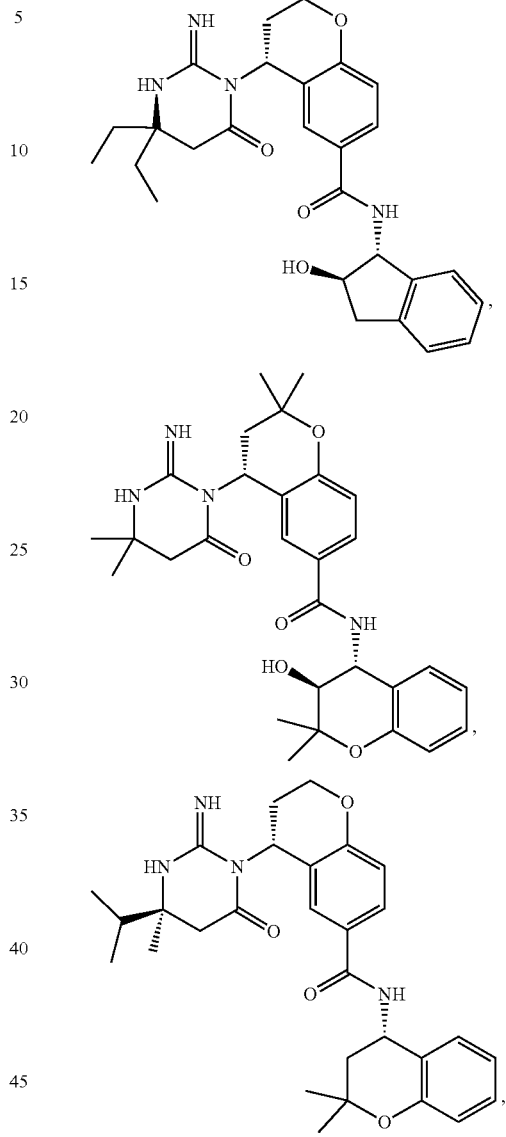
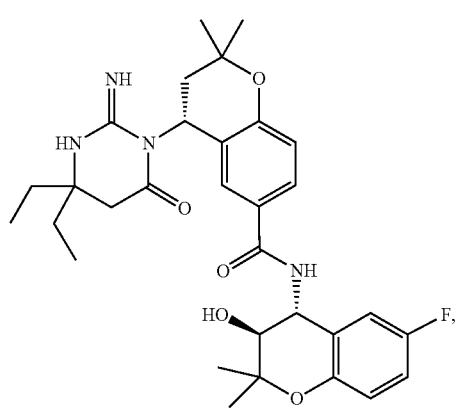
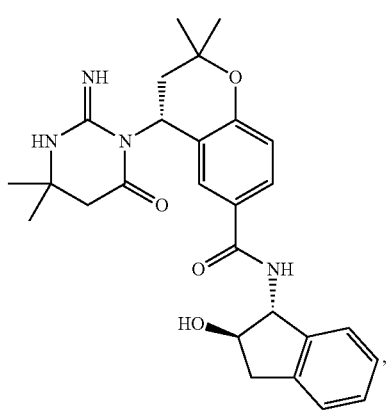

31
-continued
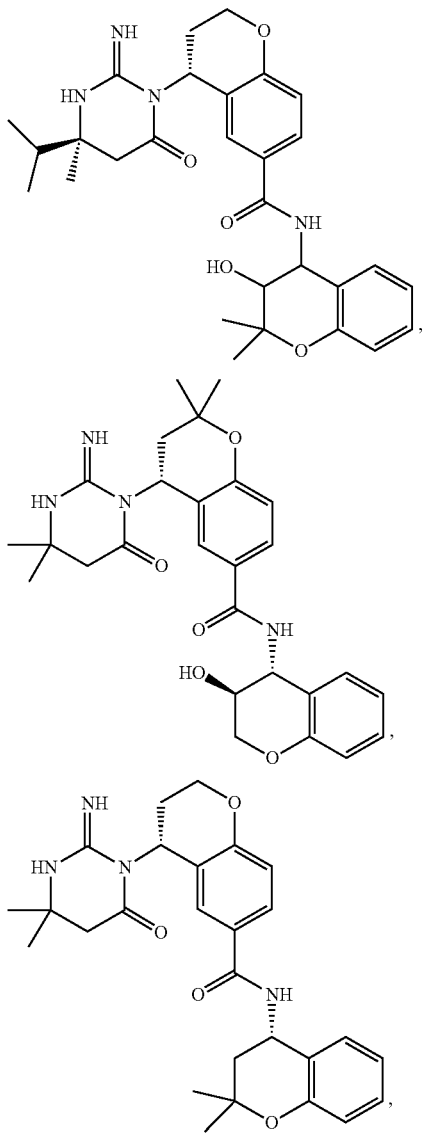
32
-continued
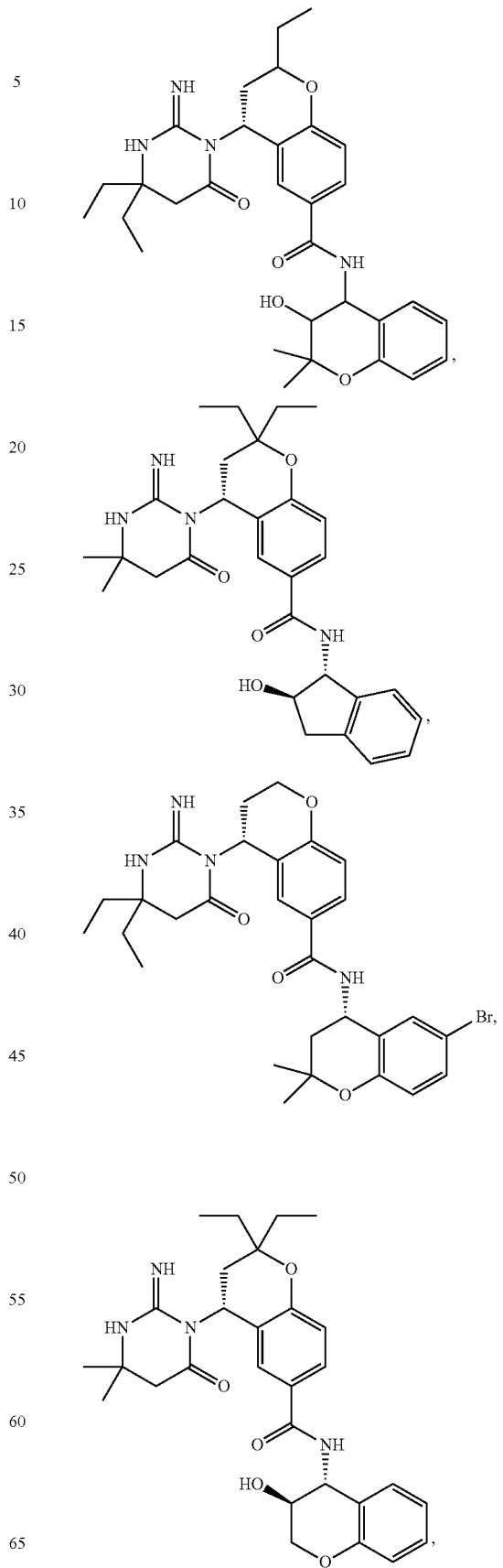

33
-continued
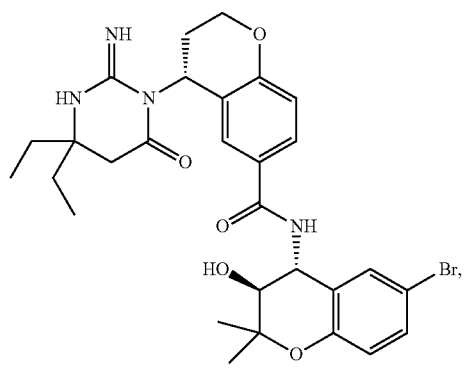
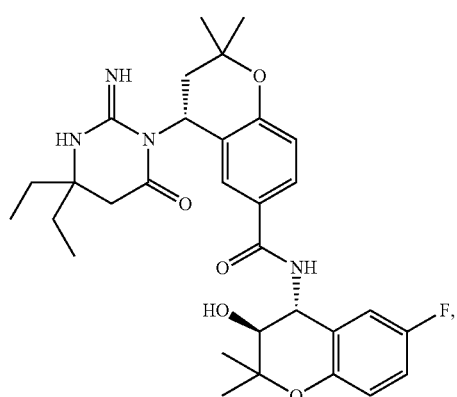
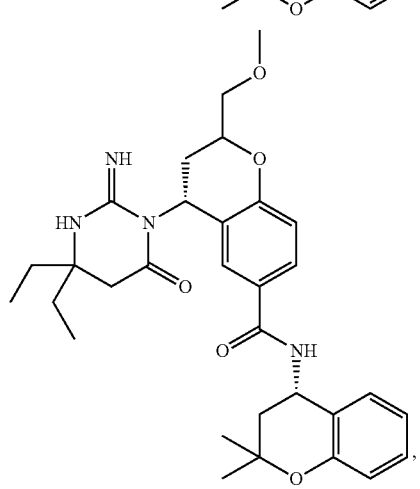
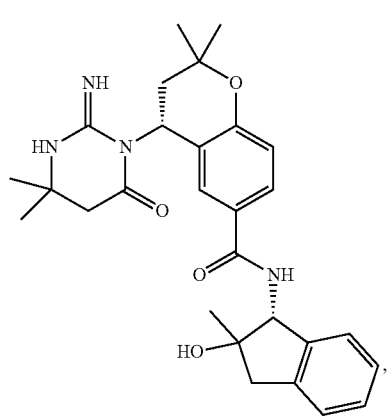
34
-continued
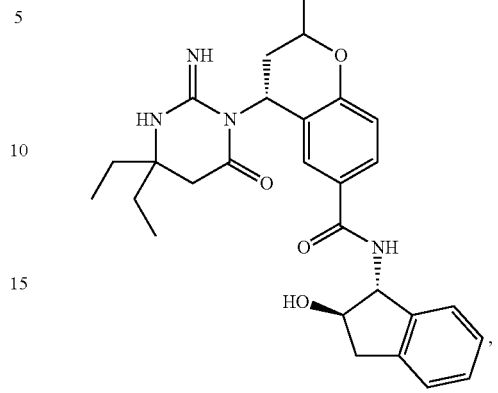
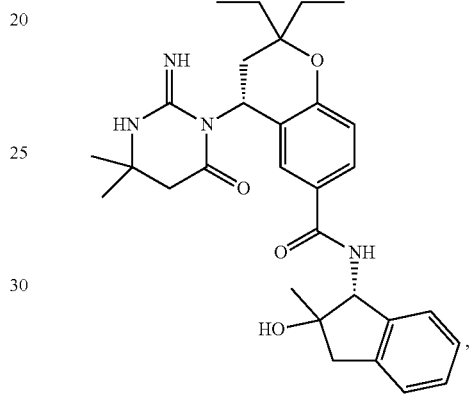
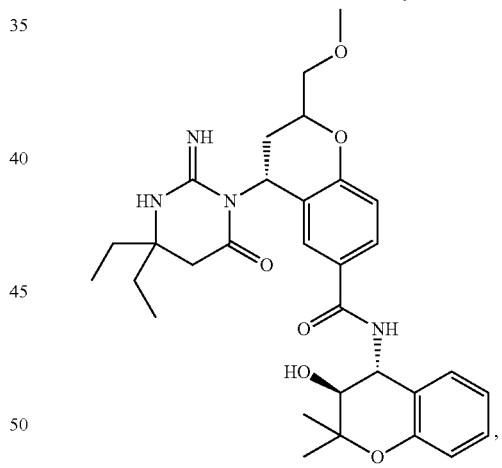
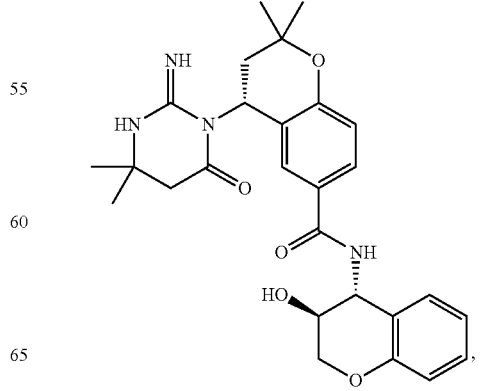

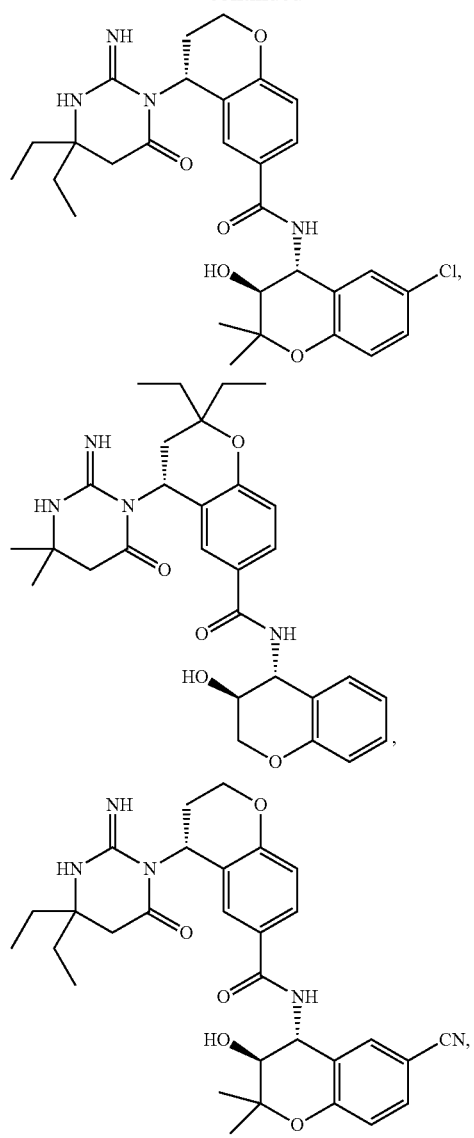
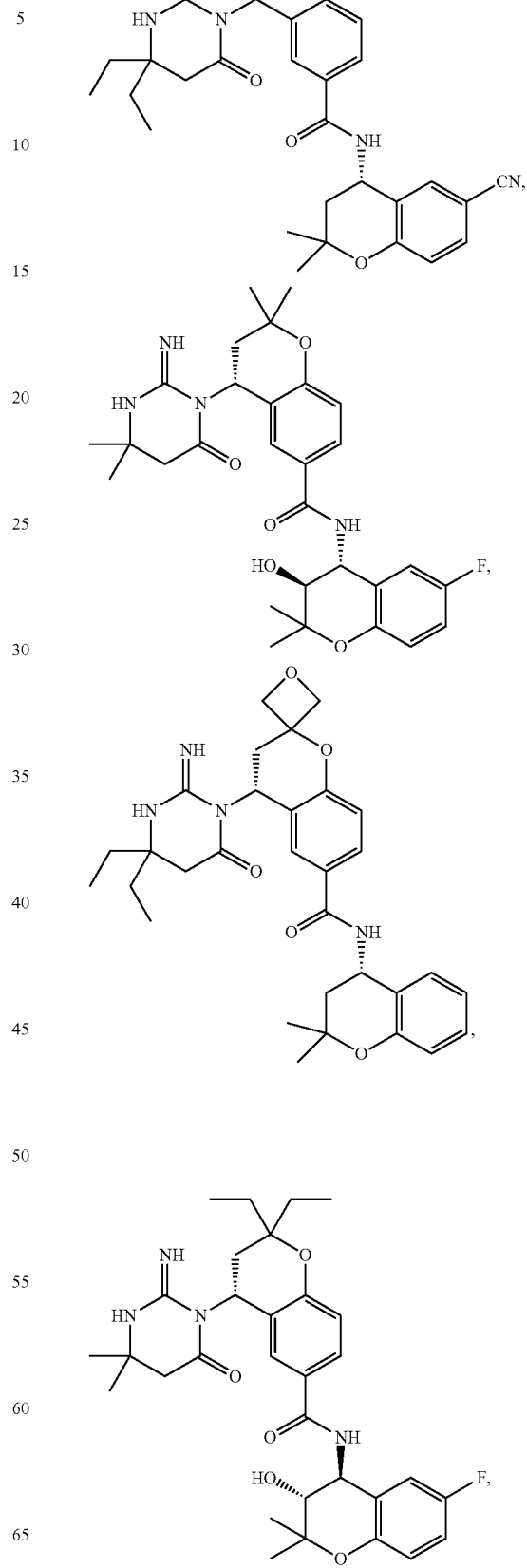

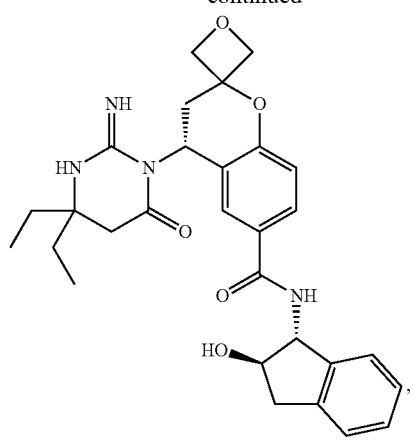
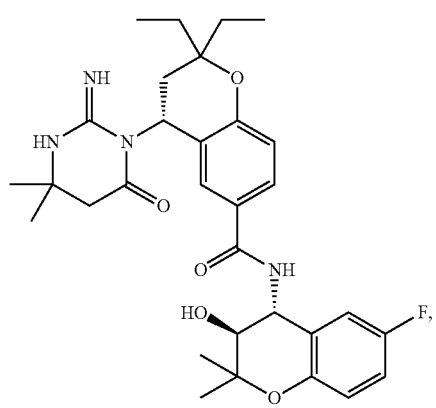
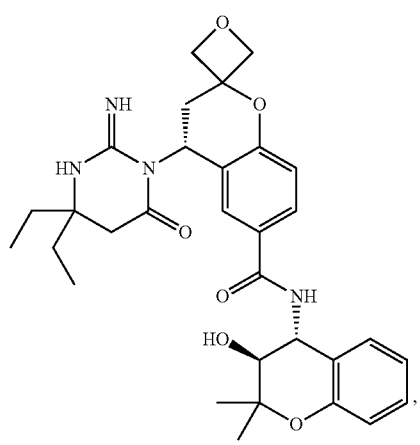
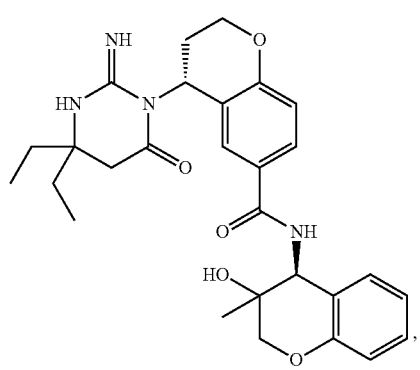
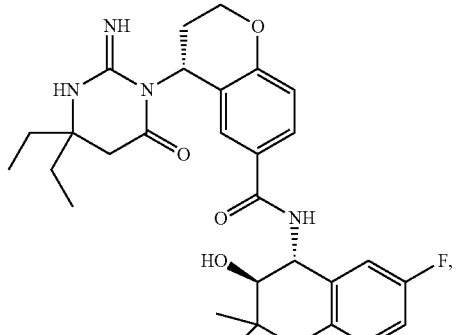
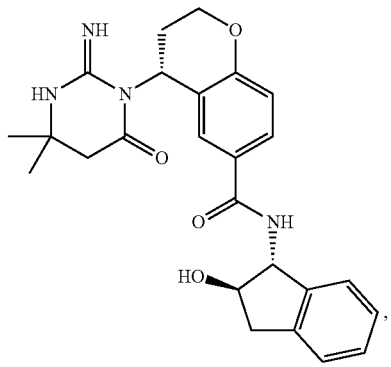
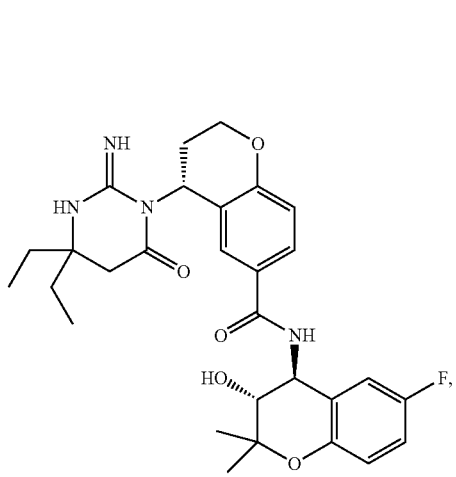
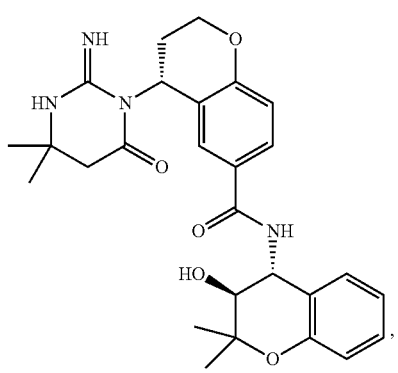

39
-continued
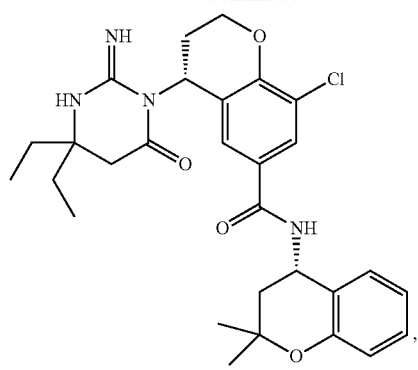
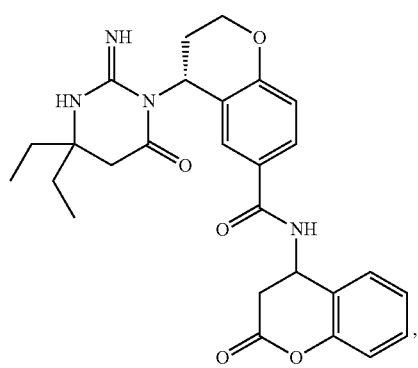
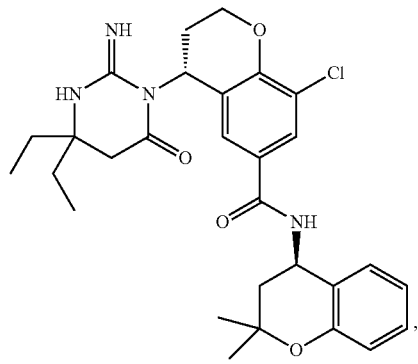
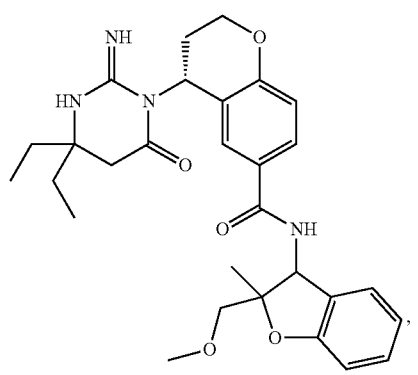
40
-continued
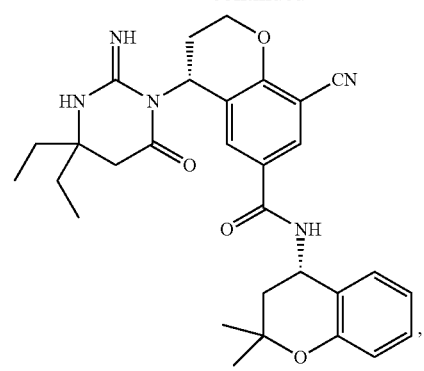
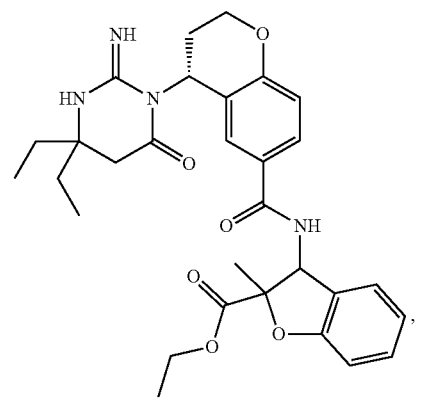
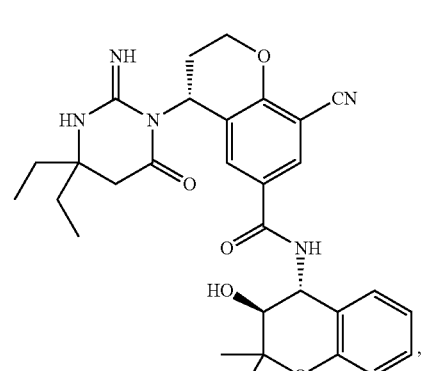
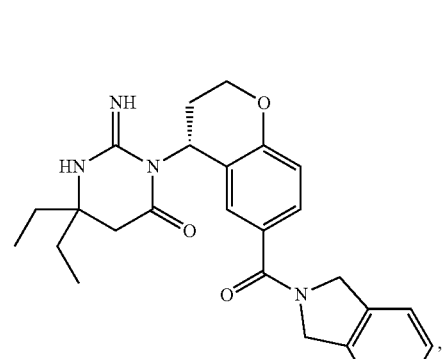

-continued
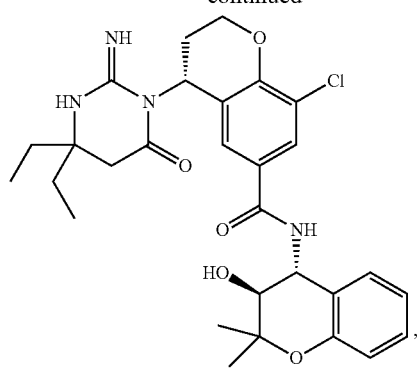
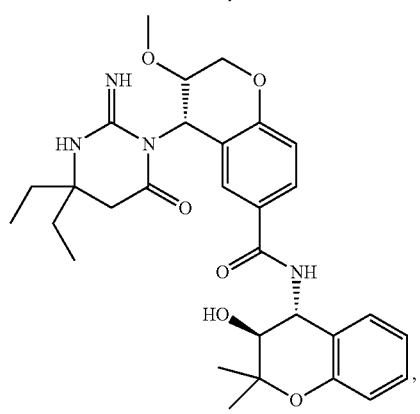
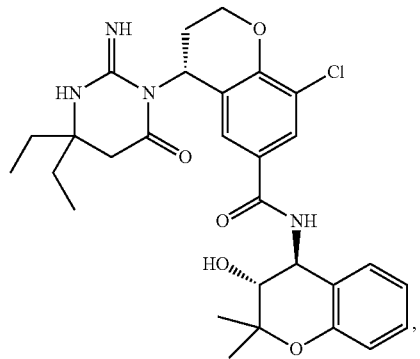
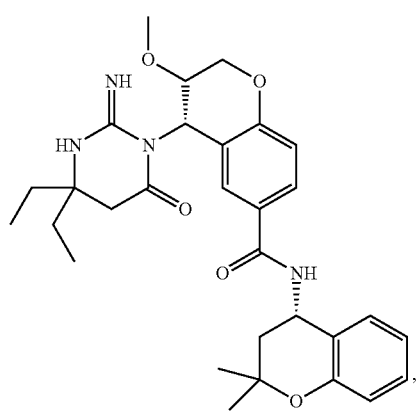
-continued
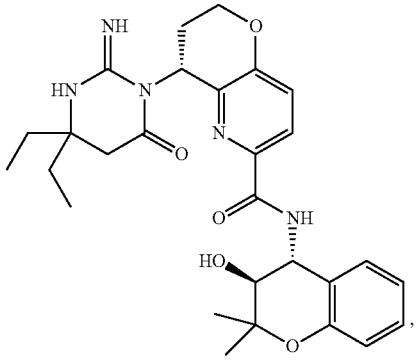
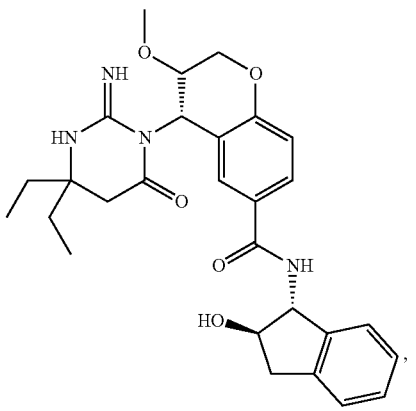
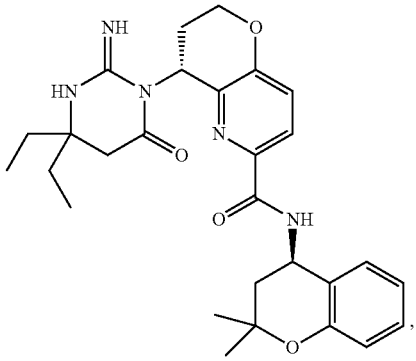
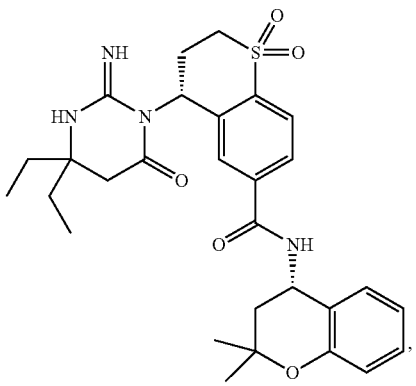

-continued
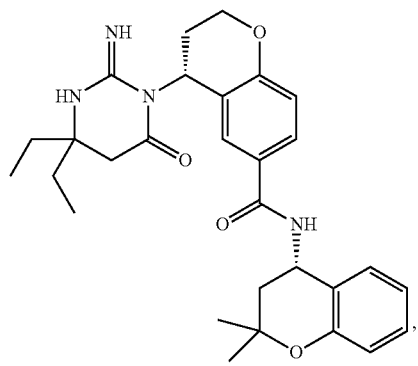
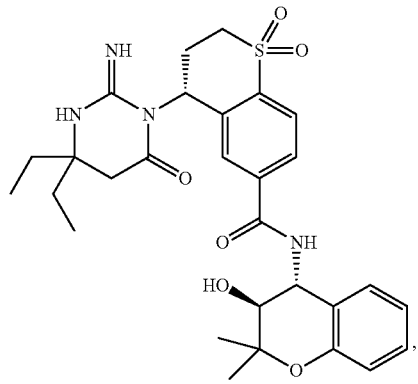
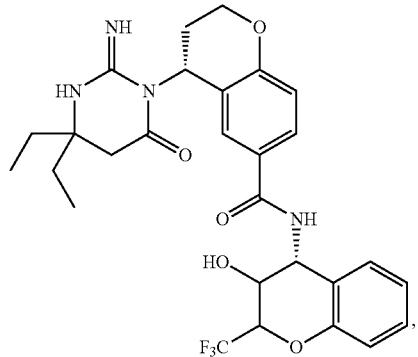
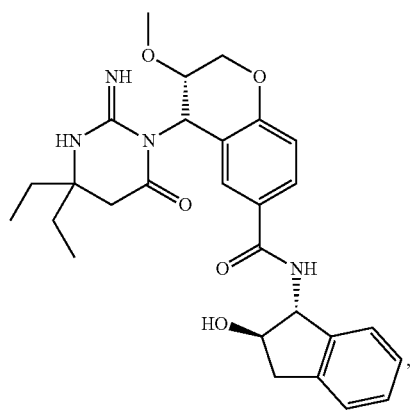
-continued
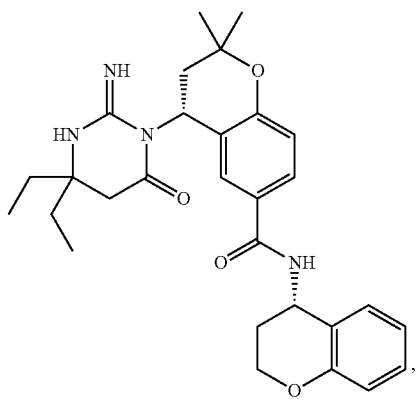
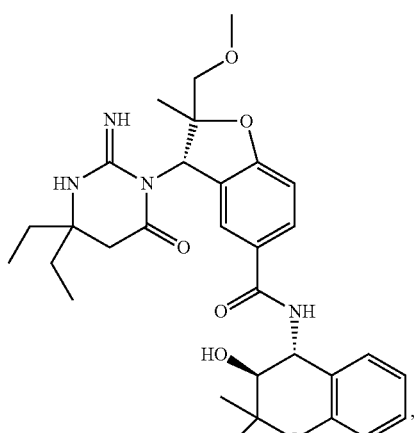
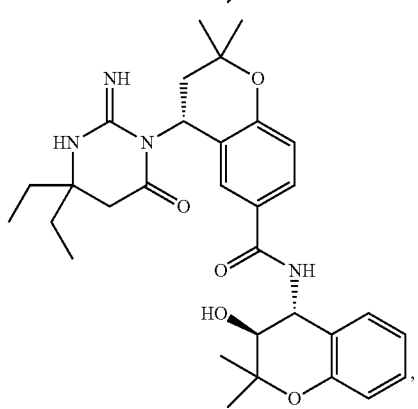
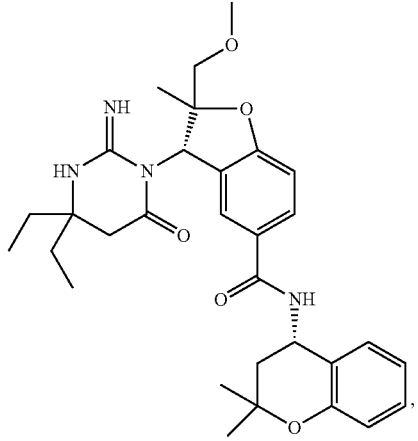

-continued
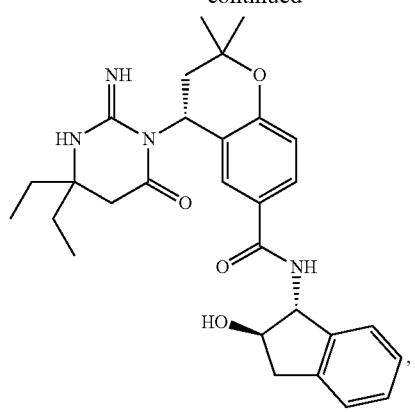
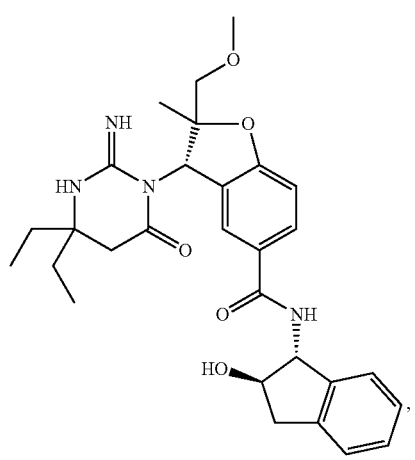
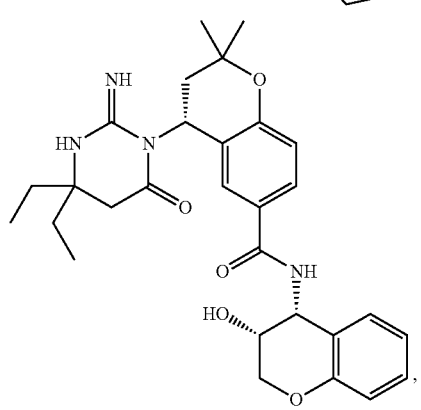
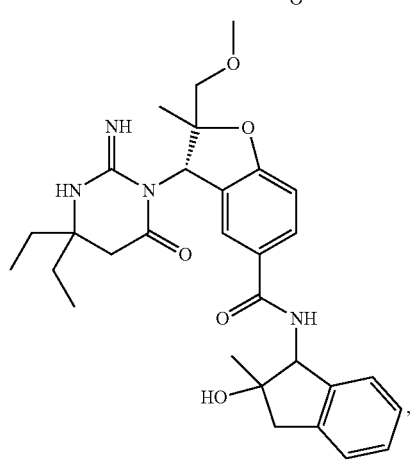
-continued
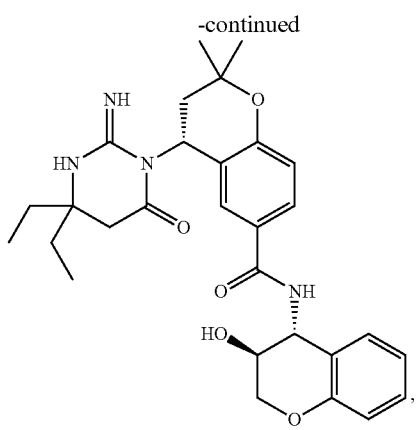
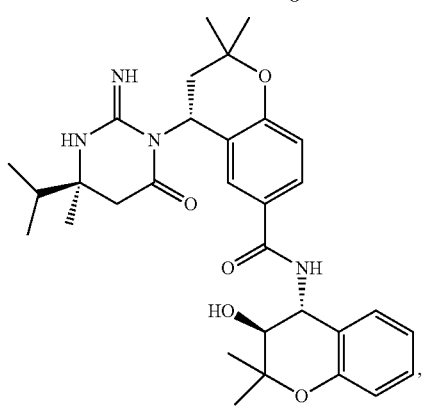
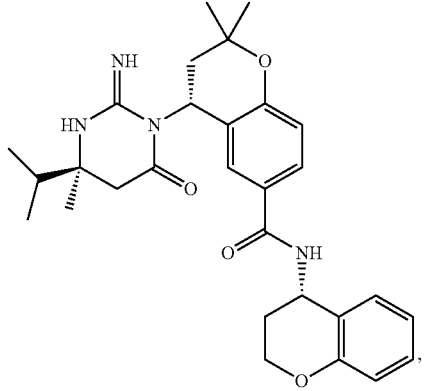
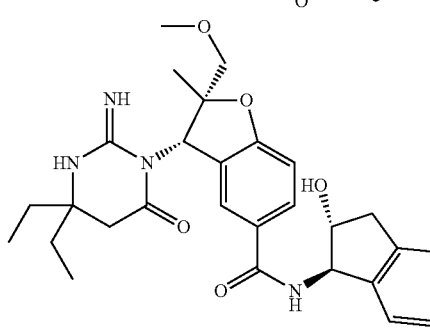
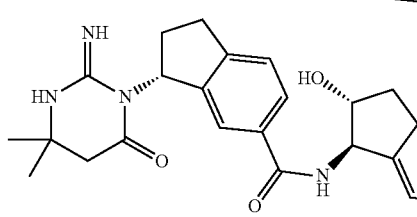

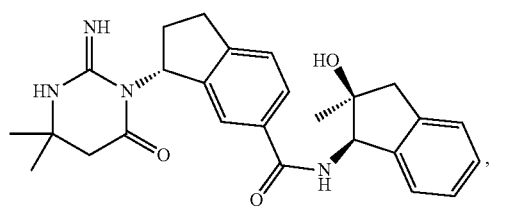
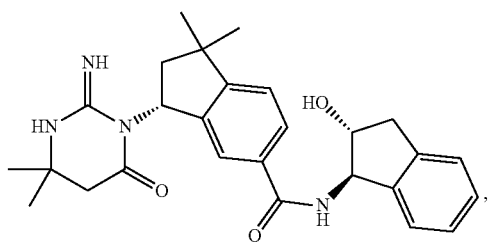
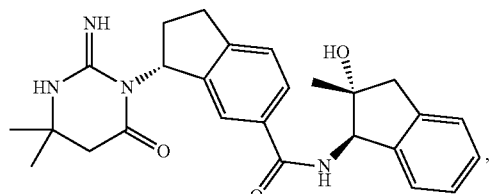
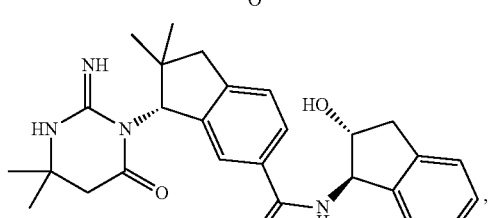
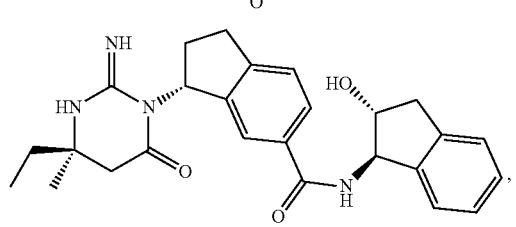
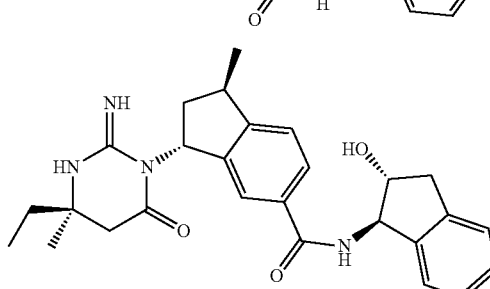
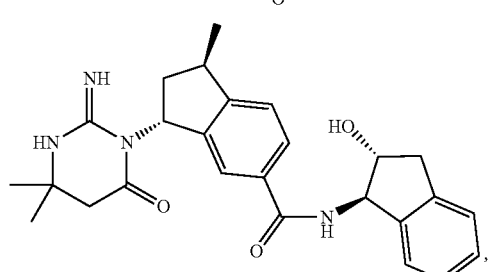
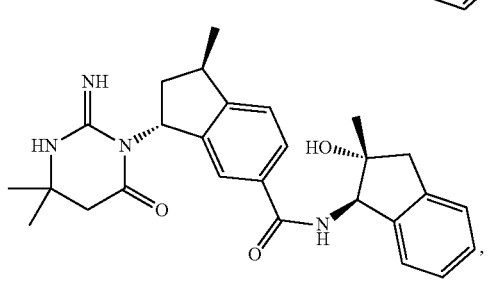
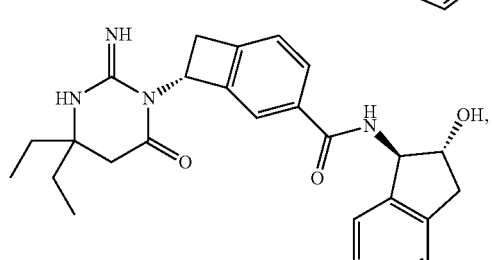
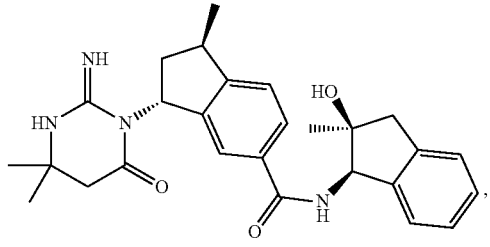
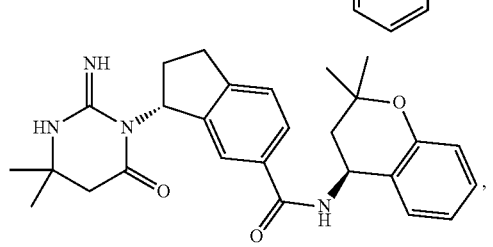
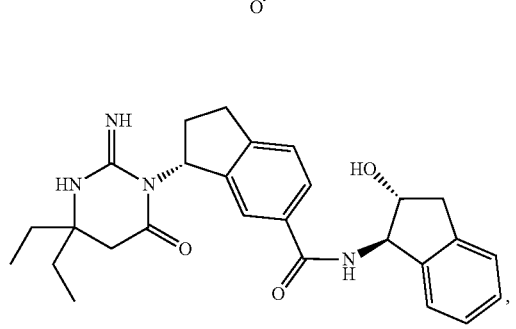
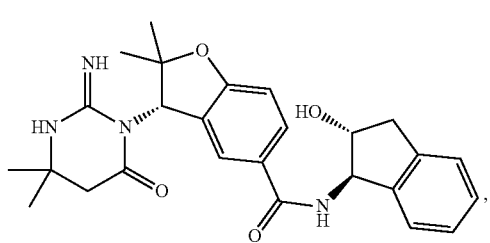

49
-continued
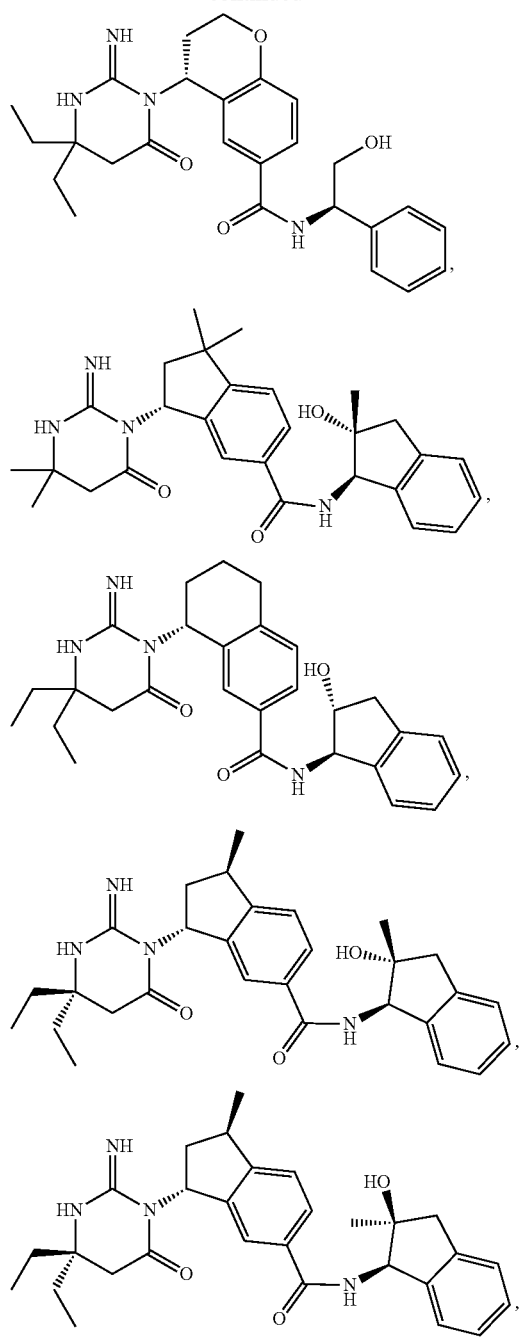
50
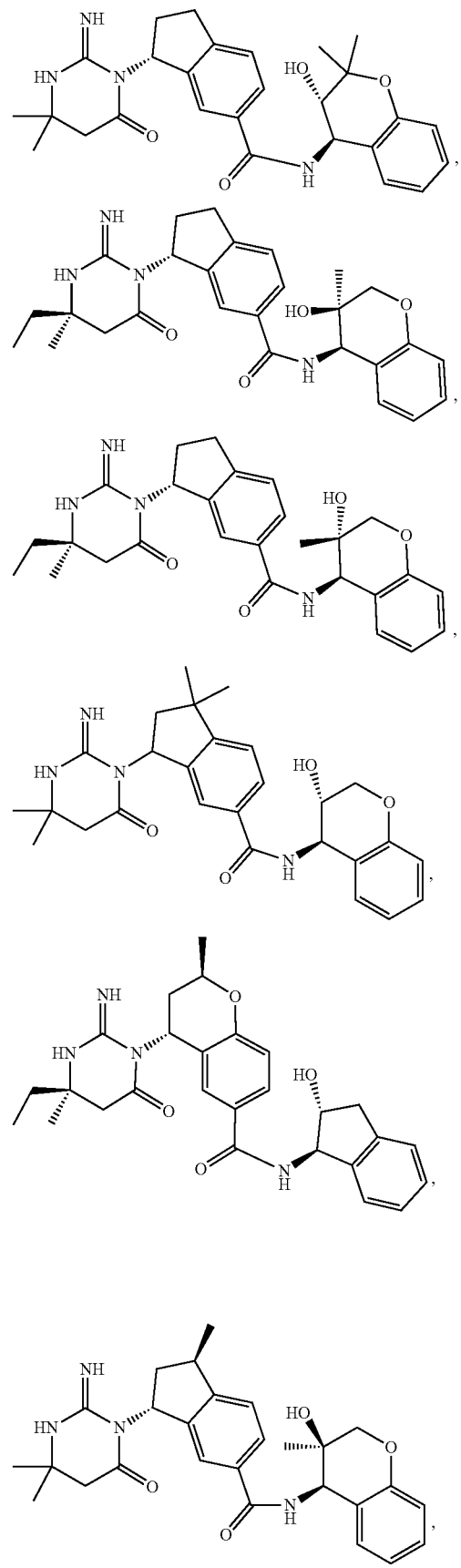

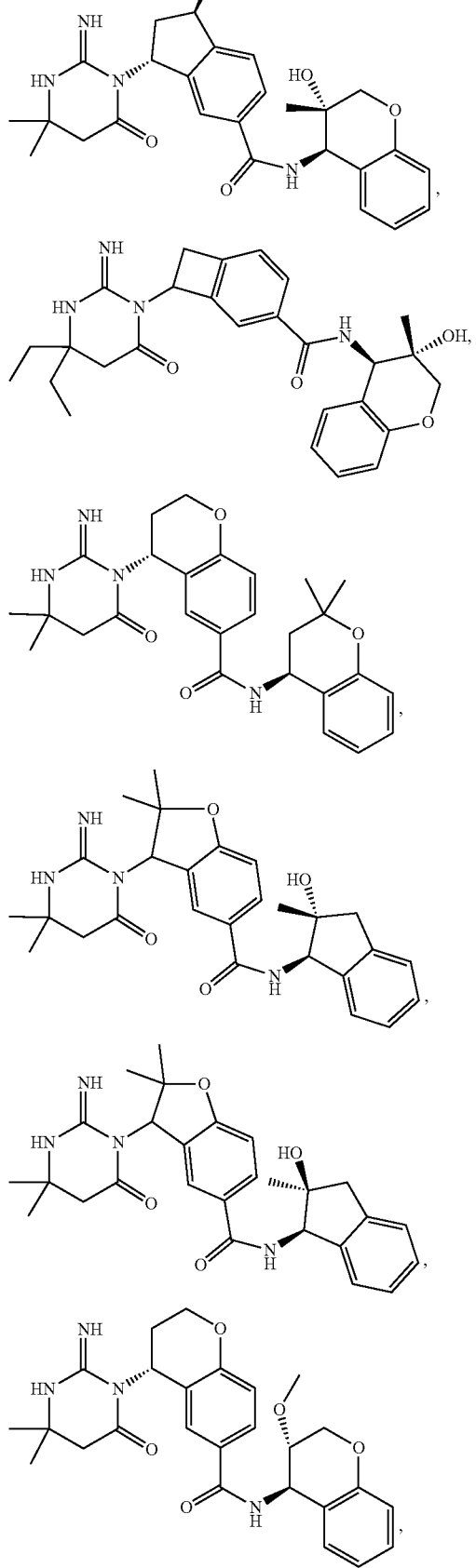
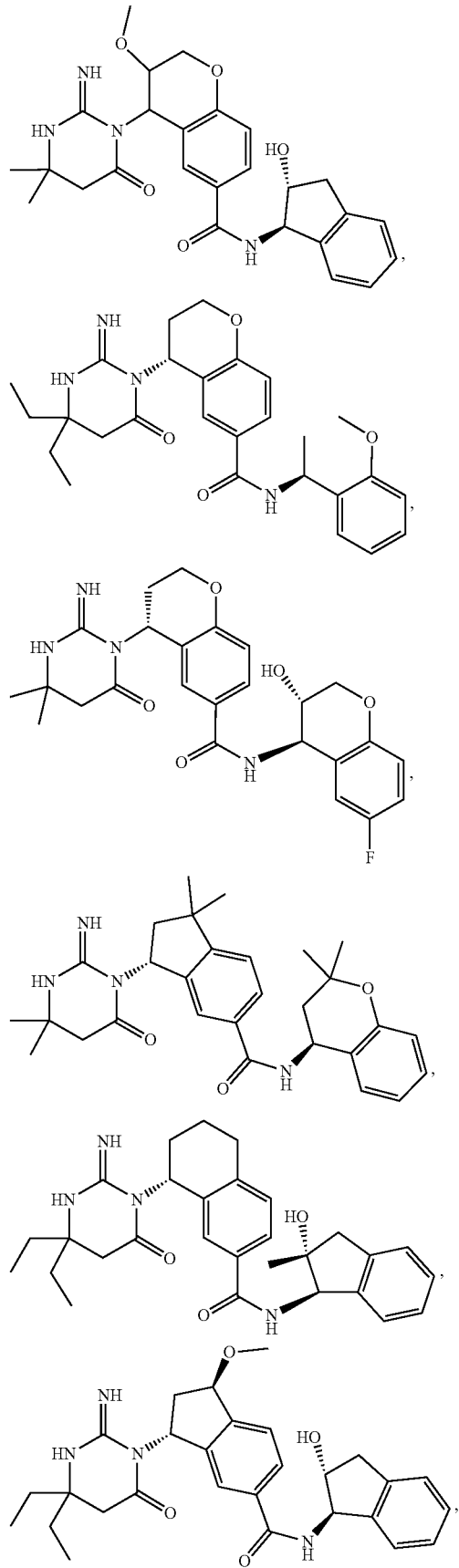

-continued
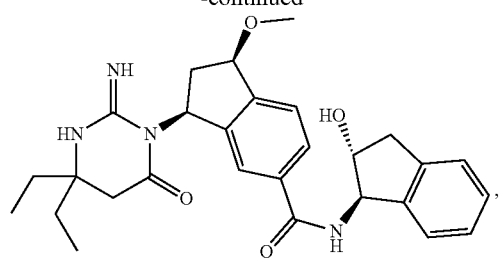
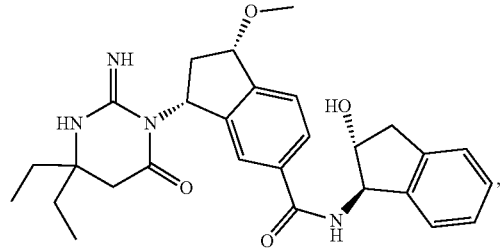
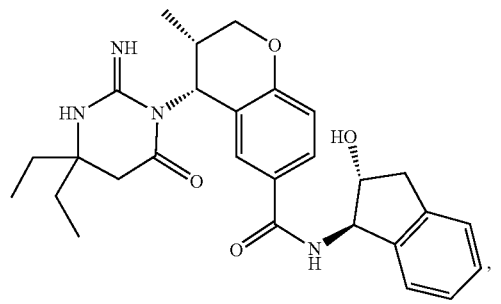
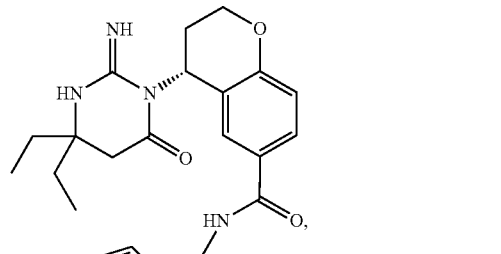
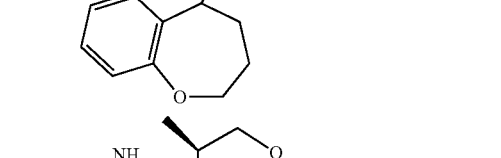
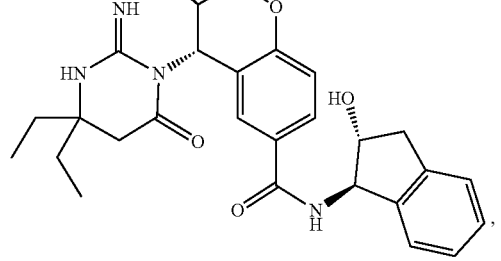
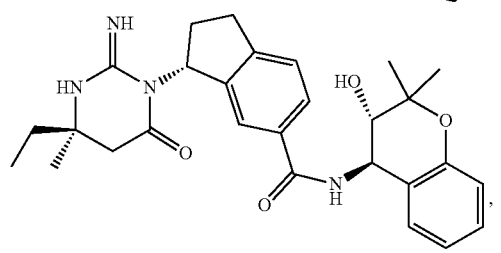
-continued
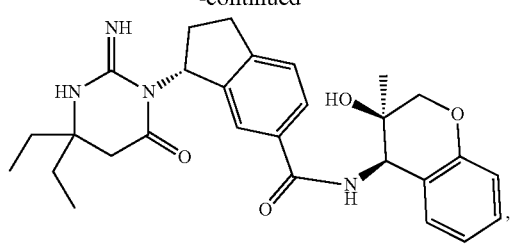
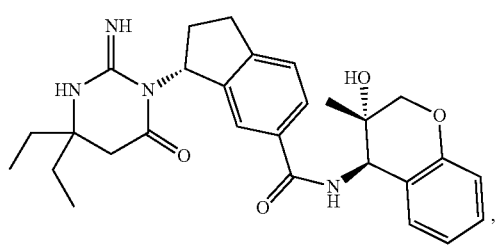
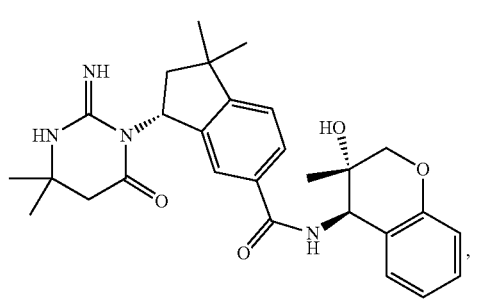
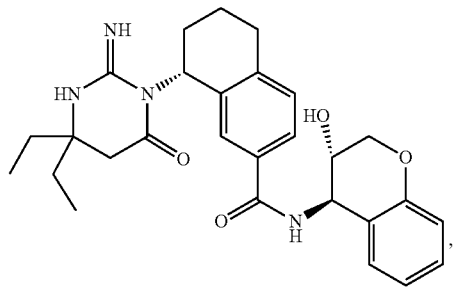
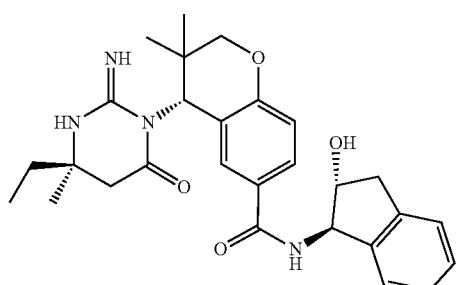
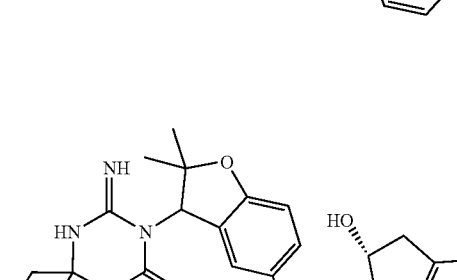
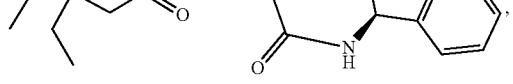

55
-continued
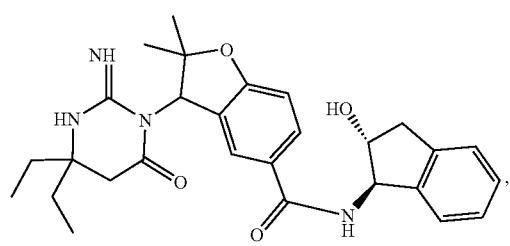
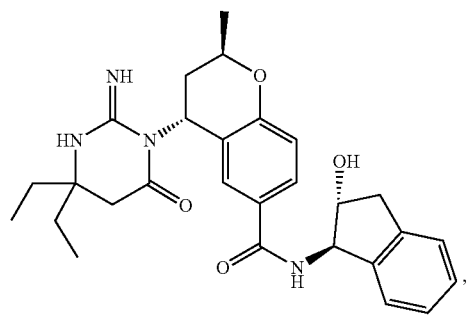
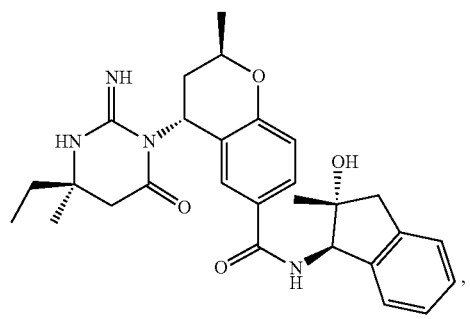
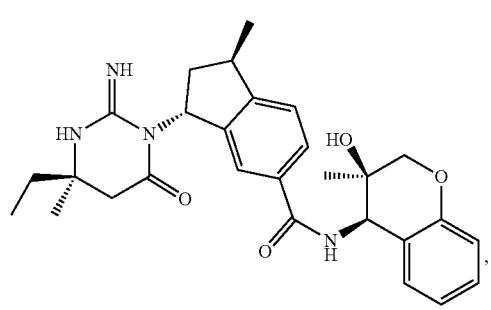
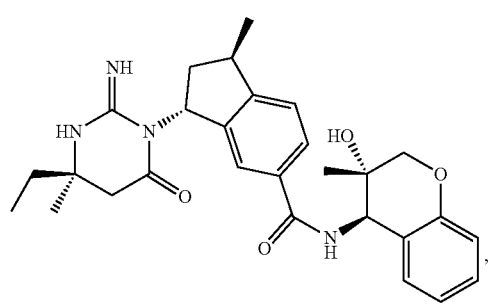
56
-continued
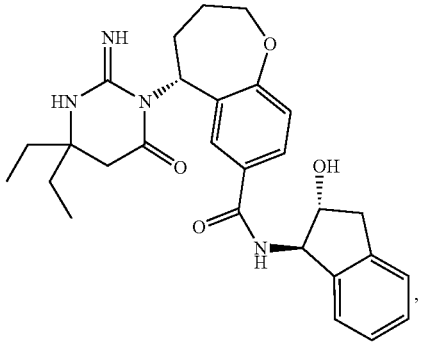
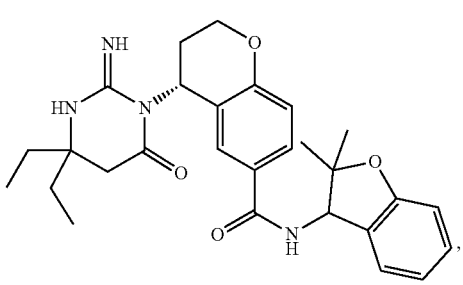
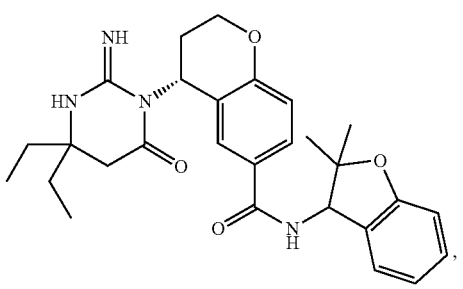
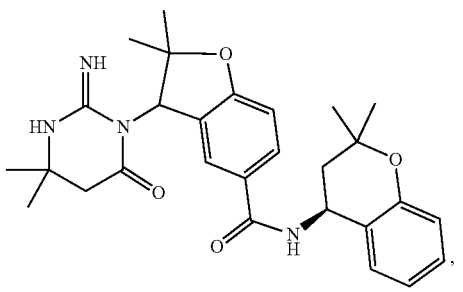
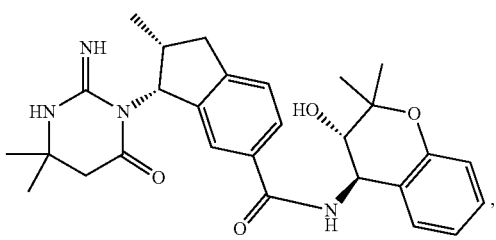
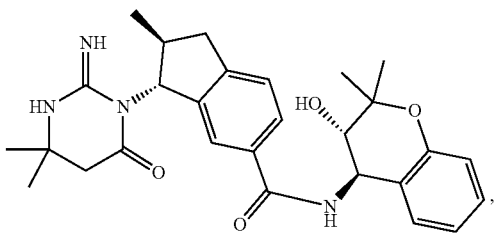

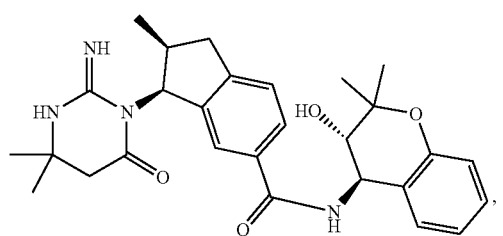
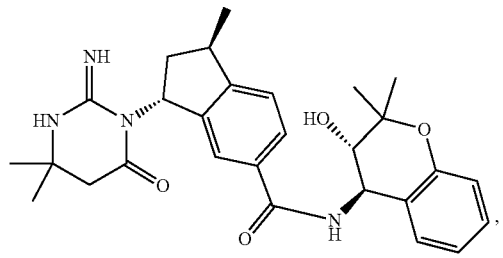
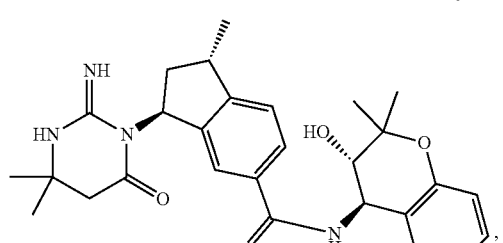
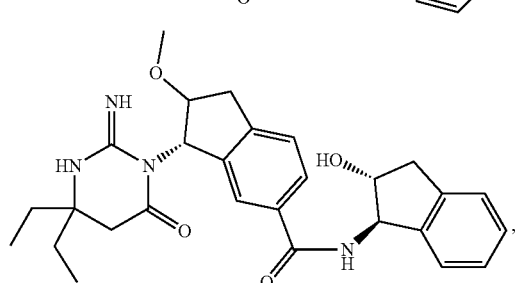
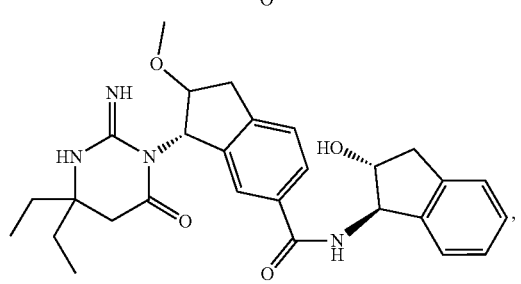
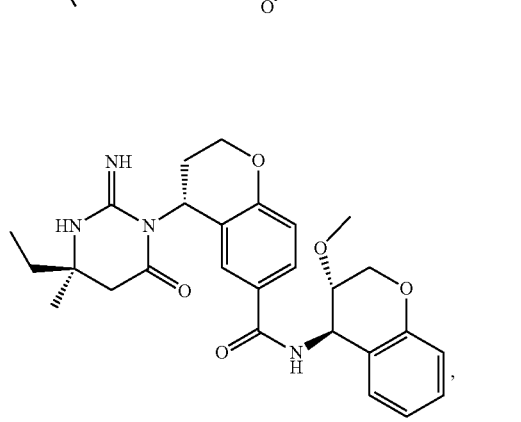
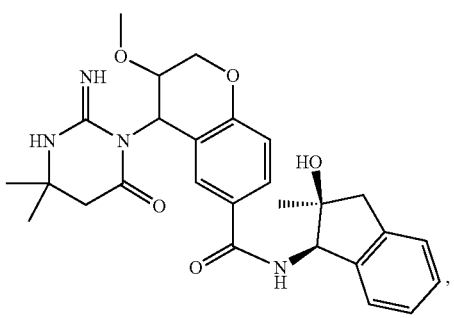
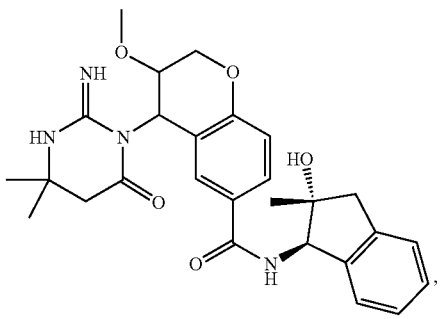
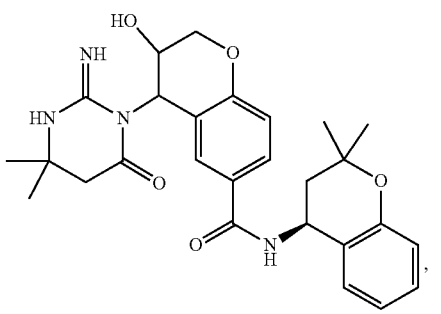
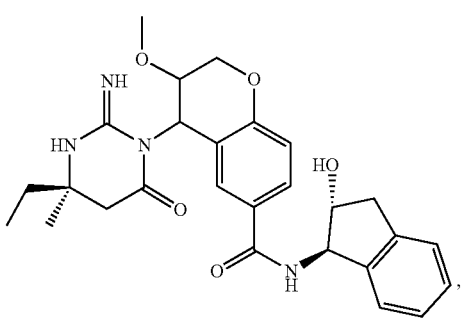
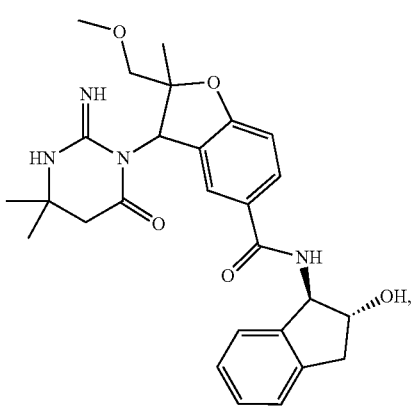

59
-continued
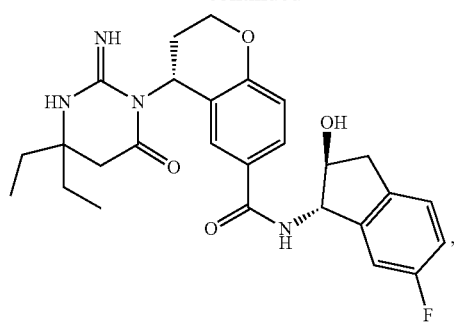
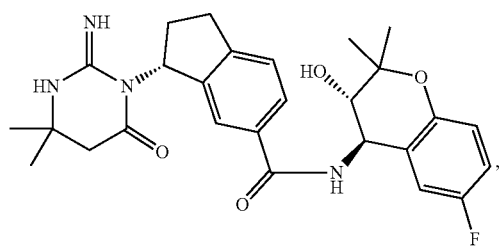
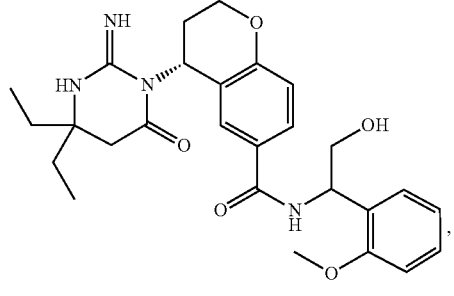
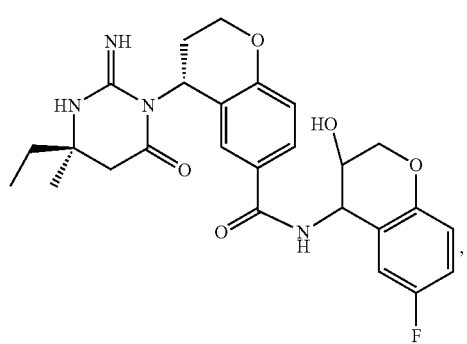
60
-continued
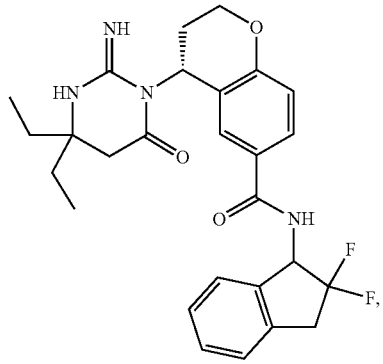
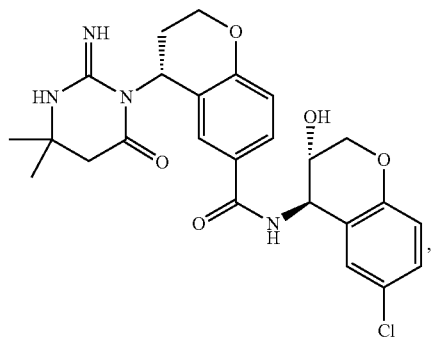
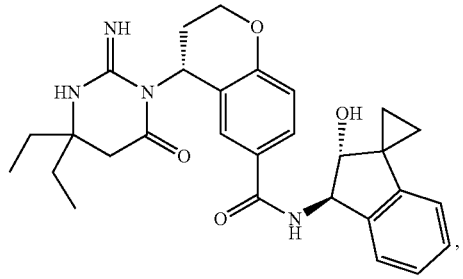
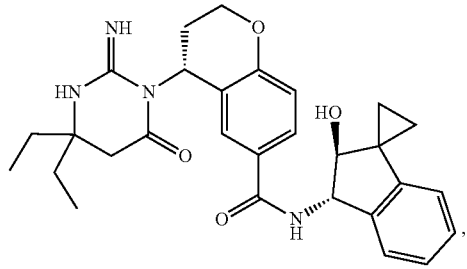
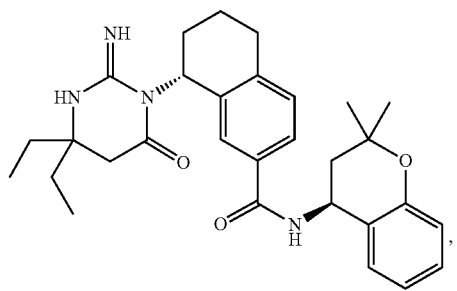

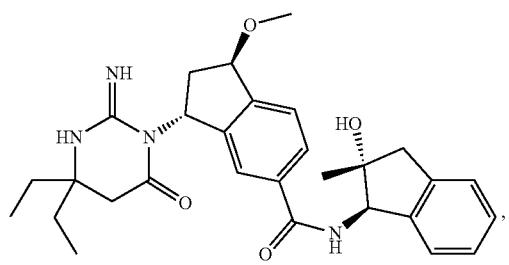
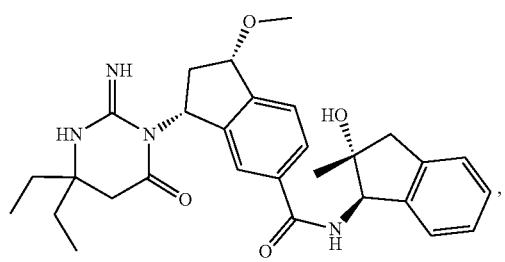
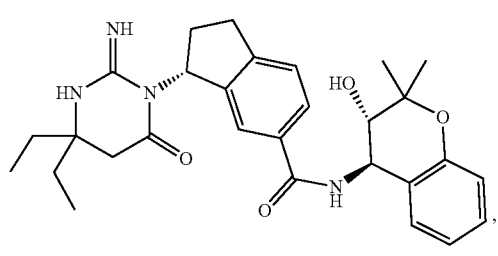
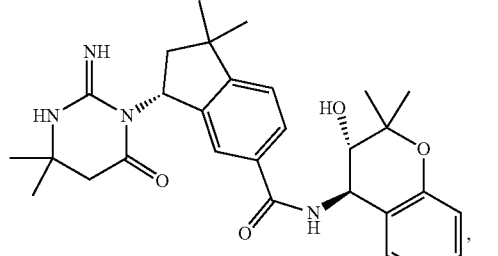
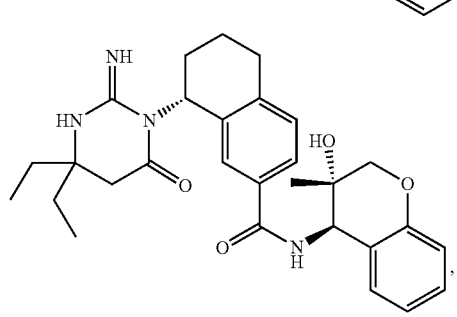
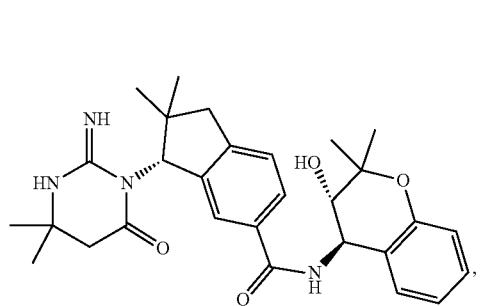
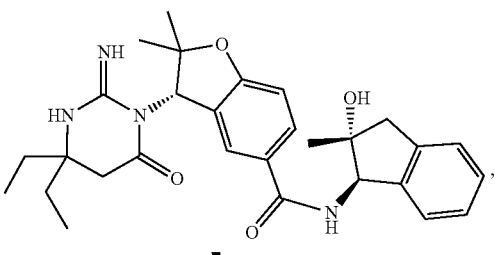
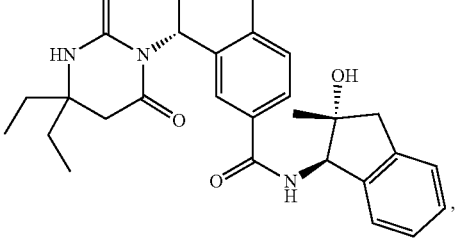
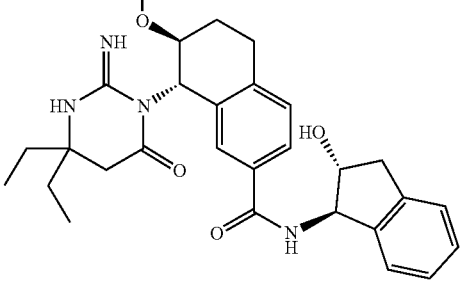
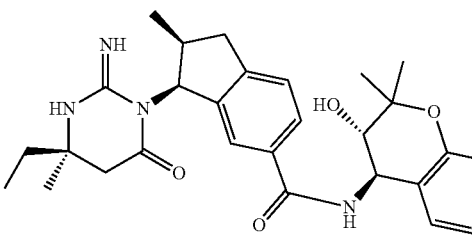
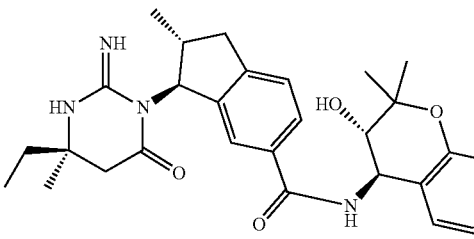
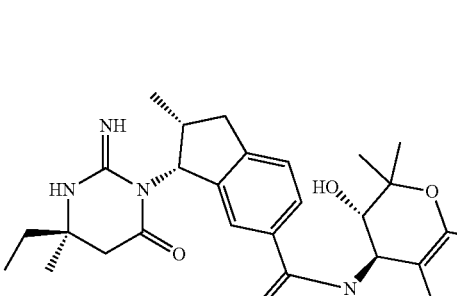

63
-continued
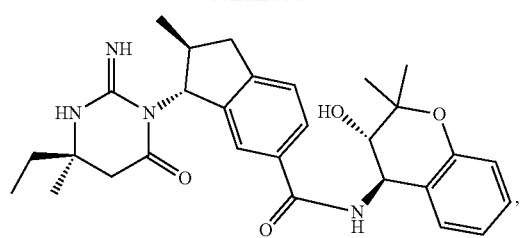
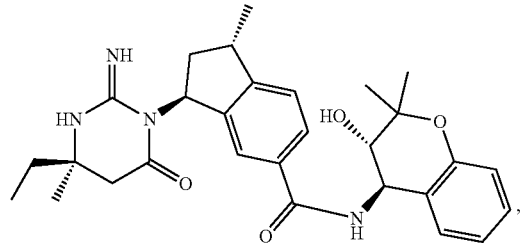
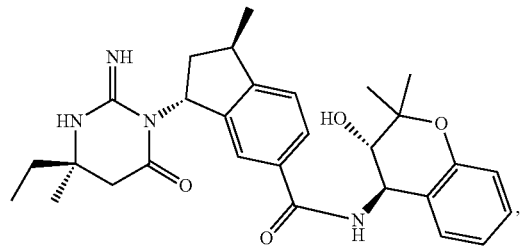
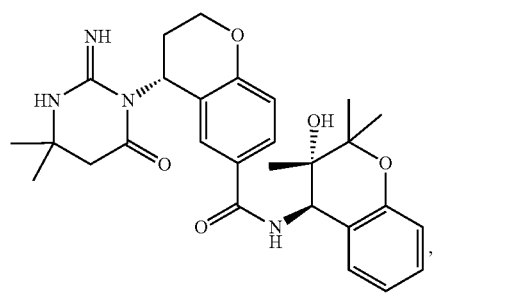
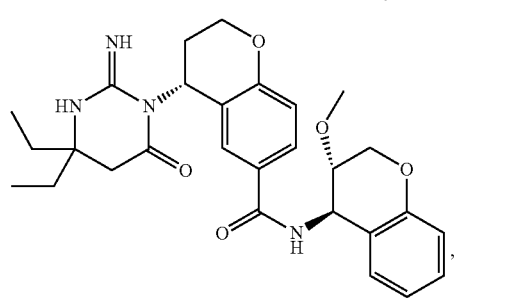
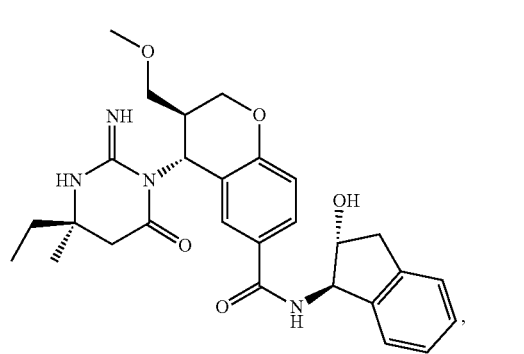
64
-continued
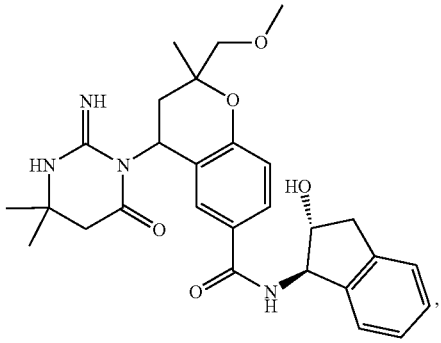
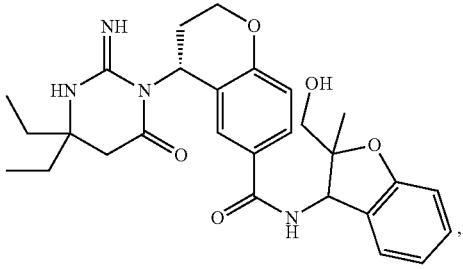
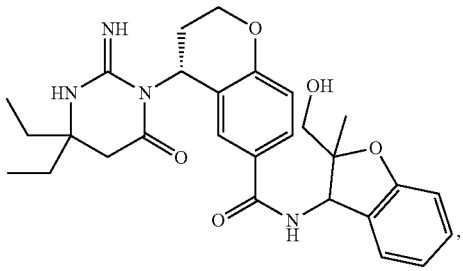
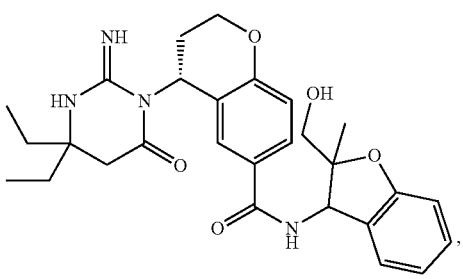
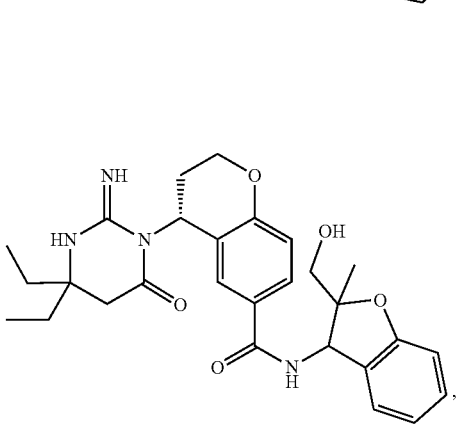

65
-continued
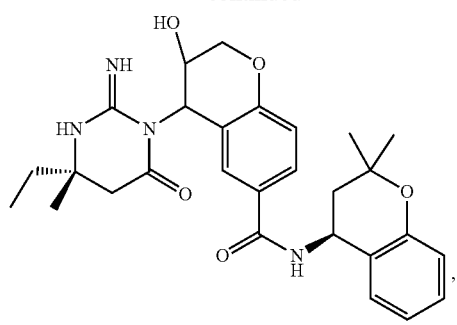
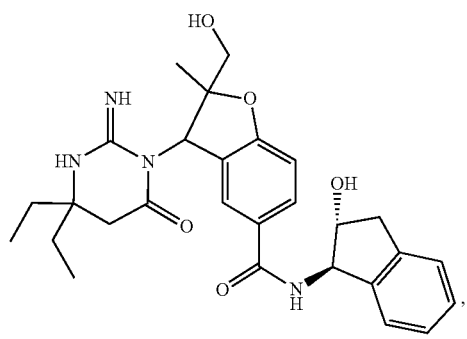
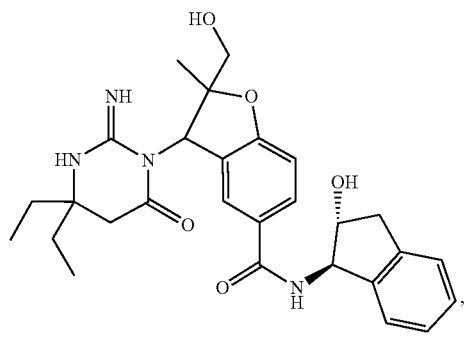
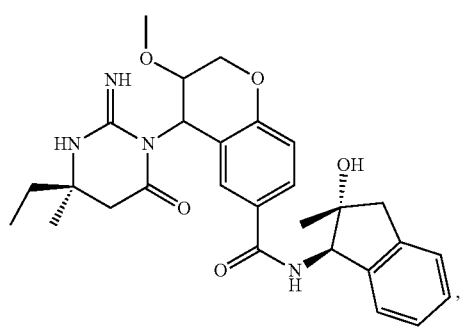
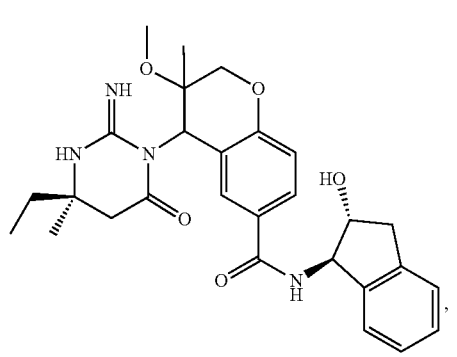
66
-continued
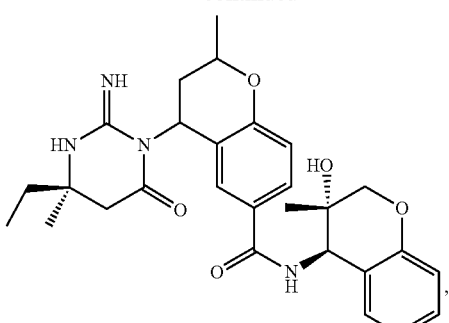
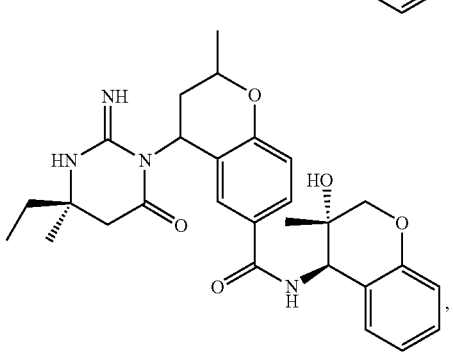
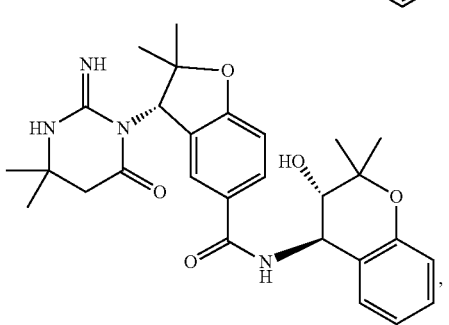
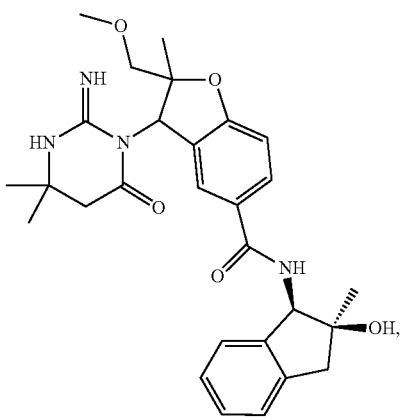
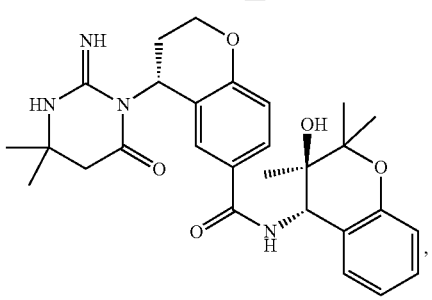

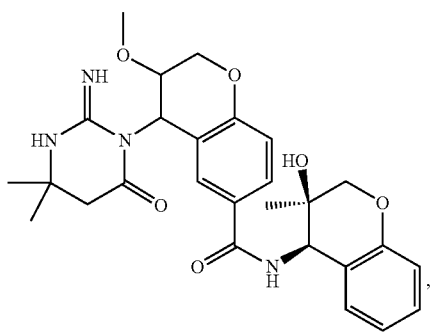
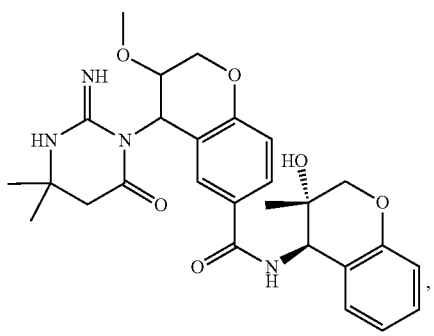
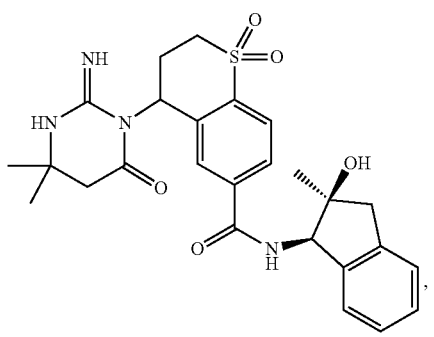
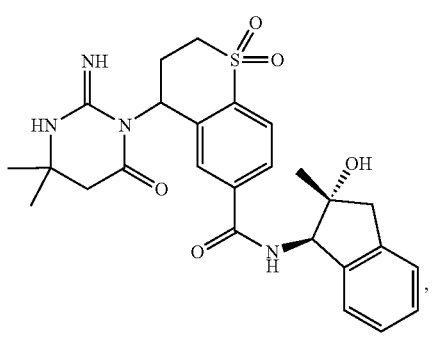
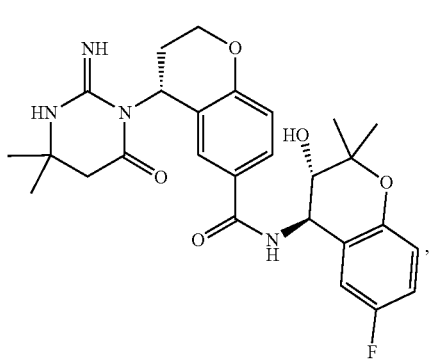
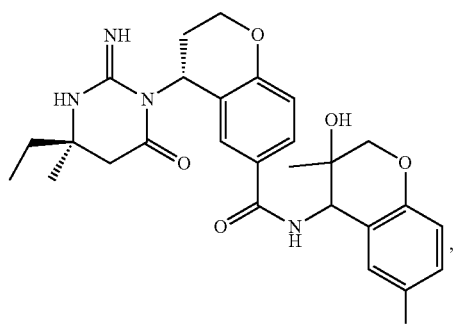
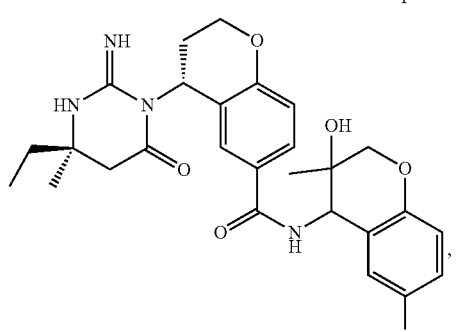
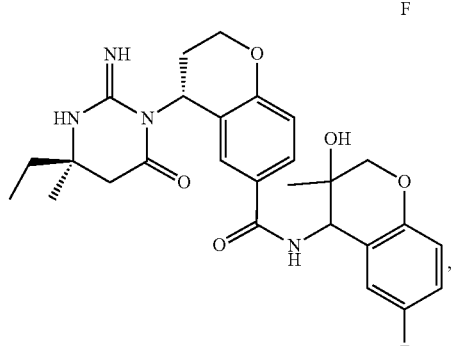
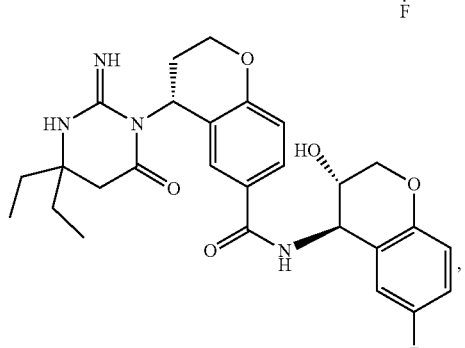
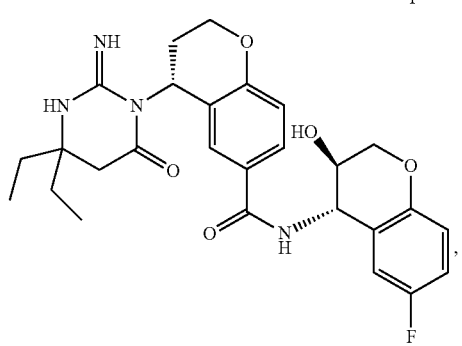

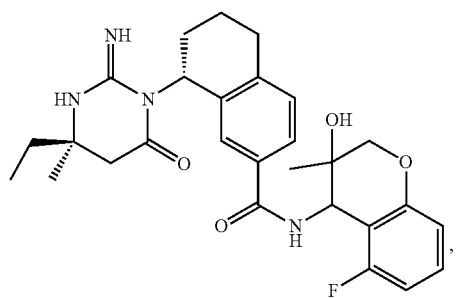
,
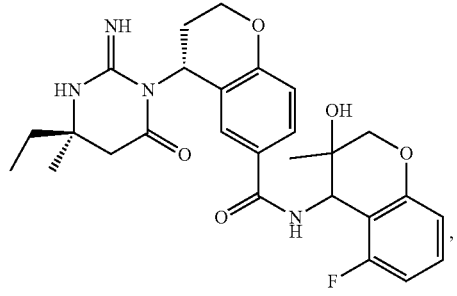
,
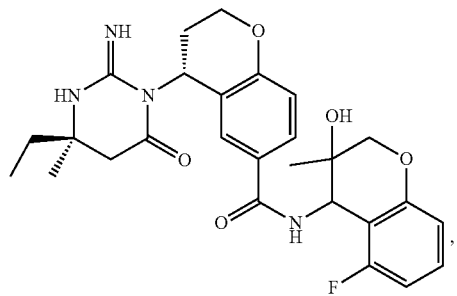
,
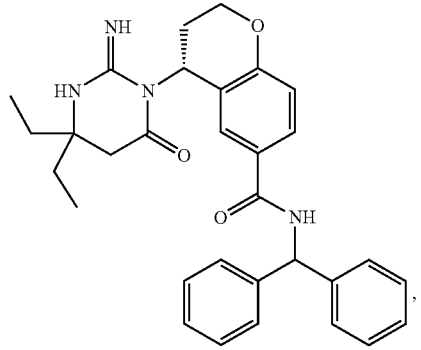
,
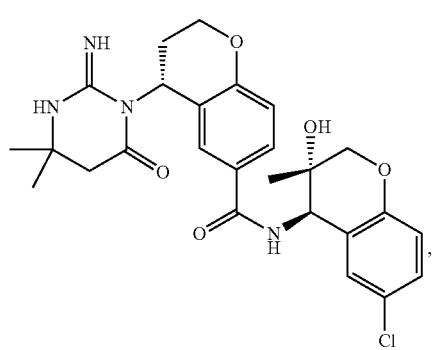
,
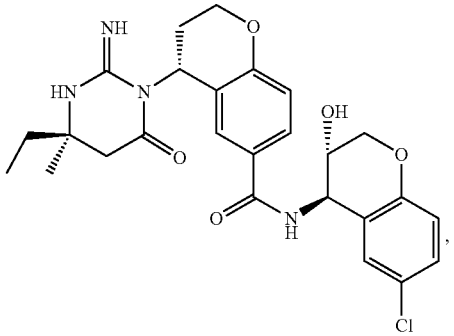
,
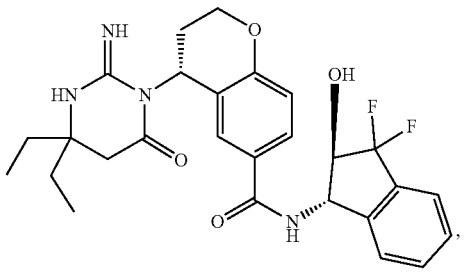
,
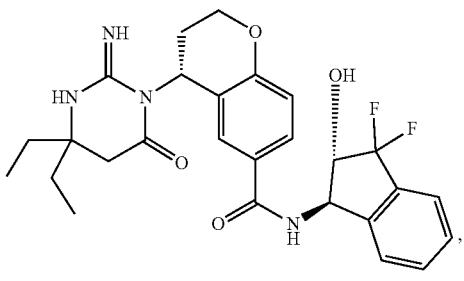
,
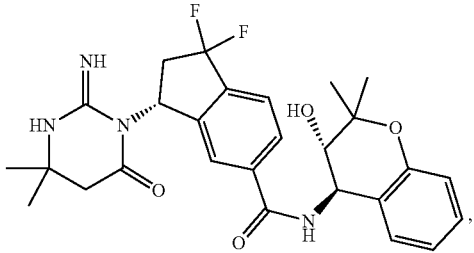
,
,
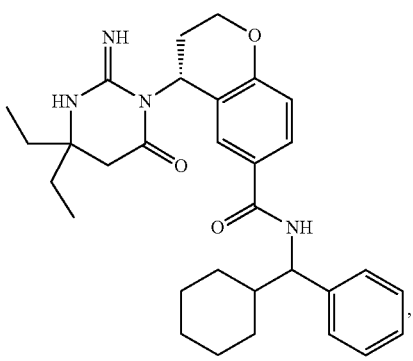
, 71
-continued
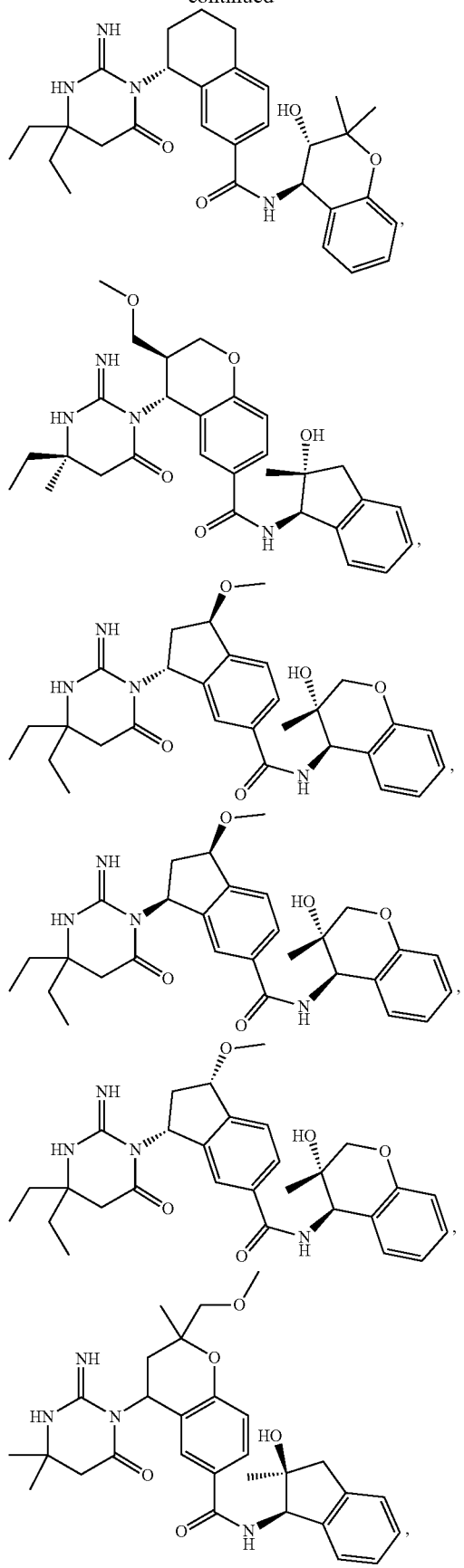
72
-continued
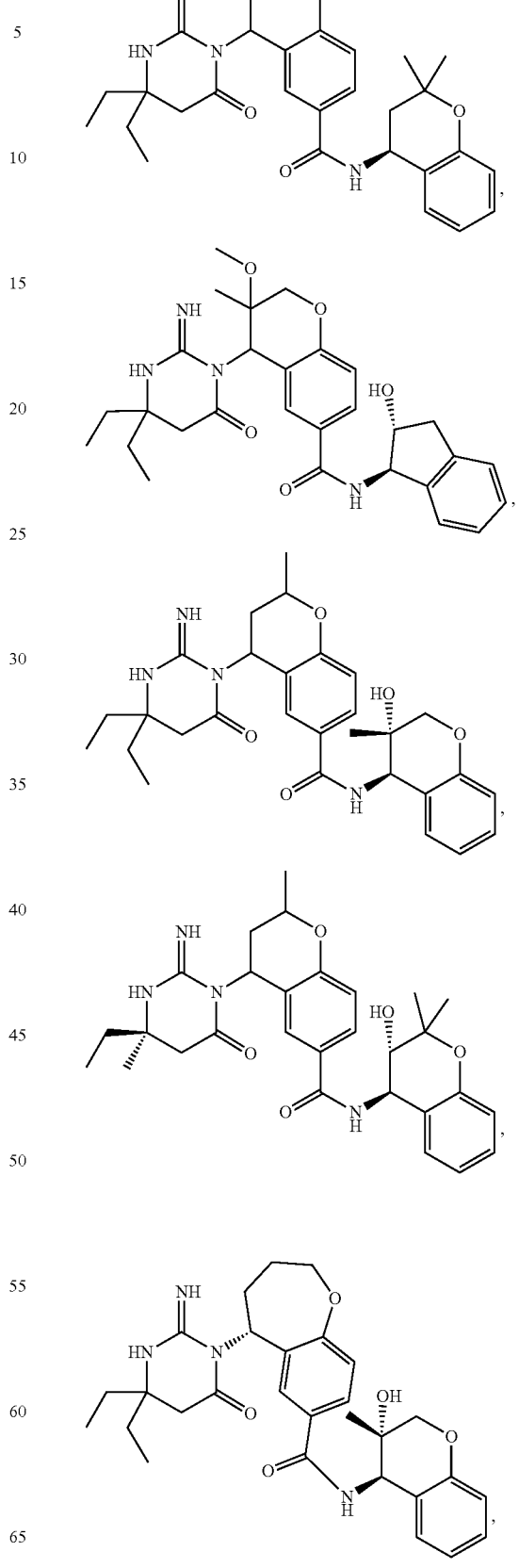

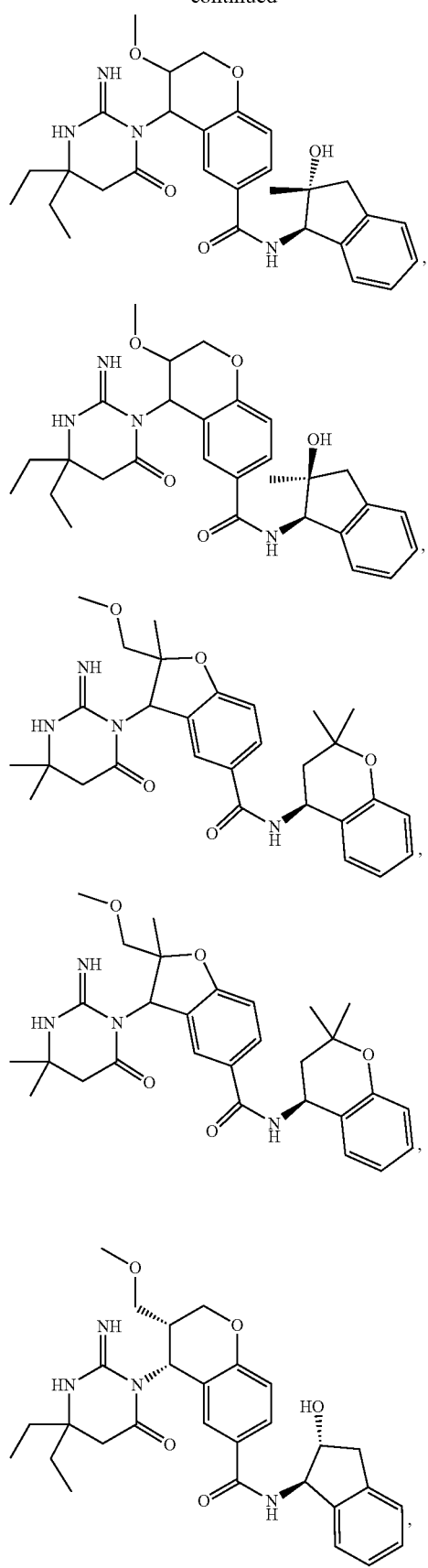
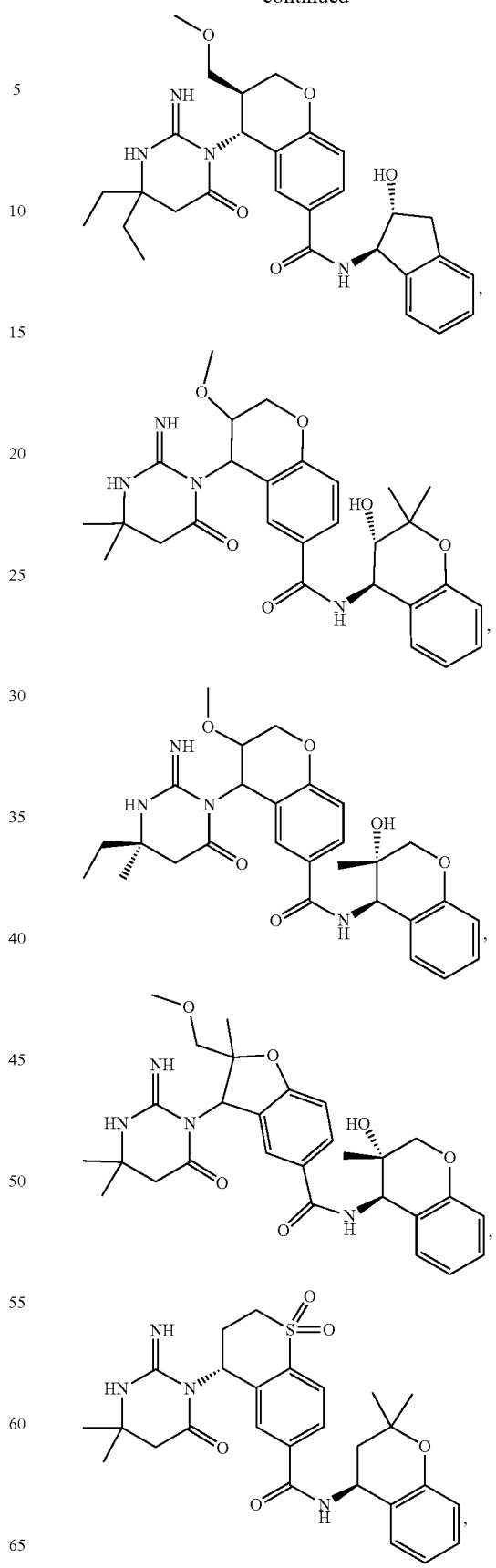

75
-continued
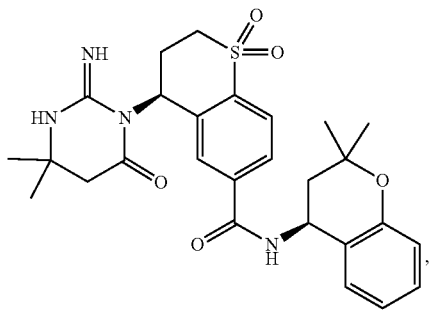
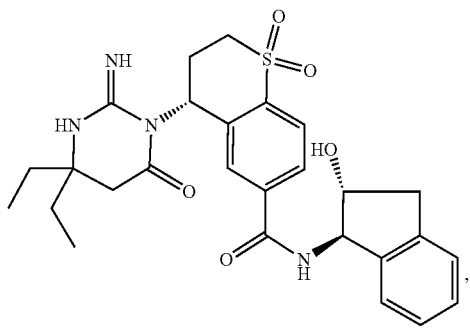
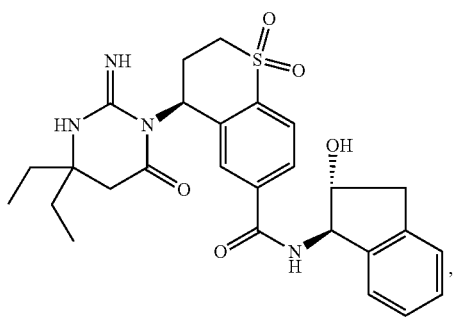
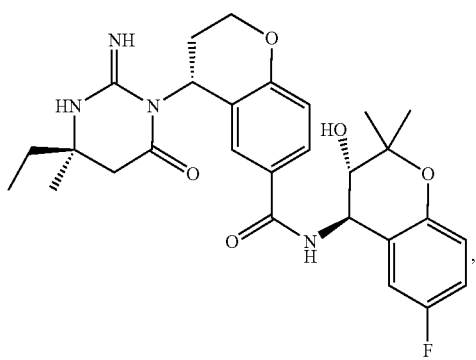
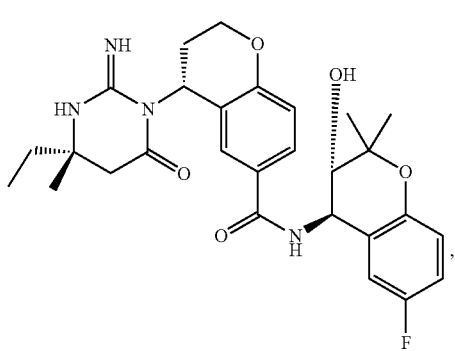
76
-continued
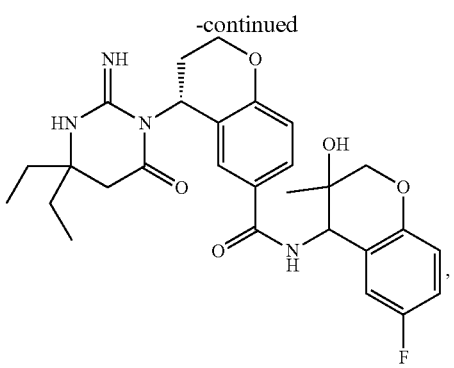
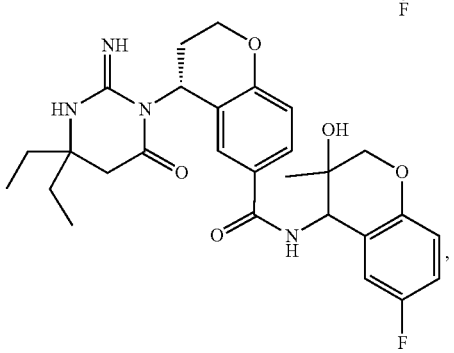
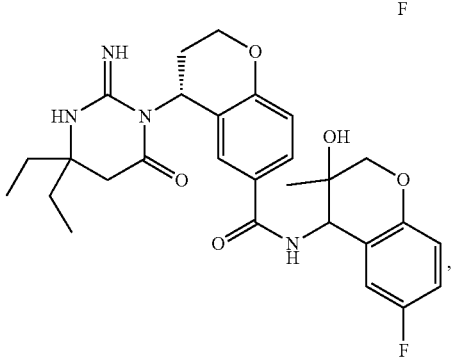
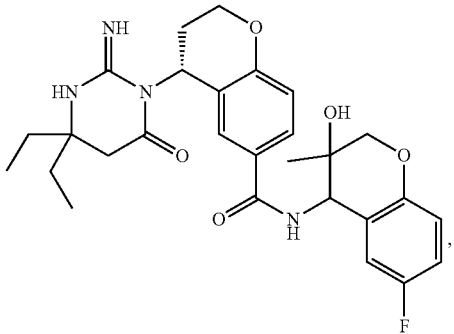
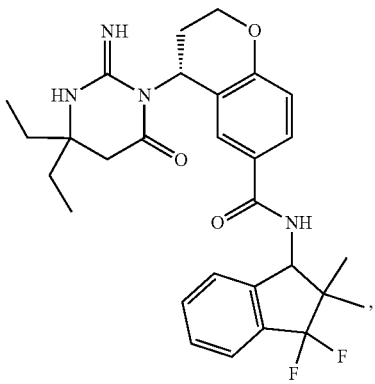

77
-continued
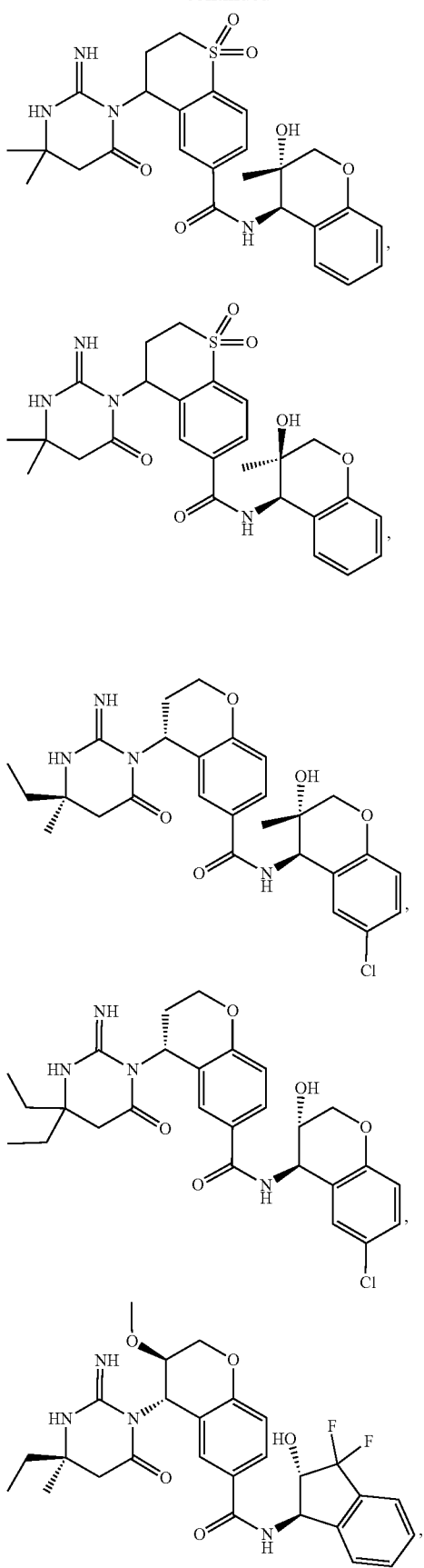
78
-continued
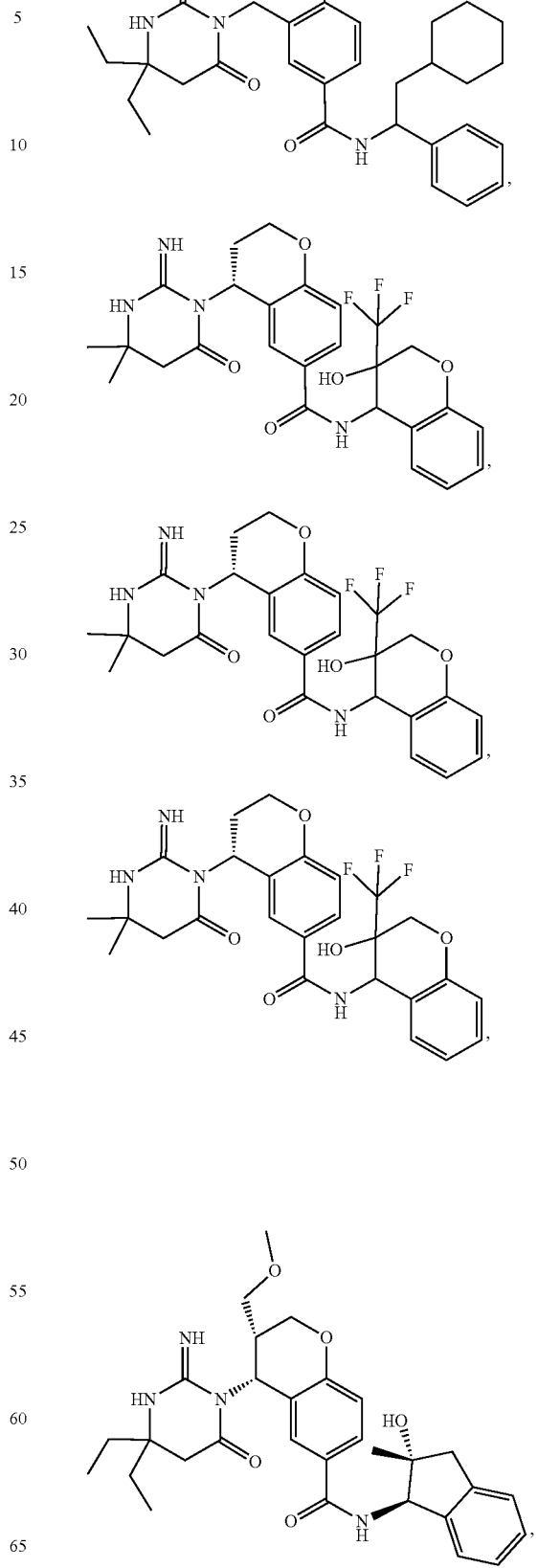

-continued
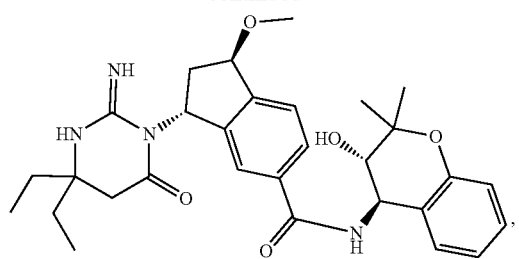
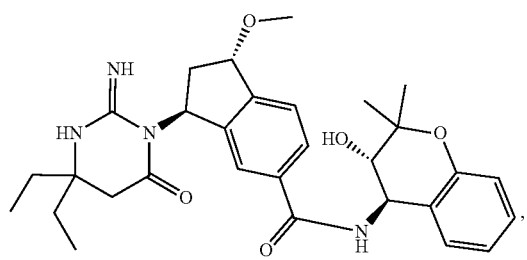
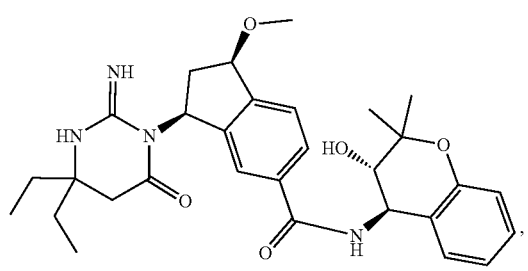
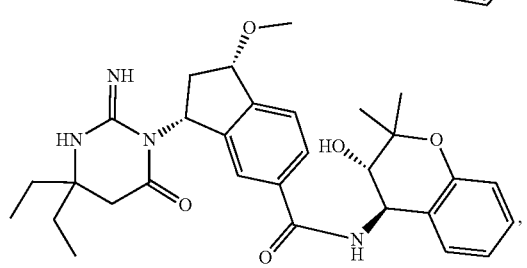
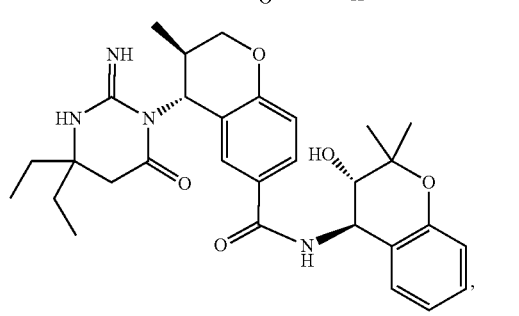
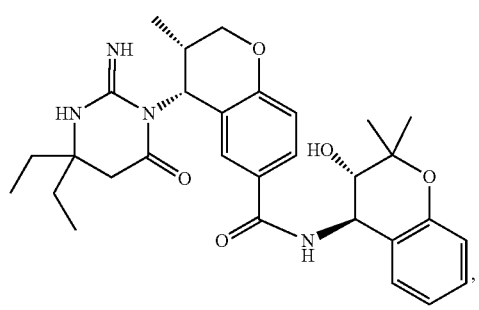
-continued
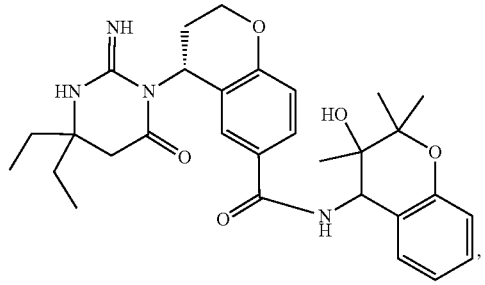
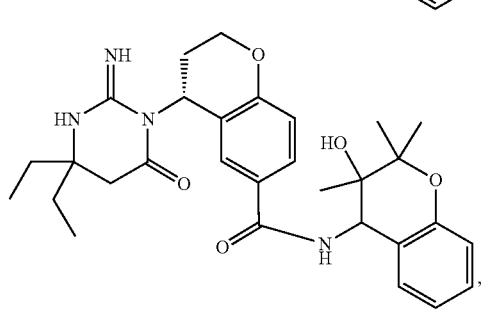
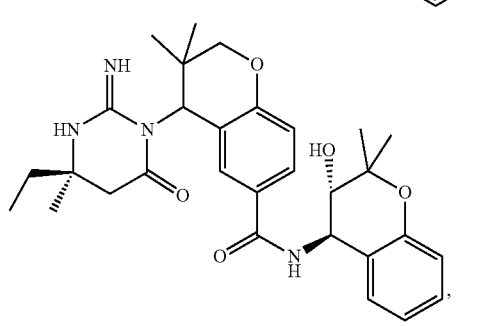
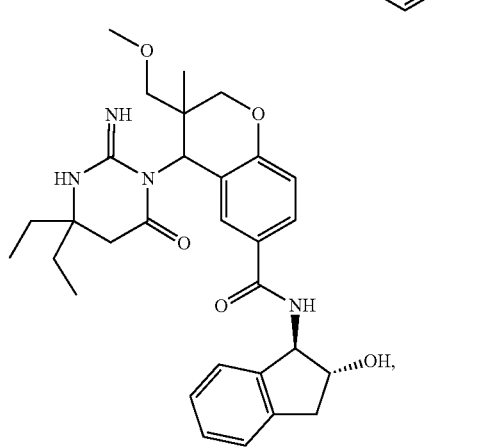
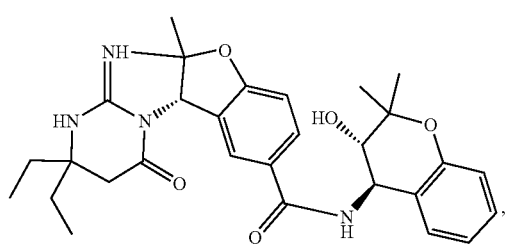

81
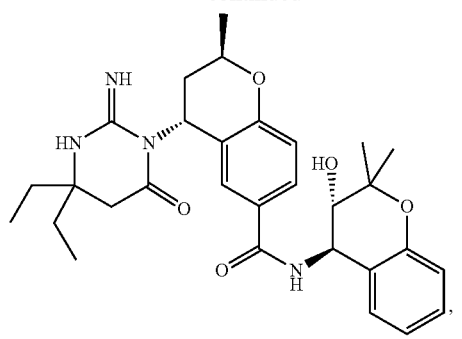
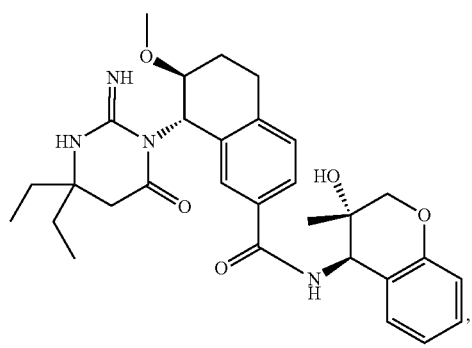
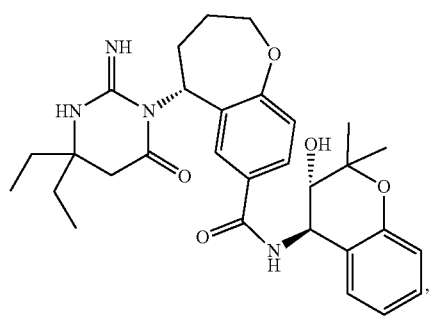
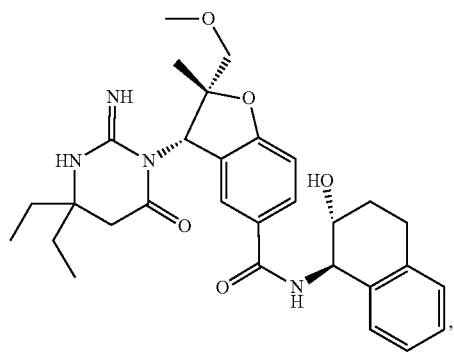
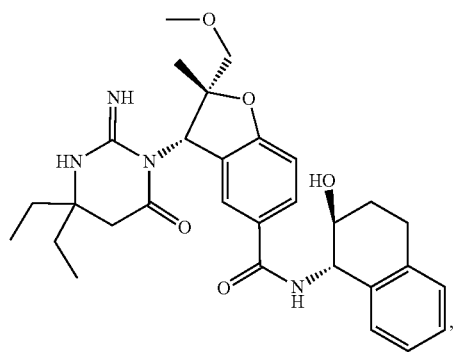
82
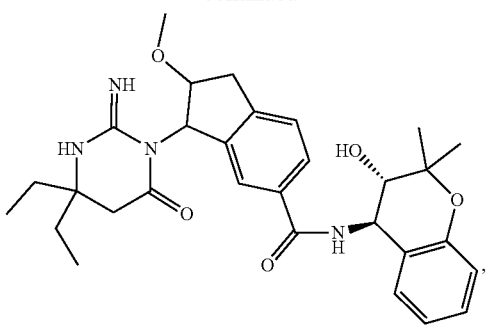
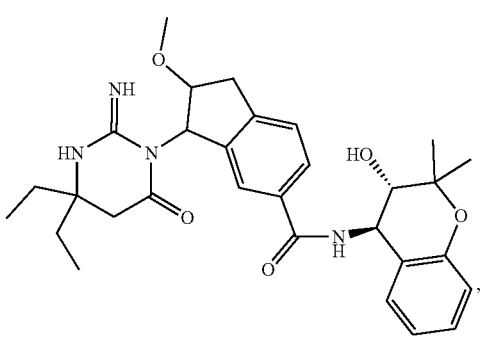
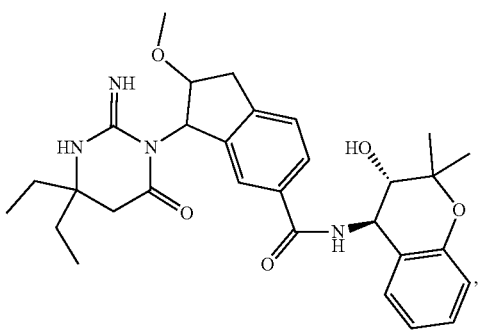
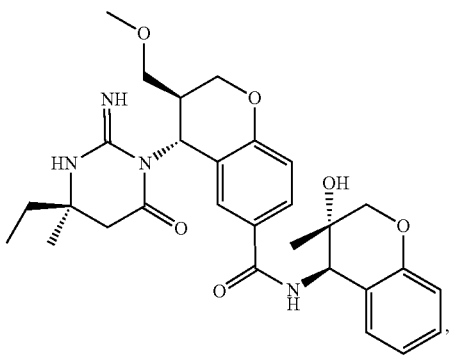
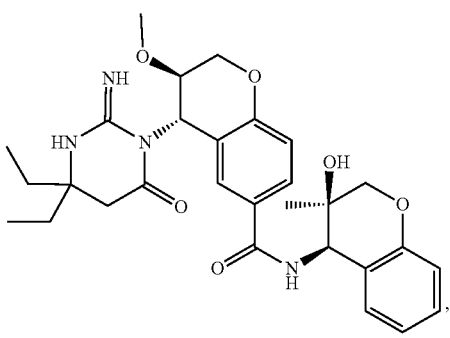

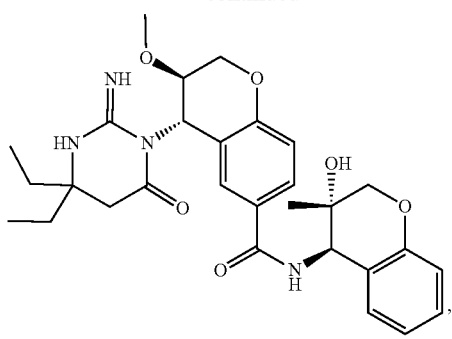
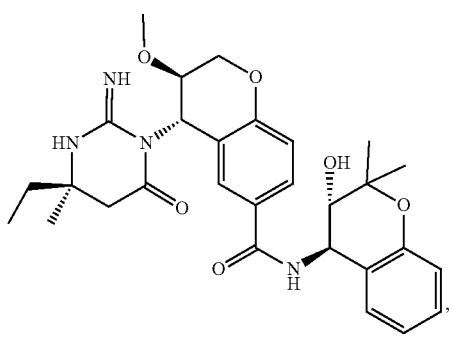
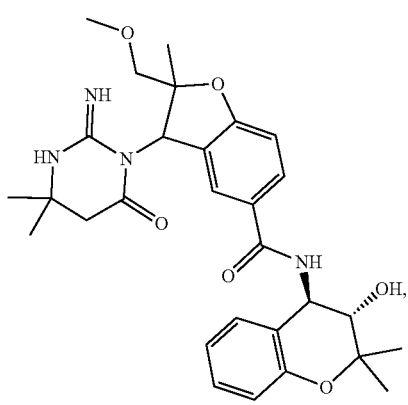
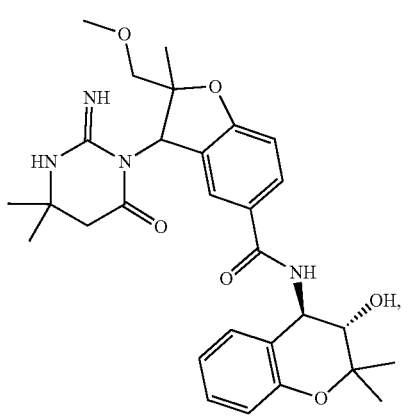
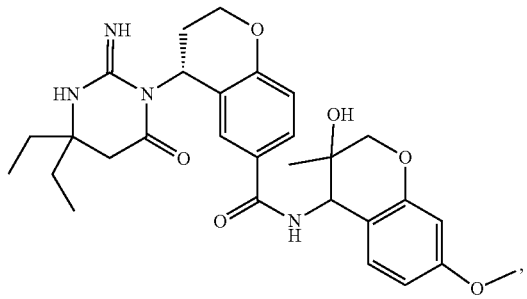
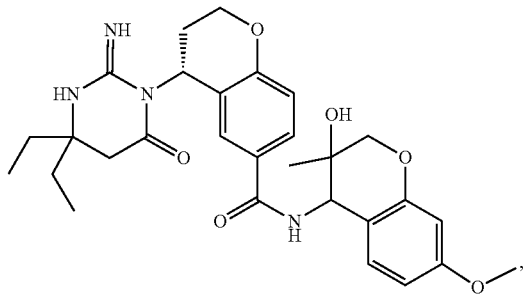
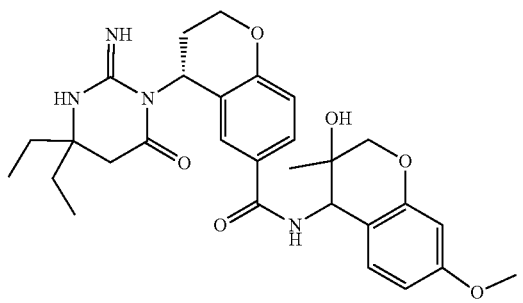
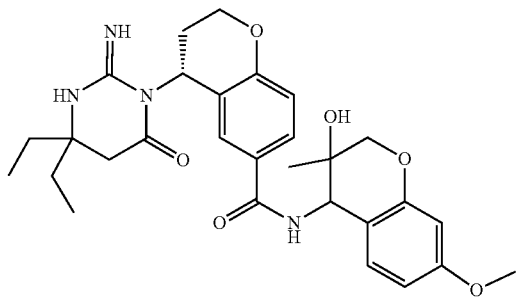
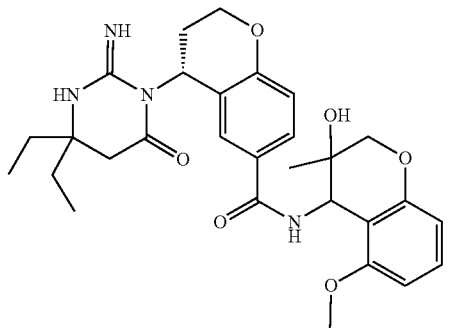

85
-continued
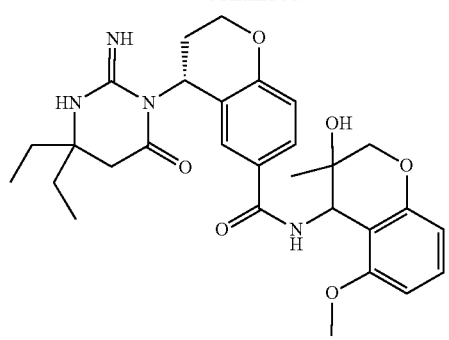
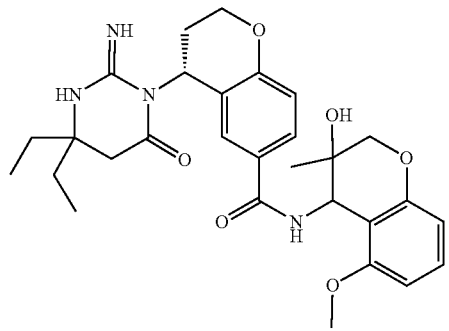
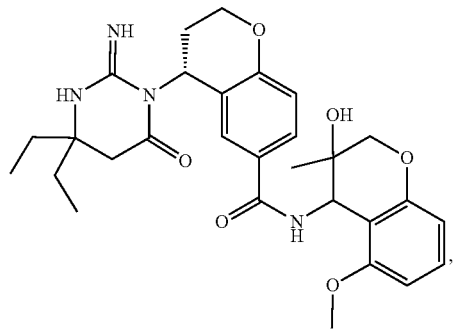
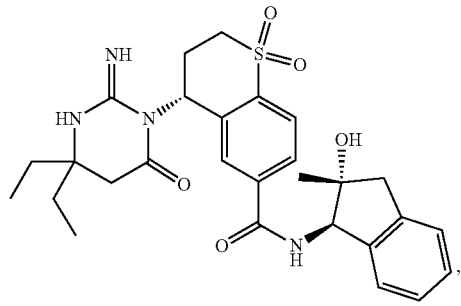
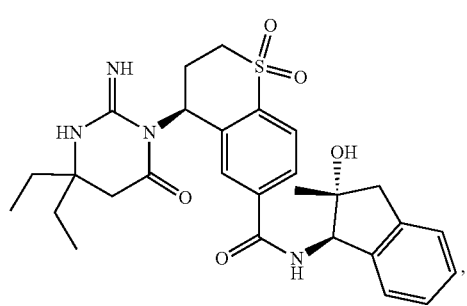
86
-continued
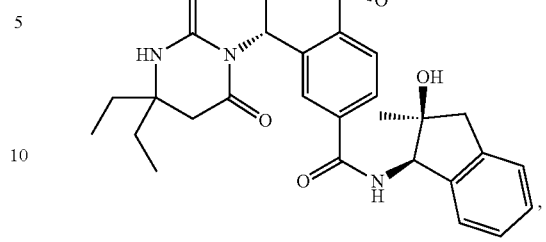
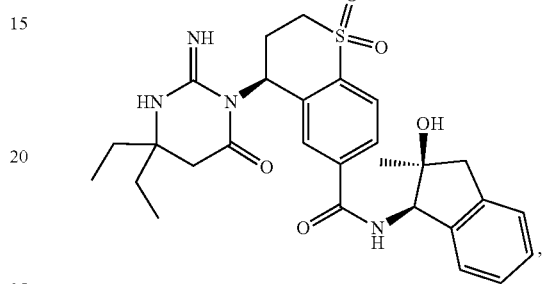
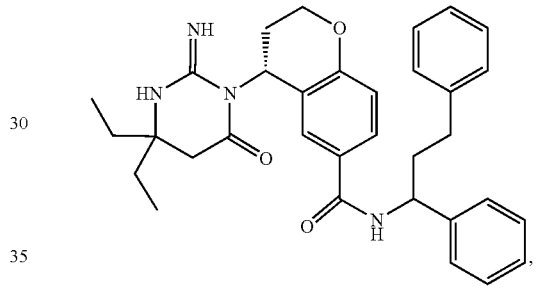
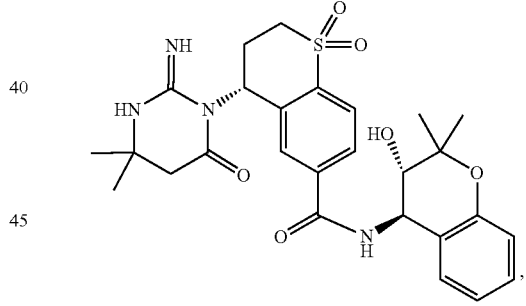
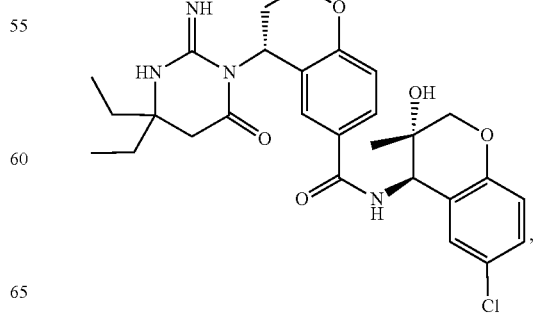

-continued
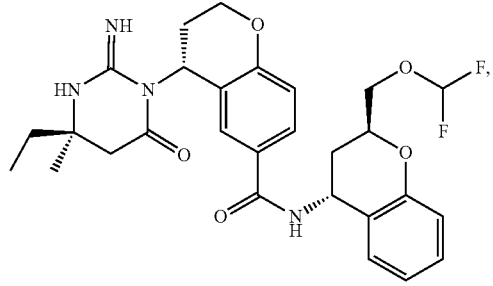
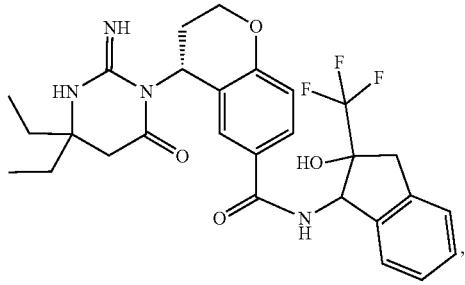
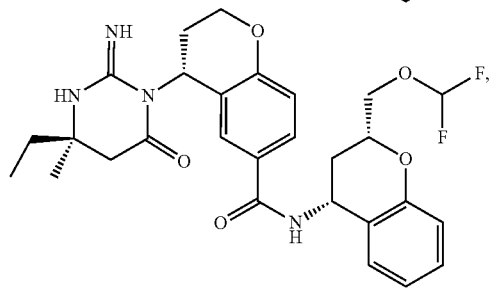
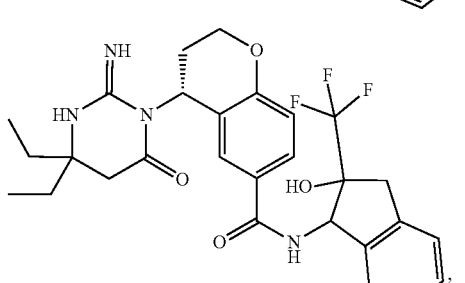
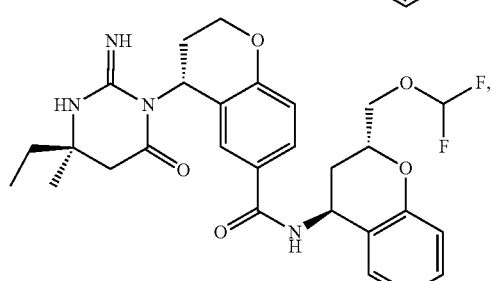
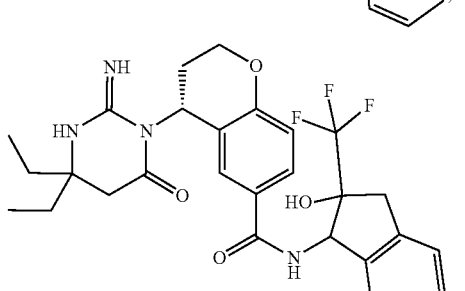
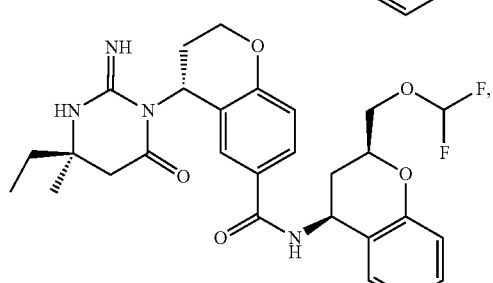
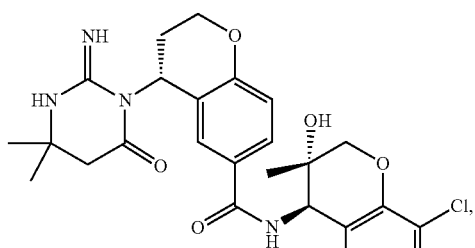
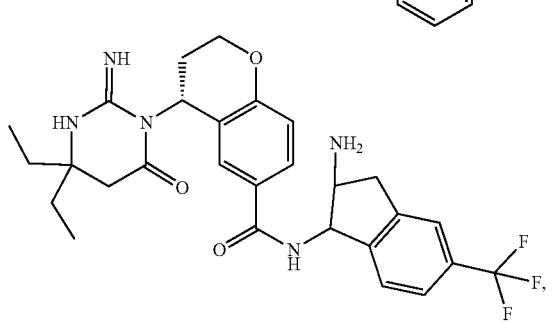
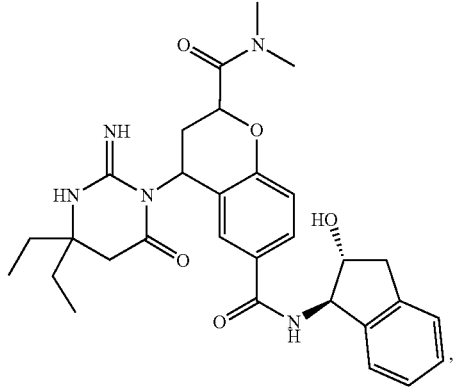

89
-continued
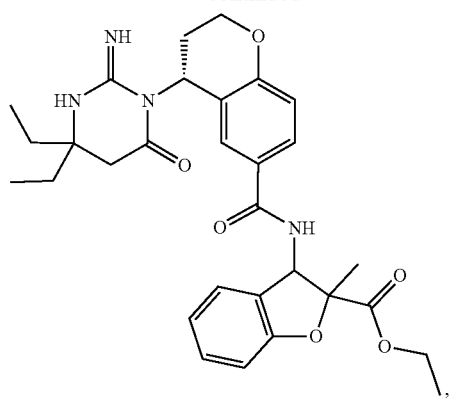
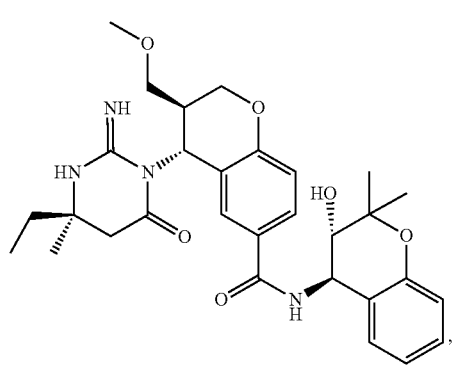
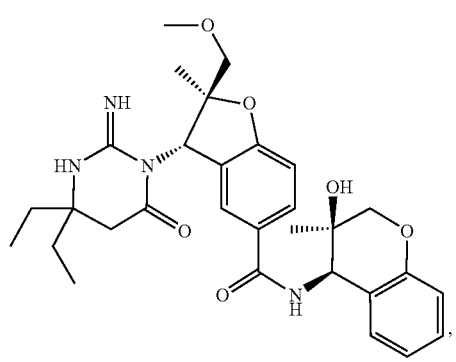
90
-continued
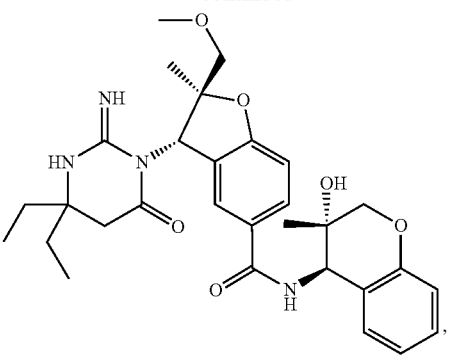
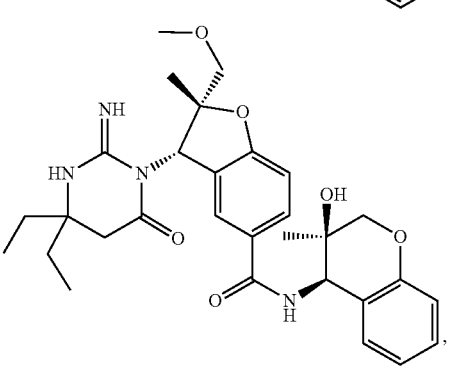
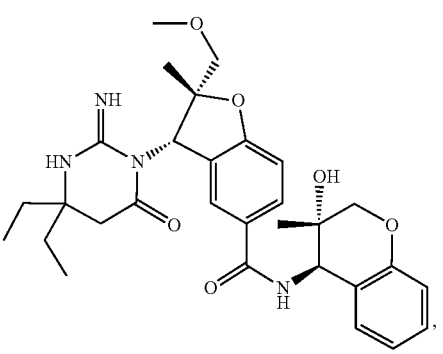
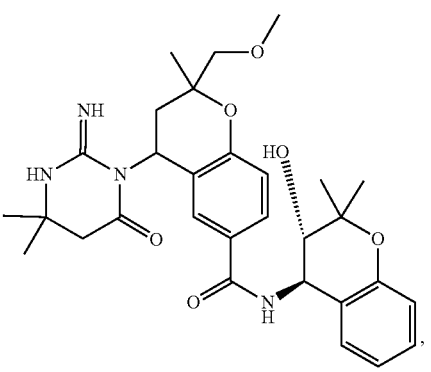

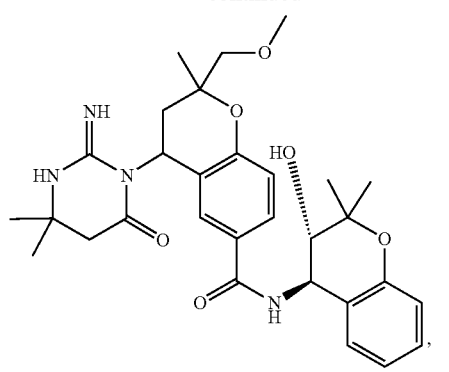
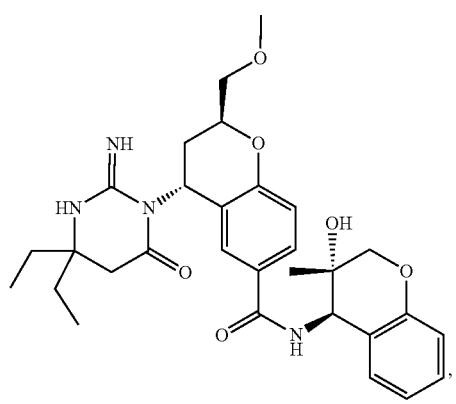
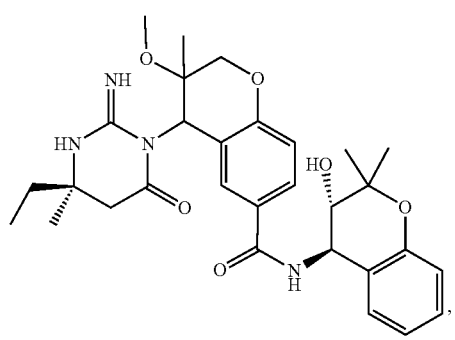
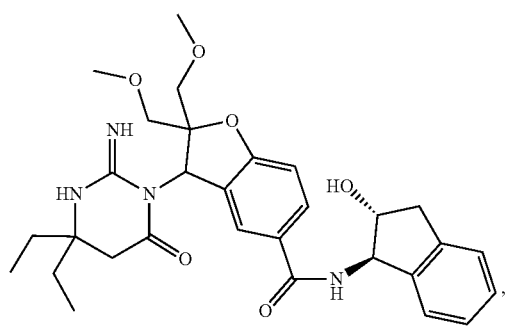
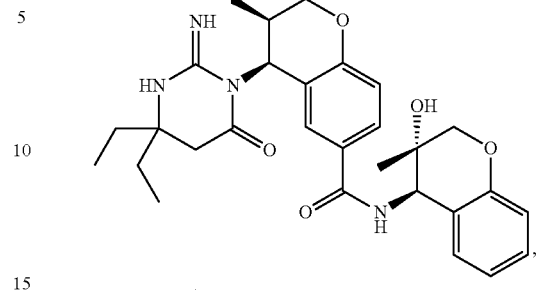
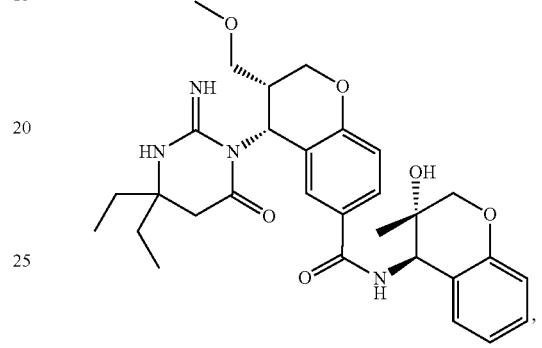
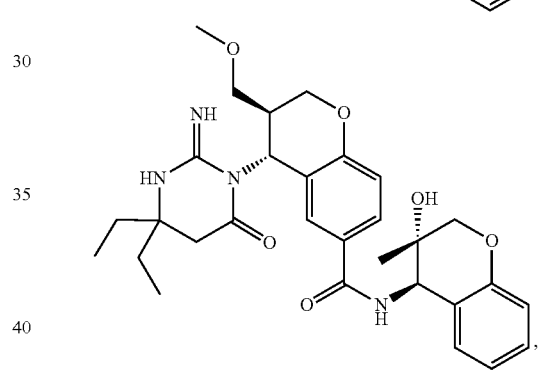
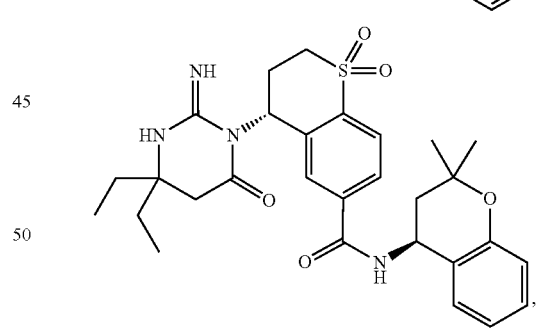
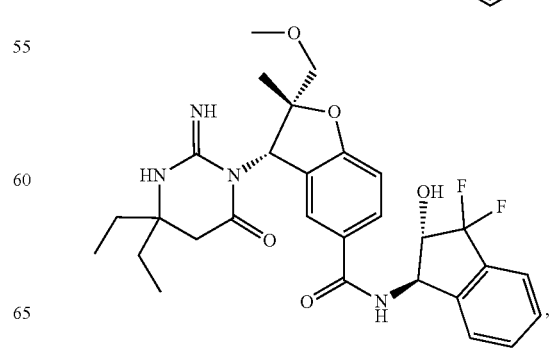

-continued
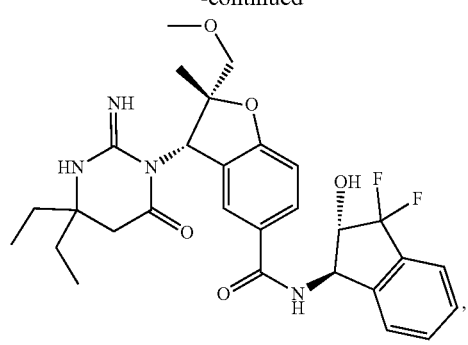
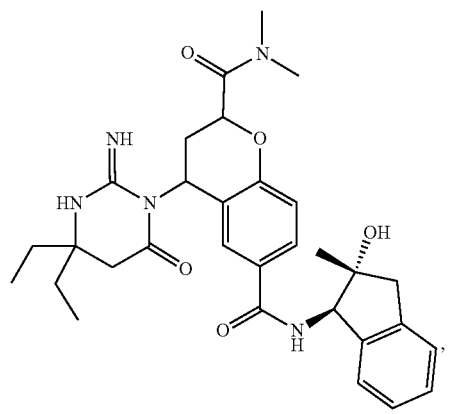
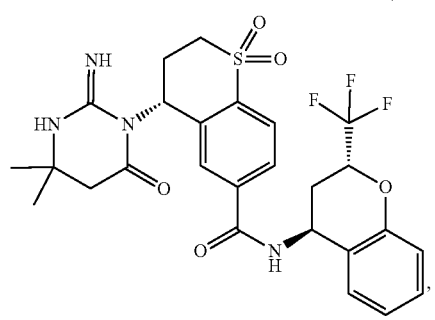
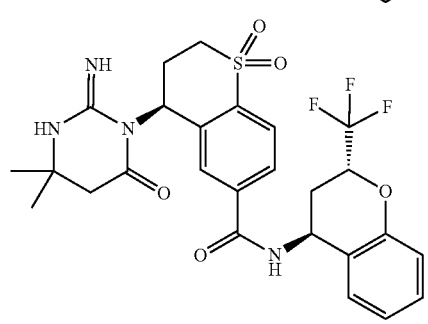
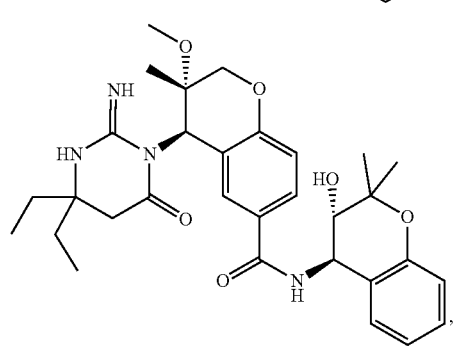
-continued
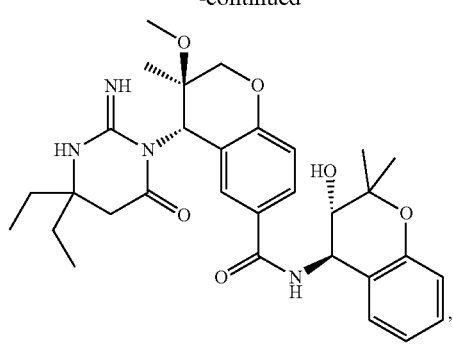
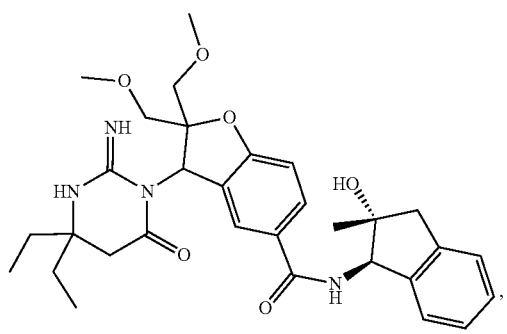
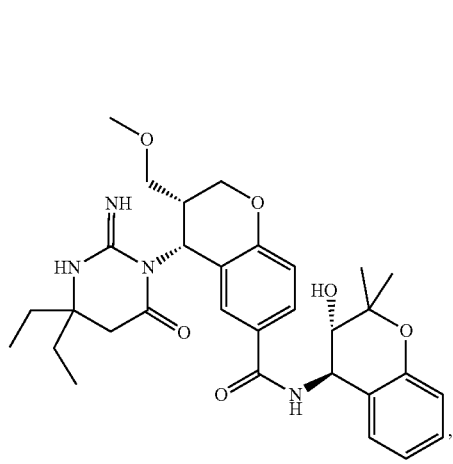
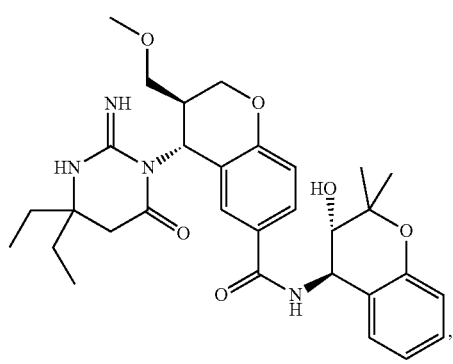

-continued
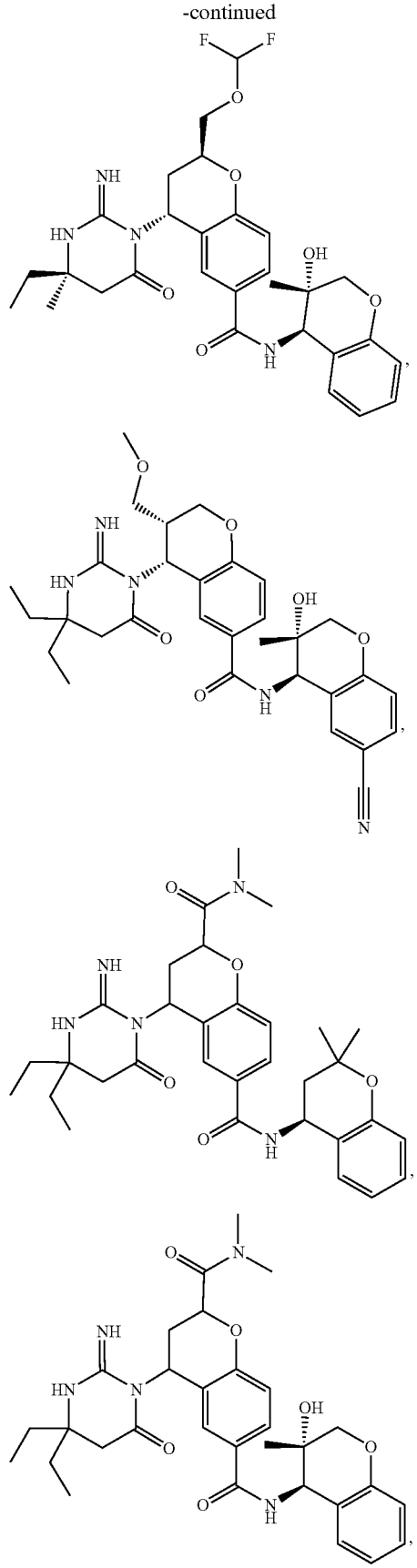
-continued
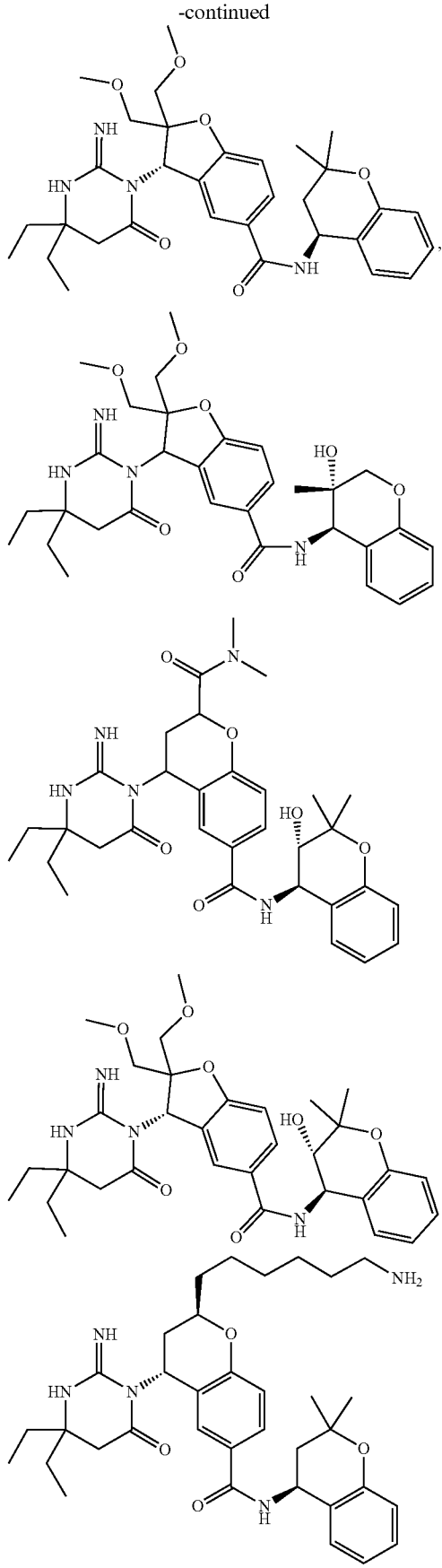

-continued
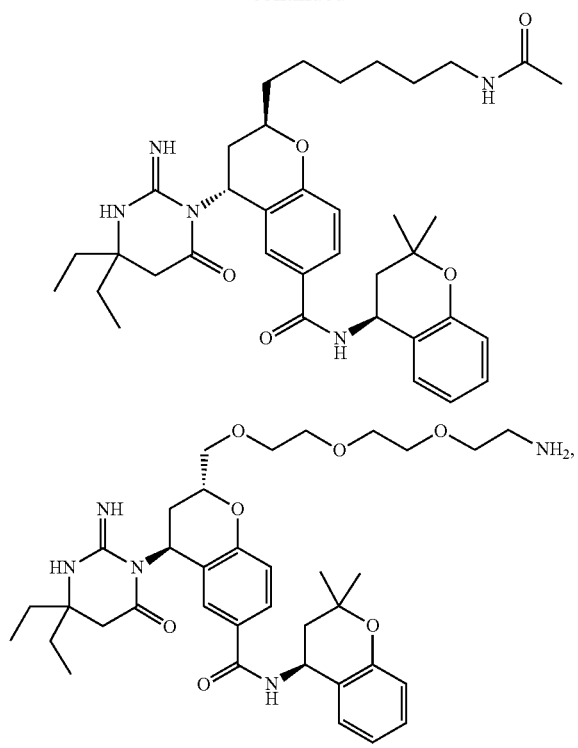
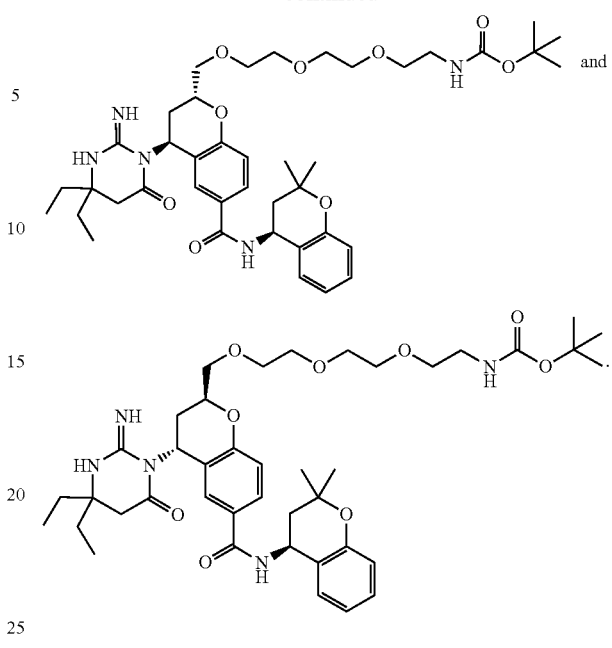
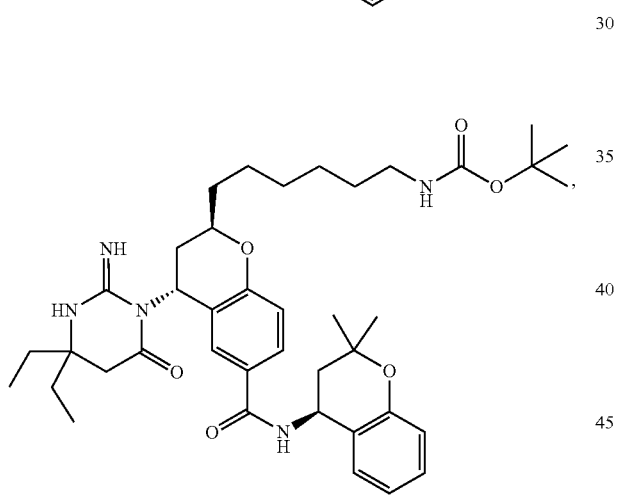
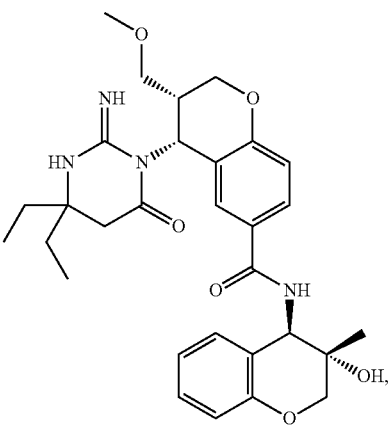
In certain embodiments, the compound is selected from the group consisting of
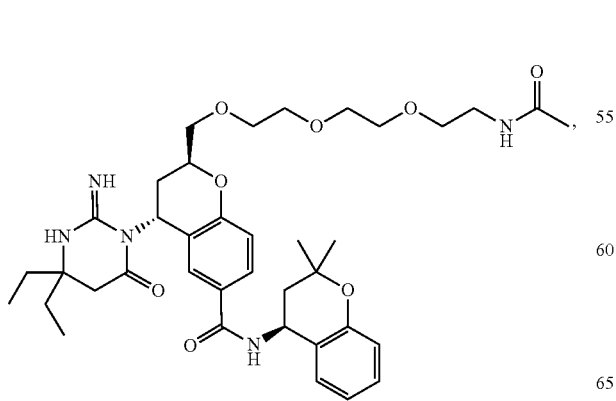
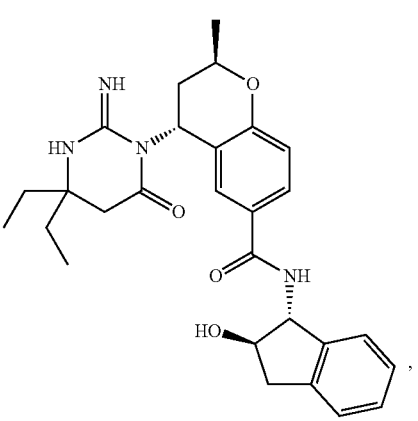

99
-continued
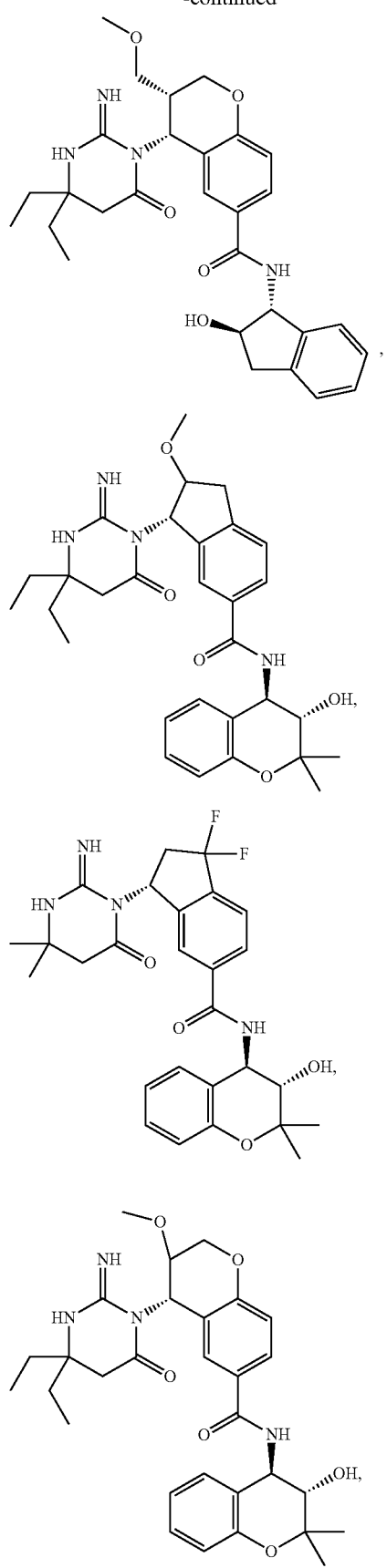
100
-continued
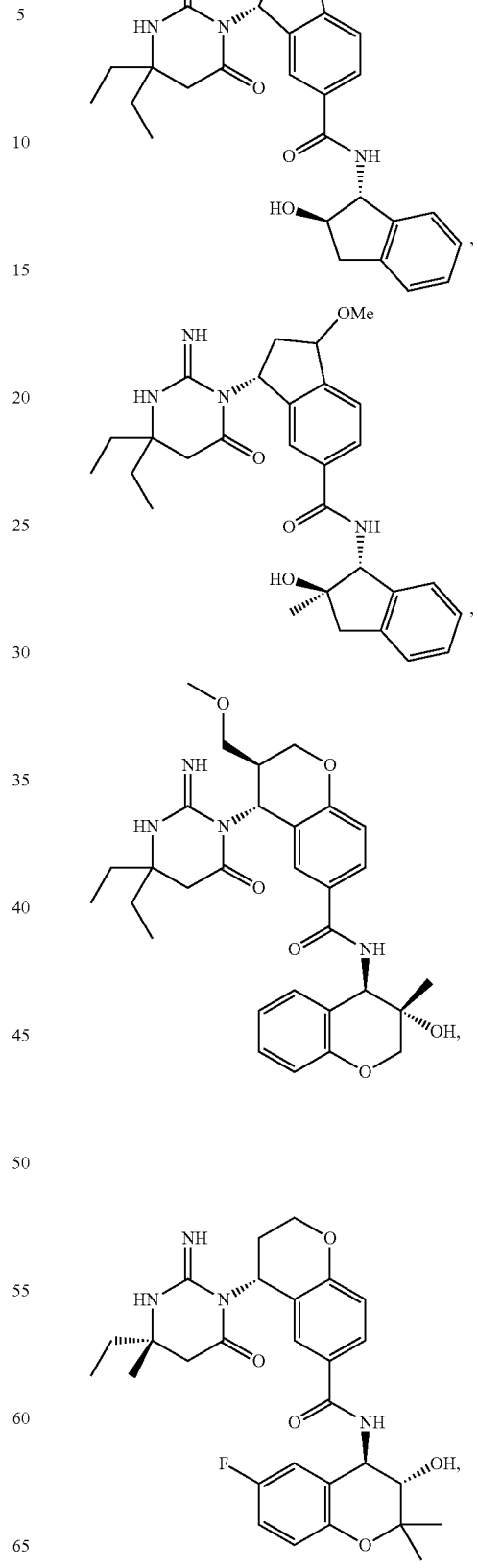

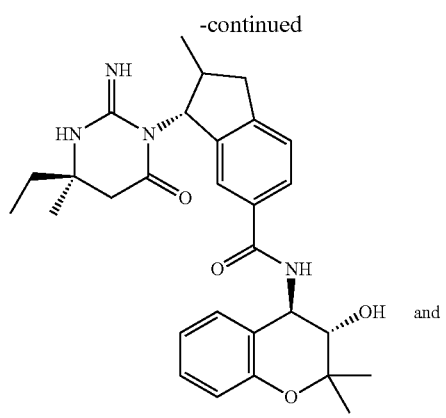
and

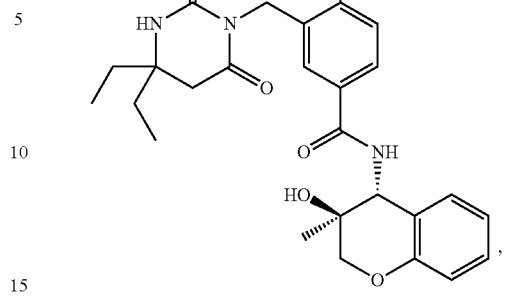

or a pharmaceutically acceptable salt thereof.

In certain embodiments described herein, the compound has the formula:

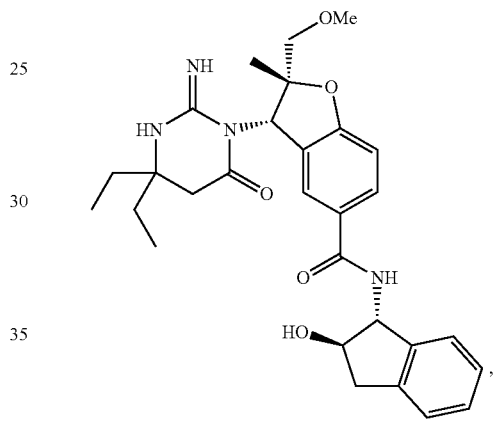

or a pharmaceutically acceptable salt thereof.

In certain embodiments described herein, the compound has the formula:

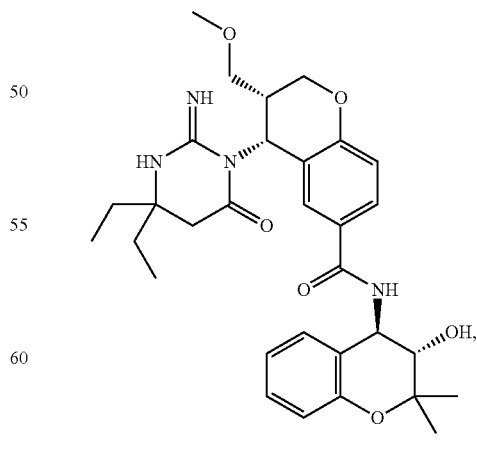

or a pharmaceutically acceptable salt thereof.

In other embodiments, the compound is selected from the group consisting of

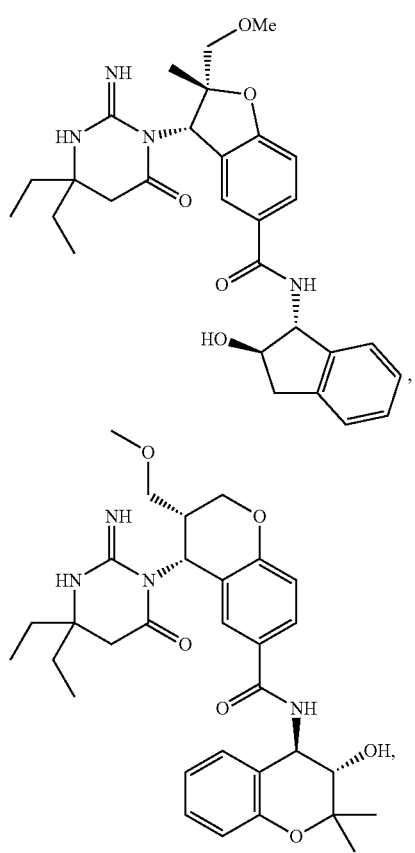

In certain embodiments described herein, the compound has the formula:

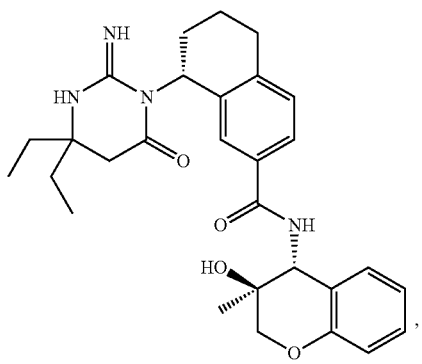 [SMILES: CCC1(CC)CC(=O)N([C@@H]2CCCc3ccc(C(=O)N[C@@H]4c5ccccc5OC[C@@]4(C)O)cc32)C(=N)N1]

or a pharmaceutically acceptable salt thereof.

Definitions and Abbreviations

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I').

In the various embodiments described herein, each variable is selected independently of the others unless otherwise indicated.

"Drug resistant" means, in connection with a *Plasmodium* parasite strain, a *Plasmodium* species which is no longer susceptible to at least one previously effective drug; which has developed the ability to withstand attack by at least one previously effective drug. A drug resistant strain may relay that ability to withstand to its progeny. Said resistance may be due to random genetic mutations in the bacterial cell that alters its sensitivity to a single drug or to different drugs.

"Patient" includes both human and non-human animals. Non-human animals include those research animals and companion animals such as mice, rats, primates, monkeys, chimpanzees, great apes, dogs, and house cats.

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, and one or more pharmaceutically acceptable carriers or diluents. The term "pharmaceutical composition" is also intended to encompass both the bulk composition and individual dosage units comprised of one or more (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the aforesaid "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" and "halo" mean fluorine, chlorine, bromine, or iodine. Preferred are fluorine, chlorine and bromine.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl and t-butyl.

"Haloalkyl" means an alkyl as defined above wherein one or more hydrogen atoms on the alkyl is replaced by a halo group defined above.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Cycloalkyl" means a non-aromatic mono- or multicyclic ring system comprising about 3 to about 12 carbon atoms, preferably about 3 to about 10 carbon atoms. Preferred cycloalkyl rings contain about 5 to about 10 ring atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Multicyclic cycloalkyls refers to multicyclic, including bicyclic, rings that include a non-aromatic ring. Non-limiting examples of suitable multicyclic cycloalkyls include 1-decalinyl, norbornyl, adamantyl and the like. In certain embodiments, a non-aromatic ring is fused to an aromatic ring. Further non-limiting examples of cycloalkyl include the following:

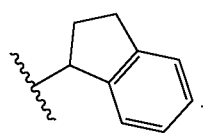 [SMILES: *C1CCc2ccccc21]

"Heterocycloalkyl" (or "heterocyclyl") means a non-aromatic, saturated or partially saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

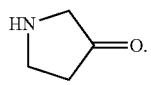

As used herein, the term "monocyclic heterocycloalkyl" refers monocyclic versions of the heterocycloalkyl moieties described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. A non-limiting example of a monocyclic heterocycloalkyl group include the moiety:

Non-limiting examples of multicyclic heterocycloalkyl groups include, bicyclic heterocycloalkyl groups. Specific examples include, but are not limited to,

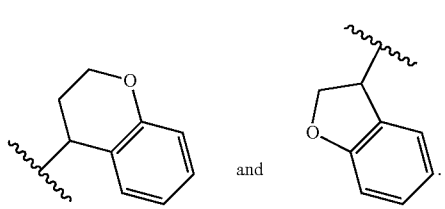 [SMILES: *C1CCOc2ccccc21 ; *C1COc2ccccc21]

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

When a variable appears more than once in a group, e.g., $R^8$ in —N($R^8$)$_2$, or a variable appears more than once in a structure presented herein, the variables can be the same or different.

A solid line ———, as a bond generally indicates a mixture of, or either of, the possible isomers, e.g., containing (R)- and (S)-stereochemistry. For example:

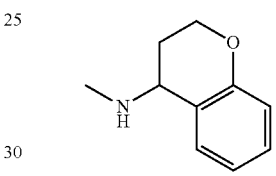

means containing either one of or both

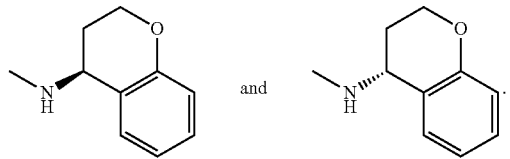

The wavy line ∼∼∼∼, as used herein shown crossing a line representing a chemical bond, indicates a point of attachment to the rest of the compound. Lines drawn into the ring systems, such as, for example

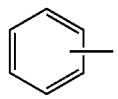

indicates that the indicated line (bond) may be attached to any of the substitutable ring atoms.

"Oxo" is defined as an oxygen atom that is double bonded to a ring carbon in a cycloalkyl, cycloalkenyl, heterocycloalkyl, heterocycloalkenyl, or another ring described herein, e.g.

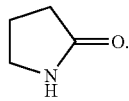

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

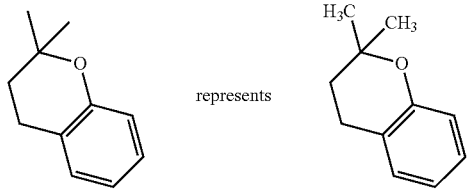

In another embodiment, the compounds useful in the methods of the invention, and/or compositions comprising them useful in said methods, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

It shall be understood that any carbon as well as heteroatom with unsatisfied valences in the text, schemes, examples and tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in Organic Synthesis* (1991), Wiley, New York.

Another embodiment provides prodrugs and/or solvates of the compounds of the invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound useful in the methods of the invention or a pharmaceutically acceptable salt thereof, contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound used in the methods of the invention contains an alcohol functional group, a prodrug can be formed by the replacement of the hydrogen atom of the alcohol group with a group such as, for example, $(C_1-C_6)$alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, $(C_1-C_6)$alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O$($C_1$-$C_6$)alkyl$)_2$ or glycosyl (the radical resulting from the removal of a hydroxyl group of the hemiacetal form of a carbohydrate), and the like.

If a compound used in the methods of the invention incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$ alkyl, carboxy $(C_1-C_6)$alkyl, amino($C_1$-$C_4$)alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N, N—($C_1$-$C_6$)alkylamino morpholino, piperidin-1-yl or pyrrolidin-1-yl, and the like.

One or more compounds used in the methods of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of the invention with one or more solvent molecules. This physical association involves varying degrees of ionic and covalent bonding, including hydrogen bonding. In certain instances, the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds used in the methods of the invention may optionally be converted to a solvate. Preparation of solvates is generally known. Thus, for example M. Caira et al, *J. Pharmaceutical Sci.*, 1993, 3, 601-611, describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition used in the methods of the present invention effective in inhibiting the above-noted diseases or enzyme activity and thus producing the desired therapeutic, ameliorative, inhibitory or preventative effect.

Another embodiment provides pharmaceutically acceptable salts of the compounds to be used in the methods of the invention. Thus, reference to a compound used in the methods of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds used in the methods of the invention may be formed, for example, by reacting a compound of the invention with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Another embodiment provides pharmaceutically acceptable esters of the compounds used in the methods of the invention. Such esters include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, another embodiment provides tautomers of the compounds of the invention to be used in the methods herein, and salts, solvates, esters and prodrugs of said tautomers. It shall be understood that all tautomeric forms of such compounds are within the scope of the compounds used in the methods of the invention. For example, all keto-enol and imine-enamine forms of the compounds, when present, are included in the invention.

The compounds used in the methods of the invention may contain asymmetric or chiral centers, and, therefore, exist in different stereoisomeric forms. It is intended that all stereoisomeric forms of the compounds used in the methods of the invention as well as mixtures thereof, including racemic mixtures, form part of the present invention. In addition, the present invention embraces use of all geometric and positional isomers. For example, if a compound used in the methods of the invention incorporates a double bond or a fused ring, both the cis- and trans-forms, as well as mixtures, are embraced within the scope of the invention.

Another embodiment provides for diastereomeric mixtures and individual enantiomers of the compounds used in the methods of the invention. Diastereomeric mixtures can be separated into their individual diastereomers based on their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds used in the methods of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds used in the methods of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the methods of the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment provides isotopically-labelled compounds to be used in the methods the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of the invention (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the Schemes and/or in the Examples hereinbelow, by substituting an appropriate isotopically labelled reagent for a non-isotopically labelled reagent.

In the compounds used in the methods of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^{1}H$) and deuterium ($^{2}H$). The presence of deuterium in the compounds of the invention is indicated by "D". Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds used in the methods of the invention, and of the salts, solvates, esters and prodrugs of the compounds of the invention, are intended to be included in the present invention.

Methods of Treatment

The present invention is directed to methods of treatment of *Plasmodium* infections comprising administering to a subject in need thereof a compound described herein, or a pharmaceutically acceptable salt thereof. More specifically, the methods of the invention comprise administration of a compound of Formula (I') or (I), or a pharmaceutically acceptable salt thereof. In certain embodiments, the compounds of Formula (I') or (I), or a pharmaceutically acceptable salt thereof, are administered in the form of a pharmaceutical composition, further comprising a pharmaceutically acceptable carrier or excipient.

The present invention provides a method for treating a *Plasmodium* infection, or for treating malaria, or for inhibiting plasmepsin X which comprises administering to a subject in need of such treatment a therapeutically effective amount of a compound, or a pharmaceutically acceptable salt thereof, said compound having the structural Formula (I') or (I) described in the Summary of the Invention. In some embodiments, the compounds of Formula (I') or (I), or pharmaceutically acceptable salts thereof, are administered with a pharmaceutically acceptable carrier, as a pharmaceutical composition. Also provided herein are various embodiments of these methods, as described, infra.

The invention also relates to the use of a compound of Formula (I'), (I), (IA), (IB), (IC), (ID) or (IE) or a pharmaceutically acceptable salt thereof for inhibiting plasmepsin X activity, for treating a *Plasmodium* infection, or for treating malaria. The invention further relates to the use of a compound of Formula (I'), (I), (IA), (IB), (IC), (ID) or (IE) or a pharmaceutically acceptable salt thereof in the manufacture of a medicament for inhibiting plasmepsin X activity, for treating a *Plasmodium* infection, or for treating malaria. The compounds of Formula (I'), (I), (IA), (IB), (IC), (ID) or (IE) or pharmaceutically acceptable salts thereof described in any of the embodiments of the invention herein are useful for any of the uses above.

The present invention provides a method for treating a *Plasmodium* infection, or for treating malaria, or for inhibiting plasmepsin IX which comprises administering to a subject in need of such treatment a therapeutically effective amount of a compound, or a pharmaceutically acceptable salt thereof, said compound having the structural Formula (I') or (I) described in the Summary of the Invention. In some embodiments, the compounds of Formula (I') or (I), or pharmaceutically acceptable salts thereof, are administered with a pharmaceutically acceptable carrier, as a pharmaceutical composition. Also provided herein are various embodiments of these methods, as described, infra.

The invention also relates to the use of a compound of Formula (I'), (I), (IA), (IB), (IC), (ID) or (IE) or a pharmaceutically acceptable salt thereof for inhibiting plasmepsin IX activity, for treating a *Plasmodium* infection, or for treating malaria. The invention further relates to the use of a compound of Formula (I'), (I), (IA), (IB), (IC), (ID) or (IE) or a pharmaceutically acceptable salt thereof in the manufacture of a medicament for inhibiting plasmepsin IX activity, for treating a *Plasmodium* infection, or for treating malaria. The compounds of Formula (I'), (I), (IA), (IB), (IC), (ID) or (IE) or pharmaceutically acceptable salts thereof described in any of the embodiments of the invention herein are useful for any of the uses above.

The present invention provides a method for treating a *Plasmodium* infection, or for treating malaria, or for inhibiting plasmepsin X and plasmepsin IX which comprises administering to a subject in need of such treatment a therapeutically effective amount of a compound, or a pharmaceutically acceptable salt thereof, said compound having the structural Formula (I') or (I) described in the Summary of the Invention. In some embodiments, the compounds of Formula (I') or (I), or pharmaceutically acceptable salts thereof, are administered with a pharmaceutically acceptable carrier, as a pharmaceutical composition. Also provided herein are various embodiments of these methods, as described, infra.

The invention also relates to the use of a compound of Formula (I'), (I), (IA), (IB), (IC), (ID) or (IE) or a pharmaceutically acceptable salt thereof for inhibiting plasmepsin X and plasmepsin IX activity, for treating a *Plasmodium* infection, or for treating malaria. The invention further relates to the use of a compound of Formula (I'), (I), (IA), (IB), (IC), (ID) or (IE) or a pharmaceutically acceptable salt thereof in the manufacture of a medicament for inhibiting plasmepsin X and plasmepsin IX activity, for treating a *Plasmodium* infection, or for treating malaria. The compounds of Formula (I'), (I), (IA), (IB), (IC), (ID) or (IE) or pharmaceutically acceptable salts thereof described in any of the embodiments of the invention herein are useful for any of the uses above.

The methods of the present invention are useful for treating malaria in that they inhibit the onset, growth, or progression of the condition, ameliorate the symptoms of the condition, cause regression of the condition, cure the condition, or otherwise improve the general well-being of a subject afflicted with, or at risk of, contracting the condition. Thus, in accordance with the presently disclosed subject matter, the terms "treat", "treating", and grammatical variations thereof, as well as the phrase "method of treating", are meant to encompass any desired therapeutic intervention, including but not limited to a method for treating an existing infection in a subject of infection, such as in a subject that has been exposed to a parasite as disclosed herein.

Embodiments of the invention also include one or more of the compounds of Formula (I'), (I), (IA), (IB), (IC), (ID) or (IE) or a pharmaceutically acceptable salt thereof (i) for use in, (ii) for use as a medicament or composition for, or (iii) for use in the preparation of a medicament for: (a) therapy (e.g., of the human body); (b) medicine; (c) inhibition of parasite/*Plasmodium* growth, (d) treatment or prophylaxis of infection by *Plasmodium* species; (e) reduction of the progression, onset or severity of pathological symptoms associated with *Plasmodium* infection and/or reduction of the likelihood of severe *Plasmodium* infection or, (f) treatment, prophylaxis of, or delay in the onset, severity, or progression of *Plasmodium*-associated disease(s), including, but not limited to: malaria.

Accordingly, another embodiment provides methods for the treatment of malaria or for the treatment of *Plasmodium* infection, comprising administration of combinations comprising an amount of at least one compound of Formula (I'), (I), (IA), (IB), (IC), (ID) or (IE), or a pharmaceutically acceptable salt, solvate, ester or prodrug thereof, and an effective amount of one or more additional agents described below. In certain embodiments, described herein are methods for the treatment of malaria or for the treatment of *Plasmodium* infection, comprising administration of combinations comprising an amount of at least one compound of Formula (I'), (I), (IA), (IB), (IC), (ID) or (IE), or a pharmaceutically acceptable salt, solvate, ester or prodrug thereof, and an effective amount of one or more additional anti-malarial agents. In certain embodiments, described herein are methods for the treatment of malaria by inhibition of plasmepsin X, IX and at least one other mechanism, comprising administration of combinations comprising an amount of at least one compound of Formula (I'), (I), (IA), (IB), (IC), (ID) or (IE), or a pharmaceutically acceptable salt, solvate, ester or prodrug thereof, and an effective amount of one or more additional anti-malarial agents, wherein the additional anti-malarial agents act through a different mechanism than inhibiting plasmepsin IX or plasmepsin X. The pharmacological properties of the compounds of Formula (I'), (I), (IA), (IB), (IC), (ID) or (IE), or a pharmaceutically acceptable salt thereof may be confirmed by several pharmacological assays. Certain assays are exemplified herein.

Dosage and Administration

Another embodiment provides suitable dosages and dosage forms of the compounds used in the methods of the invention. Suitable doses for administering compounds used in the methods of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, in specific embodiments from about 1 mg to about 50 mg, in specific embodiments from about 1 mg to about 25 mg, according to the particular application. In another embodiment, a typical recommended daily dosage regimen for oral administration can range from about 1 mg/day to about 500 mg/day, in specific embodiments 1 mg/day to 200 mg/day, in two to four divided doses.

As discussed above, the amount and frequency of administration of the compounds of the invention and/or the pharmaceutically acceptable salts thereof will be regulated according to the judgment of the attending clinician considering such factors as age, condition and size of the patient as well as severity of the symptoms being treated.

Liquid form preparations include solutions, suspensions and emulsions. As an example, may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment provides for use of compositions comprising a compound of Formula (I'), (I), (IA), (IB), (IC), (ID) or (IE), or a pharmaceutically acceptable salt thereof formulated for transdermal delivery. The transdermal compositions can take the form of creams, lotions, aerosols and/or emulsions and can be included in a transdermal patch of the matrix or reservoir type as are conventional in the art for this purpose.

Another embodiment provides for use of compositions comprising a compound of Formula (I'), (I), (IA), (IB), (IC), (ID) or (IE), or a pharmaceutically acceptable salt thereof formulated for subcutaneous delivery. Another embodiment provides for use of compositions suitable for oral delivery. In some embodiments, it may be advantageous for the pharmaceutical preparation comprising one or more compounds of Formula (I'), (I), (IA), (IB), (IC), (ID) or (IE), or a pharmaceutically acceptable salt thereof to be prepared in a unit dosage form. In such forms, the preparation is subdivided into suitably sized unit doses containing appropriate quantities of the active component, e.g., an effective amount to achieve the desired purpose. Each of the foregoing alternatives is considered as included in the various embodiments of the invention.

When used in combination with one or more additional therapeutic agents ("combination therapy"), the compounds used in the methods of this invention, i.e. the compounds of Formula (I'), (I), (IA), (IB), (IC), (ID) or (IE), may be administered together or sequentially. When administered sequentially, compounds of the invention may be administered before or after the one or more additional therapeutic agents, as determined by those skilled in the art or patient preference.

If formulated as a fixed dose, such combination products employ the compounds of Formula (I'), (I), (IA), (IB), (IC), (ID) or (IE), or a pharmaceutically acceptable salt thereof within the dosage range described herein and the other pharmaceutically active agent or treatment within its dosage range.

Combination Therapy

Another embodiment provides for methods of treatment using pharmaceutically acceptable compositions comprising a compound of the invention, either as the neat chemical or optionally further comprising additional ingredients. Such compositions are contemplated for preparation and use alone or in combination therapy. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pennsylvania.

Non-limiting examples of additional drugs and active agents useful in combination therapies for the treatment of malaria, include the following: Coartem® (Novartis International AG, Basel, Switzerland; artemether+lumefantrine), Eurartesim® (Sigma-Tau Pharmaceuticals, Inc., Rome, Italy; dihydroartemisinin-piperaquine), Pyramax® (Shin Poong Pharmaceutical Co., Ltd., Seoul, Korea; pyronaridine-artesunate), ASAQ Winthrop® (Sanofi SA (Gentilly, France)/DNDi (Geneva, Switzerland); artesunate+amodiaquine), ASMQ (Cipla Limited (Mumbai, India)/DNDi, artesunate+mefloquine), SPAQ-CO™ (Guilin Pharmaceutical Co., Ltd. (Shanghai), amodiaquine+sulfadoxine, pyrimethamine), Artesun® (Guilin Pharmaceutical, artesunate), artemether, artesunate, dihydroartemisinin, lumefantrine, amodiaquine, mefloquine, piperaquine, quinine, chloroquine, atovaquone and proguanil and sulfadoxine-pyrimethamine, Tafenoquine (Glaxosmithkline), OZ439/PQP (Sanofi), OZ439/FQ (Sanofi), KAE609 (Novartis), KAF156 (Novartis), DSM265 (NIH/Takeda), and MK-4815 (Merck & Co., Inc., Powles et al., *Antimicrobial Agents and Chemotherapy* 56(5): 2414-2419(2012)). Selection of such additional active ingredients will be according to the diseases or disorders present for which treatment is desired, as determined by the attending physician or other health care provider.

Thus, the invention also provides methods of using the compounds of Formula (I'), (I), (IA), (IB), (IC), (ID) or (IE), or a pharmaceutically acceptable salt thereof to inhibit plasmepsin X, plasmepsin IX or plasmepsin X and IX, to treat *Plasmodium* infection or treat malaria wherein the method further comprises administering to a subject in need thereof, one or more additional anti-malarial agents. In some embodiments, the one or more additional anti-malarial agents are selected from the group consisting of: artemether, lumefantrine, dihydroartemisinin, piperaquine, pyronaridine, artesunate, amodiaquine, mefloquine, sulfadoxine, pyrimethamine, lumefantrine, quinine, chloroquine, atovaquone, and proguanil.

EXAMPLES

ACN=acetonitrile
AcOEt=ethylacetate
Bu$_3$P=Bis(tri-tert-butylphosphine)palladium(0)
DCM=dichloromethane
DIAD=Diisopropyl azodicarboxylate
DIEA=N, N-Diisopropylethylamine, or Hünig's base
DMF=N,N-Dimethylformamide
DIVIP=Dess-Martin periodinane
DMSO=dimethyl sulfoxide
EDC=EDCI=1-ethyl-3-(3-dimethylaminopropyl)carbodiimide
EtOAc=ethyl acetate
h=hours
HOBt=Hydroxybenzotriazole
LCMS=Liquid chromatography-mass spectrometry
LHMDS=LiHMDS=lithium bis(trimethylsilyl)amide
LiAlH$_4$=lithium aluminum hydride
min=minutes
Me=methyl
MeOH=CH$_3$OH=methanol
NaBH$_4$=sodium borohydride
Na$_2$SO$_4$=sodium sulfate
NH$_4$Cl=Ammonium chloride
Pd(dppf)Cl$_2$=[1,1'-Bis(diphenylphosphino)ferrocene]palladium(II) dichloride
SFC=Supercritical Fluid Chromatography
TBAF=tetra-n-butylammonium fluoride
TEA=triethylamine
TFA=trifluoroacetic acid
THF=tetrahydrofuran
TMS=Trimethylsilyl CDCl₃=heavy chloroform CD₃OD=heavy methanol 1 Standard atmosphere [atm]=101325 pascal [Pa]=14.6959488 psi The meanings of the abbreviations in the nuclear magnetic resonance spectra are shown below: s=singlet, d=doublet, dd=double doublet, dt=double triplet, ddd=double double doublet, sept=septet, t=triplet, m=multiplet, br=broad, brs=broad singlet, q=quartet, J=coupling constant and Hz=hertz.

Several methods for preparing the compounds of this disclosure are described in the following Schemes and Examples. Starting materials and intermediates were purchased commercially from common catalog sources or were made using known procedures, or as otherwise illustrated. Some frequently applied routes to the compounds of Formula (I') or (I) are described in in the Schemes that follow. In some cases, the order of carrying out the reaction steps in the schemes may be varied to facilitate the reaction or to avoid unwanted reaction products. An asterisk (*) may be used in a chemical structure drawing that indicates the location of a chiral center.

SCHEME 1

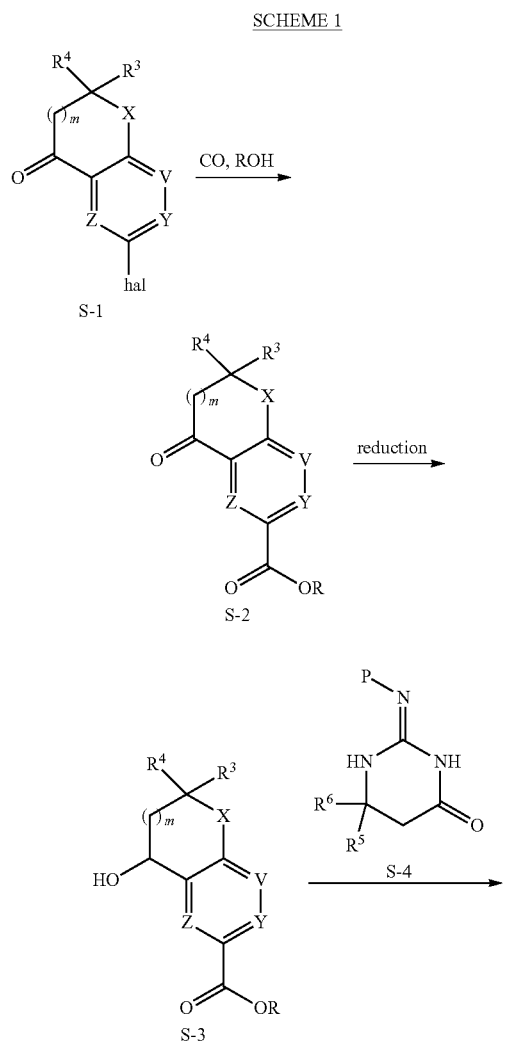

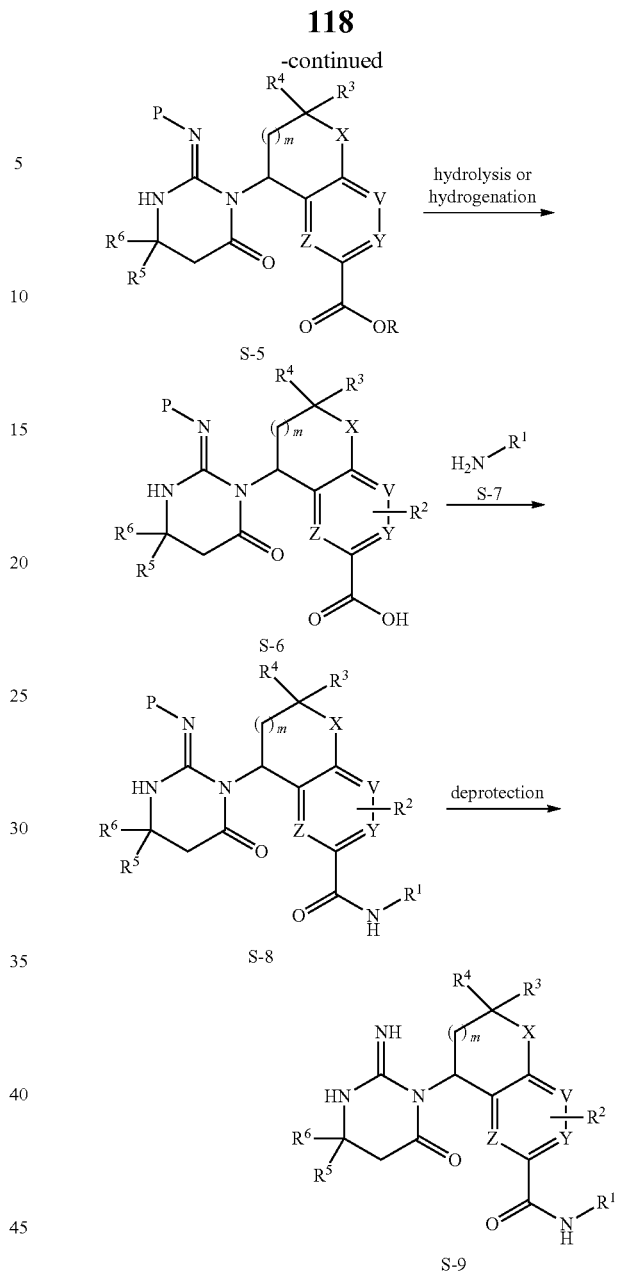

Intermediate compounds of Formula S-2, in which hal is a halogen such as Cl, Br and I, are prepared from S-1 after carbonylation in the presence of an alcohol. Ketone reduction in S-2 can be performed racemically using a hydride source such as NaBH₄ or LiAlH₄ or stereoselectivity using catalytic asymmetric hydrogenation or biocatalysis (ketoreductases) to yield alcohols S-3. Treatment of S-3 with N-protected iminopyrimidone S-4 (WO2017142825) under Mitsunobu conditions gives intermediates S-5. Alternatively, alcohol in intermediates S-3 could be transformed into a leaving group such as a mesylate, tosylate or halogen which can be displaced with iminopyrimidones S-4 to give intermediates S-5. Acid or base catalyzed hydrolysis or hydrogenation of the S-5 ester followed by coupling with amines S-7 provides intermediates S-8 which after protecting group removal yields the products of Formula S-9.

Reactions sensitive to moisture or air were performed inside a glove-box or under nitrogen or argon using anhydrous solvents and reagents. The progress of reactions was determined by either analytical thin layer chromatography (TLC) usually performed with pre-coated TLC plates or liquid chromatography-mass spectrometry (LC/MS).

Typically, the analytical LC-MS system used consisted of a Waters ZQ™ platform with electrospray ionization in positive ion detection mode with an Agilent 1100 series HPLC with autosampler. The column was commonly a Waters Xterra MS C18, 3.0×50 mm, 5 µm or a Waters Acquity UPLC® BEH C18 1.0×50 mm, 1.7 µm. The flow rate was 1 mL/min, and the injection volume was 10 µL. UV detection was in the range 210-400 nm. The mobile phase consisted of solvent A (water plus 0.05% TFA) and solvent B (MeCN plus 0.05% TFA) with a gradient of 100% solvent A for 0.7 min changing to 100% solvent B over 3.75 min, maintained for 1.1 min, then reverting to 100% solvent A over 0.2 min.

Preparative HPLC purifications were usually performed using either a mass spectrometry directed system or a non-mass guided system. Usually they were performed on a Waters Chromatography Workstation configured with LC-MS System consisting of: Waters ZQ™ single quad MS system with Electrospray Ionization, Waters 2525 Gradient Pump, Waters 2767 Injecto/Collector, Waters 996 PDA Detector, the MS Conditions of: 150-750 amu, Positive Electrospray, Collection Triggered by MS, and a Waters SUNFIRE® C-18 5-micron, 30 mm (id)×100 mm column. The mobile phases consisted of mixtures of acetonitrile (10-100%) in water containing 0.1% TFA. Flow rates were maintained at 50 mL/min, the injection volume was 1800 µL, and the UV detection range was 210-400 nm. An alternate preparative HPLC system used was a Gilson Workstation consisting of: Gilson GX-281 Injector/Collector, Gilson UV/VIS-155 Detector, Gilson 333 and 334 Pumps, and either a Phenomenex Gemini-NX C-18 5-micron, 50 mm (id)×250 mm column or a Waters XBridge™ C-18 5-micron OBD™, 30 mm (id)×250 mm column. The mobile phases consisted of mixtures of acetonitrile (0-75%) in water containing 5 mmol $(NH_4)HCO_3$. Flow rates were maintained at 50 mL/min for the Waters Xbridge™ column and 90 mL/min for the Phenomenex Gemini column. The injection volume ranged from 1000-8000 µL, and the UV detection range was 210-400 nm. Mobile phase gradients were optimized for the individual compounds. Reactions performed using microwave irradiation were normally carried out using an Emrys Optimizer manufactured by Personal Chemistry, or an Initiator manufactured by Biotage. Concentration of solutions was carried out on a rotary evaporator under reduced pressure. Flash chromatography was usually performed using either a Biotage® Flash Chromatography apparatus (Dyax Corp.), an ISCO CombiFlash® Rf apparatus, or an ISCO CombiFlash® Companion XL on silica gel (32-63 µM, 60 Å pore size) in pre-packed cartridges of the size noted. $^1$H NMR spectra were acquired at 500 MHz spectrometers in $CDCl_3$ solutions unless otherwise noted. Chemical shifts were reported in parts per million (ppm). Tetramethylsilane (TMS) was used as internal reference in $CDCl_3$ solutions, and residual $CH_3OH$ peak or TMS was used as internal reference in $CD_3OD$ solutions. Coupling constants (J) were reported in hertz (Hz). Chiral analytical chromatography was most commonly performed on one of CHIRALPAK® AS, CHIRALPAK® AD, CHIRALCEL® OD, CHIRALCEL® IA, or CHIRALCEL® OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of CHIRALPAK AS, of CHIRALPAK AD, CHIRAL-CEL® OD, CHIRALCEL® IA, CHIRALCEL® OJ columns (20×250 mm) (Daicel Chemical Industries, Ltd.) with desired isocratic solvent systems identified on chiral analytical chromatography or by supercritical fluid (SFC) conditions.

It is understood that a chiral center in a compound may exist in the "S" or "R" stereo-configuration, or as a mixture of both. Within a molecule, each bond drawn as a straight line from a chiral center includes both the (R) and (S) stereoisomers as well as mixtures thereof.

Example 1A 4-(4,4-diethyl-2-imino-6-oxotetrahydropyrimidin-1 (2H)-yl)-N—((S)-2,2-dimethylchroman-4-yl)chroman-6-carboxamide

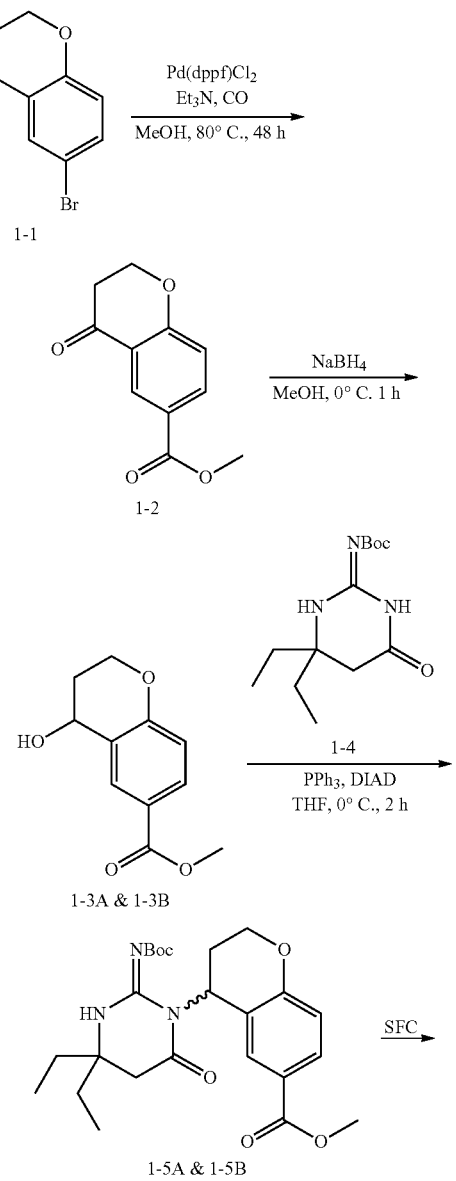

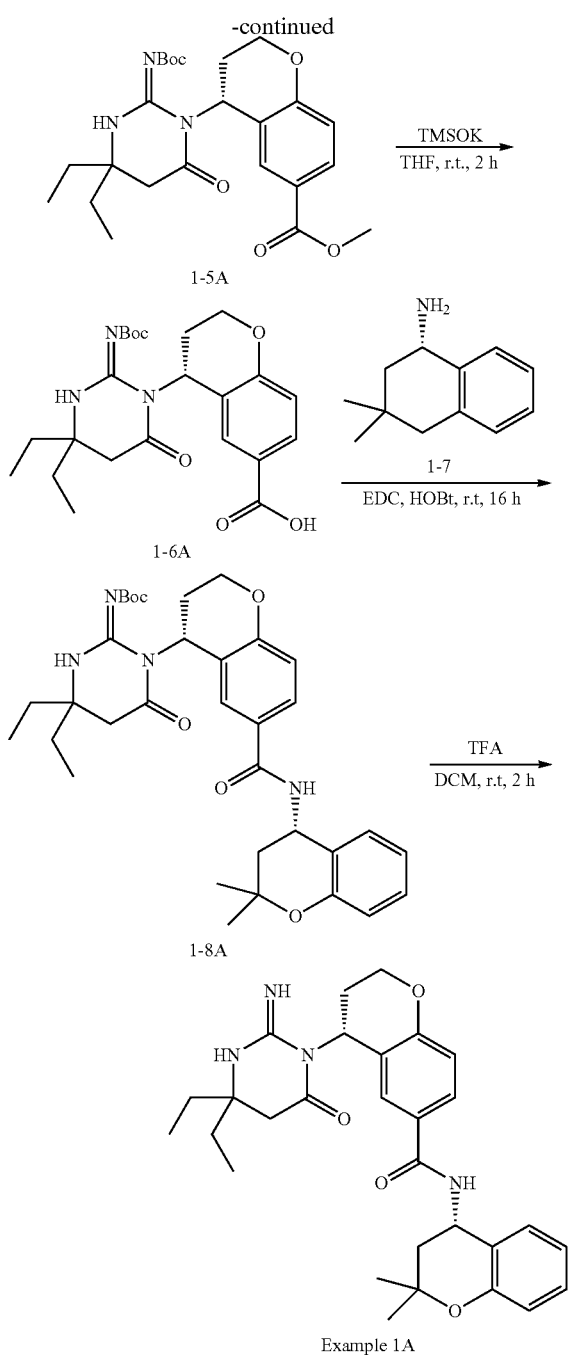

¹H NMR (400 MHz, CD₃OD) δ 8.49 (d, J=2.0 Hz, 1H), 8.12 (dd, J=8.8, 2.0 Hz, 1H), 7.08 (d, J=8.8 Hz, 1H), 4.60-4.65 (m, 2H), 3.89 (s, 3H), 2.85 (t, J=6.4 Hz, 2H).

Step B: methyl 4-hydroxychroman-6-carboxylate 1-3A & 1-3B

Sodium borohydride (3.03 g, 80 mmol) at 0° C. was added in portions to a solution of methyl 4-oxochroman-6-carboxylate 1-2 (15 g, 72.7 mmol) in MeOH (100 mL). Then the mixture was stirred at 0° C. for 1 h. Then the mixture was quenched by addition of saturated NH₄Cl (50 mL), then concentrated under reduced pressure to give a residue, added water (100 mL), extracted with EtOAc (50 mL*2). The combined organic extracts were washed with brine (50 mL), dried over Na₂SO₄, filtered and concentrated under reduced pressure, which was purified by flash silica gel chromatography (ISCO®; Agela® Flash Column Silica-CS (40 g), Eluent of 0-22% Ethyl acetate/petroleum ether gradient @50 mL/min) to give methyl 4-hydroxychroman-6-carboxylate 1-3A & 1-3B.

MS (ESI) m/z: 209.0 (M+H⁺).

¹H NMR (400 MHz, chloroform-d) δ 8.03 (d, J=2.0 Hz, 1H), 7.86 (dd, J=2.0, 8.8 Hz, 1H), 6.85 (d, J=8.8 Hz, 1H), 4.82 (s, 1H), 4.41-4.24 (m, 2H), 3.87 (s, 3H), 2.20-2.05 (m, 3H)

Step C: (E)-methyl 4-(2-((tert-butoxycarbonyl)imino)-4,4-diethyl-6-oxotetrahydropyrimidin-1(2H)-yl)chroman-6-carboxylate 1-5A & 1-5B DIAD (18.86 mL, 96 mmol) was added dropwise to a solution of (Z)-tert-butyl (4,4-diethyl-6-oxotetrahydropyrimidin-2(1H)-ylidene)carbamate 1-4 (12.94 g, 48.0 mmol), methyl 4-hydroxychroman-6-carboxylate 1-3A & 1-3B (10 g, 48.0 mmol) and triphenylphosphine (25.2 g, 96 mmol) in THF (50 mL) at 0° C. under N₂ atmosphere. The mixture was stirred at 0° C. for 2 h. The reaction was quenched by water (60 mL) and extracted with ethyl acetate (50 mL*2). The combined organic extracts were washed with brine (50 mL), dried over Na₂SO₄, filtered and concentrated under reduced pressure to give a residue, which was purified by flash silica gel chromatography (ISCO®; Agela® Flash Column Silica-CS (40 g), Eluent of 0~25% Ethyl acetate/petroleum ether gradient @50 mL/min) to give (E)-methyl 4-(2-((tert-butoxycarbonyl)imino)-4,4-diethyl-6-oxotetrahydropyrimidin-1(2H)-yl)chroman-6-carboxylate 1-5A & 1-5B.

MS (ESI) m/z: 460.2 (M+H⁺).

¹H NMR (500 MHz, chloroform-d) δ 7.75 (dd, J=2.0, 8.5 Hz, 1H), 7.60 (s, 1H), 6.82 (d, J=8.5 Hz, 1H), 6.37 (dd, J=7.0, 10.1 Hz, 1H), 4.43 (m, 1H), 4.22 (m, 1H), 3.85-3.78 (m, 3H), 2.84-2.70 (m, 1H), 2.62-2.44 (m, 2H), 2.11-2.03 (m, 1H), 1.79-1.59 (m, 5H), 1.50 (s, 9H), 1.02-0.89 (m, 6H)

Step D: of methyl 4-(2-((tert-butoxycarbonyl)imino)-4,4-diethyl-6-oxotetrahydropyrimidin-1(2H)-yl)chroman-6-carboxylate 1-5A Methyl 4-(2-((tert-butoxycarbonyl)imino)-4,4-diethyl-6-oxotetrahydropyrimidin-1(2H)-yl)chroman-6-carboxylate 1-5A (6.5 g, 14.14 mmol) was purified by SFC on (Instrument SFC 5, Method Column DAICEL CHIRALCEL OD (250 mm*50 mm, 10 um), Condition 0.1% aqNH₃ MeOH, begin B 40%, end B 40%, FlowRate (mL/min) 200, Injections 150) to afford methyl 4-(2-((tert-butoxycarbonyl)

Step A: methyl 4-oxochroman-6-carboxylate 1-2

Pd(dppf)Cl₂ (11.28 g, 15.41 mmol) and triethylamine (64.5 mL, 462 mmol) were added to a solution of 6-bromochroman-4-one 1-1 (35 g, 154 mmol) in MeOH (120 mL) at 25° C. The solution was stirred at 80° C. for 48 h under CO atmosphere (50 psi). The reaction mixture was cooled to room temperature, then concentrated under reduced pressure to give a residue. The residue was purified by flash silica gel chromatography (ISCO®; Agela® Flash Column Silica-CS (120 g), Eluent of 10% Ethyl acetate/petroleum ether gradient @55 mL/min) to give methyl 4-oxochroman-6-carboxylate 1-2.

MS (ESI) m/z: 248.1 (M+41+H⁺)

imino)-4,4-diethyl-6-oxotetrahydropyrimidin-1(2H)-yl)
chroman-6-carboxylate 1-5A (Rt=6.460 min).

MS (ESI) m/z: 460.2 (M+H⁺).

1-5A: ¹H NMR (500 MHz, chloroform-d) δ 10.10 (s, 1H), 7.75 (dd, J=2.0, 8.5 Hz, 1H), 7.61 (s, 1H), 6.83 (d, J=8.5 Hz, 1H), 6.45-6.31 (m, 1H), 4.51-4.39 (m, 1H), 4.25-4.20 (m, 1H), 3.82 (s, 3H), 2.82-2.70 (m, 1H), 2.61-2.48 (m, 2H), 2.11-2.03 (m, 1H), 1.79-1.61 (m, 4H), 1.51 (s, 9H), 1.03-0.90 (m, 6H)

Step E: 4-(2-((tert-butoxycarbonyl)imino)-4,4-diethyl-6-oxotetrahydropyrimidin-1(2H)-yl)chroman-6-carboxylic acid 1-6A Potassium trimethylsilanolate (1.842 g, 14.36 mmol) was added to a solution of methyl 4-(2-((tert-butoxycarbonyl)imino)-4,4-diethyl-6-oxotetrahydropyrimidin-1(2H)-yl)chroman-6-carboxylate 1-5A (2.2 g, 4.79 mmol) in THF (35 mL). The reaction was stirred at 22° C. for 1 h. The solution of 4-(2-((tert-butoxycarbonyl)imino)-4,4-diethyl-6-oxotetrahydropyrimidin-1(2H)-yl)chroman-6-carboxylic acid 1-6A was used for next step directly without any further manipulation or purification.

MS (ESI) m/z: 446.1 (M+H⁺)

Step F: tert-butyl (1-(6-(((S)-2,2-dimethylchroman-4-yl)carbamoyl)chroman-4-yl)-4,4-diethyl-6-oxotetrahydropyrimidin-2(1H)-ylidene)carbamate 1-8A DIEA (3.14 mL, 17.96 mmol) was added to a solution of 4-(2-((tert-butoxycarbonyl)imino)-4,4-diethyl-6-oxotetrahydropyrimidin-1(2H)-yl)chroman-6-carboxylic acid 1-6A (2.0 g, 4.49 mmol), EDC (1.721 g, 8.98 mmol), 1H-benzo[d][1,2,3]triazol-1-ol 7 (1.213 g, 8.98 mmol) and (S)-2,2-dimethylchroman-4-amine (1.591 g, 8.98 mmol) in THF (35 mL). The reaction was stirred at 22° C. for 5 h. The mixture was quenched with water (10 mL), and extracted with EtOAc (30 mL*3). The organic layers were washed with brine (30 mL), dried over Na₂SO₄, filtered, and concentrated in vacuo to afford crude product, which was purified by flash silica gel chromatography (ISCO®; Agela® Flash Column Silica-CS (40 g), Eluent of 0~26% AcOEt/petroleum ether gradient @50 mL/min) to give tert-butyl (1-(6-(((S)-2,2-dimethylchroman-4-yl)carbamoyl)chroman-4-yl)-4,4-diethyl-6-oxotetrahydropyrimidin-2(1H)-ylidene)carbamate 1-8A.

MS (ESI) m/z: 605.4 (M+H⁺)

¹H NMR (400 MHz, chloroform-d) δ 10.10 (s, 1H), 7.51 (s, 1H), 7.39 (d, J=8.4 Hz, 1H), 7.25-7.22 (m, 1H), 7.16 (t, J=7.6 Hz, 1H), 6.92-6.75 (m, 3H), 6.48-6.34 (m, 1H), 6.07 (d, J=8.8 Hz, 1H), 5.53-5.39 (m, 1H), 4.44 (d, J=11.2 Hz, 1H), 4.20 (t, J=11.2 Hz, 1H), 2.83-2.67 (m, 1H), 2.58-2.46 (m, 2H), 2.27 (m, 1H), 2.07 (m, 1H), 1.84-1.56 (m, 7H), 1.50 (s, 9H), 1.43 (s, 3H), 1.35 (s, 3H), 0.92 (m, 6H)

Step G: 4-(4,4-diethyl-2-imino-6-oxotetrahydropyrimidin-1(2H)-yl)-N—((S)-2,2-dimethylchroman-4-yl)chroman-6-carboxamide Example 1A A solution of tert-butyl (1-(6-(((S)-2,2-dimethylchroman-4-yl)carbamoyl)chroman-4-yl)-4,4-diethyl-6-oxotetrahydropyrimidin-2(1H)-ylidene)carbamate 1-8A (2.4 g, 3.97 mmol) in DCM (15 mL) and TFA (3 mL) was stirred at 20° C. for 2 h. The mixture was concentrated in vacuo to give the crude product which was purified by Prep-HPLC (0.1% TFA) (Instrument EG Method Column Waters XSELECT C18 150*30 mm*5um Condition water (0.1% TFA)-ACN Begin B 22 End B 55 Gradient Time (min) 11 100% B Hold Time (min) 2 FlowRate (mL/min) 25 Injections 10) to afford 4-(4,4-diethyl-2-imino-6-oxotetrahydropyrimidin-1(2H)-yl)-N—((S)-2,2-dimethylchroman-4-yl)chroman-6-carboxamide Example 1A.

MS (ESI) m/z: 505.3 (M+H⁺)

¹H NMR (400 MHz, methanol-d₄) δ 8.54 (d, J=8.8 Hz, 1H), 7.70 (d, J=8.0 Hz, 1H), 7.64 (s, 1H), 7.18-7.08 (m, 2H), 6.90 (d, J=8.4 Hz, 1H), 6.83 (t, J=7.2 Hz, 1H), 6.74 (d, J=8.0 Hz, 1H), 5.54-5.38 (m, 1H), 4.57-4.44 (m, 1H), 4.22 (t, J=10.8 Hz, 1H), 2.93-2.67 (m, 3H), 2.27-2.17 (m, 1H), 2.12-2.10 (m, 1H), 2.10-2.00 (m, 1H), 1.83-1.63 (m, 4H), 1.44 (s, 3H), 1.34 (s, 3H), 0.98-0.93 (m, 6H)

Example 2A 4-(4,4-diethyl-2-imino-6-oxotetrahydropyrimidin-1(2H)-yl)-N-((3S,4R)-3-hydroxy-2,2-dimethylchroman-4-yl)chroman-6-carboxamide

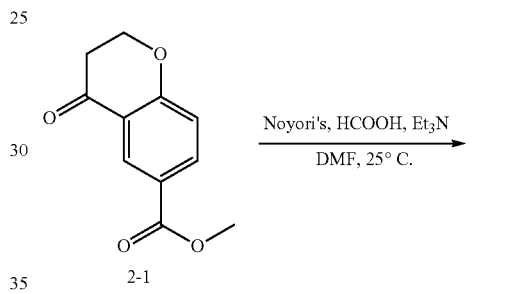

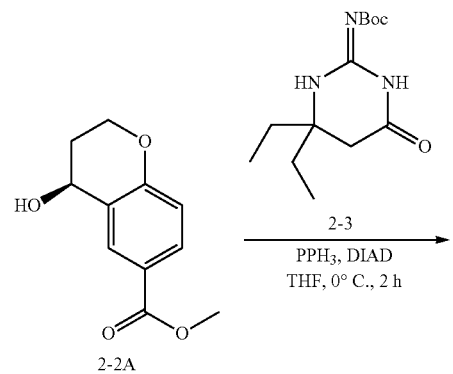

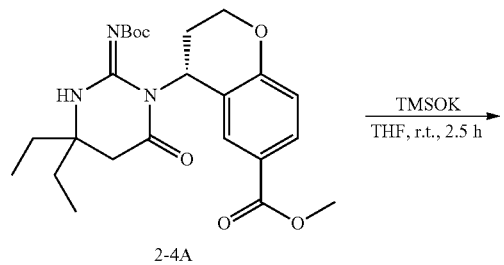

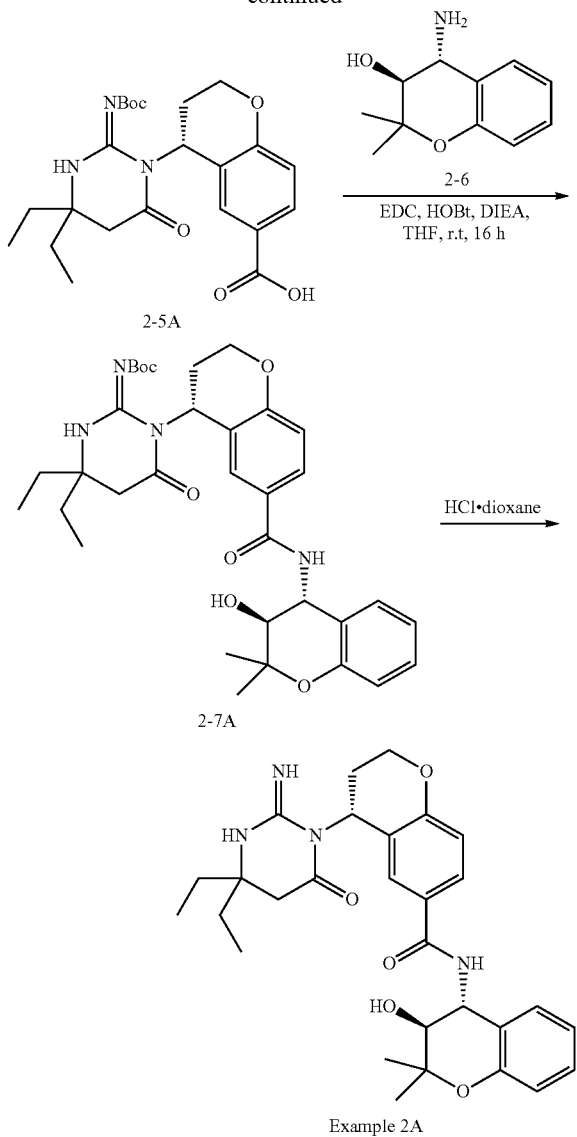

2-5A 2-7A

Example 2A

Step A: (9-methyl 4-hydroxychroman-6-carboxylate 2-2A

A solution of formic acid (30 g, 652 mmol) and triethylamine (120 g, 1186 mmol) in DMF (320 mL) was stirred for 15 min, then methyl 4-oxochroman-6-carboxylate 2-1 (40 g, 194 mmol) and (S,S)—N-(p-toluenesulfonyl)-1,2-diphenylethanediamine(chloro)([-cymene)ruthenium(II) (1.234 g, 1.940 mmol) were added, and the mixture was stirred for 10 h at 25° C. The mixture was diluted with water (300 mL), and extracted with EtOAc (250 mL*3). The organic layers were washed with brine (300 mL), dried over anhydrous Na$_2$SO$_4$, filtered and concentrated. The residue was purified by flash silica gel chromatography (ISCO®; Agela® Flash Column Silica-CS (150 g), Eluent of 0-30% Ethyl acetate/petroleum ether gradient @65 mL/min) to afford (9-methyl 4-hydroxychroman-6-carboxylate 2-2A.

MS (ESI) m/z: 209.0 (M+H$^+$)

$^1$H NMR (500 MHz, chloroform-d) δ 8.02 (s, 1H), 7.84 (d, J=8.50 Hz, 1H), 6.83 (d, J=8.0 Hz, 1H), 4.81 (q, J=4.0 Hz, 1H), 4.26-4.39 (m, 2H), 3.85 (s, 3H), 2.59 (d, J=4.0 Hz, 1H), 2.02-2.15 (m, 2H).

Step B: methyl 4-(2-((tert-butoxycarbonyl)imino)-4,4-diethyl-6-oxotetrahydropyrimidin-1(2H)-yl)chroman-6-carboxylate 2-4A (E)-diisopropyl diazene-1,2-dicarboxylate (34.0 mL, 173 mmol) was added dropwise to a solution of (Z)-tert-butyl (4,4-diethyl-6-oxotetrahydropyrimidin-2(1H)-ylidene)carbamate 2-3 (40 g, 149 mmol), methyl 4-hydroxychroman-6-carboxylate 2-2A (30 g, 144 mmol) and triphenylphosphine (48 g, 183 mmol) in THF (500 mL) at 0° C. under N$_2$ atmosphere. Then the mixture was stirred at 25° C. for 3 h. The mixture was concentrated in vacuo, then purified by flash silica gel chromatography (ISCO®; Agela® Flash Column Silica-CS (150 g), Eluent of 0~5% AcOEt/DCM gradient @65 mL/min) to give methyl 4-(2-((tert-butoxycarbonyl)imino)-4,4-diethyl-6-oxotetrahydropyrimidin-1(2H)-yl)chroman-6-carboxylate 2-4A.

MS (ESI) m/z: 460.2 (M+H$^+$).

$^1$H NMR (400 MHz, chloroform-d) δ 10.48-10.83 (m, 1H), 7.78 (d, J=8.8 Hz, 1H), 7.60 (s, 1H), 6.85 (d, J=8.8 Hz, 1H), 5.93-6.04 (m, 1H), 4.43 (d, J=11.2 Hz, 1H), 4.18 (t, J=11.2 Hz, 1H), 3.82 (s, 3H), 2.72-2.77 (m, 1H), 2.51-2.56 (m, 2H), 2.04-2.08 (m, 1H), 1.60-1.70 (m, 4H), 1.49 (s, 9H), 0.90-0.99 (m, 6H).

Step C: (R)-4-(2-((tert-butoxycarbonyl)imino)-4,4-diethyl-6-oxotetrahydropyrimidin-1(2H)-yl)chroman-6-carboxylic acid 2-5A Potassium trimethylsilanolate (7.54 g, 58.8 mmol) was added to a solution of (R)-methyl 4-(2-((tert-butoxycarbonyl)imino)-4,4-diethyl-6-oxotetrahydropyrimidin-1(2H)-yl)chroman-6-carboxylate 2-4A (9.0 g, 19.59 mmol) in THF (300 mL). The reaction was stirred at 22° C. for 2.5 h. The solution of (R)-4-(2-((tert-butoxycarbonyl)imino)-4,4-diethyl-6-oxotetrahydropyrimidin-1(2H)-yl)chroman-6-carboxylic acid 2-5A was used for next step directly without any further manipulation or purification.

MS (ESI) m/z: 446.0 (M+H$^+$)

Step D: tert-butyl (4,4-diethyl-1-((R)-6-(((3S,4R)-3-hydroxy-2,2-dimethylchroman-4-yl)carbamoyl)chroman-4-yl)-6-oxotetrahydropyrimidin-2(1H)-ylidene)carbamate 2-7A DIEA (13.69 mL, 78 mmol) was added to a solution of (R)-4-(2-((tert-butoxycarbonyl)imino)-4,4-diethyl-6-oxotetrahydropyrimidin-1(2H)-yl)chroman-6-carboxylic acid 2-5A (8.73 g, 19.60 mmol), EDC (9.39 g, 49.0 mmol), 1H-benzo[d][1,2,3]triazol-1-ol (5.30 g, 39.2 mmol) and (3S,4R)-4-amino-2,2-dimethylchroman-3-ol 2-6 (4.54 g, 23.51 mmol) in THF (300 mL). The reaction was stirred at 22° C. for 16 h. The mixture was quenched with water (80 mL), and extracted with EtOAc (80 mL×3). The organic layers were washed with brine (100 mL), dried over Na$_2$SO$_4$, filtered, and concentrated in vacuo to afford crude product as colorless oil, which was purified by flash silica gel chromatography (ISCO®; Agela® Flash Column Silica-CS (150 g), Eluent of 0-30% Ethyl acetate/petroleum ether gradient @65 mL/min) to give tert-butyl (4,4-diethyl-1-((R)-6-(((3S,4R)-

3-hydroxy-2,2-dimethylchroman-4-yl)carbamoyl)chroman-4-yl)-6-oxotetrahydropyrimidin-2(1H)-ylidene)carbamate 2-7A.

MS (ESI) m/z: 621.3 (M+H$^+$)

$^1$H NMR (500 MHz, chloroform-d) δ 10.12 (br, 1H), 7.55 (s, 1H), 7.36-7.43 (m, 1H), 7.25-7.27 (m, 1H), 7.18-7.23 (m, 1H), 6.94 (dt, J=1.0, 7.5 Hz, 1H), 6.80-6.87 (m, 2H), 6.34-6.43 (m, 2H), 5.11-5.12 (m, 1H), 4.84 (s, 1H), 4.39-4.49 (m, 1H), 4.23 (dt, J=2.0, 11.5 Hz, 1H), 3.73 (d, J=8.0 Hz, 1H), 2.68-2.83 (m, 1H), 2.45-2.56 (m, 2H), 2.05-2.09 (m, 1H), 1.60-1.74 (m, 4H), 1.49-1.50 (m, 12H), 1.28 (s, 3H), 0.90-0.98 (m, 6H).

Step E: 4-(4,4-diethyl-2-imino-6-oxotetrahydropyrimidin-1(2H)-yl)-N-((3S,4R)-3-hydroxy-2,2-dimethylchroman-4-yl)chroman-6-carboxamide Example 2A A solution of tert-butyl (4,4-diethyl-1-(6-4(3S,4R)-3-hydroxy-2,2-dimethylchroman-4-yl)carbamoyl)chroman-4-yl)-6-oxotetrahydropyrimidin-2(1H)-ylidene)carbamate 2-7A (14 g, 22.55 mmol) in HCl-dioxane (4M) (200 mL) was stirred at 25° C. for 10 h. The mixture was concentrated in vacuo. The crude was purified by Prep-HPLC (Instrument ACSSH-PrepL-K2 Method Column YMC-Triart Prep C18 250*50 mm*10 um Condition water (0.1% TFA)-ACN Begin B 20 End B 50 Gradient Time (min) 25 100% B Hold Time (min) 3 FlowRate (mL/min) 120) to afford 4-(4,4-diethyl-2-imino-6-oxotetrahydropyrimidin-1(2H)-yl)-N-((3S,4R)-3-hydroxy-2,2-dimethylchroman-4-yl)chroman-6-carboxamide Example 2A.

MS (ESI) m/z 521.3 (M+H$^+$)

$^1$H NMR (400 MHz, methanol-d$_4$) δ 8.56 (d, J=8.8 Hz, 1H), 7.72 (d, J=8.4 Hz, 1H), 7.66 (s, 1H), 7.06-7.14 (m, 2H), 6.89 (d, J=8.4 Hz, 1H), 6.80-6.85 (m, 1H), 6.74 (d, J=8.0 Hz, 1H), 5.30-5.88 (m, 1H), 5.22 (t, J=8.8 Hz, 1H), 4.49 (td, J=3.6, 11.6 Hz, 1H), 4.21 (t, J=10.8 Hz, 1H), 3.75 (d, J=9.6 Hz, 1H), 2.65-2.87 (m, 3H), 2.16-2.24 (m, 1H), 1.62-1.81 (m, 4H), 1.46 (s, 3H), 1.24 (s, 3H), 0.91-0.98 (m, 6H).

The compounds in Table 1-4 were prepared in an analogous fashion to that described in Scheme 1 and the experimentals described herein. The isomers were separated by preparative HPLC or/and preparative chiral SFC.

TABLE 1

| Example | Structure | LC/MS (M + 1)$^+$ | Name |
|---|---|---|---|
| 3A | 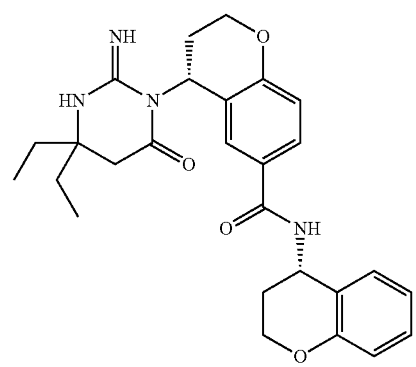 [SMILES: CCC1(CC)CC(=O)N([C@@H]2CCOc3ccc(C(=O)N[C@H]4CCOc5ccccc54)cc32)C(=N)N1] | 477.5 | (R)-N-((S)-chroman-4-yl)-4-(4,4-diethyl-2-imino-6-oxotetrahydropyrimidin-1(2H)-yl)chromane-6-carboxamide |
| 4A | 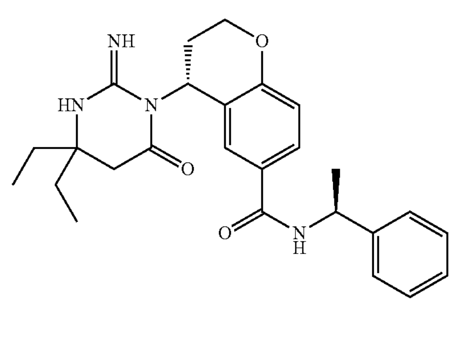 [SMILES: CCC1(CC)CC(=O)N([C@@H]2CCOc3ccc(C(=O)N[C@@H](C)c4ccccc4)cc32)C(=N)N1] | 449.2 | (R)-4-(4,4-di ethyl-2-imino-6-oxotetrahydropyrimidin-1(2H)-yl)-N-((S)-1-phenyl ethyl)chromane-6-carboxamide |

TABLE 1-continued

| Example | Structure | LC/MS (M + 1)+ | Name |
|---------|-----------|----------------|------|
| 5A | 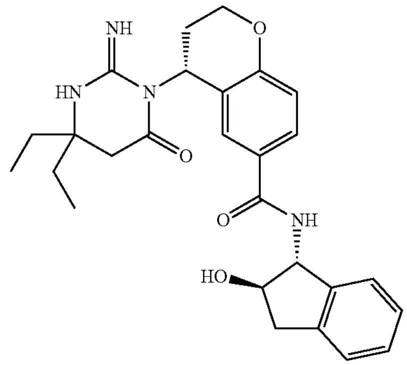 [SMILES: CCC1(CC)CC(=O)N([C@@H]2CCOc3ccc(C(=O)N[C@@H]4c5ccccc5C[C@H]4O)cc32)C(=N)N1] | 477.3 | (R)-4-(4,4-diethyl-2-imino-6-oxotetrahydropyrimidin-1(2H)-yl)-N-((1R,2R)-2-hydroxy-2,3-dihydro-1H-inden-1-yl)chromane-6-carboxamide |
| 6A | 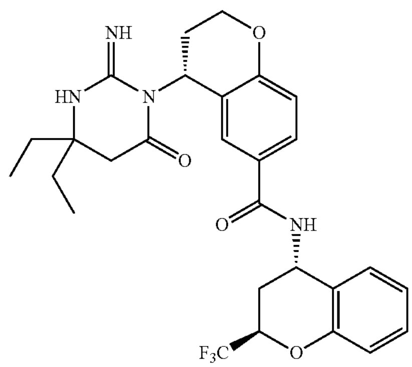 [SMILES: CCC1(CC)CC(=O)N([C@@H]2CCOc3ccc(C(=O)N[C@H]4C[C@H](C(F)(F)F)Oc5ccccc54)cc32)C(=N)N1] | 545.2 | (R)-4-(4,4-di ethyl-2-imino-6-oxotetrahydropyrimidin-1(2H)-yl)-N-((2R,4S)-2-(trifluoromethyl)chroman-4-yl)chromane-6-carboxamide |
| 6B | 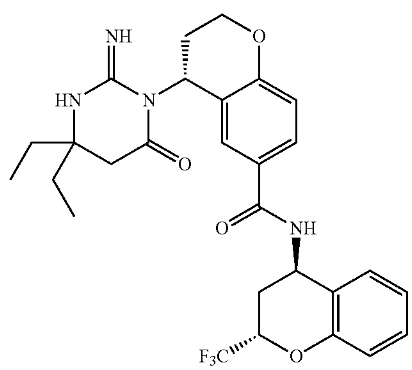 [SMILES: CCC1(CC)CC(=O)N([C@@H]2CCOc3ccc(C(=O)N[C@@H]4C[C@@H](C(F)(F)F)Oc5ccccc54)cc32)C(=N)N1] | 545.2 | (R)-4-(4,4-diethyl-2-imino-6-oxotetrahydropyrimidin-1(2H)-yl)-N-((2S,4R)-2-(trifluoromethyl)chroman-4-yl)chromane-6-carboxamide |
| 7A | 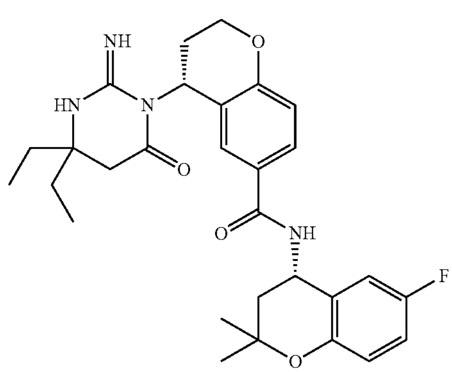 [SMILES: CCC1(CC)CC(=O)N([C@@H]2CCOc3ccc(C(=O)N[C@H]4CC(C)(C)Oc5ccc(F)cc54)cc32)C(=N)N1] | 523.2 | (R)-4-(4,4-diethyl-2-imino-6-oxotetrahydropyrimidin-1(2H)-yl)-N-((S)-6-fluoro-2,2-dimethylchroman-4-yl)chromane-6-carboxamide |

TABLE 1-continued

| Example | Structure | LC/MS (M + 1)+ | Name |
|---|---|---|---|
| 7B | 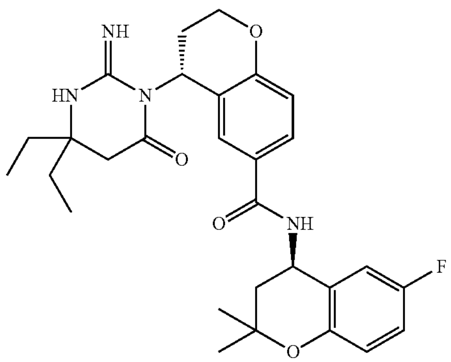 [SMILES: CCC1(CC)CC(=O)N([C@@H]2CCOc3ccc(C(=O)N[C@@H]4CC(C)(C)Oc5ccc(F)cc54)cc32)C(=N)N1] | 523.2 | (R)-4-(4,4-diethyl-2-imino-6-oxotetrahydropyrimidin-1(2H)-yl)-N-((R)-6-fluoro-2,2-dimethylchroman-4-yl)chromane-6-carboxamide |
| 8A | 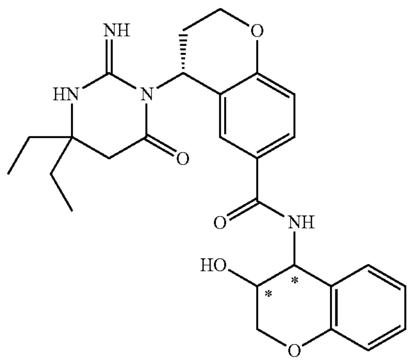 [SMILES: CCC1(CC)CC(=O)N([C@@H]2CCOc3ccc(C(=O)NC4c5ccccc5OCC4O)cc32)C(=N)N1] | 493.3 | (4R)-4-(4,4-diethyl-2-imino-6-oxotetrahydropyrimidin-1(2H)-yl)-N-(3-hydroxychroman-4-yl)chromane-6-carboxamide |
| 8B | 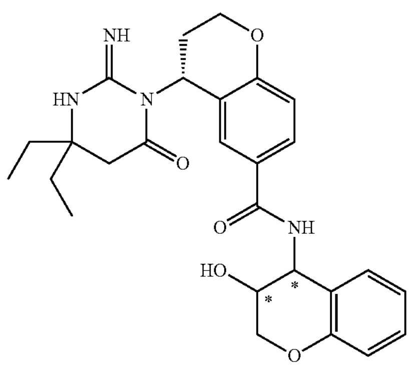 [SMILES: CCC1(CC)CC(=O)N([C@@H]2CCOc3ccc(C(=O)NC4c5ccccc5OCC4O)cc32)C(=N)N1] | 493.3 | (4R)-4-(4,4-diethyl-2-imino-6-oxotetrahydropyrimidin-1(2H)-yl)-N-(3-hydroxychroman-4-yl)chromane-6-carboxamide |
| 8C | 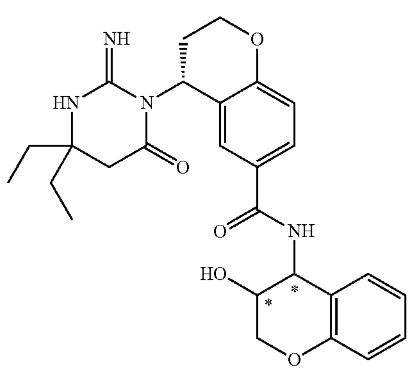 [SMILES: CCC1(CC)CC(=O)N([C@@H]2CCOc3ccc(C(=O)NC4c5ccccc5OCC4O)cc32)C(=N)N1] | 493.1 | (4R)-4-(4,4-diethyl-2-imino-6-oxotetrahydropyrimidin-1(2H)-yl)-N-(3-hydroxychroman-4-yl)chromane-6-carboxamide |

TABLE 1-continued

| Example | Structure | LC/MS (M + 1)+ | Name |
|---|---|---|---|
| 8D | 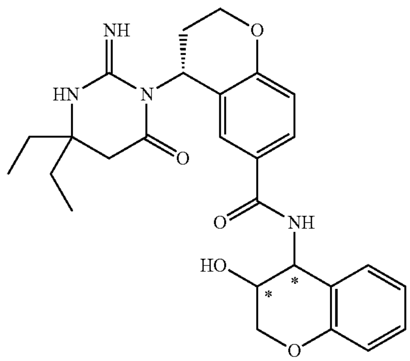 [SMILES: CCC1(CC)CC(=O)N([C@@H]2CCOc3ccc(C(=O)NC4c5ccccc5OCC4O)cc32)C(=N)N1] | 493.3 | (4R)-4-(4,4-diethyl-2-imino-6-oxotetrahydropyrimidin-1(2H)-yl)-N-(3-hydroxychroman-4-yl)chromane-6-carboxamide |
| 9A | 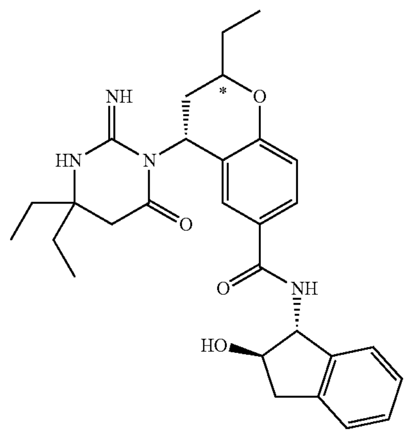 | 505.3 | (4R)-4-(4,4-diethyl-2-imino-6-oxotetrahydropyrimidin-1(2H)-yl)-2-ethyl-N-((1R,2R)-2-hydroxy-2,3-dihydro-1H-inden-1-yl)chromane-6-carboxamide |
| 9B | 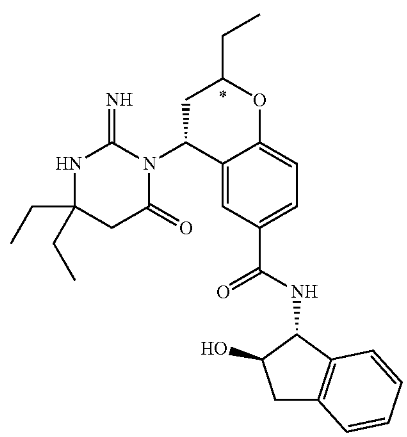 | 505.3 | (4R)-4-(4,4-diethyl-2-imino-6-oxotetrahydropyrimidin-1(2H)-yl)-2-ethyl-N-((1R,2R)-2-hydroxy-2,3-dihydro-1H-inden-1-yl)chromane-6-carboxamide |
| 10A | 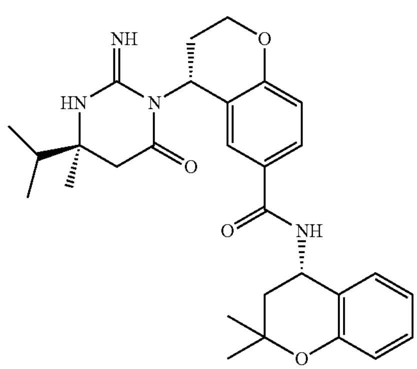 [SMILES: CC(C)[C@]1(C)CC(=O)N([C@@H]2CCOc3ccc(C(=O)N[C@H]4CC(C)(C)Oc5ccccc54)cc32)C(=N)N1] | 505.3 | (R)-N-((S)-2,2-dimethylchroman-4-yl)-4-((S)-2-imino-4-isopropyl-4-methyl-6-oxotetrahydropyrimidin-1(2H)-yl)chromane-6-carboxamide |

TABLE 1-continued

| Example | Structure | LC/MS (M + 1)+ | Name |
|---|---|---|---|
| 11A | 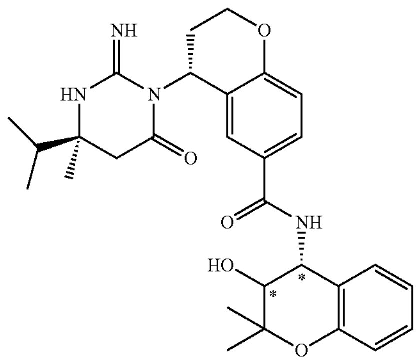 [SMILES: CC(C)[C@]1(C)CC(=O)N([C@@H]2CCOc3ccc(C(=O)N[C@@H]4c5ccccc5OC(C)(C)C4O)cc32)C(=N)N1] | 521.4 | (4R)-N-(3-hydroxy-2,2-dimethylchroman-4-yl)-4-((S)-2-imino-4-isopropyl-4-methyl-6-oxotetrahydropyrimidin-1(2H)-yl)chromane-6-carboxamide |
| 11B | 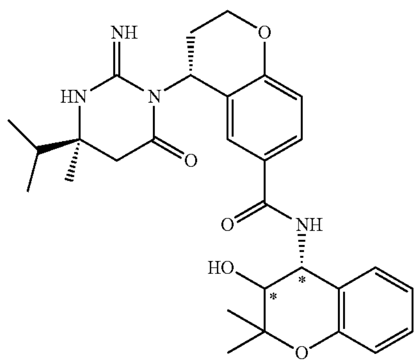 [SMILES: CC(C)[C@]1(C)CC(=O)N([C@@H]2CCOc3ccc(C(=O)N[C@@H]4c5ccccc5OC(C)(C)C4O)cc32)C(=N)N1] | 521.3 | (4R)-N-(3-hydroxy-2,2-dimethylchroman-4-yl)-4-((S)-2-imino-4-isopropyl-4-methyl-6-oxotetrahydropyrimidin-1(2H)-yl)chromane-6-carboxamide |
| 12A | 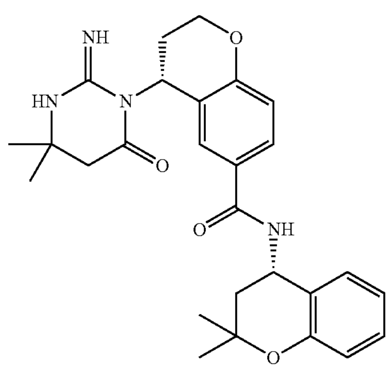 [SMILES: CC1(C)CC(=O)N([C@@H]2CCOc3ccc(C(=O)N[C@H]4CC(C)(C)Oc5ccccc54)cc32)C(=N)N1] | 477.3 | (R)-N-((S)-2,2-dimethylchroman-4-yl)-4-(2-imino-4,4-dimethyl-6-oxotetrahydropyrimidin-1(2H)-yl)chromane-6-carboxamide |
| 13A | 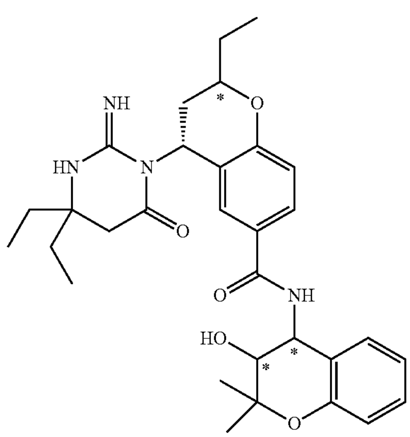 | 549.3 | (4R)-4-(4,4-diethyl-2-imino-6-oxotetrahydropyrimidin-1(2H)-yl)-2-ethyl-N-(3-hydroxy-2,2-dimethylchroman-4-yl)chromane-6-carboxamide |

TABLE 1-continued

| Example | Structure | LC/MS (M + 1)+ | Name |
|---|---|---|---|
| 13B | 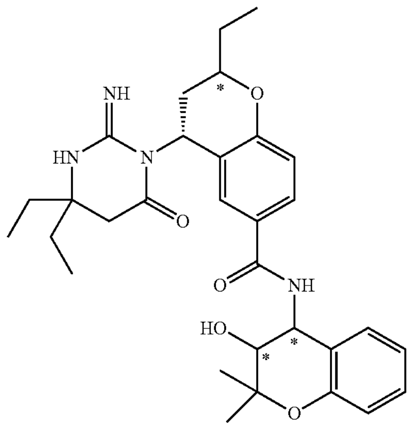 | 549.3 | (4R)-4-(4,4-diethyl-2-imino-6-oxotetrahydropyrimidin-1(2H)-yl)-2-ethyl-N-(3-hydroxy-2,2-dimethylchroman-4-yl)chromane-6-carboxamide |
| 14A | 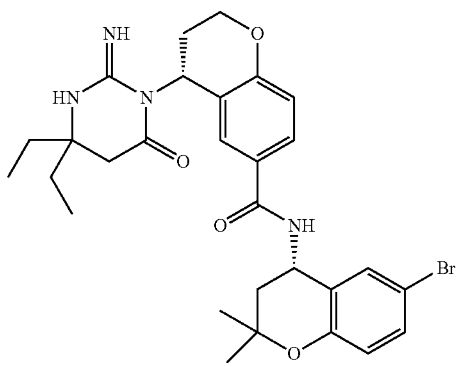 [SMILES: CCC1(CC)CC(=O)N([C@@H]2CCOc3ccc(C(=O)N[C@H]4CC(C)(C)Oc5ccc(Br)cc54)cc32)C(=N)N1] | 583.1, 585.2 | (R)-N-((S)-6-bromo-2,2-dimethylchroman-4-yl)-4-(4,4-diethyl-2-imino-6-oxotetrahydropyrimidin-1(2H)-yl)chromane-6-carboxamide |
| 15A | 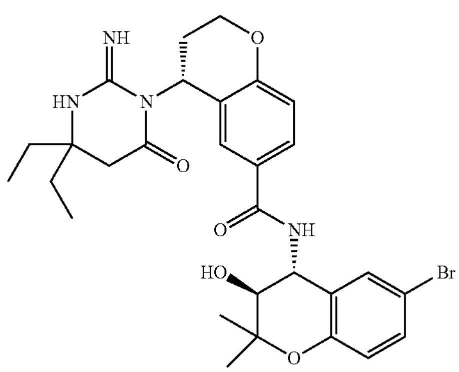 [SMILES: CCC1(CC)CC(=O)N([C@@H]2CCOc3ccc(C(=O)N[C@@H]4c5cc(Br)ccc5OC(C)(C)[C@H]4O)cc32)C(=N)N1] | 599.2, 601.3 | (R)-N-((3S,4R)-6-bromo-3-hydroxy-2,2-dimethylchroman-4-yl)-4-(4,4-diethyl-2-imino-6-oxotetrahydropyrimidin-1(2H)-yl)chromane-6-carboxamide |

TABLE 1-continued

| Example | Structure | LC/MS (M + 1)+ | Name |
|---|---|---|---|
| 16A | 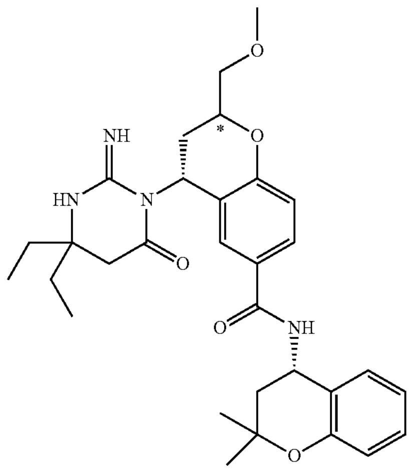 | 549.3 | (4R)-4-(4,4-diethyl-2-imino-6-oxotetrahydropyrimidin-1(2H)-yl)-N-((S)-2,2-dimethylchroman-4-yl)-2-(methoxymethyl)chromane-6-carboxamide |
| 16B | 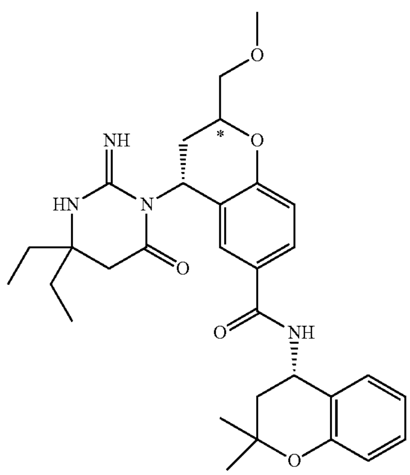 | 549.3 | (4R)-4-(4,4-diethyl-2-imino-6-oxotetrahydropyrimidin-1(2H)-yl)-N-((S)-2,2-dimethylchroman-4-yl)-2-(methoxymethyl)chromane-6-carboxamide |
| 17A | 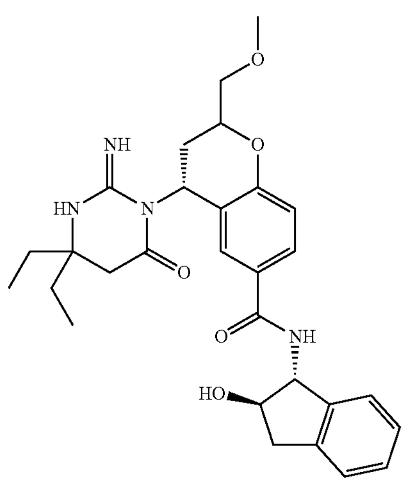 | 521.3 | (4R)-4-(4,4-diethyl-2-imino-6-oxotetrahydropyrimidin-1(2H)-yl)-N-((1R,2R)-2-hydroxy-2,3-dihydro-1H-inden-1-yl)-2-(methoxymethyl)chromane-6-carboxamide |

TABLE 1-continued

| Example | Structure | LC/MS (M + 1)+ | Name |
|---|---|---|---|
| 18A | 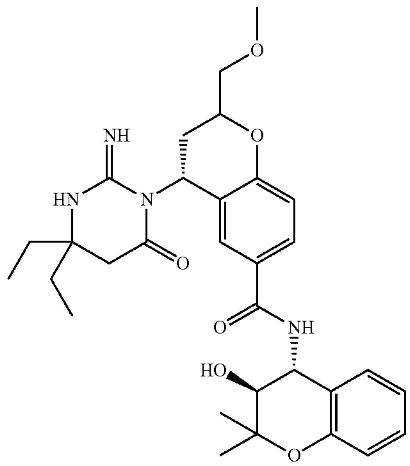 | 565.3 | (4R)-4-(4,4-diethyl-2-imino-6-oxotetrahydropyrimidin-1(2H)-yl)-N-((3S,4R)-3-hydroxy-2,2-dimethylchroman-4-yl)-2-(methoxymethyl)chromane-6-carboxamide |
| 19A | 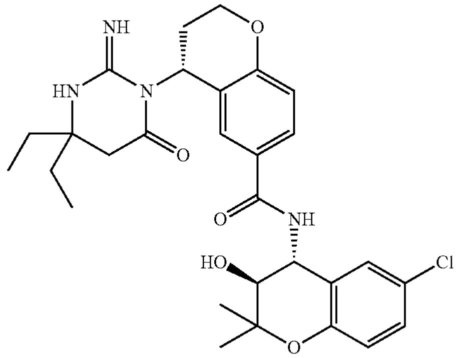 [SMILES: CCC1(CC)CC(=O)N([C@@H]2CCOc3ccc(C(=O)N[C@@H]4c5cc(Cl)ccc5OC(C)(C)[C@H]4O)cc32)C(=N)N1] | 555.2, 557.3 | (R)-N-((3S,4R)-6-chloro-3-hydroxy-2,2-dimethylchroman-4-yl)-4-(4,4-diethyl-2-imino-6-oxotetrahydropyrimidin-1(2H)-yl)chromane-6-carboxamide |
| 20A | 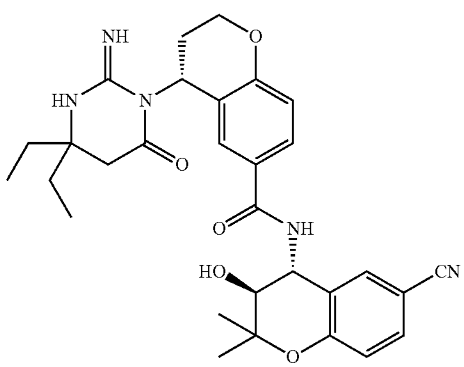 [SMILES: CCC1(CC)CC(=O)N([C@@H]2CCOc3ccc(C(=O)N[C@@H]4c5cc(C#N)ccc5OC(C)(C)[C@H]4O)cc32)C(=N)N1] | 546.3 | (R)-N-((3S,4R)-6-cyano-3-hydroxy-2,2-dimethylchroman-4-yl)-4-(4,4-diethyl-2-imino-6-oxotetrahydropyrimidin-1(2H)-yl)chromane-6-carboxamide |
| 21A | 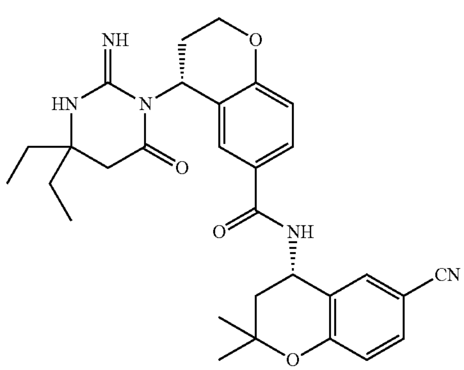 [SMILES: CCC1(CC)CC(=O)N([C@@H]2CCOc3ccc(C(=O)N[C@H]4CC(C)(C)Oc5ccc(C#N)cc54)cc32)C(=N)N1] | 530.3 | (R)-N-((S)-6-cyano-2,2-dimethylchroman-4-yl)-4-(4,4-diethyl-2-imino-6-oxotetrahydropyrimidin-1(2H)-yl)chromane-6-carboxamide |

TABLE 1-continued

| Example | Structure | LC/MS (M + 1)+ | Name |
|---|---|---|---|
| 22A | 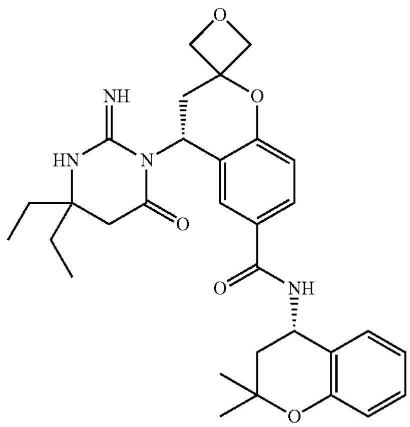 [SMILES: CCC1(CC)CC(=O)N([C@@H]2CC3(COC3)Oc3ccc(C(=O)N[C@H]4CC(C)(C)Oc5ccccc54)cc32)C(=N)N1] | 547.4 | (R)-4-(4,4-diethyl-2-imino-6-oxotetrahydropyrimidin-1(2H)-yl)-N-((S)-2,2-dimethylchroman-4-yl)spiro[chromane-2,3'-oxetane]-6-carboxamide |
| 23A | 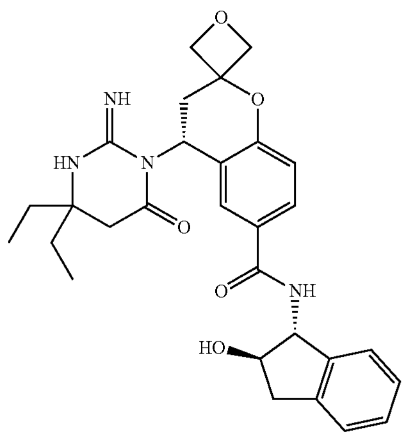 [SMILES: CCC1(CC)CC(=O)N([C@@H]2CC3(COC3)Oc3ccc(C(=O)N[C@@H]4c5ccccc5C[C@H]4O)cc32)C(=N)N1] | 519.2 | (R)-4-(4,4-diethyl-2-imino-6-oxotetrahydropyrimidin-1(2H)-yl)-N-((1R,2R)-2-hydroxy-2,3-dihydro-1H-inden-1-yl)spiro[chromane-2,3'-oxetane]-6-carboxamide |
| 24A | 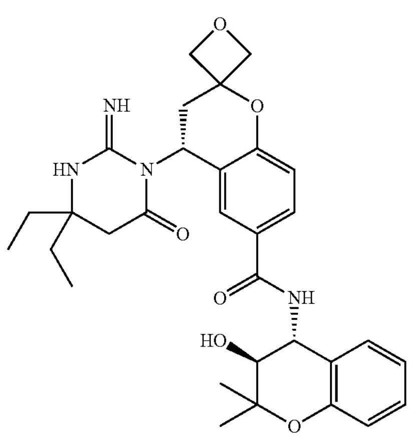 [SMILES: CCC1(CC)CC(=O)N([C@@H]2CC3(COC3)Oc3ccc(C(=O)N[C@@H]4c5ccccc5OC(C)(C)[C@H]4O)cc32)C(=N)N1] | 563.3 | (R)-4-(4,4-diethyl-2-imino-6-oxotetrahydropyrimidin-1(2H)-yl)-N-((3S,4R)-3-hydroxy-2,2-dimethylchroman-4-yl)spiro[chromane-2,3'-oxetane]-6-carboxamide |

TABLE 1-continued

| Example | Structure | LC/MS (M + 1)+ | Name |
|---|---|---|---|
| 25A | 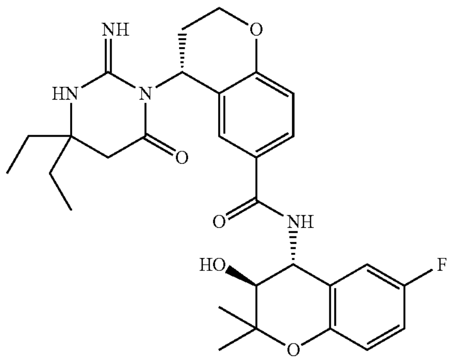 [SMILES: CCC1(CC)CC(=O)N([C@@H]2CCOc3ccc(C(=O)N[C@@H]4c5cc(F)ccc5OC(C)(C)[C@H]4O)cc32)C(=N)N1] | 539.3 | (R)-4-(4,4-diethyl-2-imino-6-oxotetrahydropyrimidin-1(2H)-yl)-N-((3S,4R)-6-fluoro-3-hydroxy-2,2-dimethylchroman-4-yl)chromane-6-carboxamide |
| 25B | 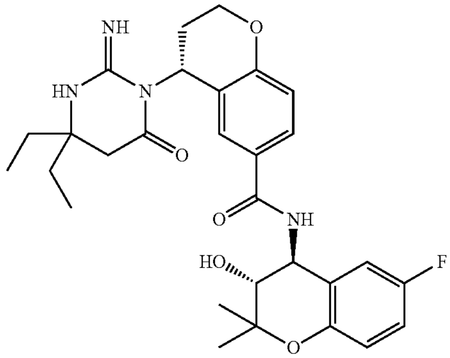 [SMILES: CCC1(CC)CC(=O)N([C@@H]2CCOc3ccc(C(=O)N[C@H]4c5cc(F)ccc5OC(C)(C)[C@@H]4O)cc32)C(=N)N1] | 539.3 | (R)-4-(4,4-diethyl-2-imino-6-oxotetrahydropyrimidin-1(2H)-yl)-N-((3R,4S)-6-fluoro-3-hydroxy-2,2-dimethylchroman-4-yl)chromane-6-carboxamide |
| 26A | 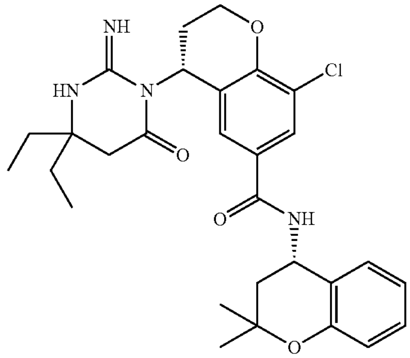 [SMILES: CCC1(CC)CC(=O)N([C@@H]2CCOc3c(Cl)cc(C(=O)N[C@H]4CC(C)(C)Oc5ccccc54)cc32)C(=N)N1] | 539.3, 541.3 | (R)-8-chloro-4-(4,4-diethyl-2-imino-6-oxotetrahydropyrimidin-1(2H)-yl)-N-((S)-2,2-dimethylchroman-4-yl)chromane-6-carboxamide |
| 26B | 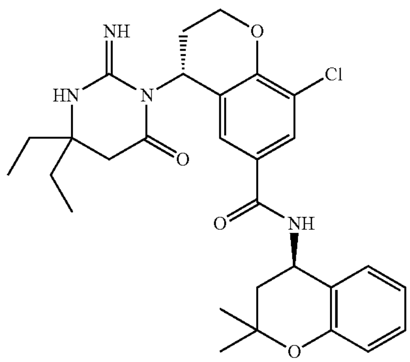 [SMILES: CCC1(CC)CC(=O)N([C@@H]2CCOc3c(Cl)cc(C(=O)N[C@@H]4CC(C)(C)Oc5ccccc54)cc32)C(=N)N1] | 539.2, 541.3 | (R)-8-chloro-4-(4,4-diethyl-2-imino-6-oxotetrahydropyrimidin-1(2H)-yl)-N-((R)-2,2-dimethylchroman-4-yl)chromane-6-carboxamide |

TABLE 1-continued

| Example | Structure | LC/MS (M + 1)+ | Name |
|---------|-----------|----------------|------|
| 27A | 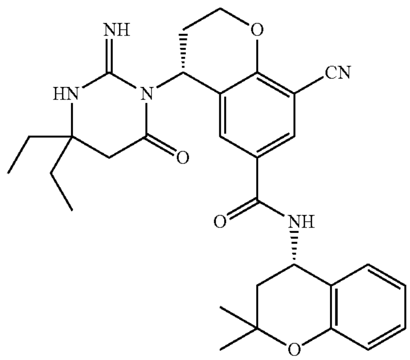 [SMILES: CCC1(CC)CC(=O)N([C@@H]2CCOc3c(C#N)cc(C(=O)N[C@H]4CC(C)(C)Oc5ccccc54)cc32)C(=N)N1] | 530.3 | (R)-8-cyano-4-(4,4-diethyl-2-imino-6-oxotetrahydropyrimidin-1yl)-N-((S)-2,2-dimethylchroman-4-yl)chromane-6-carboxamide |
| 28A | 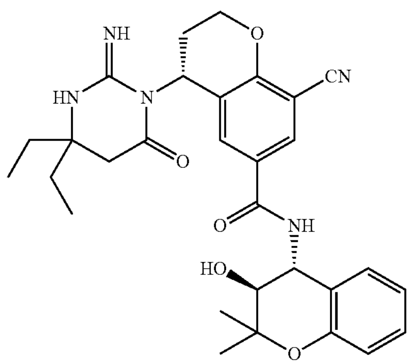 [SMILES: CCC1(CC)CC(=O)N([C@@H]2CCOc3c(C#N)cc(C(=O)N[C@@H]4c5ccccc5OC(C)(C)[C@H]4O)cc32)C(=N)N1] | 546.3 | (R)-8-cyano-4-(4,4-diethyl-2-imino-6-oxotetrahydropyrimidin-1(2H)-yl)-N-((3S,4R)-3-hydroxy-2,2-dimethylchroman-4-yl)chromane-6-carboxamide |
| 29A | 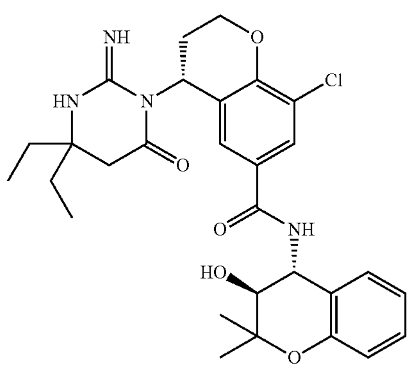 [SMILES: CCC1(CC)CC(=O)N([C@@H]2CCOc3c(Cl)cc(C(=O)N[C@@H]4c5ccccc5OC(C)(C)[C@H]4O)cc32)C(=N)N1] | 555.3, 557.3 | (R)-8-chloro-4-(4,4-diethyl-2-imino-6-oxotetrahydropyrimidin-1(2H)-yl)-N-((3S,4R)-3-hydroxy-2,2-dimethylchroman-4-yl)chromane-6-carboxamide |
| 29B | 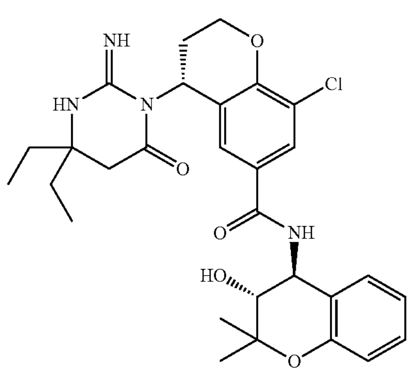 [SMILES: CCC1(CC)CC(=O)N([C@@H]2CCOc3c(Cl)cc(C(=O)N[C@H]4c5ccccc5OC(C)(C)[C@@H]4O)cc32)C(=N)N1] | 555.3, 557.3 | (R)-8-chloro-4-(4,4-diethyl-2-imino-6-oxotetrahydropyrimidin-1(2H)-yl)-N-((3R,4S)-3-hydroxy-2,2-dimethylchroman-4-yl)chromane-6-carboxamide |

TABLE 1-continued

| Example | Structure | LC/MS (M + 1)+ | Name |
|---|---|---|---|
| 30A | 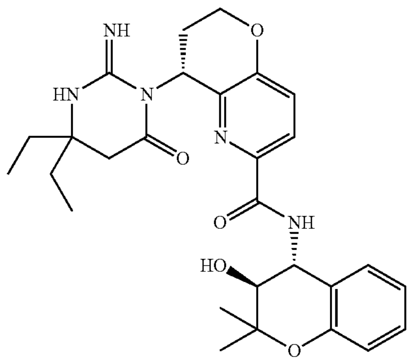 [SMILES: CCC1(CC)CC(=O)N([C@@H]2CCOc3ccc(C(=O)N[C@@H]4c5ccccc5OC(C)(C)[C@H]4O)nc32)C(=N)N1] | 522.3 | (R)-4-(4,4-diethyl-2-imino-6-oxotetrahydropyrimidin-1(2H)-yl)-N-((3S,4R)-3-hydroxy-2,2-dimethylchroman-4-yl)-3,4-dihydro-2H-pyrano[3,2-b]pyridine-6-carboxamide |
| 31A | 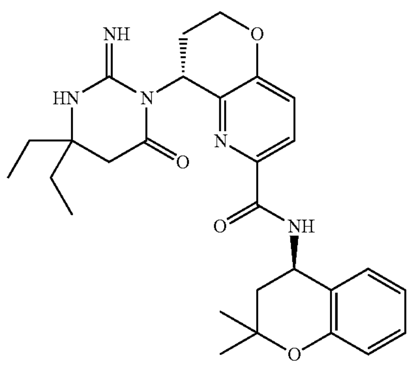 [SMILES: CCC1(CC)CC(=O)N([C@@H]2CCOc3ccc(C(=O)N[C@@H]4CC(C)(C)Oc5ccccc54)nc32)C(=N)N1] | 506.3 | (R)-4-(4,4-diethyl-2-imino-6-oxotetrahydropyrimidin-1(2H)-yl)-N-((R)-2,2-dimethylchroman-4-yl)-3,4-dihydro-2H-pyrano[3,2-b]pyridine-6-carboxamide |
| 31B | 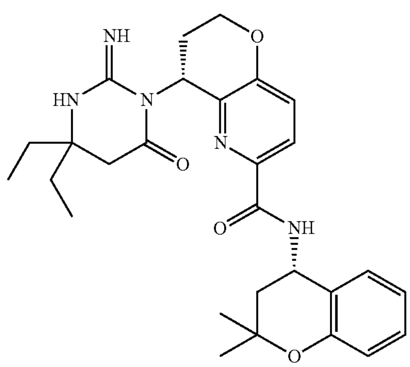 [SMILES: CCC1(CC)CC(=O)N([C@@H]2CCOc3ccc(C(=O)N[C@H]4CC(C)(C)Oc5ccccc54)nc32)C(=N)N1] | 506.3 | (R)-4-(4,4-diethyl-2-imino-6-oxotetrahydropyrimidin-1(2H)-yl)-N-((S)-2,2-dimethylchroman-4-yl)-3,4-dihydro-2H-pyrano[3,2-b]pyridine-6-carboxamide |
| 32A | 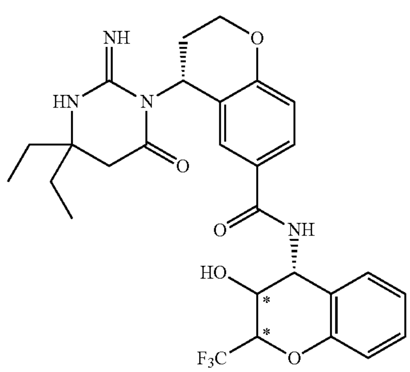 [SMILES: CCC1(CC)CC(=O)N([C@@H]2CCOc3ccc(C(=O)N[C@@H]4c5ccccc5OC(C(F)(F)F)C4O)cc32)C(=N)N1] | 561.3 | (4R)-4-(4,4-diethyl-2-imino-6-oxotetrahydropyrimidin-1(2H)-yl)-N-44R)-3-hydroxy-2-(trifluoromethyl)chroman-4-yl)chromane-6-carboxamide |

TABLE 1-continued

| Example | Structure | LC/MS (M + 1)+ | Name |
|---|---|---|---|
| 32B | 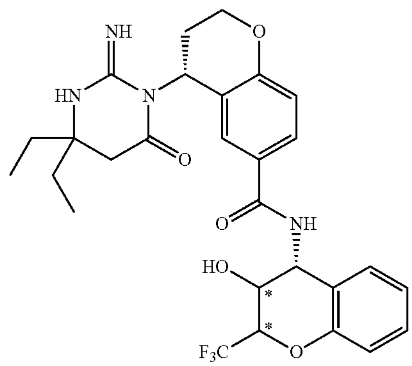 [SMILES: CCC1(CC)CC(=O)N([C@@H]2CCOc3ccc(C(=O)N[C@@H]4c5ccccc5OC(C(F)(F)F)C4O)cc32)C(=N)N1] | 561.3 | (4R)-4-(4,4-diethyl-2-imino-6-oxotetrahydropyrimidin-1(2H)-yl)-N-44R)-3-hydroxy-2-(trifluoromethyl)chroman-4-yl)chromane-6-carboxamide |
| 33A | 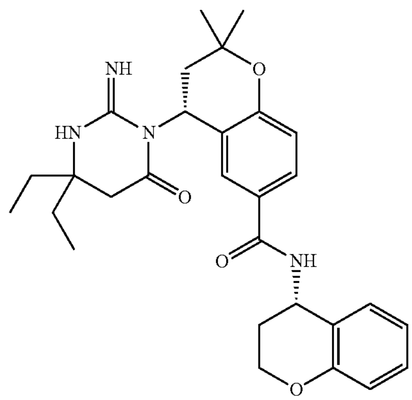 [SMILES: CCC1(CC)CC(=O)N([C@@H]2CC(C)(C)Oc3ccc(C(=O)N[C@H]4CCOc5ccccc54)cc32)C(=N)N1] | 505.3 | (R)-N-((S)-chroman-4-yl)-4-(4,4-diethyl-2-imino-6-oxotetrahydropyrimidin-1(2H)-yl)-2,2-dimethylchromane-6-carboxamide |
| 34A | 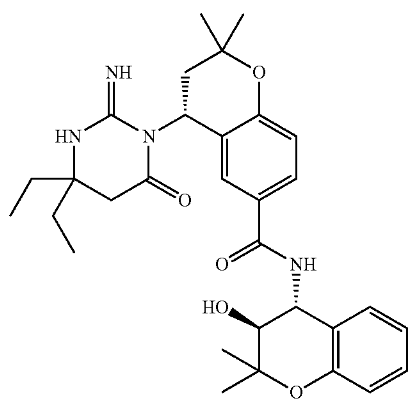 [SMILES: CCC1(CC)CC(=O)N([C@@H]2CC(C)(C)Oc3ccc(C(=O)N[C@@H]4c5ccccc5OC(C)(C)[C@H]4O)cc32)C(=N)N1] | 549.3 | (R)-4-(4,4-diethyl-2-imino-6-oxotetrahydropyrimidin-1(2H)-yl)-N-((3S,4R)-3-hydroxy-2,2-dimethylchroman-4-yl)-2,2-dimethylchromane-6-carboxamide |
| 35A | 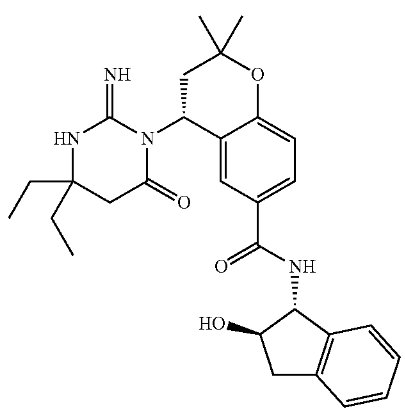 [SMILES: CCC1(CC)CC(=O)N([C@@H]2CC(C)(C)Oc3ccc(C(=O)N[C@@H]4c5ccccc5C[C@H]4O)cc32)C(=N)N1] | 505.3 | (R)-4-(4,4-diethyl-2-imino-6-oxotetrahydropyrimidin-1(2H)-yl)-N-((1R,2R)-2-hydroxy-2,3-dihydro-1H-inden-1-yl)-2,2-dimethylchromane-6-carboxamide |

TABLE 1-continued

| Example | Structure | LC/MS (M + 1)+ | Name |
|---|---|---|---|
| 36A | 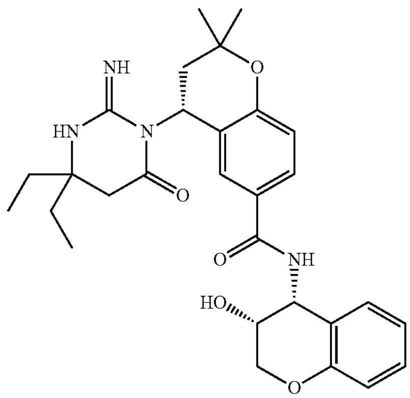 [SMILES: CCC1(CC)CC(=O)N([C@@H]2CC(C)(C)Oc3ccc(C(=O)N[C@@H]4c5ccccc5OC[C@@H]4O)cc32)C(=N)N1] | 521.3 | (R)-4-(4,4-diethyl-2-imino-6-oxotetrahydropyrimidin-1(2H)-yl)-N-((3R,4R)-3-hydroxychroman-4-yl)-2,2-dimethylchromane-6-carboxamide |
| 36B | 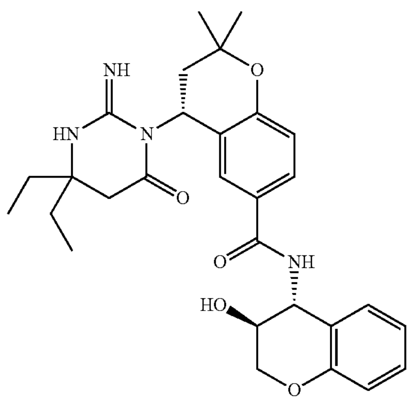 [SMILES: CCC1(CC)CC(=O)N([C@@H]2CC(C)(C)Oc3ccc(C(=O)N[C@@H]4c5ccccc5OC[C@H]4O)cc32)C(=N)N1] | 521.6 | (R)-4-(4,4-diethyl-2-imino-6-oxotetrahydropyrimidin-1(2H)-yl)-N-((3 S,4R)-3-hydroxychroman-4-yl)-2,2-dimethylchromane-6-carboxamide |
| 37A | 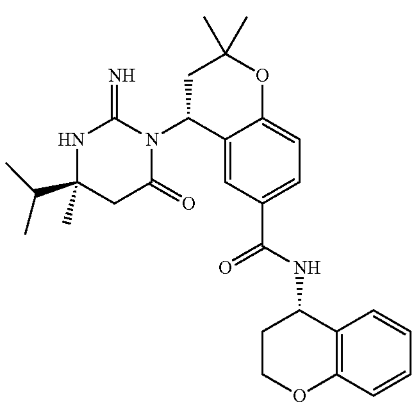 [SMILES: CC(C)[C@]1(C)CC(=O)N([C@@H]2CC(C)(C)Oc3ccc(C(=O)N[C@H]4CCOc5ccccc54)cc32)C(=N)N1] | 521.2 | (R)-N-((S)-chroman-4-yl)-4-((S)-2-imino-4-isopropyl-4-methyl-6-oxotetrahydropyrimidin-1(2H)-yl)-2,2-dimethylchromane-6-carboxamide |
| 38A | 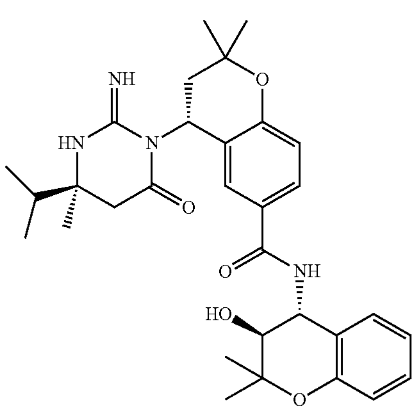 [SMILES: CC(C)[C@]1(C)CC(=O)N([C@@H]2CC(C)(C)Oc3ccc(C(=O)N[C@@H]4c5ccccc5OC(C)(C)[C@H]4O)cc32)C(=N)N1] | 549.3 | (R)-N-((3 S,4R)-3-hydroxy-2,2-dimethylchroman-4-yl)-4-((S)-2-imino-4-isopropyl-4-methyl-6-oxotetrahydropyrimidin-1(2H)-yl)-2,2-dimethylchromane-6-carboxamide |

TABLE 1-continued

| Example | Structure | LC/MS (M + 1)+ | Name |
|---|---|---|---|
| 39A | 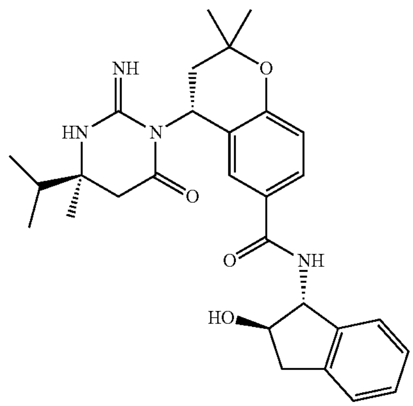 [SMILES: CC(C)[C@]1(C)CC(=O)N([C@@H]2CC(C)(C)Oc3ccc(C(=O)N[C@@H]4c5ccccc5C[C@H]4O)cc32)C(=N)N1] | 505.3 | (R)-N-((1R,2R)-2-hydroxy-2,3-dihydro-1H-inden-1-yl)-4-((S)-2-imino-4-isopropyl-4-methyl-6-oxotetrahydropyrimidin-1(2H)-yl)-2,2-dimethylchromane-6-carboxamide |
| 40A | 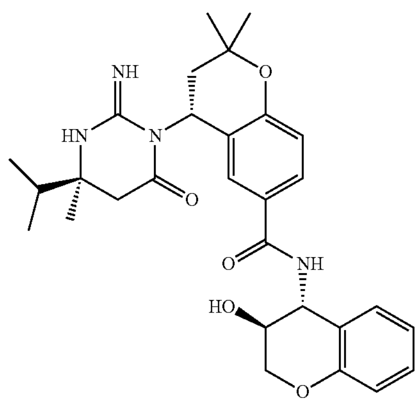 [SMILES: CC(C)[C@]1(C)CC(=O)N([C@@H]2CC(C)(C)Oc3ccc(C(=O)N[C@@H]4c5ccccc5OC[C@H]4O)cc32)C(=N)N1] | 521.3 | (R)-N-((3S,4R)-3-hydroxychroman-4-yl)-4-((S)-2-imino-4-isopropyl-4-methyl-6-oxotetrahydropyrimidin-1(2H)-yl)-2,2-dimethylchromane-6-carboxamide |
| 41A | 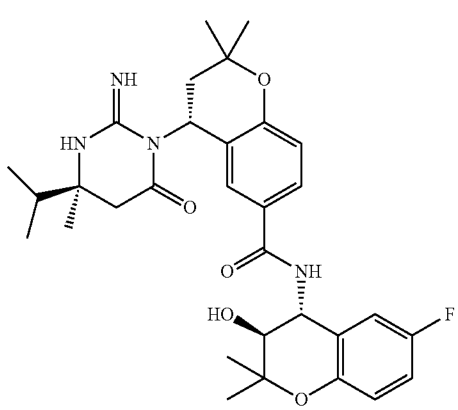 [SMILES: CC(C)[C@]1(C)CC(=O)N([C@@H]2CC(C)(C)Oc3ccc(C(=O)N[C@@H]4c5cc(F)ccc5OC(C)(C)[C@H]4O)cc32)C(=N)N1] | 567.3 | (R)-N-((3S,4R)-6-fluoro-3-hydroxy-2,2-dimethylchroman-4-yl)-4-((S)-2-imino-4-isopropyl-4-methyl-6-oxotetrahydropyrimidin-1(2H)-yl)-2,2-dimethylchromane-6-carboxamide |

TABLE 1-continued

| Example | Structure | LC/MS (M + 1)+ | Name |
|---|---|---|---|
| 42A | 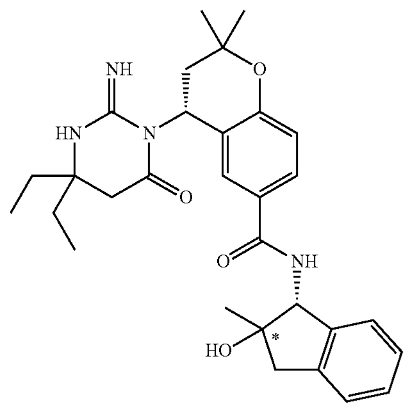 [SMILES: CCC1(CC)CC(=O)N([C@@H]2CC(C)(C)Oc3ccc(C(=O)N[C@@H]4c5ccccc5CC4(C)O)cc32)C(=N)N1] | 519.3 | (4R)-4-(4,4-diethyl-2-imino-6-oxotetrahydropyrimidin-1(2H)-yl)-N-((1R)-2-hydroxy-2-methyl-2,3-dihydro-1H-inden-1-yl)-2,2-dimethylchromane-6-carboxamide |
| 42B | 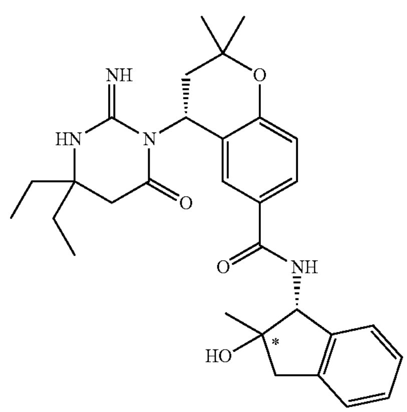 [SMILES: CCC1(CC)CC(=O)N([C@@H]2CC(C)(C)Oc3ccc(C(=O)N[C@@H]4c5ccccc5CC4(C)O)cc32)C(=N)N1] | 519.2 | (4R)-4-(4,4-diethyl-2-imino-6-oxotetrahydropyrimidin-1(2H)-yl)-N-((1R)-2-hydroxy-2-methyl-2,3-dihydro-1H-inden-1-yl)-2,2-dimethylchromane-6-carboxamide |
| 43A | 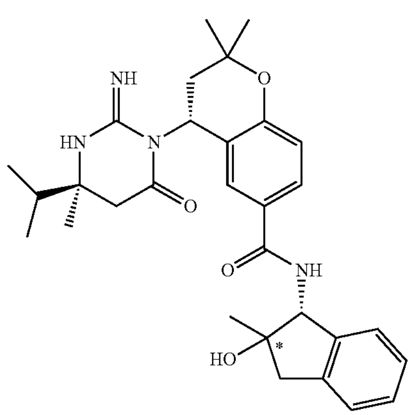 [SMILES: CC(C)[C@]1(C)CC(=O)N([C@@H]2CC(C)(C)Oc3ccc(C(=O)N[C@@H]4c5ccccc5CC4(C)O)cc32)C(=N)N1] | 519.2 | (4R)-N-((1R)-2-hydroxy-2-methyl-2,3-dihydro-1H-inden-1-yl)-4-((S)-2-imino-4-isopropyl-4-methyl-6-oxotetrahydropyrimidin-1(2H)-yl)-2,2-dimethylchromane-6-carboxamide |

TABLE 1-continued

| Example | Structure | LC/MS (M + 1)+ | Name |
|---|---|---|---|
| 43B | 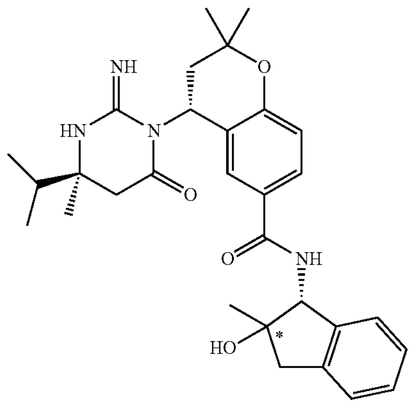 [SMILES: CC(C)[C@]1(C)CC(=O)N([C@@H]2CC(C)(C)Oc3ccc(C(=O)N[C@@H]4c5ccccc5CC4(C)O)cc32)C(=N)N1] | 519.2 | (4R)-N-((1R)-2-hydroxy-2-methyl-2,3-dihydro-1H-inden-1-yl)-4-((S)-2-imino-4-isopropyl-4-methyl-6-oxotetrahydropyrimidin-1(2H)-yl)-2,2-dimethylchromane-6-carboxamide |
| 44A | 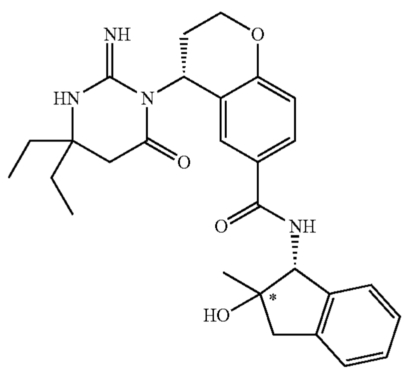 [SMILES: CCC1(CC)CC(=O)N([C@@H]2CCOc3ccc(C(=O)N[C@@H]4c5ccccc5CC4(C)O)cc32)C(=N)N1] | 491.2 | (4R)-4-(4,4-diethyl-2-imino-6-oxotetrahydropyrimidin-1(2H)-yl)-N-((1R)-2-hydroxy-2-methyl-2,3-dihydro-1H-inden-1-yl)chromane-6-carboxamide |
| 44B | 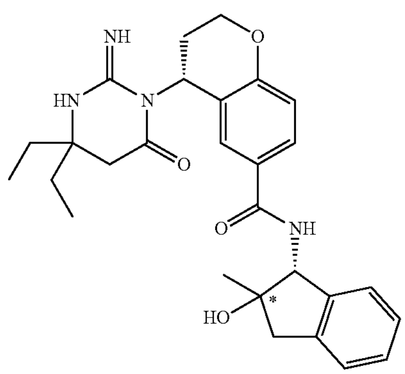 [SMILES: CCC1(CC)CC(=O)N([C@@H]2CCOc3ccc(C(=O)N[C@@H]4c5ccccc5CC4(C)O)cc32)C(=N)N1] | 491.2 | (4R)-4-(4,4-diethyl-2-imino-6-oxotetrahydropyrimidin-1(2H)-yl)-N-((1R)-2-hydroxy-2-methyl-2,3-dihydro-1H-inden-1-yl)chromane-6-carboxamide |
| 45A | 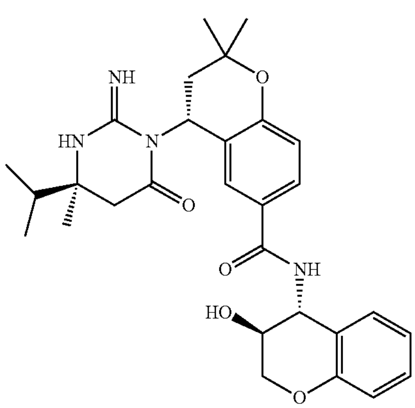 [SMILES: CC(C)[C@]1(C)CC(=O)N([C@@H]2CC(C)(C)Oc3ccc(C(=O)N[C@@H]4c5ccccc5OC[C@H]4O)cc32)C(=N)N1] | 521.2 | (R)-N-((3S,4R)-3-hydroxychroman-4-yl)-4-((S)-2-imino-4-isopropyl-4-methyl-6-oxotetrahydropyrimidin-1(2H)-yl)-2,2-dimethylchromane-6-carboxamide |

TABLE 1-continued

| Example | Structure | LC/MS (M + 1)+ | Name |
|---|---|---|---|
| 46A | 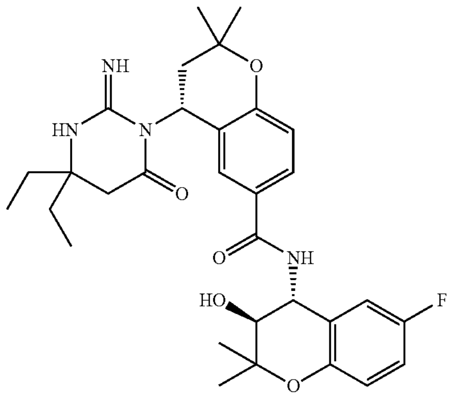 [SMILES: CCC1(CC)CC(=O)N([C@@H]2CC(C)(C)Oc3ccc(C(=O)N[C@@H]4c5cc(F)ccc5OC(C)(C)[C@H]4O)cc32)C(=N)N1] | 567.3 | (R)-4-(4,4-diethyl-2-imino-6-oxotetrahydropyrimidin-1(2H)-yl)-N-((3S,4R)-6-fluoro-3-hydroxy-2,2-dimethylchroman-4-yl)-2,2-dimethylchromane-6-carboxamide |
| 47A | 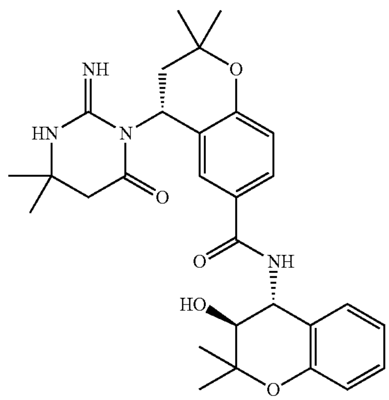 [SMILES: CC1(C)CC(=O)N([C@@H]2CC(C)(C)Oc3ccc(C(=O)N[C@@H]4c5ccccc5OC(C)(C)[C@H]4O)cc32)C(=N)N1] | 521.3 | (R)-N-((3S,4R)-3-hydroxy-2,2-dimethylchroman-4-yl)-4-(2-imino-4,4-dimethyl-6-oxotetrahydropyrimidin-1(2H)-yl)-2,2-dimethylchromane-6-carboxamide |
| 48A | 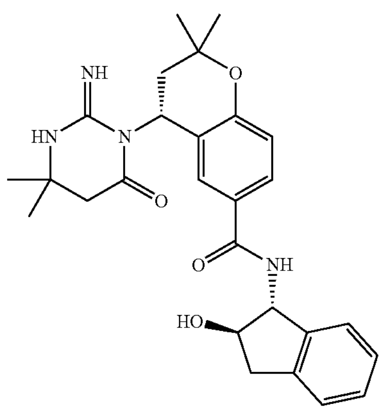 [SMILES: CC1(C)CC(=O)N([C@@H]2CC(C)(C)Oc3ccc(C(=O)N[C@@H]4c5ccccc5C[C@H]4O)cc32)C(=N)N1] | 477.3 | (R)-N-((1R,2R)-2-hydroxy-2,3-dihydro-1H-inden-1-yl)-4-(2-imino-4,4-dimethyl-6-oxotetrahydropyrimidin-1(2H)-yl)-2,2-dimethylchromane-6-carboxamide |
| 49A | 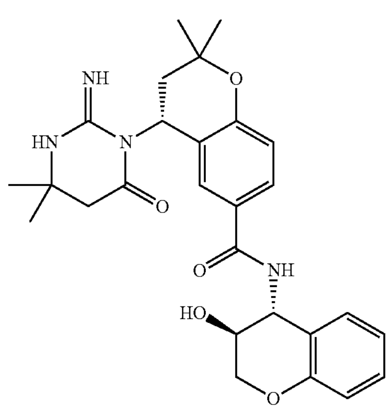 [SMILES: CC1(C)CC(=O)N([C@@H]2CC(C)(C)Oc3ccc(C(=O)N[C@@H]4c5ccccc5OC[C@H]4O)cc32)C(=N)N1] | 493.3 | (R)-N-((3S,4R)-3-hydroxychroman-4-yl)-4-(2-imino-4,4-dimethyl-6-oxotetrahydropyrimidin-1(2H)-yl)-2,2-dimethylchromane-6-carboxamide |

TABLE 1-continued

| Example | Structure | LC/MS (M + 1)+ | Name |
|---|---|---|---|
| 50A | 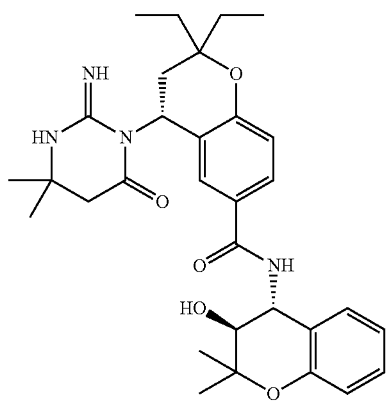 [SMILES: CCC1(CC)C[C@@H](N2C(=N)NC(C)(C)CC2=O)c2cc(C(=O)N[C@@H]3c4ccccc4OC(C)(C)[C@H]3O)ccc2O1] | 549.3 | (R)-2,2-diethyl-N-((3S,4R)-3-hydroxy-2,2-dimethylchroman-4-yl)-4-(2-imino-4,4-dimethyl-6-oxotetrahydropyrimidin-1(2H)-yl)chromane-6-carboxamide |
| 51A | 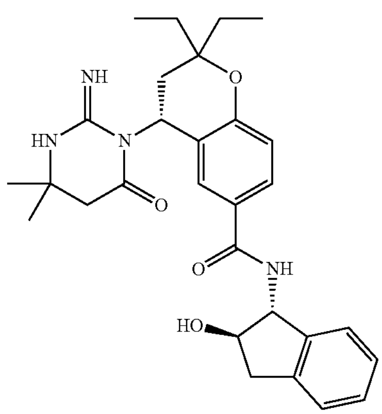 [SMILES: CCC1(CC)C[C@@H](N2C(=N)NC(C)(C)CC2=O)c2cc(C(=O)N[C@@H]3c4ccccc4C[C@H]3O)ccc2O1] | 505.3 | (R)-2,2-diethyl-N-((1R,2R)-2-hydroxy-2,3-dihydro-1H-inden-1-yl)-4-(2-imino-4,4-dimethyl-6-oxotetrahydropyrimidin-1(2H)-yl)chromane-6-carboxamide |
| 52A | 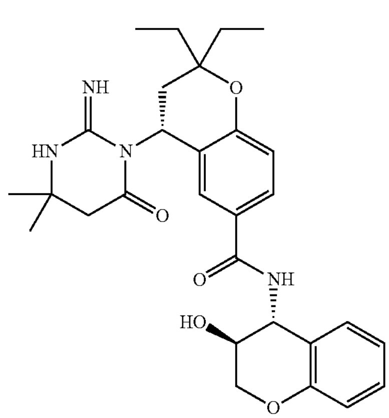 [SMILES: CCC1(CC)C[C@@H](N2C(=N)NC(C)(C)CC2=O)c2cc(C(=O)N[C@@H]3c4ccccc4OC[C@H]3O)ccc2O1] | 521.3 | (R)-2,2-diethyl-N-((3S,4R)-3-hydroxychroman-4-yl)-4-(2-imino-4,4-dimethyl-6-oxotetrahydropyrimidin-1(2H)-yl)chromane-6-carboxamide |

TABLE 1-continued

| Example | Structure | LC/MS (M + 1)+ | Name |
|---|---|---|---|
| 53A | 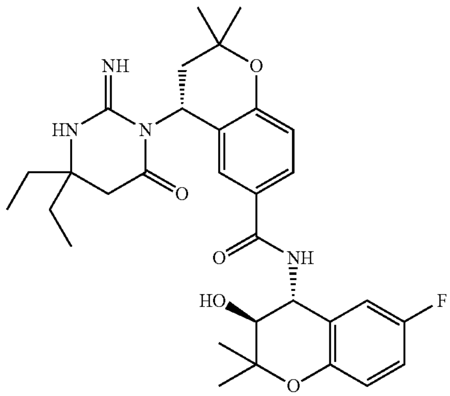 [SMILES: CCC1(CC)CC(=O)N([C@@H]2CC(C)(C)Oc3ccc(C(=O)N[C@@H]4c5cc(F)ccc5OC(C)(C)[C@H]4O)cc32)C(=N)N1] | 567.4 | (R)-4-(4,4-diethyl-2-imino-6-oxotetrahydropyrimidin-1(2H)-yl)-N-((3S,4R)-6-fluoro-3-hydroxy-2,2-dimethylchroman-4-yl)-2,2-dimethylchromane-6-carboxamide |
| 54A | 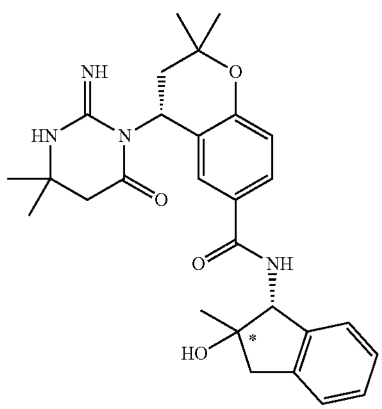 [SMILES: CC1(C)CC(=O)N([C@@H]2CC(C)(C)Oc3ccc(C(=O)N[C@@H]4c5ccccc5CC4(C)O)cc32)C(=N)N1] | 491.3 | (4R)-N-((1R)-2-hydroxy-2-methyl-2,3-dihydro-1H-inden-1-yl)-4-(2-imino-4,4-dimethyl-6-oxotetrahydropyrimidin-1(2H)-yl)-2,2-dimethylchromane-6-carboxamide |
| 54B | 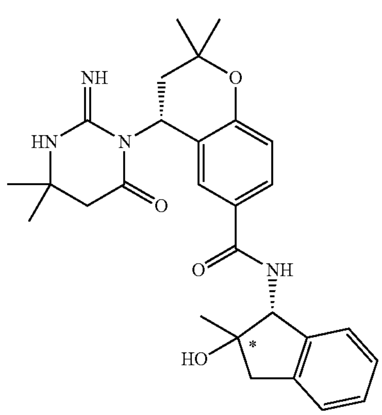 [SMILES: CC1(C)CC(=O)N([C@@H]2CC(C)(C)Oc3ccc(C(=O)N[C@@H]4c5ccccc5CC4(C)O)cc32)C(=N)N1] | 491.6 | (4R)-N-((1R)-2-hydroxy-2-methyl-2,3-dihydro-1H-inden-1-yl)-4-(2-imino-4,4-dimethyl-6-oxotetrahydropyrimidin-1(2H)-yl)-2,2-dimethylchromane-6-carboxamide |

TABLE 1-continued

| Example | Structure | LC/MS (M + 1)+ | Name |
|---|---|---|---|
| 55A | 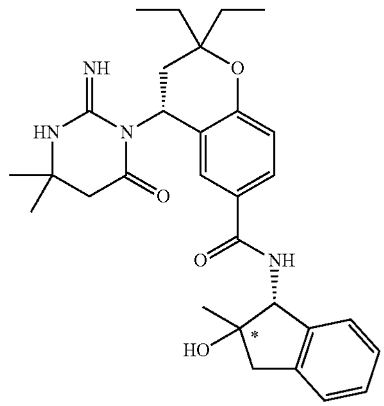 [SMILES: CCC1(CC)C[C@@H](N2C(=N)NC(C)(C)CC2=O)c2cc(C(=O)N[C@@H]3c4ccccc4CC3(C)O)ccc2O1] | 519.3 | (4R)-2,2-diethyl-N-((1R)-2-hydroxy-2-methyl-2,3-dihydro-1H-inden-1-yl)-4-(2-imino-4,4-dimethyl-6-oxotetrahydropyrimidin-1(2H)-yl)chromane-6-carboxamide |
| 55B | 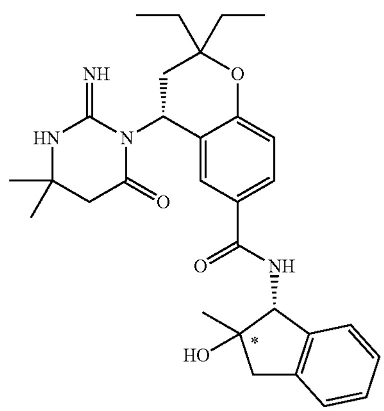 [SMILES: CCC1(CC)C[C@@H](N2C(=N)NC(C)(C)CC2=O)c2cc(C(=O)N[C@@H]3c4ccccc4CC3(C)O)ccc2O1] | 519.4 | (4R)-2,2-diethyl-N-((1R)-2-hydroxy-2-methyl-2,3-dihydro-1H-inden-1-yl)-4-(2-imino-4,4-dimethyl-6-oxotetrahydropyrimidin-1(2H)-yl)chromane-6-carboxamide |
| 56A | 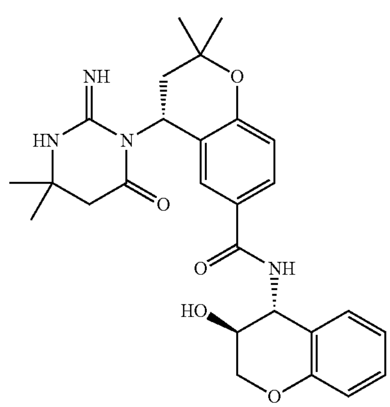 [SMILES: CC1(C)CC(=O)N([C@@H]2CC(C)(C)Oc3ccc(C(=O)N[C@@H]4c5ccccc5OC[C@H]4O)cc32)C(=N)N1] | 493.2 | (R)-N-((3S,4R)-3-hydroxychroman-4-yl)-4-(2-imino-4,4-dimethyl-6-oxotetrahydropyrimidin-1(2H)-yl)-2,2-dimethylchromane-6-carboxamide |

TABLE 1-continued

| Example | Structure | LC/MS (M + 1)+ | Name |
|---|---|---|---|
| 57A | 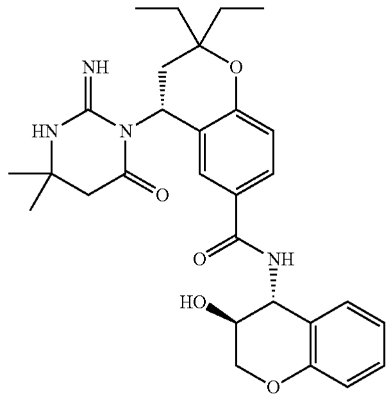 [SMILES: CCC1(CC)C[C@@H](N2C(=N)NC(C)(C)CC2=O)c2cc(C(=O)N[C@@H]3c4ccccc4OC[C@H]3O)ccc2O1] | 521.3 | (R)-2,2-diethyl-N-((3S,4R)-3-hydroxychroman-4-yl)-4-(2-imino-4,4-dimethyl-6-oxotetrahydropyrimidin-1(2H)-yl)chromane-6-carboxamide |
| 58A | 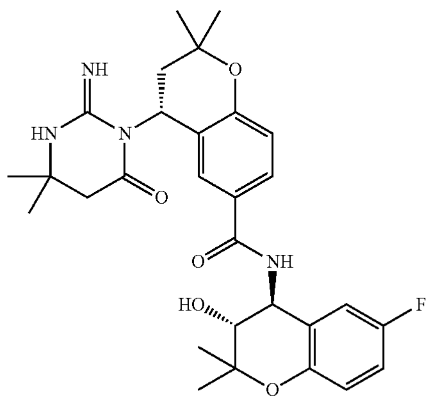 [SMILES: CC1(C)CC(=O)N([C@@H]2CC(C)(C)Oc3ccc(C(=O)N[C@H]4c5cc(F)ccc5OC(C)(C)[C@@H]4O)cc32)C(=N)N1] | 539.3 | (R)-N-((3R,4S)-6-fluoro-3-hydroxy-2,2-dimethylchroman-4-yl)-4-(2-imino-4,4-dimethyl-6-oxotetrahydropyrimidin-1(2H)-yl)-2,2-dimethylchromane-6-carboxamide |
| 58B | 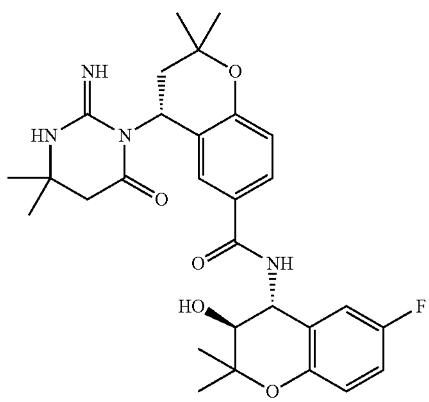 [SMILES: CC1(C)CC(=O)N([C@@H]2CC(C)(C)Oc3ccc(C(=O)N[C@@H]4c5cc(F)ccc5OC(C)(C)[C@H]4O)cc32)C(=N)N1] | 539.3 | (R)-N-((3S,4R)-6-fluoro-3-hydroxy-2,2-dimethylchroman-4-yl)-4-(2-imino-4,4-dimethyl-6-oxotetrahydropyrimidin-1(2H)-yl)-2,2-dimethylchromane-6-carboxamide |
| 59A | 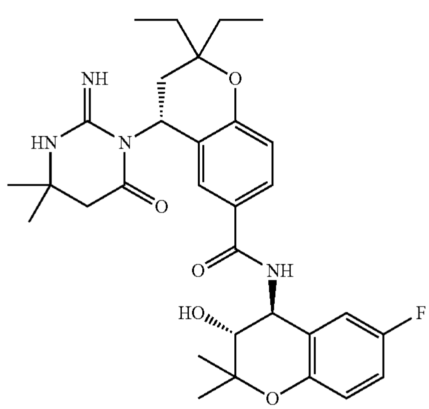 [SMILES: CCC1(CC)C[C@@H](N2C(=N)NC(C)(C)CC2=O)c2cc(C(=O)N[C@H]3c4cc(F)ccc4OC(C)(C)[C@@H]3O)ccc2O1] | 567.3 | (R)-2,2-diethyl-N-((3R,4S)-6-fluoro-3-hydroxy-2,2-dimethylchroman-4-yl)-4-(2-imino-4,4-dimethyl-6-oxotetrahydropyrimidin-yl)chromane-6-carboxamide |

TABLE 1-continued

| Example | Structure | LC/MS (M + 1)+ | Name |
|---|---|---|---|
| 59B | 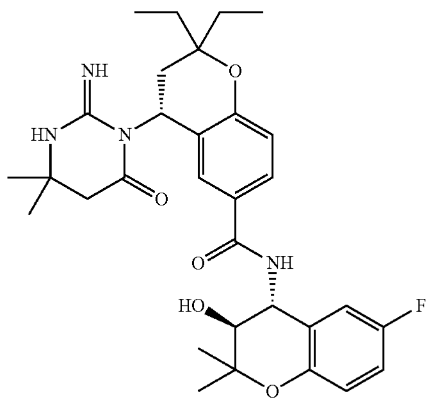 [SMILES: CCC1(CC)C[C@@H](N2C(=N)NC(C)(C)CC2=O)c2cc(C(=O)N[C@@H]3c4cc(F)ccc4OC(C)(C)[C@H]3O)ccc2O1] | 567.3 | (R)-2,2-diethyl-N-((3S,4R)-6-fluoro-3-hydroxy-2,2-dimethylchroman-4-yl)-4-(2-imino-4,4-dimethyl-6-oxotetrahydropyrimidin-1(2H)-yl)chromane-6-carboxamide |
| 60A | 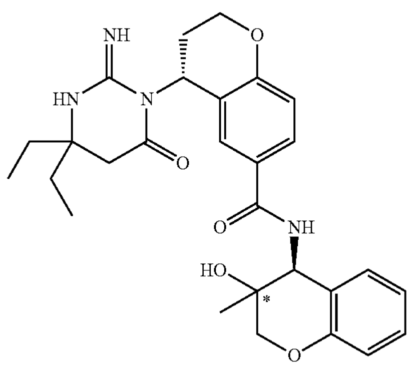 [SMILES: CCC1(CC)CC(=O)N([C@@H]2CCOc3ccc(C(=O)N[C@H]4c5ccccc5OCC4(C)O)cc32)C(=N)N1] | 507.2 | (4R)-4-(4,4-diethyl-2-imino-6-oxotetrahydropyrimidin-1(2H)-yl)-N-((4 S)-3-hydroxy-3-methylchroman-4-yl)chromane-6-carboxamide |
| 60B | 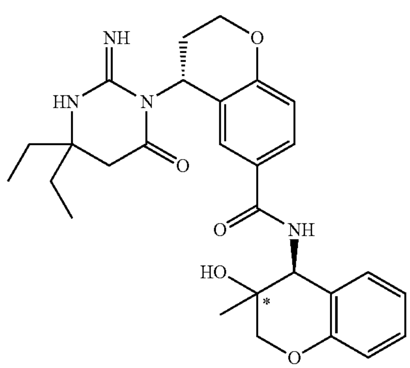 [SMILES: CCC1(CC)CC(=O)N([C@@H]2CCOc3ccc(C(=O)N[C@H]4c5ccccc5OCC4(C)O)cc32)C(=N)N1] | 507.3 | (4R)-4-(4,4-diethyl-2-imino-6-oxotetrahydropyrimidin-1(2H)-yl)-N-((4 S)-3-hydroxy-3-methylchroman-4-yl)chromane-6-carboxamide |
| 61A | 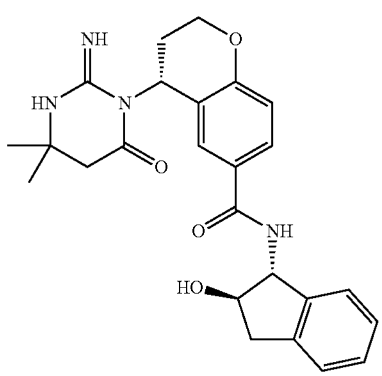 [SMILES: CC1(C)CC(=O)N([C@@H]2CCOc3ccc(C(=O)N[C@@H]4c5ccccc5C[C@H]4O)cc32)C(=N)N1] | 449.3 | (R)-N-((1R,2R)-2-hydroxy-2,3-dihydro-1H-inden-1-yl)-4-(2-imino-4,4-dimethyl-6-oxotetrahydropyrimidin-1(2H)-yl)chromane-6-carboxamide |

TABLE 1-continued

| Example | Structure | LC/MS (M + 1)+ | Name |
|---|---|---|---|
| 62A | 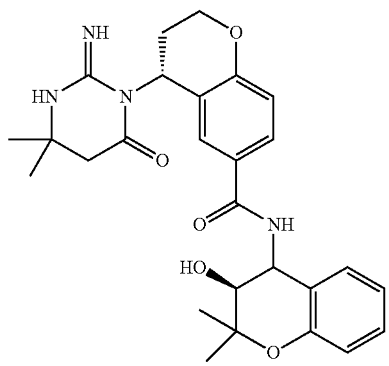 [SMILES: CC1(C)CC(=O)N([C@@H]2CCOc3ccc(C(=O)NC4c5ccccc5OC(C)(C)[C@H]4O)cc32)C(=N)N1] | 493.3 | (R)-N-((3S,4R)-3-hydroxy-2,2-dimethylchroman-4-yl)-4-(2-imino-4,4-dimethyl-6-oxotetrahydropyrimidin-1(2H)-yl)chromane-6-carboxamide |
| 63A | 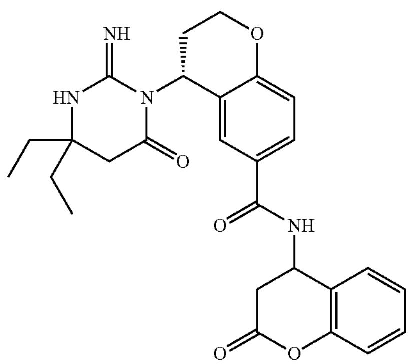 [SMILES: CCC1(CC)CC(=O)N([C@@H]2CCOc3ccc(C(=O)NC4CC(=O)Oc5ccccc54)cc32)C(=N)N1] | 491.3 | (4R)-4-(4,4-diethyl-2-imino-6-oxotetrahydropyrimidin-1(2H)-yl)-N-(2-oxochroman-4-yl)chromane-6-carboxamide |
| 64A | 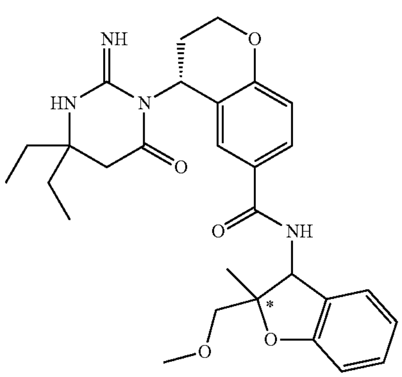 [SMILES: CCC1(CC)CC(=O)N([C@@H]2CCOc3ccc(C(=O)NC4c5ccccc5OC4(C)COC)cc32)C(=N)N1] | 521.3 | (4R)-4-(4,4-diethyl-2-imino-6-oxotetrahydropyrimidin-1(2H)-yl)-N-(2-(methoxymethyl)-2-methyl-2,3-dihydrobenzofuran-3-yl)chromane-6-carboxamide |
| 64B | 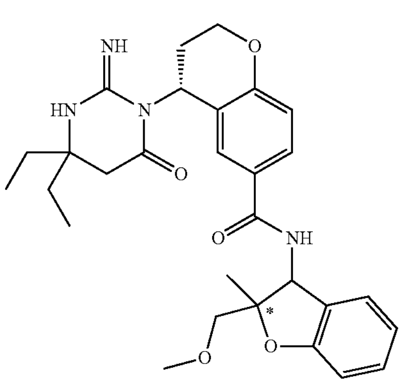 [SMILES: CCC1(CC)CC(=O)N([C@@H]2CCOc3ccc(C(=O)NC4c5ccccc5OC4(C)COC)cc32)C(=N)N1] | 521.3 | (4R)-4-(4,4-diethyl-2-imino-6-oxotetrahydropyrimidin-1(2H)-yl)-N-(2-(methoxymethyl)-2-methyl-2,3-dihydrobenzofuran-3-yl)chromane-6-carboxamide |

TABLE 1-continued

| Example | Structure | LC/MS (M + 1)+ | Name |
|---|---|---|---|
| 64C | 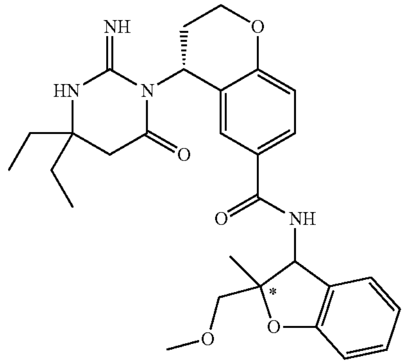 [SMILES: CCC1(CC)CC(=O)N([C@@H]2CCOc3ccc(C(=O)NC4c5ccccc5OC4(C)COC)cc32)C(=N)N1] | 521.3 | (4R)-4-(4,4-diethyl-2-imino-6-oxotetrahydropyrimidin-1(2H)-yl)-N-(2-(methoxymethyl)-2-methyl-2,3-dihydrobenzofuran-3-yl)chromane-6-carboxamide |
| 64D | 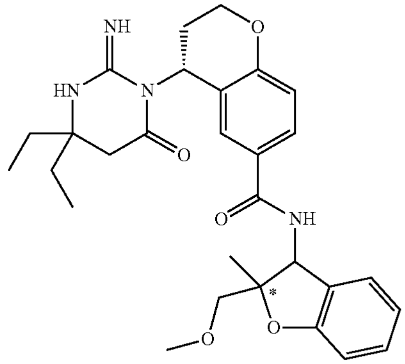 [SMILES: CCC1(CC)CC(=O)N([C@@H]2CCOc3ccc(C(=O)NC4c5ccccc5OC4(C)COC)cc32)C(=N)N1] | 521.3 | (4R)-4-(4,4-diethyl-2-imino-6-oxotetrahydropyrimidin-1(2H)-yl)-N-(2-(methoxymethyl)-2-methyl-2,3-dihydrobenzofuran-3-yl)chromane-6-carboxamide |
| 65A | 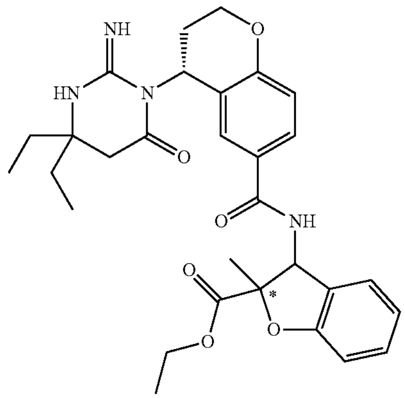 [SMILES: CCOC(=O)C1(C)Oc2ccccc2C1NC(=O)c1ccc2c(c1)[C@H](N1C(=N)NC(CC)(CC)CC1=O)CCO2] | 549.3 | ethyl 3-((R)-4-(4,4-diethyl-2-imino-6-oxotetrahydropyrimidin-1(2H)-yl)chromane-6-carboxamido)-2-methyl-2,3-dihydrobenzofuran-2-carboxylate |
| 65B | 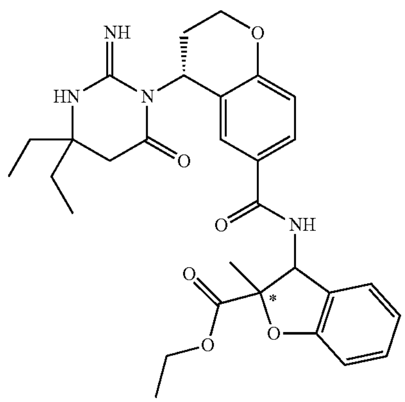 [SMILES: CCOC(=O)C1(C)Oc2ccccc2C1NC(=O)c1ccc2c(c1)[C@H](N1C(=N)NC(CC)(CC)CC1=O)CCO2] | 549.3 | ethyl 3-((R)-4-(4,4-diethyl-2-imino-6-oxotetrahydropyrimidin-1(2H)-yl)chromane-6-carboxamido)-2-methyl-2,3-dihydrobenzofuran-2-carboxylate |

TABLE 1-continued

| Example | Structure | LC/MS (M + 1)+ | Name |
|---|---|---|---|
| 65C | 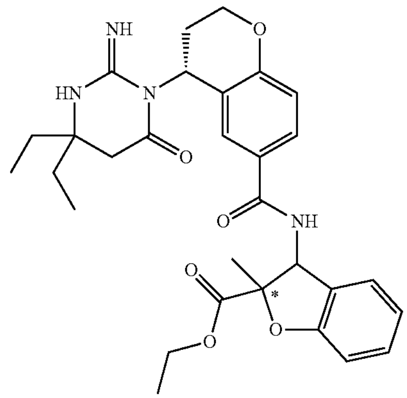 [SMILES: CCOC(=O)C1(C)Oc2ccccc2C1NC(=O)c1ccc2c(c1)[C@H](N1C(=N)NC(CC)(CC)CC1=O)CCO2] | 549.3 | ethyl 3-((R)-4-(4,4-diethyl-2-imino-6-oxotetrahydropyrimidin-1(2H)-yl)chromane-6-carboxamido)-2-methyl-2,3-dihydrobenzofuran-2-carboxylate |
| 66A | 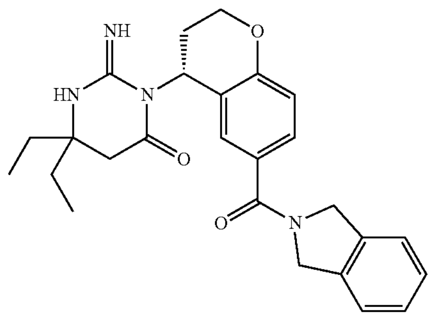 [SMILES: CCC1(CC)CC(=O)N([C@@H]2CCOc3ccc(C(=O)N4Cc5ccccc5C4)cc32)C(=N)N1] | 447.3 | (R)-6,6-diethyl-2-imino-3-(6-(isoindoline-2-carbonyl)chroman-4-yl)tetrahydropyrimidin-4(1H)-one |
| 67A | 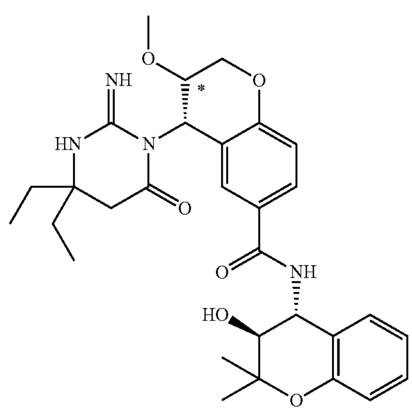 | 551.3 | (3R,4S)-4-(4,4-diethyl-2-imino-6-oxotetrahydropyrimidin-1(2H)-yl)-N-((3S,4R)-3-hydroxy-2,2-dimethylchroman-4-yl)-3-methoxychromane-6-carboxamide |
| 67B | 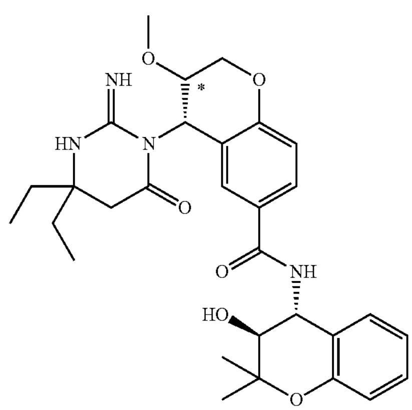 | 551.3 | (3R,4S)-4-(4,4-diethyl-2-imino-6-oxotetrahydropyrimidin-1(2H)-yl)-N-((3S,4R)-3-hydroxy-2,2-dimethylchroman-4-yl)-3-methoxychromane-6-carboxamide |

TABLE 1-continued

| Example | Structure | LC/MS (M + 1)+ | Name |
|---|---|---|---|
| 68A | 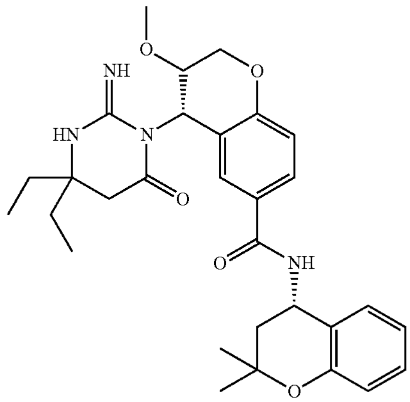 | 535.3 | (3R,4S)-4-(4,4-diethyl-2-imino-6-oxotetrahydropyrimidin-1(2H)-yl)-N-((S)-2,2-dimethylchroman-4-yl)-3-methoxychromane-6-carboxamide |
| 69A | 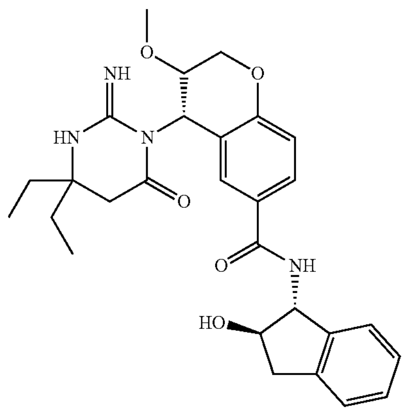 | 507.3 | (3R,4S)-4-(4,4-diethyl-2-imino-6-oxotetrahydropyrimidin-1(2H)-yl)-N-((1R,2R)-2-hydroxy-2,3-dihydro-1H-inden-1-yl)-3-methoxychromane-6-carboxamide |
| 70A | 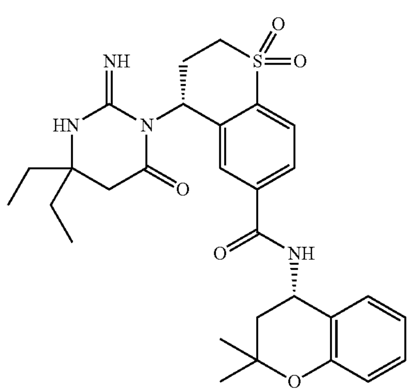 [SMILES: CCC1(CC)CC(=O)N([C@@H]2CCS(=O)(=O)c3ccc(C(=O)N[C@H]4CC(C)(C)Oc5ccccc54)cc32)C(=N)N1] | 553.3 | (R)-4-(4,4-diethyl-2-imino-6-oxotetrahydropyrimidin-1(2H)-yl)-N-((S)-2,2-dimethylchroman-4-yl)thiochromane-6-carboxamide 1,1-dioxide |
| 71A | 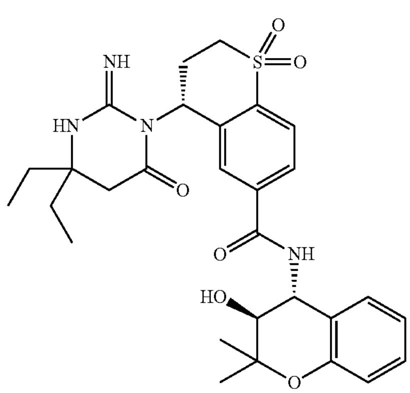 [SMILES: CCC1(CC)CC(=O)N([C@@H]2CCS(=O)(=O)c3ccc(C(=O)N[C@@H]4c5ccccc5OC(C)(C)[C@H]4O)cc32)C(=N)N1] | 569.3 | (R)-4-(4,4-diethyl-2-imino-6-oxotetrahydropyrimidin-1(2H)-yl)-N-((3S,4R)-3-hydroxy-2,2-dimethylchroman-4-yl)thiochromane-6-carboxamide 1,1-dioxide |

TABLE 1-continued

| Example | Structure | LC/MS (M + 1)+ | Name |
|---|---|---|---|
| 72A | 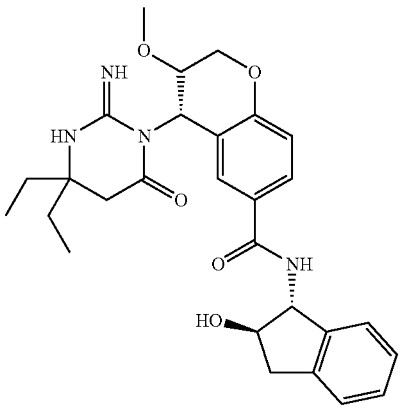 | 507.3 | (3R,4S)-4-(4,4-diethyl-2-imino-6-oxotetrahydropyrimidin-1(2H)-yl)-N-((1R,2R)-2-hydroxy-2,3-dihydro-1H-inden-1-yl)-3-methoxychromane-6-carboxamide |
| 73A | 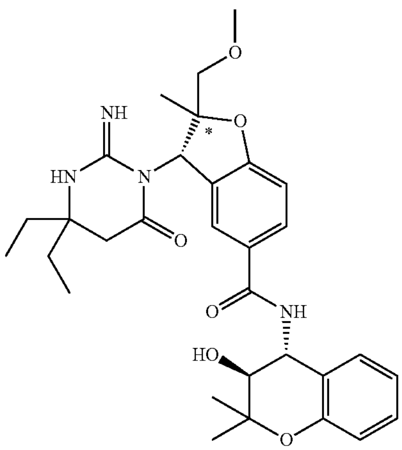 | 565.3 | (2S,3S)-3-(4,4-diethyl-2-imino-6-oxotetrahydropyrimidin-1(2H)-yl)-N-((3S,4R)-3-hydroxy-2,2-dimethylchroman-4-yl)-2-(methoxymethyl)-2-methyl-2,3-dihydrobenzofuran-5-carboxamide |
| 73B | 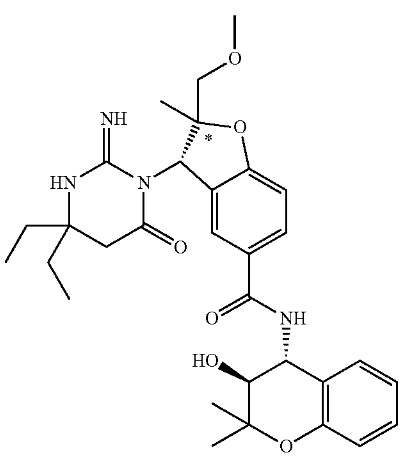 | 565.2 | (2S,3S)-3-(4,4-diethyl-2-imino-6-oxotetrahydropyrimidin-1(2H)-yl)-N-((3S,4R)-3-hydroxy-2,2-dimethylchroman-4-yl)-2-(methoxymethyl)-2-methyl-2,3-dihydrobenzofuran-5-carboxamide |

TABLE 1-continued
| Example | Structure | LC/MS (M + 1)+ | Name |
|---|---|---|---|
| 74A | 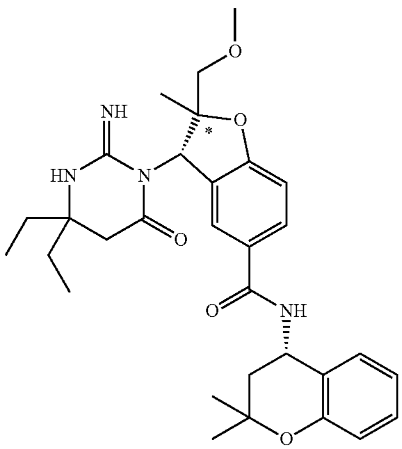 | 549.2 | (2S,3S)-3-(4,4-diethyl-2-imino-6-oxotetrahydropyrimidin-1(2H)-yl)-N-((S)-2,2-dimethylchroman-4-yl)-2-(methoxymethyl)-2-methyl-2,3-dihydrobenzofuran-5-carboxamide |
| 74B | 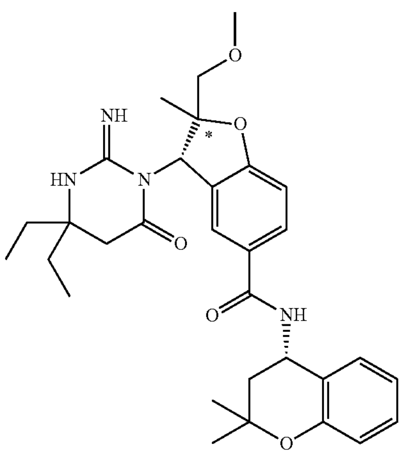 | 549.2 | (2S,3 S)-3-(4,4-diethyl-2-imino-6-oxotetrahydropyrimidin-1(2H)-yl)-N-((S)-2,2-dimethylchroman-4-yl)-2-(methoxymethyl)-2-methyl-2,3-dihydrobenzofuran-5-carboxamide |
Example 75A
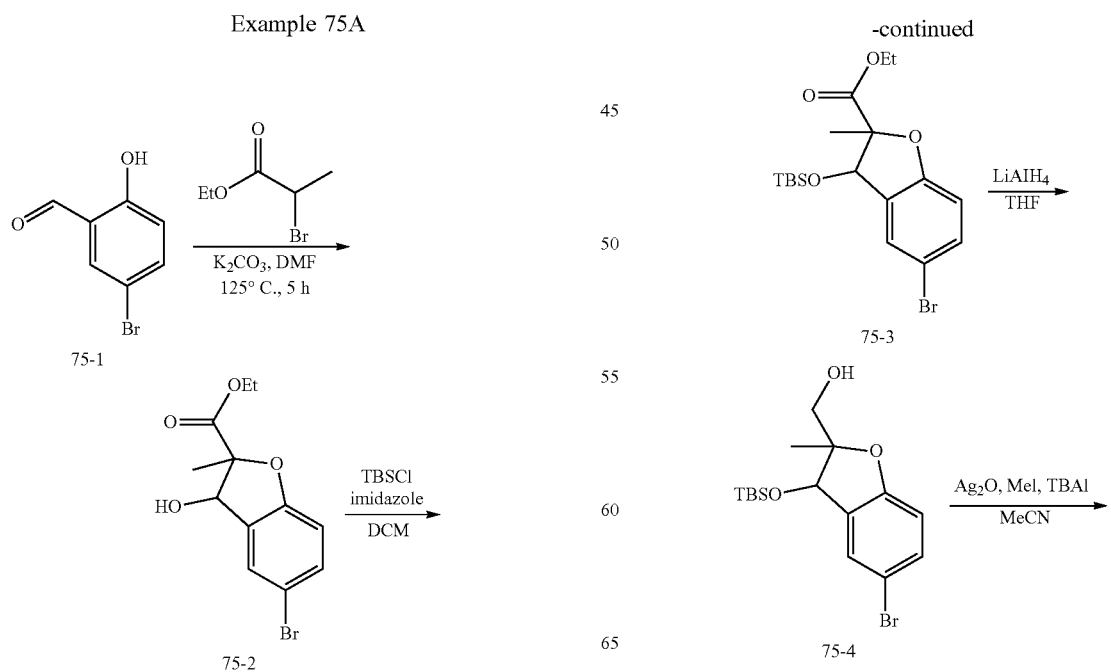

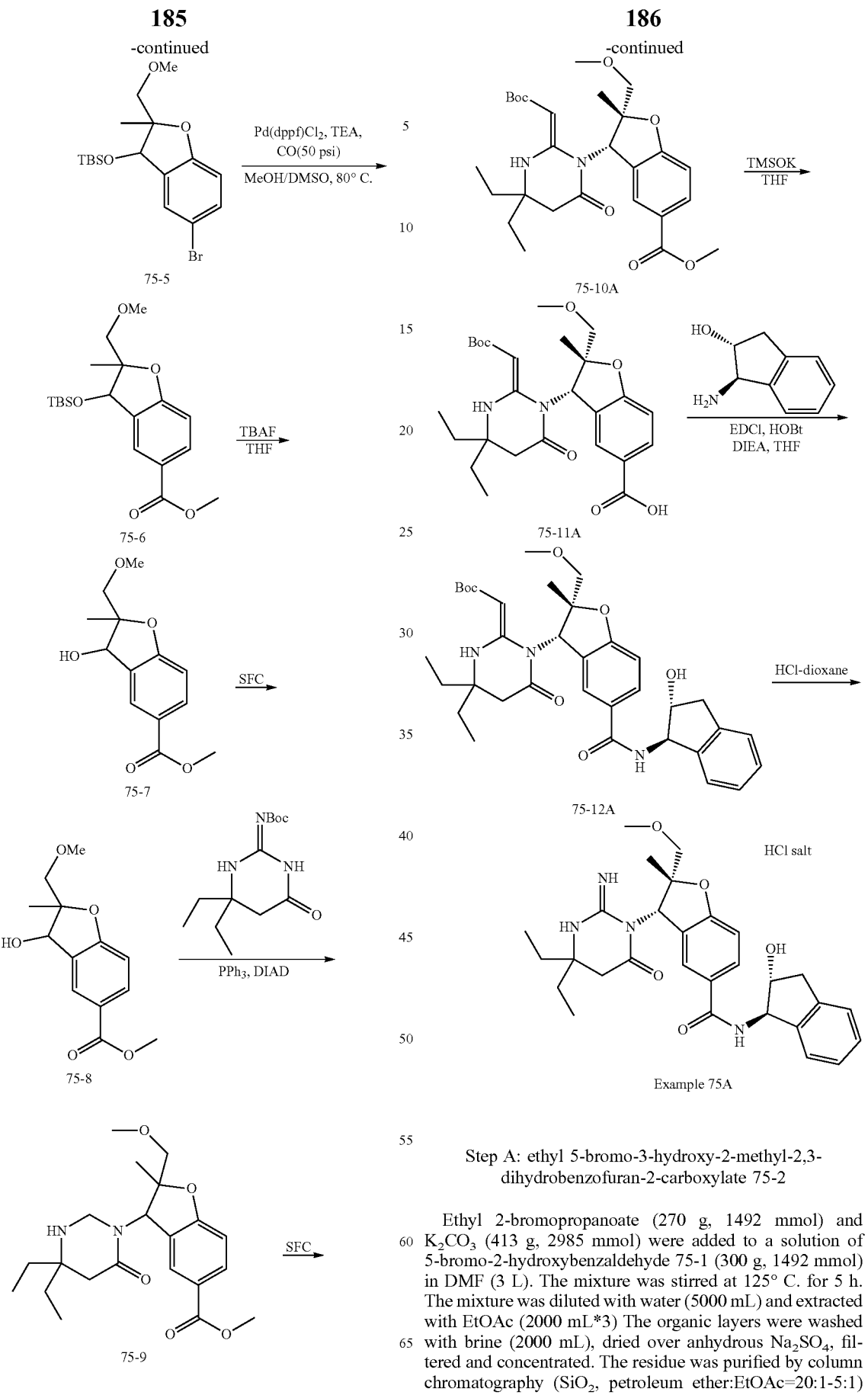

Step A: ethyl 5-bromo-3-hydroxy-2-methyl-2,3-dihydrobenzofuran-2-carboxylate 75-2

Ethyl 2-bromopropanoate (270 g, 1492 mmol) and K₂CO₃ (413 g, 2985 mmol) were added to a solution of 5-bromo-2-hydroxybenzaldehyde 75-1 (300 g, 1492 mmol) in DMF (3 L). The mixture was stirred at 125° C. for 5 h. The mixture was diluted with water (5000 mL) and extracted with EtOAc (2000 mL*3) The organic layers were washed with brine (2000 mL), dried over anhydrous Na₂SO₄, filtered and concentrated. The residue was purified by column chromatography (SiO₂, petroleum ether:EtOAc=20:1-5:1)

to afford product ethyl 5-bromo-3-hydroxy-2-methyl-2,3-dihydrobenzofuran-2-carboxylate 75-2.

¹H NMR (400 MHz, chloroform-d) δ 7.45 (d, J=1.6 Hz, 1H), 7.34 (dd, J=2.0, 8.4 Hz, 1H), 6.79 (d, J=8.4 Hz, 1H), 5.27 (s, 1H), 4.12-4.20 (m, 2H), 2.42-2.44 (m, 1H), 1.64 (s, 3H), 1.22 (t, J=7.2 Hz, 3H).

Step B: ethyl 5-bromo-3-((tert-butyldimethylsilyl)oxy)-2-methyl-2,3-dihydrobenzofuran-2-carboxylate 75-3

Ethyl 5-bromo-3-hydroxy-2-methyl-2,3-dihydrobenzofuran-2-carboxylate 75-2 (300 g, 996 mmol) in DCM (3000 mL) was added to chlorotrimethylsilane (70 g, 644 mmol) and 1H-imidazole (60 g, 881 mmol). The mixture was stirred at 25° C. for 10 h under $N_2$ atmosphere. Water (3000 mL) was added to the mixture, and the mixture was extracted with DCM (500 mL*2). The organic layers were washed with brine (1000 mL), dried over $Na_2SO_4$, filtered and concentrated in vacuo, then purified by flash column (petroleum ether/EtOAc=50:1) to give the product ethyl 5-bromo-3-((tert-butyldimethylsilyl)oxy)-2-methyl-2,3-dihydrobenzofuran-2-carboxylate 75-3.

¹H NMR (400 MHz, chloroform-d) δ 7.26-7.35 (m, 2H), 6.78 (d, J=8.4 Hz, 1H), 5.35 (s, 1H), 4.14-4.23 (m, 2H), 1.60 (s, 3H), 1.22-1.27 (m, 3H), 0.93 (s, 9H), 0.18 (s, 6H)

Step C: (5-bromo-3-((tert-butyldimethylsilyl)oxy)-2-methyl-2,3-dihydrobenzofuran-2-yl)methanol 75-4

LiAlH₄ (64.0 g, 1685 mmol) was added to a solution of ethyl 5-bromo-3-((tert-butyldimethylsilyl)oxy)-2-methyl-2,3-dihydrobenzofuran-2-carboxylate 75-3 (350 g, 843 mmol) in THF (3000 mL), in portions at 0° C. for 30 min. Then the mixture was stirred at 27° C. for another 30 min. The mixture was quenched with water (100 mL), diluted with EtOAc (5000 mL), dried over anhydrous $Na_2SO_4$ and $MgSO_4$, filtered and concentrated to afford product (5-bromo-3-((tert-butyldimethylsilyl)oxy)-2-methyl-2,3-dihydrobenzofuran-2-yl)methanol 75-4. The product was used for the next step without purification.

¹H NMR (400 MHz, chloroform-d) δ 7.27-7.32 (m, 2H), 6.60-6.70 (m, 1H), 5.23 (s, 1H), 3.55-3.66 (m, 2H), 1.77-1.86 (m, 1H), 1.35 (s, 3H), 0.93 (s, 9H), 0.21 (s, 3H), 0.16 (s, 3H).

Step D: ((5-bromo-2-(methoxymethyl)-2-methyl-2,3-dihydrobenzofuran-3-yl)oxy)(tert-butyl)dimethylsilane 75-5

Iodomethane (968.150 g, 6821 mmol) and TBAI (20 g, 54.1 mmol) was added to a solution of (5-bromo-3-((tert-butyldimethylsilyl)oxy)-2-methyl-2,3-dihydrobenzofuran-2-yl)methanol 75-4 (270 g, 723 mmol) and monosilver(I) monosilver(III) monooxide (335 g, 1446 mmol) in MeCN (2.0 L mL) at 27° C. The mixture was stirred at 50° C. for 15 h under $N_2$ atmosphere. The mixture was filtered and concentrated. The residue was purified by flash column ($SiO_2$, petroleum ether/EtOAc=100:1) to afford product ((5-bromo-2-(methoxymethyl)-2-methyl-2,3-dihydrobenzofuran-3-yl)oxy)(tert-butyl)dimethylsilane 75-5.

¹H NMR (500 MHz, chloroform-d) δ 7.20-7.29 (m, 2H), 6.63 (d, J=8.5 Hz, 1H), 5.14 (s, 1H), 3.14-3.46 (m, 5H), 1.34 (s, 3H), 0.89 (s, 9H), 0.07-0.19 (m, 6H).

Step E: methyl 3-((tert-butyldimethylsilyl)oxy)-2-(methoxymethyl)-2-methyl-2,3-dihydrobenzofuran-5-carboxylate 75-6

Pd(dppf)Cl₂ (18.9 g, 25.8 mmol) and triethylamine (131 g, 1291 mmol) was added to a solution of ((5-bromo-2-(methoxymethyl)-2-methyl-2,3-dihydrobenzofuran-3-yl)oxy)(tert-butyl)dimethylsilane 75-5 (100 g, 258 mmol) in MeOH (1000 mL) and DMSO (500 mL). The mixture was stirred at 80° C. for 12 h under 50 psi CO atmosphere. The mixture was filtered and concentrated. The residue was added water (500 mL), and extracted with EtOAc (300 mL×2). The organic layers were washed with brine (300 mL), dried over $Na_2SO_4$, filtered and concentrated in vacuo, then purified by flash column (petroleum ether/EtOAc=100:0 to 10:1) to afford product methyl 3-((tert-butyldimethylsilyl)oxy)-2-(methoxymethyl)-2-methyl-2,3-dihydrobenzofuran-5-carboxylate 75-6.

¹H NMR (500 MHz, chloroform-d) δ 7.91-7.99 (m, 2H), 6.79 (d, J=9.5 Hz, 1H), 5.21 (s, 1H), 3.87 (s, 3H), 3.41-3.46 (m, 1H), 3.36 (s, 3H), 3.32-3.35 (m, 1H), 1.41 (s, 3H), 0.92 (s, 9H), 0.22 (s, 3H), 0.17 (s, 3H).

Step F: methyl 3-hydroxy-2-(methoxymethyl)-2-methyl-2,3-dihydrobenzofuran-5-carboxylate 75-7

TBAF (355 mL, 355 mmol) was added to a solution of methyl 3-((tert-butyldimethylsilyl)oxy)-2-(methoxymethyl)-2-methyl-2,3-dihydrobenzofuran-5-carboxylate 75-6 (65 g, 177 mmol) in THF (100 mL). The mixture was stirred at 27° C. for 0.5 hours. The mixture was diluted with water (200 mL) and extracted with EtOAc (100 mL*3). The organic layers were washed with brine (100 mL), dried over anhydrous $Na_2SO_4$, filtered and concentrated. The residue was purified by column chromatography ($SiO_2$, petroleum ether:EtOAc=10:1 to 3:1) to afford product methyl 3-hydroxy-2-(methoxymethyl)-2-methyl-2,3-dihydrobenzofuran-5-carboxylate 75-7.

¹H NMR (400 MHz, chloroform-d) δ 8.04 (d, J=2.0 Hz, 1H), 7.90 (dd, 8.5 Hz, 1H), 6.78 (d, J=8.5 Hz, 1H), 5.08 (s, 1H), 3.85 (s, 3H), 3.30-3.47 (m, 5H), 2.61 (br, 1H), 1.49 (s, 3H).

Step G: methyl (2S,3R)-3-hydroxy-2-(methoxymethyl)-2-methyl-2,3-dihydrobenzofuran-5-carboxylate 75-8 (P1) and methyl (2R,3S)-3-hydroxy-2-(methoxymethyl)-2-methyl-2,3-dihydrobenzofuran-5-carboxylate 75-8 (P2)

The methyl 3-hydroxy-2-(methoxymethyl)-2-methyl-2,3-dihydrobenzofuran-5-carboxylate 75-7 (40 g, 159 mmol) was purified by SFC (SFC-7 Method Column DAICEL CHIRALPAK AD (250 mm×50 mm, 10 um). Condition 0.1% NH₃H₂O IPA Begin B 25% End B 25%. Gradient time (min) 100% B Hold Time (min) FlowRate (mL/min) 200) to give methyl (2S,3R)-3-hydroxy-2-(methoxymethyl)-2-methyl-2,3-dihydrobenzofuran-5-carboxylate 75-8 (P1) (Rt=3.450) and methyl (2R,3S)-3-hydroxy-2-(methoxymethyl)-2-methyl-2,3-dihydrobenzofuran-5-carboxylate 75-8 (P2) (Rt=3.951). 75-8 (P1): MS (ESI) m/z 253.1 (M+H⁺)

¹H NMR (400 MHz, chloroform-d) δ 8.04 (s, 1H), 7.91 (dd, 8.5 Hz, 1H), 6.78 (d, J=8.5 Hz, 1H), 5.07 (d, J=4.5 Hz, 1H), 3.84 (s, 3H), 3.27-3.46 (m, 5H), 2.47 (br, J=7.5 Hz, 1H), 1.47 (s, 3H). 75-8 (P2): MS (ESI) m/z 253.1 (M+H⁺)

¹H NMR (400 MHz, chloroform-d) δ 8.01 (d, J=1.2 Hz, 1H), 7.87 (dd, J=1.6, 8.4 Hz, 1H), 6.76 (d, J=8.4 Hz, 1H), 5.05 (s, 1H), 3.82 (s, 3H), 3.39-3.46 (m, 1H), 3.28-3.33 (m, 4H), 2.74 (br, 1H), 1.46 (s, 3H).

Step H: methyl 3-(2-((tert-butoxycarbonyl)imino)-4,4-diethyl-6-oxotetrahydropyrimidin-1(2H)-yl)-2-(methoxymethyl)-2-methyl-2,3-dihydrobenzofuran-5-carboxylate 75-9

DIAD (10.58 mL, 54.4 mmol) was added dropwise to a solution of tert-butyl (4,4-diethyl-6-oxotetrahydropyrimidin-2(1H)-ylidene)carbamate (11 g, 40.8 mmol), methyl (2S,3R)-3-hydroxy-2-(methoxymethyl)-2-methyl-2,3-dihydrobenzofuran-5-carboxylate 75-8 (10 g, 39.6 mmol) and triphenylphosphine (14 g, 53.4 mmol) in THF (150 mL), at 25° C. under $N_2$ atmosphere. Then the mixture was stirred at 27° C. for 2 h. The mixture was concentrated and added EtOAc (100 mL) to dissolved and added pet. ether slowly to white solid appear. The mixture filtered and concentrated in vacuo. The residue was purified by column chromatography ($SiO_2$, petroleum ether:EtOAc:DCM=100:10:1-100:10:10) to afford product methyl 3-(2-((tert-butoxycarbonyl)imino)-4,4-diethyl-6-oxotetrahydropyrimidin-1(2H)-yl)-2-(methoxymethyl)-2-methyl-2,3-dihydrobenzofuran-5-carboxylate 75-9.

MS (ESI) m/z: 504.2 (M+H$^+$)

$^1$H NMR (400 MHz, chloroform-d) δ 9.78-10.08 (m, 1H), 7.87-7.99 (m, 1H), 7.68-7.79 (m, 1H), 6.79-6.89 (m, 1H), 6.44-6.47 (m, 1H), 3.83-3.84 (m, 3H), 3.52-3.58 (m, 2H), 3.40 (s, 3H), 2.45-2.49 (m, 2H), 1.57-1.68 (m, 4H), 1.35-1.54 (m, 11H), 0.89-0.98 (m, 6H).

Step I: (2R,3S)-methyl 3-(2-((tert-butoxycarbonyl)imino)-4,4-diethyl-6-oxotetrahydropyrimidin-1(2H)-yl)-2-(methoxymethyl)-2-methyl-2,3-dihydrobenzofuran-5-carboxylate 75-10A and methyl 3-(2-((tert-butoxycarbonyl)imino)-4,4-diethyl-6-oxotetrahydropyrimidin-1(2H)-yl)-2-(methoxymethyl)-2-methyl-2,3-dihydrobenzofuran-5-carboxylate 75-10B The methyl 3-(2-((tert-butoxycarbonyl)imino)-4,4-diethyl-6-oxotetrahydropyrimidin-1(2H)-yl)-2-(methoxymethyl)-2-methyl-2,3-dihydrobenzofuran-5-carboxylate 75-9 (25.5 g, 50.6 mmol) was purified by SFC (Instrument SFC-17 Method Column DAICEL CHIRALPAK AD-H (250 mm×30 mm, 5 um), Condition 0.1% NH$_3$H$_2$O IPA Begin B 30% End B 30% Gradient Time (min) 100% B Hold Time (min) FlowRate (mL/min) 60 Injections 100) to give (2R,3S)-methyl 3-(2-((tert-butoxycarbonyl)imino)-4,4-diethyl-6-oxotetrahydropyrimidin-1(2H)-yl)-2-(methoxymethyl)-2-methyl-2,3-dihydrobenzofuran-5-carboxylate 75-10A (P1) (9.0 g, 17.87 mmol, 35.3% yield) (Rt=1.869) as a colorless oil and methyl 3-(2-((tert-butoxycarbonyl)imino)-4,4-diethyl-6-oxotetrahydropyrimidin-1(2H)-yl)-2-(methoxymethyl)-2-methyl-2,3-dihydrobenzofuran-5-carboxylate 75-10B (P2).

75-10A (P1): MS (ESI) m/z 504.3 (M+H$^+$)

$^1$H NMR (500 MHz, chloroform-d) δ 10.00 (s, 1H), 7.93 (dd, J=1.5, 8.5 Hz, 1H), 7.76 (s, 1H), 6.84 (d, J=8.5 Hz, 1H), 6.44 (s, 1H), 3.84 (s, 3H), 3.54 (s, 2H), 3.39 (s, 3H), 2.45 (s, 2H), 1.58-1.64 (m, 4H), 1.50-1.54 (m, 12H), 0.91-0.94 (m, 6H).

75-10B (P2): MS (ESI) m/z 504.3 (M+H$^+$)

$^1$H NMR (500 MHz, chloroform-d) δ 9.91 (s, 1H), 7.91 (dd, 8.5 Hz, 1H), 7.71 (s, 1H), 6.83 (d, J=8.5 Hz, 1H), 6.47 (s, 1H), 3.83 (s, 3H), 3.53-3.59 (m, 2H), 3.40 (s, 3H), 2.50 (s, 2H), 1.60-1.66 (m, 4H), 1.51 (s, 9H), 1.37 (s, 3H), 0.90-0.97 (m, 6H).

Step J: (2R,3S)-3-(2-((tert-butoxycarbonyl)imino)-4,4-diethyl-6-oxotetrahydropyrimidin-1(2H)-yl)-2-(methoxymethyl)-2-methyl-2,3-dihydrobenzofuran-5-carboxylic acid 75-11A Potassium trimethylsilanolate (5.60 g, 43.7 mmol) was added to a solution of (2R,3S)-methyl 3-(2-((tert-butoxycarbonyl)imino)-4,4-diethyl-6-oxotetrahydropyrimidin-1(2H)-yl)-2-(methoxymethyl)-2-methyl-2,3-dihydrobenzofuran-5-carboxylate 75-10A (5.5 g, 10.92 mmol) in THF (100 mL). The reaction was stirred at 27° C. for 1 h under $N_2$ atmosphere. The solution of (2R,3S)-3-(2-((tert-butoxycarbonyl)imino)-4,4-diethyl-6-oxotetrahydropyrimidin-1(2H)-yl)-2-(methoxymethyl)-2-methyl-2,3-dihydrobenzofuran-5-carboxylic acid 75-11A was used for next step directly without any further manipulation or purification.

MS (ESI) m/z: 490.1 (M+H$^+$)

Step K: tert-butyl(4,4-diethyl-1-((2R,3S)-5-(((1R,2R)-2-hydroxy-2,3-dihydro-1H-inden-1-yl)carbamoyl)-2-(methoxymethyl)-2-methyl-2,3-dihydrobenzofuran-3-yl)-6-oxotetrahydropyrimidin-2(1H)-ylidene)carbamate 75-12A N-ethyl-N-isopropylpropan-2-amine (7.06 g, 54.6 mmol) was added to a solution of (2R,3S)-3-(2-((tert-butoxycarbonyl)imino)-4,4-diethyl-6-oxotetrahydropyrimidin-1(2H)-yl)-2-(methoxymethyl)-2-methyl-2,3-dihydrobenzofuran-5-carboxylic acid 75-11A (5.35 g, 10.93 mmol), N1-((ethylimino)methylene)-N3,N3-dimethylpropane-1,3-diamine hydrochloride (4.19 g, 21.86 mmol), (1R,2R)-1-amino-2,3-dihydro-1H-inden-2-ol (1.956 g, 13.11 mmol) and 1H-benzo[d][1,2,3]triazol-1-ol (2.95 g, 21.86 mmol) in THF (100 mL). The reaction was stirred at 27° C. for 3 h under $N_2$ atmosphere. The mixture was quenched with water (100 mL), and extracted with EtOAc (100 mL×2). The organic layers were washed with brine (100 mL), dried over $Na_2SO_4$, filtered, and concentrated in vacuo. The residue was purified by column chromatography ($SiO_2$, petroleum ether:EtOAc:DCM=100:10:10-20:10:10) to give tert-butyl (4,4-diethyl-1-((2R,3S)-5-(((1R,2R)-2-hydroxy-2,3-dihydro-1H-inden-1-yl)carbamoyl)-2-(methoxymethyl)-2-methyl-2,3-dihydrobenzofuran-3-yl)-6-oxotetrahydropyrimidin-2(1H)-ylidene)carbamate 75-12A.

MS (ESI) m/z: 621.5 (M+H$^+$)

$^1$H NMR (500 MHz, chloroform-d) δ 10.00 (s, 1H), 7.68 (s, 1H), 7.61 (dd, J=1.5, 8.5 Hz, 1H), 7.26-7.32 (m, 3H), 6.85 (d, J=8.5 Hz, 1H), 6.51 (s, 1H), 6.44 (d, J=6.0 Hz, 1H), 5.28-5.29 (m, 1H), 4.82 (s, 1H), 4.47 (q, J=7.5 Hz, 1H), 3.55 (d, J=1.5 Hz, 2H), 3.39 (s, 3H), 3.30-3.37 (m, 1H), 2.98 (dd, J=8.0, 15.5 Hz, 1H), 2.45 (d, J=2.5 Hz, 2H), 1.58-1.66 (m, 4H), 1.49-1.56 (m, 12H), 0.94 (q, J=7.5 Hz, 6H).

Step L: (2R,3S)-3-(4,4-diethyl-2-imino-6-oxotetrahydropyrimidin-1(2H)-yl)-N-((1R,2R)-2-hydroxy-2,3-dihydro-1H-inden-1-yl)-2-(methoxymethyl)-2-methyl-2,3-dihydrobenzofuran-5-carboxamide Example 75A A solution of tert-butyl (4,4-diethyl-1-((2R,3S)-5-(((1R,2R)-2-hydroxy-2,3-dihydro-1H-inden-1-yl)carbamoyl)-2-(methoxymethyl)-2-methyl-2,3-dihydrobenzofuran-3-yl)-6-oxotetrahydropyrimidin-2(1H)-ylidene)carbamate 75-12A (5.5 g, 8.86 mmol) in 4N HCl-dioxane (100 mL) was stirred at 27° C. for 1 h. The mixture was concentrated and purified by HPLC (Instrument ACSSH-prepL-K3 Method Column YMC-Triart Prep C18 250*50 mm*10 um Condition water (0.05% ammonia hydroxide v/v)-ACN Begin B 35 End B 55 Gradient Time (min) 15 100% B Hold Time (min) 5 Flow-Rate (mL/min) 110) then freeze-drying to give free base of desired product. The free base product was dissolved in MeCN (50 mL) and conc HCl (2 mL) in water (150 mL) and freeze-drying to afford product (2R,3S)-3-(4,4-diethyl-2-imino-6-oxotetrahydropyrimidin-1(2H)-yl)-N-((1R,2R)-2-hydroxy-2,3-dihydro-1H-inden-1-yl)-2-(methoxymethyl)-2-methyl-2,3-dihydrobenzofuran-5-carboxamide Example 75A.

MS (ESI) m/z: 521.2 (M+H$^+$)

$^1$H NMR (500 MHz, methanol-d$_4$) δ 7.81-8.05 (m, 2H), 7.15-7.30 (m, 4H), 7.06 (d, J=8.5 Hz, 0.38H), 6.89 (d, J=9.0 Hz, 0.6H), 6.38 (s, 0.4H), 5.40-5.47 (m, 1.6H), 4.47-4.53 (m, 1H), 3.66-3.79 (m, 1.4H), 3.53 (d, J=9.5 Hz, 0.6H), 3.40-3.46 (m, 3H), 3.27-3.31 (m, 1H), 2.84-3.09 (m, 2H), 2.56-2.81 (m, 1H), 1.64-1.94 (m, 4H), 1.55 (d, J=14.5 Hz, 3H), 0.93-1.04 (m, 6H).

TABLE 2

| Example | Structure | LC/MS (M + 1)$^+$ | Name |
|---------|-----------|-------------------|------|
| 75B | 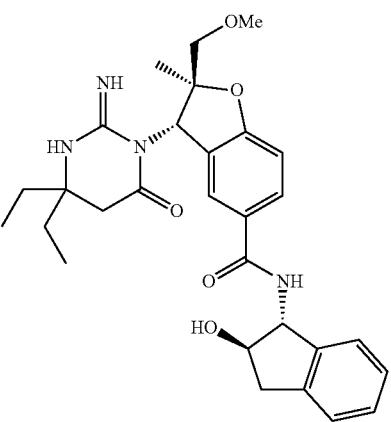 [SMILES: CCC1(CC)CC(=O)N([C@H]2c3cc(C(=O)N[C@@H]4c5ccccc5C[C@H]4O)ccc3O[C@]2(C)COC)C(=N)N1] | 521.2 | (2S,3S)-3-(4,4-diethyl-2-imino-6-oxotetrahydropyrimidin-1(2H)-yl)-N-((1R,2R)-2-hydroxy-2,3-dihydro-1H-inden-1-yl)-2-(methoxymethyl)-2-methyl-2,3-dihydrobenzofuran-5-carboxamide |
| 76A | 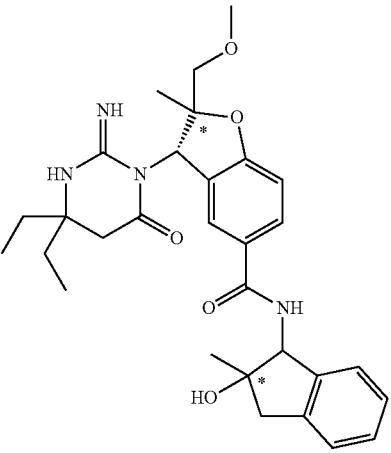 | 535.3 | (2S,3S)-3-(4,4-diethyl-2-imino-6-oxotetrahydropyrimidin-1(2H)-yl)-N-(2-hydroxy-2-methyl-2,3-dihydro-1H-inden-1-yl)-2-(methoxymethyl)-2-methyl-2,3-dihydrobenzofuran-5-carboxamide |

TABLE 2-continued

| Example | Structure | LC/MS (M + 1)+ | Name |
|---|---|---|---|
| 76B | 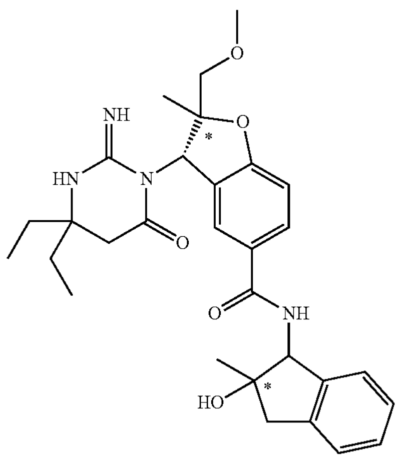 | 535.4 | (2S,3S)-3-(4,4-diethyl-2-imino-6-oxotetrahydropyrimidin-1(2H)-yl)-N-(2-hydroxy-2-methyl-2,3-dihydro-1H-inden-1-yl)-2-(methoxymethyl)-2-methyl-2,3-dihydrobenzofuran-5-carboxamide |
| 77A | 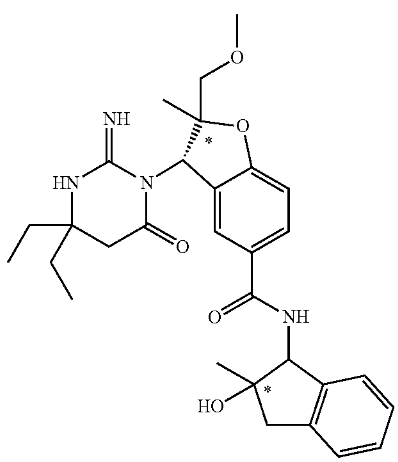 | 535.3 | (2S,3S)-3-(4,4-diethyl-2-imino-6-oxotetrahydropyrimidin-1(2H)-yl)-N-(2-hydroxy-2-methyl-2,3-dihydro-1H-inden-1-yl)-2-(methoxymethyl)-2-methyl-2,3-dihydrobenzofuran-5-carboxamide |
| 77B | 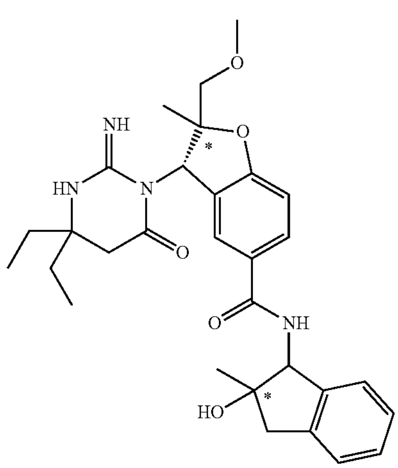 | 535.3 | (2S,3S)-3-(4,4-diethyl-2-imino-6-oxotetrahydropyrimidin-1(2H)-yl)-N-(2-hydroxy-2-methyl-2,3-dihydro-1H-inden-1-yl)-2-(methoxymethyl)-2-methyl-2,3-dihydrobenzofuran-5-carboxamide |

TABLE 2-continued

| Example | Structure | LC/MS (M + 1)+ | Name |
|---|---|---|---|
| 78 | 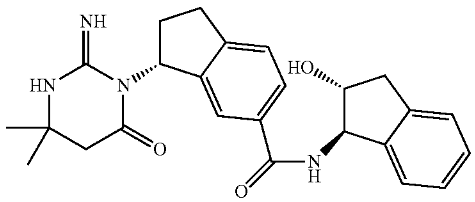 [SMILES: CC1(C)CC(=O)N([C@@H]2CCc3ccc(C(=O)N[C@@H]4c5ccccc5C[C@H]4O)cc32)C(=N)N1] | 433.0 | (3R)-N-[(1R,2R)-2-hydroxyindan-1-yl]-3-(2-imino-4,4-dimethyl-6-oxo-hexahydropyrimidin-1-yl)indane-5-carboxamide |
| 79 | 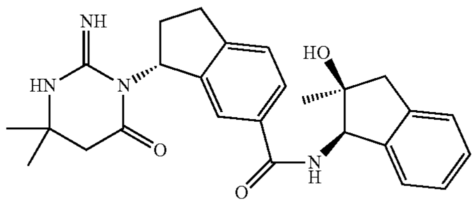 [SMILES: CC1(C)CC(=O)N([C@@H]2CCc3ccc(C(=O)N[C@@H]4c5ccccc5C[C@]4(C)O)cc32)C(=N)N1] | 447.3 | (3R)-N-[(1R,2S)-2-hydroxy-2-methyl-indan-1-yl]-3-(2-imino-4,4-dimethyl-6-oxo-hexahydropyrimidin-1-yl)indane-5-carboxamide |
| 80 | 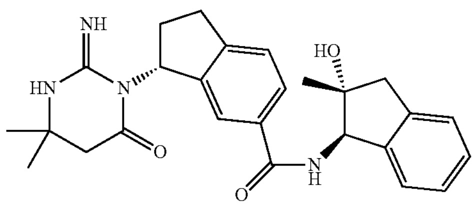 [SMILES: CC1(C)CC(=O)N([C@@H]2CCc3ccc(C(=O)N[C@@H]4c5ccccc5C[C@@]4(C)O)cc32)C(=N)N1] | 447.0 | (3R)-N-[(1R,2R)-2-hydroxy-2-methyl-indan-1-yl]-3-(2-imino-4,4-dimethyl-6-oxo-hexahydropyrimidin-1-yl)indane-5-carboxamide |
| 81 | 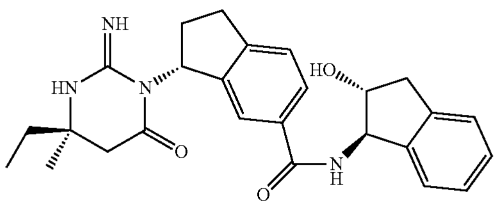 [SMILES: CC[C@]1(C)CC(=O)N([C@@H]2CCc3ccc(C(=O)N[C@@H]4c5ccccc5C[C@H]4O)cc32)C(=N)N1] | 447.3 | (3R)-3-[(4R)-4-ethyl-2-imino-4-methyl-6-oxo-hexahydropyrimidin-1-yl]-N-[(1R,2R)-2-hydroxyindan-1-yl]indane-5-carboxamide |
| 82 | 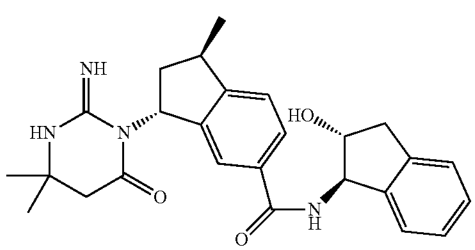 [SMILES: C[C@@H]1C[C@@H](N2C(=N)NC(C)(C)CC2=O)c2cc(C(=O)N[C@@H]3c4ccccc4C[C@H]3O)ccc21] | 447.3 | (1R,3R)-N-[(1R,2R)-2-hydroxyindan-1-yl]-3-(2-imino-4,4-dimethyl-6-oxo-hexahydropyrimidin-1-yl)-1-methyl-indane-5-carboxamide |
| 83 | 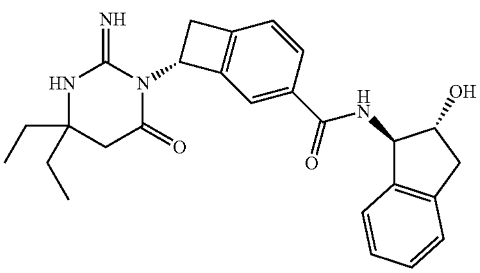 [SMILES: CCC1(CC)CC(=O)N([C@@H]2Cc3ccc(C(=O)N[C@@H]4c5ccccc5C[C@H]4O)cc32)C(=N)N1] | 447.1 | (8R)-8-(4,4-diethyl-2-imino-6-oxo-hexahydropyrimidin-1-yl)-N-[(1R,2R)-2-hydroxyindan-1-yl]bicyclo[4.2.0]octa-1(6),2,4-triene-3-carboxamide |

TABLE 2-continued

| Example | Structure | LC/MS (M + 1)+ | Name |
|---|---|---|---|
| 84 | 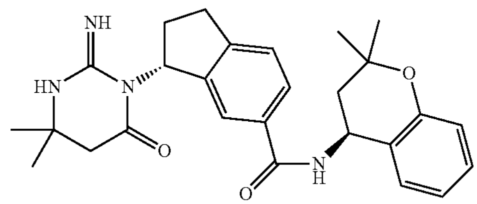 [SMILES: CC1(C)CC(=O)N([C@@H]2CCc3ccc(C(=O)N[C@H]4CC(C)(C)Oc5ccccc54)cc32)C(=N)N1] | 461.1 | (3R)-N-[(4S)-2,2-dimethylchroman-4-yl]-3-(2-imino-4,4-dimethyl-6-oxo-hexahydropyrimidin-1-yl)indane-5-carboxamide |
| 85 | 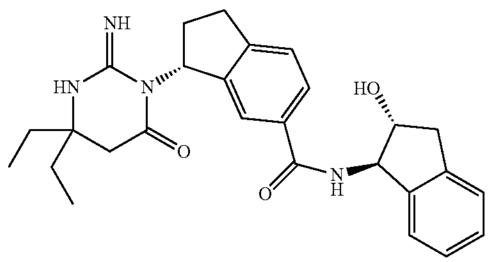 [SMILES: CCC1(CC)CC(=O)N([C@@H]2CCc3ccc(C(=O)N[C@@H]4c5ccccc5C[C@H]4O)cc32)C(=N)N1] | 461.3 | (3R)-3-(4,4-diethyl-2-imino-6-oxo-hexahydropyrimidin-1-yl)-N-[(1R,2R)-2-hydroxyindan-1-yl]indane-5-carboxamide |
| 86 | 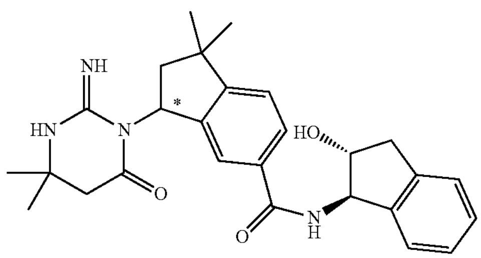 [SMILES: CC1(C)CC(=O)N(C2CC(C)(C)c3ccc(C(=O)N[C@@H]4c5ccccc5C[C@H]4O)cc32)C(=N)N1] | 461.3 | N-[(1R,2R)-2-hydroxyindan-1-yl]-3-(2-imino-4,4-dimethyl-6-oxo-hexahydropyrimidin-1-yl)-1,1-dimethyl-indane-5-carboxamide |
| 87 | 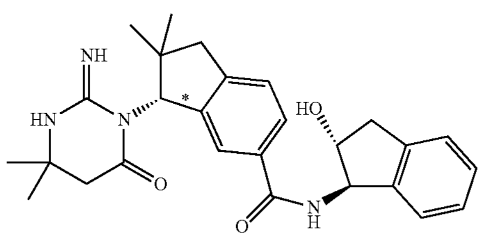 [SMILES: CC1(C)CC(=O)N([C@H]2c3cc(C(=O)N[C@@H]4c5ccccc5C[C@H]4O)ccc3CC2(C)C)C(=N)N1] | 461.3 | N-[(1R,2R)-2-hydroxyindan-1-yl]-3-(2-imino-4,4-dimethyl-6-oxo-hexahydropyrimidin-1-yl)-2,2-dimethyl-indane-5-carboxamide |
| 88 | 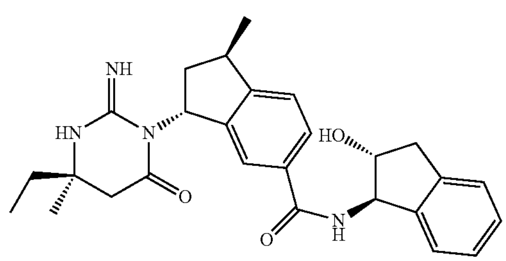 [SMILES: CC[C@]1(C)CC(=O)N([C@@H]2C[C@@H](C)c3ccc(C(=O)N[C@@H]4c5ccccc5C[C@H]4O)cc32)C(=N)N1] | 461.3 | (1R,3R)-3-[(4R)-4-ethyl-2-imino-4-methyl-6-oxo-hexahydropyrimidin-1-yl]-N-[(1R,2R)-2-hydroxyindan-1-yl]-1-methyl-indane-5-carboxamide |
| 89 | 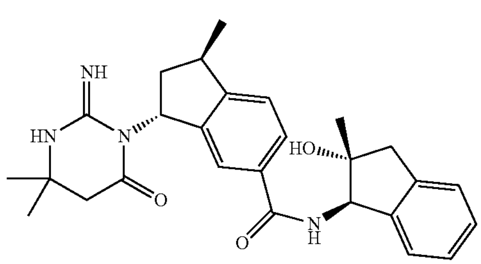 [SMILES: C[C@@H]1C[C@@H](N2C(=N)NC(C)(C)CC2=O)c2cc(C(=O)N[C@@H]3c4ccccc4C[C@@]3(C)O)ccc21] | 461.3 | (1R,3R)-N-[(1R,2R)-2-hydroxy-2-methyl-indan-1-yl]-3-(2-imino-4,4-dimethyl-6-oxo-hexahydropyrimidin-1-yl)-1-methyl-indane-5-carboxamide |

TABLE 2-continued

| Example | Structure | LC/MS (M + 1)+ | Name |
|---|---|---|---|
| 90 | 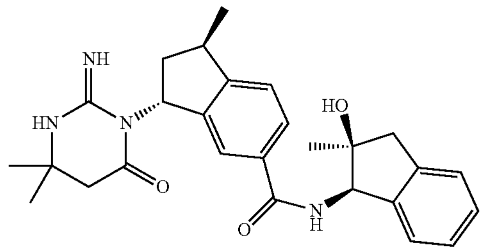 [SMILES: C[C@@H]1C[C@@H](N2C(=N)NC(C)(C)CC2=O)c2cc(C(=O)N[C@@H]3c4ccccc4C[C@]3(C)O)ccc21] | 461.3 | (1R,3R)-N-[(1R,2S)-2-hydroxy-2-methyl-indan-1-yl]-3-(2-imino-4,4-dimethyl-6-oxo-hexahydropyrimidin-1-yl)-1-methyl-indane-5-carboxamide |
| 91 | 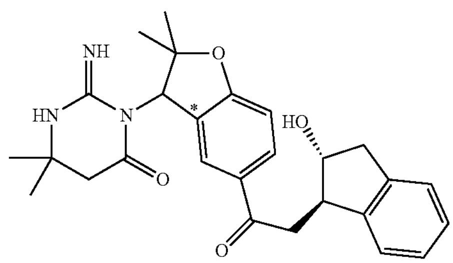 [SMILES: CC1(C)CC(=O)N(C2c3cc(C(=O)C[C@@H]4c5ccccc5C[C@H]4O)ccc3OC2(C)C)C(=N)N1] | 463.1 | N-[(1R,2R)-2-hydroxyindan-1-yl]-3-(2-imino-4,4-dimethyl-6-oxo-hexahydropyrimidin-1-yl)-2,2-dimethyl-3H-benzofuran-5-carboxamide |
| 92 | 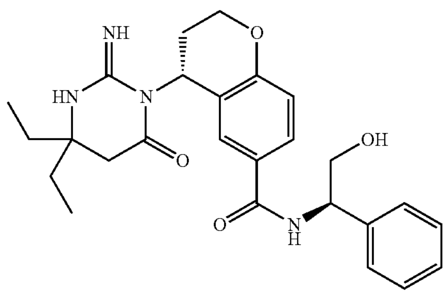 [SMILES: CCC1(CC)CC(=O)N([C@@H]2CCOc3ccc(C(=O)N[C@@H](CO)c4ccccc4)cc32)C(=N)N1] | 465.3 | (4R)-4-(4,4-diethyl-2-imino-6-oxo-hexahydropyrimidin-1-yl)-N-[(1R)-2-hydroxy-1-phenyl-ethyl]chromane-6-carboxamide |
| 93 | 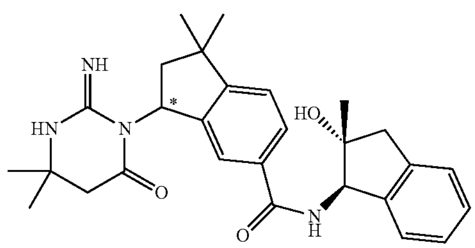 [SMILES: CC1(C)CC(=O)N(C2CC(C)(C)c3ccc(C(=O)N[C@@H]4c5ccccc5C[C@@]4(C)O)cc32)C(=N)N1] | 475.3 | N-[(1R,2R)-2-hydroxy-2-methyl-indan-1-yl]-3-(2-imino-4,4-dimethyl-6-oxo-hexahydropyrimidin-1-yl)-1,1-dimethyl-indane-5-carboxamide |
| 94 | 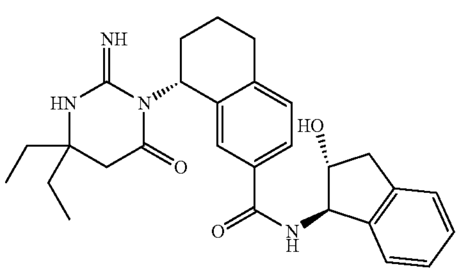 [SMILES: CCC1(CC)CC(=O)N([C@@H]2CCCc3ccc(C(=O)N[C@@H]4c5ccccc5C[C@H]4O)cc32)C(=N)N1] | 475.3 | (4R)-4-(4,4-diethyl-2-imino-6-oxo-hexahydropyrimidin-1-yl)-N-[(1R,2R)-2-hydroxyindan-1-yl]tetralin-6-carboxamide |

TABLE 2-continued

| Example | Structure | LC/MS (M + 1)+ | Name |
|---|---|---|---|
| 95 | 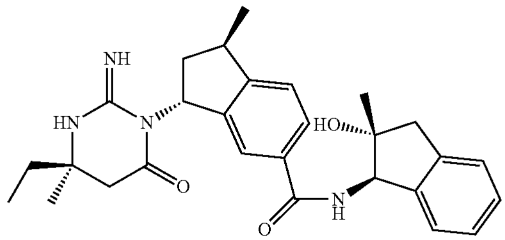 [SMILES: CC[C@]1(C)CC(=O)N([C@@H]2C[C@@H](C)c3ccc(C(=O)N[C@@H]4c5ccccc5C[C@@]4(C)O)cc32)C(=N)N1] | 475.3 | (1R,3R)-3-[(4R)-4-ethyl-2-imino-4-methyl-6-oxo-hexahydropyrimidin-1-yl]-N-[(1R,2R)-2-hydroxy-2-methyl-indan-1-yl]-1-methyl-indane-5-carboxamide |
| 96 | 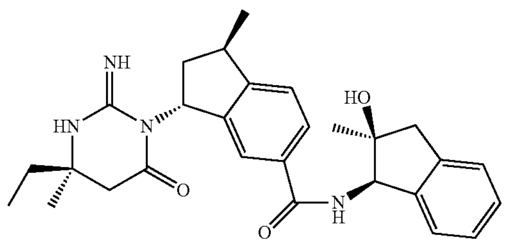 [SMILES: CC[C@]1(C)CC(=O)N([C@@H]2C[C@@H](C)c3ccc(C(=O)N[C@@H]4c5ccccc5C[C@]4(C)O)cc32)C(=N)N1] | 475.3 | (1R,3R)-3-[(4R)-4-ethyl-2-imino-4-methyl-6-oxo-hexahydropyrimidin-1-yl]-N-[(1R,2S)-2-hydroxy-2-methyl-indan-1-yl]-1-methyl-indane-5-carboxamide |
| 97 | 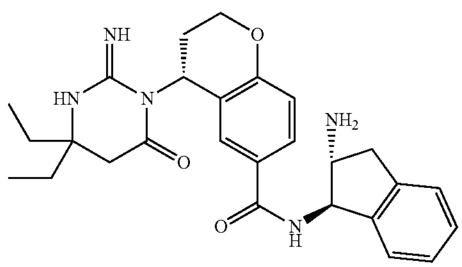 [SMILES: CCC1(CC)CC(=O)N([C@@H]2CCOc3ccc(C(=O)N[C@@H]4c5ccccc5C[C@H]4N)cc32)C(=N)N1] | 476.2 | (4R)-N-[(1R,2R)-2-aminoindan-1-yl]-4-(4,4-diethyl-2-imino-6-oxo-hexahydropyrimidin-1-yl)chromane-6-carboxamide |
| 98 | 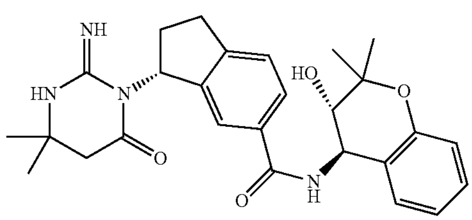 [SMILES: CC1(C)CC(=O)N([C@@H]2CCc3ccc(C(=O)N[C@@H]4c5ccccc5OC(C)(C)[C@H]4O)cc32)C(=N)N1] | 477.1 | (3R)-N-[(3S,4R)-3-hydroxy-2,2-dimethyl-chroman-4-yl]-3-(2-imino-4,4-dimethyl-6-oxo-hexahydropyrimidin-1-yl)indane-5-carboxamide |
| 99 | 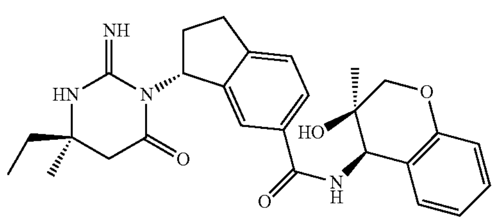 [SMILES: CC[C@]1(C)CC(=O)N([C@@H]2CCc3ccc(C(=O)N[C@@H]4c5ccccc5OC[C@]4(C)O)cc32)C(=N)N1] | 477.4 | (3R)-3-[(4R)-4-ethyl-2-imino-4-methyl-6-oxo-hexahydropyrimidin-1-yl]-N-[(3R,4R)-3-hydroxy-3-methyl-chroman-4-yl]indane-5-carboxamide |
| 100 | 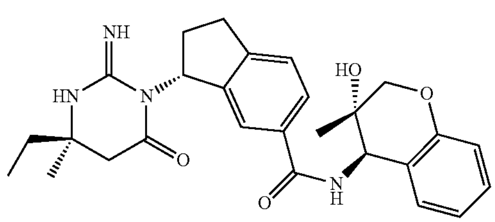 [SMILES: CC[C@]1(C)CC(=O)N([C@@H]2CCc3ccc(C(=O)N[C@@H]4c5ccccc5OC[C@@]4(C)O)cc32)C(=N)N1] | 477.3 | (3R)-3-[(4R)-4-ethyl-2-imino-4-methyl-6-oxo-hexahydropyrimidin-1-yl]-N-[(3S,4R)-3-hydroxy-3-methyl-chroman-4-yl]indane-5-carboxamide |

TABLE 2-continued

| Example | Structure | LC/MS (M + 1)+ | Name |
|---|---|---|---|
| 101 | 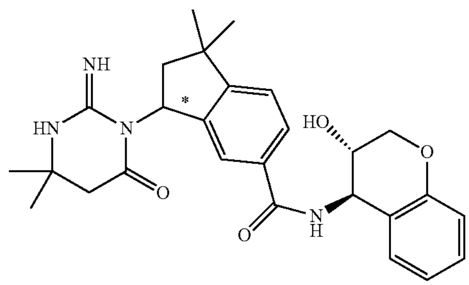 [SMILES: CC1(C)CC(=O)N(C2CC(C)(C)c3ccc(C(=O)N[C@@H]4c5ccccc5OC[C@H]4O)cc32)C(=N)N1] | 477.3 | N-[(3S,4R)-3-hydroxychroman-4-yl]-3-(2-imino-4,4-dimethyl-6-oxo-hexahydropyrimidin-1-yl)-1,1-dimethyl-indane-5-carboxamide |
| 102 | 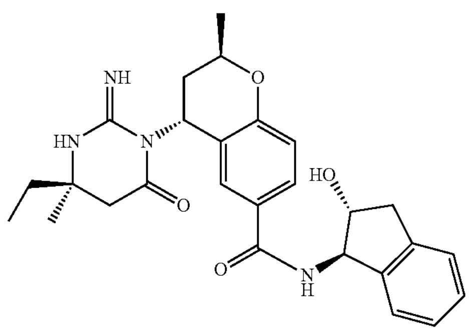 [SMILES: CC[C@]1(C)CC(=O)N([C@@H]2C[C@@H](C)Oc3ccc(C(=O)N[C@@H]4c5ccccc5C[C@H]4O)cc32)C(=N)N1] | 477.3 | (2R,4R)-4-[(4R)-4-ethyl-2-imino-4-methyl-6-oxo-hexahydropyrimidin-1-yl]-N-[(1R,2R)-2-hydroxyindan-1-yl]-2-methyl-chromane-6-carboxamide |
| 103 | 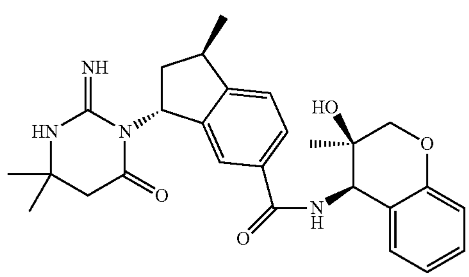 [SMILES: C[C@@H]1C[C@@H](N2C(=N)NC(C)(C)CC2=O)c2cc(C(=O)N[C@@H]3c4ccccc4OC[C@]3(C)O)ccc21] | 477.3 | (1R,3R)-N-[(3R,4R)-3-hydroxy-3-methyl-chroman-4-yl]-3-(2-imino-4,4-dimethyl-6-oxo-hexahydropyrimidin-1-yl)-1-methyl-indane-5-carboxamide |
| 104 | 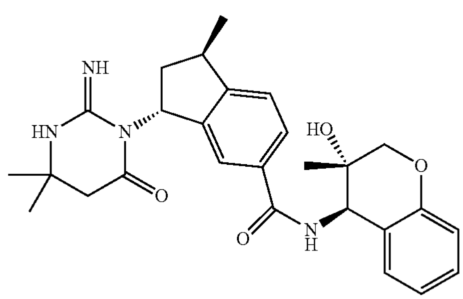 [SMILES: C[C@@H]1C[C@@H](N2C(=N)NC(C)(C)CC2=O)c2cc(C(=O)N[C@@H]3c4ccccc4OC[C@@]3(C)O)ccc21] | 477.2 | (1R,3R)-N-[(3S,4R)-3-hydroxy-3-methyl-chroman-4-yl]-3-(2-imino-4,4-dimethyl-6-oxo-hexahydropyrimidin-1-yl)-1-methyl-indane-5-carboxamide |
| 105 | 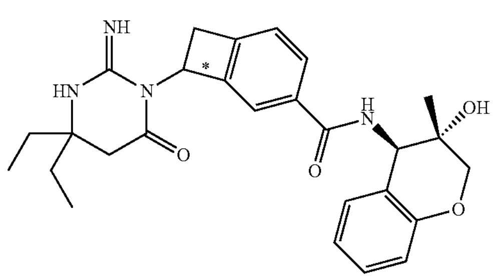 [SMILES: CCC1(CC)CC(=O)N(C2Cc3ccc(C(=O)N[C@@H]4c5ccccc5OC[C@@]4(C)O)cc32)C(=N)N1] | 477.1 | 8-(4,4-diethyl-2-imino-6-oxo-hexahydropyrimidin-1-yl)-N-[(3S,4R)-3-hydroxy-3-methyl-chroman-4-yl]bicyclo[4.2.0]octa-1(6),2,4-triene-3-carboxamide |

TABLE 2-continued

| Example | Structure | LC/MS (M + 1)+ | Name |
|---|---|---|---|
| 106 | 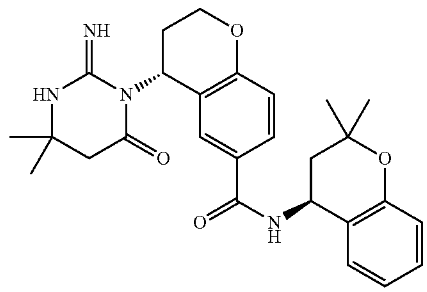 [SMILES: CC1(C)CC(=O)N([C@@H]2CCOc3ccc(C(=O)N[C@H]4CC(C)(C)Oc5ccccc54)cc32)C(=N)N1] | 477.3 | (4R)-N-[(4S)-2,2-dimethylchroman-4-yl]-4-(2-imino-4,4-dimethyl-6-oxo-hexahydropyrimidin-1-yl)chromane-6-carboxamide |
| 107 | 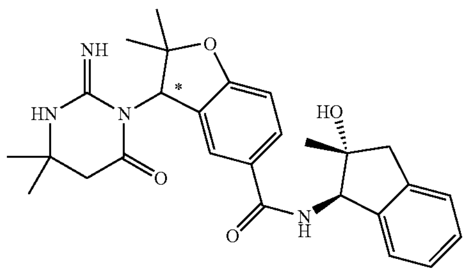 [SMILES: CC1(C)CC(=O)N(C2c3cc(C(=O)N[C@@H]4c5ccccc5C[C@@]4(C)O)ccc3OC2(C)C)C(=N)N1] | 477.3 | N-[(1R,2R)-2-hydroxy-2-methyl-indan-1-yl]-3-(2-imino-4,4-dimethyl-6-oxo-hexahydropyrimidin-1-yl)-2,2-dimethyl-3H-benzofuran-5-carboxamide |
| 108 | 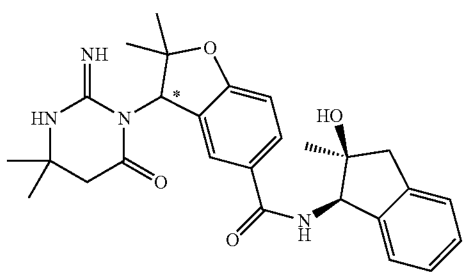 [SMILES: CC1(C)CC(=O)N(C2c3cc(C(=O)N[C@@H]4c5ccccc5C[C@]4(C)O)ccc3OC2(C)C)C(=N)N1] | 477.3 | N-[(1R,2S)-2-hydroxy-2-methyl-indan-1-yl]-3-(2-imino-4,4-dimethyl-6-oxo-hexahydropyrimidin-1-yl)-2,2-dimethyl-3H-benzofuran-5-carboxamide |
| 109 | 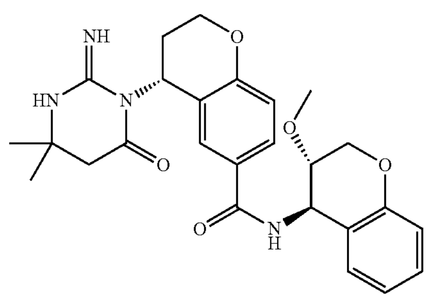 [SMILES: CO[C@@H]1COc2ccccc2[C@H]1NC(=O)c1ccc2c(c1)[C@H](N1C(=N)NC(C)(C)CC1=O)CCO2] | 479.2 | (4R)-4-(2-imino-4,4-dimethyl-6-oxo-hexahydropyrimidin-1-yl)-N-[(3S,4R)-3-methoxychroman-4-yl]chromane-6-carboxamide |
| 110 | 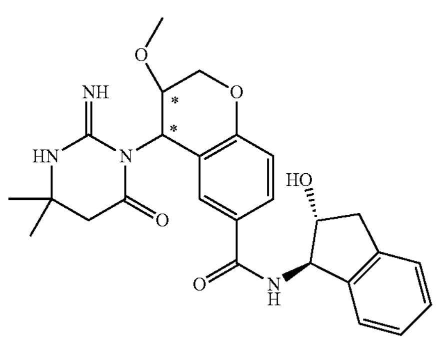 [SMILES: COC1COc2ccc(C(=O)N[C@@H]3c4ccccc4C[C@H]3O)cc2C1N1C(=N)NC(C)(C)CC1=O] | 479.2 | N-[(1R,2R)-2-hydroxyindan-1-yl]-4-(2-imino-4,4-dimethyl-6-oxo-hexahydropyrimidin-1-yl)-3-methoxy-chromane-6-carboxamide |

TABLE 2-continued

| Example | Structure | LC/MS (M + 1)+ | Name |
|---|---|---|---|
| 111 | 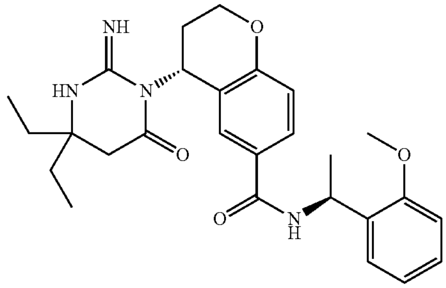 [SMILES: CCC1(CC)CC(=O)N([C@@H]2CCOc3ccc(C(=O)N[C@@H](C)c4ccccc4OC)cc32)C(=N)N1] | 479.3 | (4R)-4-(4,4-diethyl-2-imino-6-oxo-hexahydropyrimidin-1-yl)-N-[(1S)-1-(2-methoxyphenyl)ethyl]chromane-6-carboxamide |
| 112 | 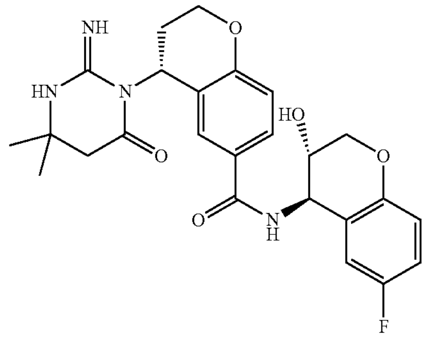 [SMILES: CC1(C)CC(=O)N([C@@H]2CCOc3ccc(C(=O)N[C@@H]4c5cc(F)ccc5OC[C@H]4O)cc32)C(=N)N1] | 483.3 | (4R)-N-[(3S,4R)-6-fluoro-3-hydroxy-chroman-4-yl]-4-(2-imino-4,4-dimethyl-6-oxo-hexahydropyrimidin-1-yl)chromane-6-carboxamide |
| 113 | 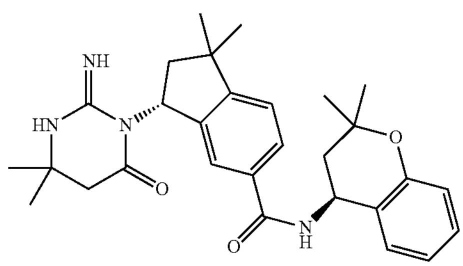 [SMILES: CC1(C)CC(=O)N([C@@H]2CC(C)(C)c3ccc(C(=O)N[C@H]4CC(C)(C)Oc5ccccc54)cc32)C(=N)N1] | 489.3 | (3R)-N-[(4S)-2,2-dimethylchroman-4-yl]-3-(2-imino-4,4-dimethyl-6-oxo-hexahydropyrimidin-1-yl)-1,1-dimethyl-indane-5-carboxamide |
| 114 | 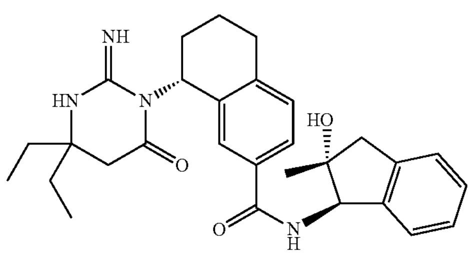 [SMILES: CCC1(CC)CC(=O)N([C@@H]2CCCc3ccc(C(=O)N[C@@H]4c5ccccc5C[C@@]4(C)O)cc32)C(=N)N1] | 489.3 | (4R)-4-(4,4-diethyl-2-imino-6-oxo-hexahydropyrimidin-1-yl)-N-[(1R,2R)-2-hydroxy-2-methyl-indan-1-yl]tetralin-6-carboxamide |
| 115 | 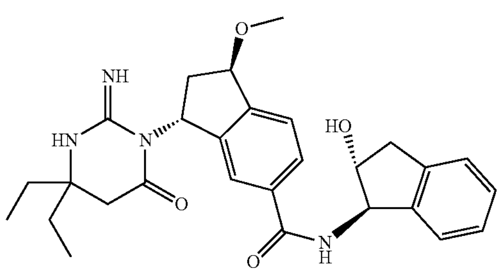 [SMILES: CCC1(CC)CC(=O)N([C@@H]2C[C@@H](OC)c3ccc(C(=O)N[C@@H]4c5ccccc5C[C@H]4O)cc32)C(=N)N1] | 491.3 | (1R,3R)-3-(4,4-diethyl-2-imino-6-oxo-hexahydropyrimidin-1-yl)-N-[(1R,2R)-2-hydroxyindan-1-yl]-1-methoxy-indane-5-carboxamide |

TABLE 2-continued

| Example | Structure | LC/MS (M + 1)+ | Name |
|---|---|---|---|
| 116 | 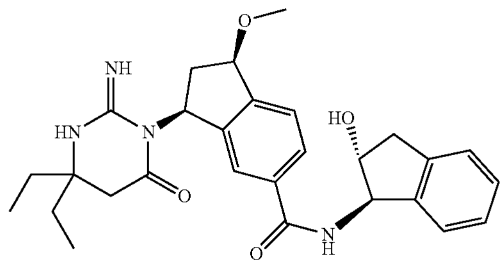 [SMILES: CCC1(CC)CC(=O)N([C@H]2C[C@@H](OC)c3ccc(C(=O)N[C@@H]4c5ccccc5C[C@H]4O)cc32)C(=N)N1] | 491.3 | (1R,3S)-3-(4,4-diethyl-2-imino-6-oxo-hexahydropyrimidin-1-yl)-N-[(1R,2R)-2-hydroxyindan-1-yl]-1-methoxy-indane-5-carboxamide |
| 117 | 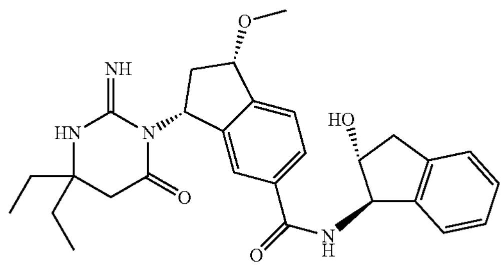 [SMILES: CCC1(CC)CC(=O)N([C@@H]2C[C@H](OC)c3ccc(C(=O)N[C@@H]4c5ccccc5C[C@H]4O)cc32)C(=N)N1] | 491.3 | (1S,3R)-3-(4,4-diethyl-2-imino-6-oxo-hexahydropyrimidin-1-yl)-N-[(1R,2R)-2-hydroxyindan-1-yl]-1-methoxy-indane-5-carboxamide |
| 118 | 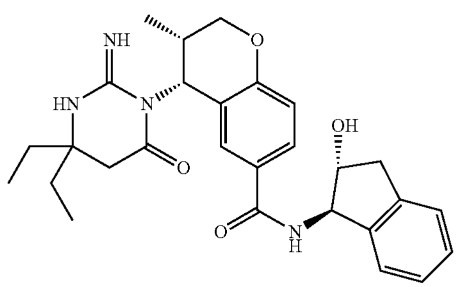 [SMILES: CCC1(CC)CC(=O)N([C@H]2c3cc(C(=O)N[C@@H]4c5ccccc5C[C@H]4O)ccc3OC[C@H]2C)C(=N)N1] | 491.3 | (3S,4R)-4-(4,4-diethyl-2-imino-6-oxo-hexahydropyrimidin-1-yl)-N-[(1R,2R)-2-hydroxyindan-1-yl]-3-methyl-chromane-6-carboxamide |
| 119 | 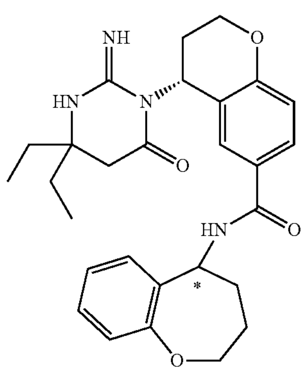 [SMILES: CCC1(CC)CC(=O)N([C@@H]2CCOc3ccc(C(=O)NC4CCCOc5ccccc54)cc32)C(=N)N1] | 491.3 | (4R)-4-(4,4-diethyl-2-imino-6-oxo-hexahydropyrimidin-1-yl)-N-(2,3,4,5-tetrahydro-1-benzoxepin-5-yl)chromane-6-carboxamide |
| 120 | 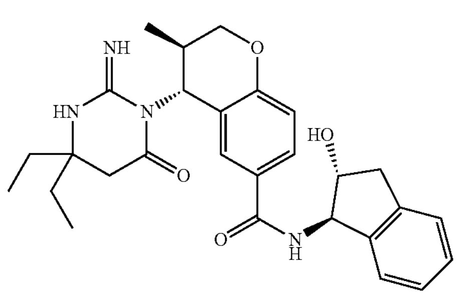 [SMILES: CCC1(CC)CC(=O)N([C@H]2c3cc(C(=O)N[C@@H]4c5ccccc5C[C@H]4O)ccc3OC[C@@H]2C)C(=N)N1] | 491.3 | (3R,4R)-4-(4,4-diethyl-2-imino-6-oxo-hexahydropyrimidin-1-yl)-N-[(1R,2R)-2-hydroxyindan-1-yl]-3-methyl-chromane-6-carboxamide |

TABLE 2-continued

| Example | Structure | LC/MS (M + 1)+ | Name |
|---|---|---|---|
| 121 | 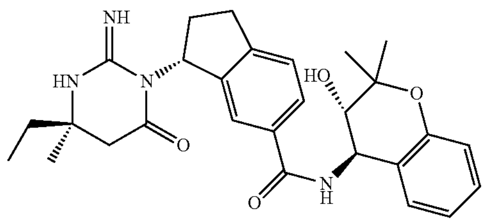 [SMILES: CC[C@]1(C)CC(=O)N([C@@H]2CCc3ccc(C(=O)N[C@@H]4c5ccccc5OC(C)(C)[C@H]4O)cc32)C(=N)N1] | 491.3 | (3R)-3-[(4R)-4-ethyl-2-imino-4-methyl-6-oxo-hexahydropyrimidin-1-yl]-N-[(3S,4R)-3-hydroxy-2,2-dimethyl-chroman-4-yl]indane-5-carboxamide |
| 122 | 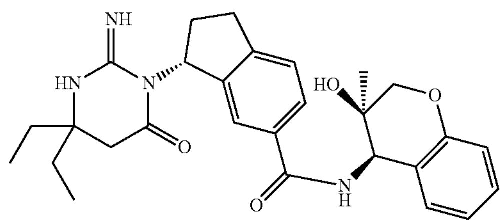 [SMILES: CCC1(CC)CC(=O)N([C@@H]2CCc3ccc(C(=O)N[C@@H]4c5ccccc5OC[C@]4(C)O)cc32)C(=N)N1] | 491.3 | (3R)-3-(4,4-diethyl-2-imino-6-oxo-hexahydropyrimidin-1-yl)-N-[(3R,4R)-3-hydroxy-3-methyl-chroman-4-yl]indane-5-carboxamide |
| 123 | 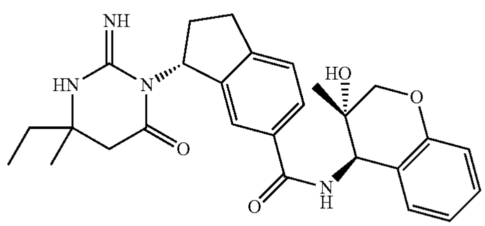 [SMILES: CCC1(C)CC(=O)N([C@@H]2CCc3ccc(C(=O)N[C@@H]4c5ccccc5OC[C@@]4(C)O)cc32)C(=N)N1] | 491.3 | (3R)-3-(4,4-diethyl-2-imino-6-oxo-hexahydropyrimidin-1-yl)-N-[(3S,4R)-3-hydroxy-3-methyl-chroman-4-yl]indane-5-carboxamide |
| 124 | 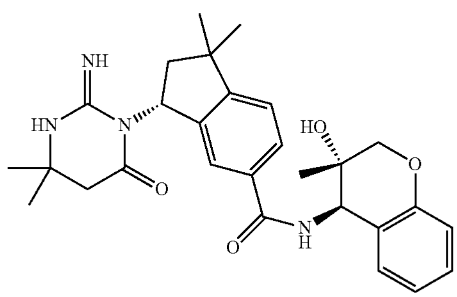 [SMILES: CC1(C)CC(=O)N([C@@H]2CC(C)(C)c3ccc(C(=O)N[C@@H]4c5ccccc5OC[C@@]4(C)O)cc32)C(=N)N1] | 491.3 | (3R)-N-[(3S,4R)-3-hydroxy-3-methyl-chroman-4-yl]-3-(2-imino-4,4-dimethyl-6-oxo-hexahydropyrimidin-1-yl)-1,1-dimethyl-indane-5-carboxamide |
| 125 | 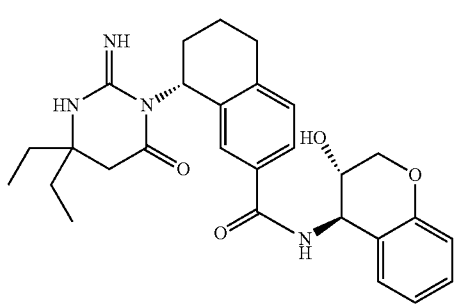 [SMILES: CCC1(CC)CC(=O)N([C@@H]2CCCc3ccc(C(=O)N[C@@H]4c5ccccc5OC[C@H]4O)cc32)C(=N)N1] | 491.3 | (4R)-4-(4,4-diethyl-2-imino-6-oxo-hexahydropyrimidin-1-yl)-N-[(3S,4R)-3-hydroxychroman-4-yl]tetralin-6-carboxamide |

TABLE 2-continued

| Example | Structure | LC/MS (M + 1)+ | Name |
|---|---|---|---|
| 126 | 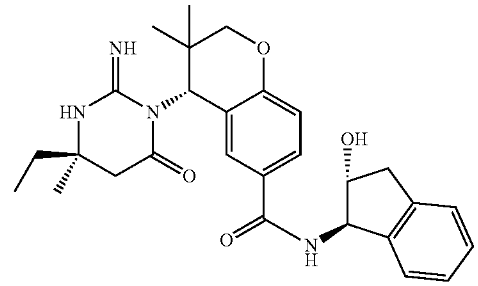 [SMILES: CC[C@]1(C)CC(=O)N([C@H]2c3cc(C(=O)N[C@@H]4c5ccccc5C[C@H]4O)ccc3OCC2(C)C)C(=N)N1] | 491.3 | (4R)-4-[(4R)-4-ethyl-2-imino-4-methyl-6-oxo-hexahydropyrimidin-1-yl]-N-[(1R,2R)-2-hydroxyindan-1-yl]-3,3-dimethyl-chromane-6-carboxamide |
| 127A | 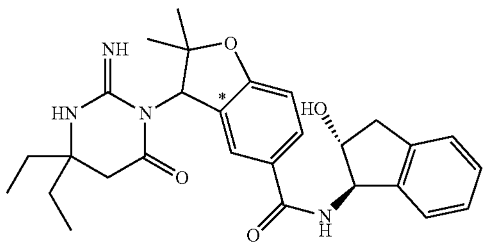 [SMILES: CCC1(CC)CC(=O)N(C2c3cc(C(=O)N[C@@H]4c5ccccc5C[C@H]4O)ccc3OC2(C)C)C(=N)N1] | 491.3 | 3-(4,4-diethyl-2-imino-6-oxo-hexahydropyrimidin-1-yl)-N-[(1R,2R)-2-hydroxyindan-1-yl]-2,2-dimethyl-3H-benzofuran-5-carboxamide |
| 127B | 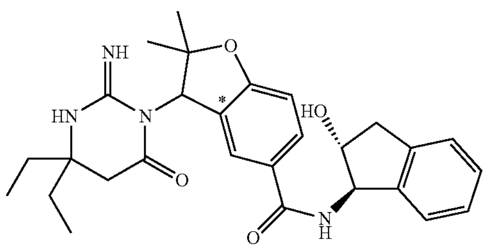 [SMILES: CCC1(CC)CC(=O)N(C2c3cc(C(=O)N[C@@H]4c5ccccc5C[C@H]4O)ccc3OC2(C)C)C(=N)N1] | 491.3 | 3-(4,4-diethyl-2-imino-6-oxo-hexahydropyrimidin-1-yl)-N-[(1R,2R)-2-hydroxyindan-1-yl]-2,2-dimethyl-3H-benzofuran-5-carboxamide |
| 128 | 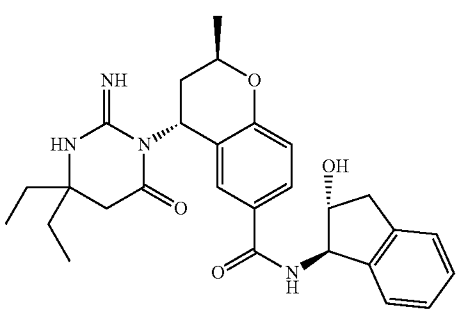 [SMILES: CCC1(CC)CC(=O)N([C@@H]2C[C@@H](C)Oc3ccc(C(=O)N[C@@H]4c5ccccc5C[C@H]4O)cc32)C(=N)N1] | 491.3 | (2R,4R)-4-(4,4-diethyl-2-imino-6-oxo-hexahydropyrimidin-1-yl)-N-[(1R,2R)-2-hydroxyindan-1-yl]-2-methyl-chromane-6-carboxamide |
| 129 | 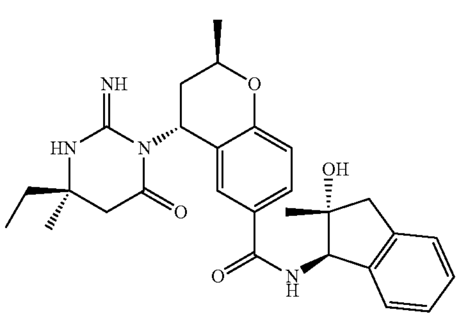 [SMILES: CC[C@]1(C)CC(=O)N([C@@H]2C[C@@H](C)Oc3ccc(C(=O)N[C@@H]4c5ccccc5C[C@@]4(C)O)cc32)C(=N)N1] | 491.3 | (2R,4R)-4-[(4R)-4-ethyl-2-imino-4-methyl-6-oxo-hexahydropyrimidin-1-yl]-N-[(1R,2R)-2-hydroxy-2-methyl-indan-1-yl]-2-methyl-chromane-6-carboxamide |

TABLE 2-continued

| Example | Structure | LC/MS (M + 1)+ | Name |
|---|---|---|---|
| 130 | 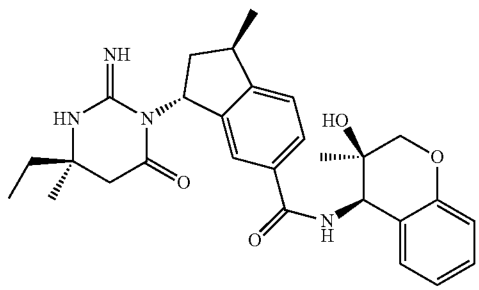 [SMILES: CC[C@]1(C)CC(=O)N([C@@H]2C[C@@H](C)c3ccc(C(=O)N[C@@H]4c5ccccc5OC[C@]4(C)O)cc32)C(=N)N1] | 491.3 | (1R,3R)-3-[(4R)-4-ethyl-2-imino-4-methyl-6-oxo-hexahydropyrimidin-1-yl]-N-[(3R,4R)-3-hydroxy-3-methyl-chroman-4-yl]-1-methyl-indane-5-carboxamide |
| 131 | 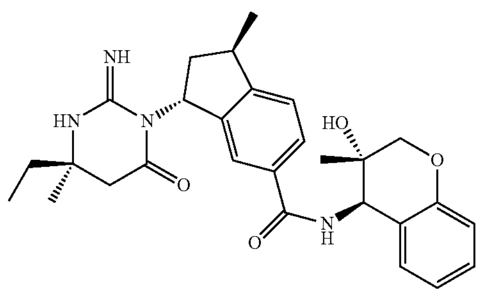 [SMILES: CC[C@]1(C)CC(=O)N([C@@H]2C[C@@H](C)c3ccc(C(=O)N[C@@H]4c5ccccc5OC[C@@]4(C)O)cc32)C(=N)N1] | 491.2 | (1R,3R)-3-[(4R)-4-ethyl-2-imino-4-methyl-6-oxo-hexahydropyrimidin-1-yl]-N-[(3S,4R)-3-hydroxy-3-methyl-chroman-4-yl]-1-methyl-indane-5-carboxamide |
| 132 | 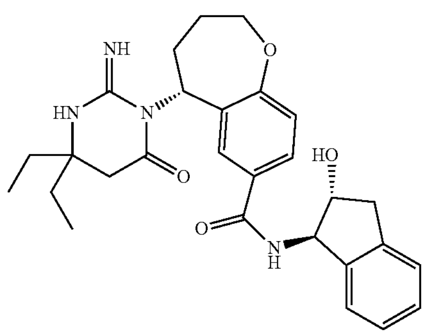 [SMILES: CCC1(CC)CC(=O)N([C@@H]2CCCOc3ccc(C(=O)N[C@@H]4c5ccccc5C[C@H]4O)cc32)C(=N)N1] | 491.1 | (5R)-5-(4,4-diethyl-2-imino-6-oxo-hexahydropyrimidin-1-yl)-N-[(1R,2R)-2-hydroxyindan-1-yl]-2,3,4,5-tetrahydro-1-benzoxepine-7-carboxamide |
| 133A | 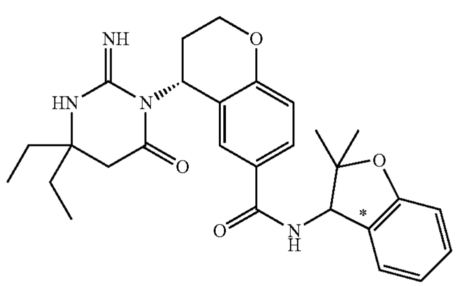 [SMILES: CCC1(CC)CC(=O)N([C@@H]2CCOc3ccc(C(=O)NC4c5ccccc5OC4(C)C)cc32)C(=N)N1] | 491.3 | (4R)-4-(4,4-diethyl-2-imino-6-oxo-hexahydropyrimidin-1-yl)-N-(2,2-dimethyl-3H-benzofuran-3-yl)chromane-6-carboxamide |
| 133B | 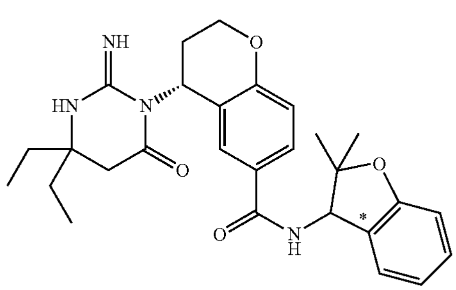 [SMILES: CCC1(CC)CC(=O)N([C@@H]2CCOc3ccc(C(=O)NC4c5ccccc5OC4(C)C)cc32)C(=N)N1] | 491.3 | (4R)-4-(4,4-diethyl-2-imino-6-oxo-hexahydropyrimidin-1-yl)-N-(2,2-dimethyl-3H-benzofuran-3-yl)chromane-6-carboxamide |

TABLE 2-continued

| Example | Structure | LC/MS (M + 1)+ | Name |
|---|---|---|---|
| 134 | 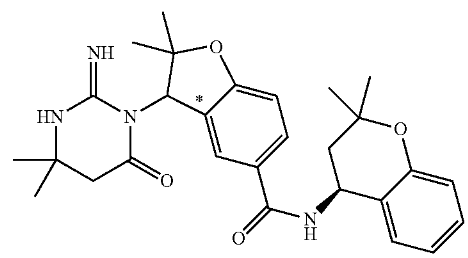 [SMILES: CC1(C)CC(=O)N(C2c3cc(C(=O)N[C@H]4CC(C)(C)Oc5ccccc54)ccc3OC2(C)C)C(=N)N1] | 491.3 | N-[(4S)-2,2-dimethylchroman-4-yl]-3-(2-imino-4,4-dimethyl-6-oxo-hexahydropyrimidin-1-yl)-2,2-dimethyl-3H-benzofuran-5-carboxamide |
| 135 | 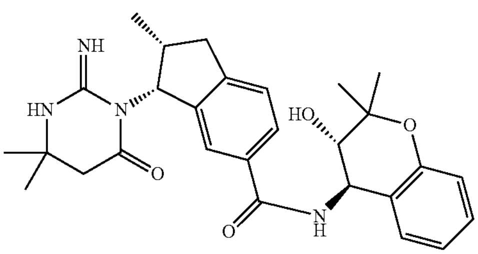 [SMILES: C[C@@H]1Cc2ccc(C(=O)N[C@@H]3c4ccccc4OC(C)(C)[C@H]3O)cc2[C@@H]1N1C(=N)NC(C)(C)CC1=O] | 491.3 | (2R,3R)-N-[(3S,4R)-3-hydroxy-2,2-dimethyl-chroman-4-yl]-3-(2-imino-4,4-dimethyl-6-oxo-hexahydropyrimidin-1-yl)-2-methyl-indane-5-carboxamide |
| 136 | 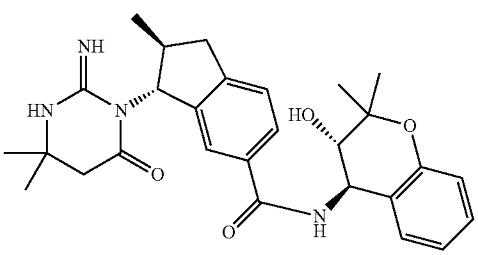 [SMILES: C[C@H]1Cc2ccc(C(=O)N[C@@H]3c4ccccc4OC(C)(C)[C@H]3O)cc2[C@@H]1N1C(=N)NC(C)(C)CC1=O] | 491.3 | (2S,3R)-N-[(3S,4R)-3-hydroxy-2,2-dimethyl-chroman-4-yl]-3-(2-imino-4,4-dimethyl-6-oxo-hexahydropyrimidin-1-yl)-2-methyl-indane-5-carboxamide |
| 137 | 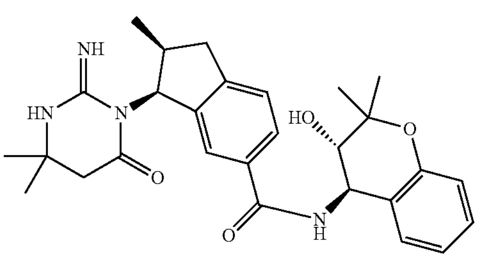 [SMILES: C[C@H]1Cc2ccc(C(=O)N[C@@H]3c4ccccc4OC(C)(C)[C@H]3O)cc2[C@H]1N1C(=N)NC(C)(C)CC1=O] | 491.3 | (2S,3S)-N-[(3S,4R)-3-hydroxy-2,2-dimethyl-chroman-4-yl]-3-(2-imino-4,4-dimethyl-6-oxo-hexahydropyrimidin-1-yl)-2-methyl-indane-5-carboxamide |
| 138 | 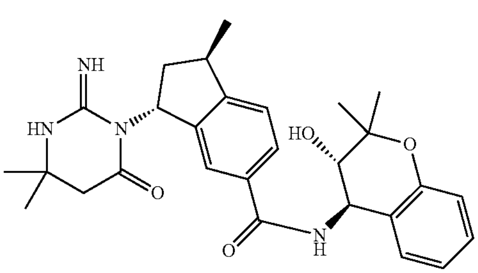 [SMILES: C[C@@H]1C[C@@H](N2C(=N)NC(C)(C)CC2=O)c2cc(C(=O)N[C@@H]3c4ccccc4OC(C)(C)[C@H]3O)ccc21] | 491.3 | (1R,3R)-N-[(3S,4R)-3-hydroxy-2,2-dimethyl-chroman-4-yl]-3-(2-imino-4,4-dimethyl-6-oxo-hexahydropyrimidin-1-yl)-1-methyl-indane-5-carboxamide |

TABLE 2-continued

| Example | Structure | LC/MS (M + 1)+ | Name |
|---|---|---|---|
| 139 | 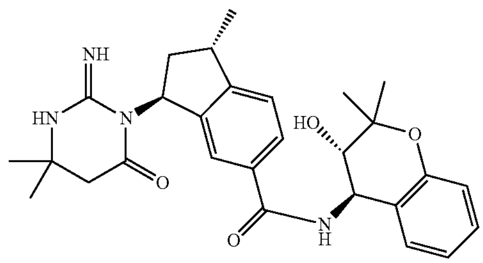 [SMILES: C[C@H]1C[C@H](N2C(=N)NC(C)(C)CC2=O)c2cc(C(=O)N[C@@H]3c4ccccc4OC(C)(C)[C@H]3O)ccc21] | 491.3 | (1S,3S)-N-[(3S,4R)-3-hydroxy-2,2-dimethyl-chroman-4-yl]-3-(2-imino-4,4-dimethyl-6-oxo-hexahydropyrimidin-1-yl)-1-methyl-indane-5-carboxamide |
| 140A | 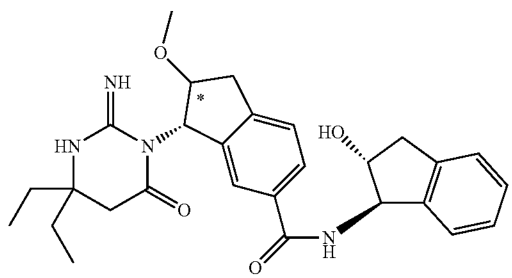 [SMILES: CCC1(CC)CC(=O)N([C@H]2c3cc(C(=O)N[C@@H]4c5ccccc5C[C@H]4O)ccc3CC2OC)C(=N)N1] | 491.3 | (3S)-3-(4,4-diethyl-1-imino-6-oxo-hexahydropyrimidin-1-yl)-N-[(1R,2R)-2-hydroxyindan-1-yl]-2-methoxy-indane-5-carboxamide |
| 140B | 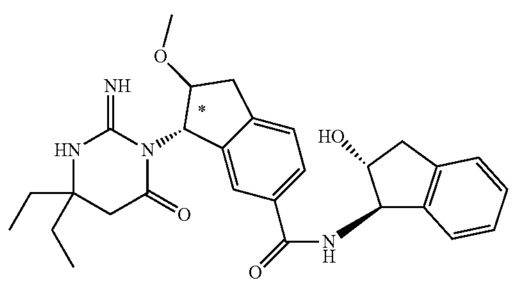 [SMILES: CCC1(CC)CC(=O)N([C@H]2c3cc(C(=O)N[C@@H]4c5ccccc5C[C@H]4O)ccc3CC2OC)C(=N)N1] | 491.3 | (3S)-3-(4,4-diethyl-2-imino-6-oxo-hexahydropyrimidin-1-yl)-N-[(1R,2R)-2-hydroxyindan-1-yl]-2-methoxy-indane-5-carboxamide |
| 141 | 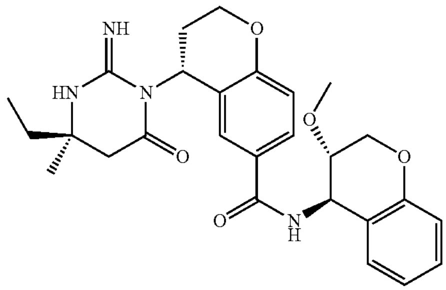 [SMILES: CC[C@]1(C)CC(=O)N([C@@H]2CCOc3ccc(C(=O)N[C@@H]4c5ccccc5OC[C@H]4OC)cc32)C(=N)N1] | 493.2 | (4R)-4-[(4R)-4-ethyl-2-imino-4-methyl-6-oxo-hexahydropyrimidin-1-yl]-N-[(3S,4R)-3-methoxychroman-4-yl]chromane-6-carboxamide |
| 142 | 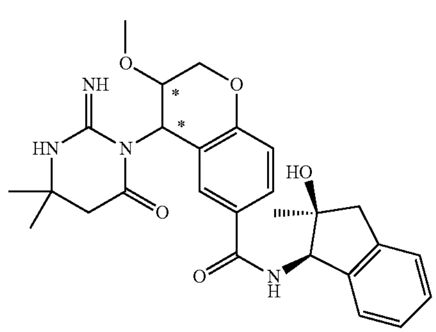 [SMILES: COC1COc2ccc(C(=O)N[C@@H]3c4ccccc4C[C@]3(C)O)cc2C1N1C(=N)NC(C)(C)CC1=O] | 493.2 | N-[(1R,2S)-2-hydroxy-2-methyl-indan-1-yl]-4-(2-imino-4,4-dimethyl-6-oxo-hexahydropyrimidin-1-yl)-3-methoxy-chromane-6-carboxamide |

TABLE 2-continued

| Example | Structure | LC/MS (M + 1)+ | Name |
|---|---|---|---|
| 143 | 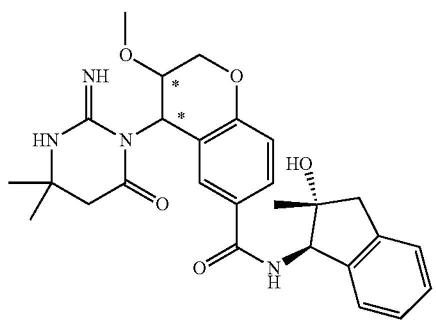 [SMILES: COC1COc2ccc(C(=O)N[C@@H]3c4ccccc4C[C@@]3(C)O)cc2C1N1C(=N)NC(C)(C)CC1=O] | 493.2 | N-[(1R,2R)-2-hydroxy-2-methyl-indan-1-yl]-4-(1-imino-4,4-dimethyl-6-oxo-hexahydropyrimidin-1-yl)-3-methoxy-chromane-6-carboxamide |
| 144 | 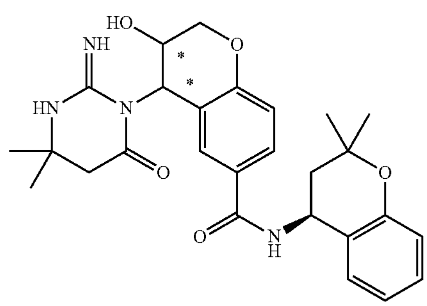 [SMILES: CC1(C)CC(=O)N(C2c3cc(C(=O)N[C@H]4CC(C)(C)Oc5ccccc54)ccc3OCC2O)C(=N)N1] | 493.3 | N-[(4S)-2,2-dimethylchroman-4-yl]-3-hydroxy-4-(2-imino-4,4-dimethyl-6-oxo-hexahydropyrimidin-1-yl)chromane-6-carboxamide |
| 145 | 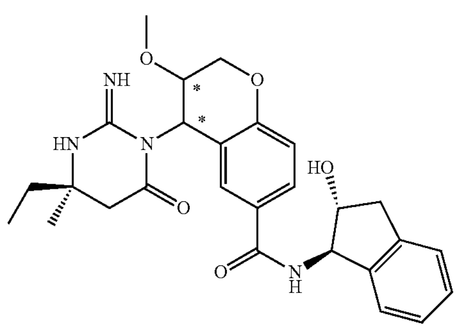 [SMILES: CC[C@]1(C)CC(=O)N(C2c3cc(C(=O)N[C@@H]4c5ccccc5C[C@H]4O)ccc3OCC2OC)C(=N)N1] | 493.2 | 4-[(4R)-4-ethyl-2-imino-4-methyl-6-oxo-hexahydropyrimidin-1-yl]-N-[(1R,2R)-2-hydroxyindan-1-yl]-3-methoxy-chromane-6-carboxamide |
| 146 | 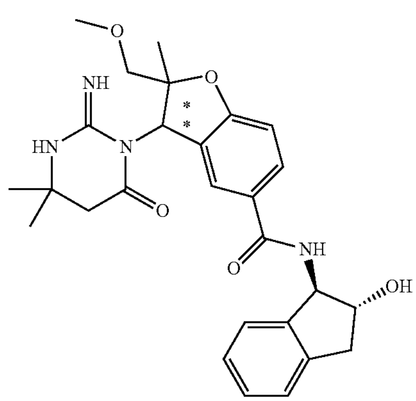 [SMILES: COCC1(C)Oc2ccc(C(=O)N[C@@H]3c4ccccc4C[C@H]3O)cc2C1N1C(=N)NC(C)(C)CC1=O] | 493.1 | N-[(1R,2R)-2-hydroxyindan-1-yl]-3-(2-imino-4,4-dimethyl-6-oxo-hexahydropyrimidin-1-yl)-2-(methoxymethyl)-2-methyl-3H-benzofuran-5-carboxamide |

TABLE 2-continued

| Example | Structure | LC/MS (M + 1)+ | Name |
|---|---|---|---|
| 147 | 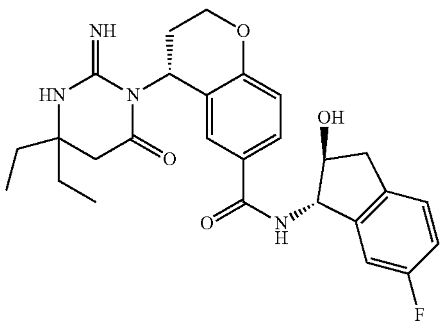 [SMILES: CCC1(CC)CC(=O)N([C@@H]2CCOc3ccc(C(=O)N[C@H]4c5cc(F)ccc5C[C@@H]4O)cc32)C(=N)N1] | 495.3 | (4R)-4-(4,4-diethyl-2-imino-6-oxo-hexahydropyrimidin-1-yl)-N-[(1S,2S)-6-fluoro-2-hydroxy-indan-1-yl]chromane-6-carboxamide |
| 148 | 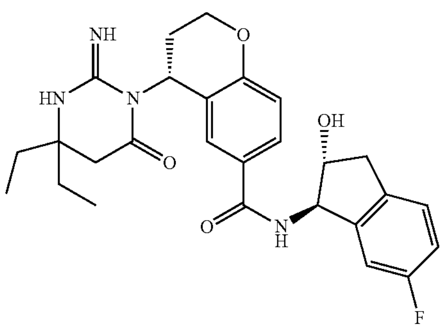 [SMILES: CCC1(CC)CC(=O)N([C@@H]2CCOc3ccc(C(=O)N[C@@H]4c5cc(F)ccc5C[C@H]4O)cc32)C(=N)N1] | 495.3 | (4R)-4-(4,4-diethyl-2-imino-6-oxo-hexahydropyrimidin-1-yl)-N-[(1R,2R)-6-fluoro-2-hydroxy-indan-1-yl]chromane-6-carboxamide |
| 149 | 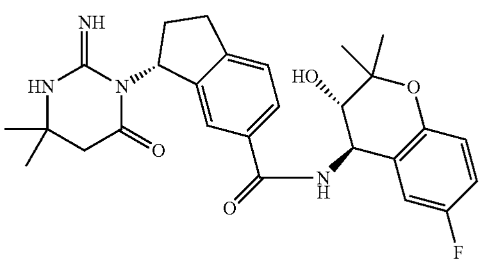 [SMILES: CC1(C)CC(=O)N([C@@H]2CCc3ccc(C(=O)N[C@@H]4c5cc(F)ccc5OC(C)(C)[C@H]4O)cc32)C(=N)N1] | 495.1 | (3R)-N-[(3S,4R)-6-fluoro-3-hydroxy-2,2-dimethyl-chroman-4-yl]-3-(2-imino-4,4-dimethyl-6-oxo-hexahydropyrimidin-1-yl)indane-5-carboxamide |
| 150 | 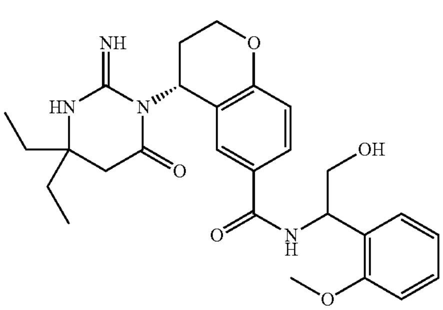 [SMILES: CCC1(CC)CC(=O)N([C@@H]2CCOc3ccc(C(=O)NC(CO)c4ccccc4OC)cc32)C(=N)N1] | 495.3 | (4R)-4-(4,4-diethyl-2-imino-6-oxo-hexahydropyrimidin-1-yl)-N-[2-hydroxy-1-(2-methoxyphenyl)ethyl]chromane-6-carboxamide |

TABLE 2-continued

| Example | Structure | LC/MS (M + 1)+ | Name |
|---|---|---|---|
| 151 | 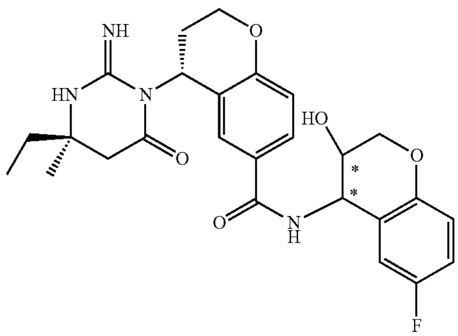 [SMILES: CC[C@]1(C)CC(=O)N([C@@H]2CCOc3ccc(C(=O)NC4c5cc(F)ccc5OCC4O)cc32)C(=N)N1] | 497.2 | (4R)-4-[(4R)-4-ethyl-2-imino-4-methyl-6-oxo-hexahydropyrimidin-1-yl]-N-(6-fluoro-3-hydroxy-chroman-4-yl)chromane-6-carboxamide |
| 152 | 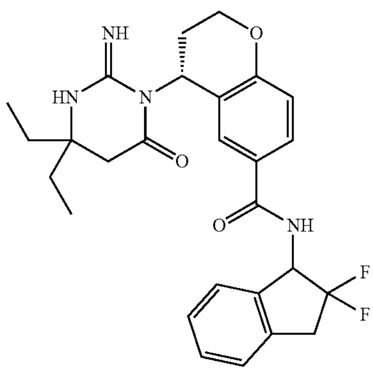 [SMILES: CCC1(CC)CC(=O)N([C@@H]2CCOc3ccc(C(=O)NC4c5ccccc5CC4(F)F)cc32)C(=N)N1] | 497.2 | (4R)-4-(4,4-diethyl-2-imino-6-oxo-hexahydropyrimidin-1-yl)-N-(2,2-difluoroindan-1-yl)chromane-6-carboxamide |
| 153 | 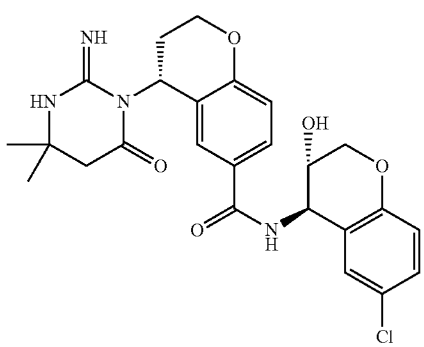 [SMILES: CC1(C)CC(=O)N([C@@H]2CCOc3ccc(C(=O)N[C@@H]4c5cc(Cl)ccc5OC[C@H]4O)cc32)C(=N)N1] | 499.1 | (4R)-N-[(3S,4R)-6-chloro-3-hydroxy-chroman-4-yl]-4-(2-imino-4,4-dimethyl-6-oxo-hexahydropyrimidin-1-yl)chromane-6-carboxamide |
| 154 | 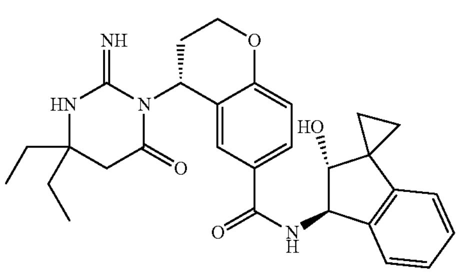 [SMILES: CCC1(CC)CC(=O)N([C@@H]2CCOc3ccc(C(=O)N[C@@H]4c5ccccc5C5(CC5)[C@H]4O)cc32)C(=N)N1] | 503.2 | (4R)-4-(4,4-diethyl-2-imino-6-oxo-hexahydropyrimidin-1-yl)-N-[(1'R,2'R)-2'-hydroxyspiro[cyclopropane-1,3'-indane]-1'-yl]chromane-6-carboxamide |

TABLE 2-continued

| Example | Structure | LC/MS (M + 1)+ | Name |
|---|---|---|---|
| 155 | 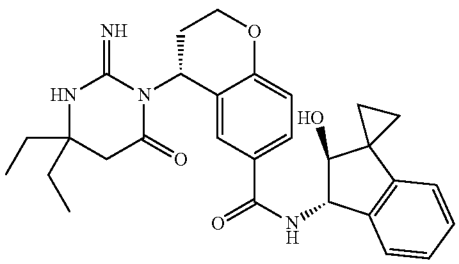 [SMILES: CCC1(CC)CC(=O)N([C@@H]2CCOc3ccc(C(=O)N[C@H]4c5ccccc5C5(CC5)[C@@H]4O)cc32)C(=N)N1] | 503.3 | (4R)-4-(4,4-diethyl-2-imino-6-oxo-hexahydropyrimidin-1-yl)-N-[(1'S,2'S)-2'-hydroxyspiro[cyclopropane-1,3'-indane]-1'-yl]chromane-6-carboxamide |
| 156 | 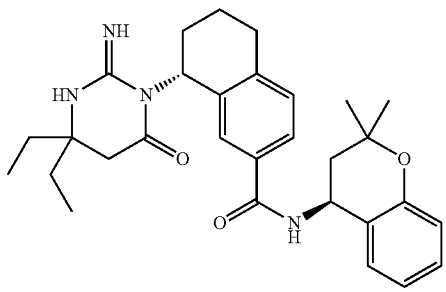 [SMILES: CCC1(CC)CC(=O)N([C@@H]2CCCc3ccc(C(=O)N[C@H]4CC(C)(C)Oc5ccccc54)cc32)C(=N)N1] | 503.3 | (4R)-4-(4,4-diethyl-2-imino-6-oxo-hexahydropyrimidin-1-yl)-N-[(4S)-2,2-dimethylchroman-4-yl]tetralin-6-carboxamide |
| 157 | 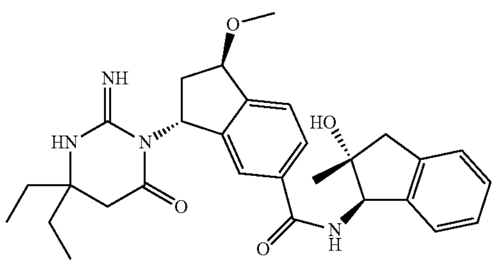 [SMILES: CCC1(CC)CC(=O)N([C@@H]2C[C@@H](OC)c3ccc(C(=O)N[C@@H]4c5ccccc5C[C@@]4(C)O)cc32)C(=N)N1] | 505.3 | (1R,3R)-3-(4,4-diethyl-2-imino-6-oxo-hexahydropyrimidin-1-yl)-N-[(1R,2R)-2-hydroxy-2-methyl-indan-1-yl]-1-methoxy-indane-5-carboxamide |
| 158 | 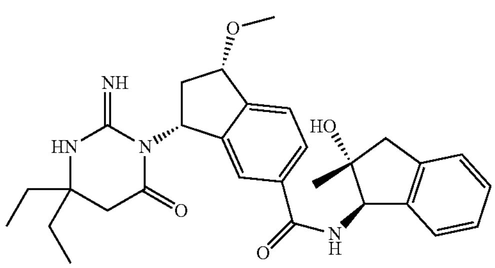 [SMILES: CCC1(CC)CC(=O)N([C@@H]2C[C@H](OC)c3ccc(C(=O)N[C@@H]4c5ccccc5C[C@@]4(C)O)cc32)C(=N)N1] | 505.3 | (1S,3R)-3-(4,4-diethyl-2-imino-6-oxo-hexahydropyrimidin-1-yl)-N-[(1R,2R)-2-hydroxy-2-methyl-indan-1-yl]-1-methoxy-indane-5-carboxamide |
| 159 | 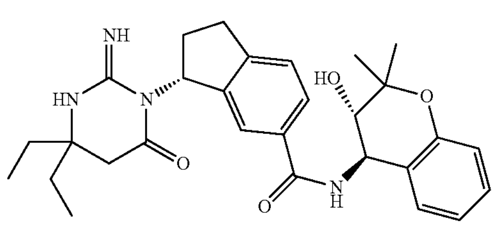 [SMILES: CCC1(CC)CC(=O)N([C@@H]2CCc3ccc(C(=O)N[C@@H]4c5ccccc5OC(C)(C)[C@H]4O)cc32)C(=N)N1] | 505.4 | (3R)-3-(4,4-diethyl-2-imino-6-oxo-hexahydropyrimidin-1-yl)-N-[(3S,4R)-3-hydroxy-2,2-dimethyl-chroman-4-yl]indane-5-carboxamide |

TABLE 2-continued

| Example | Structure | LC/MS (M + 1)+ | Name |
|---|---|---|---|
| 160 | 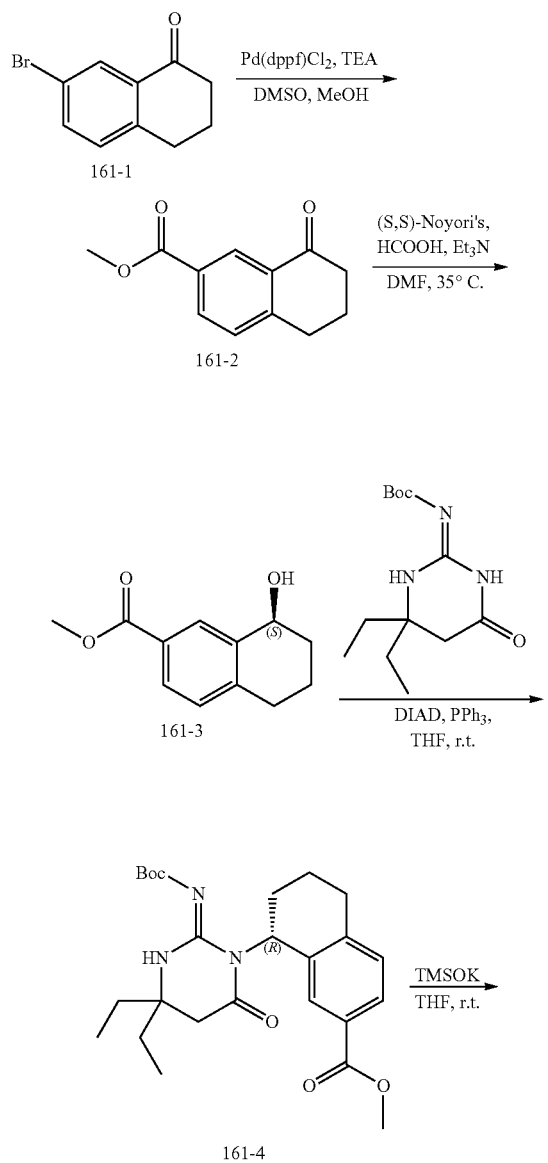 | 505.2 | (3R)-N-[(3S,4R)-3-hydroxy-2,2-dimethyl-chroman-4-yl]-3-(2-imino-4,4-dimethyl-6-oxo-hexahydropyrimidin-1-yl)-1,1-dimethyl-indane-5-carboxamide |

Example 161

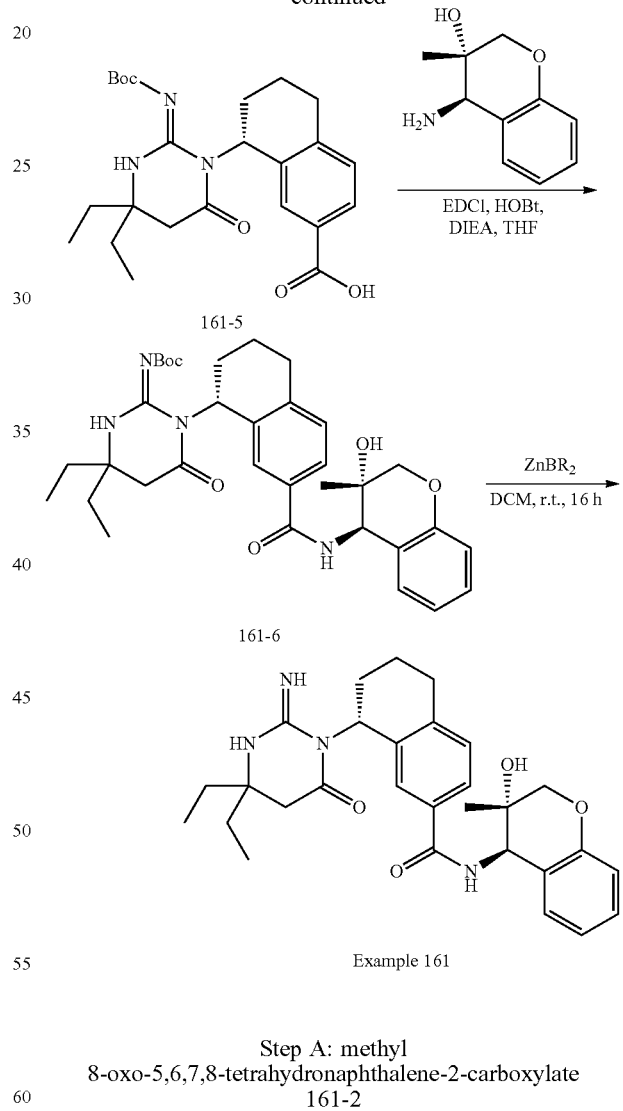

Example 161

Step A: methyl 8-oxo-5,6,7,8-tetrahydronaphthalene-2-carboxylate 161-2

PdCl$_2$(dppf) (11 g, 15.03 mmol) and triethylamine (108 mL, 777 mmol) was added to a solution of 7-bromo-1-tetralone 161-1 (35 g, 155 mmol) in MeOH (200 mL) and DMSO (100 mL). The mixture was stirred at 80° C. for 48 h under 50 psi CO atmosphere. After cooled, the mixture was concentrated in vacuo. The residue was diluted with water (200 mL), and extracted with EtOAc (200 mL*3). The combined organic layers were washed with water (400 mL) and brine (400 mL), dried over Na$_2$SO$_4$, filtered and concentrated in vacuo. The crude was purified by column chromatography (SiO$_2$, petroleum ether:EtOAc=3:1) to afford methyl 8-oxo-5,6,7,8-tetrahydronaphthalene-2-carboxylate 161-2.

$^1$H NMR (400 MHz, chloroform-d) δ 8.63 (d, J=1.2 Hz, 1H), 8.08 (dd, J=2.0, 6.0 Hz, 1H), 7.31 (d, J=8.0 Hz, 1H), 3.90 (s, 3H), 2.99 (t, J=6.0 Hz, 2H), 2.66 (t, J=6.4 Hz, 2H), 2.10-2.17 (m, 2H)

Step B: methyl (S)-8-hydroxy-5,6,7,8-tetrahydronaphthalene-2-carboxylate 161-3

A solution of formic acid (27.7 mL, 734 mmol) and TEA (205 mL, 1469 mmol) in DMF (400 mL) was stirred for 15 min, then methyl 8-oxo-5,6,7,8-tetrahydronaphthalene-2-carboxylate 161-2 (50 g, 245 mmol) and (S,S)—N-(p-toluenesulfonyl)-1,2-diphenylethanediamine(chloro)(p-cymene)ruthenium(II) (6.23 g, 9.79 mmol) were added and the mixture was stirred at 35° C. for 16 h. The mixture was diluted with water (800 mL) and extracted with EtOAc (500 mL×3). The combined organic layers were washed with water (500 mL) and brine (500 mL), dried over anhydrous Na$_2$SO$_4$, filtered and concentrated. The residue which was purified by flash silica gel chromatography (ISCO®; Agela® Flash Column Silica-CS (330 g), Eluent of 0-30% Ethyl acetate/petroleum ether gradient @85 mL/min) to afford methyl (S)-8-hydroxy-5,6,7,8-tetrahydronaphthalene-2-carboxylate 161-3.

$^1$H NMR (400 MHz, chloroform-d) δ 8.13 (s, 1H), 7.84 (d, J=7.6 Hz, 1H), 7.16 (d, J=8.4 Hz, 1H), 4.82-4.83 (m, 1H), 3.90 (s, 3H), 2.85-2.92 (m, 1H), 2.73-2.80 (m, 1H), 2.00-2.05 (m, 2H), 1.89-1.91 (m, 1H), 1.76-1.84 (m, 1H)

Step C: give methyl (R,E)-8-(2-((tert-butoxycarbonyl)imino)-4,4-diethyl-6-oxotetrahydropyrimidin-1(2H)-yl)-5,6,7,8-tetrahydronaphthalene-2-carboxylate 161-4

DIAD (36.8 mL, 189 mmol) was added dropwise to a solution of tert-butyl (E)-(4,4-diethyl-6-oxotetrahydropyrimidin-2(1H)-ylidene)carbamate (43.1 g, 160 mmol), methyl (S)-8-hydroxy-5,6,7,8-tetrahydronaphthalene-2-carboxylate 161-3 (30 g, 145 mmol) and triphenylphosphane (49.6 g, 189 mmol) in THF (500 mL) at 0° C. under N$_2$ atmosphere. The mixture was stirred at 27° C. for 2 h. The product was diluted with EtOAc (100 mL) and petroleum ether (500 mL) was slowly added while stirring. The mixture was filtered. The filtrate was concentrated in vacuo and purified by flash silica gel chromatography (ISCO®; Agela® Flash Column Silica-CS (330 g), Eluent of 10% Ethyl acetate/petroleum ether gradient @85 mL/min to give methyl (R,E)-8-(2-((tert-butoxycarbonyl)imino)-4,4-diethyl-6-oxotetrahydropyrimidin-1(2H)-yl)-5,6,7,8-tetrahydronaphthalene-2-carboxylate 161-4. MS (ESI) m/z: 458.3 (M+H$^+$)

$^1$H NMR (400 MHz, chloroform-d) δ 10.11 (br s, 1H), 7.72 (d, J=8.0 Hz, 1H), 7.62 (s, 1H), 7.13 (d, J=8.4 Hz, 1H), 6.17-6.33 (m, 1H), 3.85 (s, 3H), 2.90-3.08 (m, 1H), 2.75-2.78 (m, 1H), 2.47-2.59 (m, 2H), 2.23-2.35 (m, 1H), 2.01-2.10 (m, 2H), 1.77-1.88 (m, 2H), 1.62-1.76 (m, 4H), 1.51 (br s, 9H), 0.92-1.01 (m, 6H).

Step D: (E)-8-(2-((tert-butoxycarbonyl)imino)-4,4-diethyl-6-oxotetrahydropyrimidin-1(2H)-yl)-5,6,7,8-tetrahydronaphthalene-2-carboxylic acid 161-5

Potassium trimethylsilanolate (21.31 g, 166 mmol) was added to a solution of methyl (E)-8-(2-((tert-butoxycarbonyl)imino)-4,4-diethyl-6-oxotetrahydropyrimidin-1(2H)-yl)-5,6,7,8-tetrahydronaphthalene-2-carboxylate 161-4 (19 g, 41.5 mmol) in THF (450 mL). The reaction was stirred at 25° C. for 0.5 h. The solution of (E)-8-(2-((tert-butoxycarbonyl)imino)-4,4-diethyl-6-oxotetrahydropyrimidin-1(2H)-yl)-5,6,7,8-tetrahydronaphthalene-2-carboxylic acid 161-5 was used for next step directly without any further manipulation or purification.

MS (ESI) m/z 444.7 (M+H$^+$)

Step E: tert-butyl((E)-4,4-diethyl-1-(7-(((3S,4R)-3-hydroxy-3-methylchroman-4-yl)carbamoyl)-1,2,3,4-tetrahydronaphthalen-1-yl)-6-oxotetrahydropyrimidin-2(1H)-ylidene)carbamate 161-6

DIEA (36.4 mL, 209 mmol) was added to a solution of (E)-8-(2-((tert-butoxycarbonyl)imino)-4,4-diethyl-6-oxotetrahydropyrimidin-1(2H)-yl)-5,6,7,8-tetrahydronaphthalene-2-carboxylic acid 161-5 (18.5 g, 41.7 mmol), EDCI (40.0 g, 209 mmol), HOBt (16.91 g, 125 mmol) and (3S,4R)-4-amino-3-methylchroman-3-ol (8.22 g, 45.9 mmol) in THF (450 mL). The reaction was stirred at 25° C. for 2.5 h. The mixture was quenched with water (400 mL), and extracted with EtOAc (500 mL*3). The combined organic layers were washed with brine (350 mL), dried over Na$_2$SO$_4$, filtered and concentrated in vacuo. The crude was purified by flash silica gel chromatography (ISCO®; Agela® Flash Column Silica-CS (120 g), Eluent of 0-30% Ethyl acetate/petroleum ether gradient @85 mL/min) to afford tert-butyl ((E)-4,4-diethyl-1-(7-(((3S,4R)-3-hydroxy-3-methylchroman-4-yl)carbamoyl)-1,2,3,4-tetrahydronaphthalen-1-yl)-6-oxotetrahydropyrimidin-2(1H)-ylidene)carbamate 161-6. MS (ESI) m/z 605.3 (M+H$^+$)

$^1$H NMR (400 MHz, chloroform-d) δ 10.15 (br s, 1H), 7.56 (br s, 1H), 7.42 (d, J=8.0 Hz, 1H), 7.27-7.31 (m, 1H), 7.23 (d, J=7.6 Hz, 1H), 7.15 (d, J=8.0 Hz, 1H), 6.99 (t, J=7.6 Hz, 1H), 6.91 (d, J=8.0 Hz, 1H), 6.36 (d, J=7.2 Hz, 1H), 6.25-6.28 (m, 1H), 5.31 (d, J=7.2 Hz, 1H), 4.96 (s, 1H), 3.96-4.04 (m, 2H), 2.91-3.09 (m, 1H), 2.76-2.80 (m, 1H), 2.53 (br s, 2H), 2.28-2.32 (m, 1H), 2.00-2.11 (m, 2H), 1.73-1.88 (m, 1H), 1.62-1.67 (m, 4H), 1.50 (s, 9H), 1.24 (s, 3H), 0.88-0.97 (m, 6H).

Step F: 8-(4,4-diethyl-2-imino-6-oxotetrahydropyrimidin-1(2H)-yl)-N-((3S,4R)-3-hydroxy-3-methylchroman-4-yl)-5,6,7,8-tetrahydronaphthalene-2-carboxamide Example 161

A solution of tert-butyl ((E)-4,4-diethyl-1-(7-(((3S,4R)-3-hydroxy-3-methylchroman-4-yl)carbamoyl)-1,2,3,4-tetrahydronaphthalen-1-yl)-6-oxotetrahydropyrimidin-2(1H)-ylidene)carbamate 161-6 (25 g, 41.3 mmol) and zinc(II) bromide (37.17 g, 165.2 mmol) in DCM (300 mL) at 25° C. under N$_2$ atmosphere was stirred at 25° C. for 16 h. The mixture was concentrated in vacuo at room temperature. MeCN (300 mL) was added and the mixture was stirred and then filtered. The filtrate was concentrated and purified by prep-HPLC (Instrument PREPL-X Method Column YMC-Triart Prep C18 250*50 mm*10 um Condition water (0.05% HCl)-ACN Begin B 10 End B 40 Gradient Time (min) 20

100% B Hold Time (min) 3 FlowRate(ml/min) 120 Injections 6) to afford 8-(4,4-diethyl-2-imino-6-oxotetrahydropyrimidin-1(2H)-yl)-N-((3S,4R)-3-hydroxy-3-methylchroman-4-yl)-5,6,7,8-tetrahydronaphthalene-2-carboxamide Example 161. MS (ESI) m/z 505.2 (M+H$^+$)

$^1$H NMR (400 MHz, methanol-d$_4$) δ 7.63 (br s, 1H), 7.59 (s, 1H), 720-7.24 (m, 1H), 7.17 (d, J=8.0 Hz, 2H), 6.88-6.94 (m, 1H), 6.86 (d, J=8.00 Hz, 1H), 5.19-5.64 (m, 2H), 3.94-4.05 (m, 2H), 2.67-2.97 (m, 4H), 2.08-2.45 (m, 3H), 1.64-1.89 (m, 5H), 1.28 (s, 3H), 0.98 (t, J=7.2 Hz, 6H).

The compounds in Table 1-4 were prepared in an analogous fashion to that described in Scheme 1 and the experimentals described herein. The isomers were separated by preparative HPLC or/and preparative chiral SFC.

TABLE 3

| Example | Structure | LC/MS (M + 1)$^+$ | Name |
|---|---|---|---|
| 162 | 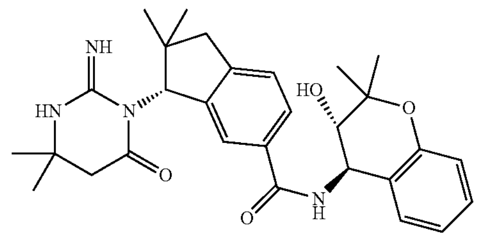 [SMILES: CC1(C)CC(=O)N([C@H]2c3cc(C(=O)N[C@@H]4c5ccccc5OC(C)(C)[C@H]4O)ccc3CC2(C)C)C(=N)N1] | 505.3 | (3R)-N-[(3S,4R)-3-hydroxy-2,2-dimethyl-chroman-4-yl]-3-(2-imino-4,4-dimethyl-6-oxo-hexahydropyrimidin-1-yl)-2,2-dimethyl-indane-5-carboxamide |
| 163 | 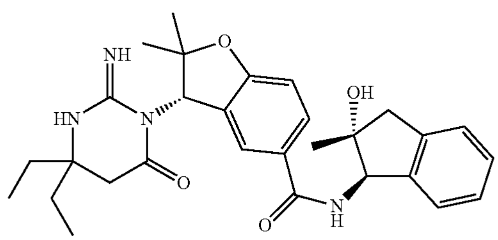 [SMILES: CCC1(CC)CC(=O)N([C@H]2c3cc(C(=O)N[C@@H]4c5ccccc5C[C@@]4(C)O)ccc3OC2(C)C)C(=N)N1] | 505.3 | (3S)-3-(4,4-diethyl-2-imino-6-oxo-hexahydropyrimidin-1-yl)-N-[(1R,2R)-2-hydroxy-2-methyl-indan-1-yl]-2,2-dimethyl-3H-benzofuran-5-carboxamide |
| 164 | 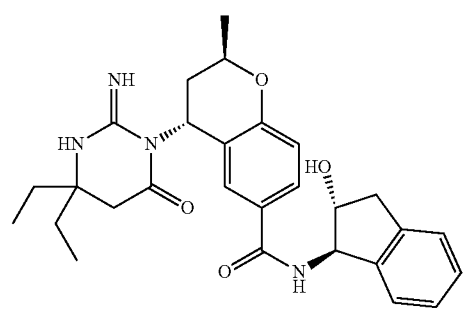 [SMILES: CCC1(CC)CC(=O)N([C@@H]2C[C@@H](C)Oc3ccc(C(=O)N[C@@H]4c5ccccc5C[C@H]4O)cc32)C(=N)N1] | 505.3 | (2R,4R)-4-(4,4-diethyl-2-imino-6-oxo-hexahydropyrimidin-1-yl)-N-[(1R,2R)-2-hydroxy-2-methyl-indan-1-yl]-2-methyl-chromane-6-carboxamide |
| 165 | 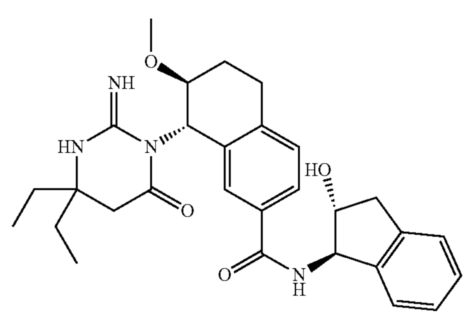 [SMILES: CCC1(CC)CC(=O)N([C@H]2c3cc(C(=O)N[C@@H]4c5ccccc5C[C@H]4O)ccc3CC[C@@H]2OC)C(=N)N1] | 505.1 | (3S,4S)-4-(4,4-diethyl-2-imino-6-oxo-hexahydropyrimidin-1-yl)-N-[(1R,2R)-2-hydroxyindan-1-yl]-3-methoxy-tetralin-6-carboxamide |
| 166 | 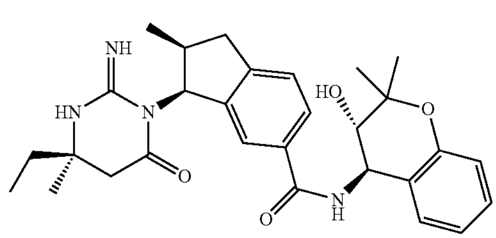 [SMILES: CC[C@]1(C)CC(=O)N([C@@H]2c3cc(C(=O)N[C@@H]4c5ccccc5OC(C)(C)[C@H]4O)ccc3C[C@@H]2C)C(=N)N1] | 505.3 | (2S,3S)-3-[(4R)-4-ethyl-2-imino-4-methyl-6-oxo-hexahydropyrimidin-1-yl]-N-[(3S,4R)-3-hydroxy-2,2-dimethyl-chroman-4-yl]-2-methyl-indane-5-carboxamide |

| Example | Structure | LC/MS (M + 1)+ | Name |
|---|---|---|---|
| 167 | 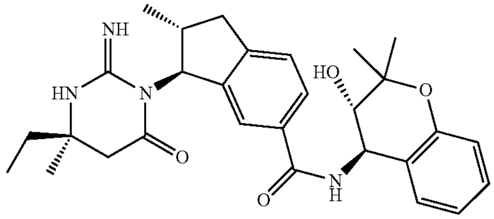 [SMILES: CC[C@]1(C)CC(=O)N([C@@H]2c3cc(C(=O)N[C@@H]4c5ccccc5OC(C)(C)[C@H]4O)ccc3C[C@H]2C)C(=N)N1] | 505.3 | (2R,3S)-3-[(4R)-4-ethyl-2-imino-4-methyl-6-oxo-hexahydropyrimidin-1-yl]-N-[(3S,4R)-3-hydroxy-2,2-dimethyl-chroman-4-yl]-2-methyl-indane-5-carboxamide |
| 168 | 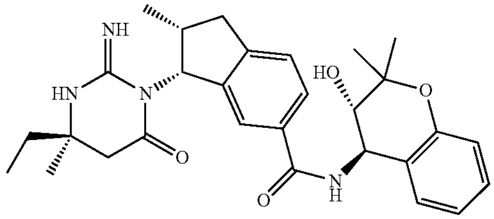 [SMILES: CC[C@]1(C)CC(=O)N([C@H]2c3cc(C(=O)N[C@@H]4c5ccccc5OC(C)(C)[C@H]4O)ccc3C[C@H]2C)C(=N)N1] | 505.3 | (2R,3R)-3-[(4R)-4-ethyl-2-imino-4-methyl-6-oxo-hexahydropyrimidin-1-yl]-N-[(3S,4R)-3-hydroxy-2,2-dimethyl-chroman-4-yl]-2-methyl-indane-5-carboxamide |
| 169 | 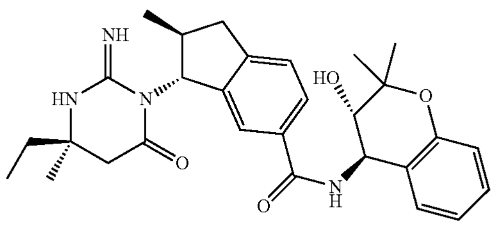 [SMILES: CC[C@]1(C)CC(=O)N([C@H]2c3cc(C(=O)N[C@@H]4c5ccccc5OC(C)(C)[C@H]4O)ccc3C[C@@H]2C)C(=N)N1] | 505.3 | (2S,3R)-3-[(4R)-4-ethyl-2-imino-4-methyl-6-oxo-hexahydropyrimidin-1-yl]-N-[(3S,4R)-3-hydroxy-2,2-dimethyl-chroman-4-yl]-2-methyl-indane-5-carboxamide |
| 170 | 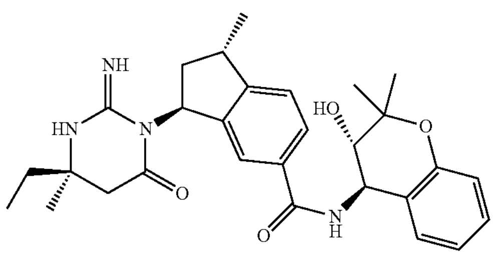 [SMILES: CC[C@]1(C)CC(=O)N([C@H]2C[C@H](C)c3ccc(C(=O)N[C@@H]4c5ccccc5OC(C)(C)[C@H]4O)cc32)C(=N)N1] | 505.3 | (1S,3S)-3-[(4R)-4-ethyl-2-imino-4-methyl-6-oxo-hexahydropyrimidin-1-yl]-N-[(3S,4R)-3-hydroxy-2,2-dimethyl-chroman-4-yl]-1-methyl-indane-5-carboxamide |
| 171 | 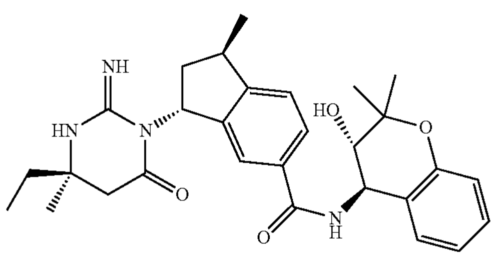 [SMILES: CC[C@]1(C)CC(=O)N([C@@H]2C[C@@H](C)c3ccc(C(=O)N[C@@H]4c5ccccc5OC(C)(C)[C@H]4O)cc32)C(=N)N1] | 505.3 | (1R,3R)-3-[(4R)-4-ethyl-2-imino-4-methyl-6-oxo-hexahydropyrimidin-1-yl]-N-[(3S,4R)-3-hydroxy-2,2-dimethyl-chroman-4-yl]-1-methyl-indane-5-carboxamide |
| 172 | 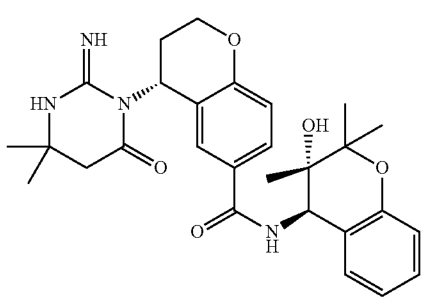 [SMILES: CC1(C)CC(=O)N([C@@H]2CCOc3ccc(C(=O)N[C@@H]4c5ccccc5OC(C)(C)[C@@]4(C)O)cc32)C(=N)N1] | 507.3 | (4R)-N-[(3S,4R)-3-hydroxy-2,2,3-trimethyl-chroman-4-yl]-4-(2-imino-4,4-dimethyl-6-oxo-hexahydropyrimidin-1-yl)chromane-6-carboxamide |

TABLE 3-continued

| Example | Structure | LC/MS (M + 1)+ | Name |
|---|---|---|---|
| 173 | 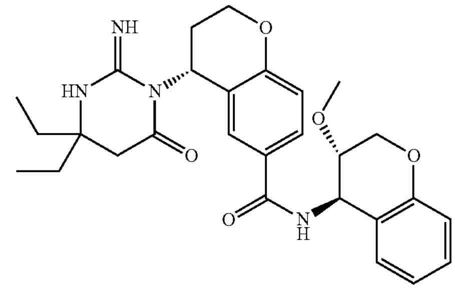 [SMILES: CCC1(CC)CC(=O)N([C@@H]2CCOc3ccc(C(=O)N[C@@H]4c5ccccc5OC[C@H]4OC)cc32)C(=N)N1] | 507.3 | (4R)-4-(4,4-diethyl-2-imino-6-oxo-hexahydropyrimidin-1-yl)-N-[(3S,4R)-3-methoxychroman-4-yl]chromane-6-carboxamide |
| 174 | 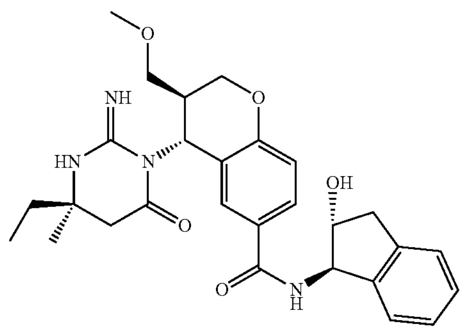 [SMILES: CC[C@]1(C)CC(=O)N([C@H]2c3cc(C(=O)N[C@@H]4c5ccccc5C[C@H]4O)ccc3OC[C@@H]2COC)C(=N)N1] | 507.1 | (3S,4R)-4-[(4R)-4-ethyl-2-imino-4-methyl-6-oxo-hexahydropyrimidin-1-yl]-N-[(1R,2R)-2-hydroxyindan-1-yl]-3-(methoxymethyl)chromane-6-carboxamide |
| 175 | 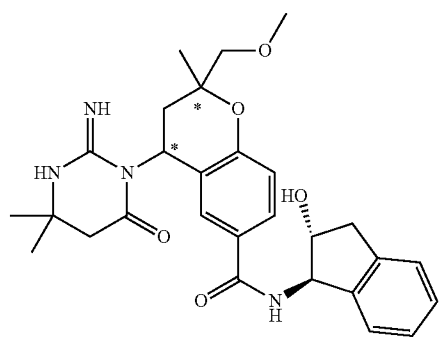 [SMILES: COCC1(C)CC(N2C(=N)NC(C)(C)CC2=O)c2cc(C(=O)N[C@@H]3c4ccccc4C[C@H]3O)ccc2O1] | 507.3 | N-[(1R,2R)-2-hydroxyindan-1-yl]-4-(2-imino-4,4-dimethyl-6-oxo-hexahydropyrimidin-1-yl)-2-(methoxymethyl)-2-methyl-chromane-6-carboxamide |
| 176A | 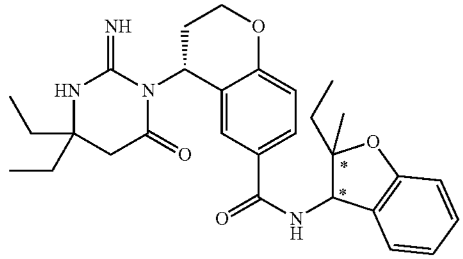 [SMILES: CCC1(CC)CC(=O)N([C@@H]2CCOc3ccc(C(=O)NC4c5ccccc5OC4(C)CC)cc32)C(=N)N1] | 507.2 | (4R)-4-(4,4-diethyl-2-imino-6-oxo-hexahydropyrimidin-1-yl)-N-[2-(hydroxymethyl)-2-methyl-3H-benzofuran-3-yl]chromane-6-carboxamide |
| 176B | 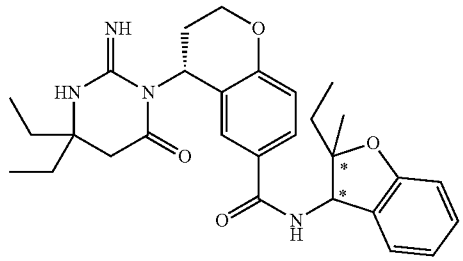 [SMILES: CCC1(CC)CC(=O)N([C@@H]2CCOc3ccc(C(=O)NC4c5ccccc5OC4(C)CC)cc32)C(=N)N1] | 507.3 | (4R)-4-(4,4-diethyl-2-imino-6-oxo-hexahydropyrimidin-1-yl)-N-[2-(hydroxymethyl)-methyl-3H-benzofuran-3-yl]chromane-6-carboxamide |

TABLE 3-continued

| Example | Structure | LC/MS (M + 1)+ | Name |
|---|---|---|---|
| 176C | 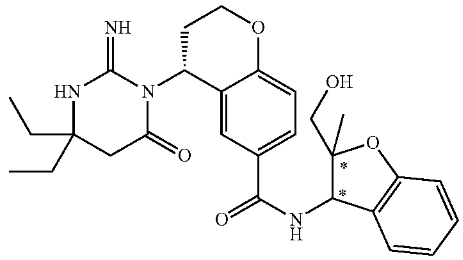 [SMILES: CCC1(CC)CC(=O)N([C@@H]2CCOc3ccc(C(=O)NC4c5ccccc5OC4(C)CO)cc32)C(=N)N1] | 507.3 | (4R)-4-(4,4-diethyl-2-imino-6-oxo-hexahydropyrimidin-1-yl)-N-[2-(hydroxymethyl)-2-methyl-3H-benzofuran-3-yl]chromane-6-carboxamide |
| 176D | 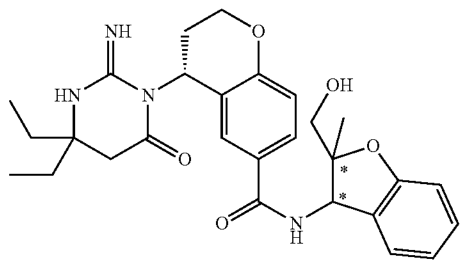 [SMILES: CCC1(CC)CC(=O)N([C@@H]2CCOc3ccc(C(=O)NC4c5ccccc5OC4(C)CO)cc32)C(=N)N1] | 507.3 | (4R)-4-(4,4-diethyl-2-imino-6-oxo-hexahydropyrimidin-1-yl)-N-[2-(hydroxymethyl)-2-methyl-3H-benzofuran-3-yl]chromane-6-carboxamide |
| 177 | 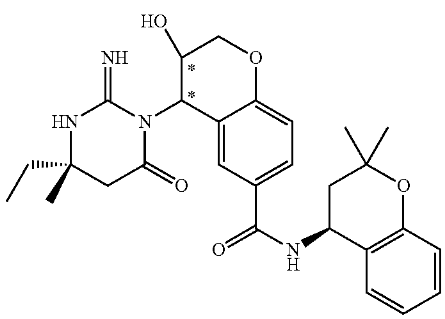 [SMILES: CC[C@@]1(C)CC(=O)N(C2c3cc(C(=O)N[C@H]4CC(C)(C)Oc5ccccc54)ccc3OCC2O)C(=N)N1] | 507.3 | N-[(4S)-2,2-dimethylchroman-4-yl]-4-[(4S)-4-ethyl-2-imino-4-methyl-6-oxo-hexahydropyrimidin-1-yl]-3-hydroxy-chromane-6-carboxamide |
| 178A | 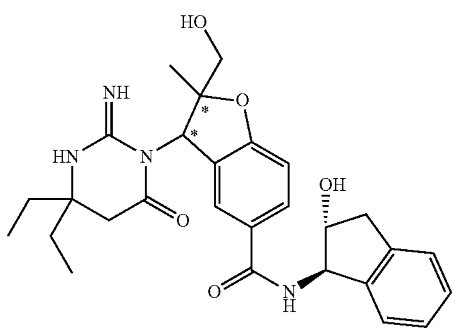 [SMILES: CCC1(CC)CC(=O)N(C2c3cc(C(=O)N[C@@H]4c5ccccc5C[C@H]4O)ccc3OC2(C)CO)C(=N)N1] | 507.3 | 3-(4,4-diethyl-2-imino-6-oxo-hexahydropyrimidin-1-yl)-N-[(1R,2R)-2-hydroxyindan-1-yl]-2-(hydroxymethyl)-2-methyl-3H-benzofuran-5-carboxamide |
| 178B | 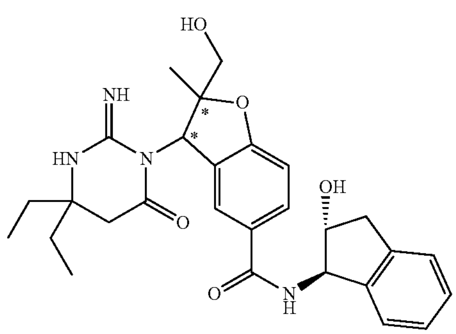 [SMILES: CCC1(CC)CC(=O)N(C2c3cc(C(=O)N[C@@H]4c5ccccc5C[C@H]4O)ccc3OC2(C)CO)C(=N)N1] | 507.3 | 3-(4,4-diethyl-2-imino-6-oxo-hexahydropyrimidin-1-yl)-N-[(1R,2R)-2-hydroxyindan-1-yl]-2-(hydroxymethyl)-2-methyl-3H-benzofuran-5-carboxamide |

TABLE 3-continued

| Example | Structure | LC/MS (M + 1)+ | Name |
|---|---|---|---|
| 179 | 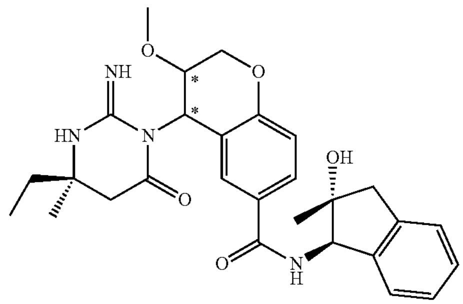 [SMILES: CC[C@]1(C)CC(=O)N(C2c3cc(C(=O)N[C@@H]4c5ccccc5C[C@@]4(C)O)ccc3OCC2OC)C(=N)N1] | 507.3 | 4-[(4R)-4-ethyl-2-imino-4-methyl-6-oxo-hexahydropyrimidin-1-yl]-N-[(1R,2R)-2-hydroxy-2-methyl-indan-1-yl]-3-methoxy-chromane-6-carboxamide |
| 180 | 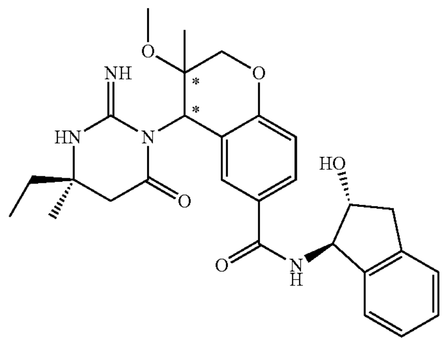 [SMILES: CC[C@]1(C)CC(=O)N(C2c3cc(C(=O)N[C@@H]4c5ccccc5C[C@H]4O)ccc3OCC2(C)OC)C(=N)N1] | 507.3 | 4-[(4R)-4-ethyl-2-imino-4-methyl-6-oxo-hexahydropyrimidin-1-yl]-N-[(1R,2R)-2-hydroxyindan-1-yl]-3-methoxy-3-methyl-chromane-6-carboxamide |
| 181A | 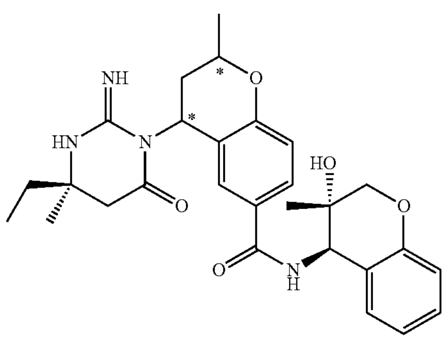 [SMILES: CC[C@]1(C)CC(=O)N(C2CC(C)Oc3ccc(C(=O)N[C@@H]4c5ccccc5OC[C@@]4(C)O)cc32)C(=N)N1] | 507.3 | 4-[(4R)-4-ethyl-2-imino-4-methyl-6-oxo-hexahydropyrimidin-1-yl]-N-[(3S,4R)-3-hydroxy-3-methyl-chroman-4-yl]-2-methyl-chromane-6-carboxamide |
| 181B | 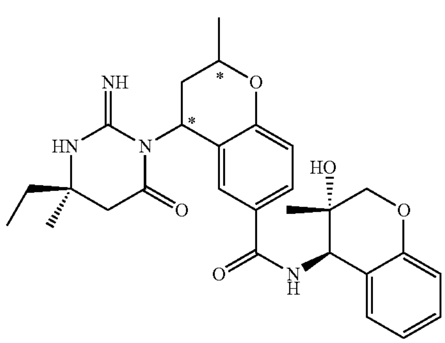 [SMILES: CC[C@]1(C)CC(=O)N(C2CC(C)Oc3ccc(C(=O)N[C@@H]4c5ccccc5OC[C@@]4(C)O)cc32)C(=N)N1] | 507.3 | 4-[(4R)-4-ethyl-2-imino-4-methyl-6-oxo-hexahydropyrimidin-1-yl]-N-[(3S,4R)-3-hydroxy-3-methyl-chroman-4-yl]-2-methyl-chromane-6-carboxamide |

TABLE 3-continued

| Example | Structure | LC/MS (M + 1)+ | Name |
|---|---|---|---|
| 182 | 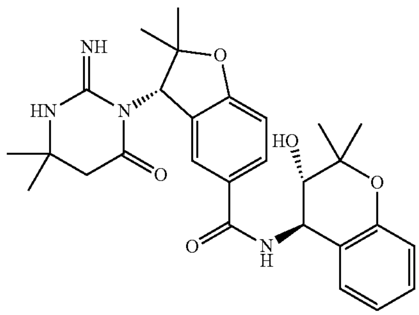 [SMILES: CC1(C)CC(=O)N([C@H]2c3cc(C(=O)N[C@@H]4c5ccccc5OC(C)(C)[C@H]4O)ccc3OC2(C)C)C(=N)N1] | 507.3 | (3S)-N-[(3S,4R)-3-hydroxy-2,2-dimethyl-chroman-4-yl]-3-(2-imino-4,4-dimethyl-6-oxo-hexahydropyrimidin-1-yl)-2,2-dimethyl-3H-benzofuran-5-carboxamide |
| 183 | 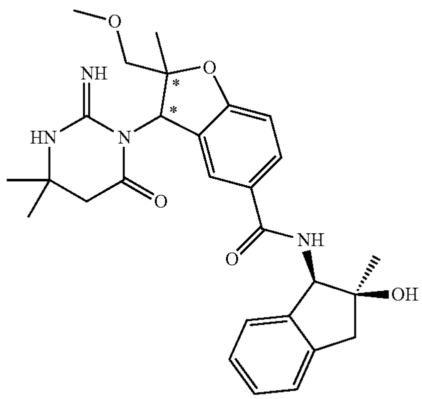 [SMILES: COCC1(C)Oc2ccc(C(=O)N[C@@H]3c4ccccc4C[C@]3(C)O)cc2C1N1C(=N)NC(C)(C)CC1=O] | 507.3 | N-[(1R,2S)-2-hydroxy-2-methyl-indan-1-yl]-3-(2-imino-4,4-dimethyl-6-oxo-hexahydropyrimidin-1-yl)-2-(methoxymethyl)-2-methyl-3H-benzofuran-5-carboxamide |
| 184 | 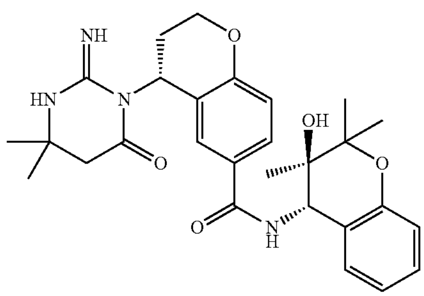 [SMILES: CC1(C)CC(=O)N([C@@H]2CCOc3ccc(C(=O)N[C@H]4c5ccccc5OC(C)(C)[C@]4(C)O)cc32)C(=N)N1] | 507.3 | (4R)-N-[(3R,4S)-3-hydroxy-2,2,3-trimethyl-chroman-4-yl]-4-(2-imino-4,4-dimethyl-6-oxo-hexahydropyrimidin-1-yl)chromane-6-carboxamide |
| 185 | 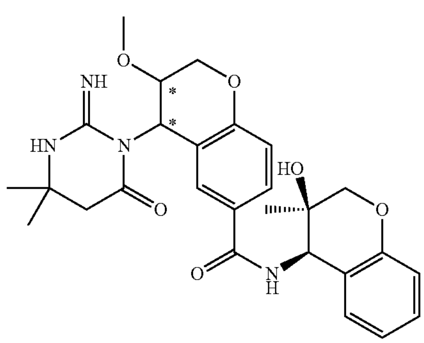 [SMILES: COC1COc2ccc(C(=O)N[C@@H]3c4ccccc4OC[C@]3(C)O)cc2C1N1C(=N)NC(C)(C)CC1=O] | 509.2 | N-[(3R,4R)-3-hydroxy-3-methyl-chroman-4-yl]-4-(2-imino-4,4-dimethyl-6-oxo-hexahydropyrimidin-1-yl)-3-methoxy-chromane-6-carboxamide |

TABLE 3-continued

| Example | Structure | LC/MS (M + 1)+ | Name |
|---|---|---|---|
| 186 | 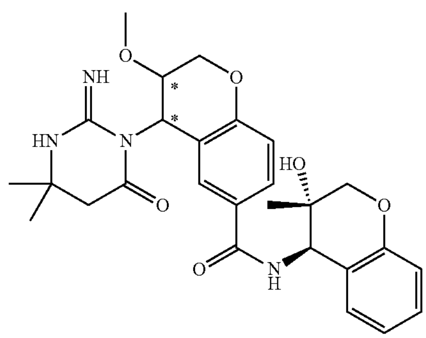 [SMILES: COC1COc2ccc(C(=O)N[C@@H]3c4ccccc4OC[C@@]3(C)O)cc2C1N1C(=N)NC(C)(C)CC1=O] | 509.2 | N-[(3S,4R)-3-hydroxy-3-methyl-chroman-4-yl]-4-(2-imino-4,4-dimethyl-6-oxo-hexahydropyrimidin-1-yl)-3-methoxy-chromane-6-carboxamide |
| 187 | 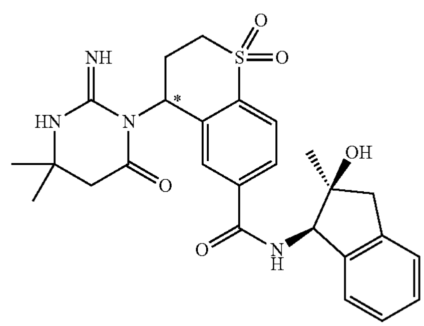 [SMILES: CC1(C)CC(=O)N(C2CCS(=O)(=O)c3ccc(C(=O)N[C@@H]4c5ccccc5C[C@]4(C)O)cc32)C(=N)N1] | 511.3 | N-[(1R,2S)-2-hydroxy-2-methyl-indan-1-yl]-4-(2-imino-4,4-dimethyl-6-oxo-hexahydropyrimidin-1-yl)-1,1-dioxo-3,4-dihydro-2H-thiochromane-6-carboxamide |
| 188 | 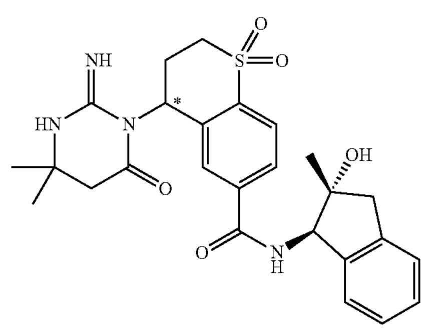 [SMILES: CC1(C)CC(=O)N(C2CCS(=O)(=O)c3ccc(C(=O)N[C@@H]4c5ccccc5C[C@@]4(C)O)cc32)C(=N)N1] | 511.2 | N-[(1R,2R)-2-hydroxy-2-methyl-indan-1-yl]-4-(2-imino-4,4-dimethyl-6-oxo-hexahydropyrimidin-1-yl)-1,1-dioxo-3,4-dihydro-2H-thiochromene-6-carboxamide |
| 189 | 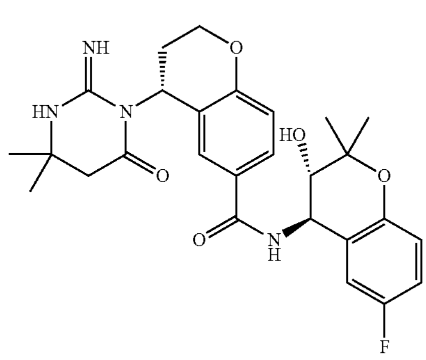 [SMILES: CC1(C)CC(=O)N([C@@H]2CCOc3ccc(C(=O)N[C@@H]4c5cc(F)ccc5OC(C)(C)[C@H]4O)cc32)C(=N)N1] | 511.3 | (4R)-N-[(3S,4R)-6-fluoro-3-hydroxy-2,2-dimethyl-chroman-4-yl]-4-(2-imino-4,4-dimethyl-6-oxo-hexahydropyrimidin-1-yl)chromane-6-carboxamide |

TABLE 3-continued

| Example | Structure | LC/MS (M + 1)+ | Name |
|---|---|---|---|
| 190A | 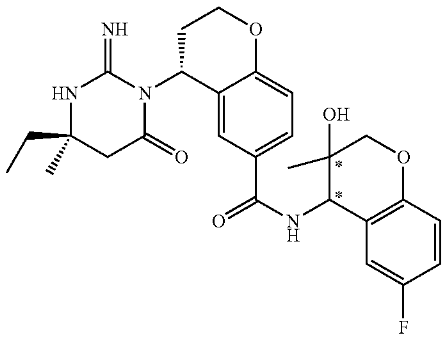 [SMILES: CC[C@]1(C)CC(=O)N([C@@H]2CCOc3ccc(C(=O)NC4c5cc(F)ccc5OCC4(C)O)cc32)C(=N)N1] | 511.2 | (4R)-4-[(4R)-4-ethyl-2-imino-4-methyl-6-oxo-hexahydropyrimidin-1-yl]-N-(6-fluoro-3-hydroxy-3-methyl-chroman-4-yl)chromane-6-carboxamide |
| 190B | 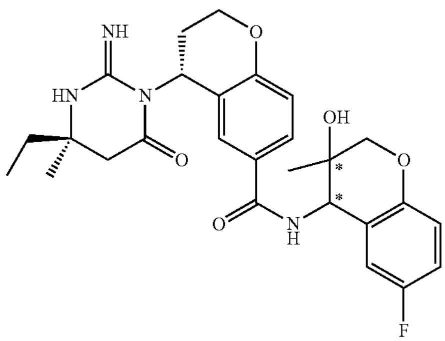 [SMILES: CC[C@]1(C)CC(=O)N([C@@H]2CCOc3ccc(C(=O)NC4c5cc(F)ccc5OCC4(C)O)cc32)C(=N)N1] | 511.2 | (4R)-4-[(4R)-4-ethyl-2-imino-4-methyl-6-oxo-hexahydropyrimidin-1-yl]-N-(6-fluoro-3-hydroxy-3-methyl-chroman-4-yl)chromane-6-carboxamide |
| 190C | 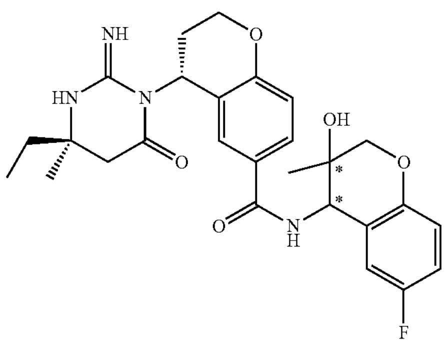 [SMILES: CC[C@]1(C)CC(=O)N([C@@H]2CCOc3ccc(C(=O)NC4c5cc(F)ccc5OCC4(C)O)cc32)C(=N)N1] | 511.2 | (4R)-4-[(4R)-4-ethyl-2-imino-4-methyl-6-oxo-hexahydropyrimidin-1-yl]-N-(6-fluoro-3-hydroxy-3-methyl-chroman-4-yl)chromane-6-carboxamide |
| 191 | 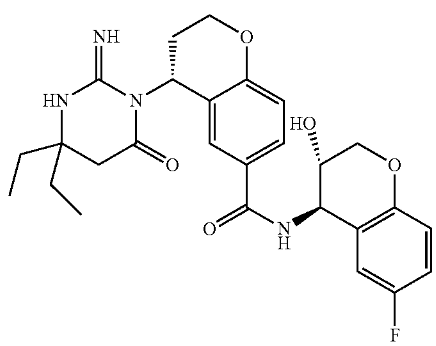 [SMILES: CCC1(CC)CC(=O)N([C@@H]2CCOc3ccc(C(=O)N[C@@H]4c5cc(F)ccc5OC[C@H]4O)cc32)C(=N)N1] | 511.2 | (4R)-4-(4,4-diethyl-2-imino-6-oxo-hexahydropyrimidin-1-yl)-N-[(3S,4R)-6-fluoro-3-hydroxy-chroman-4-yl]chromane-6-carboxamide |

TABLE 3-continued

| Example | Structure | LC/MS (M + 1)+ | Name |
|---|---|---|---|
| 192 | 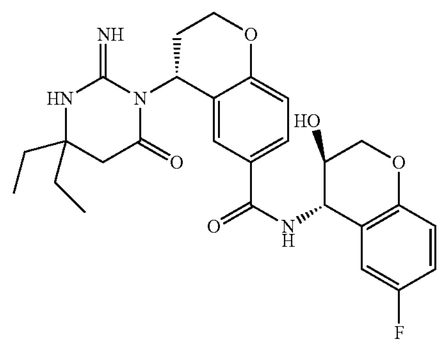 [SMILES: CCC1(CC)CC(=O)N([C@@H]2CCOc3ccc(C(=O)N[C@H]4c5cc(F)ccc5OC[C@@H]4O)cc32)C(=N)N1] | 511.3 | (4R)-4-(4,4-diethyl-2-imino-6-oxo-hexahydropyrimidin-1-yl)-N-[(3R,4S)-6-fluoro-3-hydroxy-chroman-4-yl]chromane-6-carboxamide |
| 193A | 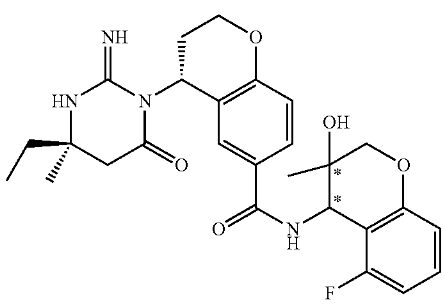 [SMILES: CC[C@]1(C)CC(=O)N([C@@H]2CCOc3ccc(C(=O)NC4c5c(F)cccc5OCC4(C)O)cc32)C(=N)N1] | 511.3 | (4R)-4-[(4R)-4-ethyl-2-imino-4-methyl-6-oxo-hexahydropyrimidin-1-yl]-N-(5-fluoro-3-hydroxy-3-methyl-chroman-4-yl)chromane-6-carboxamide |
| 193B | 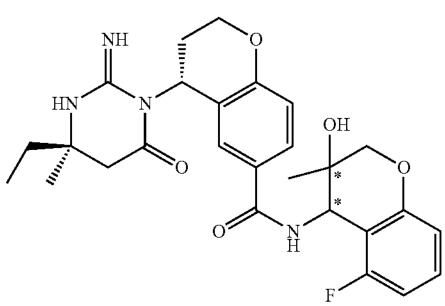 [SMILES: CC[C@]1(C)CC(=O)N([C@@H]2CCOc3ccc(C(=O)NC4c5c(F)cccc5OCC4(C)O)cc32)C(=N)N1] | 511.3 | (4R)-4-[(4R)-4-ethyl-2-imino-4-methyl-6-oxo-hexahydropyrimidin-1-yl]-N-(5-fluoro-3-hydroxy-3-methyl-chroman-4-yl)chromane-6-carboxamide |
| 193C | 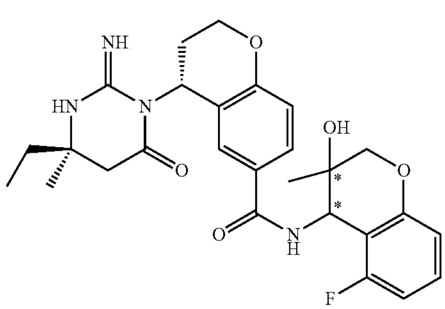 [SMILES: CC[C@]1(C)CC(=O)N([C@@H]2CCOc3ccc(C(=O)NC4c5c(F)cccc5OCC4(C)O)cc32)C(=N)N1] | 511.3 | (4R)-4-[(4R)-4-ethyl-2-imino-4-methyl-6-oxo-hexahydropyrimidin-1-yl]-N-(5-fluoro-3-hydroxy-3-methyl-chroman-4-yl)chromane-6-carboxamide |

TABLE 3-continued

| Example | Structure | LC/MS (M + 1)+ | Name |
|---|---|---|---|
| 194 | 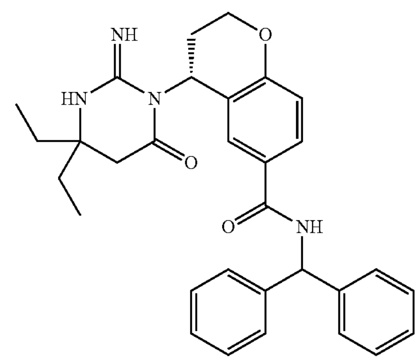 [SMILES: CCC1(CC)CC(=O)N([C@@H]2CCOc3ccc(C(=O)NC(c4ccccc4)c4ccccc4)cc32)C(=N)N1] | 511.3 | (4R)-N-benzhydryl-4-(4,4-diethyl-2-imino-6-oxo-hexahydropyrimidin-1-yl)chromane-6-carboxamide |
| 195 | 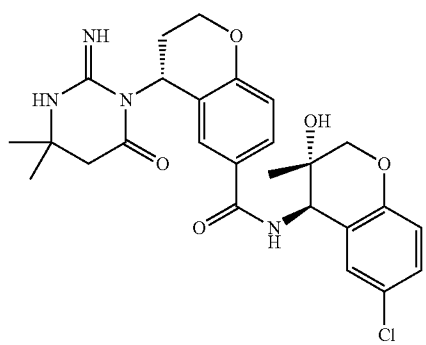 [SMILES: CC1(C)CC(=O)N([C@@H]2CCOc3ccc(C(=O)N[C@@H]4c5cc(Cl)ccc5OC[C@@]4(C)O)cc32)C(=N)N1] | 513.1 | (4R)-N-[(3S,4R)-6-chloro-3-hydroxy-3-methyl-chroman-4-yl]-4-(2-imino-4,4-dimethyl-6-oxo-hexahydropyrimidin-1-y)chromane-6-carboxamide |
| 196 | 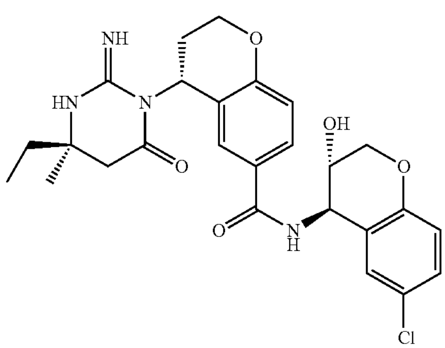 [SMILES: CC[C@]1(C)CC(=O)N([C@@H]2CCOc3ccc(C(=O)N[C@@H]4c5cc(Cl)ccc5OC[C@H]4O)cc32)C(=N)N1] | 513.2 | (4R)-N-[(3S,4R)-6-chloro-3-hydroxy-chroman-4-yl]-4-[(4R)-4-ethyl-2-imino-4-methyl-6-oxo-hexahydropyrimidin-1-yl]chromane-6-carboxamide |
| 197 | 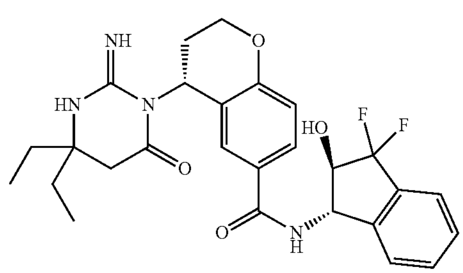 [SMILES: CCC1(CC)CC(=O)N([C@@H]2CCOc3ccc(C(=O)N[C@H]4c5ccccc5C(F)(F)[C@@H]4O)cc32)C(=N)N1] | 513.2 | (4R)-4-(4,4-diethyl-2-imino-6-oxo-hexahydropyrimidin-1-yl)-N-[(1S,2R)-3,3-difluoro-2-hydroxy-indan-1-yl]chromane-6-carboxamide |

TABLE 3-continued

| Example | Structure | LC/MS (M + 1)+ | Name |
|---|---|---|---|
| 198 | 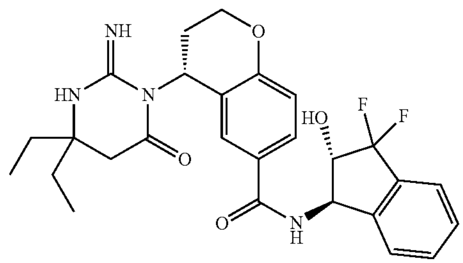 [SMILES: CCC1(CC)CC(=O)N([C@@H]2CCOc3ccc(C(=O)N[C@@H]4c5ccccc5C(F)(F)[C@H]4O)cc32)C(=N)N1] | 513.2 | (4R)-4-(4,4-diethyl-2-imino-6-oxo-hexahydropyrimidin-1-yl)-N-[(1R,2S)-3,3-difluoro-2-hydroxy-indan-1-yl]chromane-6-carboxamide |
| 199 | 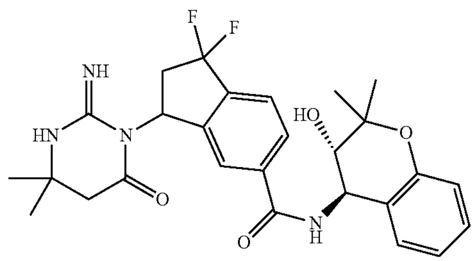 [SMILES: CC1(C)CC(=O)N(C2CC(F)(F)c3ccc(C(=O)N[C@@H]4c5ccccc5OC(C)(C)[C@H]4O)cc32)C(=N)N1] | 513.3 | (3R)-1,1-difluoro-N-[(3S,4R)-3-hydroxy-2,2-dimethyl-chroman-4-yl]-3-(2-imino-4,4-dimethyl-6-oxo-hexahydropyrimidin-1-yl)indane-5-carboxamide |
| 200 | 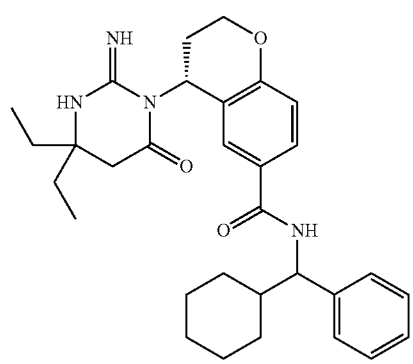 [SMILES: CCC1(CC)CC(=O)N([C@@H]2CCOc3ccc(C(=O)NC(c4ccccc4)C4CCCCC4)cc32)C(=N)N1] | 517.3 | (4R)-N-[cyclohexyl(phenyl)methyl]-4-(4,4-diethyl-2-imino-6-oxo-hexahydropyrimidin-1-yl)chromane-6-carboxamide |
| 201 | 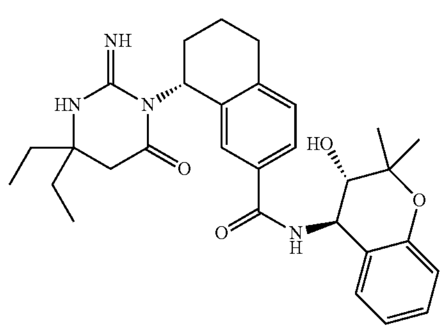 [SMILES: CCC1(CC)CC(=O)N([C@@H]2CCCc3ccc(C(=O)N[C@@H]4c5ccccc5OC(C)(C)[C@H]4O)cc32)C(=N)N1] | 519.3 | (4R)-4-(4,4-diethyl-2-imino-6-oxo-hexahydropyrimidin-1-yl)-N-[(3S,4R)-3-hydroxy-2,2-dimethyl-chroman-4-yl]tetralin-6-carboxamide |
| 202 | 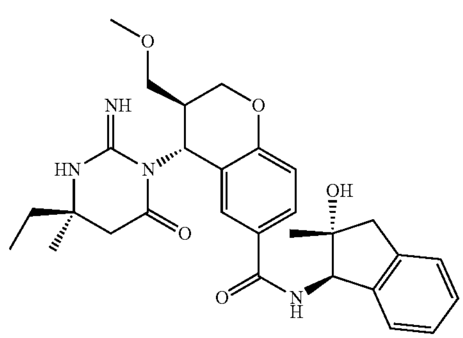 [SMILES: CC[C@]1(C)CC(=O)N([C@H]2c3cc(C(=O)N[C@@H]4c5ccccc5C[C@@]4(C)O)ccc3OC[C@@H]2COC)C(=N)N1] | 521.2 | (3S,4R)-4-[(4R)-4-ethyl-2-imino-4-methyl-6-oxo-hexahydropyrimidin-1-yl]-N-[(1R,2R)-2-hydroxy-2-methyl-indan-1-yl]-3-(methoxymethyl)chromane-6-carboxamide |

TABLE 3-continued

| Example | Structure | LC/MS (M + 1)+ | Name |
|---|---|---|---|
| 203 | 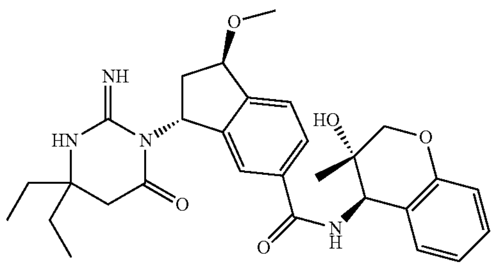 [SMILES: CCC1(CC)CC(=O)N([C@@H]2C[C@@H](OC)c3ccc(C(=O)N[C@@H]4c5ccccc5OC[C@@]4(C)O)cc32)C(=N)N1] | 521.3 | (1R,3R)-3-(4,4-diethyl-2-imino-6-oxo-hexahydropyrimidin-1-yl)-N-[(3S,4R)-3-hydroxy-3-methyl-chroman-4-yl]-1-methoxy-indane-6-carboxamide |
| 204 | 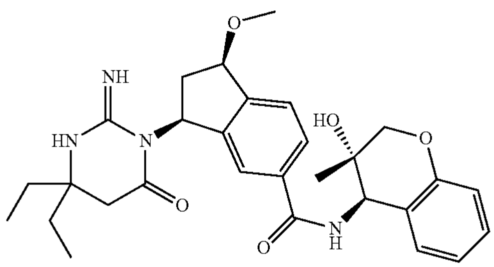 [SMILES: CCC1(CC)CC(=O)N([C@H]2C[C@@H](OC)c3ccc(C(=O)N[C@@H]4c5ccccc5OC[C@@]4(C)O)cc32)C(=N)N1] | 521.3 | (1R,3S)-3-(4,4-diethyl-2-imino-6-oxo-hexahydropyrimidin-1-yl)-N-[(3S,4R)-3-hydroxy-3-methyl-chroman-4-yl]-1-methoxy-indane-5-carboxamide |
| 205 | 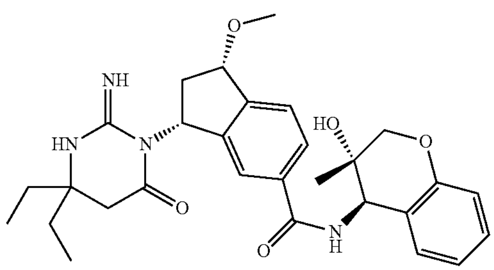 [SMILES: CCC1(CC)CC(=O)N([C@@H]2C[C@H](OC)c3ccc(C(=O)N[C@@H]4c5ccccc5OC[C@@]4(C)O)cc32)C(=N)N1] | 521.3 | (1S,3R)-3-(4,4-diethyl-2-imino-6-oxo-hexahydropyrimidin-1-yl)-N-[(3S,4R)-3-hydroxy-3-methyl-chroman-4-yl]-1-methoxy-indane-5-carboxamide |
| 206 | 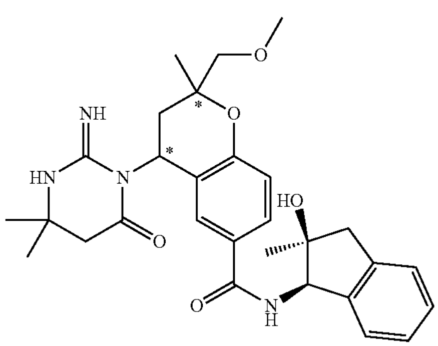 [SMILES: COCC1(C)CC(N2C(=N)NC(C)(C)CC2=O)c2cc(C(=O)N[C@@H]3c4ccccc4C[C@]3(C)O)ccc2O1] | 521.3 | N-[(1R,2S)-2-hydroxy-2-methyl-indan-1-yl]-4-(2-imino-4,4-dimethyl-6-oxo-hexahydropyrimidin-1-yl)-2-(methoxymethyl)-2-methyl-chromane-6-carboxamide |
| 207 | 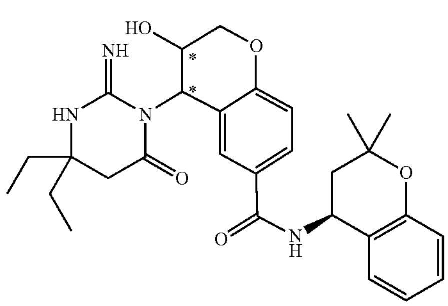 [SMILES: CCC1(CC)CC(=O)N(C2c3cc(C(=O)N[C@H]4CC(C)(C)Oc5ccccc54)ccc3OCC2O)C(=N)N1] | 521.2 | 4-(4,4-diethyl-2-imino-6-oxo-hexahydropyrimidin-1-yl)-N-[(4S)-2,2-dimethylchroman-4-yl]-3-hydroxy-chromane-6-carboxamide |

TABLE 3-continued

| Example | Structure | LC/MS (M + 1)+ | Name |
|---|---|---|---|
| 208 | 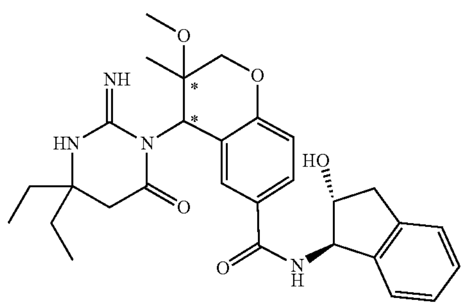 [SMILES: CCC1(CC)CC(=O)N(C2c3cc(C(=O)N[C@@H]4c5ccccc5C[C@H]4O)ccc3OCC2(C)OC)C(=N)N1] | 521.3 | 4-(4,4-diethyl-2-imino-6-oxo-hexahydropyrimidin-1-yl)-N-[(1R,2R)-2-hydroxyindan-1-yl]-3-methoxy-3-methyl-chromane-6-carboxamide |
| 209 | 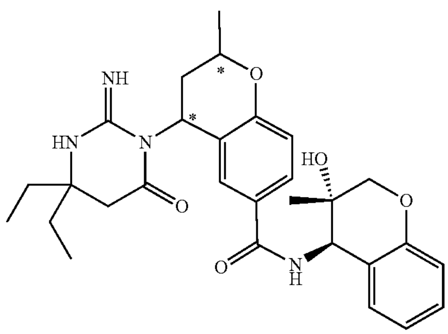 [SMILES: CCC1(CC)CC(=O)N(C2CC(C)Oc3ccc(C(=O)N[C@@H]4c5ccccc5OC[C@@]4(C)O)cc32)C(=N)N1] | 521.3 | 4-(4,4-diethyl-2-imino-6-oxo-hexahydropyrimidin-1-yl)-N-[(3S,4R)-3-hydroxy-3-methyl-chroman-4-yl]-2-methyl-chromane-6-carboxamide |
| 210 | 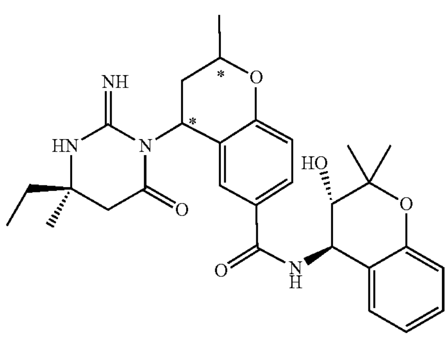 [SMILES: CC[C@]1(C)CC(=O)N(C2CC(C)Oc3ccc(C(=O)N[C@@H]4c5ccccc5OC(C)(C)[C@H]4O)cc32)C(=N)N1] | 521.3 | 4-[(4R)-4-ethyl-2-imino-4-methyl-6-oxo-hexahydropyrimidin-1-yl]-N-[(3S,4R)-3-hydroxy-2,2-dimethyl-chroman-4-yl]-2-methyl-chromane-6-carboxamide |
| 211 | 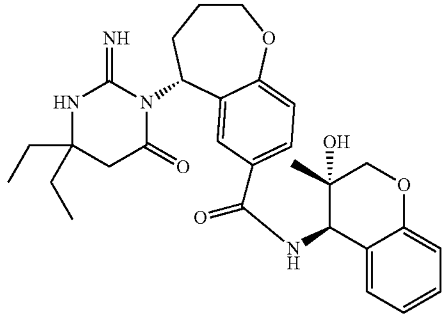 [SMILES: CCC1(CC)CC(=O)N([C@@H]2CCCOc3ccc(C(=O)N[C@@H]4c5ccccc5OC[C@@]4(C)O)cc32)C(=N)N1] | 521.2 | (5R)-5-(4,4-diethyl-2-imino-6-oxo-hexahydropyrimidin-1-yl)-N-[(3S,4R)-3-hydroxy-3-methyl-chroman-4-yl]-2,3,4,5-tetrahydro-1-benzoxepine-7-carboxamide |

TABLE 3-continued

| Example | Structure | LC/MS (M + 1)+ | Name |
|---|---|---|---|
| 212 | 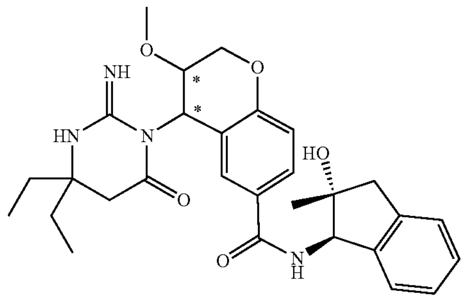 [SMILES: CCC1(CC)CC(=O)N(C2c3cc(C(=O)N[C@@H]4c5ccccc5C[C@@]4(C)O)ccc3OCC2OC)C(=N)N1] | 521.3 | 4-(4,4-diethyl-2-imino-6-oxo-hexahydropyrimidin-1-yl)-N-[(1R,2R)-2-hydroxy-2-methyl-indan-1-yl]-3-methoxy-chromane-6-carboxamide |
| 213 | 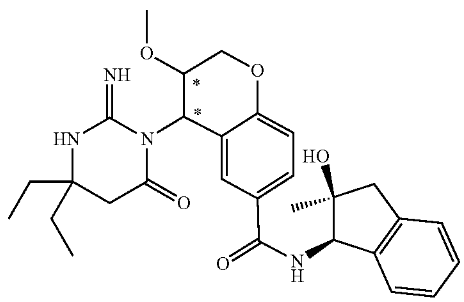 [SMILES: CCC1(CC)CC(=O)N(C2c3cc(C(=O)N[C@@H]4c5ccccc5C[C@]4(C)O)ccc3OCC2OC)C(=N)N1] | 521.3 | 4-(4,4-diethyl-2-imino-6-oxo-hexahydropyrimidin-1-yl)-N-[(1R,2S)-2-hydroxy-2-methyl-indan-1-yl]-3-methoxy-chromane-6-carboxamide |
| 214A | 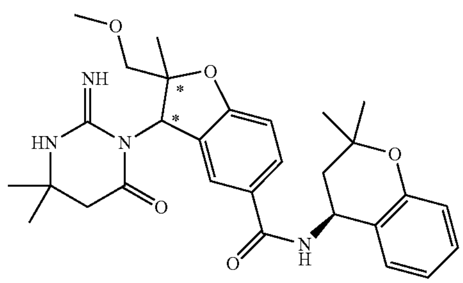 [SMILES: COCC1(C)Oc2ccc(C(=O)N[C@H]3CC(C)(C)Oc4ccccc43)cc2C1N1C(=N)NC(C)(C)CC1=O] | 521.3 | N-[(4S)-2,2-dimethylchroman-4-yl]-3-(2-imino-4,4-dimethyl-6-oxo-hexahydropyrimidin-1-yl)-2-(methoxymethyl)-2-methyl-3H-benzofuran-5-carboxamide |
| 214B | 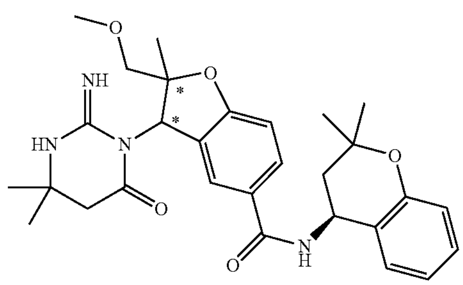 [SMILES: COCC1(C)Oc2ccc(C(=O)N[C@H]3CC(C)(C)Oc4ccccc43)cc2C1N1C(=N)NC(C)(C)CC1=O] | 521.3 | N-[(4S)-2,2-dimethylchroman-4-yl]-3-(2-imino-4,4-dimethyl-6-oxo-hexahydropyrimidin-1-yl)-2-(methoxymethyl)-2-methyl-3H-benzofuran-5-carboxamide |
| 215 | 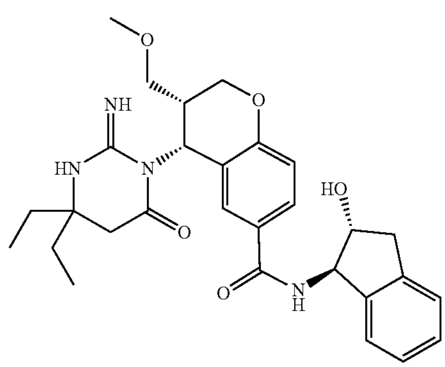 [SMILES: CCC1(CC)CC(=O)N([C@H]2c3cc(C(=O)N[C@@H]4c5ccccc5C[C@H]4O)ccc3OC[C@H]2COC)C(=N)N1] | 521.3 | (3R,4R)-4-(4,4-diethyl-2-imino-6-oxo-hexahydropyrimidin-1-yl)-N-[(1R,2R)-2-hydroxyindan-1-yl]-3-(methoxymethyl)chromane-6-carboxamide |

TABLE 3-continued

| Example | Structure | LC/MS (M + 1)+ | Name |
|---|---|---|---|
| 216 | 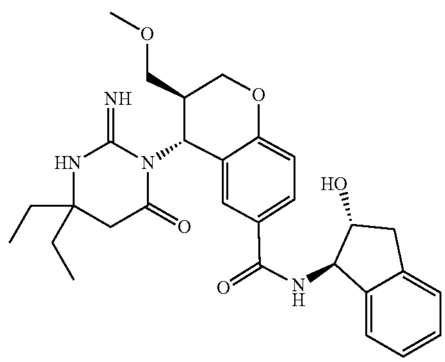 [SMILES: CCC1(CC)CC(=O)N([C@H]2c3cc(C(=O)N[C@@H]4c5ccccc5C[C@H]4O)ccc3OC[C@@H]2COC)C(=N)N1] | 521.3 | (3S,4R)-4-(4,4-diethyl-2-imino-6-oxo-hexahydropyrimidin-1-yl)-N-[(1R,2R)-2-hydroxyindan-1-yl]-3-(methoxymethyl)chromane-6-carboxamide |
| 217 | 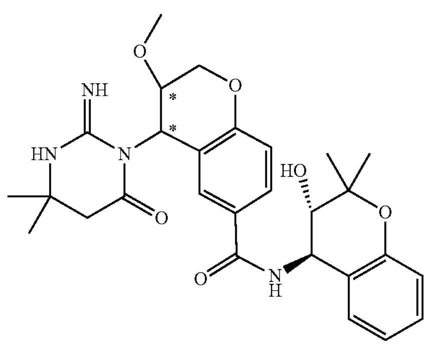 [SMILES: COC1COc2ccc(C(=O)N[C@@H]3c4ccccc4OC(C)(C)[C@H]3O)cc2C1N1C(=N)NC(C)(C)CC1=O] | 523.3 | N-[(3S,4R)-3-hydroxy-2,2-dimethyl-chroman-4-yl]-4-(2-imino-4,4-dimethyl-6-oxo-hexahydropyrimidin-1-yl)-3-methoxy-chromane-6-carboxamide |
| 218 | 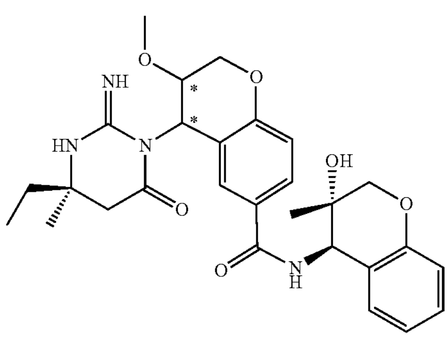 [SMILES: CC[C@]1(C)CC(=O)N(C2c3cc(C(=O)N[C@@H]4c5ccccc5OC[C@@]4(C)O)ccc3OCC2OC)C(=N)N1] | 523.2 | 4-[(4R)-4-ethyl-2-imino-4-methyl-6-oxo-hexahydropyrimidin-1-yl]-N-[(3S,4R)-3-hydroxy-3-methyl-chroman-4-yl]-3-methoxy-chromane-6-carboxamide |
| 219 | 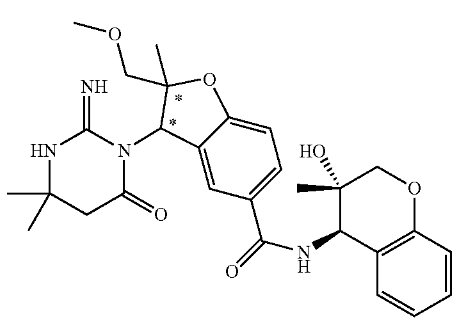 [SMILES: COCC1(C)Oc2ccc(C(=O)N[C@@H]3c4ccccc4OC[C@@]3(C)O)cc2C1N1C(=N)NC(C)(C)CC1=O] | 523.3 | N-[(3S,4R)-3-hydroxy-3-methyl-chroman-4-yl]-3-(2-imino-4,4-dimethyl-6-oxo-hexahydropyrimidin-1-yl)-2-(methoxymethyl)-2-methyl-3H-benzofuran-5-carboxamide |

TABLE 3-continued

| Example | Structure | LC/MS (M + 1)+ | Name |
|---|---|---|---|
| 220 | 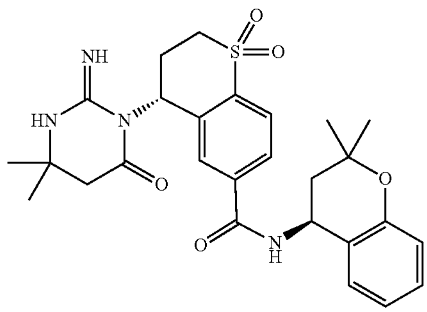 [SMILES: CC1(C)CC(=O)N([C@@H]2CCS(=O)(=O)c3ccc(C(=O)N[C@H]4CC(C)(C)Oc5ccccc54)cc32)C(=N)N1] | 525.2 | (4R)-N-[(4S)-2,2-dimethylchroman-4-yl]-4-(2-imino-4,4-dimethyl-6-oxo-hexahydropyrimidin-1-yl)-1,1-dioxo-3,4-dihydro-2H-thiochromene-6-carboxamide |
| 221 | 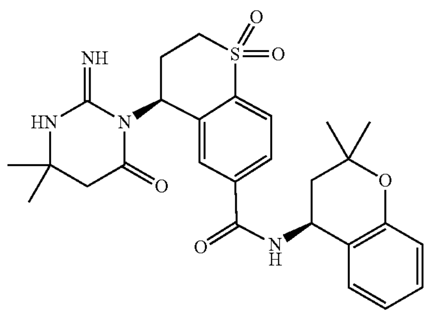 [SMILES: CC1(C)CC(=O)N([C@H]2CCS(=O)(=O)c3ccc(C(=O)N[C@H]4CC(C)(C)Oc5ccccc54)cc32)C(=N)N1] | 525.3 | (4S)-N-[(4S)-2,2-dimethylchroman-4-yl]-4-(2-imino-4,4-dimethyl-6-oxo-hexahydropyrimidin-1-yl)-1,1-dioxo-3,4-dihydro-2H-thiochromene-6-carboxamide |
| 222 | 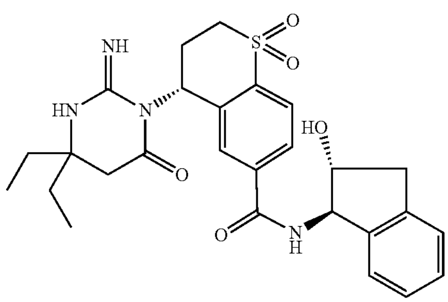 [SMILES: CCC1(CC)CC(=O)N([C@@H]2CCS(=O)(=O)c3ccc(C(=O)N[C@@H]4c5ccccc5C[C@H]4O)cc32)C(=N)N1] | 525.2 | (4R)-4-(4,4-diethyl-2-imino-6-oxo-hexahydropyrimidin-1-yl)-N-[(1R,2R)-2-hydroxyindan-1-yl]-1,1-dioxo-3,4-dihydro-2H-thiochromene-6-carboxamide |
| 223 | 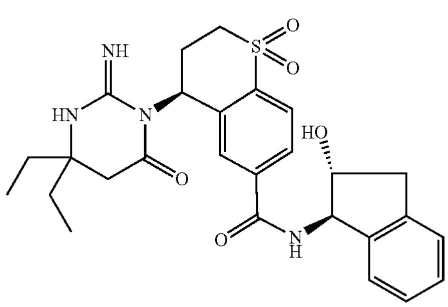 [SMILES: CCC1(CC)CC(=O)N([C@H]2CCS(=O)(=O)c3ccc(C(=O)N[C@@H]4c5ccccc5C[C@H]4O)cc32)C(=N)N1] | 525.3 | (4S)-4-(4,4-diethyl-2-imino-6-oxo-hexahydropyrimidin-1-yl)-N-[(1R,2R)-2-hydroxyindan-1-yl]-1,1-dioxo-3,4-dihydro-2H-thiochromene-6-carboxamide |

TABLE 3-continued

| Example | Structure | LC/MS (M + 1)+ | Name |
|---|---|---|---|
| 224 | 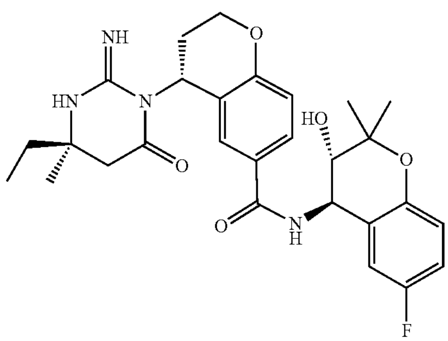 [SMILES: CC[C@]1(C)CC(=O)N([C@@H]2CCOc3ccc(C(=O)N[C@@H]4c5cc(F)ccc5OC(C)(C)[C@H]4O)cc32)C(=N)N1] | 525.3 | (4R)-4-[(4R)-4-ethyl-2-imino-4-methyl-6-oxo-hexahydropyrimidin-1-yl]-N-[(3S,4R)-6-fluoro-3-hydroxy-2,2-dimethyl-chroman-4-yl]chromane-6-carboxamide |
| 225 | 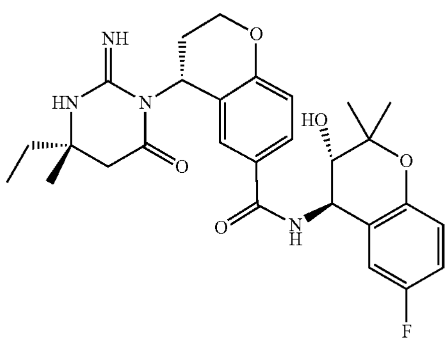 [SMILES: CC[C@@]1(C)CC(=O)N([C@@H]2CCOc3ccc(C(=O)N[C@@H]4c5cc(F)ccc5OC(C)(C)[C@H]4O)cc32)C(=N)N1] | 525.2 | (4R)-4-[(4S)-4-ethyl-2-imino-4-methyl-6-oxo-hexahydropyrimidin-1-yl]-N-[(3S,4R)-6-fluoro-3-hydroxy-2,2-dimethyl-chroman-4-yl]chromane-6-carboxamide |
| 226A | 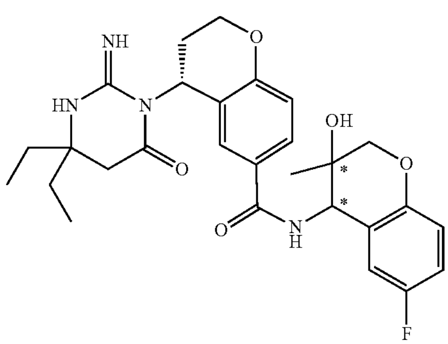 [SMILES: CCC1(CC)CC(=O)N([C@@H]2CCOc3ccc(C(=O)NC4c5cc(F)ccc5OCC4(C)O)cc32)C(=N)N1] | 525.3 | (4R)-4-(4,4-diethyl-2-imino-6-oxo-hexahydropyrimidin-1-yl)-N-(6-fluoro-3-hydroxy-3-methyl-chroman-4-yl)chromane-6-carboxamide |
| 226B | 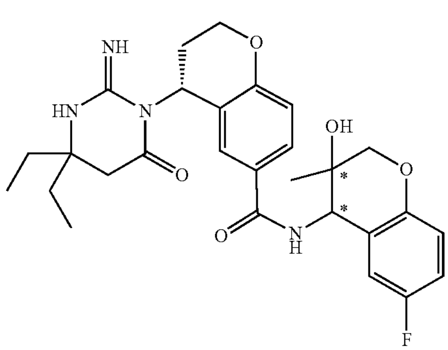 [SMILES: CCC1(CC)CC(=O)N([C@@H]2CCOc3ccc(C(=O)NC4c5cc(F)ccc5OCC4(C)O)cc32)C(=N)N1] | 525.3 | (4R)-4-(4,4-diethyl-2-imino-6-oxo-hexahydropyrimidin-1-yl)-N-(6-fluoro-3-hydroxy-3-methyl-chroman-4-yl)chromane-6-carboxamide |

TABLE 3-continued

| Example | Structure | LC/MS (M + 1)+ | Name |
|---|---|---|---|
| 226C | 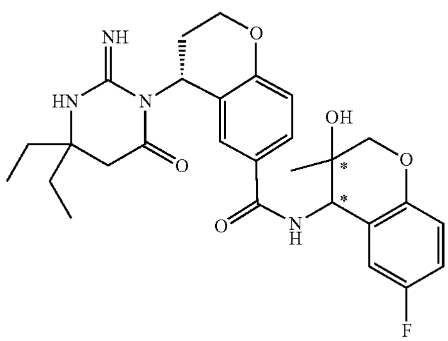 [SMILES: CCC1(CC)CC(=O)N([C@@H]2CCOc3ccc(C(=O)NC4c5cc(F)ccc5OCC4(C)O)cc32)C(=N)N1] | 525.3 | (4R)-4-(4,4-diethyl-2-imino-6-oxo-hexahydropyrimidin-1-yl)-N-(6-fluoro-3-hydroxy-3-methyl-chroman-4-yl)chromane-6-carboxamide |
| 226D | 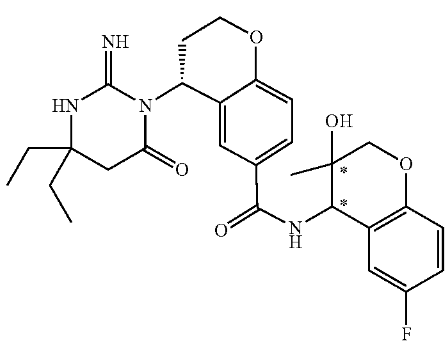 [SMILES: CCC1(CC)CC(=O)N([C@@H]2CCOc3ccc(C(=O)NC4c5cc(F)ccc5OCC4(C)O)cc32)C(=N)N1] | 525.1 | (4R)-4-(4,4-diethyl-2-imino-6-oxo-hexahydropyrimidin-1-yl)-N-(6-fluoro-3-hydroxy-3-methyl-chroman-4-yl)chromane-6-carboxamide |
| 227 | 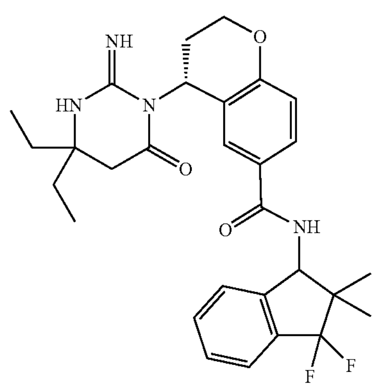 [SMILES: CCC1(CC)CC(=O)N([C@@H]2CCOc3ccc(C(=O)NC4c5ccccc5C(F)(F)C4(C)C)cc32)C(=N)N1] | 525.3 | (4R)-4-(4,4-diethyl-2-imino-6-oxo-hexahydropyrimidin-1-yl)-N-(3,3-difluoro-2,2-dimethyl-indan-1-yl)chromane-6-carboxamide |
| 228 | 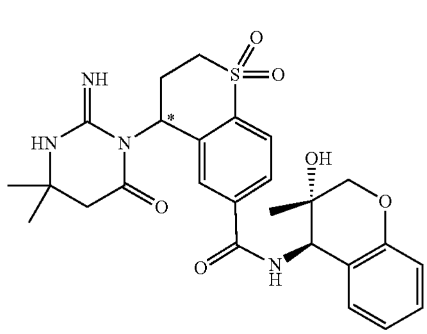 [SMILES: CC1(C)CC(=O)N(C2CCS(=O)(=O)c3ccc(C(=O)N[C@@H]4c5ccccc5OC[C@@]4(C)O)cc32)C(=N)N1] | 527.2 | N-[(3S,4R)-3-hydroxy-3-methyl-chroman-4-yl]-4-(2-imino-4,4-dimethyl-6-oxo-hexahydropyrimidin-1-yl)-1,1-dioxo-3,4-dihydro-2H-thiochromene-6-carboxamide |

TABLE 3-continued

| Example | Structure | LC/MS (M + 1)+ | Name |
|---|---|---|---|
| 229 | 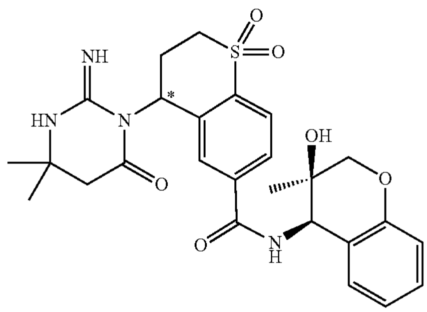 [SMILES: CC1(C)CC(=O)N(C2CCS(=O)(=O)c3ccc(C(=O)N[C@@H]4c5ccccc5OC[C@]4(C)O)cc32)C(=N)N1] | 527.2 | N-[(3R,4R)-3-hydroxy-3-methyl-chroman-4-yl]-4-(2-imino-4,4-dimethyl-6-oxo-hexahydropyrimidin-1-yl)-1,1-dioxo-3,4-dihydro-2H-thiochromene-6-carboxamide |
| 230 | 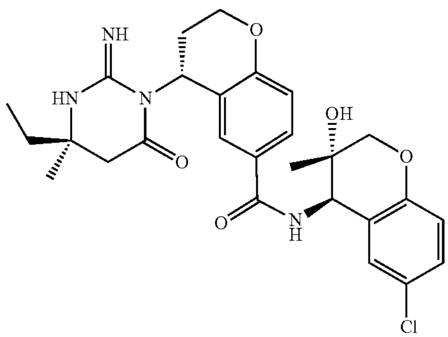 [SMILES: CC[C@]1(C)CC(=O)N([C@@H]2CCOc3ccc(C(=O)N[C@@H]4c5cc(Cl)ccc5OC[C@@]4(C)O)cc32)C(=N)N1] | 527.1 | (4R)-N-[(3S,4R)-6-chloro-3-hydroxy-3-methyl-chroman-4-yl]-4-[(4R)-4-ethyl-2-imino-4-methyl-6-oxo-hexahydropyrimidin-1-yl]chromane-6-carboxamide |
| 231 | 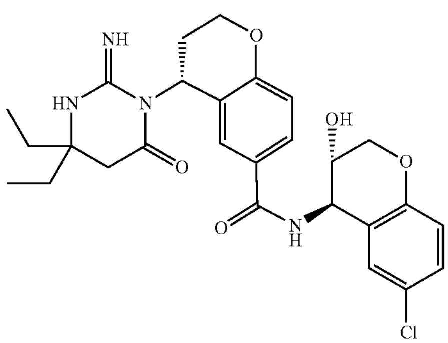 [SMILES: CCC1(CC)CC(=O)N([C@@H]2CCOc3ccc(C(=O)N[C@@H]4c5cc(Cl)ccc5OC[C@H]4O)cc32)C(=N)N1] | 527.3 | (4R)-N-[(3S,4R)-6-chloro-3-hydroxy-chroman-4-yl]-4-(4,4-diethyl-2-imino-6-oxo-hexahydropyrimidin-1-yl)chromane-6-carboxamide |
| 232 | 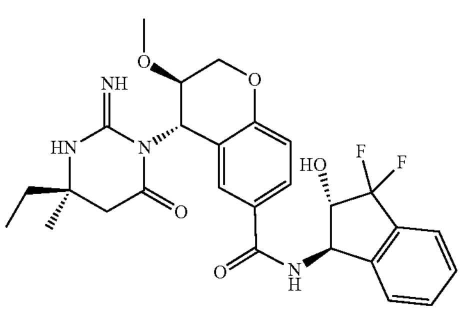 [SMILES: CC[C@]1(C)CC(=O)N([C@H]2c3cc(C(=O)N[C@@H]4c5ccccc5C(F)(F)[C@H]4O)ccc3OC[C@@H]2OC)C(=N)N1] | 529.3 | (3R,4S)-N-[(1R,2S)-3,3-difluoro-2-hydroxy-indan-1-yl]-4-[(4R)-4-ethyl-2-imino-4-methyl-6-oxo-hexahydropyrimidin-1-yl]-3-methoxy-chromane-6-carboxamide |

TABLE 3-continued

| Example | Structure | LC/MS (M + 1)+ | Name |
|---|---|---|---|
| 233 | 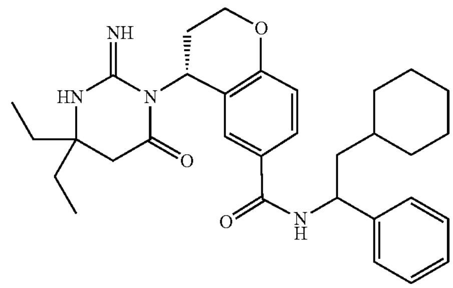 [SMILES: CCC1(CC)CC(=O)N([C@@H]2CCOc3ccc(C(=O)NC(CC4CCCCC4)c4ccccc4)cc32)C(=N)N1] | 531.3 | (4R)-N-(2-cyclohexyl-1-phenyl-ethyl)-4-(4,4-diethyl-2-imino-6-oxo-hexahydropyrimidin-1-yl)chromane-6-carboxamide |
| 234A | 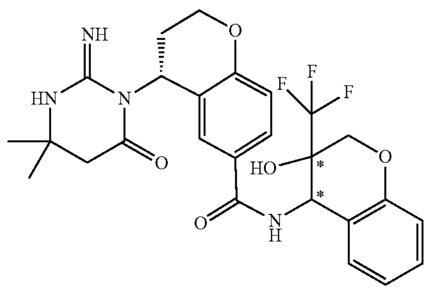 [SMILES: CC1(C)CC(=O)N([C@@H]2CCOc3ccc(C(=O)NC4c5ccccc5OCC4(O)C(F)(F)F)cc32)C(=N)N1] | 533.3 | (4R)-N-[3-hydroxy-3-(trifluoromethyl)chroman-4-yl]-4-(2-imino-4,4-dimethyl-6-oxo-hexahydropyrimidin-1-yl)chromane-6-carboxamide |
| 234B | 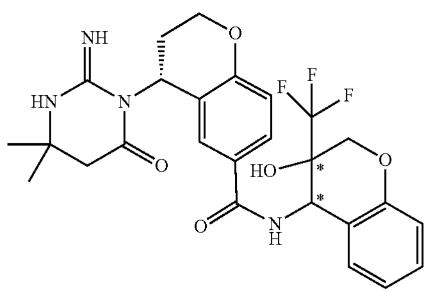 [SMILES: CC1(C)CC(=O)N([C@@H]2CCOc3ccc(C(=O)NC4c5ccccc5OCC4(O)C(F)(F)F)cc32)C(=N)N1] | 533.2 | (4R)-N-[3-hydroxy-3-(trifluoromethyl)chroman-4-yl]-4-(2-imino-4,4-dimethyl-6-oxo-hexahydropyrimidin-1-yl)chromane-6-carboxamide |
| 234C | 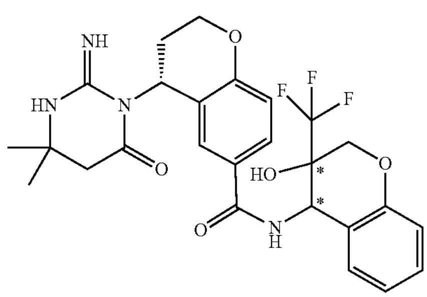 [SMILES: CC1(C)CC(=O)N([C@@H]2CCOc3ccc(C(=O)NC4c5ccccc5OCC4(O)C(F)(F)F)cc32)C(=N)N1] | 533.2 | (4R)-N-[3-hydroxy-3-(trifluoromethyl)chroman-4-yl]-4-(2-imino-4,4-dimethyl-6-oxo-hexahydropyrimidin-1-yl)chromane-6-carboxamide |
| 235 | 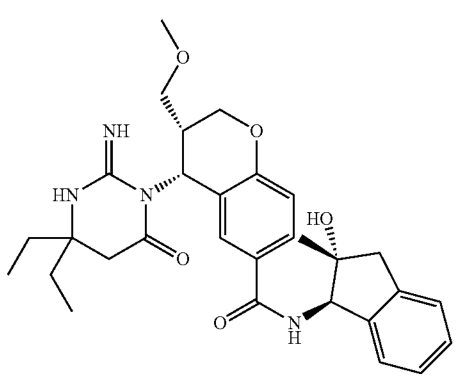 [SMILES: CCC1(CC)CC(=O)N([C@H]2c3cc(C(=O)N[C@@H]4c5ccccc5C[C@@]4(C)O)ccc3OC[C@H]2COC)C(=N)N1] | 535.1 | (3R,4R)-4-(4,4-diethyl-2-imino-6-oxo-hexahydropyrimidin-1-yl)-N-[(1R,2R)-2-hydroxy-2-methyl-indan-1-yl]-3-(methoxymethyl)chromane-6-carboxamide |

TABLE 3-continued

| Example | Structure | LC/MS (M + 1)+ | Name |
|---|---|---|---|
| 236 | 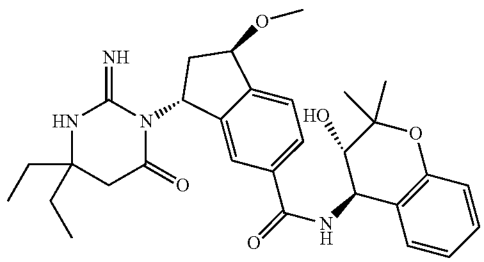 [SMILES: CCC1(CC)CC(=O)N([C@@H]2C[C@@H](OC)c3ccc(C(=O)N[C@@H]4c5ccccc5OC(C)(C)[C@H]4O)cc32)C(=N)N1] | 535.3 | (1R,3R)-3-(4,4-diethyl-2-imino-6-oxo-hexahydropyrimidin-1-yl)-N-[(3S,4R)-3-hydroxy-2,2-dimethyl-chroman-4-yl]-1-methoxy-indane-5-carboxamide |
| 237 | 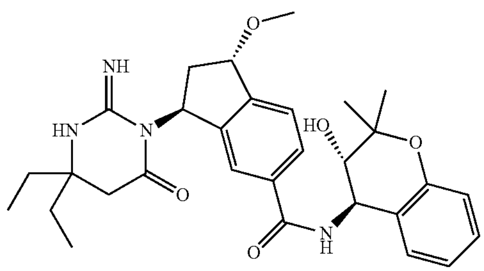 [SMILES: CCC1(CC)CC(=O)N([C@H]2C[C@H](OC)c3ccc(C(=O)N[C@@H]4c5ccccc5OC(C)(C)[C@H]4O)cc32)C(=N)N1] | 535.3 | (1S,3S)-3-(4,4-diethyl-2-imino-6-oxo-hexahydropyrimidin-1-yl)-N-[(3S,4R)-3-hydroxy-2,2-dimethyl-chroman-4-yl]-1-methoxy-indane-5-carboxamide |
| 238 | 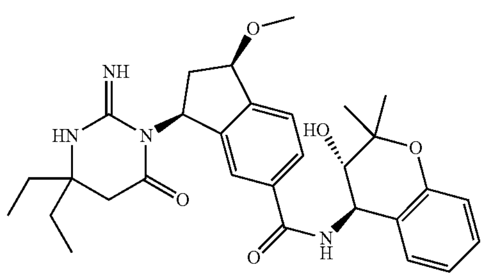 [SMILES: CCC1(CC)CC(=O)N([C@H]2C[C@@H](OC)c3ccc(C(=O)N[C@@H]4c5ccccc5OC(C)(C)[C@H]4O)cc32)C(=N)N1] | 535.4 | (1R,3S)-3-(4,4-diethyl-2-imino-6-oxo-hexahydropyrimidin-1-yl)-N-[(3S,4R)-3-hydroxy-2,2-dimethyl-chroman-4-yl]-1-methoxy-indane-5-carboxamide |
| 239 | 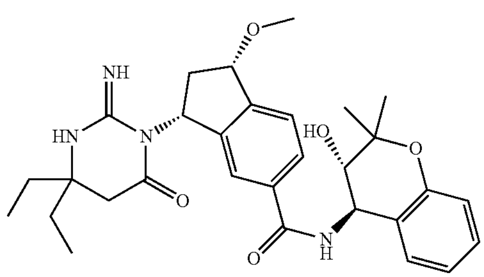 [SMILES: CCC1(CC)CC(=O)N([C@@H]2C[C@H](OC)c3ccc(C(=O)N[C@@H]4c5ccccc5OC(C)(C)[C@H]4O)cc32)C(=N)N1] | 535.3 | (1S,3R)-3-(4,4-diethyl-2-imino-6-oxo-hexahydropyrimidin-1-yl)-N-[(3S,4R)-3-hydroxy-2,2-dimethyl-chroman-4-yl]-1-methoxy-indane-5-carboxamide |
| 240 | 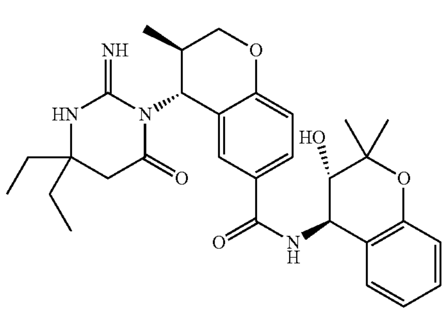 [SMILES: CCC1(CC)CC(=O)N([C@H]2c3cc(C(=O)N[C@@H]4c5ccccc5OC(C)(C)[C@H]4O)ccc3OC[C@@H]2C)C(=N)N1] | 535.4 | (3R,4R)-4-(4,4-diethyl-2-imino-6-oxo-hexahydropyrimidin-1-yl)-N-[(3S,4R)-3-hydroxy-2,2-dimethyl-chroman-4-yl]-3-methyl-chromane-6-carboxamide |

TABLE 3-continued

| Example | Structure | LC/MS (M + 1)+ | Name |
|---|---|---|---|
| 241 | 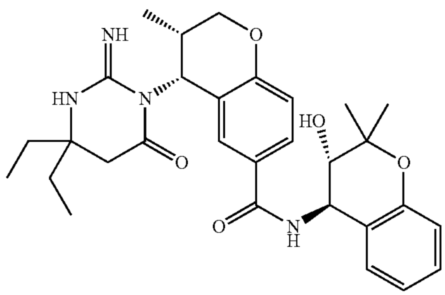 [SMILES: CCC1(CC)CC(=O)N([C@H]2c3cc(C(=O)N[C@@H]4c5ccccc5OC(C)(C)[C@H]4O)ccc3OC[C@H]2C)C(=N)N1] | 535.3 | (3S,4R)-4-(4,4-diethyl-2-imino-6-oxo-hexahydropyrimidin-1-yl)-N-[(3S,4R)-3-hydroxy-2,2-dimethyl-chroman-4-yl]-3-methyl-chromane-6-carboxamide |
| 242A | 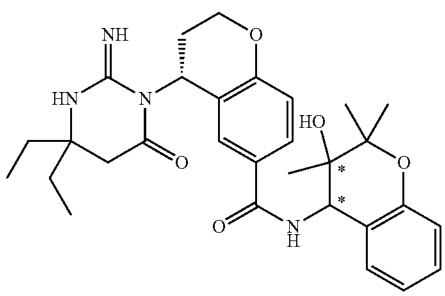 [SMILES: CCC1(CC)CC(=O)N([C@@H]2CCOc3ccc(C(=O)NC4c5ccccc5OC(C)(C)C4(C)O)cc32)C(=N)N1] | 535.3 | (4R)-4-(4,4-diethyl-2-imino-6-oxo-hexahydropyrimidin-1-yl)-N-(3-hydroxy-2,2,3-trimethyl-chroman-4-yl)chromane-6-carboxamide |
| 242B | 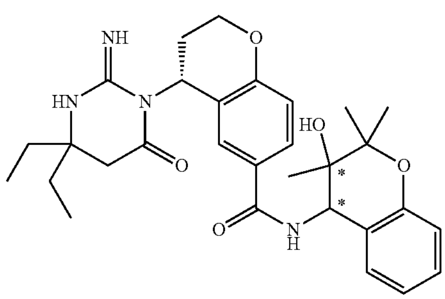 [SMILES: CCC1(CC)CC(=O)N([C@@H]2CCOc3ccc(C(=O)NC4c5ccccc5OC(C)(C)C4(C)O)cc32)C(=N)N1] | 535.3 | (4R)-4-(4,4-diethyl-2-imino-6-oxo-hexahydropyrimidin-1-yl)-N-(3-hydroxy-2,2,3-trimethyl-chroman-4-yl)chromane-6-carboxamide |
| 243 | 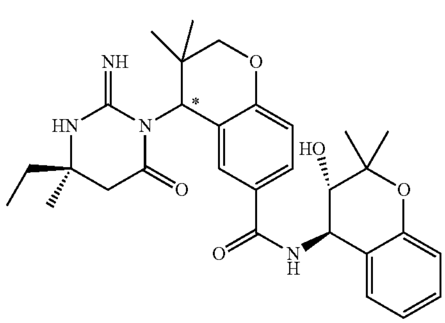 [SMILES: CC[C@]1(C)CC(=O)N(C2c3cc(C(=O)N[C@@H]4c5ccccc5OC(C)(C)[C@H]4O)ccc3OCC2(C)C)C(=N)N1] | 535.3 | 4-[(4R)-4-ethyl-2-imino-4-methyl-6-oxo-hexahydropyrimidin-1-yl]-N-[(3S,4R)-3-hydroxy-2,2-dimethyl-chroman-4-yl]-3,3-dimethyl-chromane-6-carboxamide |

TABLE 3-continued

| Example | Structure | LC/MS (M + 1)+ | Name |
|---|---|---|---|
| 244 | 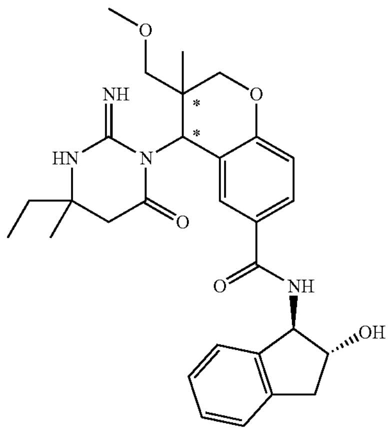 [SMILES: CCC1(C)CC(=O)N(C2c3cc(C(=O)N[C@@H]4c5ccccc5C[C@H]4O)ccc3OCC2(C)COC)C(=N)N1] | 535.3 | 4-(4,4-diethyl-2-imino-6-oxo-hexahydropyrimidin-1-yl)-N-[(1R,2R)-2-hydroxyindan-1-yl]-3-(methoxymethyl)-3-methyl-chromane-6-carboxamide |
| 245 | 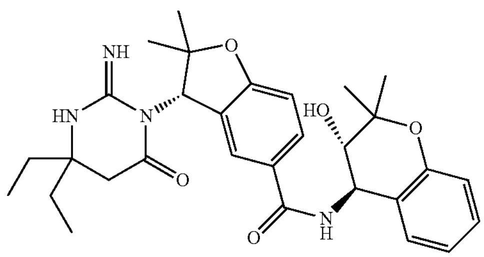 [SMILES: CCC1(CC)CC(=O)N([C@H]2c3cc(C(=O)N[C@@H]4c5ccccc5OC(C)(C)[C@H]4O)ccc3OC2(C)C)C(=N)N1] | 535.4 | (3S)-3-(4,4-diethyl-2-imino-6-oxo-hexahydropyrimidin-1-yl)-N-[(3S,4R)-3-hydroxy-2,2-dimethyl-chroman-4-yl]-2,2-dimethyl-3H-benzofuran-5-carboxamide |
| 246 | 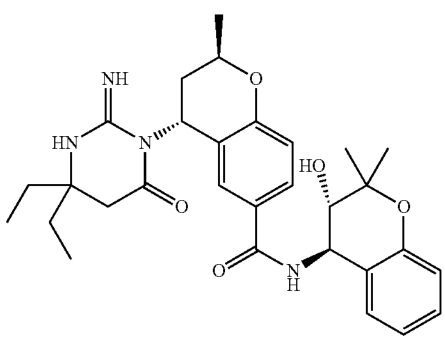 [SMILES: CCC1(CC)CC(=O)N([C@@H]2C[C@@H](C)Oc3ccc(C(=O)N[C@@H]4c5ccccc5OC(C)(C)[C@H]4O)cc32)C(=N)N1] | 535.3 | (2R,4R)-4-(4,4-diethyl-2-imino-6-oxo-hexahydropyrimidin-1-yl)-N-[(3S,4R)-3-hydroxy-2,2-dimethyl-chroman-4-yl]-2-methyl-chromane-6-carboxamide |
| 247 | 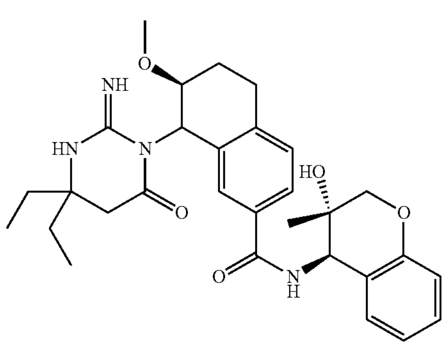 [SMILES: CCC1(CC)CC(=O)N(C2c3cc(C(=O)N[C@@H]4c5ccccc5OC[C@@]4(C)O)ccc3CC[C@@H]2OC)C(=N)N1] | 535.1 | (3S,4S)-4-(4,4-diethyl-2-imino-6-oxo-hexahydropyrimidin-1-yl)-N-[(3S,4R)-3-hydroxy-3-methyl-chroman-4-yl]-3-methoxy-tetralin-6-carboxamide |

TABLE 3-continued

| Example | Structure | LC/MS (M + 1)+ | Name |
|---|---|---|---|
| 248 | 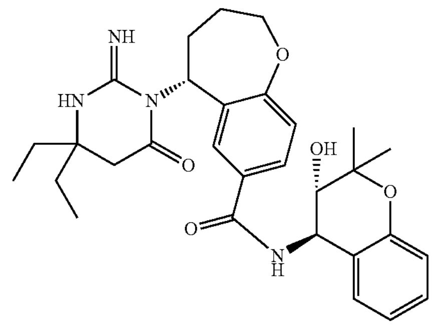 [SMILES: CCC1(CC)CC(=O)N([C@@H]2CCCOc3ccc(C(=O)N[C@@H]4c5ccccc5OC(C)(C)[C@H]4O)cc32)C(=N)N1] | 535.2 | (5R)-5-(4,4-diethyl-2-imino-6-oxo-hexahydropyrimidin-1-yl)-N-[(3S,4R)-3-hydroxy-2,2-dimethyl-chroman-4-yl]-2,3,4,5-tetrahydro-1-benzoxepine-7-carboxamide |
| 249 | 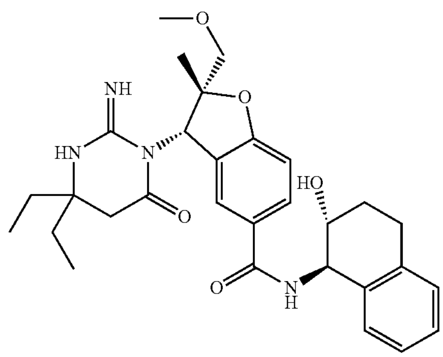 [SMILES: CCC1(CC)CC(=O)N([C@H]2c3cc(C(=O)N[C@@H]4c5ccccc5CC[C@H]4O)ccc3O[C@@]2(C)COC)C(=N)N1] | 535.3 | (2R,3S)-3-(4,4-diethyl-2-imino-6-oxo-hexahydropyrimidin-1-yl)-N-[(1R,2R)-2-hydroxytetralin-1-yl]-2-(methoxymethyl)-2-methyl-3H-benzofuran-5-carboxamide |
| 250 | 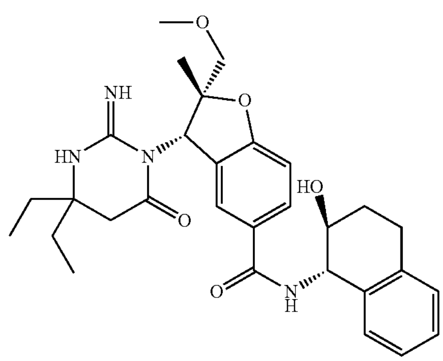 [SMILES: CCC1(CC)CC(=O)N([C@H]2c3cc(C(=O)N[C@H]4c5ccccc5CC[C@@H]4O)ccc3O[C@@]2(C)COC)C(=N)N1] | 535.3 | (2R,3S)-3-(4,4-diethyl-2-imino-6-oxo-hexahydropyrimidin-1-yl)-N-[(1S,2S)-2-hydroxytetralin-1-yl]-2-(methoxymethyl)-2-methyl-3H-benzofuran-5-carboxamide |
| 251A | 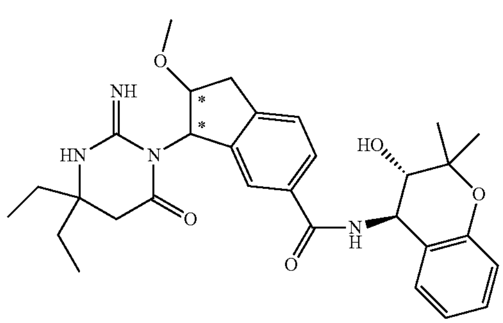 [SMILES: CCC1(CC)CC(=O)N(C2c3cc(C(=O)N[C@@H]4c5ccccc5OC(C)(C)[C@H]4O)ccc3CC2OC)C(=N)N1] | 535.3 | 3-(4,4-diethyl-2-imino-6-oxo-hexahydropyrimidin-1-yl)-N-[(3S,4R)-3-hydroxy-2,2-dimethyl-chroman-4-yl]-2-methoxy-indane-5-carboxamide |

TABLE 3-continued

| Example | Structure | LC/MS (M + 1)+ | Name |
|---|---|---|---|
| 251B | 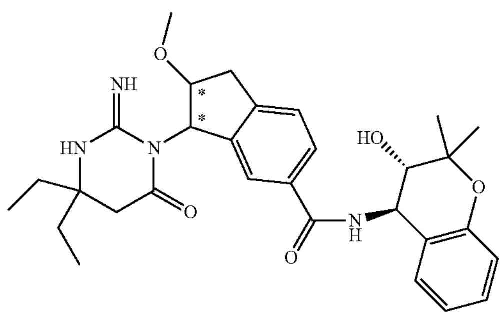 [SMILES: CCC1(CC)CC(=O)N(C2c3cc(C(=O)N[C@@H]4c5ccccc5OC(C)(C)[C@H]4O)ccc3CC2OC)C(=N)N1] | 535.3 | 3-(4,4-diethyl-2-imino-6-oxo-hexahydropyrimidin-1-yl)-N-[(3S,4R)-3-hydroxy-2,2-dimethyl-chroman-4-yl]-2-methoxy-indane-5-carboxamide |
| 251C | 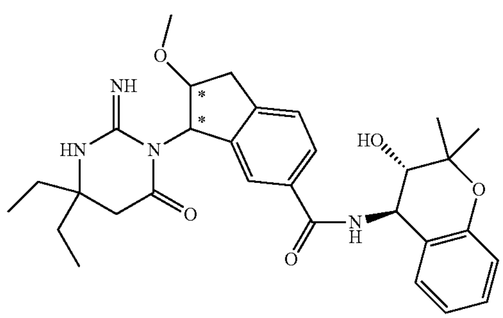 [SMILES: CCC1(CC)CC(=O)N(C2c3cc(C(=O)N[C@@H]4c5ccccc5OC(C)(C)[C@H]4O)ccc3CC2OC)C(=N)N1] | 535.4 | 3-(4,4-diethyl-2-imino-6-oxo-hexahydropyrimidin-1-yl)-N-[(3S,4R)-3-hydroxy-2,2-dimethyl-chroman-4-yl]-2-methoxy-indane-5-carboxamide |
| 252 | 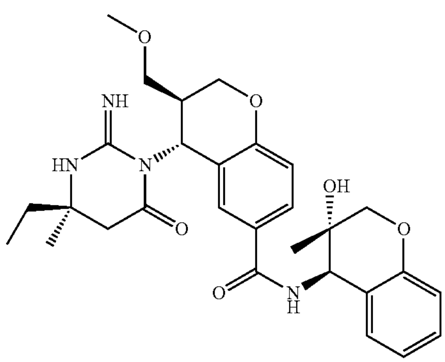 [SMILES: CC[C@]1(C)CC(=O)N([C@H]2c3cc(C(=O)N[C@@H]4c5ccccc5OC[C@@]4(C)O)ccc3OC[C@@H]2COC)C(=N)N1] | 537.2 | (3S,4R)-4-[(4R)-4-ethyl-2-imino-4-methyl-6-oxo-hexahydropyrimidin-1-yl]-N-[(3S,4R)-3-hydroxy-3-methyl-chroman-4-yl]-3-(methoxymethyl)chromane-6-carboxamide |
| 253 | 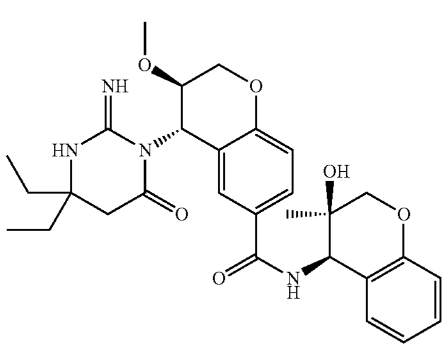 [SMILES: CCC1(CC)CC(=O)N([C@H]2c3cc(C(=O)N[C@@H]4c5ccccc5OC[C@]4(C)O)ccc3OC[C@@H]2OC)C(=N)N1] | 537.3 | (3R,4S)-4-(4,4-diethyl-2-imino-6-oxo-hexahydropyrimidin-1-yl)-N-[(3R,4R)-3-hydroxy-3-methyl-chroman-4-yl]-3-methoxy-chromane-6-carboxamide |

TABLE 3-continued

| Example | Structure | LC/MS (M + 1)+ | Name |
|---|---|---|---|
| 254 | 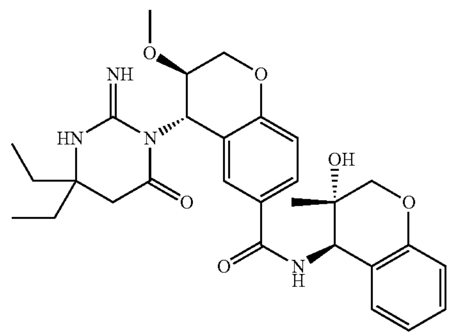 [SMILES: CCC1(CC)CC(=O)N([C@H]2c3cc(C(=O)N[C@@H]4c5ccccc5OC[C@@]4(C)O)ccc3OC[C@@H]2OC)C(=N)N1] | 537.3 | (3R,4S)-4-(4,4-diethyl-2-imino-6-oxo-hexahydropyrimidin-1-yl)-N-[(3S,4R)-3-hydroxy-3-methyl-chroman-4-yl]-3-methoxy-chromane-6-carboxamide |
| 255 | 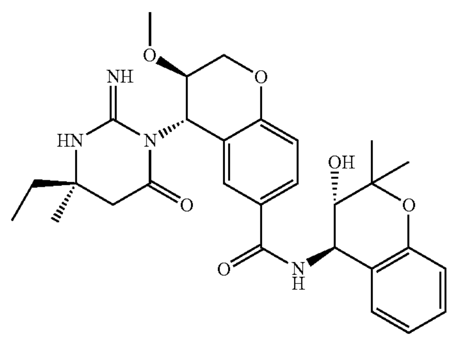 [SMILES: CC[C@]1(C)CC(=O)N([C@H]2c3cc(C(=O)N[C@@H]4c5ccccc5OC(C)(C)[C@H]4O)ccc3OC[C@@H]2OC)C(=N)N1] | 537.2 | (3R,4S)-4-[(4R)-4-ethyl-2-imino-4-methyl-6-oxo-hexahydropyrimidin-1-yl]-N-[(3S,4R)-3-hydroxy-2,2-dimethyl-chroman-4-yl]-3-methoxy-chromane-6-carboxamide |
| 256 | 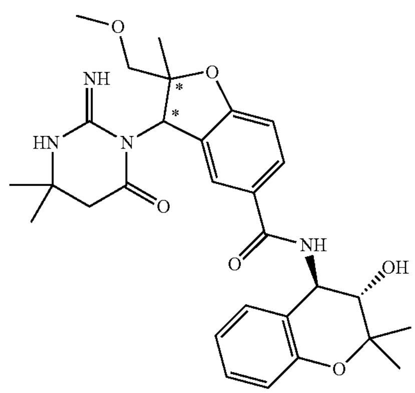 | 537.2 | N-[(3S,4R)-3-hydroxy-2,2-dimethyl-chroman-4-yl]-3-(2-imino-4,4-dimethyl-6-oxo-hexahydropyrimidin-1-yl)-2-(methoxymethyl)-2-methyl-3H-benzofuran-5-carboxamide |
| 257 | 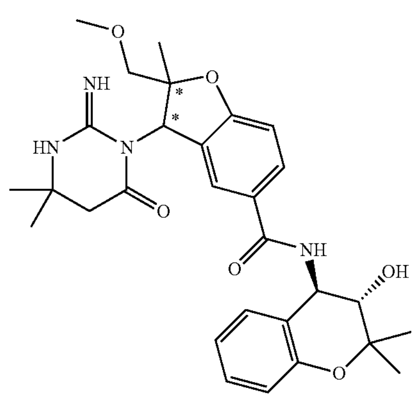 | 537.3 | N-[(3S,4R)-3-hydroxy-2,2-dimethyl-chroman-4-yl]-3-(2-imino-4,4-dimethyl-6-oxo-hexahydropyrimidin-1-yl)-2-(methoxymethyl)-2-methyl-3H-benzofuran-5-carboxamide |

TABLE 3-continued

| Example | Structure | LC/MS (M + 1)+ | Name |
|---|---|---|---|
| 258A | 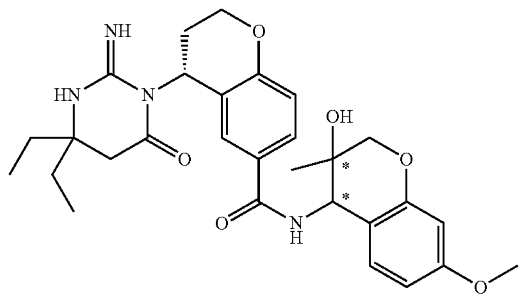 [SMILES: CCC1(CC)CC(=O)N([C@@H]2CCOc3ccc(C(=O)NC4c5ccc(OC)cc5OCC4(C)O)cc32)C(=N)N1] | 537.3 | (4R)-4-(4,4-diethyl-2-imino-6-oxo-hexahydropyrimidin-1-yl)-N-(3-hydroxy-7-methoxy-3-methyl-chroman-4-yl)chromane-6-carboxamide |
| 258B | 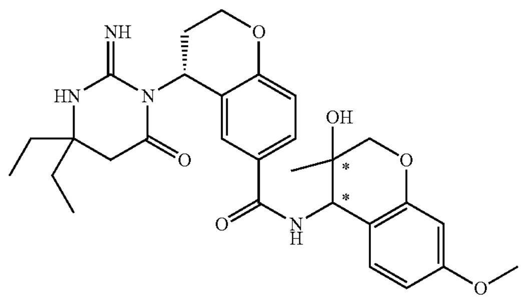 [SMILES: CCC1(CC)CC(=O)N([C@@H]2CCOc3ccc(C(=O)NC4c5ccc(OC)cc5OCC4(C)O)cc32)C(=N)N1] | 537.3 | (4R)-4-(4,4-diethyl-2-imino-6-oxo-hexahydropyrimidin-1-yl)-N-(3-hydroxy-7-methoxy-3-methyl-chroman-4-yl)chromane-6-carboxamide |
| 258C | 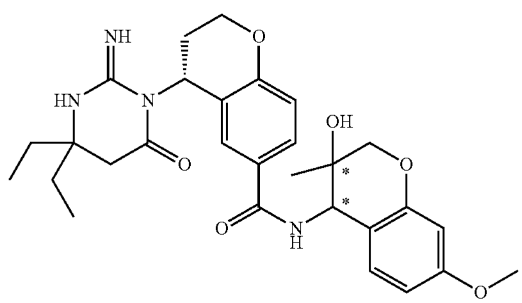 [SMILES: CCC1(CC)CC(=O)N([C@@H]2CCOc3ccc(C(=O)NC4c5ccc(OC)cc5OCC4(C)O)cc32)C(=N)N1] | 537.3 | (4R)-4-(4,4-diethyl-2-imino-6-oxo-hexahydropyrimidin-1-yl)-N-(3-hydroxy-7-methoxy-3-methyl-chroman-4-yl)chromane-6-carboxamide |
| 258D | 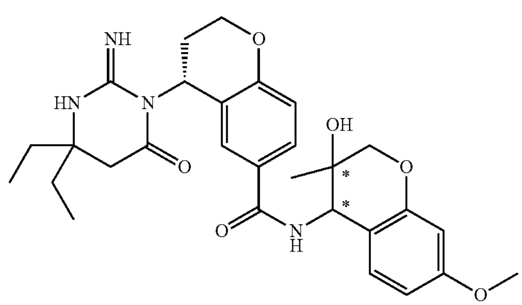 [SMILES: CCC1(CC)CC(=O)N([C@@H]2CCOc3ccc(C(=O)NC4c5ccc(OC)cc5OCC4(C)O)cc32)C(=N)N1] | 537.3 | (4R)-4-(4,4-diethyl-2-imino-6-oxo-hexahydropyrimidin-1-yl)-N-(3-hydroxy-7-methoxy-3-methyl-chroman-4-yl)chromane-6-carboxamide |
| 259A | 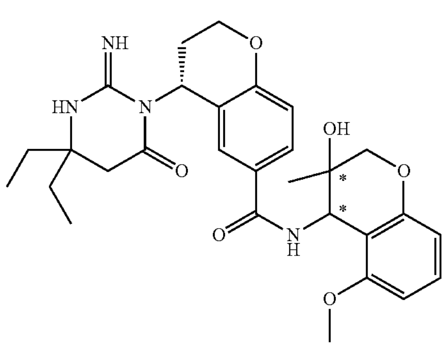 [SMILES: CCC1(CC)CC(=O)N([C@@H]2CCOc3ccc(C(=O)NC4c5c(OC)cccc5OCC4(C)O)cc32)C(=N)N1] | 537.3 | (4R)-4-(4,4-diethyl-2-imino-6-oxo-hexahydropyrimidin-1-yl)-N-(3-hydroxy-5-methoxy-3-methyl-chroman-4-yl)chromane-6-carboxamide |

TABLE 3-continued

| Example | Structure | LC/MS (M + 1)+ | Name |
|---------|-----------|----------------|------|
| 259B | 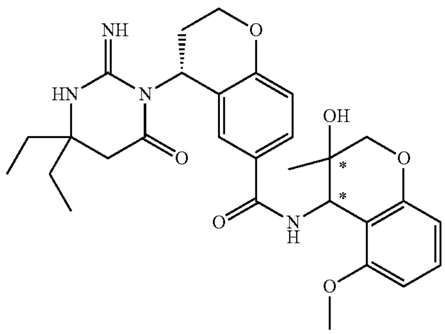 [SMILES: CCC1(CC)CC(=O)N([C@@H]2CCOc3ccc(C(=O)NC4c5c(OC)cccc5OCC4(C)O)cc32)C(=N)N1] | 537.3 | (4R)-4-(4,4-diethyl-2-imino-6-oxo-hexahydropyrimiidn-1-yl)-N-(3-hydroxy-5-methoxy-3-methyl-chroman-4-yl)chromane-6-carboxamide |
| 259C | 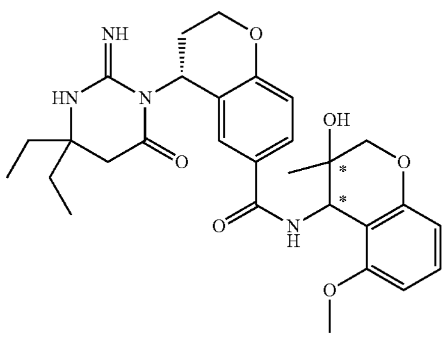 [SMILES: CCC1(CC)CC(=O)N([C@@H]2CCOc3ccc(C(=O)NC4c5c(OC)cccc5OCC4(C)O)cc32)C(=N)N1] | 537.3 | (4R)-4-(4,4-diethyl-2-imino-6-oxo-hexahydropyrimidin-1-yl)-N-(3-hydroxy-5-methoxy-3-methyl-chroman-4-yl)chromane-6-carboxamide |
| 259D | 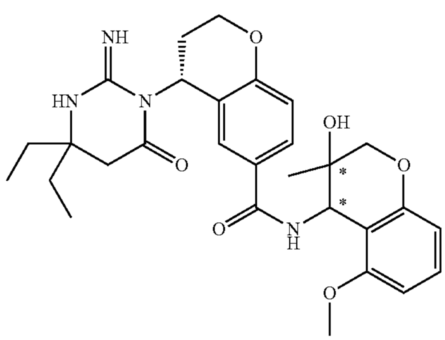 [SMILES: CCC1(CC)CC(=O)N([C@@H]2CCOc3ccc(C(=O)NC4c5c(OC)cccc5OCC4(C)O)cc32)C(=N)N1] | 537.3 | (4R)-4-(4,4-diethyl-2-imino-6-oxo-hexahydropyrimidin-1-yl)-N-(3-hydroxy-5-methoxy-3-methyl-chroman-4-yl)chromane-6-carboxamide |
| 260 | 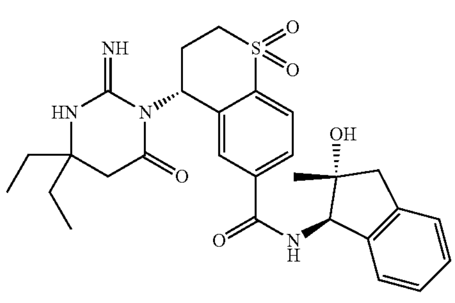 [SMILES: CCC1(CC)CC(=O)N([C@@H]2CCS(=O)(=O)c3ccc(C(=O)N[C@@H]4c5ccccc5C[C@@]4(C)O)cc32)C(=N)N1] | 539.3 | (4R)-4-(4,4-diethyl-2-imino-6-oxo-hexahydropyrimidin-1-yl)-N-[(1R,2R)-2-hydroxy-2-methyl-indan-1-yl]-1,1-dioxo-3,4-dihydro-2H-thiochromene-6-carboxamide |

TABLE 3-continued

| Example | Structure | LC/MS (M + 1)+ | Name |
|---|---|---|---|
| 261 | 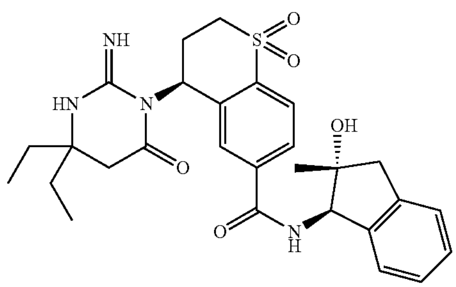 [SMILES: CCC1(CC)CC(=O)N([C@H]2CCS(=O)(=O)c3ccc(C(=O)N[C@@H]4c5ccccc5C[C@@]4(C)O)cc32)C(=N)N1] | 539.3 | (4S)-4-(4,4-diethyl-2-imino-6-oxo-hexahydropyrimidin-1-yl)-N-[(1R,2R)-2-hydroxy-2-methyl-indan-1-yl]-1,1-dioxo-3,4-dihydro-2H-thiochromene-6-carboxamide |
| 262 | 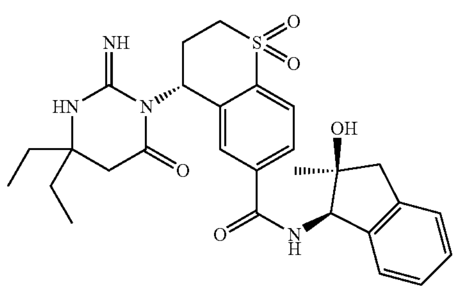 [SMILES: CCC1(CC)CC(=O)N([C@@H]2CCS(=O)(=O)c3ccc(C(=O)N[C@@H]4c5ccccc5C[C@]4(C)O)cc32)C(=N)N1] | 539.3 | (4R)-4-(4,4-diethyl-2-imino-6-oxo-hexahydropyrimidin-1-yl)-N-[(1R,2S)-2-hydroxy-2-methyl-indan-1-yl]-1,1-dioxo-3,4-dihydro-2H-thiochromene-6-carboxamide |
| 263 | 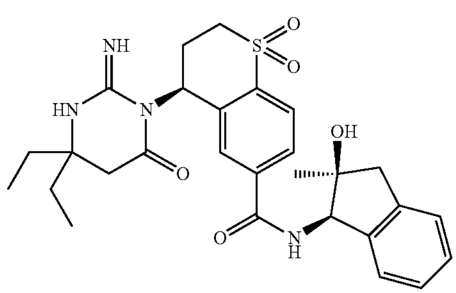 [SMILES: CCC1(CC)CC(=O)N([C@H]2CCS(=O)(=O)c3ccc(C(=O)N[C@@H]4c5ccccc5C[C@]4(C)O)cc32)C(=N)N1] | 539.3 | (4S)-4-(4,4-diethyl-2-imino-6-oxo-hexahydropyrimidin-1-yl)-N-[(1R,2S)-2-hydroxy-2-methyl-indan-1-yl]-1,1-dioxo-3,4-dihydro-2H-thiochromene-6-carboxamide |
| 264 | 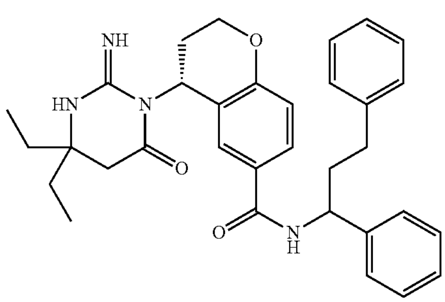 [SMILES: CCC1(CC)CC(=O)N([C@@H]2CCOc3ccc(C(=O)NC(CCc4ccccc4)c4ccccc4)cc32)C(=N)N1] | 539.3 | (4R)-4-(4,4-diethyl-2-imino-6-oxo-hexahydropyrimidin-1-yl)-N-(1,3-diphenylpropyl)chromane-6-carboxamide |
| 265 | 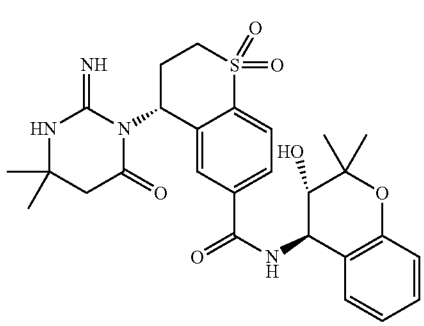 [SMILES: CC1(C)CC(=O)N([C@@H]2CCS(=O)(=O)c3ccc(C(=O)N[C@@H]4c5ccccc5OC(C)(C)[C@H]4O)cc32)C(=N)N1] | 541.3 | (4R)-N-[(3S,4R)-3-hydroxy-2,2-dimethyl-chroman-4-yl]-4-(2-imino-4,4-dimethyl-6-oxo-hexahydropyrimidin-1-yl)-1,1-dioxo-3,4-dihydro-2H-thiochromene-6-carboxamide |

TABLE 3-continued

| Example | Structure | LC/MS (M + 1)+ | Name |
|---|---|---|---|
| 266 | 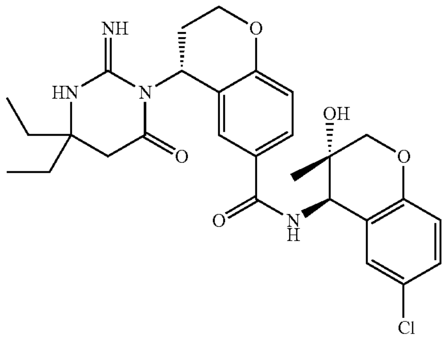 [SMILES: CCC1(CC)CC(=O)N([C@@H]2CCOc3ccc(C(=O)N[C@@H]4c5cc(Cl)ccc5OC[C@@]4(C)O)cc32)C(=N)N1] | 541.2 | (4R)-N-[(3S,4R)-6-chloro-3-hydroxy-3-methyl-chroman-4-yl]-4-(4,4-diethyl-2-imino-6-oxo-hexahydropyrimidin-1-yl)chromane-6-carboxamide |
| 267 | 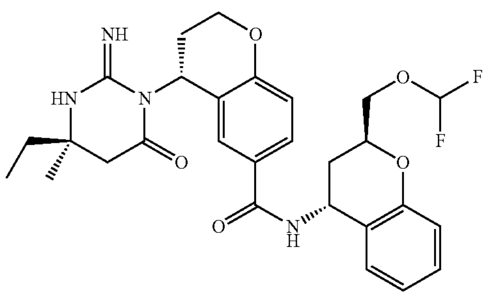 [SMILES: CC[C@]1(C)CC(=O)N([C@@H]2CCOc3ccc(C(=O)N[C@@H]4C[C@@H](COC(F)F)Oc5ccccc54)cc32)C(=N)N1] | 543.3 | (4R)-N-[(2S,4R)-2-(difluoromethoxymethyl)chroman-4-yl]-4-[(4R)-4-ethyl-2-imino-4-methyl-6-oxo-hexahydropyrimidin-1-yl]chromane-6-carboxamide |
| 268 | 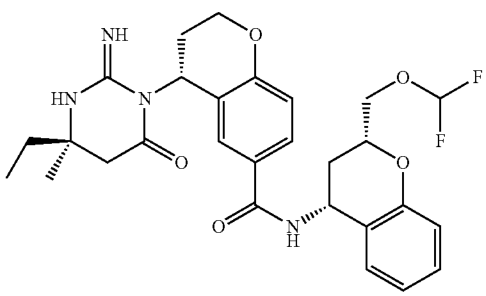 [SMILES: CC[C@]1(C)CC(=O)N([C@@H]2CCOc3ccc(C(=O)N[C@@H]4C[C@H](COC(F)F)Oc5ccccc54)cc32)C(=N)N1] | 543.3 | (4R)-N-[(2R,4R)-2-(difluoromethoxymethyl)chroman-4-yl]-4-[(4R)-4-ethyl-2-imino-4-methyl-6-oxo-hexahydropyrimidin-1-yl]chromane-6-carboxamide |
| 269 | 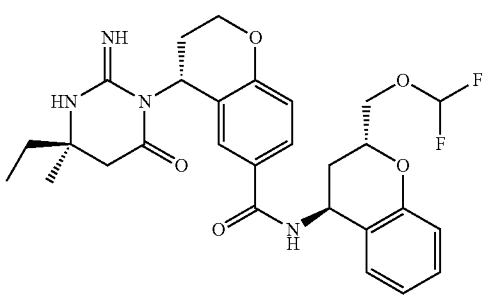 [SMILES: CC[C@]1(C)CC(=O)N([C@@H]2CCOc3ccc(C(=O)N[C@H]4C[C@H](COC(F)F)Oc5ccccc54)cc32)C(=N)N1] | 543.3 | (4R)-N-[(2R,4S)-2-(difluoromethoxymethyl)chroman-4-yl]-4-[(4R)-4-ethyl-2-imino-4-methyl-6-oxo-hexahydropyrimidin-1-yl]chromane-6-carboxamide |
| 270 | 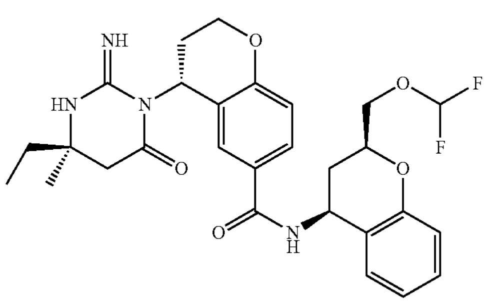 [SMILES: CC[C@]1(C)CC(=O)N([C@@H]2CCOc3ccc(C(=O)N[C@H]4C[C@@H](COC(F)F)Oc5ccccc54)cc32)C(=N)N1] | 543.3 | (4R)-N-[(2S,4S)-2-(difluoromethoxymethyl)chroman-4-yl]-4-[(4R)-4-ethyl-2-imino-4-methyl-6-oxo-hexahydropyrimidin-1-yl]chromane-6-carboxamide |

TABLE 3-continued

| Example | Structure | LC/MS (M + 1)+ | Name |
|---|---|---|---|
| 271 | 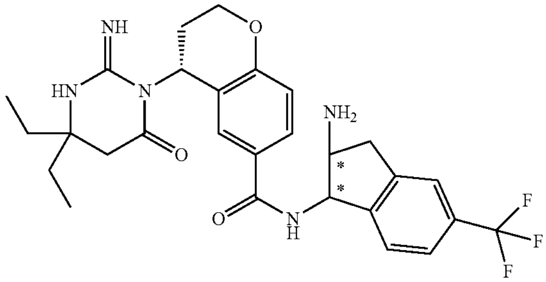 [SMILES: CCC1(CC)CC(=O)N([C@@H]2CCOc3ccc(C(=O)NC4c5ccc(C(F)(F)F)cc5CC4N)cc32)C(=N)N1] | 544.3 | (4R)-N-[2-amino-5-(trifluoromethyl)indan-1-yl]-4-(4,4-diethyl-2-imino-6-oxo-hexahydropyrimidin-1-yl)chromane-6-carboxamide |
| 272A | 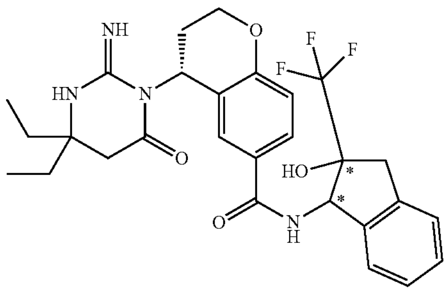 [SMILES: CCC1(CC)CC(=O)N([C@@H]2CCOc3ccc(C(=O)NC4c5ccccc5CC4(O)C(F)(F)F)cc32)C(=N)N1] | 545.3 | (4R)-4-(4,4-diethyl-2-imino-6-oxo-hexahydropyrimidin-1-yl)-N-[2-hydroxy-2-(trifluoromethyl)indan-1-yl]chromane-6-carboxamide |
| 272B | 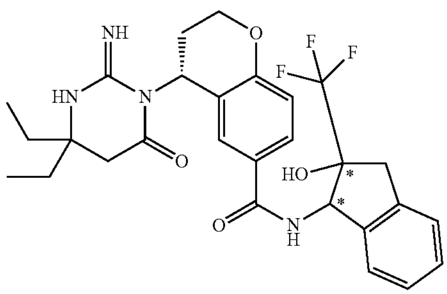 [SMILES: CCC1(CC)CC(=O)N([C@@H]2CCOc3ccc(C(=O)NC4c5ccccc5CC4(O)C(F)(F)F)cc32)C(=N)N1] | 545.3 | (4R)-4-(4,4-diethyl-2-imino-6-oxo-hexahydropyrimidin-1-yl)-N-[2-hydroxy-2-(trifluoromethyl)indan-1-yl]chromane-6-carboxamide |
| 272C | 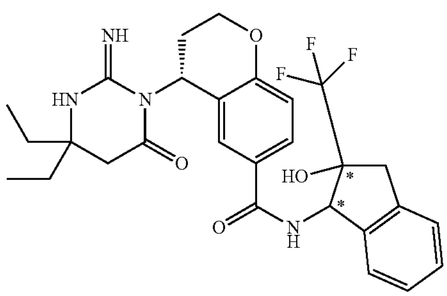 [SMILES: CCC1(CC)CC(=O)N([C@@H]2CCOc3ccc(C(=O)NC4c5ccccc5CC4(O)C(F)(F)F)cc32)C(=N)N1] | 545.3 | (4R)-4-(4,4-diethyl-2-imino-6-oxo-hexahydropyrimidin-1-yl)-N-[2-hydroxy-2-(trifluoromethyl)indan-1-yl]chromane-6-carboxamide |
| 272D | 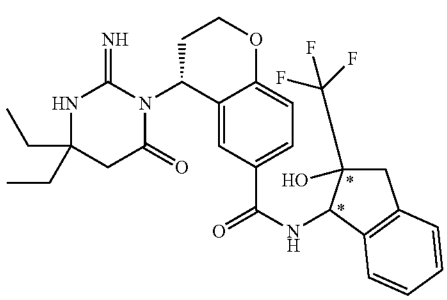 [SMILES: CCC1(CC)CC(=O)N([C@@H]2CCOc3ccc(C(=O)NC4c5ccccc5CC4(O)C(F)(F)F)cc32)C(=N)N1] | 545.3 | (4R)-4-(4,4-diethyl-2-imino-6-oxo-hexahydropyrimidin-1-yl)-N-[2-hydroxy-2-(trifluoromethyl)indan-1-yl]chromane-6-carboxamide |

TABLE 3-continued

| Example | Structure | LC/MS (M + 1)+ | Name |
|---|---|---|---|
| 273 | 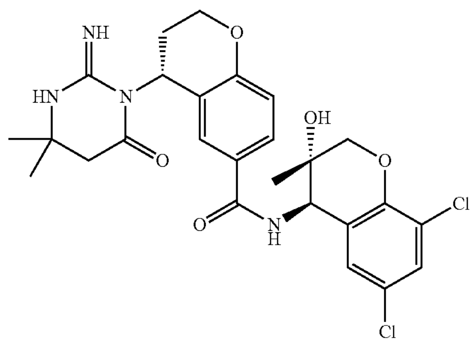 [SMILES: CC1(C)CC(=O)N([C@@H]2CCOc3ccc(C(=O)N[C@@H]4c5cc(Cl)cc(Cl)c5OC[C@@]4(C)O)cc32)C(=N)N1] | 547.1 | (4R)-N-[(3S,4R)-6,8-dichloro-3-hydroxy-3-methyl-chroman-4-yl]-4-(2-imino-4,4-dimethyl-6-oxo-hexahydropyrimidin-1-yl)chromane-6-carboxamide |
| 274 | 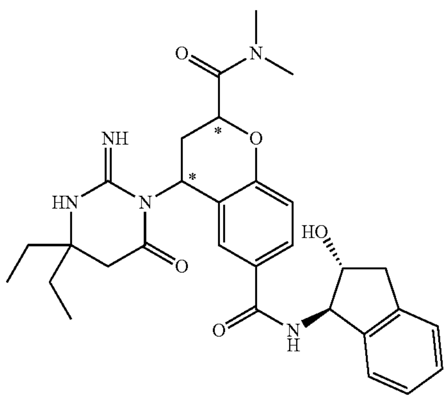 [SMILES: CCC1(CC)CC(=O)N(C2CC(C(=O)N(C)C)Oc3ccc(C(=O)N[C@@H]4c5ccccc5C[C@H]4O)cc32)C(=N)N1] | 548.3 | 4-(4,4-diethyl-2-imino-6-oxo-hexahydropyrimidin-1-yl)-N6-[(1R,2R)-2-hydroxyindan-1-yl]-N2,N2-dimethyl-chromane-26,-dicarboxamide |
| 275 | 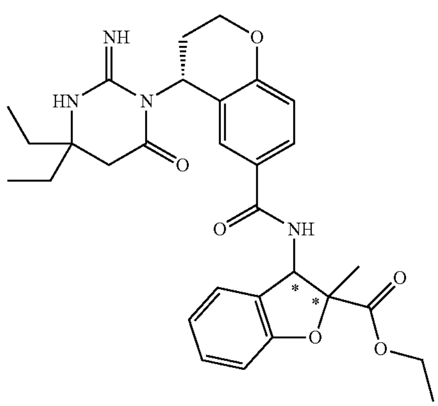 [SMILES: CCOC(=O)C1(C)Oc2ccccc2C1NC(=O)c1ccc2c(c1)[C@H](N1C(=N)NC(CC)(CC)CC1=O)CCO2] | 549.4 | ethyl 3-[[(4R)-4-(4,4-diethyl-2-imino-6-oxo-hexahydropyrimidin-1-yl)chromane-6-carbonyl]amino]-2-methyl-3H-benzofuran-2-carboxylate |
| 276 | 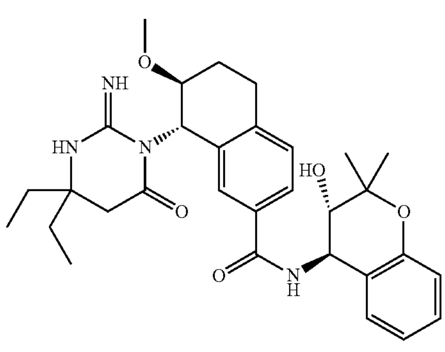 [SMILES: CCC1(CC)CC(=O)N([C@H]2c3cc(C(=O)N[C@@H]4c5ccccc5OC(C)(C)[C@H]4O)ccc3CC[C@@H]2OC)C(=N)N1] | 549.2 | (3S,4S)-4-(4,4-diethyl-2-imino-6-oxo-hexahydropyrimidin-1-yl)-N-[(3S,4R)-3-hydroxy-2,2-dimethyl-chroman-4-yl]-3-methoxy-tetralin-6-carboxamide |

TABLE 3-continued

| Example | Structure | LC/MS (M + 1)+ | Name |
|---|---|---|---|
| 277 | 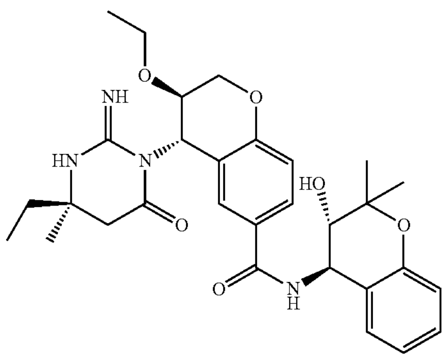 [SMILES: CCO[C@H]1COc2ccc(C(=O)N[C@@H]3c4ccccc4OC(C)(C)[C@H]3O)cc2[C@@H]1N1C(=N)N[C@](C)(CC)CC1=O] | 551.1 | (3S,4R)-4-[(4R)-4-ethyl-2-imino-4-methyl-6-oxo-hexahydropyrimidin-1-yl]-N-[(3S,4R)-3-hydroxy-2,2-dimethyl-chroman-4-yl]-3-(methoxymethyl)chromane-6-carboxamide |
| 278 | 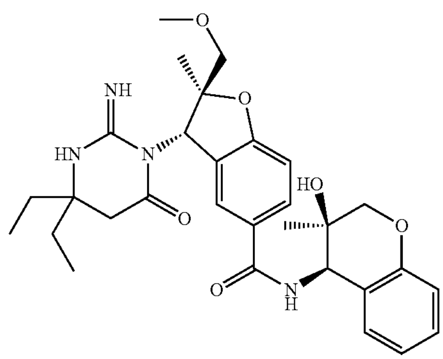 [SMILES: CCC1(CC)CC(=O)N([C@H]2c3cc(C(=O)N[C@@H]4c5ccccc5OC[C@]4(C)O)ccc3O[C@]2(C)COC)C(=N)N1] | 551.3 | (2S,3S)-3-(4,4-diethyl-2-imino-6-oxo-hexahydropyrimidin-1-yl)-N-[(3R,4R)-3-hydroxy-3-methyl-chroman-4-yl]-2-(methoxymethyl)-2-methyl-3H-benzofuran-5-carboxamide |
| 279 | 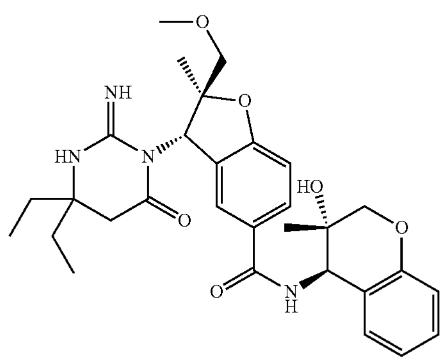 [SMILES: CCC1(CC)CC(=O)N([C@H]2c3cc(C(=O)N[C@@H]4c5ccccc5OC[C@@]4(C)O)ccc3O[C@]2(C)COC)C(=N)N1] | 551.3 | (2S,3S)-3-(4,4-diethyl-2-imino-6-oxo-hexahydropyrimidin-1-yl)-N-[(3S,4R)-3-hydroxy-3-methyl-chroman-4-yl]-2-(methoxymethyl)-2-methyl-3H-benzofuran-5-carboxamide |
| 280 | 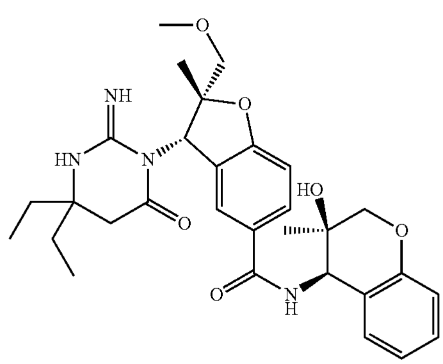 [SMILES: CCC1(CC)CC(=O)N([C@H]2c3cc(C(=O)N[C@@H]4c5ccccc5OC[C@]4(C)O)ccc3O[C@@]2(C)COC)C(=N)N1] | 551.3 | (2R,3S)-3-(4,4-diethyl-2-imino-6-oxo-hexahydropyrimidin-1-yl)-N-[(3R,4R)-3-hydroxy-3-methyl-chroman-4-yl]-2-(methoxymethyl)-2-methyl-3H-benzofuran-5-carboxamide |

TABLE 3-continued

| Example | Structure | LC/MS (M + 1)+ | Name |
|---|---|---|---|
| 281 | 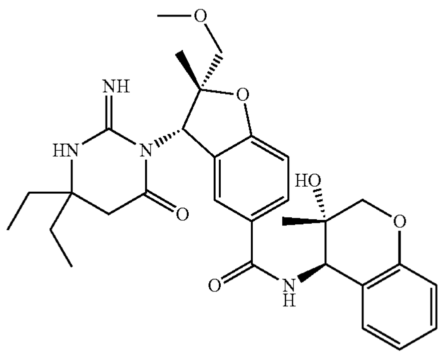 [SMILES: CCC1(CC)CC(=O)N([C@H]2c3cc(C(=O)N[C@@H]4c5ccccc5OC[C@@]4(C)O)ccc3O[C@@]2(C)COC)C(=N)N1] | 551.3 | (2R,3S)-3-(4,4-diethyl-2-imino-6-oxo-hexahydropyrimidin-1-yl)-N-[(3S,4R)-3-hydroxy-3-methyl-chroman-4-yl]-2-(methoxymethyl)-2-methyl-3H-benzofuran-5-carboxamide |
| 282A | 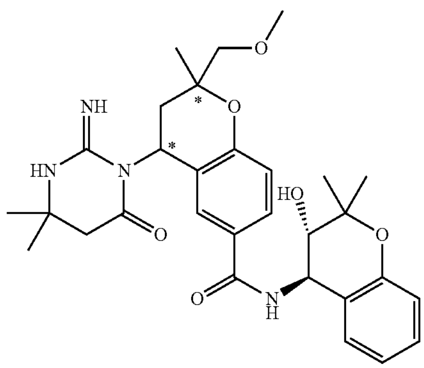 [SMILES: COCC1(C)CC(N2C(=N)NC(C)(C)CC2=O)c2cc(C(=O)N[C@@H]3c4ccccc4OC(C)(C)[C@H]3O)ccc2O1] | 551.3 | N-[(3S,4R)-3-hydroxy-2,2-dimethyl-chroman-4-yl]-4-(2-imino-4,4-dimethyl-6-oxo-hexahydropyrimidin-1-yl)-2-(methoxymethyl)-2-methyl-chromane-6-carboxamide |
| 282B | 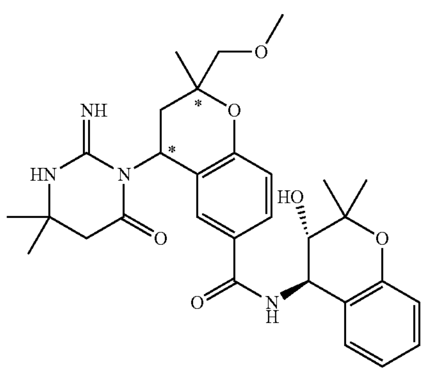 [SMILES: COCC1(C)CC(N2C(=N)NC(C)(C)CC2=O)c2cc(C(=O)N[C@@H]3c4ccccc4OC(C)(C)[C@H]3O)ccc2O1] | 551.1 | N-[(3S,4R)-3-hydroxy-2,2-dimethyl-chroman-4-yl]-4-(2-imino-4,4-dimethyl-6-oxo-hexahydropyrimidin-1-yl)-2-(methoxymethyl)-2-methyl-chromane-6-carboxamide |
| 283 | 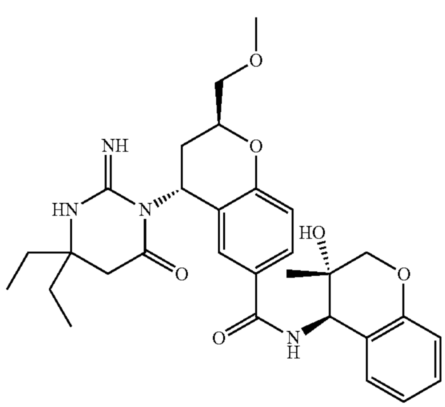 [SMILES: CCC1(CC)CC(=O)N([C@@H]2C[C@@H](COC)Oc3ccc(C(=O)N[C@@H]4c5ccccc5OC[C@@]4(C)O)cc32)C(=N)N1] | 551.2 | (2S,4R)-4-(4,4-diethyl-2-imino-6-oxo-hexahydropyrimidin-1-yl)-N-[(3S,4R)-3-hydroxy-3-methyl-chroman-4-yl]-2-(methoxymethyl)chromane-6-carboxamide |

TABLE 3-continued

| Example | Structure | LC/MS (M + 1)+ | Name |
|---|---|---|---|
| 284 | 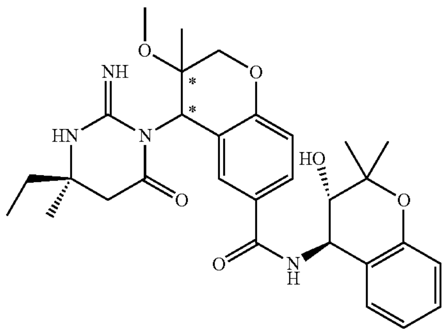 [SMILES: CC[C@]1(C)CC(=O)N(C2c3cc(C(=O)N[C@@H]4c5ccccc5OC(C)(C)[C@H]4O)ccc3OCC2(C)OC)C(=N)N1] | 551.1 | 4-[(4R)-4-ethyl-2-imino-4-methyl-6-oxo-hexahydropyrimidin-1-yl]-N-[(3S,4R)-3-hydroxy-2,2-dimethyl-chroman-4-yl]-3-methoxy-3-methyl-chromane-6-carboxamide |
| 285 | 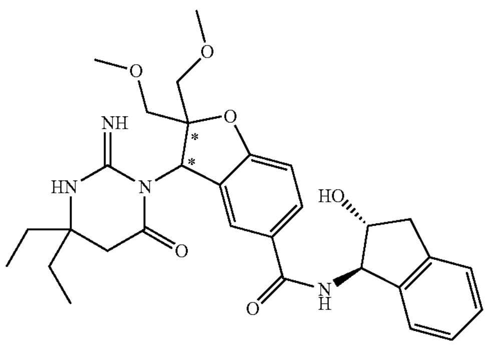 [SMILES: CCC1(CC)CC(=O)N(C2c3cc(C(=O)N[C@@H]4c5ccccc5C[C@H]4O)ccc3OC2(COC)COC)C(=N)N1] | 551.3 | 3-(4,4-diethyl-2-imino-6-oxo-hexahydropyrimidin-1-yl)-N-[(1R,2R)-2-hydroxyindan-1-yl]-2,2-bis(methoxymethyl)-3H-benzofuran-5-carboxamide |
| 286 | 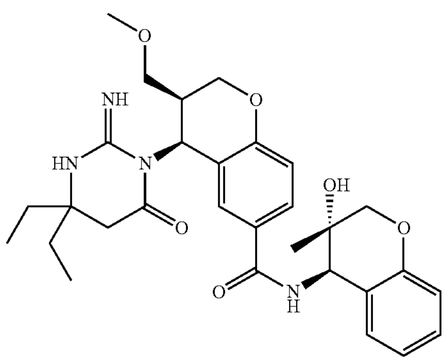 [SMILES: CCC1(CC)CC(=O)N([C@@H]2c3cc(C(=O)N[C@@H]4c5ccccc5OC[C@@]4(C)O)ccc3OC[C@@H]2COC)C(=N)N1] | 551.3 | (3S,4S)-4-(4,4-diethyl-2-imino-6-oxo-hexahydropyrimidin-1-yl)-N-[(3S,4R)-3-hydroxy-3-methyl-chroman-4-yl]-3-(methoxymethyl)chromane-6-carboxamide |
| 287 | 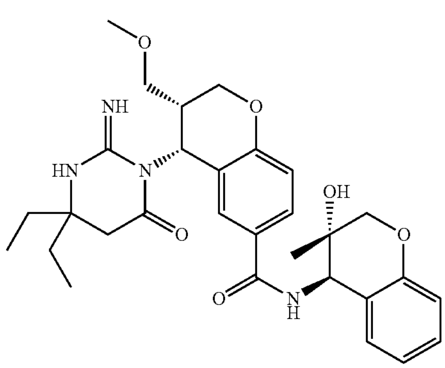 [SMILES: CCC1(CC)CC(=O)N([C@H]2c3cc(C(=O)N[C@@H]4c5ccccc5OC[C@@]4(C)O)ccc3OC[C@H]2COC)C(=N)N1] | 551.3 | (3R,4R)-4-(4,4-diethyl-2-imino-6-oxo-hexahydropyrimidin-1-yl)-N-[(3S,4R)-3-hydroxy-3-methyl-chroman-4-yl]-3-(methoxymethyl)chromane-6-carboxamide |

TABLE 3-continued

| Example | Structure | LC/MS (M + 1)+ | Name |
|---|---|---|---|
| 288 | 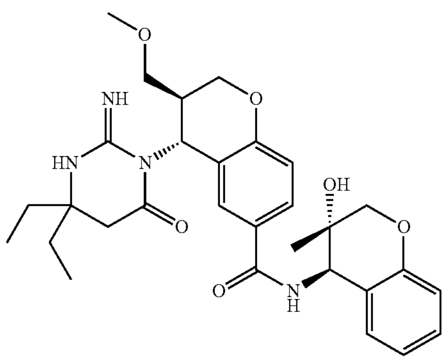 [SMILES: CCC1(CC)CC(=O)N([C@H]2c3cc(C(=O)N[C@@H]4c5ccccc5OC[C@@]4(C)O)ccc3OC[C@@H]2COC)C(=N)N1] | 551.4 | (3S,4R)-4-(4,4-diethyl-2-imino-6-oxo-hexahydropyrimidin-1-yl)-N-[(3S,4R)-3-hydroxy-3-methyl-chroman-4-yl]-3-(methoxymethyl)chromane-6-carboxamide |
| 289 | 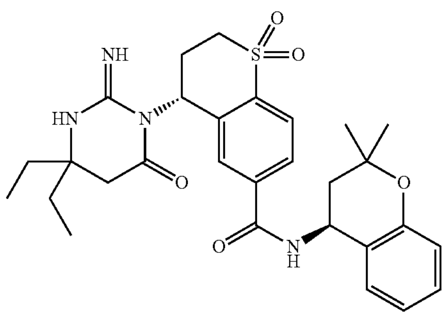 [SMILES: CCC1(CC)CC(=O)N([C@@H]2CCS(=O)(=O)c3ccc(C(=O)N[C@H]4CC(C)(C)Oc5ccccc54)cc32)C(=N)N1] | 553.3 | (4R)-4-(4,4-diethyl-2-imino-6-oxo-hexahydropyrimidin-1-yl)-N-[(4S)-2,2-dimethylchroman-4-yl]-1,1-dioxo-3,4-dihydro-2H-thiochromane-6-carboxamide |
| 290 | 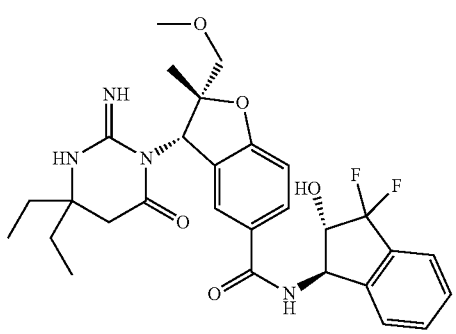 [SMILES: CCC1(CC)CC(=O)N([C@H]2c3cc(C(=O)N[C@@H]4c5ccccc5C(F)(F)[C@H]4O)ccc3O[C@@]2(C)COC)C(=N)N1] | 557.3 | (2R,3S)-3-(4,4-diethyl-2-imino-6-oxo-hexahydropyrimidin-1-yl)-N-[(1R,2S)-3,3-difluoro-2-hydroxy-indan-1-yl]-2-(methoxymethyl)-2-methyl-3H-benzofuran-5-carboxamide |
| 291 | 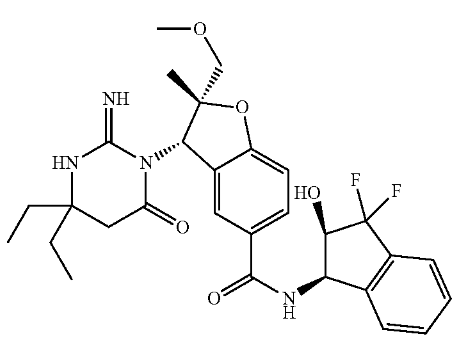 [SMILES: CCC1(CC)CC(=O)N([C@H]2c3cc(C(=O)N[C@@H]4c5ccccc5C(F)(F)[C@@H]4O)ccc3O[C@@]2(C)COC)C(=N)N1] | 557.2 | (2R,3S)-3-(4,4-diethyl-2-imino-6-oxo-hexahydropyrimidin-1-yl)-N-[(1S,2R)-3,3-difluoro-2-hydroxy-indan-1-yl]-2-(methoxymethyl)-2-methyl-3H-benzofuran-5-carboxamide |

TABLE 3-continued

| Example | Structure | LC/MS (M + 1)+ | Name |
|---|---|---|---|
| 292 | 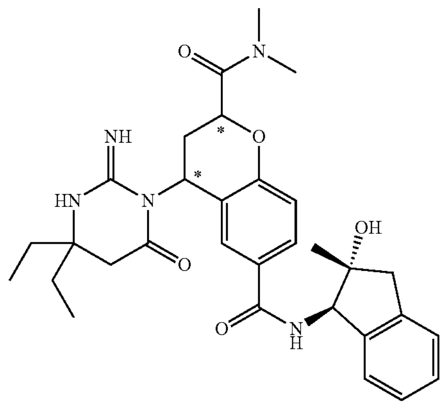 [SMILES: CCC1(CC)CC(=O)N(C2CC(C(=O)N(C)C)Oc3ccc(C(=O)N[C@@H]4c5ccccc5C[C@@]4(C)O)cc32)C(=N)N1] | 562.4 | 4-(4,4-diethyl-2-imino-6-oxo-hexahydropyrimidin-1-yl)-N6-[(1R,2R)-2-hydroxy-2-methyl-indan-1-yl]-N2,N2-dimethyl-chromane-2,6-dicarboxamide |
| 293 | 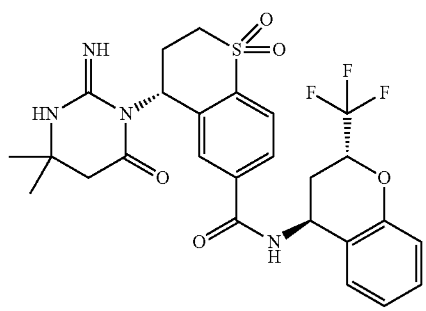 [SMILES: CC1(C)CC(=O)N([C@@H]2CCS(=O)(=O)c3ccc(C(=O)N[C@H]4C[C@H](C(F)(F)F)Oc5ccccc54)cc32)C(=N)N1] | 565.2 | (4R)-4-(2-imino-4,4-dimethyl-6-oxo-hexahydropyrimidin-1-yl)-1,1-dioxo-N-[(2R,4S)-2-(trifluoromethyl)chroman-4-yl]-3,4-dihydro-2H-thiochromene-6-carboxamide |
| 294 | 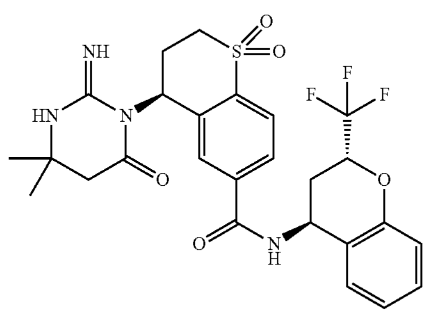 [SMILES: CC1(C)CC(=O)N([C@H]2CCS(=O)(=O)c3ccc(C(=O)N[C@H]4C[C@H](C(F)(F)F)Oc5ccccc54)cc32)C(=N)N1] | 565.2 | (4S)-4-(2-imino-4,4-dimethyl-6-oxo-hexahydropyrimidin-1-yl)-1,1-dioxo-N-[(2R,4S)-2-(trifluoromethyl)chroman-4-yl]-3,4-dihydro-2H-thiochromene-6-carboxamide |
| 295 | 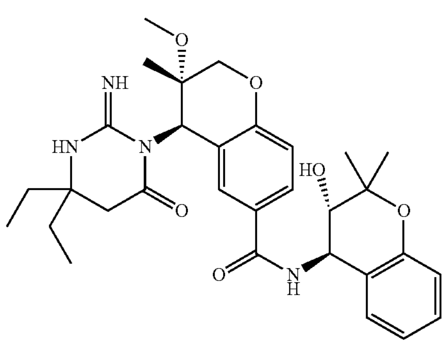 [SMILES: CCC1(CC)CC(=O)N([C@@H]2c3cc(C(=O)N[C@@H]4c5ccccc5OC(C)(C)[C@H]4O)ccc3OC[C@@]2(C)OC)C(=N)N1] | 565.3 | (3S,4R)-4-(4,4-diethyl-2-imino-6-oxo-hexahydropyrimidin-1-yl)-N-[(3S,4R)-3-hydroxy-2,2-dimethyl-chroman-4-yl]-3-methoxy-3-methyl-chromane-6-carboxamide |

TABLE 3-continued

| Example | Structure | LC/MS (M + 1)+ | Name |
|---|---|---|---|
| 296 | 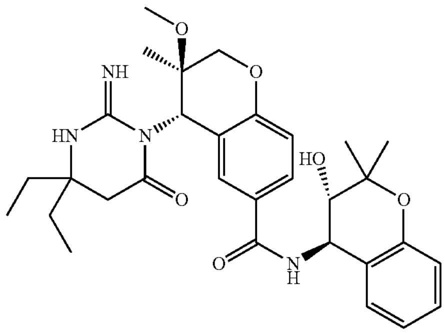 [SMILES: CCC1(CC)CC(=O)N([C@H]2c3cc(C(=O)N[C@@H]4c5ccccc5OC(C)(C)[C@H]4O)ccc3OC[C@]2(C)OC)C(=N)N1] | 565.3 | (3R,4S)-4-(4,4-diethyl-2-imino-6-oxo-hexahydropyrimidin-1-yl)-N-[(3S,4R)-3-hydroxy-2,2-dimethyl-chroman-4-yl]-3-methoxy-3-methyl-chromane-6-carboxamide |
| 297 | 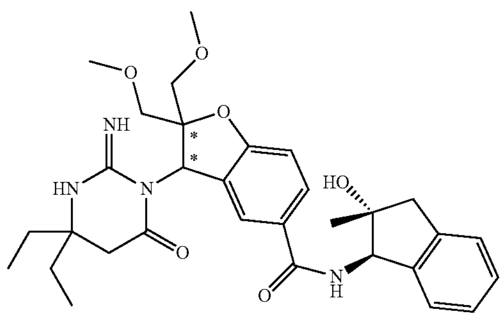 [SMILES: CCC1(CC)CC(=O)N(C2c3cc(C(=O)N[C@@H]4c5ccccc5C[C@@]4(C)O)ccc3OC2(COC)COC)C(=N)N1] | 565.3 | 3-(4,4-diethyl-2-imino-6-oxo-hexahydropyrimidin-1-yl)-N-[(1R,2R)-2-hydroxy-2-methyl-indan-1-yl]-2,2-bis(methoxymethyl)-3H-benzofuran-5-carboxamide |

Example 298

(3R,4R)-4-(4,4-diethyl-2-imino-6-oxotetrahydropyrimidin-1(2H)-yl)-N-((3S,4R)-3-hydroxy-2,2-dimethylchroman-4-yl)-3-(methoxymethyl)chromane-6-carboxamide

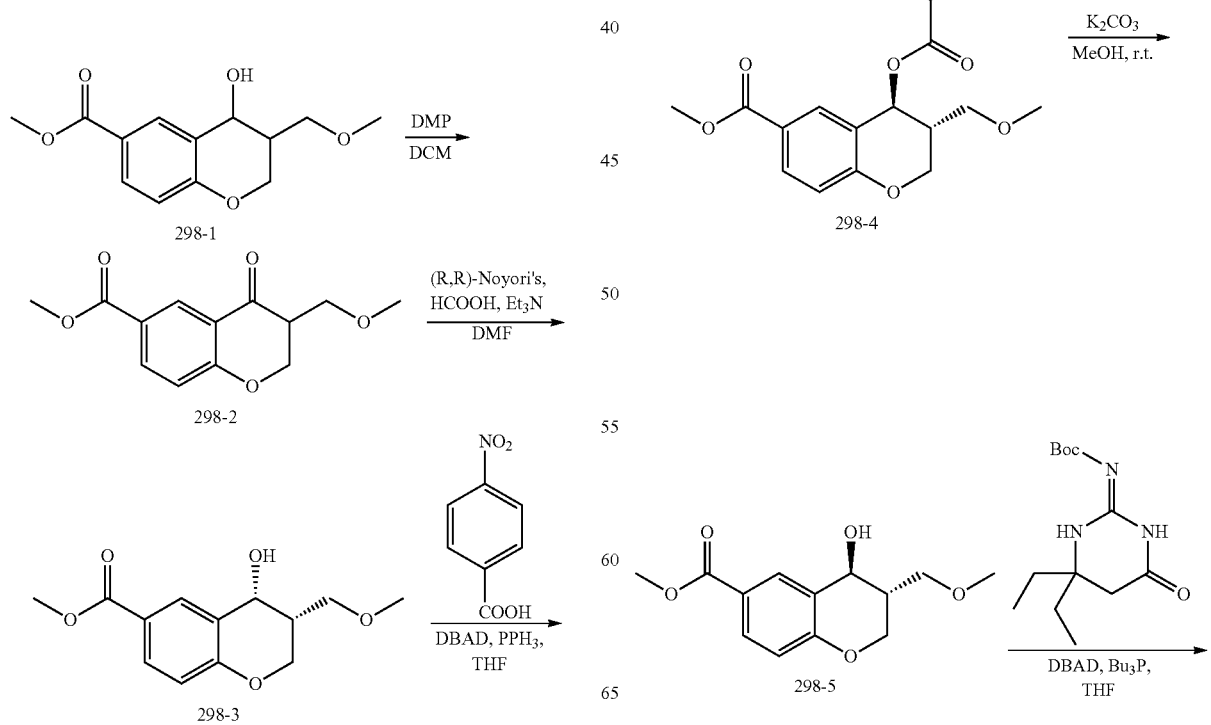

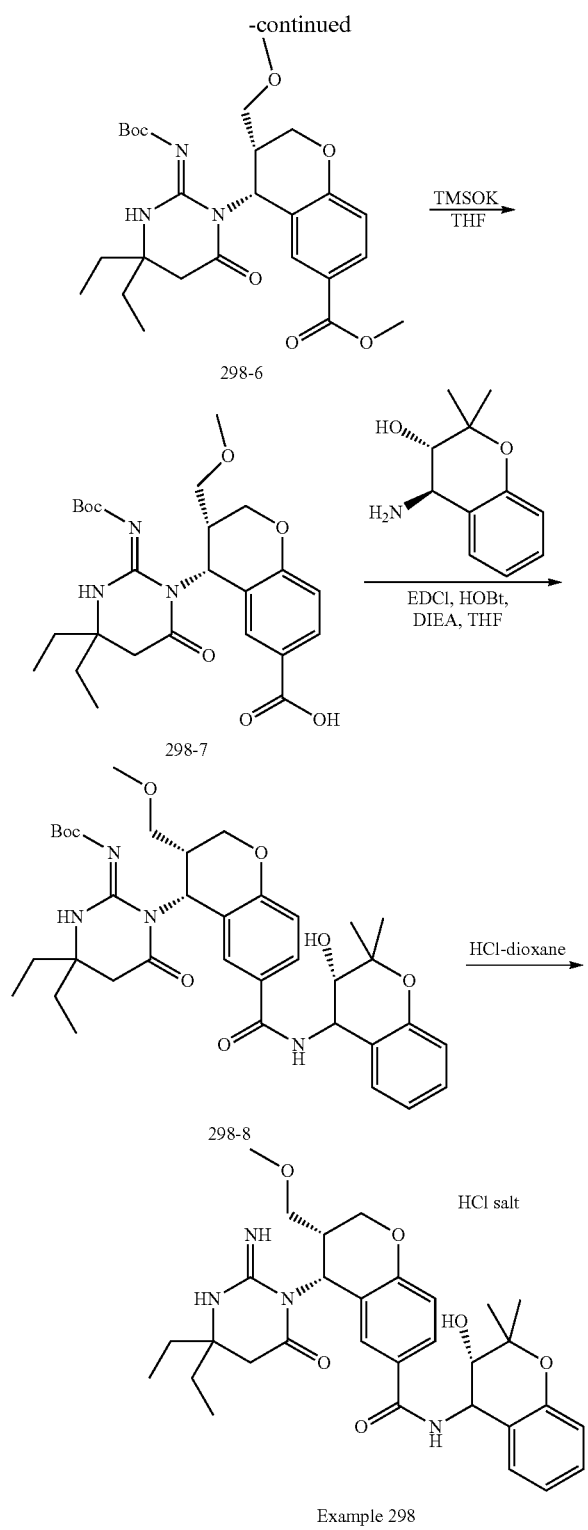

Example 298

Step A: methyl 3-(methoxymethyl)-4-oxochromane-6-carboxylate 298-2

DMP (121 g, 285 mmol) was added to a solution of methyl 4-hydroxy-3-(methoxymethyl)chromane-6-carboxylate 298-1 (60 g, 238 mmol) in $CH_2Cl_2$ (1500 mL) under nitrogen. The mixture was stirred at 25° C. for 2 h. The mixture was filtered, then concentrated and purified by column chromatography (petroleum ether/EtOAc=100:0 to 10:1) to afford product methyl 3-(methoxymethyl)-4-oxochromane-6-carboxylate 298-2.

MS (ESI) m/z 251.3 (M+H$^+$)

$^1$H NMR (400 MHz, chloroform-d) δ 8.57 (d, J=2.0 Hz, 1H), 8.13 (d, J=2.4, 8.4 Hz, 1H), 7.02 (d, J=8.4 Hz, 1H), 4.70 (dd, J=5.2, 11.2 Hz, 1H), 4.47 (dd, J=5.6, 11.6 Hz, 1H), 3.90 (s, 3H), 3.76-3.84 (m, 1H), 3.65-3.75 (m, 1H), 3.37 (s, 3H), 3.06-3.07 (m, 1H)

Step B: methyl (3R,4R)-4-hydroxy-3-(methoxymethyl)chromane-6-carboxylate 298-3

A solution of formic acid (26.7 mL, 707 mmol) and triethylamine (197 mL, 1415 mmol) in DMF (200 mL) was stirred for 15 min, then methyl 3-(methoxymethyl)-4-oxochromane-6-carboxylate 298-2 (59 g, 236 mmol) in DMF (200 mL) and RuCl(p-cymene)[(R,R)-Ts-DPEN] ($C_{31}H_{35}ClN_2O_2RuS$) (4.50 g, 7.07 mmol) was added and stirred for 12 h at 25° C. under $N_2$ atmosphere. The mixture was diluted with water (600 mL), extracted with EtOAc (600 mL*3). The organic layers were washed with water (1200 mL) and brine (800 mL), dried over anhydrous $Na_2SO_4$, filtered and concentrated. The residue which was purified by flash silica gel chromatography (ISCO®; Agela® Flash Column Silica-CS (330 g), Eluent of 20% Ethyl acetate/petroleum ether gradient @100 mL/min) to afford methyl (3R,4R)-4-hydroxy-3-(methoxymethyl)chromane-6-carboxylate 298-3.

MS (ESI) m/z 235.2 (M−18+H$^+$)

$^1$H NMR (500 MHz, chloroform-d) δ 8.05 (d, J=2.0 Hz, 1H), 7.89 (dd, J=2.0, 8.5 Hz, 1H), 6.87 (d, J=8.5 Hz, 1H), 4.86 (t, J=3.5 Hz, 1H), 4.20-4.29 (m, 2H), 3.88 (s, 3H), 3.66-3.73 (m, 1H), 3.56-3.65 (m, 1H), 3.39 (s, 3H), 2.80 (d, J=4.0 Hz, 1H), 2.32-2.47 (m, 1H)

Step C: (3R,4S)-3-(methoxymethyl)-4-((4-nitrobenzoyl)oxy)chromane-6-carboxylate 298-4

4-nitrobenzoic acid (37.1 g, 222 mmol), triphenylphosphane (116 g, 444 mmol) and di-tert-butyl azodicarboxylate (102 g, 444 mmol) were added to a solution of methyl (3R,4R)-4-hydroxy-3-(methoxymethyl)chromane-6-carboxylate 298-3 (56 g, 222 mmol) in THF (600 mL) at 0° C. under $N_2$ atmosphere. The mixture was stirred at 25° C. for 1.5 h. The solvent was evaporated under reduced pressure to give the crude product. The crude product was purified by flash silica gel chromatography (ISCO®; 330 g SepaFlash® Silica Flash Column, Eluent of 24% EtOAc/petroleum ether gradient @ 100 mL/min) to give methyl (3R,4S)-3-(methoxymethyl)-4-((4-nitrobenzoyl)oxy)chromane-6-carboxylate 298-4.

Step D: methyl (3R,4S)-4-hydroxy-3-(methoxymethyl)chromane-6-carboxylate 298-5

$K_2CO_3$ (59.6 g, 431 mmol) was added to a solution of methyl (3R,4S)-3-(methoxymethyl)-4-((4-nitrobenzoyl)oxy)chromane-6-carboxylate 298-4 (86.5 g, 216 mmol) in MeOH (500 mL) and $CH_2Cl_2$ (300 mL) at 25° C. under $N_2$ atmosphere. The mixture was stirred at 25° C. for 12 h. The mixture was diluted with water (600 mL), extracted with DCM (800 mL×3), dried over $Na_2SO_4$, and filtered. The solvent was evaporated under reduced pressure. The residue was purified by flash silica gel chromatography (ISCO®;

330 g Sepa Flash® Silica Flash Column, Eluent of 30% EtOAc/petroleum ether gradient @ 100 mL/min) to give methyl (3R,4S)-4-hydroxy-3-(methoxymethyl)chromane-6-carboxylate 298-5.

MS (ESI) m/z 253.1 (M+H⁺)

¹H NMR (500 MHz, chloroform-d) δ 8.12 (d, J=2.0 Hz, 1H), 7.87 (dd, J=2.5, 8.5 Hz, 1H), 6.83-6.89 (m, 1H), 4.69-4.75 (m, 1H), 4.33 (dd, J=3.0, 11.0 Hz, 1H), 4.09-4.13 (m, 1H), 3.88 (s, 3H), 3.44-3.50 (m, 1H), 3.39-3.43 (m, 1H), 3.37 (s, 3H), 2.68 (d, J=5.0 Hz, 1H), 2.31-2.33 (m, 1H).

Step E: methyl (3R,4R)-4-((E)-2-((tert-butoxycarbonyl)imino)-4,4-diethyl-6-oxotetrahydropyrimidin-1(2H)-yl)-3-(methoxymethyl)chromane-6-carboxylate 298-6

Di-tert-butyl azodicarboxylate (63.9 g, 277 mmol) was added to a solution of methyl (3R,4S)-4-hydroxy-3-(methoxymethyl)chromane-6-carboxylate 298-5 (35 g, 139 mmol), tert-butyl (E)-(4,4-diethyl-6-oxotetrahydropyrimidin-2(1H)-ylidene)carbamate (37.4 g, 139 mmol) and Bu₃P (56.1 g, 277 mmol) in THF (500 mL) at 0° C. under N₂ atmosphere. Then the mixture was stirred at 25° C. for 30 min. The mixture was concentrated in vacuo and purified by column chromatography (petroleum ether/EtOAc=50:1-5:1) to give a crude product, which was dissolved in pet. ether (800 mL), stirred and filtered. The filtrate was concentrated to afford product methyl (3R,4R)-4-((E)-2-((tert-butoxycarbonyl)imino)-4,4-diethyl-6-oxotetrahydropyrimidin-1(2H)-yl)-3-(methoxymethyl) chromane-6-carboxylate 298-6.

MS (ESI) m/z 504.5 (M+H⁺)

1H NMR (500 MHz, chloroform-d) δ 7.76-7.85 (m, 1H), 7.68 (d, J=2.0 Hz, 1H), 6.87 (d, J=8.5 Hz, 1H), 6.48 (d, J=7.5 Hz, 1H), 4.44-4.57 (m, 1H), 4.31-4.32 (m, 1H), 3.83 (s, 3H), 3.57-3.58 (m, 1H), 3.47-3.48 (m, 1H), 3.27 (s, 3H), 2.66-2.78 (m, 1H), 2.41-2.53 (m, 2H), 1.63-1.71 (m, 4H), 1.47 (s, 9H), 0.93-0.96 (m, 6H)

Step F: (3R,4R)-4-((E)-2-((tert-butoxycarbonyl)imino)-4,4-diethyl-6-oxotetrahydropyrimidin-1(2H)-yl)-3-(methoxymethyl)chromane-6-carboxylic acid 298-7

Potassium trimethylsilanolate (28.1 g, 219 mmol) was added to a solution of methyl (3R,4R)-4-((E)-2-((tert-butoxycarbonyl)imino)-4,4-diethyl-6-oxotetrahydropyrimidin-1(2H)-yl)-3-(methoxymethyl)chromane-6-carboxylate 298-6 (23 g, 36.5 mmol) in THF (400 mL) at 0° C. under N₂ atmosphere. The mixture was stirred at 25° C. for 1 h. (3R,4R)-4-((E)-2-((tert-butoxycarbonyl)imino)-4,4-diethyl-6-oxotetrahydropyrimidin-1 (2H)-yl)-3-(methoxymethyl) chromane-6-carboxylic acid 298-7 in THF was used for the next step directly without further purification.

MS (ESI) m/z: 490.3 (M+H⁺)

Step G: tert-butyl ((E)-4,4-diethyl-1-((3R,4R)-6-(((3S,4R)-3-hydroxy-2,2-dimethylchroman-4-yl)carbamoyl)-3-(methoxymethyl)chroman-4-yl)-6-oxotetrahydropyrimidin-2(1H)-ylidene)carbamate 298-8

DIEA (31.2 mL, 179 mmol) was added to a solution of (3R,4R)-4-((E)-2-((tert-butoxycarbonyl)imino)-4,4-diethyl-6-oxotetrahydropyrimidin-1(2H)-yl)-3-(methoxymethyl) chromane-6-carboxylic acid 298-7 (17.5 g, 35.7 mmol), EDCI (20.56 g, 107 mmol), HOBt (7.25 g, 53.6 mmol) and (3S,4R)-4-amino-2,2-dimethylchroman-3-ol (7 g, 36.2 mmol) in THF (600 mL). The reaction was stirred at 25° C. for 2 h. The mixture was quenched with water (400 mL), and extracted with EtOAc (500 mL*3). The organic layers were washed with brine (600 mL), dried over Na₂SO₄, filtered and concentrated in vacuo. The crude was purified by flash silica gel chromatography (ISCO®; 330 g Sepa Flash® Silica Flash Column, Eluent of 40% EtOAc/petroleum ether gradient @ 100 mL/min) to give tert-butyl ((E)-4,4-diethyl-1-((3R,4R)-6-(((3S,4R)-3-hydroxy-2,2-dimethylchroman-4-yl)carbamoyl)-3-(methoxymethyl)chroman-4-yl)-6-oxotetrahydropyrimidin-2(1H)-ylidene)carbamate 298-8.

MS (ESI) m/z 665.4 (M+H⁺)

¹H NMR (400 MHz, chloroform-d) δ 10.17 (s, 1H), 7.61 (d, J=1.2 Hz, 1H), 7.45-7.47 (m, 1H), 7.27-7.30 (m, 1H), 7.15-7.25 (m, 1H), 6.96 (t, J=7.34 Hz, 1H), 6.52 (br d, J=6.8 Hz, 1H), 6.34 (br d, J=7.2 Hz, 1H), 5.17 (br t, J=8.0 Hz, 1H), 4.76 (br d, J=1.6 Hz, 1H), 4.50 (t, J=10.4 Hz, 1H), 4.32 (br dd, J=4.0, 10.6 Hz, 1H), 3.69-3.78 (m, 1H), 3.58 (dd, J=4.8, 9.6 Hz, 1H), 3.44-3.53 (m, 1H), 3.27 (s, 3H), 2.69-2.78 (m, 1H), 2.43-2.55 (m, 2H), 1.63-1.69 (m, 4H), 1.53 (s, 9H), 1.29 (d, J=5.2 Hz, 6H), 0.89-1.00 (m, 6H)

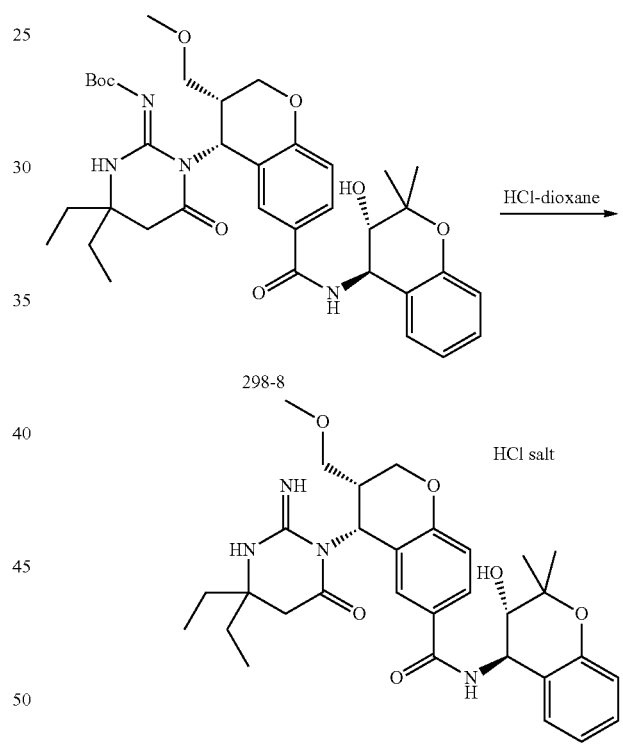

298-8

Example 298

Step H: product (3R,4R)-4-(4,4-diethyl-2-imino-6-oxotetrahydropyrimidin-1(2H)-yl)-N-((3S,4R)-3-hydroxy-2,2-dimethylchroman-4-yl)-3-(methoxymethyl)chromane-6-carboxamide Example 298

A solution of tert-butyl ((E)-4,4-diethyl-1-((3R,4R)-6-(((3S,4R)-3-hydroxy-2,2-dimethylchroman-4-yl)carbamoyl)-3-(methoxymethyl)chroman-4-yl)-6-oxotetrahydropyrimidin-2(1H)-ylidene)carbamate 298-8 (16.8 g, 25.3 mmol) in HCl-dioxane (4 N) (500 mL) was stirred at 25° C. for 12 hrs. The mixture was concentrated under reduced pressure, and the residue was purified by Prep-HPLC (Instrument L-Y Method Column YMC Exphere C18 250*50 mm*10 um Condition water (0.05% HCl)-ACN Begin B 10 End B 50 Gradient Time (min) 20 100% B Hold Time (min) 3 Flow Rate (mL/min) 120 Injections 9) to afford product (3R,4R)-4-(4,4-diethyl-2-imino-6-oxotetrahydropyrimidin-1(2H)-yl)-N-((3S,4R)-3-hydroxy-2,2-dimethylchroman-4-yl)-3-(methoxymethyl)chromane-6-carboxamide Example 298.

MS (ESI) m/z 565.2 (M+H$^+$)

$^1$H NMR (500 MHz, methanol-d$_4$) δ 8.55 (d, J=8.5 Hz, 1H), 7.77 (dd, J=2.0, 9.0 Hz, 1H), 7.74 (d, J=2.0 Hz, 1H), 7.10-7.16 (m, 2H), 6.91 (d, J=8.5 Hz, 1H), 6.83-6.88 (m, 1H), 6.76 (d, J=8.5 Hz, 1H), 5.39 (d, J=6.0 Hz, 1H), 5.20-5.28 (m, 1H), 4.29-4.38 (m, 1H), 4.24-4.25 (m, 1H), 3.78 (d, J=10.0 Hz, 1H), 3.58-3.60 (m, 1H), 3.47-3.53 (m, 1H), 3.40 (s, 3H), 2.88-2.96 (m, 1H), 2.83 (d, J=16.0 Hz, 1H), 2.63 (d, J=16.0 Hz, 1H), 1.56-1.77 (m, 4H), 1.48 (s, 3H), 1.27 (s, 3H), 0.97 (t, J=8.0 Hz, 3H), 0.92 (t, J=7.5 Hz, 3H)

TABLE 4

| Example | Structure | LC/MS (M + 1)$^+$ | Name |
| --- | --- | --- | --- |
| 299 | 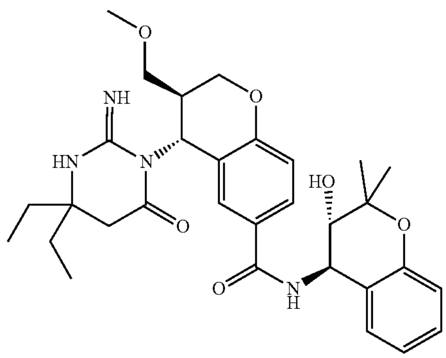 [SMILES: CCC1(CC)CC(=O)N([C@H]2c3cc(C(=O)N[C@@H]4c5ccccc5OC(C)(C)[C@H]4O)ccc3OC[C@@H]2COC)C(=N)N1] | 565.3 | (3S,4R)-4-(4,4-diethyl-2-imino-6-oxo-hexahydropyrimidin-1-yl)-N-[(3S,4R)-3-hydroxy-2,2-dimethyl-chroman-4-yl]-3-(methoxymethyl)chromane-6-carboxamide |
| 300 | 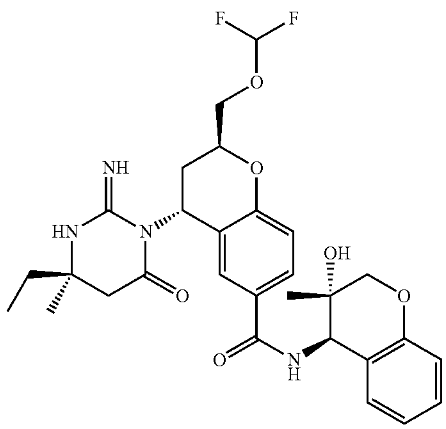 [SMILES: CC[C@]1(C)CC(=O)N([C@@H]2C[C@@H](COC(F)F)Oc3ccc(C(=O)N[C@@H]4c5ccccc5OC[C@@]4(C)O)cc32)C(=N)N1] | 573.3 | (2S,4R)-2-(difluoromethoxymethyl)-4-[(4R)-4-ethyl-2-imino-4-methyl-6-oxo-hexahydropyrimidin-1-yl]-N-[(3S,4R)-3-hydroxy-3-methyl-chroman-4-yl]chromane-6-carboxamide |
| 301 | 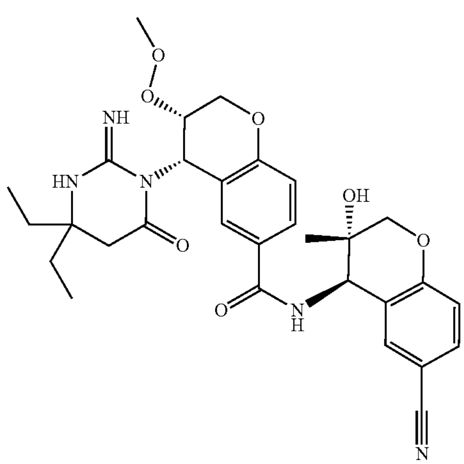 [SMILES: CCC1(CC)CC(=O)N([C@H]2c3cc(C(=O)N[C@@H]4c5cc(C#N)ccc5OC[C@@]4(C)O)ccc3OC[C@H]2OOC)C(=N)N1] | 576.2 | (3R,4R)-N-[(3S,4R)-6-cyano-3-hydroxy-3-methyl-chroman-4-yl]-4-(4,4-diethyl-2-imino-6-oxo-hexahydropyrimidin-1-yl)-3-(methoxymethyl)chromane-6-carboxamide |

TABLE 4-continued

| Example | Structure | LC/MS (M + 1)+ | Name |
|---|---|---|---|
| 302 | 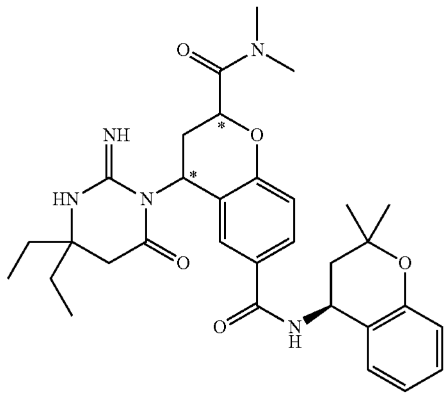 [SMILES: CCC1(CC)CC(=O)N(C2CC(C(=O)N(C)C)Oc3ccc(C(=O)N[C@H]4CC(C)(C)Oc5ccccc54)cc32)C(=N)N1] | 576.4 | 4-(4,4-diethyl-2-imino-6-oxo-hexahydropyrimidin-1-yl)-N6-[(4S)-2,2-dimethylchroman-4-yl]-N2,N2-dimethyl-chromane-2,6-dicarboxamide |
| 303 | 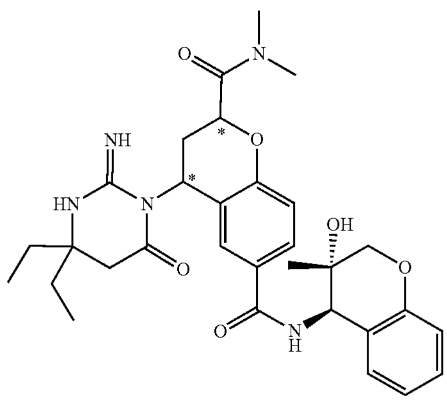 [SMILES: CCC1(CC)CC(=O)N(C2CC(C(=O)N(C)C)Oc3ccc(C(=O)N[C@@H]4c5ccccc5OC[C@@]4(C)O)cc32)C(=N)N1] | 578.3 | 4-(4,4-diethyl-2-imino-6-oxo-hexahydropyrimidin-1-yl)-N6-[(3S,4R)-3-hydroxy-3-methyl-chroman-4-yl]-N2,N2-dimethyl-chromane-2,6-dicarboxamide |
| 304 | 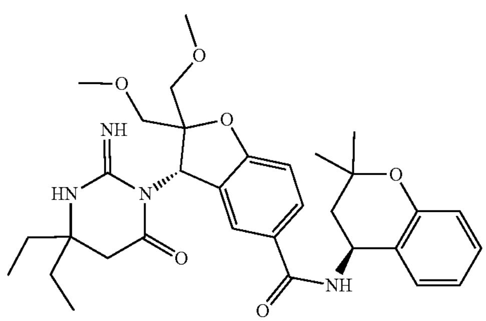 [SMILES: CCC1(CC)CC(=O)N([C@H]2c3cc(C(=O)N[C@H]4CC(C)(C)Oc5ccccc54)ccc3OC2(COC)COC)C(=N)N1] | 579.3 | (3S)-3-(4,4-diethyl-2-imino-6-oxo-hexahydropyrimidin-1-yl)-N-[(4S)-2,2-dimethylchroman-4-yl]-2,2-bis(methoxymethyl)-3H-benzofuran-5-carboxamide |
| 305 | 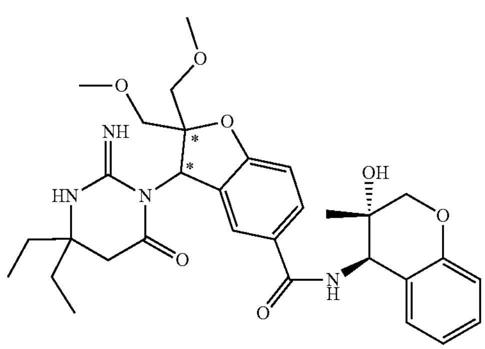 [SMILES: CCC1(CC)CC(=O)N(C2c3cc(C(=O)N[C@@H]4c5ccccc5OC[C@@]4(C)O)ccc3OC2(COC)COC)C(=N)N1] | 581.3 | 3-(4,4-diethyl-2-imino-6-oxo-hexahydropyrimidin-1-yl)-N-[(3S,4R)-3-hydroxy-3-methyl-chroman-4-yl]-2,2-bis(methoxymethyl)-3H-benzofuran-5-carboxamide |

TABLE 4-continued

| Example | Structure | LC/MS (M + 1)+ | Name |
|---|---|---|---|
| 306 | 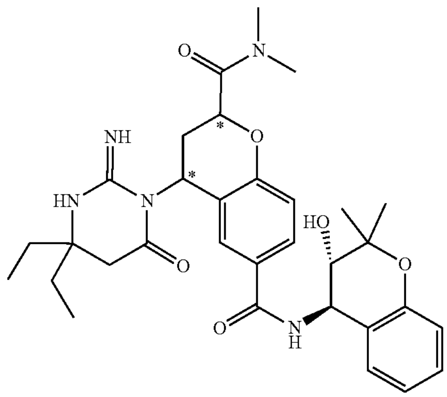 [SMILES: CCC1(CC)CC(=O)N(C2CC(C(=O)N(C)C)Oc3ccc(C(=O)N[C@@H]4c5ccccc5OC(C)(C)[C@H]4O)cc32)C(=N)N1] | 592.4 | 4-(4,4-diethyl-2-imino-6-oxo-hexahydropyrimidin-1-yl)-N6-[(3S,4R)-3-hydroxy-2,2-dimethyl-chroman-4-yl]-N2,N2-dimethyl-chromane-2,6-dicarboxamide |
| 307 | 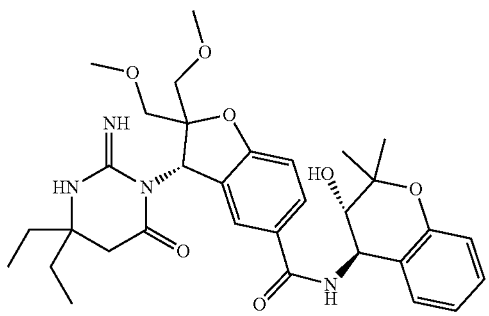 [SMILES: CCC1(CC)CC(=O)N([C@H]2c3cc(C(=O)N[C@@H]4c5ccccc5OC(C)(C)[C@H]4O)ccc3OC2(COC)COC)C(=N)N1] | 595.3 | (3S)-3-(4,4-diethyl-2-imino-6-oxo-hexahydropyrimidin-1-yl)-N-[(3-3-hydroxy-2,2-dimethyl-chroman-4-yl]-2,2-bis(methoxymethyl)-3H-benzofuran-5-carboxamide |
| 308 | 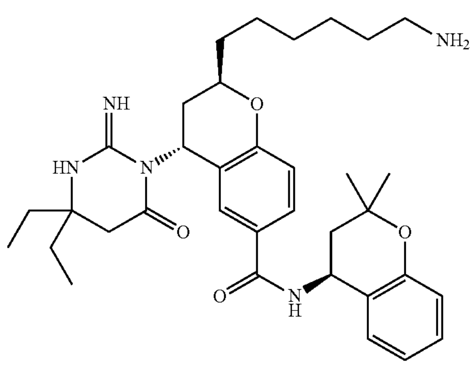 [SMILES: CCC1(CC)CC(=O)N([C@@H]2C[C@@H](CCCCCCN)Oc3ccc(C(=O)N[C@H]4CC(C)(C)Oc5ccccc54)cc32)C(=N)N1] | 604.4 | (2R,4R)-2-(6-aminohexyl)-4-(4,4-diethyl-2-imino-6-oxo-hexahydropyrimidin-1-yl)-N-[(4S)-2,2-dimethylchroman-4-yl]chromane-6-carboxamide |
| 309 | 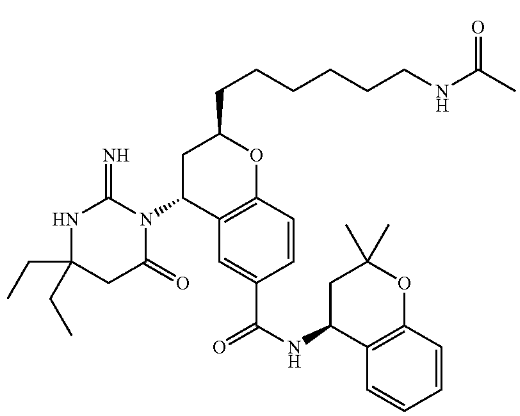 [SMILES: CCC1(CC)CC(=O)N([C@@H]2C[C@@H](CCCCCCNC(C)=O)Oc3ccc(C(=O)N[C@H]4CC(C)(C)Oc5ccccc54)cc32)C(=N)N1] | 646.3 | (2R,4R)-2-(6-acetamidohexyl)-4-(4,4-diethyl-2-imino-6-oxo-hexahydropyrimidin-1-yl)-N-[(4S)-2,2-dimethylchroman-4-yl]chromane-6-carboxamide |

TABLE 4-continued

| Example | Structure | LC/MS (M + 1)+ | Name |
|---|---|---|---|
| 310 | 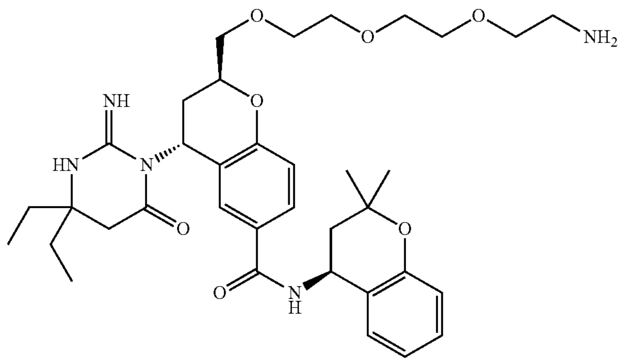 [SMILES: CCC1(CC)CC(=O)N([C@@H]2C[C@@H](COCCOCCOCCN)Oc3ccc(C(=O)N[C@H]4CC(C)(C)Oc5ccccc54)cc32)C(=N)N1] | 666.5 | (2S,4R)-2-[2-[2-(2-aminoethoxy)ethoxy]ethoxymethyl]-4-(4,4-diethyl-2-imino-6-oxo-hexahydropyrimidin-1-yl)-N-[(4S)-2,2-dimethylchroman-4-yl]chromane-6-carboxamide |
| 311 | 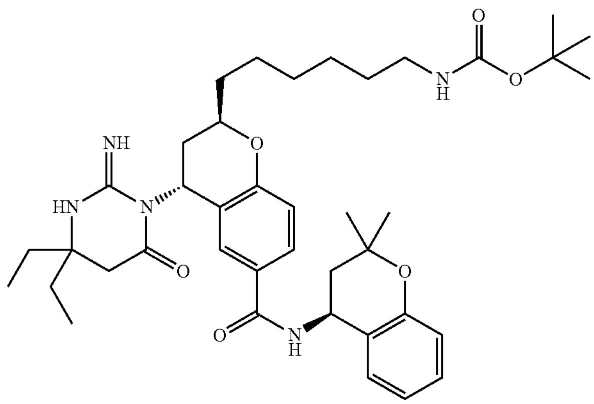 [SMILES: CCC1(CC)CC(=O)N([C@@H]2C[C@@H](CCCCCCNC(=O)OC(C)(C)C)Oc3ccc(C(=O)N[C@H]4CC(C)(C)Oc5ccccc54)cc32)C(=N)N1] | 704.5 | tert-butyl N-[6-[(2R,4R)-4-(4,4-diethyl-2-imino-6-oxo-hexahydropyrimidin-1-yl)-6-[[(4S)-2,2-dimethylchroman-4-yl]carbamoyl]chroman-2-yl]hexyl]carbamate |
| 312 | 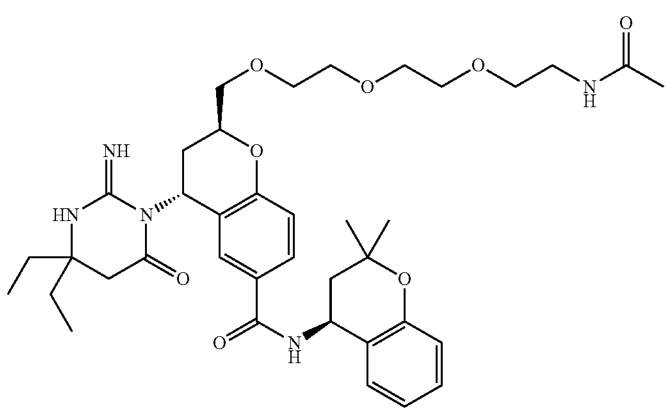 [SMILES: CCC1(CC)CC(=O)N([C@@H]2C[C@@H](COCCOCCOCCNC(C)=O)Oc3ccc(C(=O)N[C@H]4CC(C)(C)Oc5ccccc54)cc32)C(=N)N1] | 708.5 | (2S,4R)-2-[2-[2-(2-acetamidoethoxy)ethoxy]ethoxymethyl]-4-(4,4-diethyl-2-imino-6-oxo-hexahydropyrimidin-1-yl)-N-[(4S)-2,2-dimethylchroman-4-yl]chromane-6-carboxamide |
| 313 | 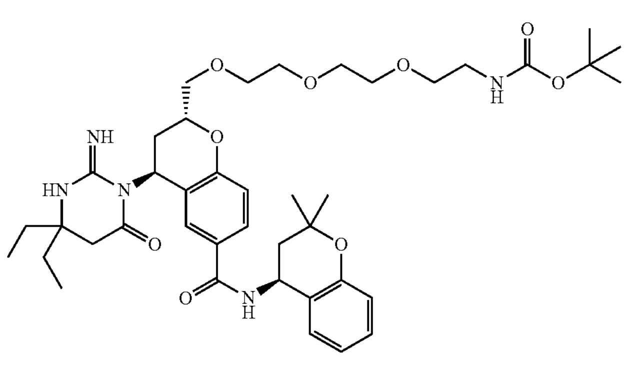 [SMILES: CCC1(CC)CC(=O)N([C@H]2C[C@H](COCCOCCOCCNC(=O)OC(C)(C)C)Oc3ccc(C(=O)N[C@H]4CC(C)(C)Oc5ccccc54)cc32)C(=N)N1] | 766.5 | tert-butyl N-[2-[2-[2-[[(2R,4S)-4-(4,4-diethyl-2-imino-6-oxo-hexahydropyrimidin-l-yl)-6-[[(4S)-2,2-dimethylchroman-4-yl]carbamoyl]chroman-2-yl]methoxy]ethoxy]ethoxy]ethyl]carbamate |

TABLE 4-continued

| Example | Structure | LC/MS (M + 1)+ | Name |
|---|---|---|---|
| 314 | 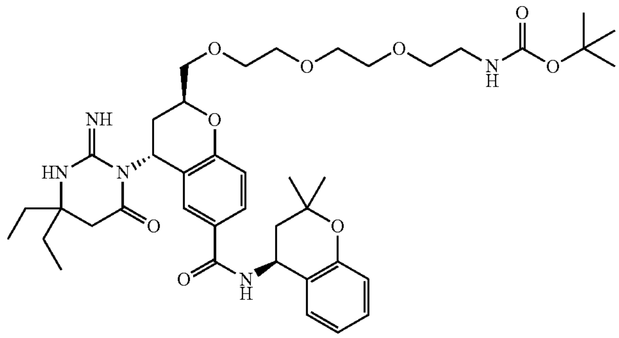 [SMILES: CCC1(CC)CC(=O)N([C@@H]2C[C@@H](COCCOCCOCCNC(=O)OC(C)(C)C)Oc3ccc(C(=O)N[C@H]4CC(C)(C)Oc5ccccc54)cc32)C(=N)N1] | 766.5 | tert-butyl N-[2-[2-[2-[[(2S,4R)-4-(4,4-diethyl-2-imino-6-oxo-hexahydropyrimidin-1-yl)-6-[[(4S)-2,2-dimethylchroman-4-yl]carbamoyl]chroman-2-yl]methoxy]ethoxy]ethoxy]ethyl]carbamate |

Example 315

Assessing Antiparasite Potency in a Parasite LDH Growth Assay (Parasite Assay)

The parasite stock was maintained at 4% haematocrit in RPMI-Hepes media buffered with sodium bicarbonate and supplemented with 5% heat inactivated human serum and 0.5% albumax.

Approximately 42 hours prior to the potency assay being set up, parasites were synchronized with 5% sorbitol to select for ring stage parasites. On the day of assay set up, a blood smear of the parasite culture was Giemsa stained and counted. The parasitemia was adjusted to 0.7% rings and the haematocrit was diluted to 2% in RPMI-Hepes media buffered with sodium bicarbonate and supplemented with 5% heat inactivated human serum and 0.5% albumax. 30 ul of diluted parasites are then added into 10 ul of media+compound in pre-prepared Greiner TC assay plates. Parasite assay plates were placed in gassed humidified boxes in single layer and allowed to incubate at 37° C. for 72 hours. After 72 hours growth, assay plates are sealed with parafilm and frozen flat, in single file at −80° C. overnight. On the following day, assay plates are allowed to thaw at room temperature for 4 hours to which an LDH assay is performed to measure parasite growth.

Assay $EC_{50}$ results are shown in Table 5.

TABLE 5

| Example | $EC_{50}$ (nM) |
|---|---|
| 1A | 0.5 |
| 1B | 163 |
| 2A | 0.5 |
| 2B | 73 |
| 3A | 2.2 |
| 4A | 87 |
| 5A | 5.9 |
| 6A | 1.1 |
| 6B | 8.8 |
| 7A | 0.4 |
| 7B | 19 |
| 8A | 10 |
| 8B | 22 |
| 8C | 120 |
| 8D | 86 |
| 9A | 0.9 |
| 9B | 170 |
| 10A | 0.5 |
| 11A | 0.9 |
| 11B | 84 |
| 12A | 1.1 |
| 13A | 0.8 |
| 13B | 54 |
| 14A | 1 |
| 15A | 0.3 |
| 16A | 0.6 |
| 16B | 95 |
| 17A | 2.7 |
| 18A | 0.8 |
| 19A | 0.3 |
| 20A | 0.8 |
| 21A | 0.8 |
| 22A | 0.7 |
| 23A | 5 |
| 24A | 9.3 |
| 25A | 0.5 |
| 25B | 59.8 |
| 26A | 1.3 |
| 26B | 180 |
| 27A | 1.3 |
| 28A | 1.8 |
| 29A | 1 |
| 29B | 39.7 |
| 30A | 0.8 |
| 31A | 22 |
| 31B | 1 |
| 32A | 7.9 |
| 32B | 290 |
| 33A | 28.3 |
| 34A | 1.2 |
| 35A | 2.4 |
| 36A | 8.9 |
| 36B | 2.2 |
| 37A | 74.4 |
| 38A | 2.8 |
| 39A | 29.9 |
| 40A | 69.5 |
| 41A | 2.8 |
| 42A | 1.0 |
| 42B | 3.2 |
| 43A | 8.1 |
| 43B | 21 |
| 44A | 1.5 |
| 44B | 2.8 |
| 45A | 2.6 |
| 46A | 130 |
| 47A | 4.7 |
| 48A | 37.5 |
| 49A | 49 |
| 50A | 3.7 |
| 51A | 22.5 |
| 52A | 14.4 |
| 53A | 0.3 |
| 54A | 190 |

TABLE 5-continued

| Example | EC$_{50}$ (nM) |
|---|---|
| 54B | 160 |
| 55A | 24.5 |
| 55B | 83.1 |
| 56A | 26.9 |
| 57A | 18.3 |
| 58A | 250 |
| 58B | 3.8 |
| 59A | 210 |
| 59B | 1.6 |
| 60A | 1.3 |
| 60B | 1.7 |
| 61A | 8.4 |
| 62A | 1.2 |
| 63A | 220 |
| 64A | 12 |
| 64B | 0.9 |
| 64C | 64 |
| 64D | 42 |
| 65A | 68 |
| 65B | 2.6 |
| 65C | 26 |
| 66A | 76 |
| 67A | 170 |
| 67B | 0.8 |
| 68A | 1.0 |
| 69A | 2.6 |
| 70A | 9.3 |
| 71A | 3.5 |
| 72A | 0.5 |
| 73A | 0.3 |
| 73B | 1.7 |
| 74A | 0.3 |
| 74B | 6.5 |
| 75A | 0.4 |
| 75B | 9.5 |
| 76A | 8.5 |
| 76B | 1.1 |
| 77A | 57.1 |
| 77B | 21.4 |
| 78 | 8.9 |
| 79 | 9.6 |
| 80 | 18.0 |
| 81 | 6.6 |
| 82 | 15.5 |
| 83 | 20.0 |
| 84 | 0.9 |
| 85 | 10.7 |
| 86 | 87.8 |
| 87 | 105 |
| 88 | 3.4 |
| 89 | 43.5 |
| 90 | 26.8 |
| 91 | 45.2 |
| 92 | 97.2 |
| 93 | 190 |
| 94 | 1.9 |
| 95 | 8.8 |
| 96 | 6.5 |
| 97 | 19.0 |
| 98 | 1.5 |
| 99 | 4.2 |
| 100 | 5.3 |
| 101 | 46.7 |
| 102 | 14.0 |
| 103 | 6.1 |
| 104 | 5.0 |
| 105 | 8.8 |
| 106 | 6.6 |
| 107 | 222 |
| 108 | 74.3 |
| 109 | 14.0 |
| 110 | 60.0 |
| 111 | 90.0 |
| 112 | 11.4 |
| 113 | 16.4 |
| 114 | 1.8 |
| 115 | 3.6 |
| 116 | 210 |
| 117 | 2.5 |
| 118 | 0.9 |
| 119 | 2.8 |
| 120 | 0.8 |
| 121 | 0.6 |
| 122 | 3.9 |
| 123 | 2.8 |
| 124 | 57.5 |
| 125 | 2.1 |
| 126 | 14.3 |
| 127A | 202 |
| 127B | 222 |
| 128 | 2.8 |
| 129 | 3.5 |
| 130 | 2.1 |
| 131 | 2.0 |
| 132 | 1.6 |
| 133A | 1.4 |
| 133B | 17.0 |
| 134 | 8.8 |
| 135 | 0.9 |
| 136 | 1.3 |
| 137 | 239 |
| 138 | 0.9 |
| 139 | 180 |
| 140A | 1.4 |
| 140B | 1.7 |
| 141 | 8.4 |
| 142 | 98.5 |
| 143 | 178 |
| 144 | 194 |
| 145 | 40.8 |
| 146 | 35.5 |
| 147 | 160 |
| 148 | 2.7 |
| 149 | 1.1 |
| 150 | 49.0 |
| 151 | 5.4 |
| 152 | 7.7 |
| 153 | 11.5 |
| 154 | 0.7 |
| 155 | 82.5 |
| 156 | 1.1 |
| 157 | 19.9 |
| 158 | 0.9 |
| 159 | 0.5 |
| 160 | 8.3 |
| 161 | 0.8 |
| 162 | 7.5 |
| 163 | 8.4 |
| 164 | 2.4 |
| 165 | 3.4 |
| 166 | 154 |
| 167 | 250 |
| 168 | 0.4 |
| 169 | 0.3 |
| 170 | 184 |
| 171 | 0.7 |
| 172 | 0.9 |
| 173 | 2.8 |
| 174 | 1.9 |
| 175 | 31.0 |
| 176A | 29.2 |
| 176B | 7.8 |
| 176C | 2.4 |
| 176D | 114 |
| 177 | 66.9 |
| 178A | 108 |
| 178B | 2.2 |
| 179 | 65.4 |
| 180 | 65.4 |
| 181A | 189 |
| 181B | 7.9 |
| 182 | 6.1 |
| 183 | 71.4 |
| 184 | 105 |
| 185 | 50.3 |
| 186 | 70.0 |

TABLE 5-continued

| Example | EC$_{50}$ (nM) |
|---|---|
| 187 | 66.7 |
| 188 | 203 |
| 189 | 1.0 |
| 190A | 261 |
| 190B | 2.6 |
| 190C | 4.9 |
| 191 | 2.6 |
| 192 | 232 |
| 193A | 96.4 |
| 193B | 0.8 |
| 193C | 19.5 |
| 194 | 0.9 |
| 195 | 3.5 |
| 196 | 8.6 |
| 197 | 125 |
| 198 | 11.3 |
| 199 | 1.1 |
| 200 | 2.9 |
| 201 | 1.4 |
| 202 | 0.8 |
| 203 | 5.9 |
| 204 | 247 |
| 205 | 2.1 |
| 206 | 66.0 |
| 207 | 22.0 |
| 208 | 3.7 |
| 209 | 7.9 |
| 210 | 195 |
| 211 | 8.9 |
| 212 | 6.5 |
| 213 | 9.0 |
| 214A | 8.2 |
| 214B | 260 |
| 215 | 4.2 |
| 216 | 2.7 |
| 217 | 4.9 |
| 218 | 64 |
| 219 | 208 |
| 220 | 2.9 |
| 221 | 190 |
| 222 | 15.6 |
| 223 | 300 |
| 224 | 0.3 |
| 225 | 0.8 |
| 226A | 2.6 |
| 226B | 69.0 |
| 226C | 273 |
| 226D | 1.0 |
| 227 | 1.3 |
| 228 | 282 |
| 229 | 59.3 |
| 230 | 2.7 |
| 231 | 7.4 |
| 232 | 21.8 |
| 233 | 7.9 |
| 234A | 22.5 |
| 234B | 3.9 |
| 234C | 43.2 |
| 235 | 0.7 |
| 236 | 0.9 |
| 237 | 240 |
| 238 | 47.8 |
| 239 | 0.9 |
| 240 | 0.6 |
| 241 | 0.4 |
| 242A | 0.6 |
| 242B | 10.5 |
| 243 | 6.1 |
| 244 | 7.8 |
| 245 | 0.8 |
| 246 | 2.0 |
| 247 | 4.5 |
| 248 | 0.8 |
| 249 | 1.1 |
| 250 | 219 |
| 251A | 0.4 |
| 251B | 1.5 |
| 251C | 84.4 |

TABLE 5-continued

| Example | EC$_{50}$ (nM) |
|---|---|
| 252 | 2.1 |
| 253 | 4.3 |
| 254 | 3.4 |
| 255 | 3.3 |
| 256 | 8.9 |
| 257 | 189 |
| 258A | 85.9 |
| 258B | 2.4 |
| 258C | 226 |
| 258D | 6.7 |
| 259A | 5.5 |
| 259B | 24.2 |
| 259C | 3.6 |
| 259D | 10.6 |
| 260 | 8.2 |
| 261 | 133 |
| 262 | 7.4 |
| 263 | 74.8 |
| 264 | 3.3 |
| 265 | 31.1 |
| 266 | 2.6 |
| 267 | 24.0 |
| 268 | 25.0 |
| 269 | 2.9 |
| 270 | 1.8 |
| 271 | 182 |
| 272A | 62.5 |
| 272B | 14.3 |
| 272C | 0.9 |
| 272D | 2.3 |
| 273 | 7.8 |
| 274 | 98.5 |
| 275 | 25.7 |
| 276 | 0.6 |
| 277 | 0.4 |
| 278 | 12.2 |
| 279 | 31.4 |
| 28 | 0.4 |
| 281 | 1.1 |
| 282A | 7.8 |
| 282B | 40.5 |
| 283 | 2.6 |
| 284 | 8.5 |
| 285 | 35.5 |
| 286 | 240 |
| 287 | 1.9 |
| 288 | 1.8 |
| 289 | 0.6 |
| 290 | 0.3 |
| 291 | 240 |
| 292 | 49.7 |
| 293 | 2.8 |
| 294 | 259 |
| 295 | 100 |
| 296 | 0.3 |
| 297 | 241 |
| 298 | 0.5 |
| 299 | 0.8 |
| 300 | 3.8 |
| 301 | 1.8 |
| 302 | 1.7 |
| 303 | 50.8 |
| 304 | 5.6 |
| 305 | 75.8 |
| 306 | 27.4 |
| 307 | 3.2 |
| 308 | 40.5 |
| 309 | 3.2 |
| 310 | 211 |
| 311 | 2.4 |
| 312 | 53.9 |
| 313 | 260 |
| 314 | 7.3 |

Example 1 as an Inhibitor of PMX and PMIX Function Whilst $C_4$ is Specific for PMX To confirm that Example 1 blocks PMX function in the *P. falciparum* parasite, the ability to inhibit cleavage of a known substrate for this protease was tested. SERAS is a 120 kDa protein required for merozoite egress and is processed by subtilisin-like protease subtilisin 1 (SUB1) to release a soluble polypeptide of approximately 50 kDa (Pino, P., Caldelari, R., Mukherjee, B., Vahokoski, J., Klages, N., Maco, B., et al. (2017). A multistage antimalarial targets the plasmepsins IX and X essential for invasion and egress. Science 358, 522-528). The protease inhibitor E64, which prevents schizont rupture, but does not affect SERAS processing was used as a negative control (Salmon, B. L., Oksman, A. and Goldberg, D. E. (2001). Malaria parasite exit from the host erythrocyte: A two-step process requiring extraerythrocytic proteolysis. Proc Natl Acad Sci USA 98, 271-276). However, following incubation with Example 1, there was an accumulation of unprocessed SERAS at 120 kDa confirming that SUB1 activation requires prior processing. SERAS was included as a control in all subsequent experiments as a proxy for PMX-mediated activation of SUB1.

To confirm that Example 1 was a dual inhibitor of PMX and PMIX function, the ability of this compound to inhibit cleavage of the known PMIX substrate Rhoptry Associated Protein 1 (RAP1) in parasite extracts was tested (Pino et al., 2017). RAP1 is a merozoite rhoptry protein that is localized to the parasitophorous vacuole after invasion and processed by both PMIX and SUB1 (Pino et al., 2017). The processed forms of RAP1 (p82 and p69) are detected in untreated and E64-treated merozoites, showing that this protein was processed normally by PMIX and SUB1 under these conditions. RAP1 was not released into the parasite supernatant because it was deposited in the parasitophorous vacuole during the invasion process (Baldi, D., Andrews, K., Waller, R., Roos, D., Howard, R., Crabb, B. and Cowman, A. (2000)). RAP1 controls rhoptry targeting of RAP2 in the malaria parasite *Plasmodium falciparum*. Embo Journal 19, 2435-2443. In parasites treated with Example 1 only the unprocessed p87 form of RAP1 was present, indicating that both SUB1 and PMIX cleavage have been blocked. Similar results were obtained for Apical Sushi Protein (ASP) which has also been shown to be cleaved by PMIX (Pino et al., 2017). ASP was processed into a 47 kDa polypeptide (p47) in untreated and E64-treated parasites. However, this cleavage event was inhibited by Example 1 and the full-length protein of 87 kDa (p87) was observed, indicating that PMIX processing of this protein was blocked by Example 1. These findings confirm that Example 1 acts as a dual inhibitor and blocks both PMX and PMIX protease activity in the *P. falciparum* parasite.

The development of Example 1 as a PMIX/PMX dual inhibitor of the *P. falciparum* parasite has allowed for the analysis of the function of these aspartic acid proteases. To do this, PMIX was processed to a 55 kDa (p55) protein and this was not inhibited by E64. Example 1 was used to inhibit this processing event, indicating that autocatalytic cleavage of PMIX was important for activation of this protease. The development of a PMX-specific inhibitor and a PMX/PIX dual inhibitor confirms the PMX specific processing of ASP and RAP1, and also shows that PMX was autocatalytically processed and activated.

What is claimed:

1. A compound having the structural Formula (I'):

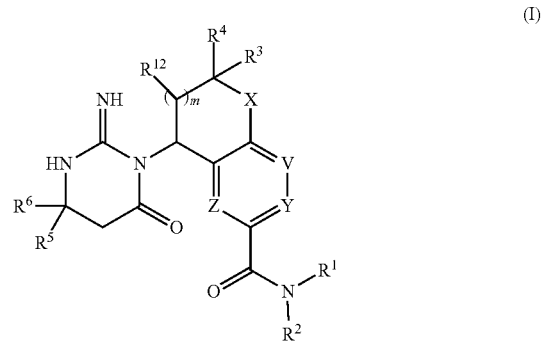

(I)

or a pharmaceutically acceptable salt thereof, wherein:

X is $CH_2$, O, S, SO, $SO_2$ or NH;

Y is $CR^9$ or N, wherein when Y is N, Z is $CR^{11}$ and V is $CR^{10}$;

V is $CR^{10}$ or N, wherein when V is N, Z is $CR^{11}$ and Y is $CR^9$;

Z is $CR^{11}$ or N, wherein when Z is N, V is $CR^{10}$ and Y is $CR^9$;

$R^1$ is a heterocycloalkyl, $C_3$-$C_{12}$cycloalkyl, aryl, or $C_1$-$C_6$alkylaryl or when taken with $R^2$ and the nitrogen to which they are bonded, forms a nitrogen-containing ring, wherein the heterocycloalkyl, $C_3$-$C_{12}$cycloalkyl, aryl, $C_1$-$C_6$alkylaryl or nitrogen-containing ring is unsubstituted or substituted with 1 to 5 substituents independently selected from the group consisting of halogen, CN, OH, $C_1$-$C_6$alkoxy, $C_1$-$C_6$alkylOC$_1$-$C_6$alkyl, $C_1$-$C_6$alkylCOOH, COOH, oxo, COOC$_1$-$C_6$alkyl, $C_1$-$C_6$alkylCOOC$_1$-$C_6$alkyl, $C_3$-$C_6$cycloalkyl, $C_1$-$C_6$alkyl, haloC$_1$-$C_6$alkyl, $C_1$-$C_6$alkylOH, CON($R^7$)($R^8$), N($R^7$)($R^8$) and $C_1$-$C_6$alkylN($R^7$)($R^8$);

$R^2$ is hydrogen, $C_1$-$C_6$alkylCOOH, COOH, $C_3$-$C_6$cycloalkyl, $C_1$-$C_6$alkyl, haloC$_1$-$C_6$alkyl or $C_1$-$C_6$alkylOH or when taken with $R^1$, and the nitrogen to which they are bonded, forms a nitrogen-containing ring, wherein the nitrogen-containing ring is unsubstituted or substituted with 1 to 5 substituents independently selected from the group halogen, CN, OH, $C_1$-$C_6$alkoxy, $C_1$-$C_6$alkylOC$_1$-$C_6$alkyl, $C_1$-$C_6$alkylCOOH, COOH, oxo, COOC$_1$-$C_6$alkyl, $C_3$-$C_6$cycloalkyl, $C_1$-$C_6$alkyl, haloC$_1$-$C_6$alkyl, $C_1$-$C_6$alkylOH, CON($R^7$)($R^8$), N($R^7$)($R^8$) and $C_1$-$C_6$alkylN($R^7$)($R^8$);

$R^3$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, haloC$_1$-$C_6$alkyl, $C_1$-$C_6$alkylOH, CON($R^7$)($R^8$), N($R^7$)($R^8$), or $C_1$-$C_6$alkylN($R^7$)($R^8$), or when taken with $R^4$ forms a $C_3$-$C_6$cycloalkyl or $C_3$-$C_6$heterocycloalkyl;

$R^4$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, haloC$_1$-$C_6$alkyl, $C_1$-$C_6$alkylOH, CON($R^7$)($R^8$), N($R^7$)($R^8$), or $C_1$-$C_6$alkylN($R^7$)($R^8$), or when taken with $R^3$ forms a $C_3$-$C_6$cycloalkyl or $C_3$-$C_6$heterocycloalkyl;

$R^5$ is hydrogen, halogen, CN, OH, $C_1$-$C_6$alkoxy, $C_1$-$C_6$alkylOC$_1$-$C_6$alkyl, $C_1$-$C_6$alkylCOOH, COOH, $C_3$-$C_6$cycloalkyl, $C_1$-$C_6$alkyl, haloC$_1$-$C_6$alkyl, $C_1$-$C_6$alkylOH, CON($R^7$)($R^8$), N($R^7$)($R^8$) or $C_1$-$C_6$alkylN($R^7$)($R^8$), or when taken with $R^6$ forms a $C_3$-$C_6$cycloalkyl or $C_3$-$C_6$heterocycloalkyl;

$R^6$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$), or when taken with $R^5$ forms a $C_3$-$C_6$cycloalkyl or $C_3$-$C_6$heterocycloalkyl;

$R^7$ is hydrogen, $C_1$-$C_6$alkylCOOH, COOH, $C_3$-$C_6$cycloalkyl, $C_1$-$C_6$alkyl, halo$C_1$-$C_6$alkyl, or $C_1$-$C_6$alkylOH;

$R^8$ is hydrogen, $C_1$-$C_6$alkylCOOH, COOH, $C_3$-$C_6$cycloalkyl, $C_1$-$C_6$alkyl, halo$C_1$-$C_6$alkyl, or $C_1$-$C_6$alkylOH;

$R^9$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$);

$R^{10}$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$);

$R^{11}$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$);

$R^{12}$ is hydrogen, halogen, CN, OH, $C_1$-$C_6$alkoxy, $C_1$-$C_6$alkylO$C_1$-$C_6$alkyl, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) or $C_1$-$C_6$alkylN($R^7$)($R^8$); and m is 0, 1 or 2.

2. The compound of claim 1, or a pharmaceutically acceptable salt thereof, wherein m is 1 and X is O.

3. The compound of claim 1, or a pharmaceutically acceptable salt thereof, wherein m is 1 and X is $CH_2$.

4. The compound of claim 1, or a pharmaceutically acceptable salt thereof, wherein m is 0 and X is O.

5. The compound of claim 1, or a pharmaceutically acceptable salt thereof, wherein m is 1 and X is $SO_2$.

6. The compound of claim 1, or a pharmaceutically acceptable salt thereof, wherein $R^1$ is selected from:

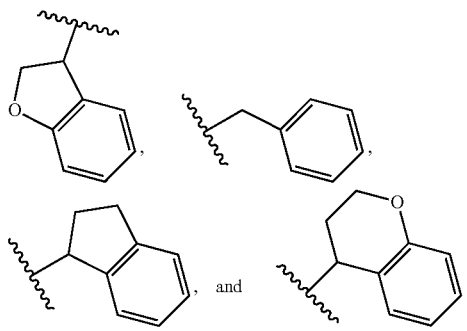

and wherein $R^1$ is unsubstituted or substituted with 1 to 5 substituents independently selected from the group halogen, CN, OH, $C_1$-$C_6$alkoxy, $C_1$-$C_6$alkylO$C_1$-$C_6$alkyl, $C_1$-$C_6$alkylCOOH, COOH, oxo, COOC$_1$-$C_6$alkyl, $C_3$-$C_6$cycloalkyl, $C_1$-$C_6$alkyl, halo$C_1$-$C_6$alkyl, $C_1$-$C_6$alkylOH, CON($R^7$)($R^8$), N($R^7$)($R^8$) and $C_1$-$C_6$alkylN($R^7$)($R^8$);

$R^7$ is hydrogen, $C_1$-$C_6$alkylCOOH, COOH, $C_3$-$C_6$cycloalkyl, $C_1$-$C_6$alkyl, halo$C_1$-$C_6$alkyl or $C_1$-$C_6$alkylOH; and $R^8$ is hydrogen, $C_1$-$C_6$alkylCOOH, COOH, $C_3$-$C_6$cycloalkyl, $C_1$-$C_6$alkyl, halo$C_1$-$C_6$alkyl or $C_1$-$C_6$alkylOH.

7. The compound of claim 6, or a pharmaceutically acceptable salt thereof, wherein $R^1$ is:

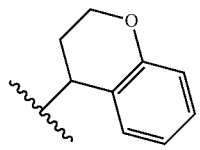 [SMILES: *C1CCOc2ccccc21]

and wherein $R^1$ is unsubstituted or substituted with 1 to 5 substituents independently selected from the group halogen, CN, OH, $C_1$-$C_6$alkoxy, $C_1$-$C_6$alkylO$C_1$-$C_6$alkyl, $C_1$-$C_6$alkylOhalo$C_1$-$C_6$alkyl, oxo, COOC$_1$-$C_6$alkyl, $C_1$-$C_6$alkyl, halo$C_1$-$C_6$alkyl and $C_1$-$C_6$alkylOH.

8. The compound of claim 6, or a pharmaceutically acceptable salt thereof, wherein $R^1$ is:

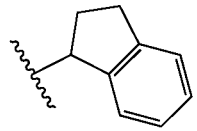 [SMILES: *C1CCc2ccccc21]

and wherein $R^1$ is unsubstituted or substituted with 1 to 5 substituents independently selected from the group halogen, CN, OH, $C_1$-$C_6$alkoxy, $C_1$-$C_6$alkylO$C_1$-$C_6$alkyl, $C_1$-$C_6$alkylOhalo$C_1$-$C_6$alkyl, oxo, COOC$_1$-$C_6$alkyl, $C_1$-$C_6$alkyl, halo$C_1$-$C_6$alkyl, $NH_2$, and $C_1$-$C_6$alkylOH.

9. The compound of claim 8, or a pharmaceutically acceptable salt thereof, wherein $R^2$ is hydrogen.

10. The compound of claim 1, or a pharmaceutically acceptable salt thereof, wherein $R^1$ is taken with $R^2$ and the nitrogen to which they are bonded, to form a nitrogen-containing ring.

11. The compound of claim 10, or a pharmaceutically acceptable salt thereof, wherein the nitrogen-containing ring is:

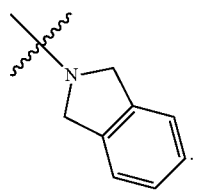 [SMILES: *N1Cc2ccccc2C1]

12. The compound of claim 1, or a pharmaceutically acceptable salt thereof, wherein $R^3$ is hydrogen, $C_1$-$C_6$alkylO$C_1$-$C_6$alkyl or $C_1$-$C_6$alkyl or when taken with $R^4$ forms a $C_3$-$C_6$heterocycloalkyl.

13. The compound of claim 1, or a pharmaceutically acceptable salt thereof, wherein $R^3$ is hydrogen or $C_1$-$C_6$alkyl, or when taken with $R^4$ forms a $C_3$-$C_6$heterocycloalkyl.

14. The compound of claim 1, or a pharmaceutically acceptable salt thereof, wherein $R^5$ is hydrogen or $C_1$-$C_6$alkyl.

15. The compound of claim 1, or a pharmaceutically acceptable salt thereof, wherein $R^6$ is hydrogen or $C_1$-$C_6$alkyl.

16. The compound of claim 1, or a pharmaceutically acceptable salt thereof, wherein $R^3$ and $R^4$ are independently selected from the group hydrogen, halogen, OH, $C_1$-$C_6$alkylOH, $C_1$-$C_6$alkylalkoxy, $C_1$-$C_6$alkylO$C_1$-$C_6$alkyl, $C_1$-$C_6$alkyl, CON($C_1$-$C_6$alkyl)$_2$, and $C_1$-$C_6$alkylN($R^7$)($R^8$)

$R^7$ is hydrogen, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CO$C_1$-$C_6$alkyl or COO$C_1$-$C_6$alkyl;

$R^8$ is hydrogen, $C_1$-$C_6$alkylCOOH, COOH, $C_3$-$C_6$cycloalkyl, $C_1$-$C_6$alkyl, halo$C_1$-$C_6$alkyl, $C_1$-$C_6$alkylOH, CO$C_1$-$C_6$alkyl or COO$C_1$-$C_6$alkyl.

17. The compound of claim 1, or a pharmaceutically acceptable salt thereof, wherein m is 1 or 2, and $R^{12}$ is selected from hydrogen, halogen, OH, $C_1$-$C_6$alkylOH, $C_1$-$C_6$alkylalkoxy, $C_1$-$C_6$alkylO$C_1$-$C_6$alkyl, and $C_1$-$C_6$alkyl.

18. The compound of claim 1, or a pharmaceutically acceptable salt thereof, wherein Y is CH.

19. The compound of claim 1, or a pharmaceutically acceptable salt thereof, wherein Z is CH.

20. The compound of claim 1, or a pharmaceutically acceptable salt thereof, wherein V is CH.

21. The compound of claim 1, or a pharmaceutically acceptable salt thereof, wherein Z is N; and Y and V are both CH.

22. The compound of claim 1, or a pharmaceutically acceptable salt thereof, wherein V is N; and Y and Z are both CH.

23. A compound selected from the group:

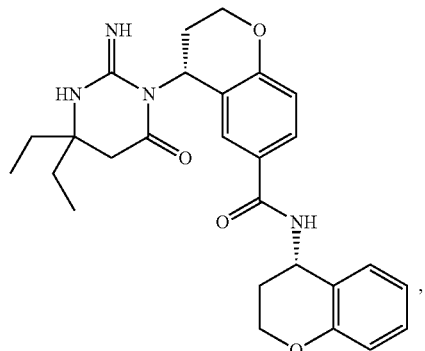

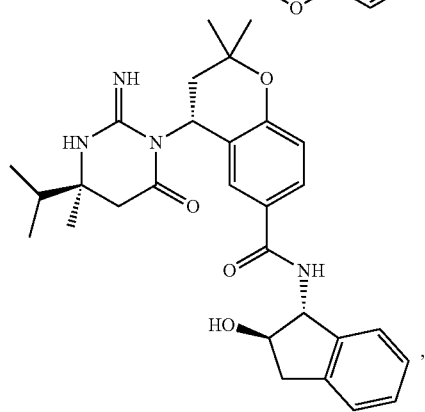

-continued

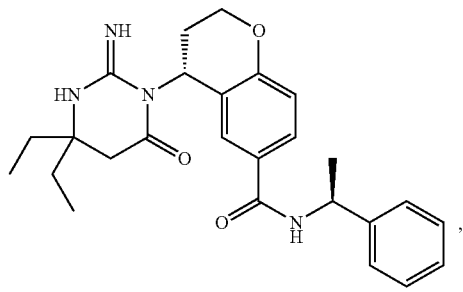

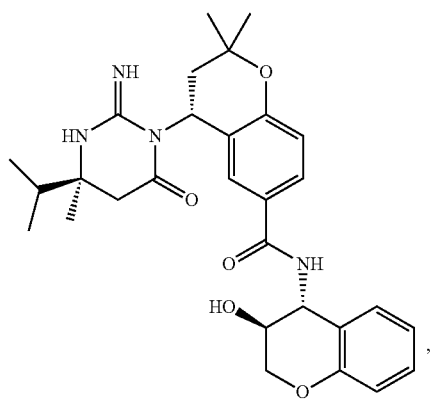

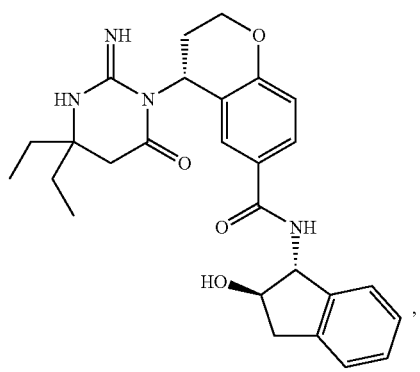

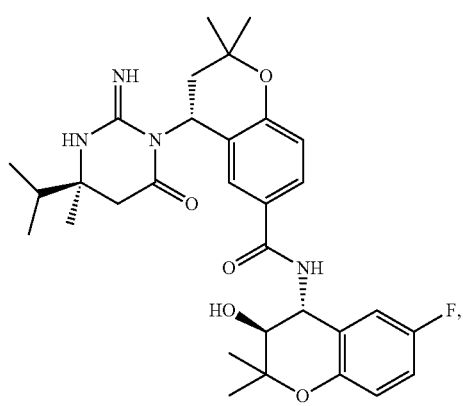

333
-continued
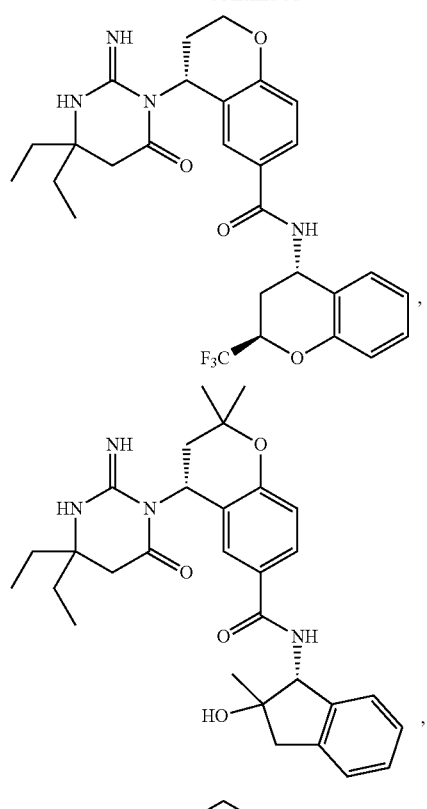
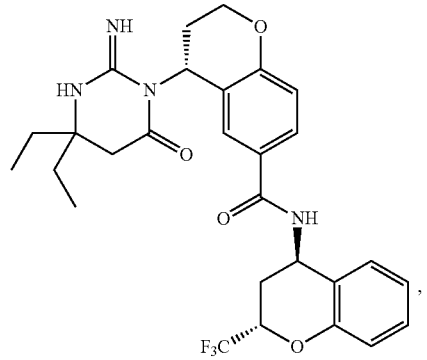
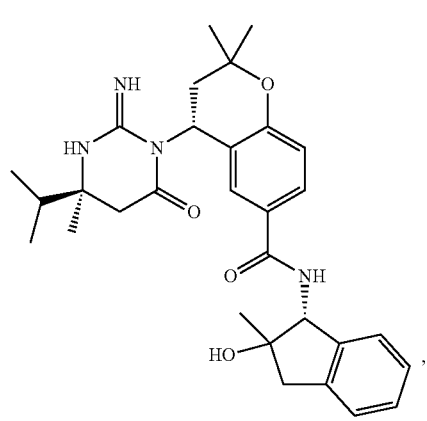
334
-continued
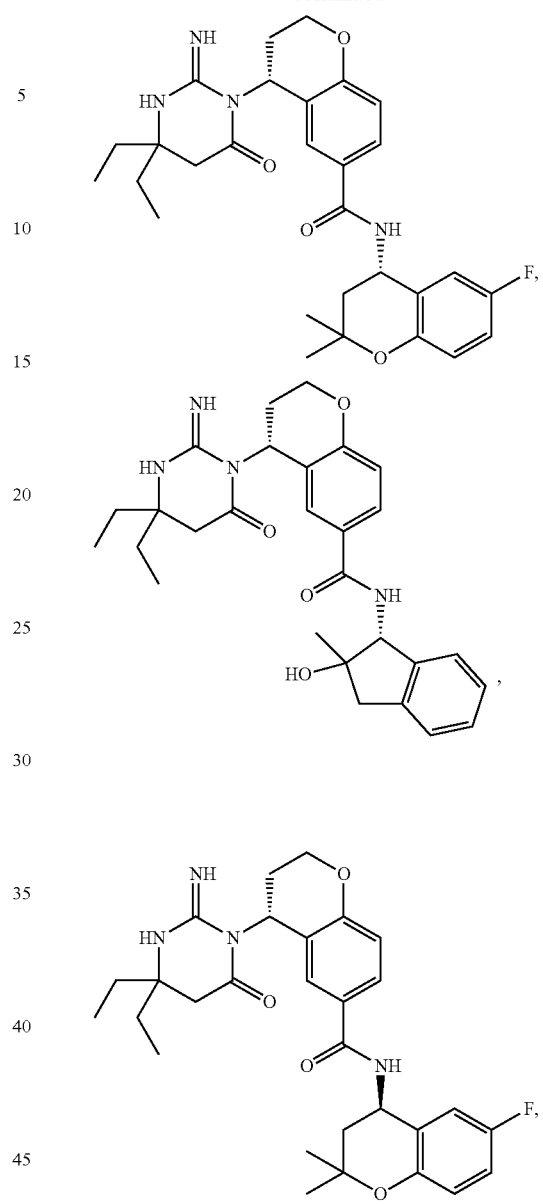
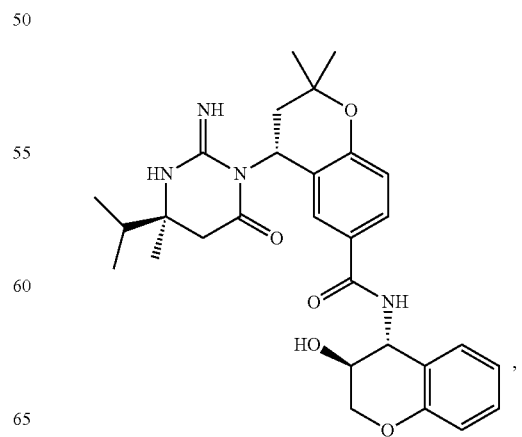

-continued
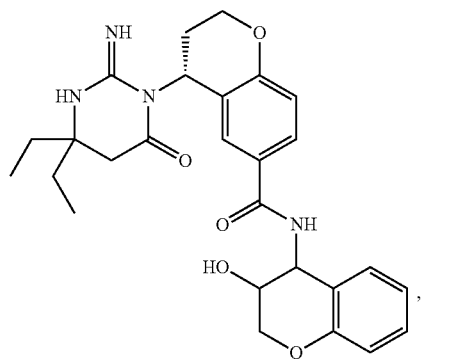
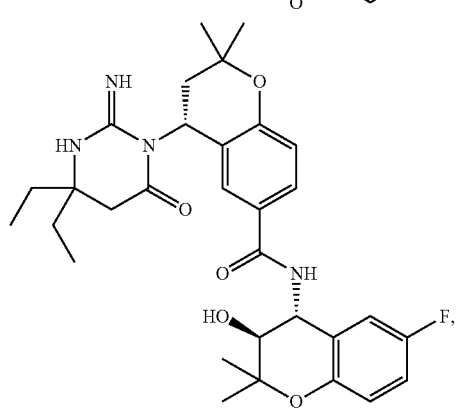
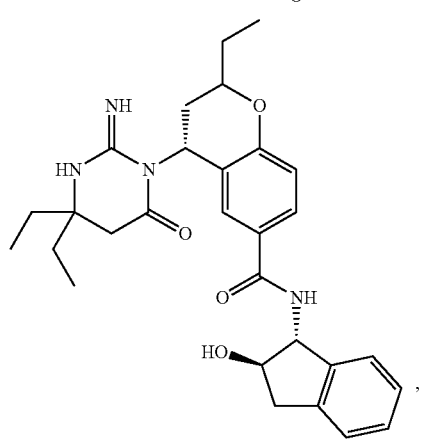
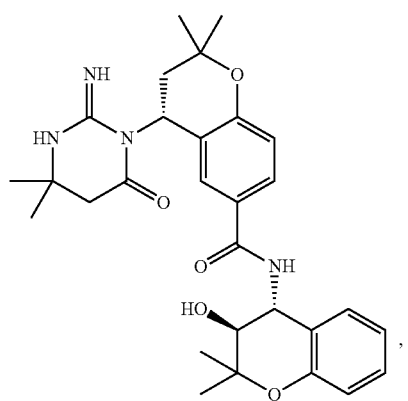
-continued
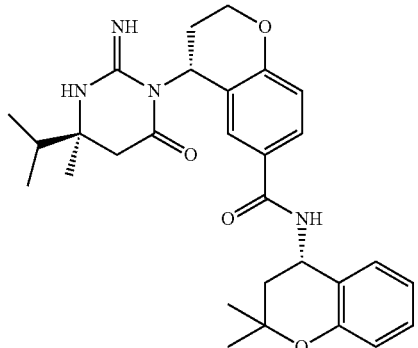
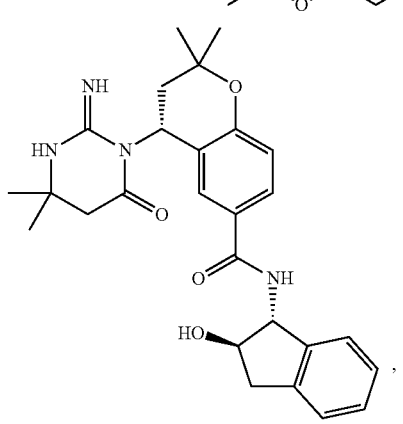
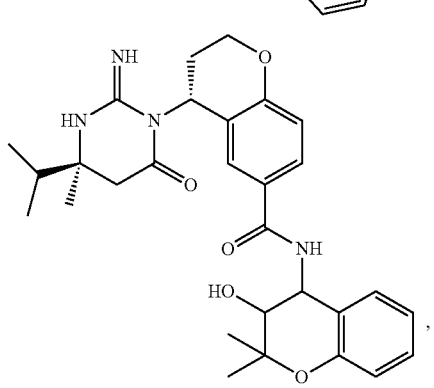
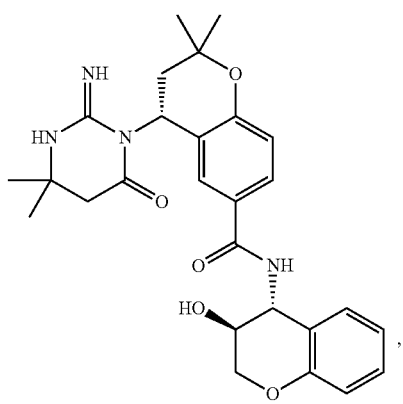

337
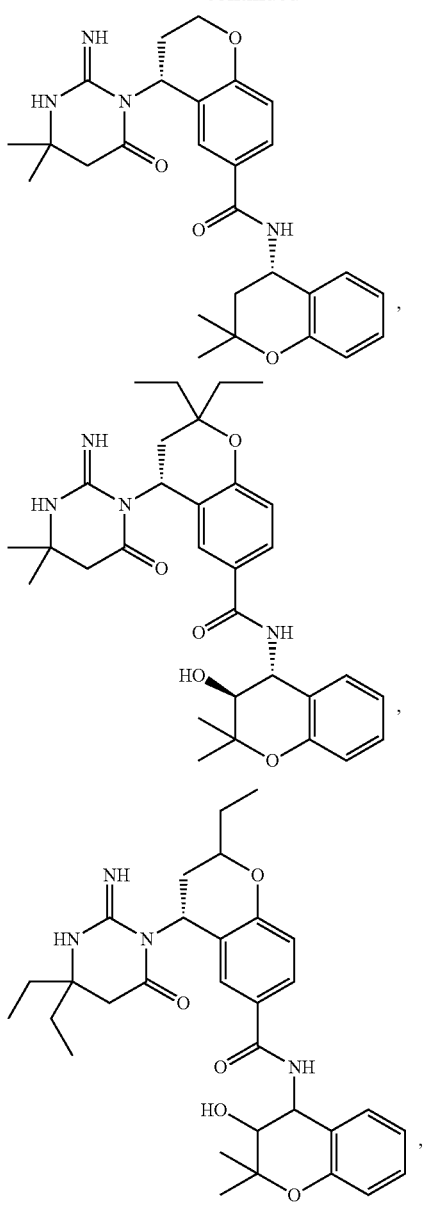
338
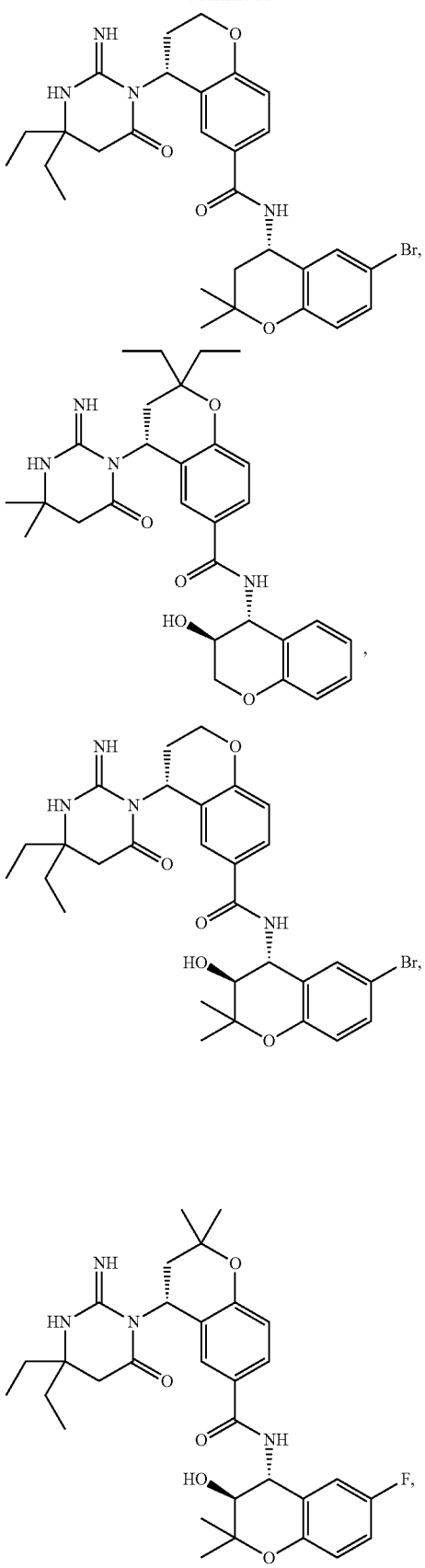

339
-continued
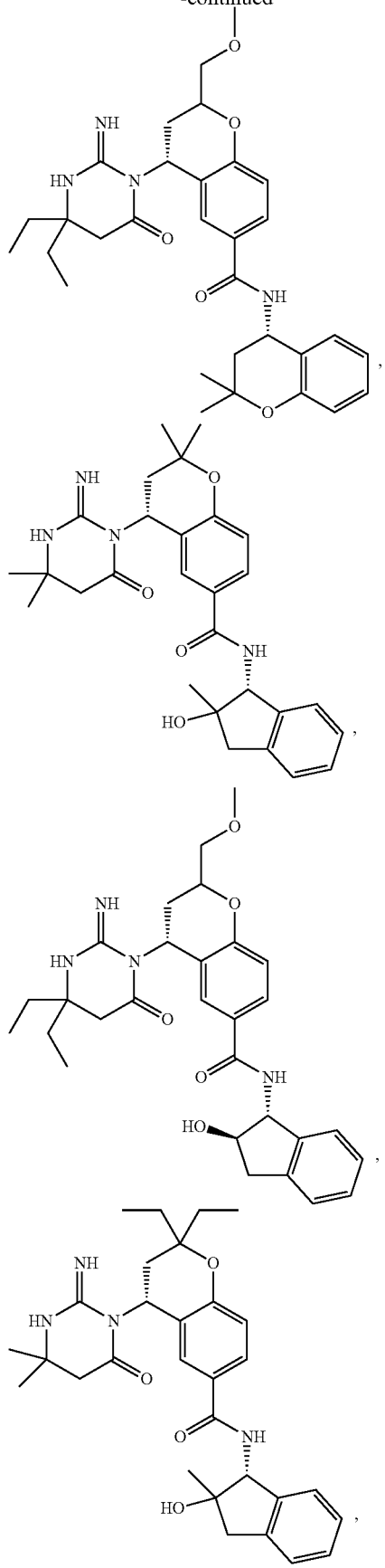
340
-continued
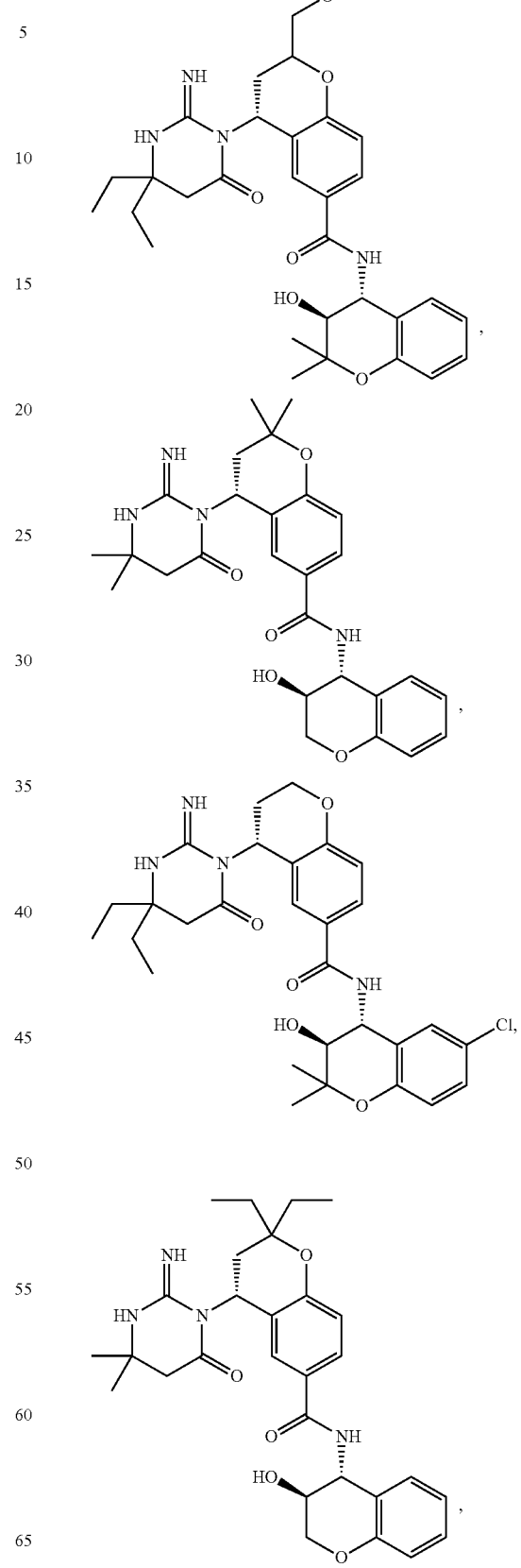

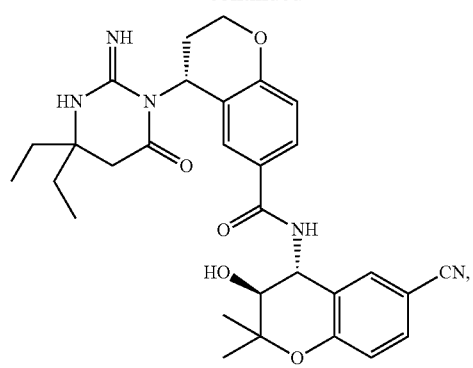
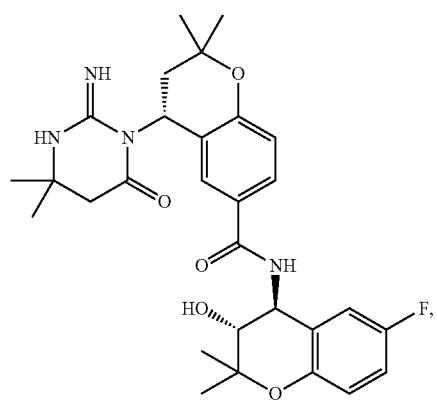
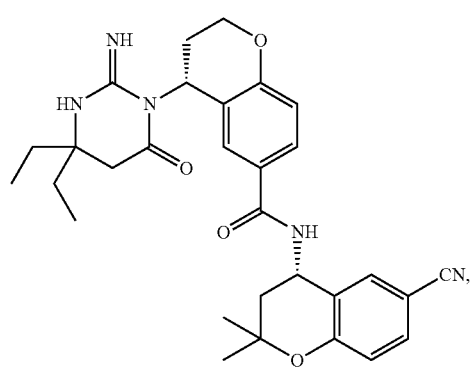
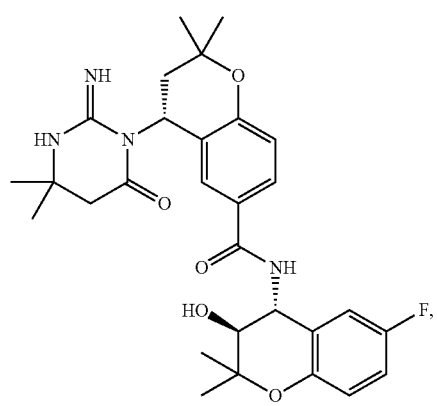
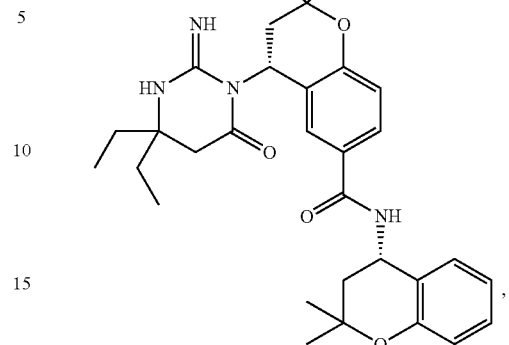
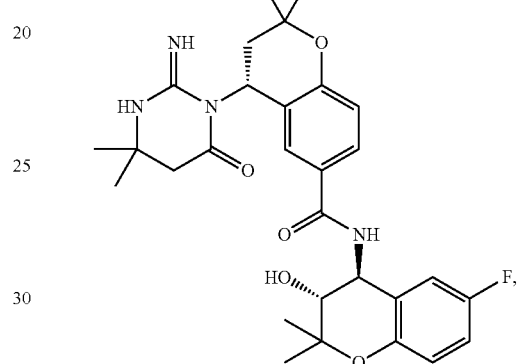
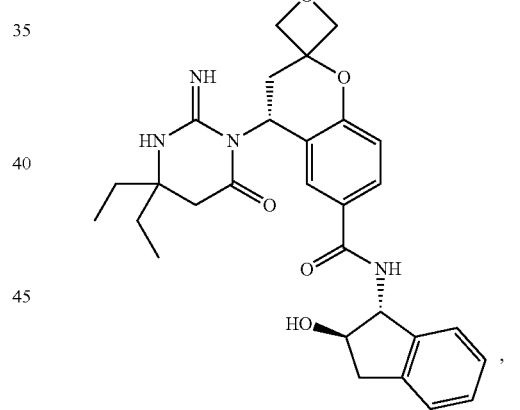
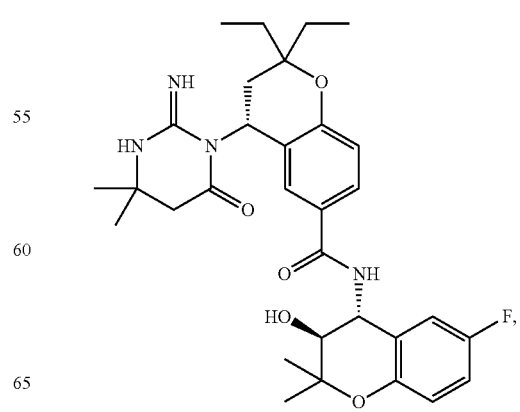

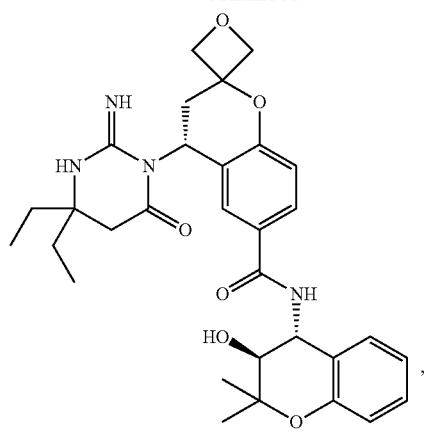
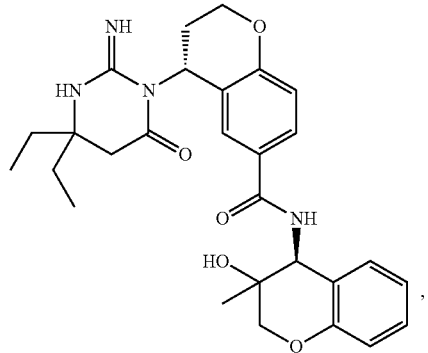
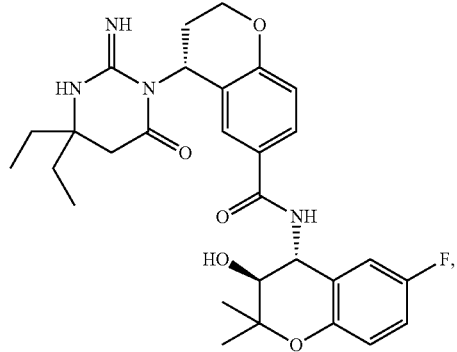
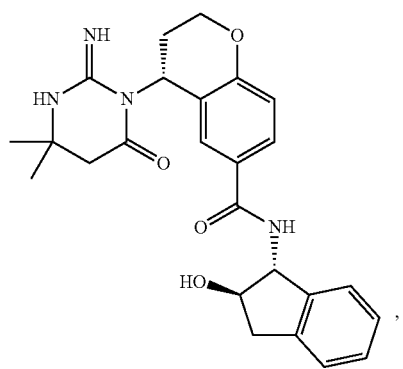
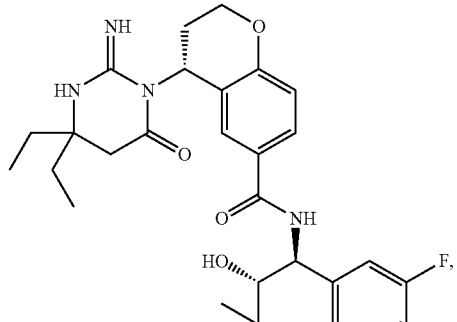
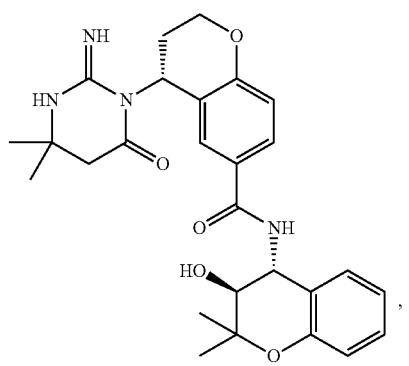
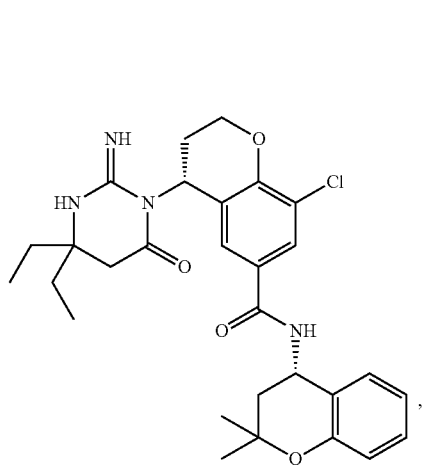
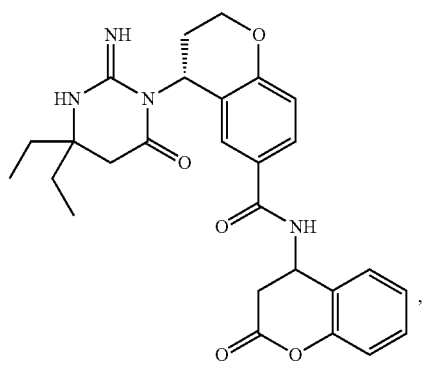

345
-continued
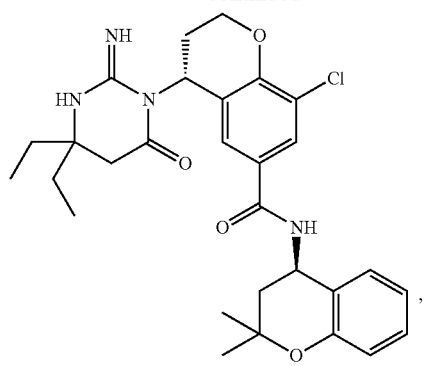
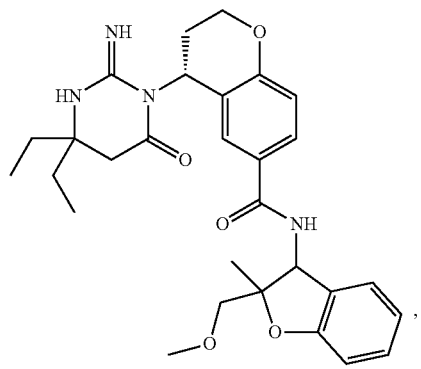
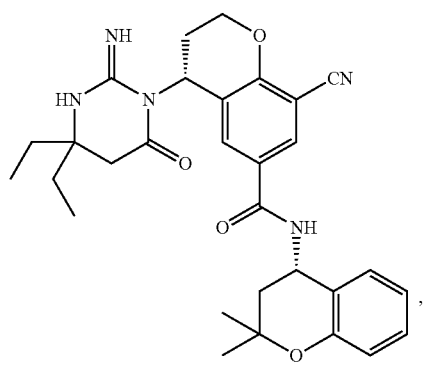
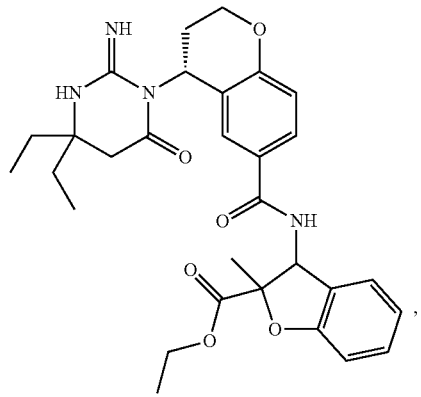
346
-continued
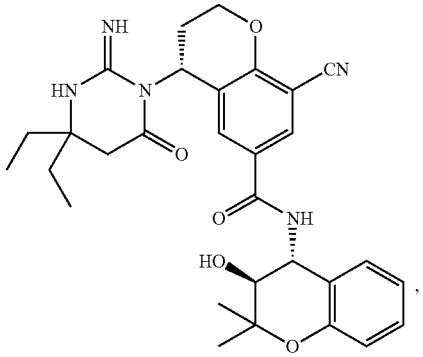
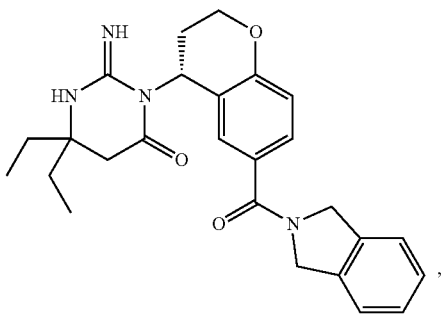
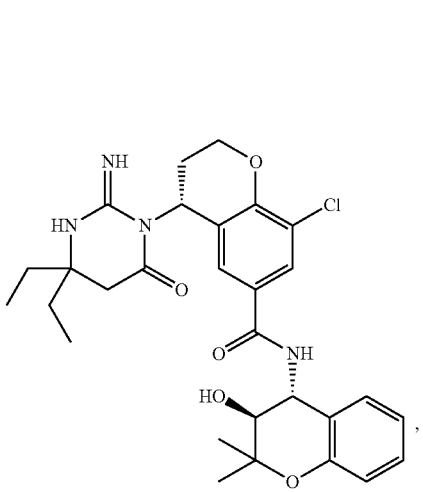
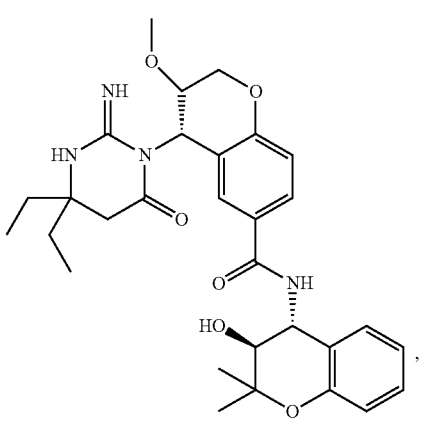

347
-continued
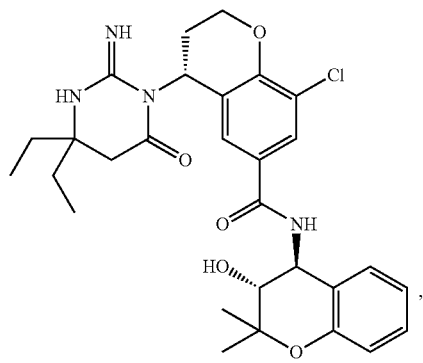
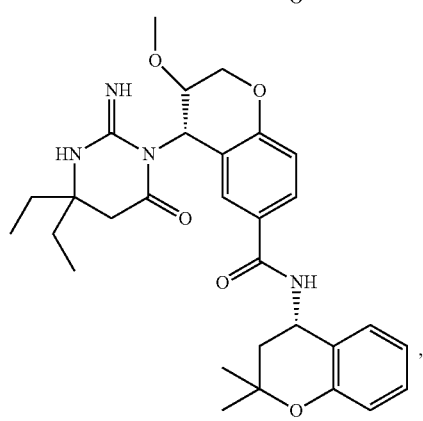
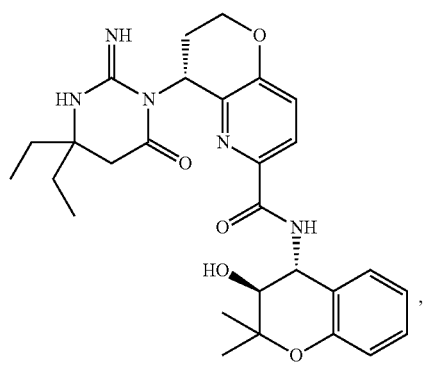
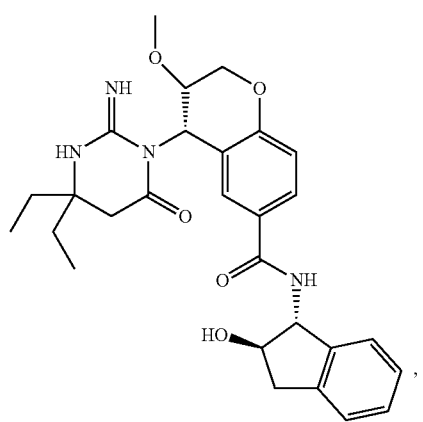
348
-continued
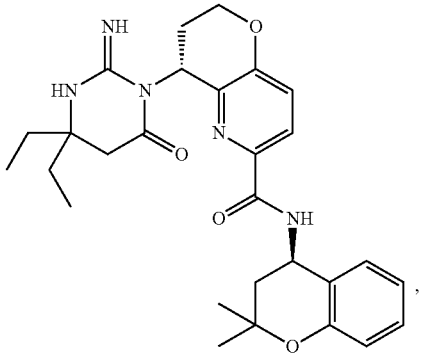
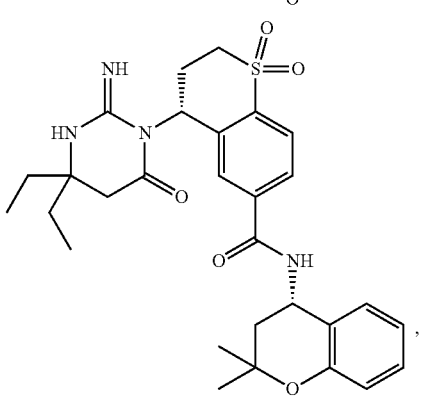
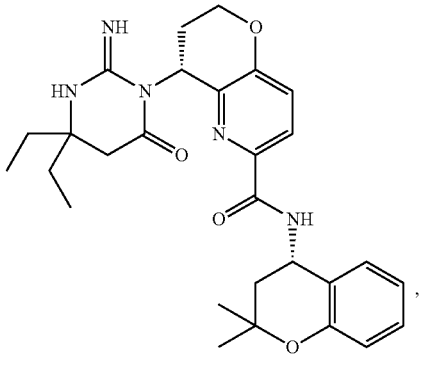
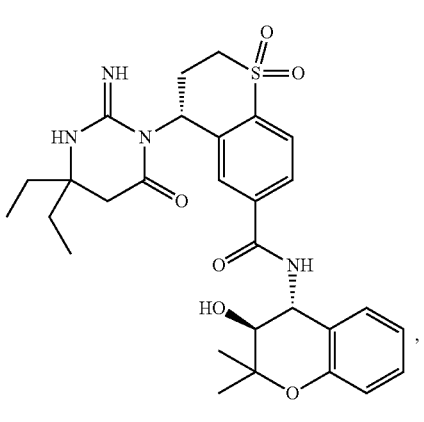

349
-continued
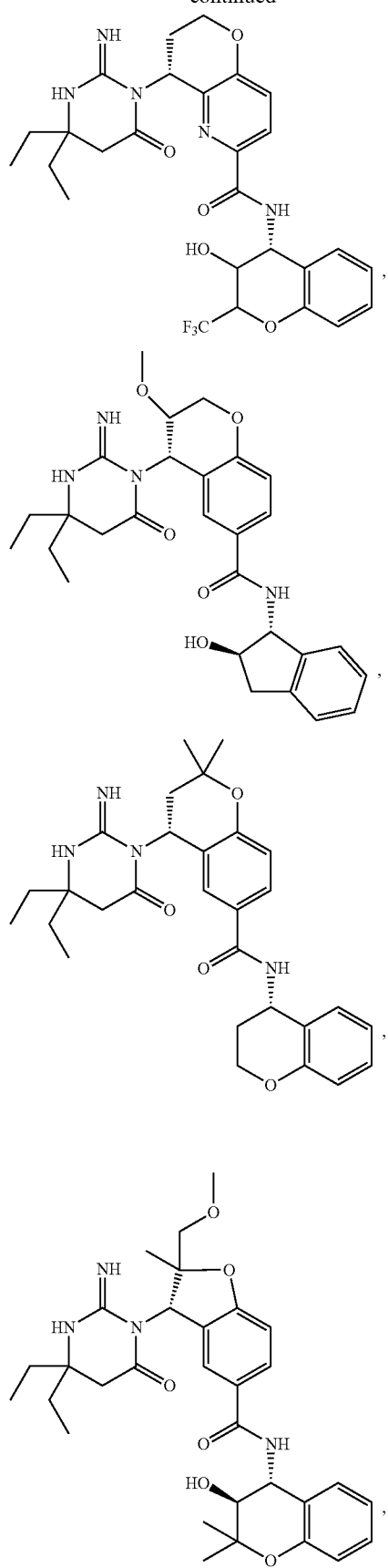
350
-continued
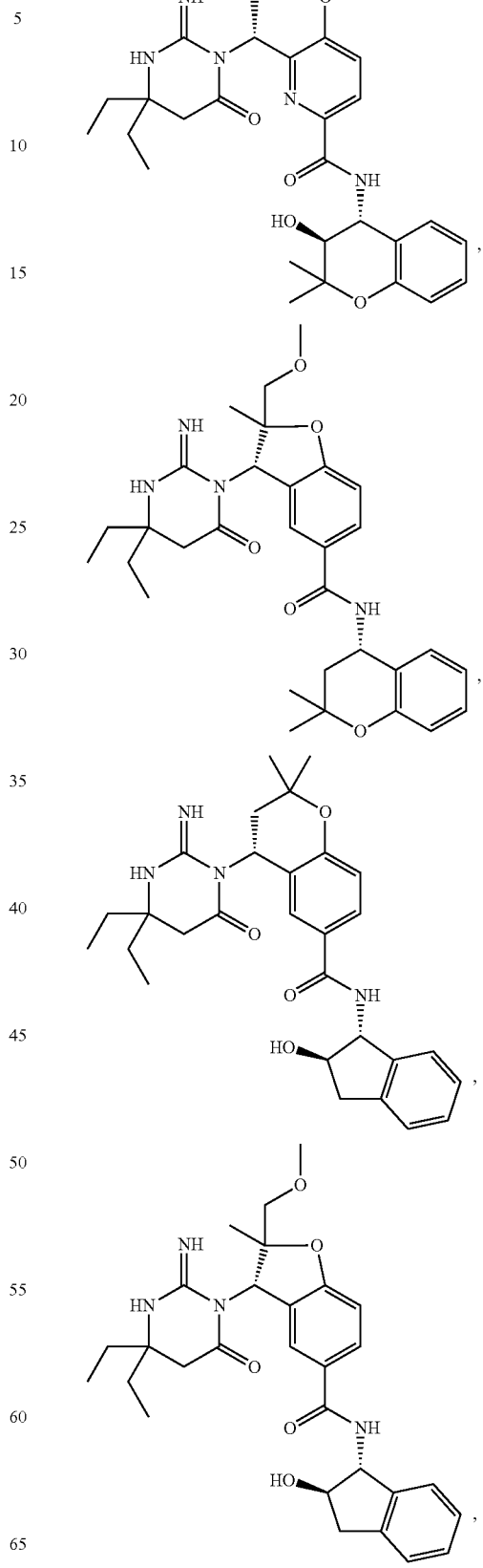

-continued
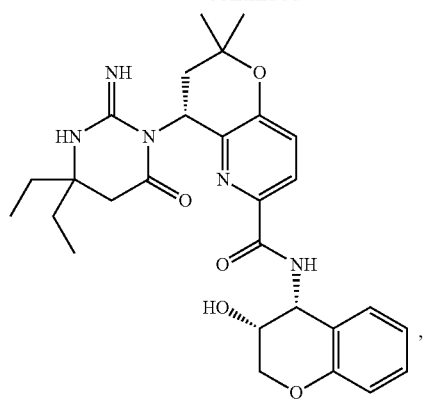
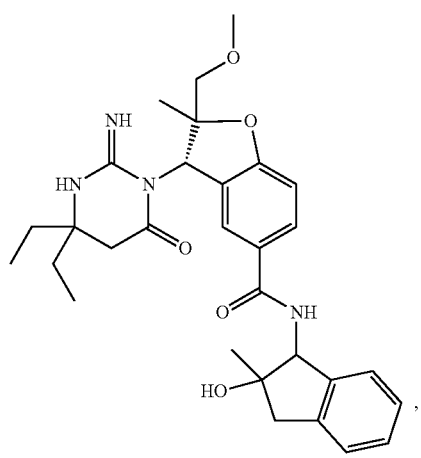
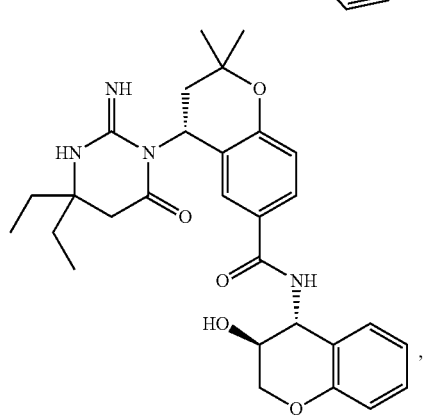
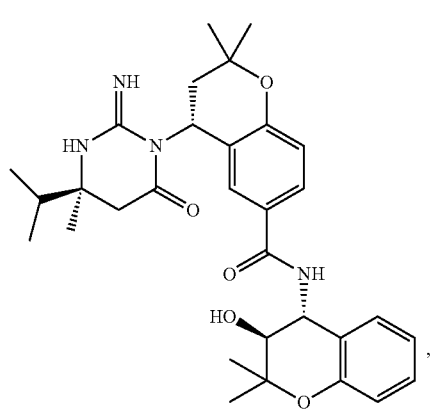
-continued
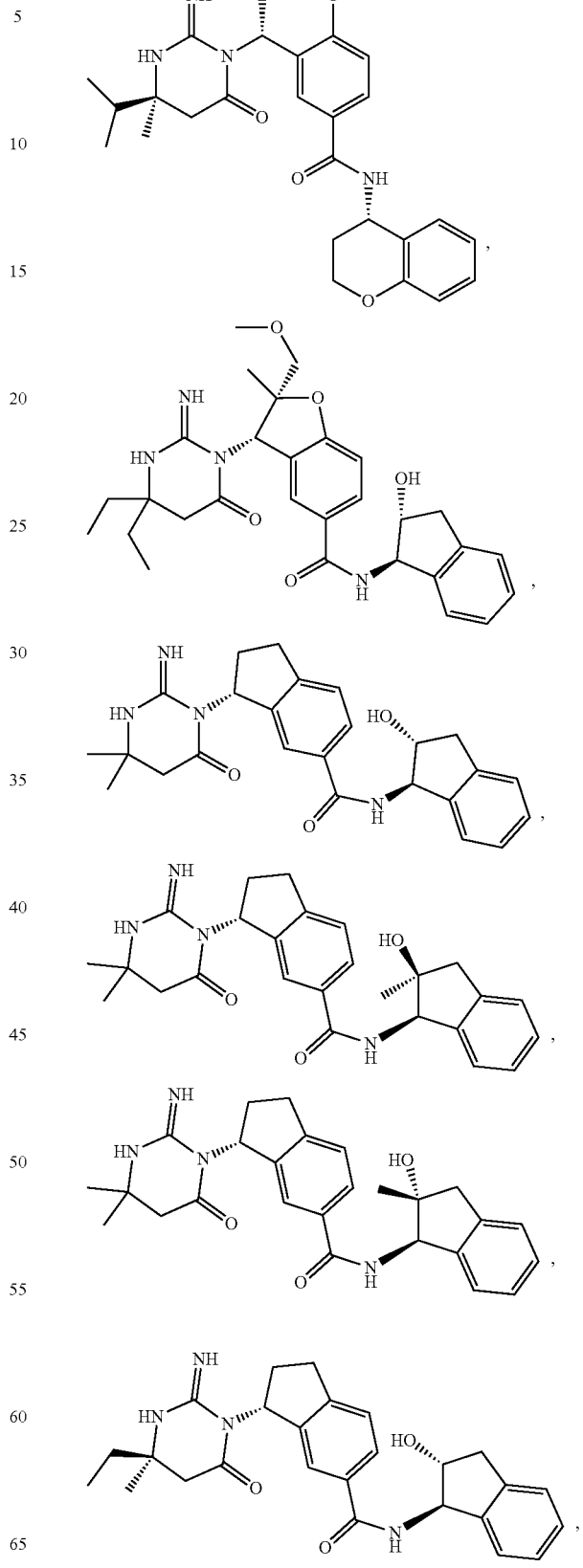

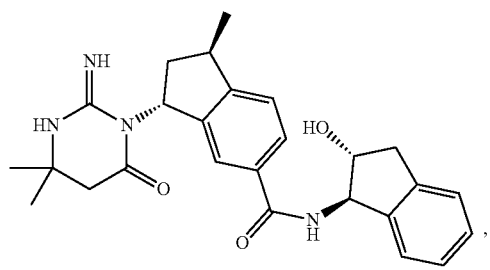,
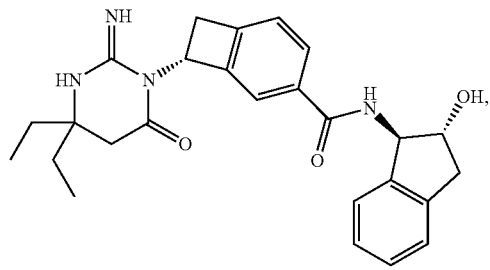,
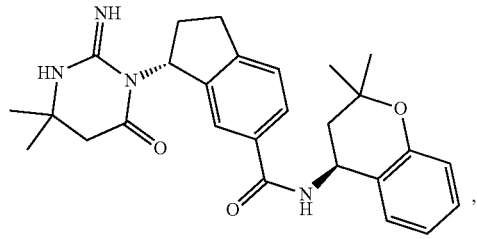,
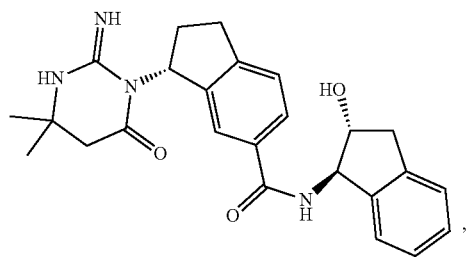,
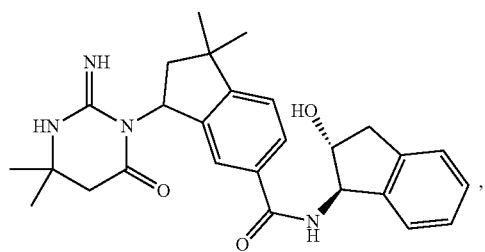,
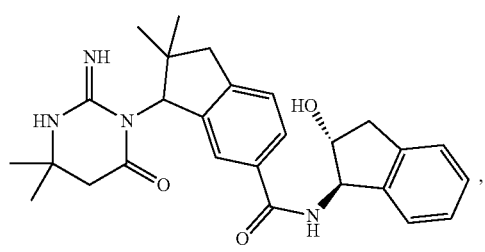,
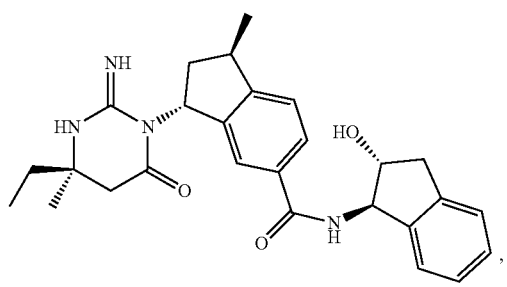,
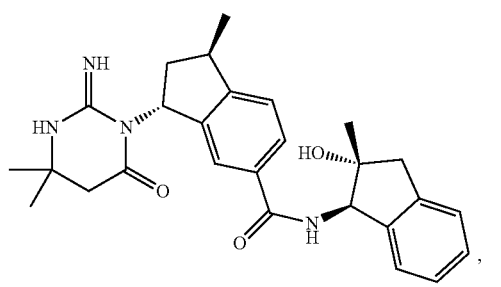,
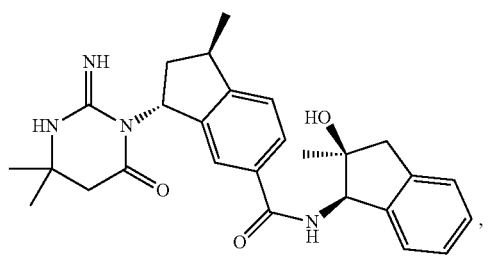,
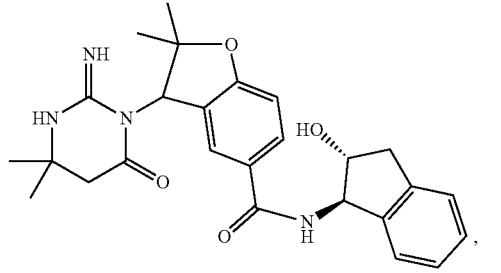,
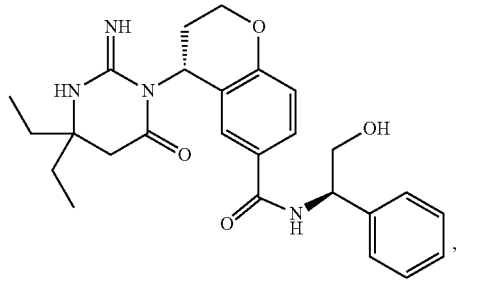,
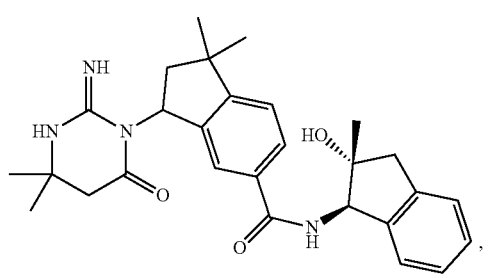, -continued
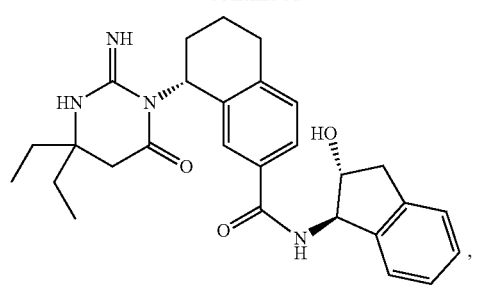
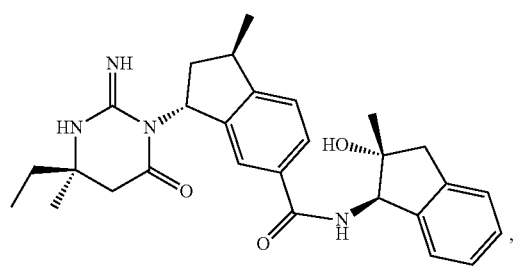
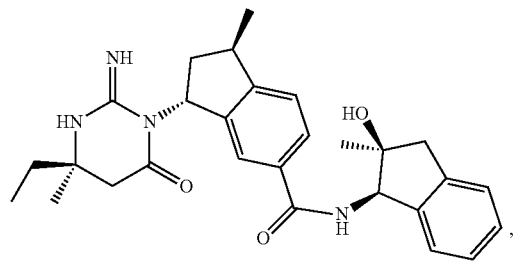
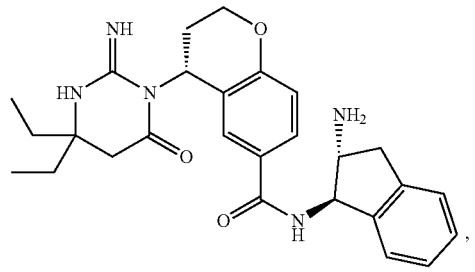
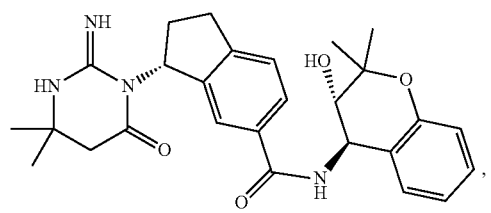
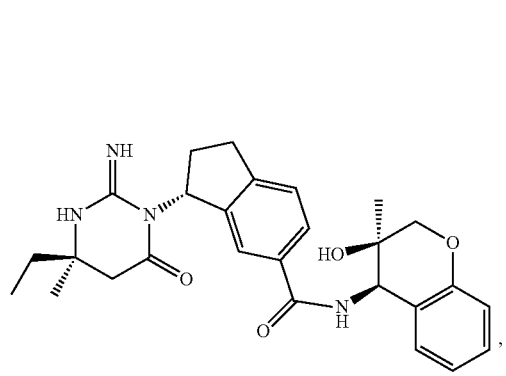
-continued
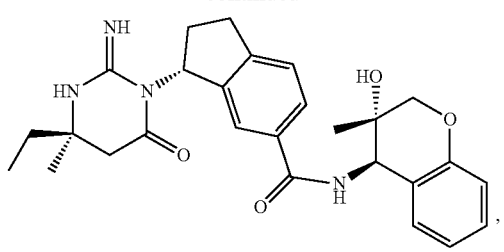
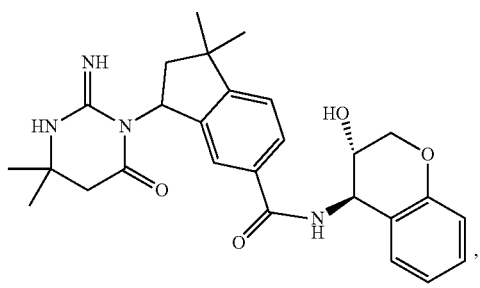
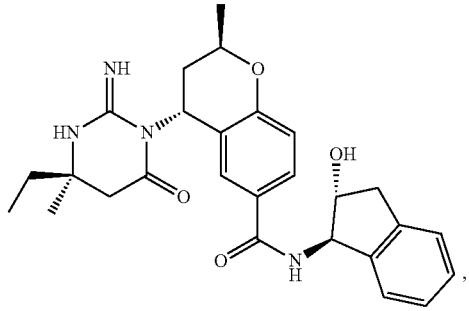
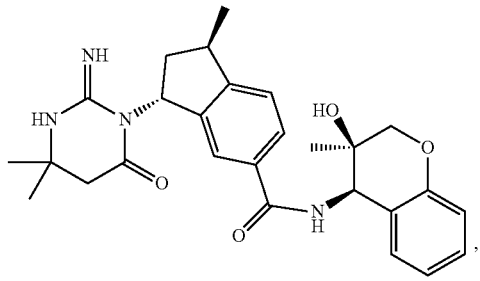
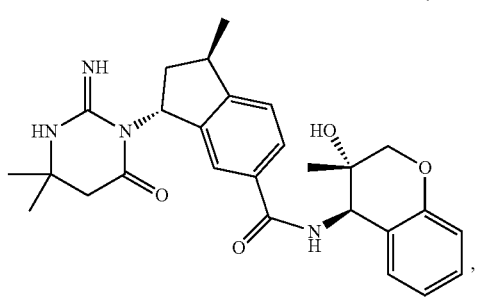
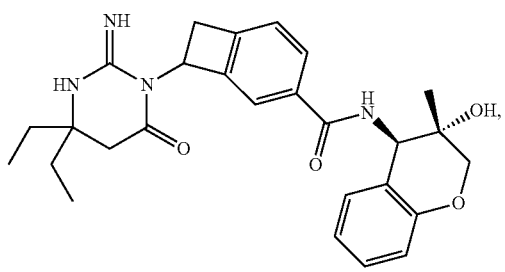

357
-continued
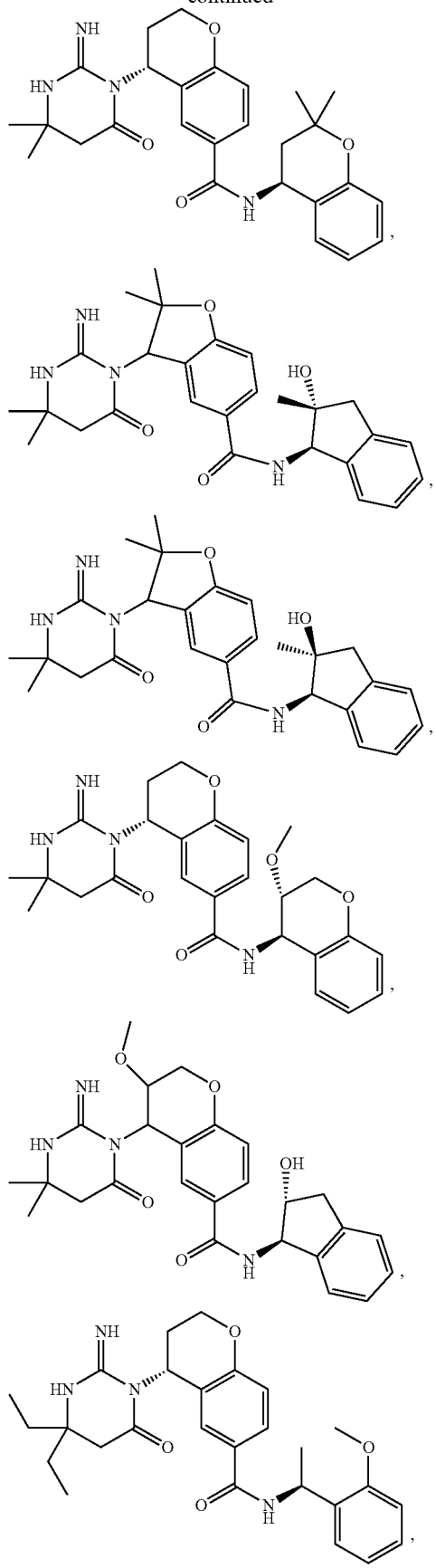
358
-continued
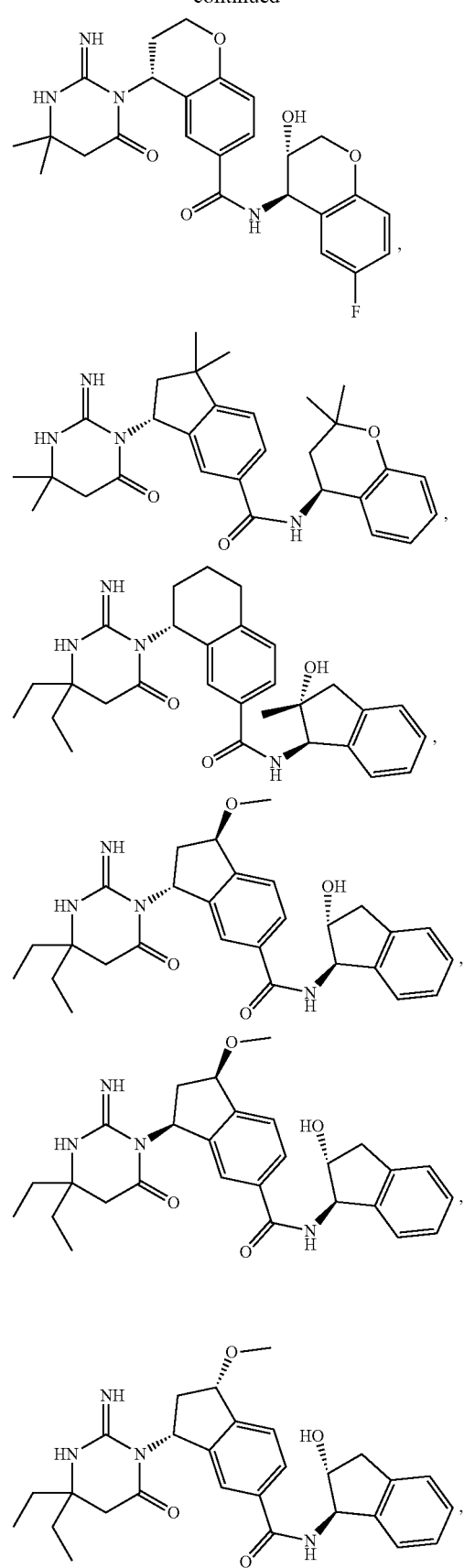

359
-continued
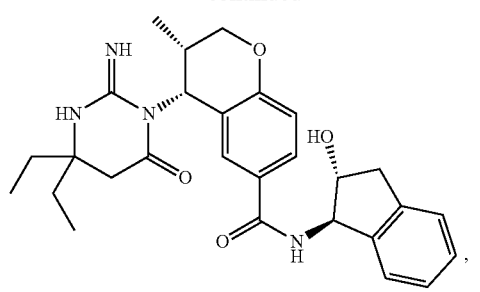
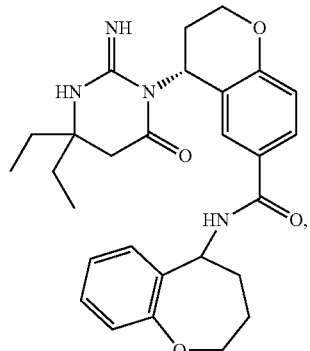
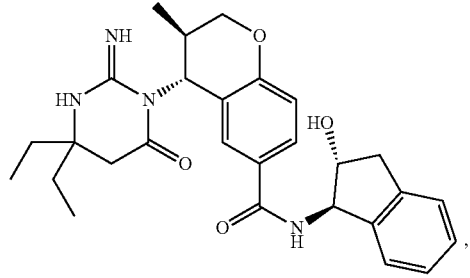
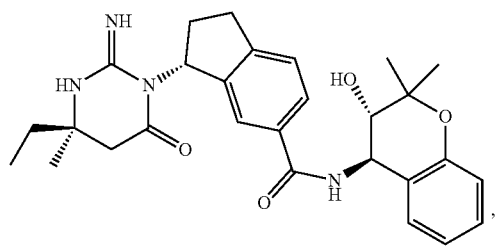
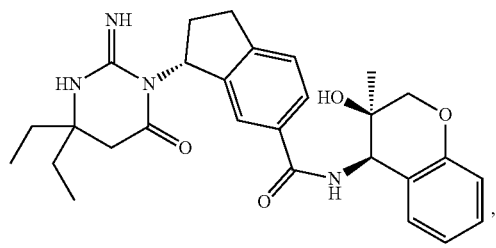
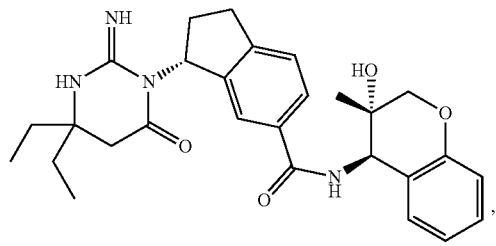
360
-continued
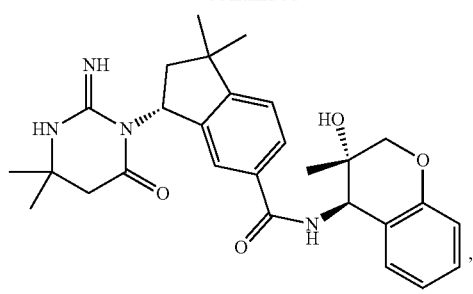
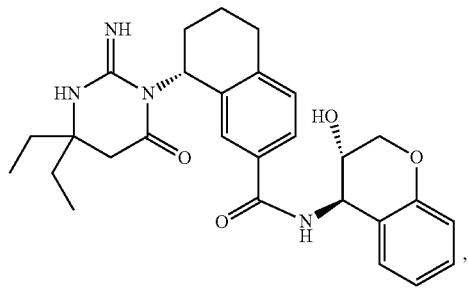
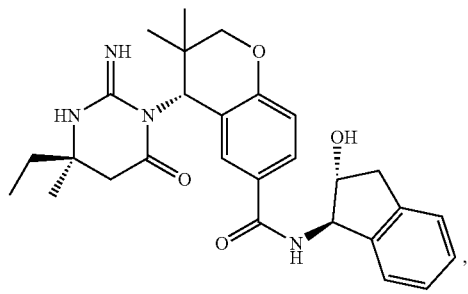
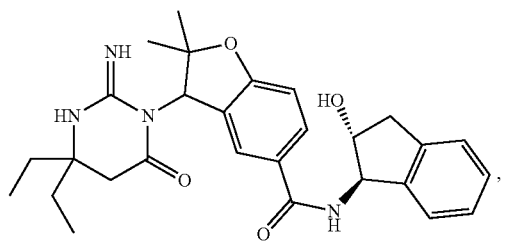
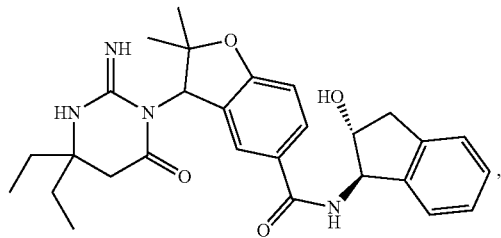
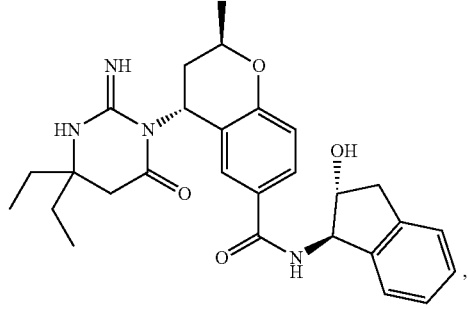

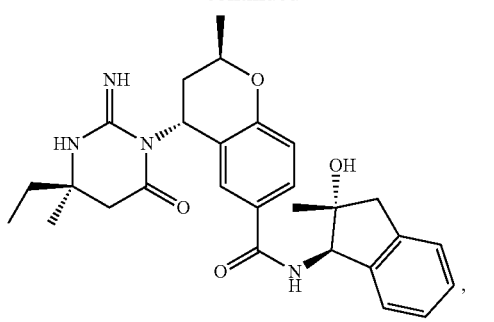
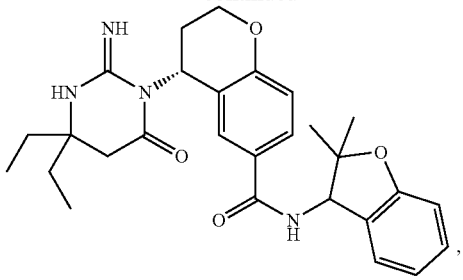
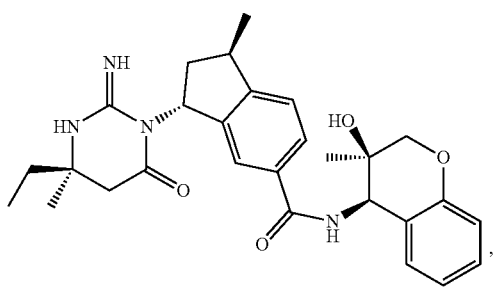
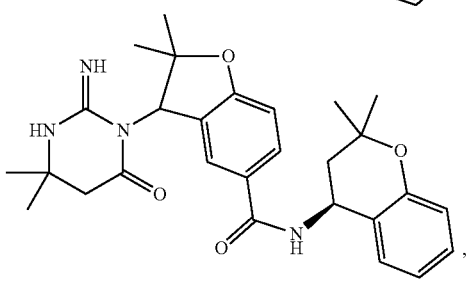
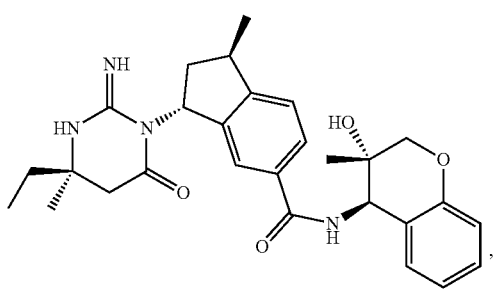
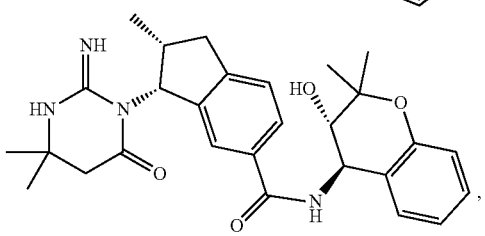
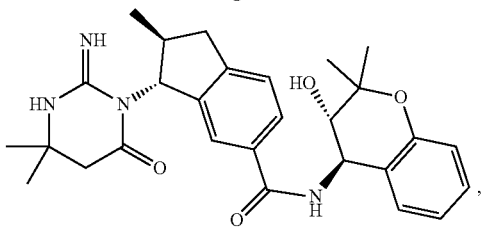
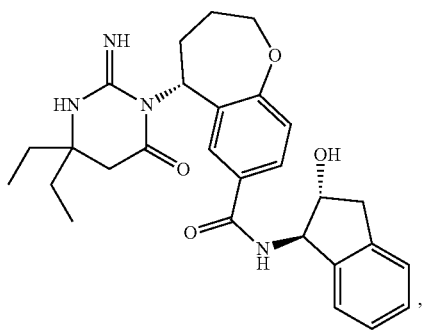
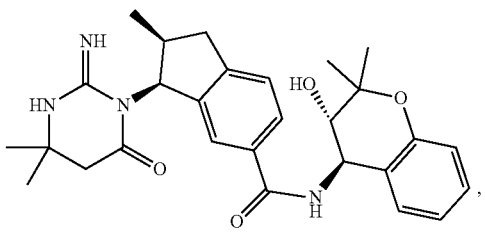
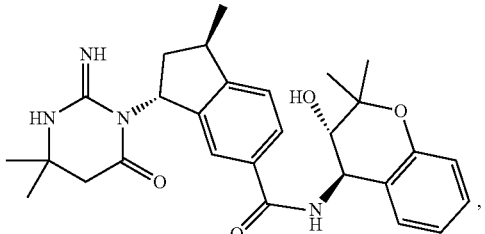
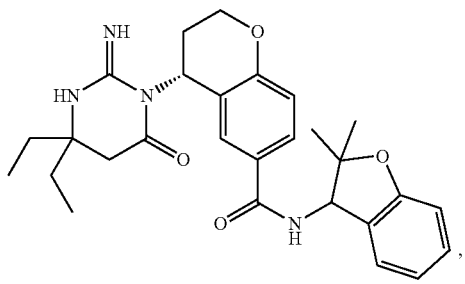
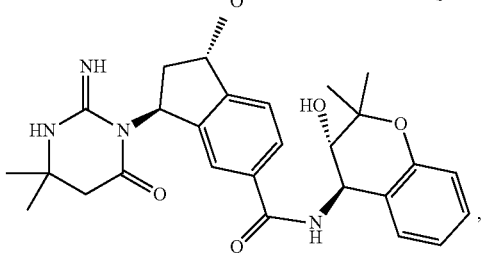

363
-continued
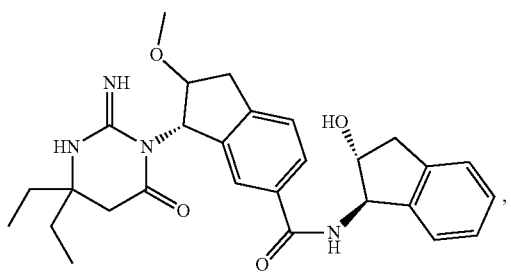
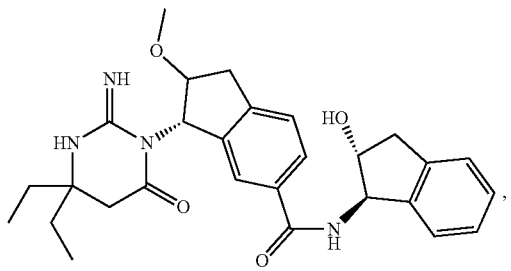
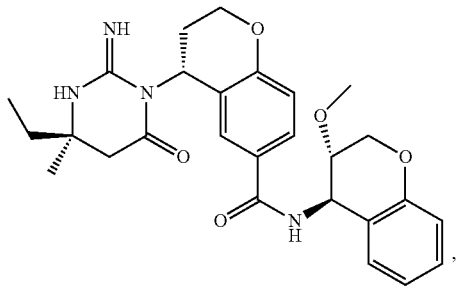
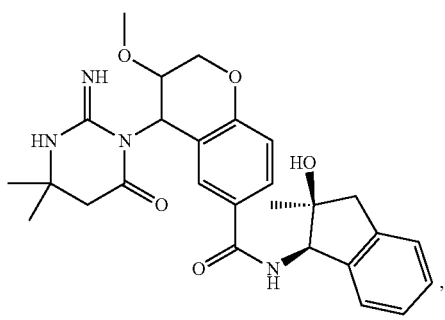
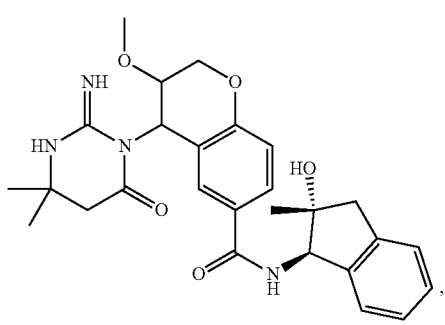
364
-continued
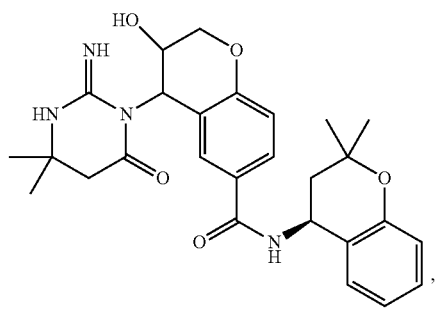
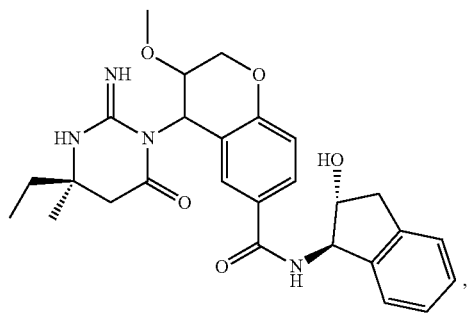
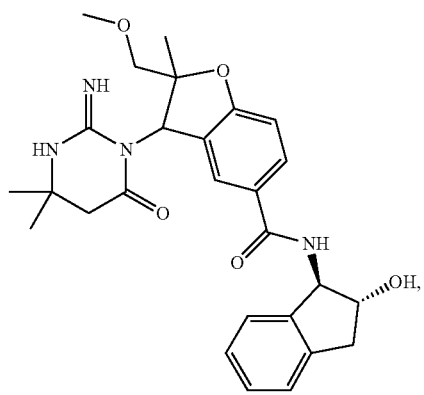
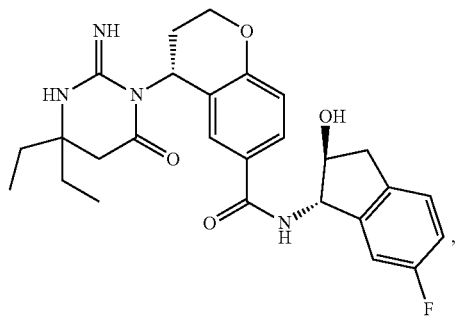
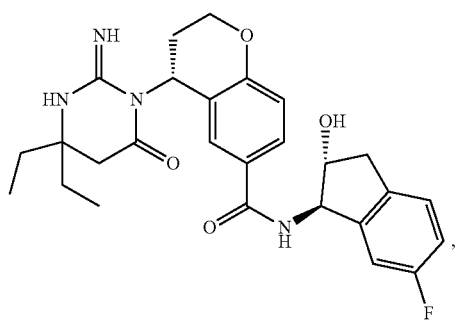

-continued
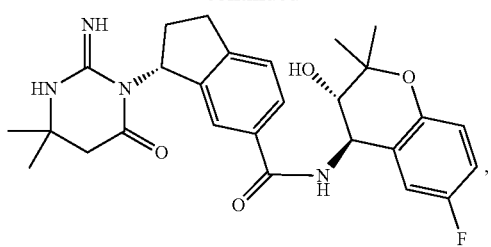
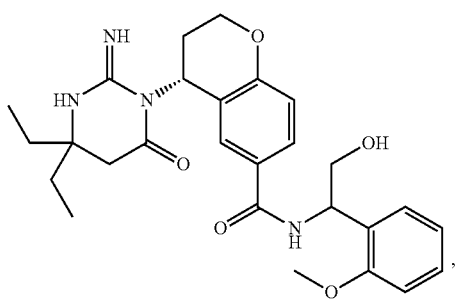
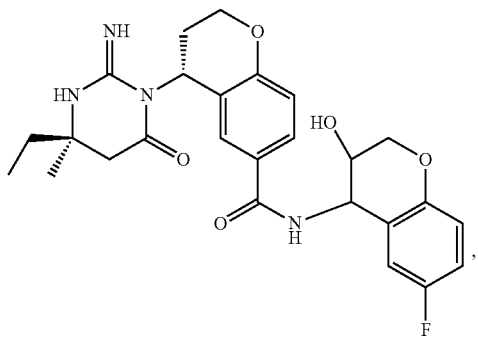
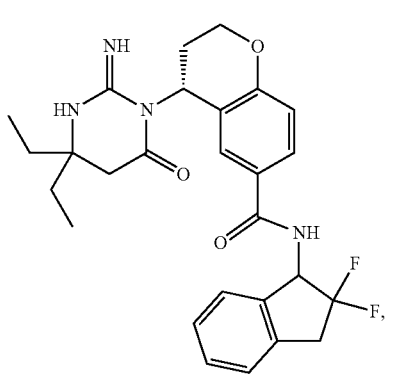
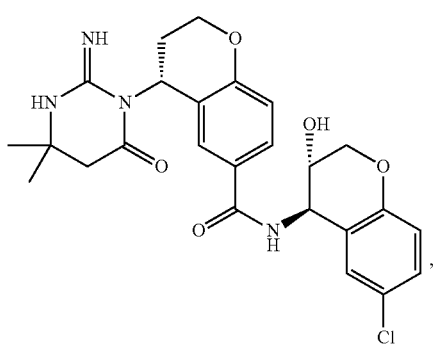
-continued
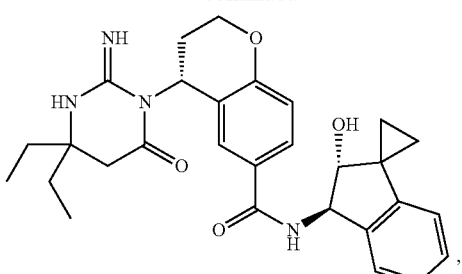
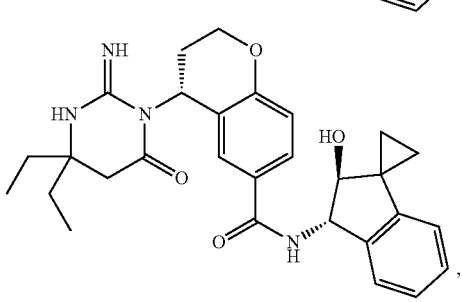
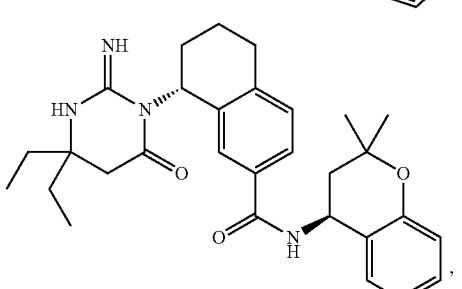
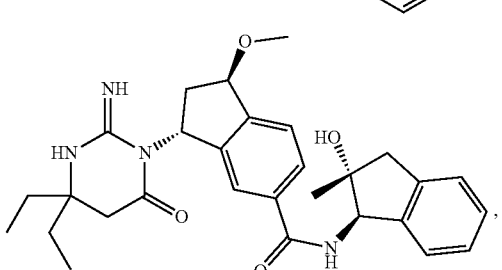
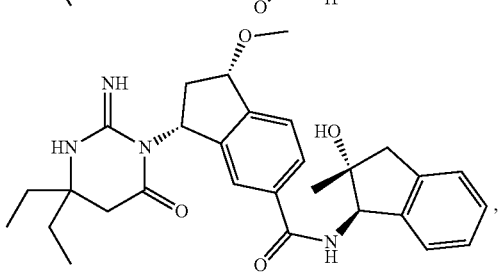
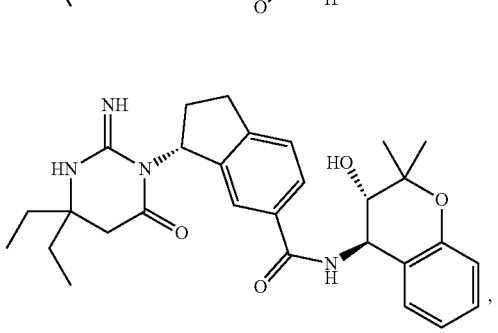

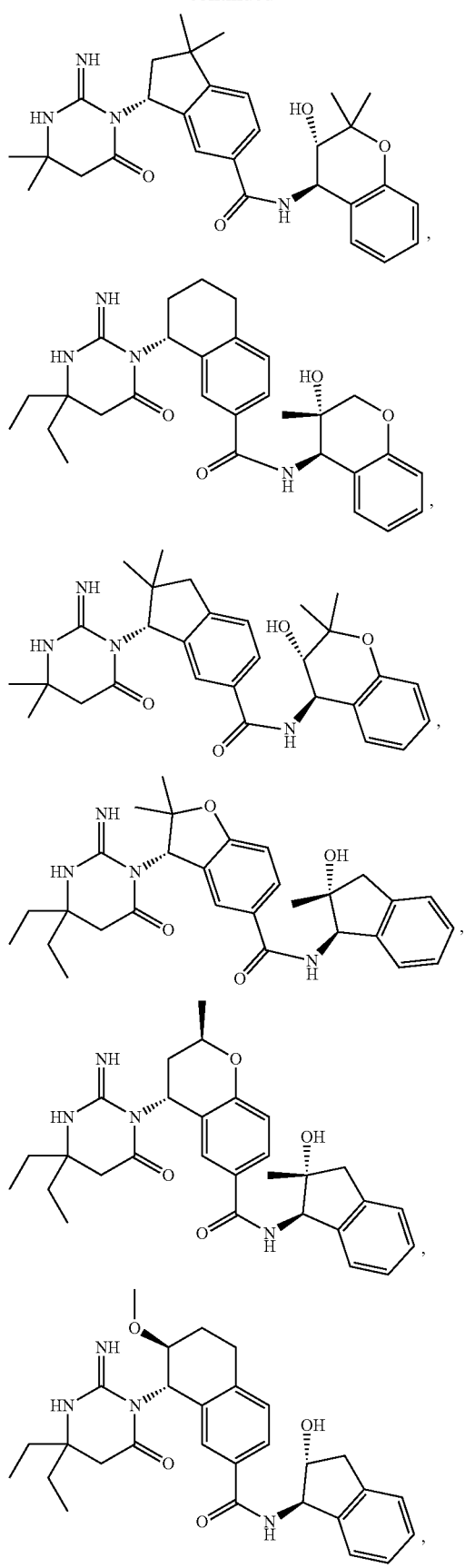
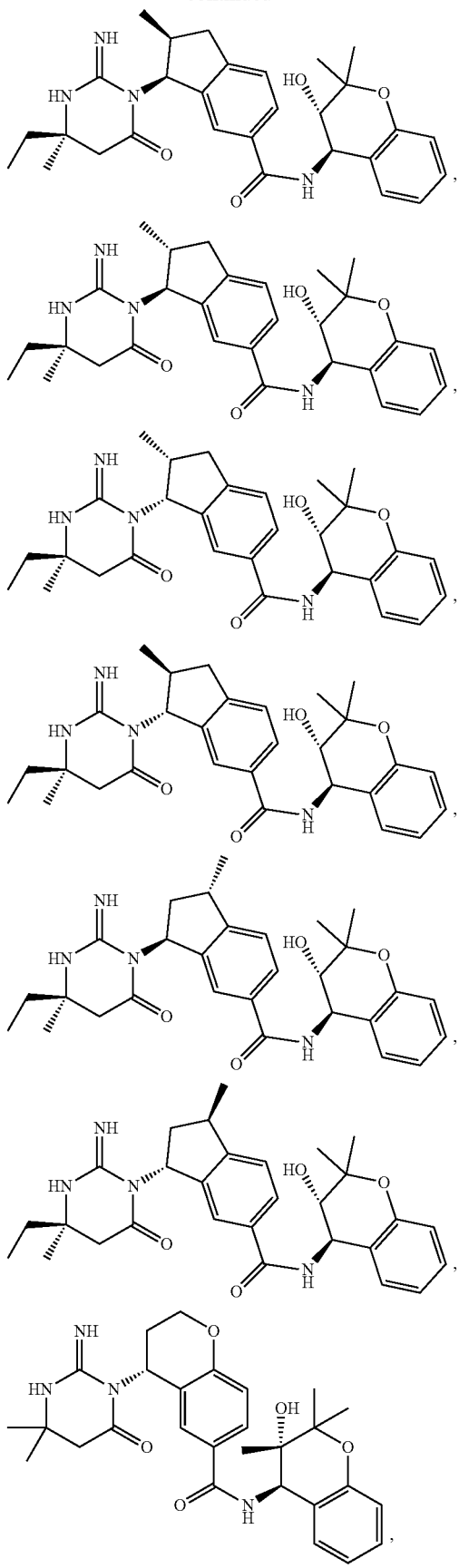

369
-continued
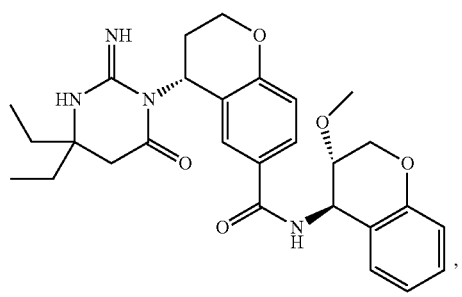,
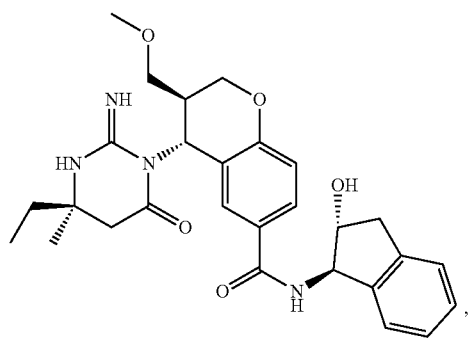,
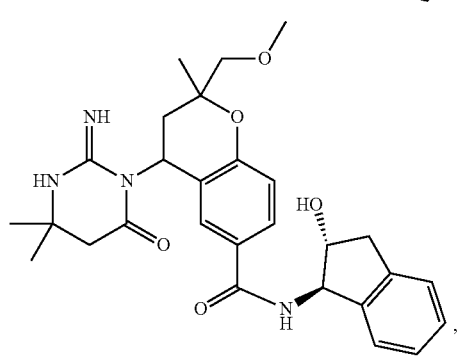,
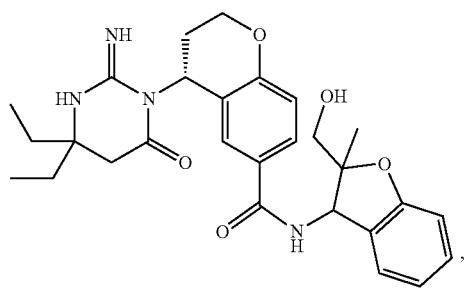,
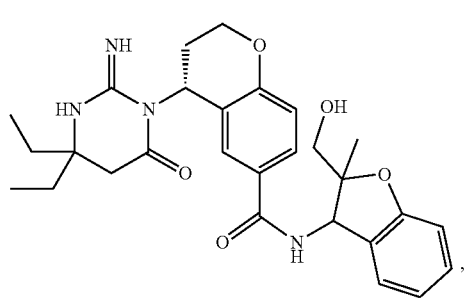,
370
-continued
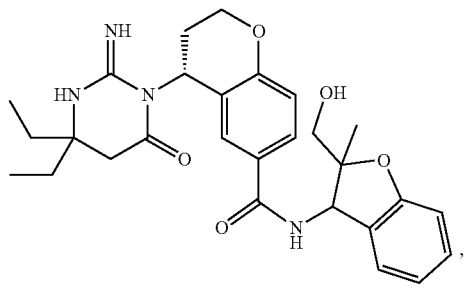,
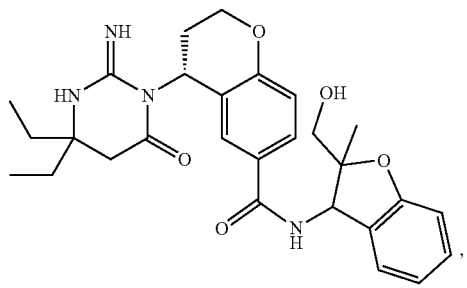,
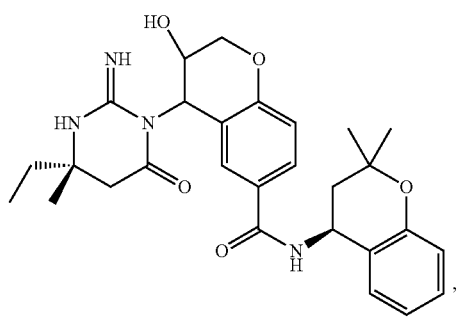,
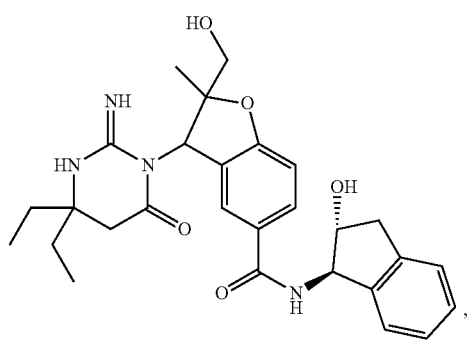,
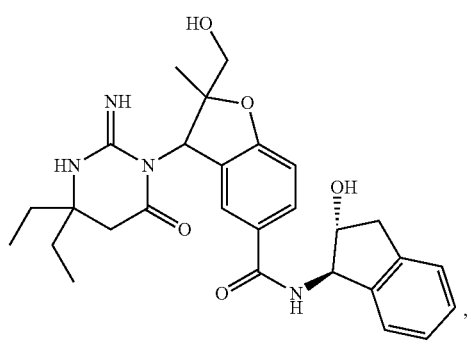, 371
-continued
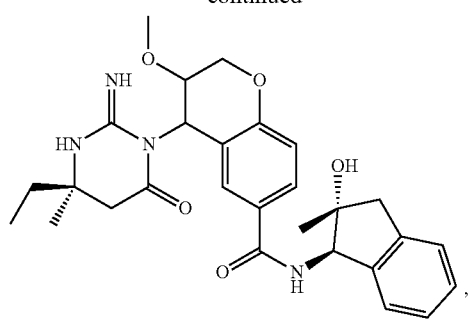
,
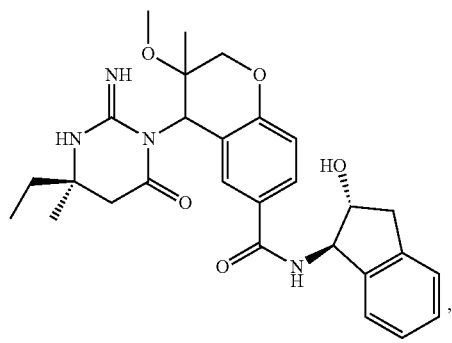
,
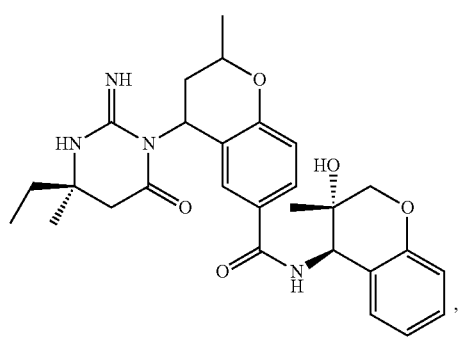
,
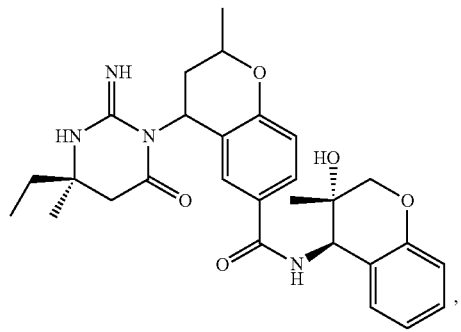
,
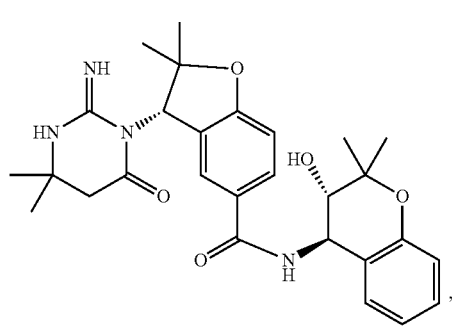
,
372
-continued
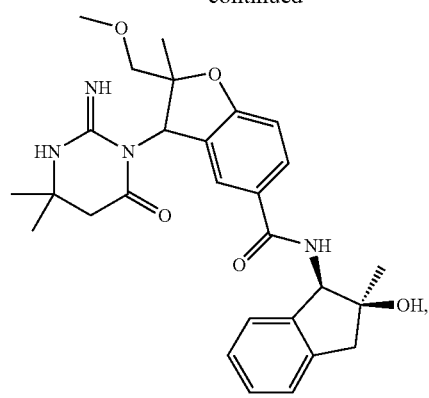
,
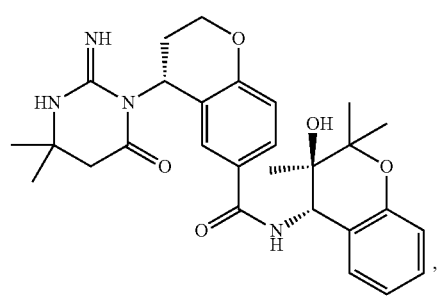
,
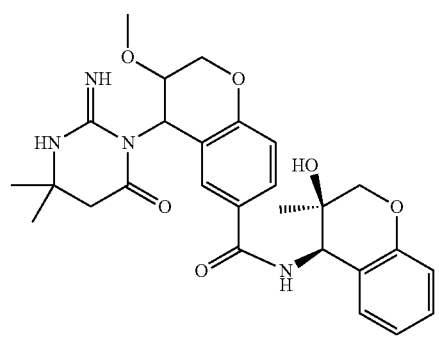
,
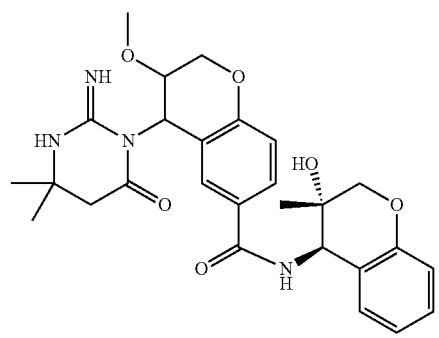
,
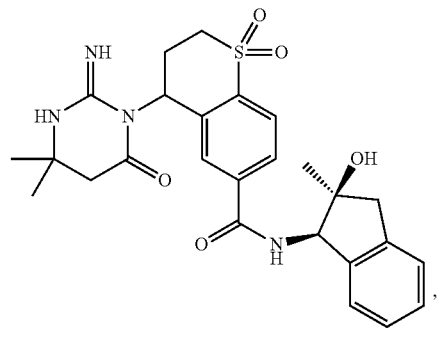
, 373
-continued
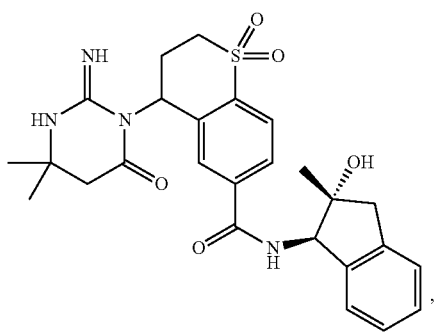
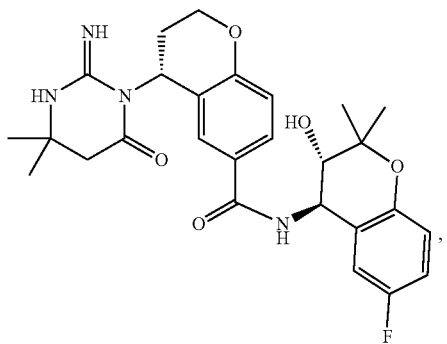
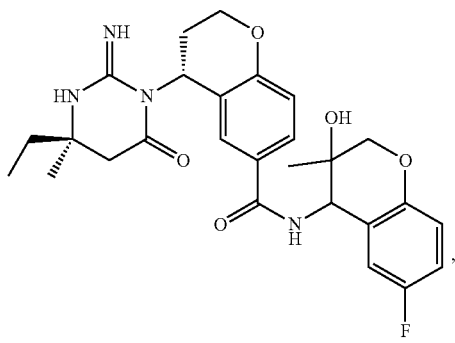
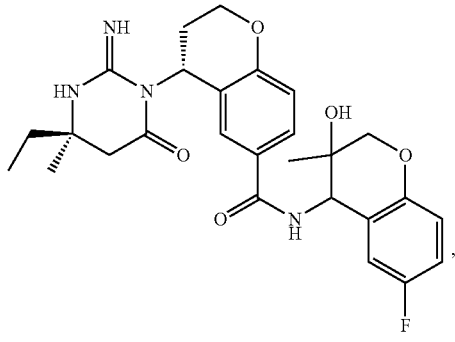
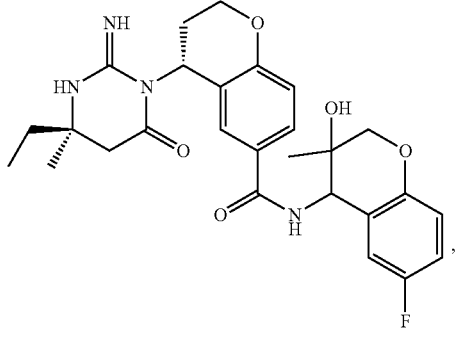
374
-continued
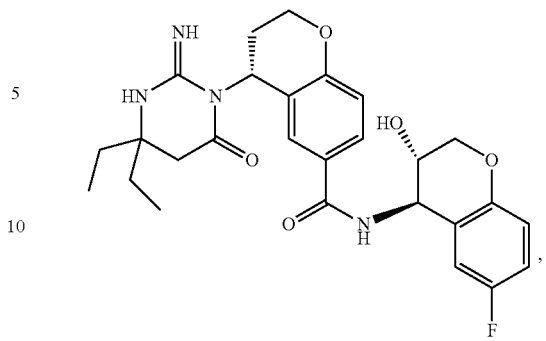
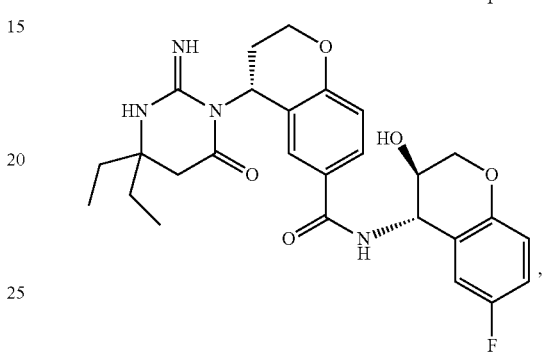
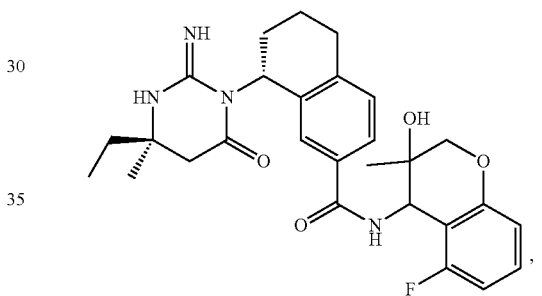
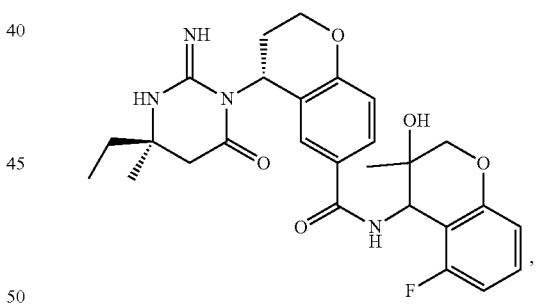
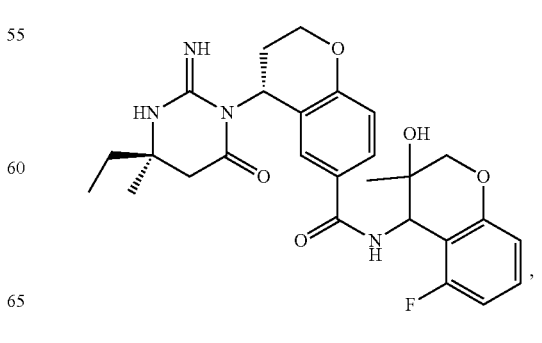

375
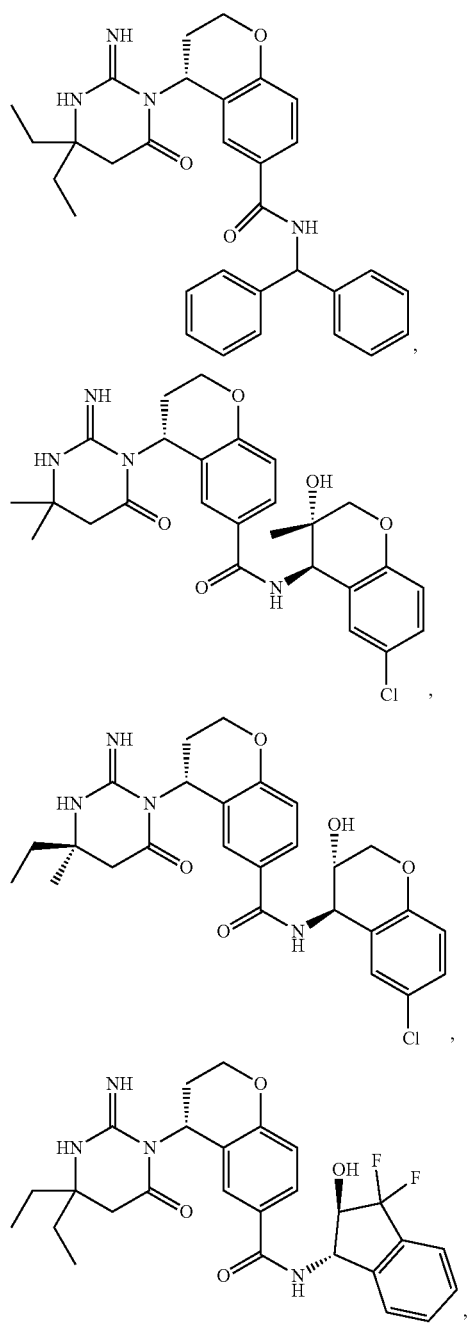
376
-continued
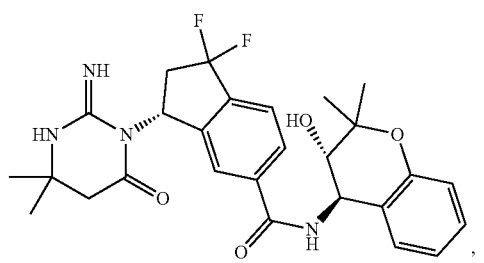
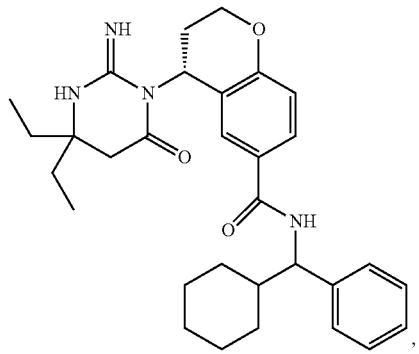
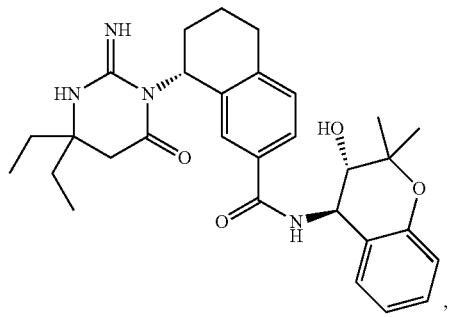
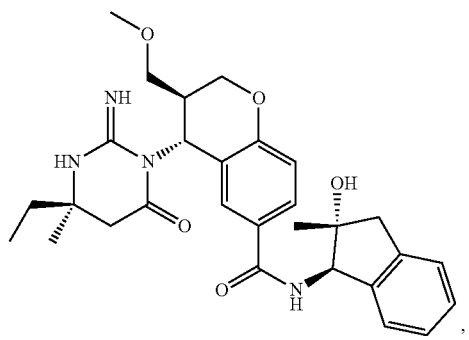
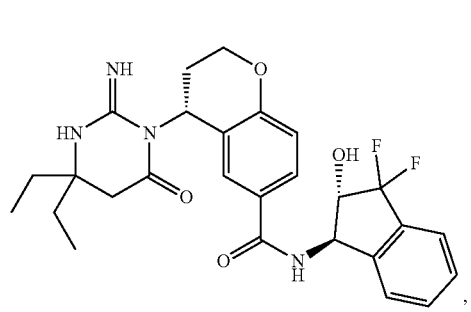
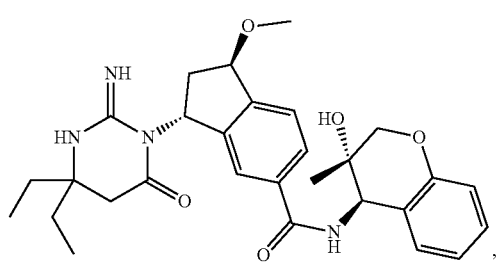

377
-continued
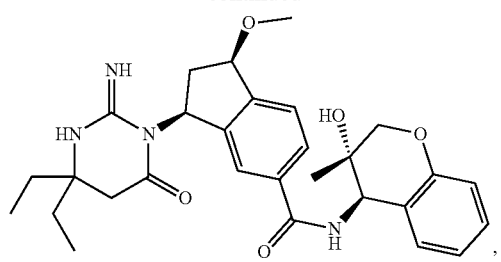
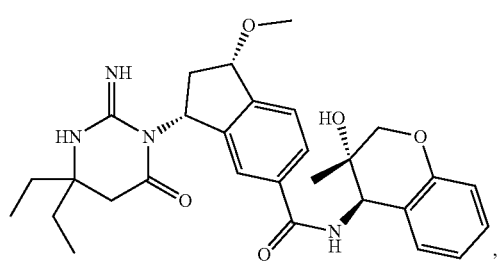
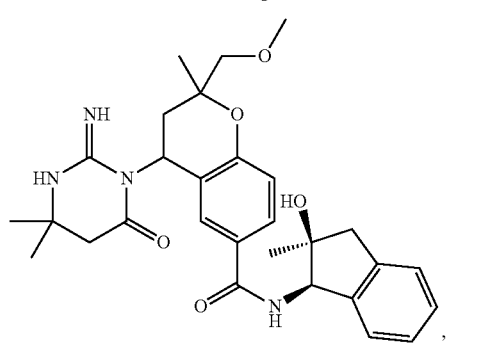
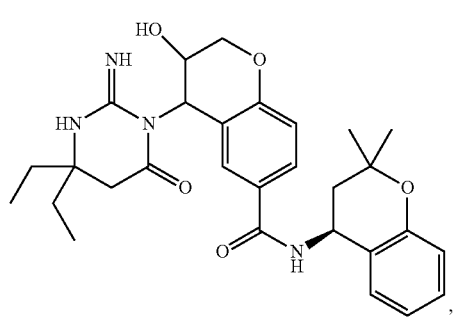
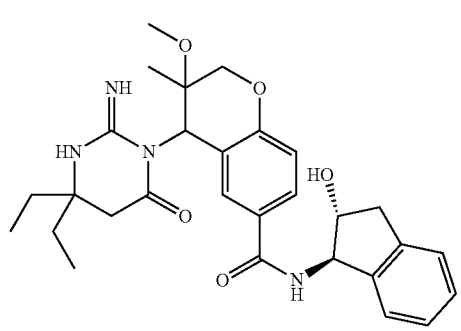
378
-continued
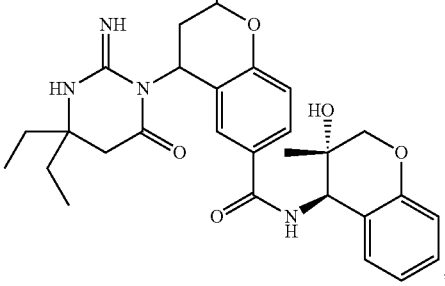
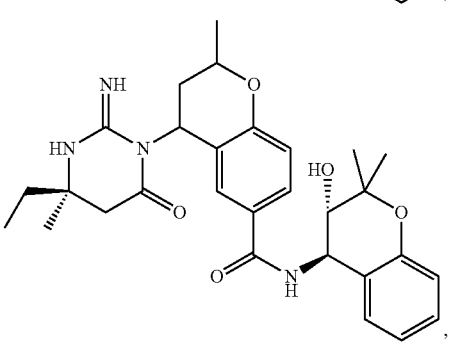
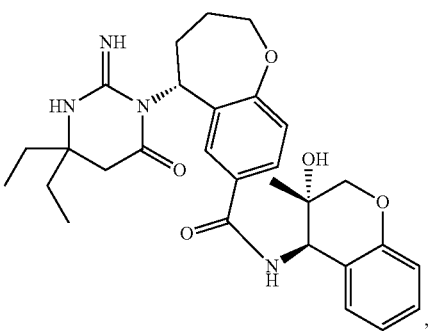
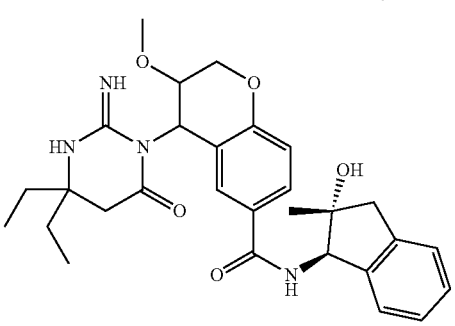
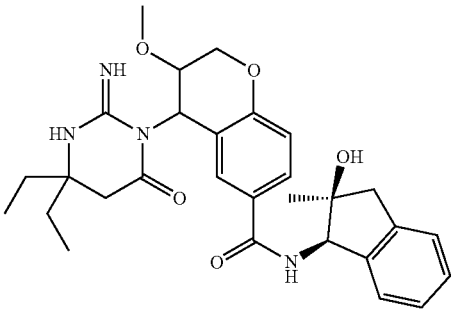

379
-continued
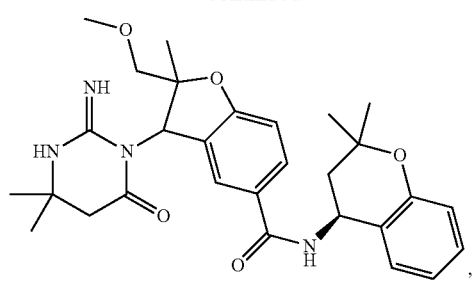
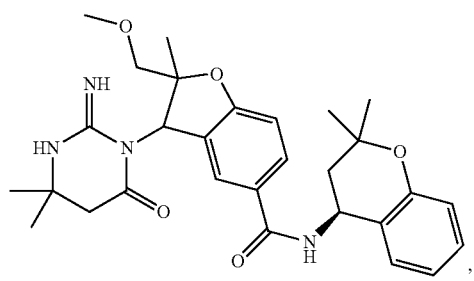
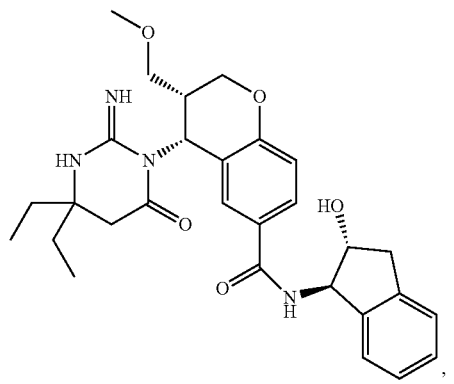
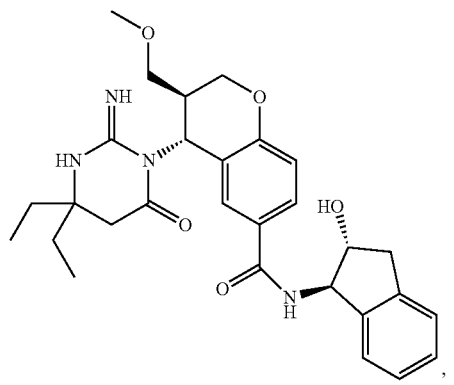
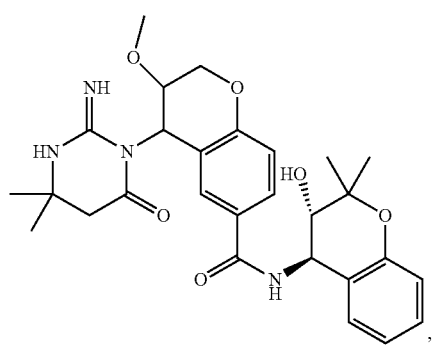
380
-continued
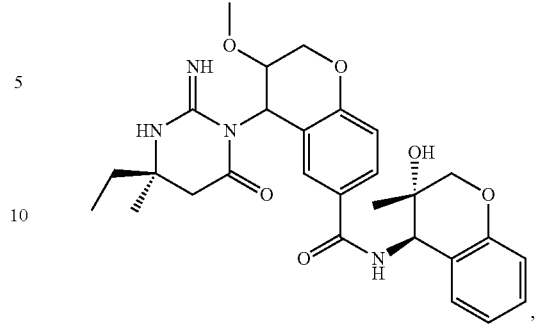
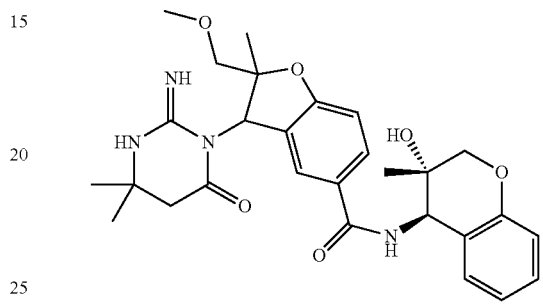
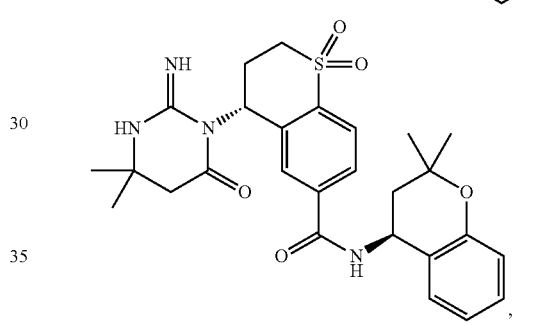
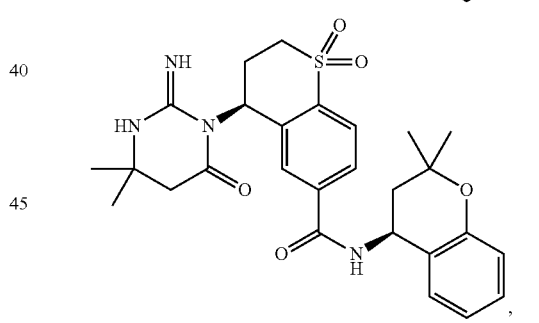
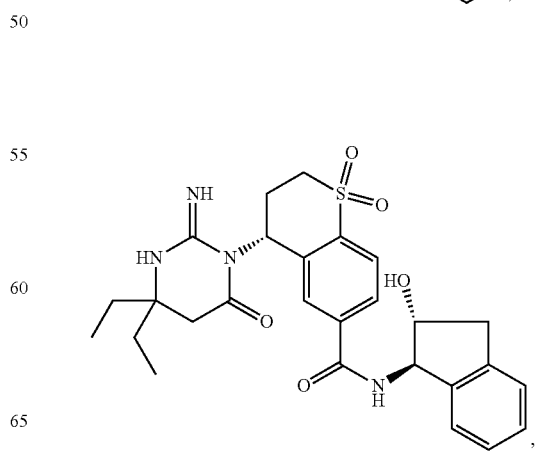

381
-continued
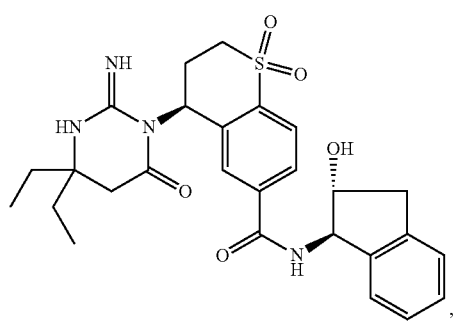
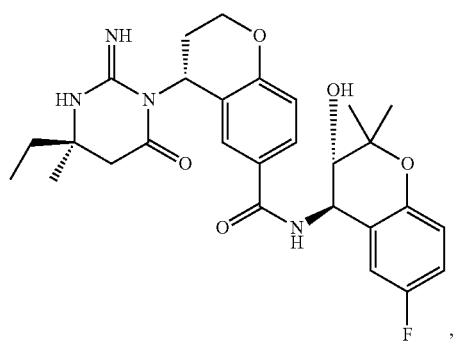
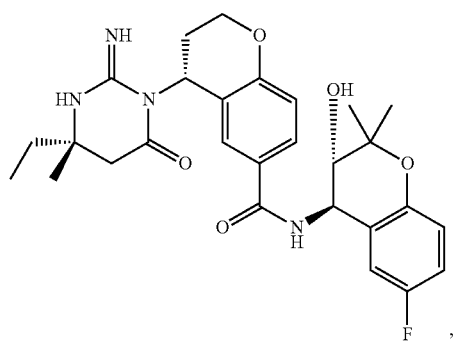
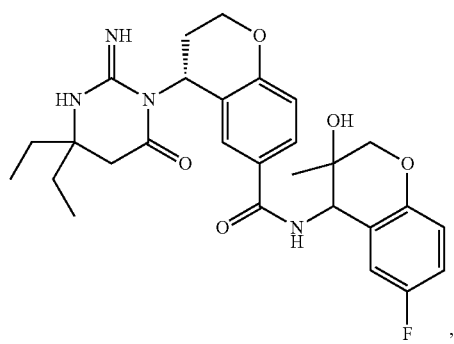
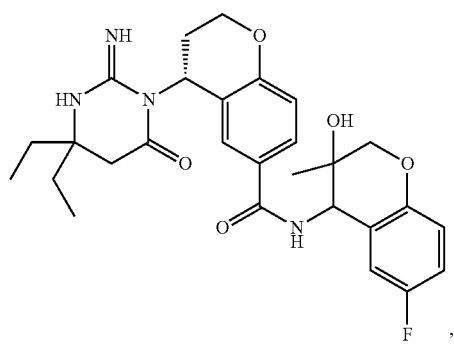
382
-continued
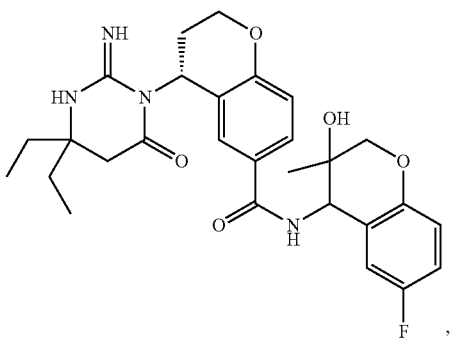
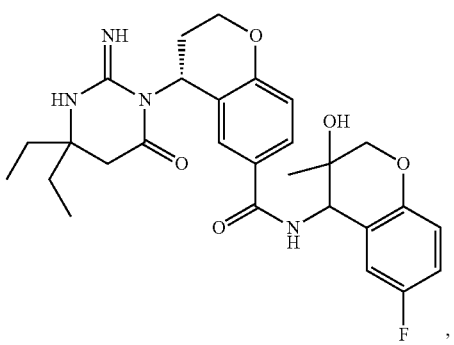
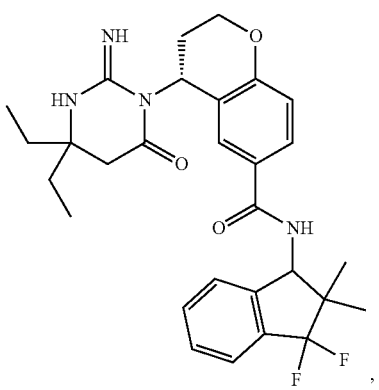
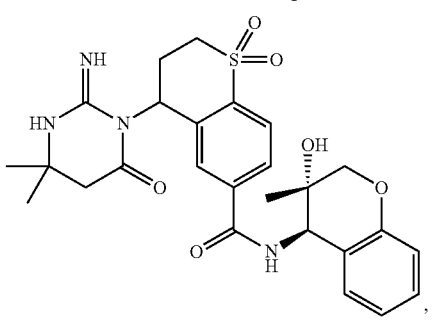
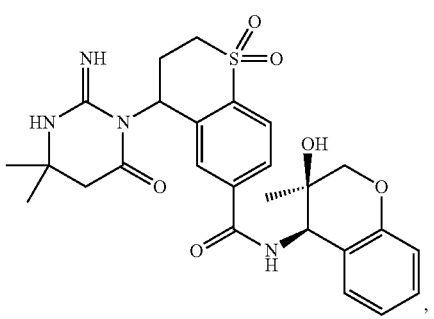

383
-continued
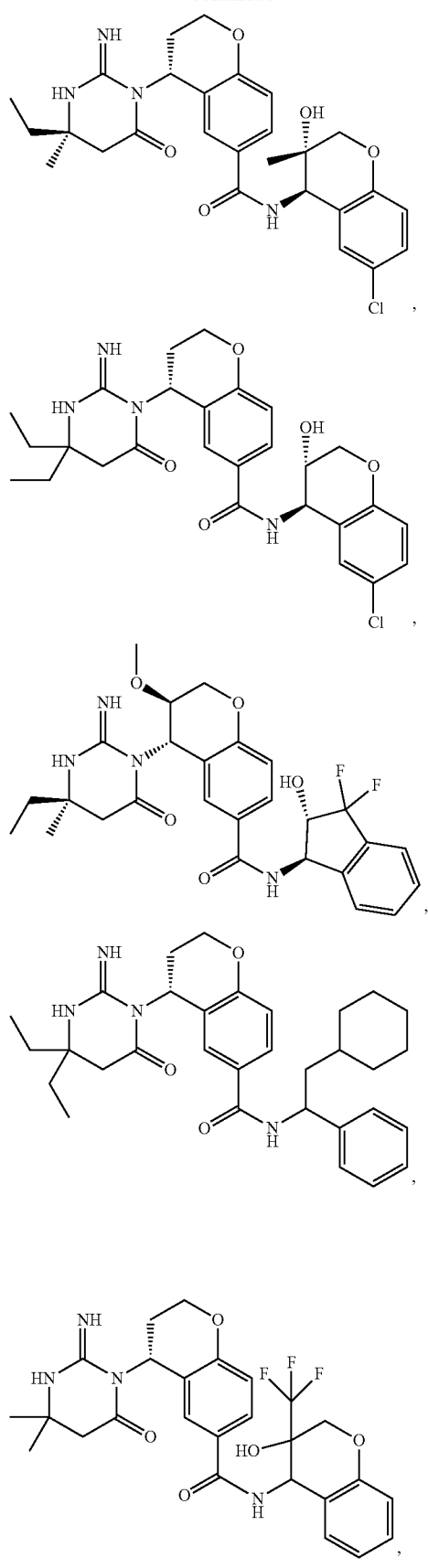
384
-continued
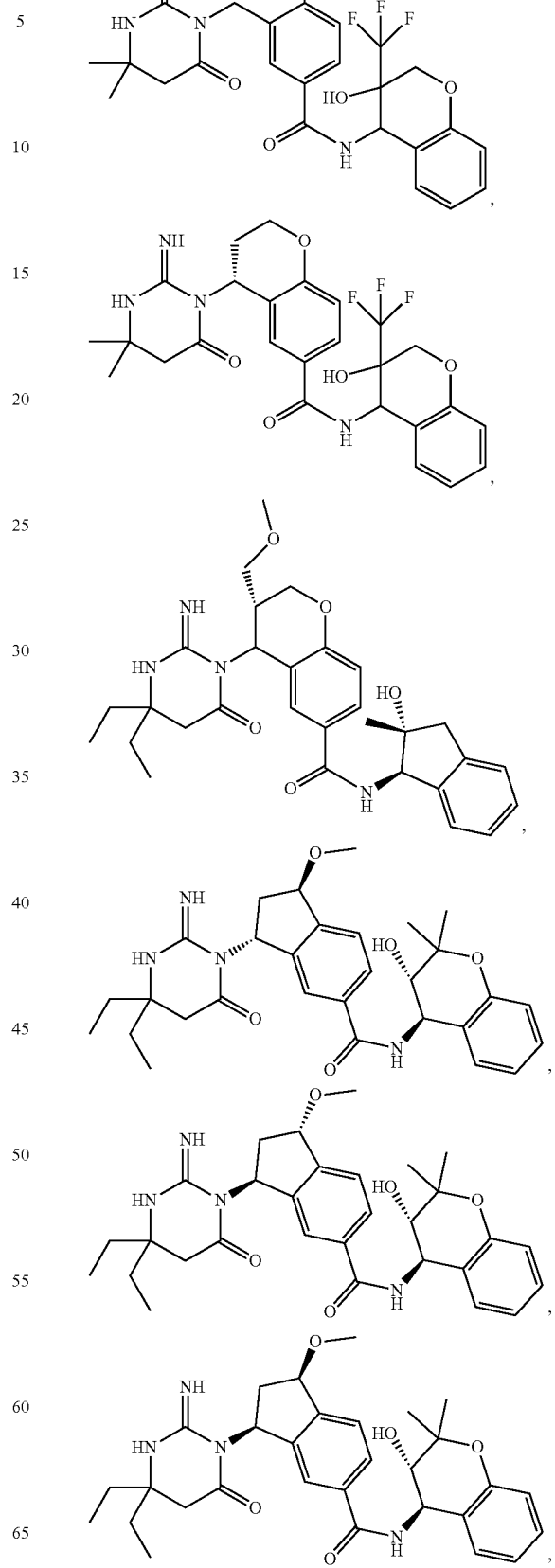

385
-continued
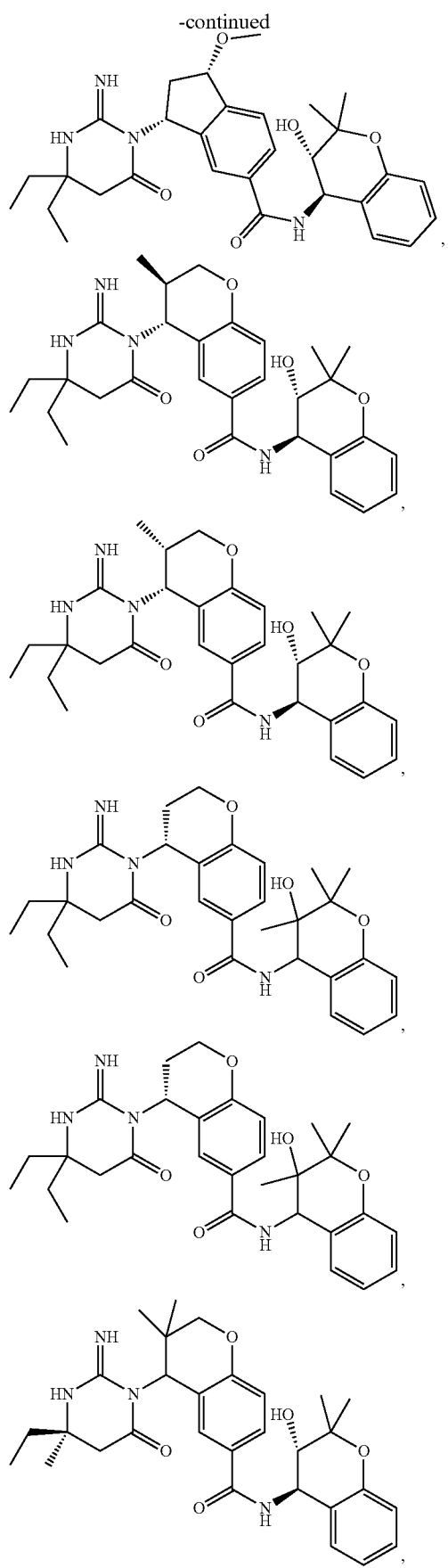
386
-continued
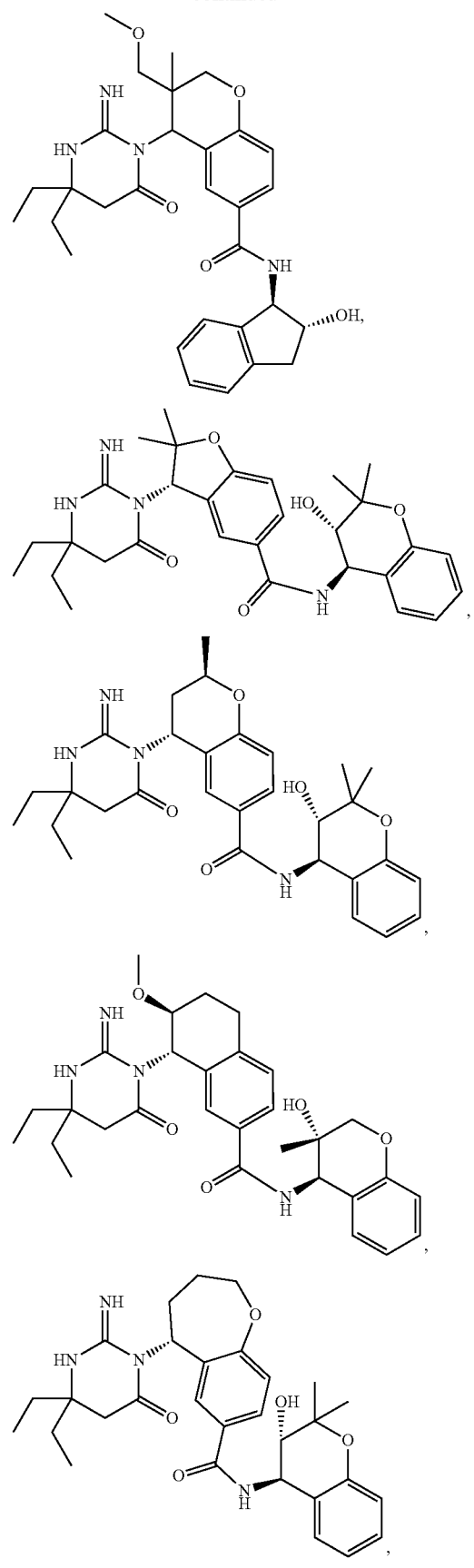

387
-continued
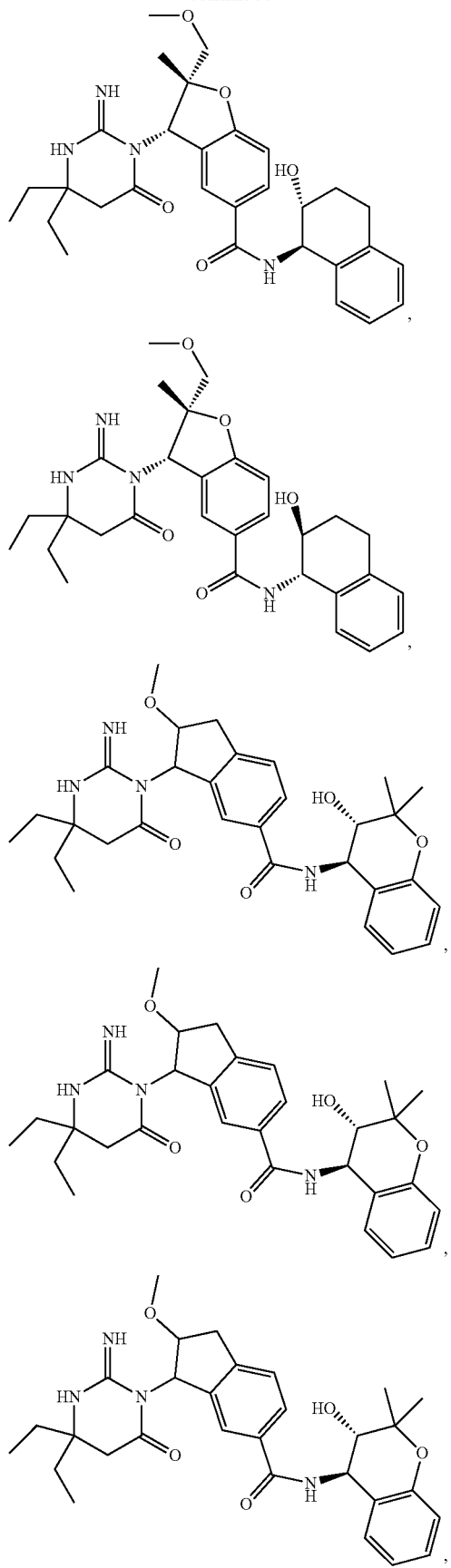
388
-continued
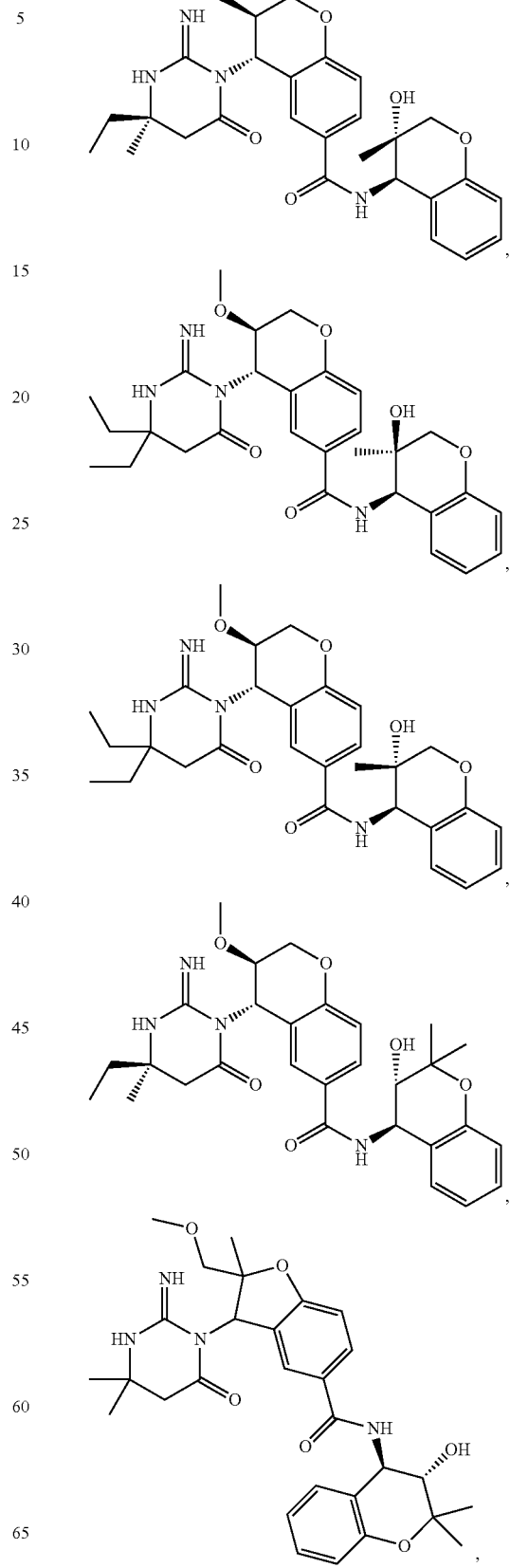

389
-continued
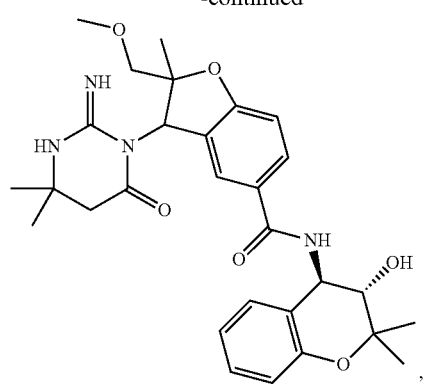
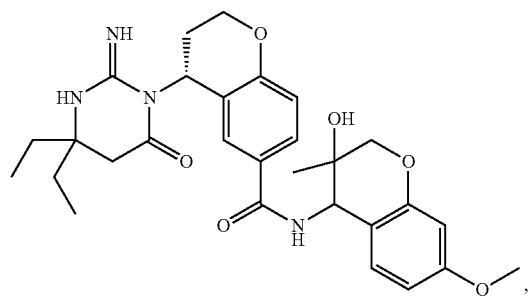
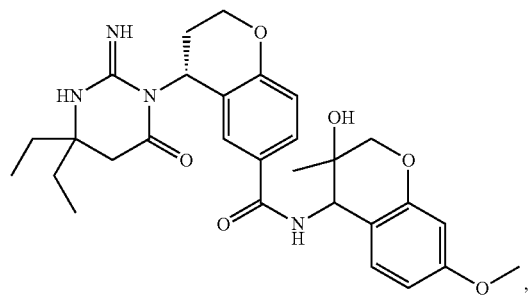
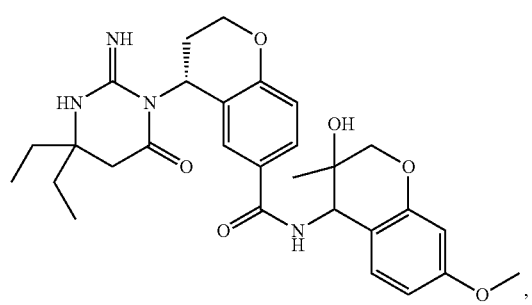
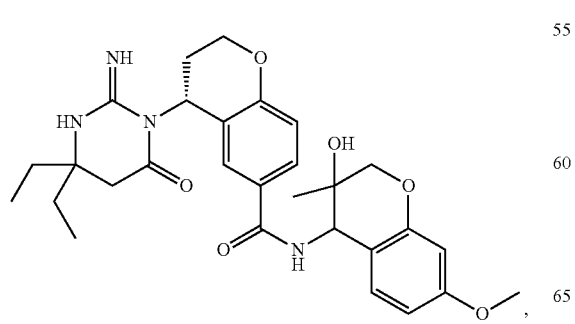
390
-continued
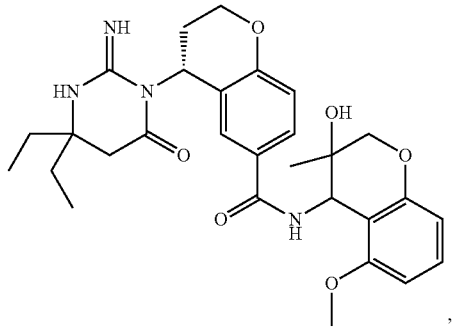
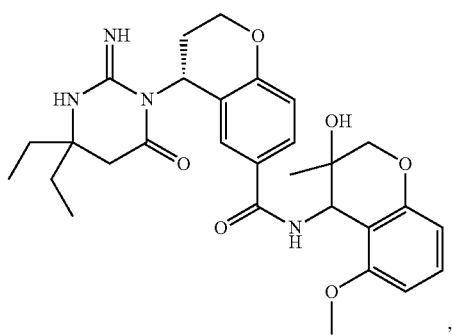
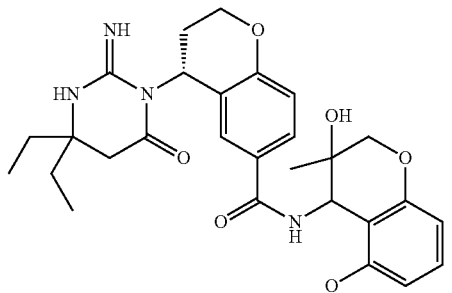
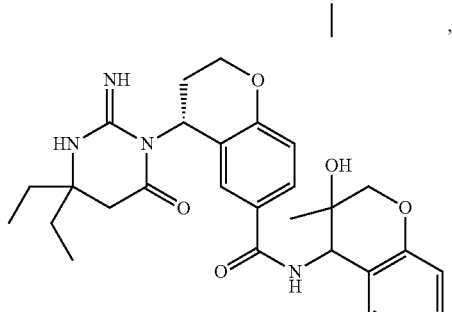
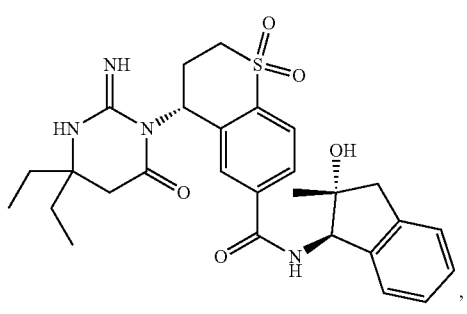

391
-continued
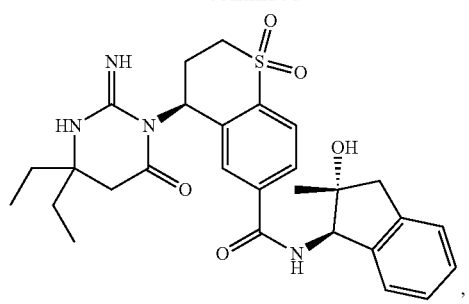
,
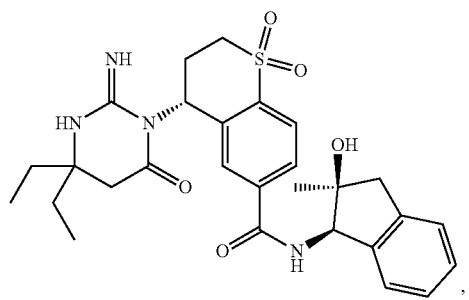
,
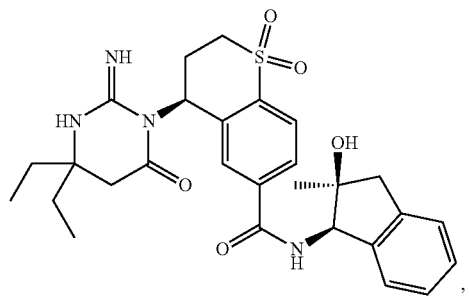
,
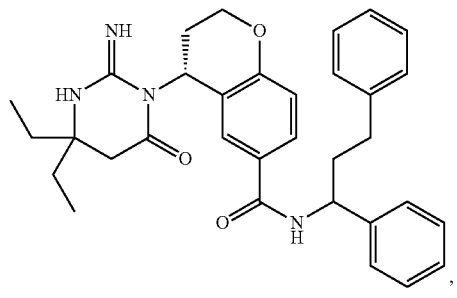
,
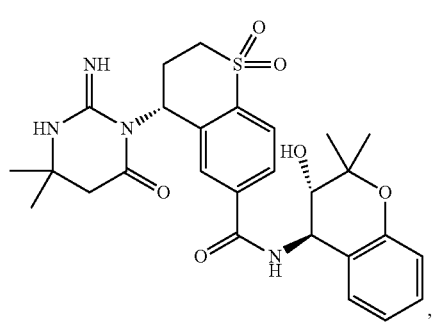
,
392
-continued
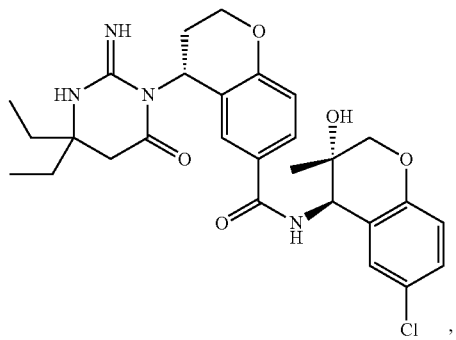
,
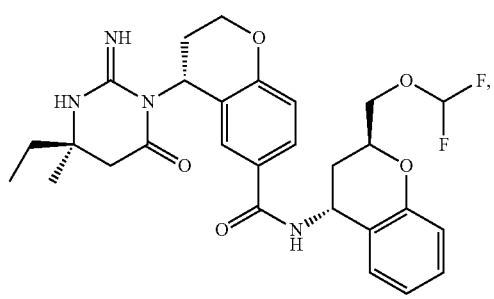
,
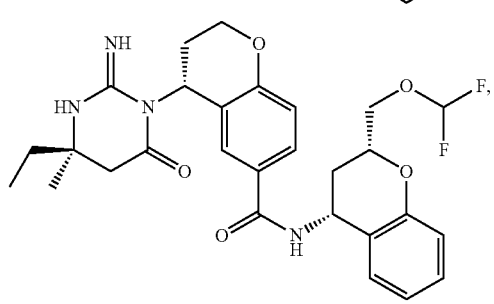
,
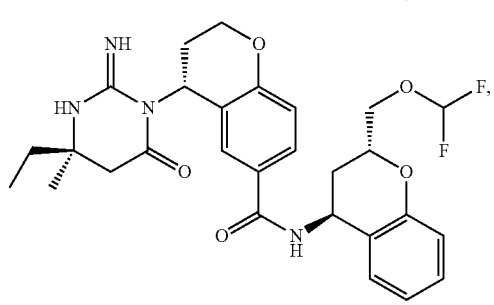

393
-continued
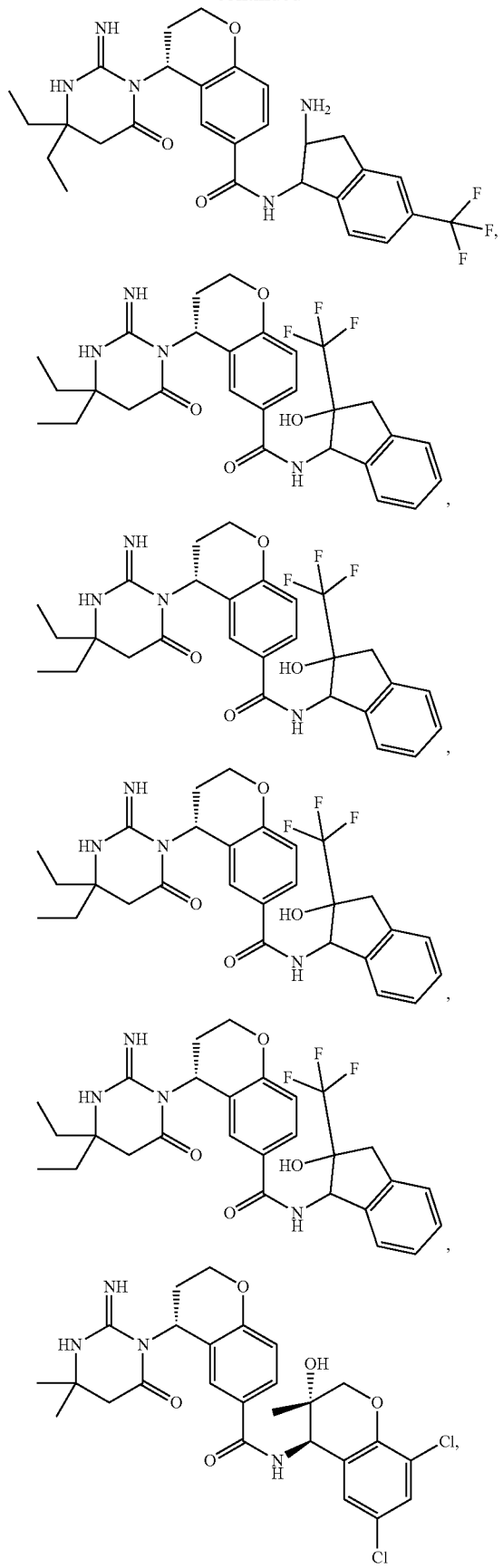
394
-continued
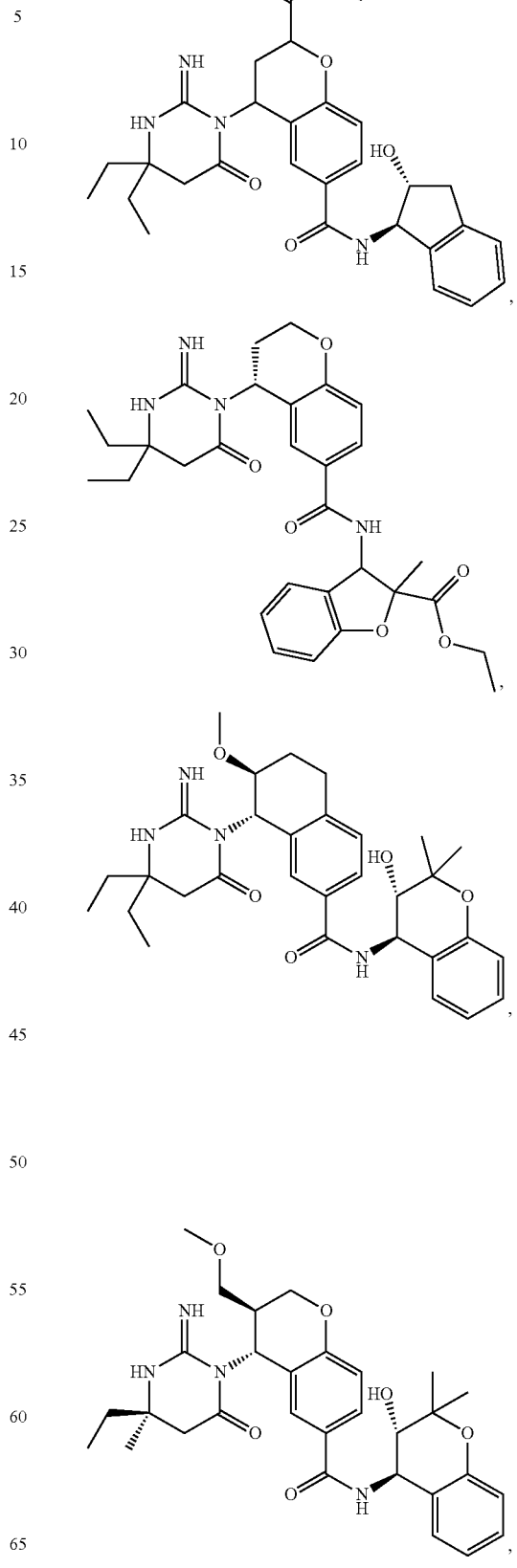

395
-continued
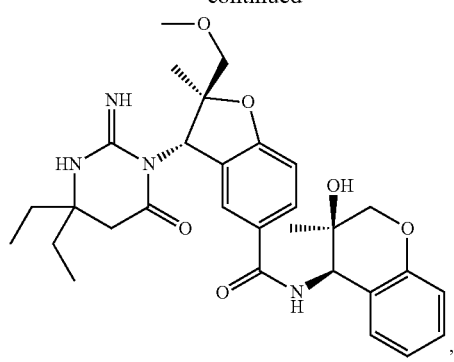
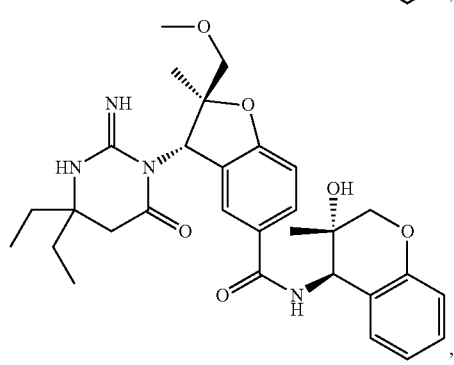
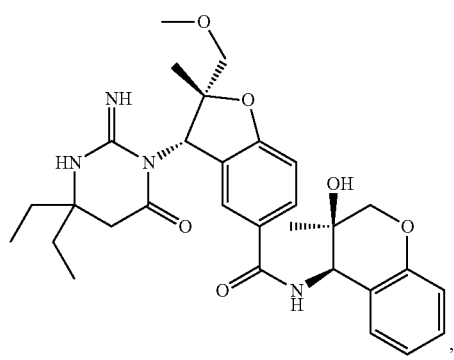
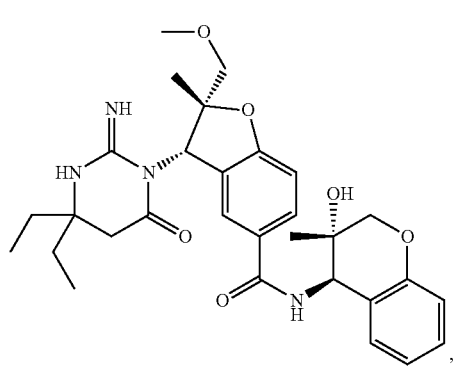
396
-continued
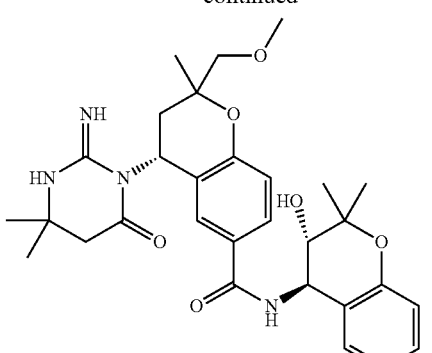
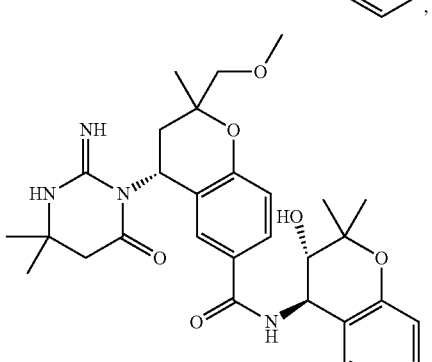
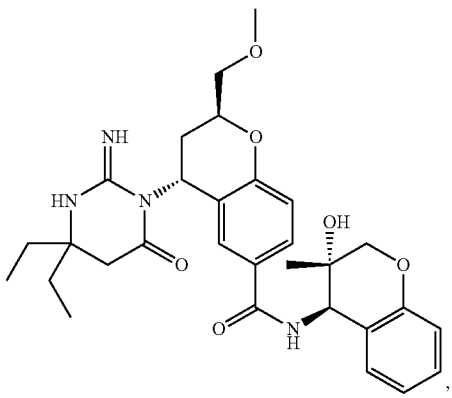

397
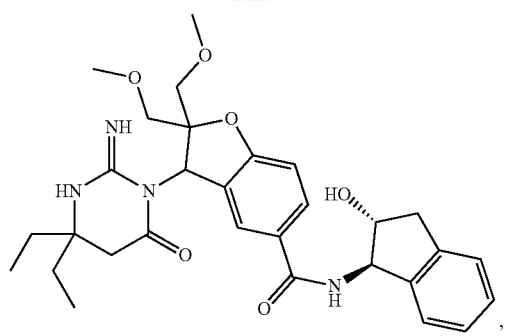
398
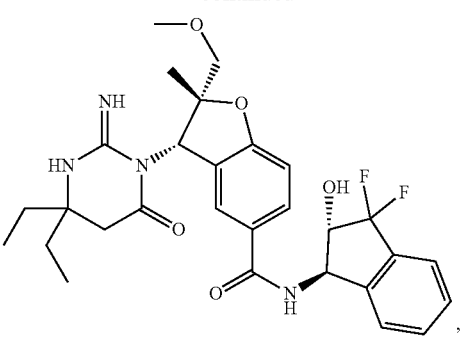
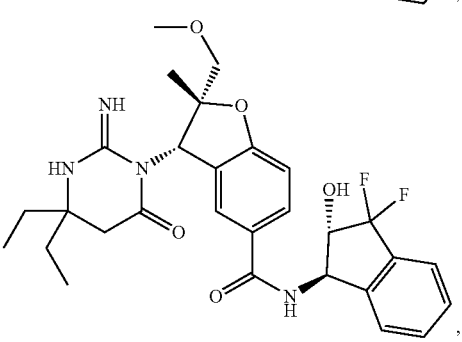
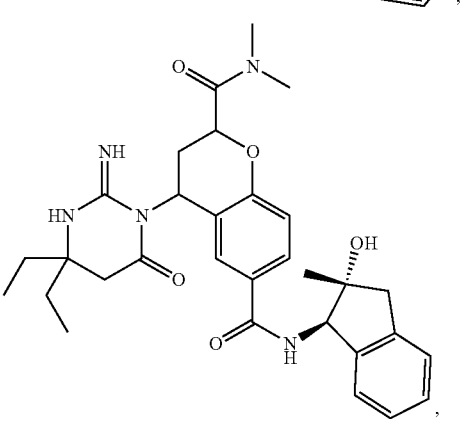
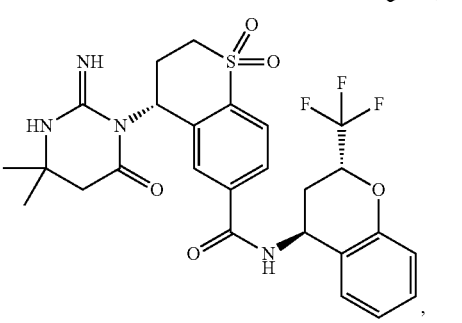
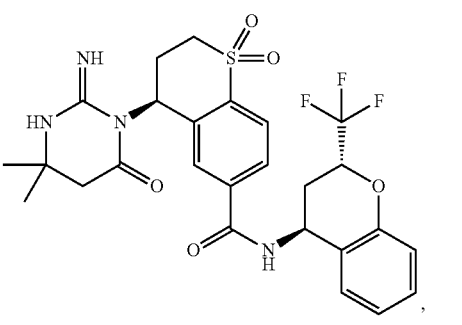

399
-continued
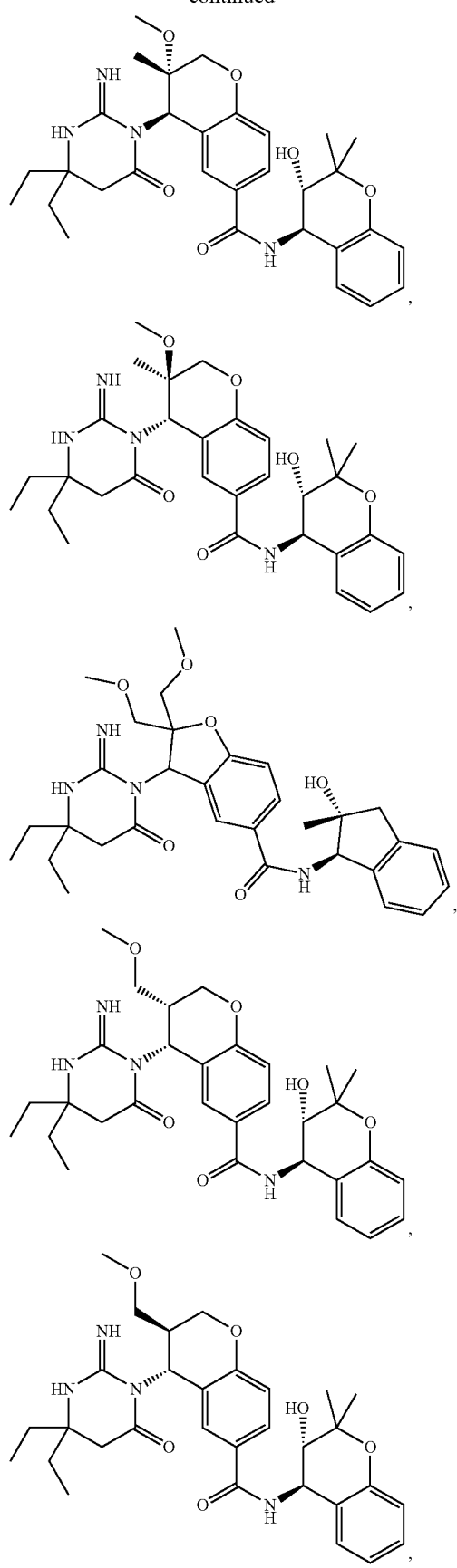
400
-continued
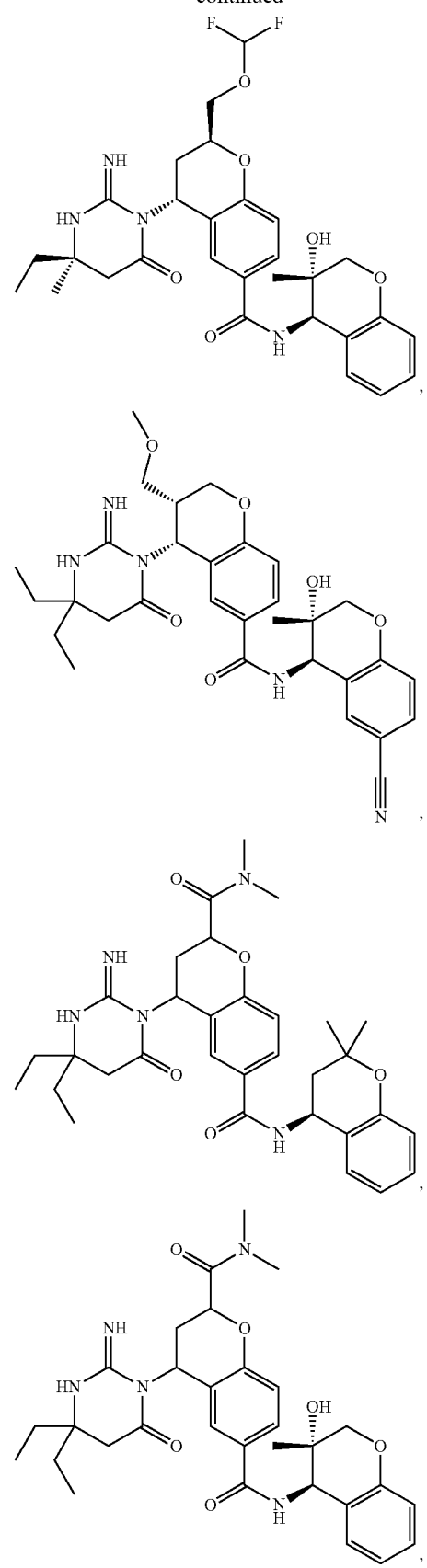

401
-continued
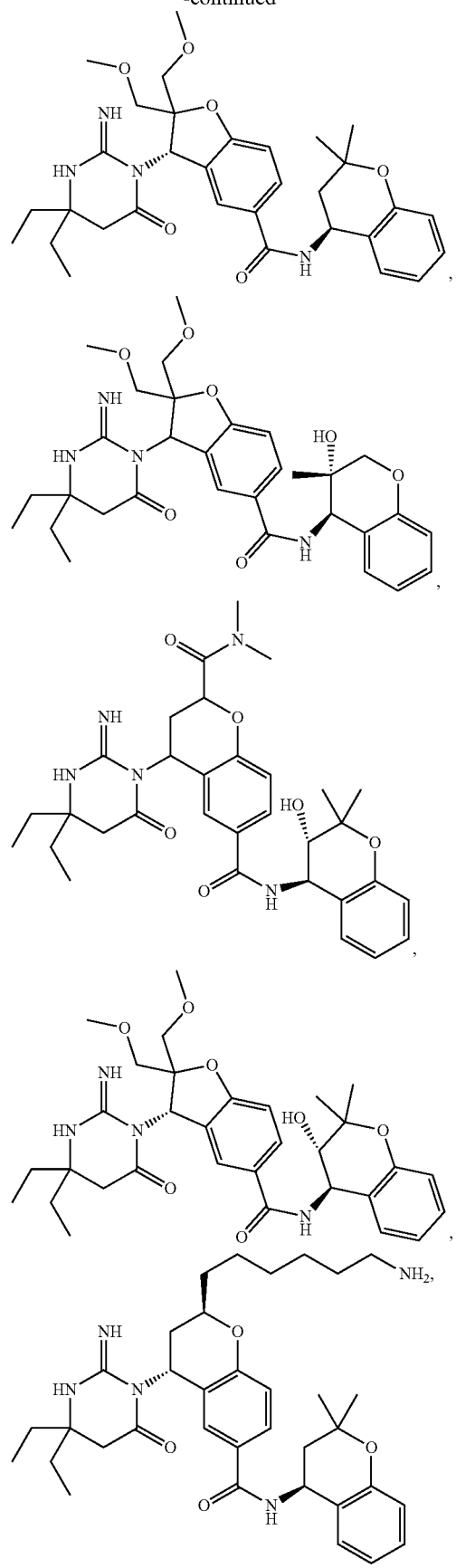
402
-continued
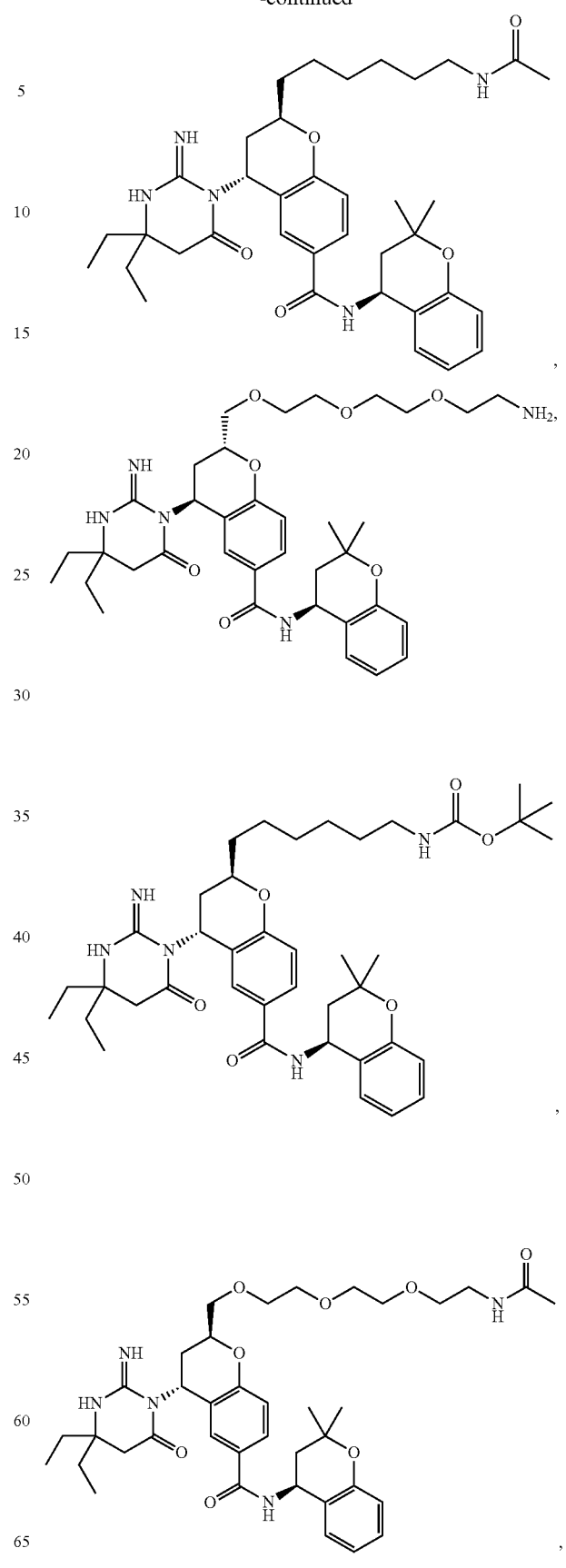

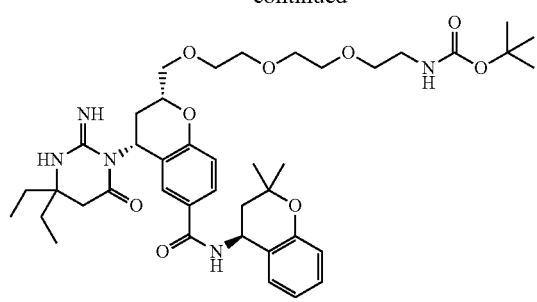
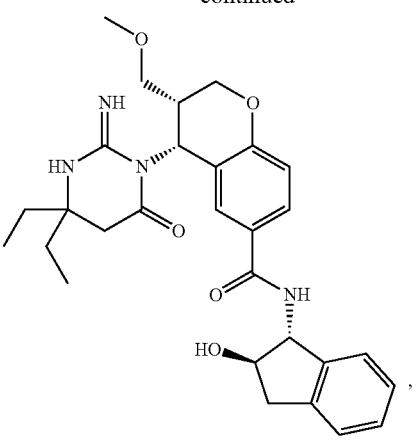
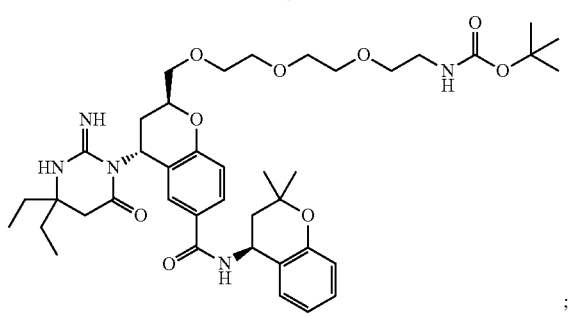
or a pharmaceutically acceptable salt thereof.
24. A compound selected from
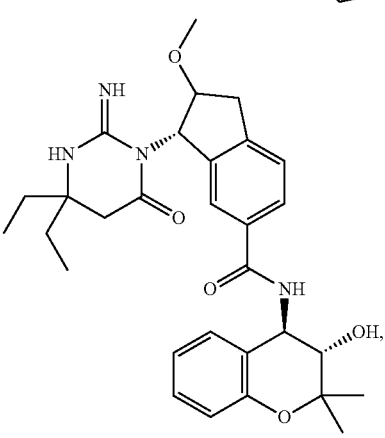
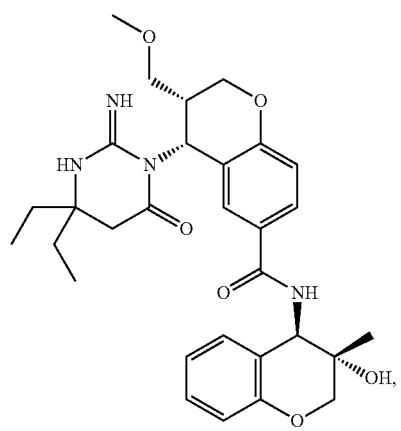
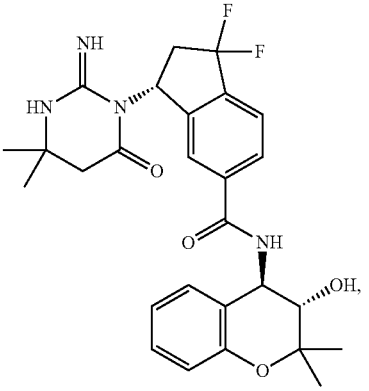
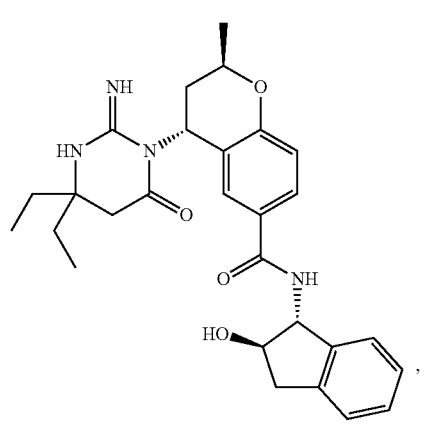
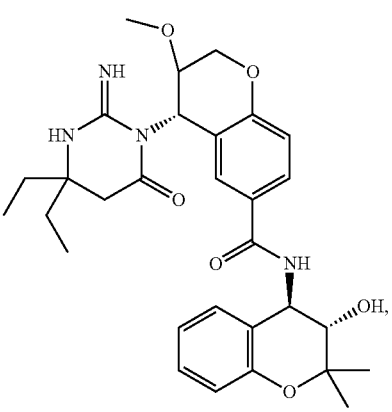

405
-continued
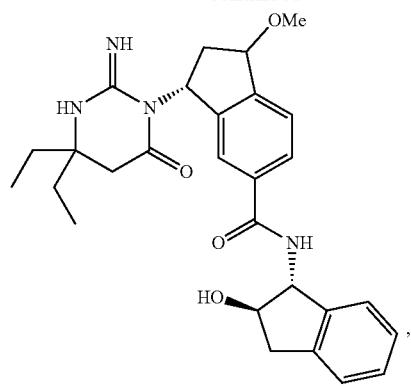
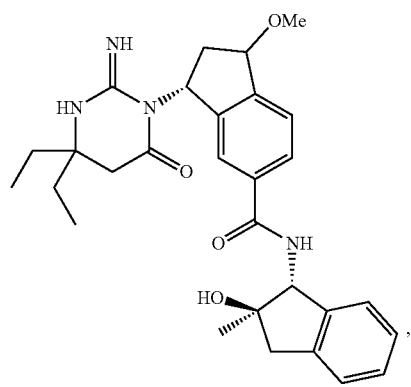
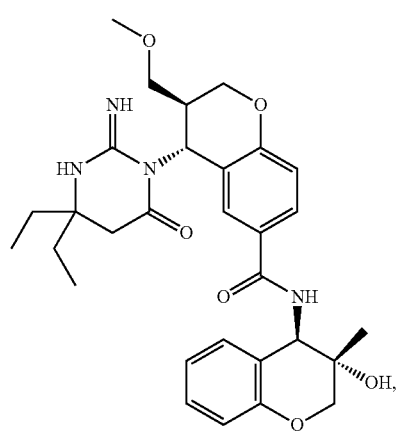
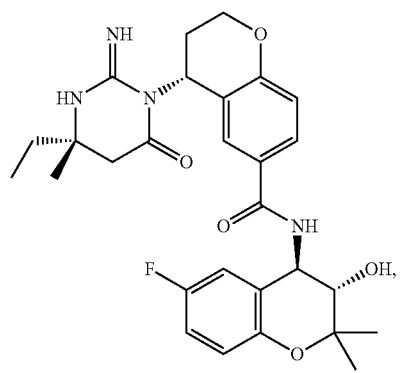
406
-continued
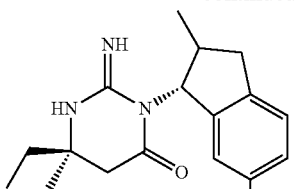
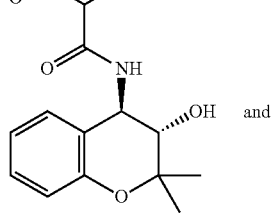 and
25. A compound selected from
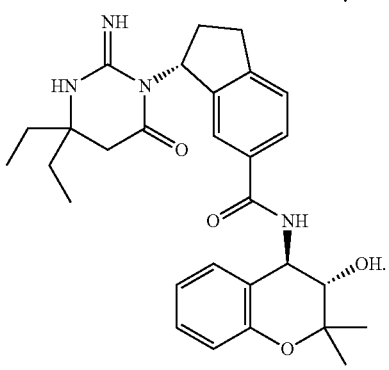
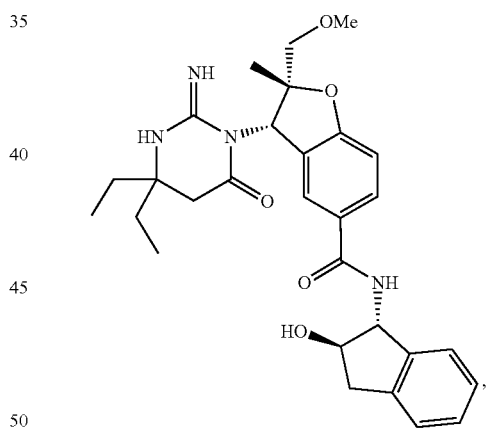
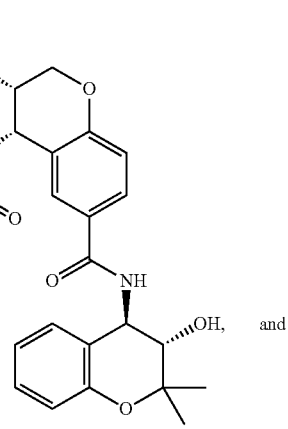 and -continued

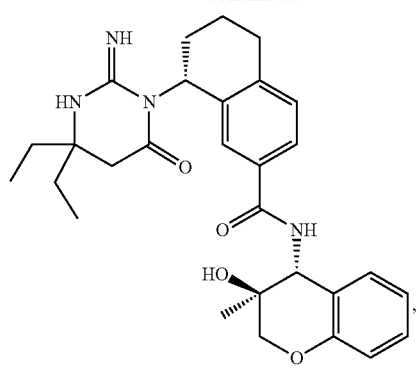

or a pharmaceutically acceptable salt thereof.

26. A compound having the formula

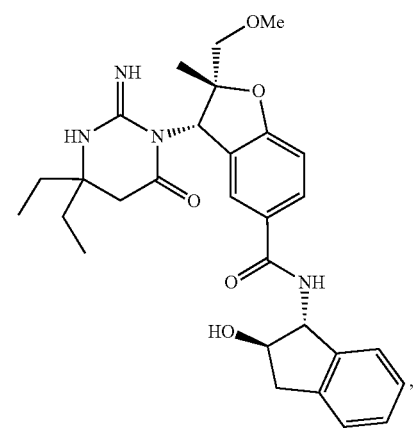 [SMILES: CCC1(CC)CC(=O)N([C@H]2c3cc(C(=O)N[C@@H]4c5ccccc5C[C@H]4O)ccc3O[C@@]2(C)COC)C(=N)N1]

or a pharmaceutically acceptable salt thereof.

27. A compound having the formula

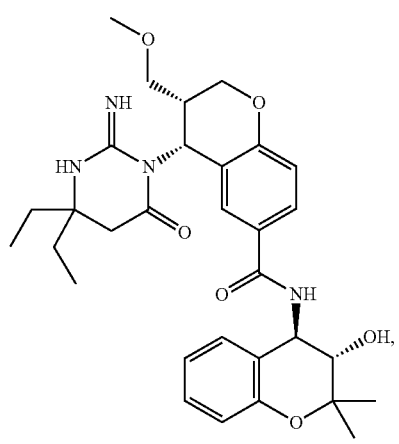 [SMILES: CCC1(CC)CC(=O)N([C@H]2c3cc(C(=O)N[C@@H]4c5ccccc5OC(C)(C)[C@H]4O)ccc3OC[C@H]2COC)C(=N)N1]

or a pharmaceutically acceptable salt thereof.

28. A compound having the formula

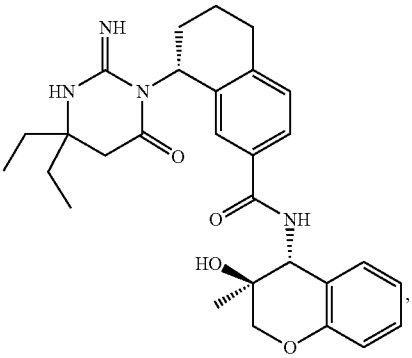 [SMILES: CCC1(CC)CC(=O)N([C@@H]2CCCc3ccc(C(=O)N[C@@H]4c5ccccc5OC[C@@]4(C)O)cc32)C(=N)N1]

or a pharmaceutically acceptable salt thereof.

29. The compound according to claim 24, which is:

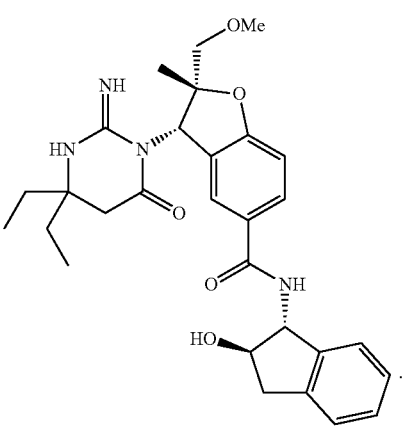 [SMILES: CCC1(CC)CC(=O)N([C@H]2c3cc(C(=O)N[C@@H]4c5ccccc5C[C@H]4O)ccc3O[C@@]2(C)COC)C(=N)N1]

30. The compound according to claim 24, which is:

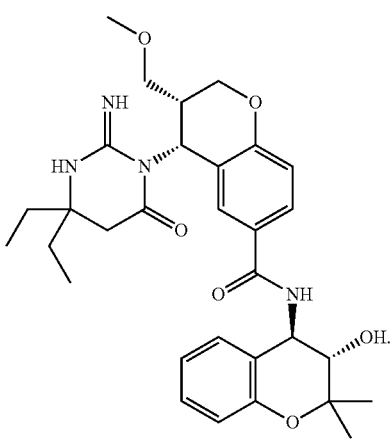 [SMILES: CCC1(CC)CC(=O)N([C@H]2c3cc(C(=O)N[C@@H]4c5ccccc5OC(C)(C)[C@H]4O)ccc3OC[C@H]2COC)C(=N)N1]

31. The compound according to claim 24, which is:

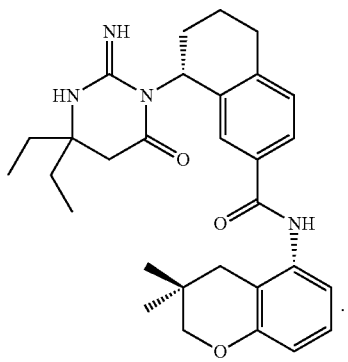

32. A pharmaceutical composition comprising a compound of claim 1, or a pharmaceutically acceptable salt thereof, and a pharmaceutically acceptable carrier.

33. A pharmaceutical composition comprising a compound of claim 1 and a pharmaceutically acceptable carrier.

34. A pharmaceutical composition comprising a compound of claim 26, and a pharmaceutically acceptable carrier.

35. The pharmaceutical composition according to claim 34, further comprising one or more additional agents selected from anti-malarial agents artemether, lumefantrine, dihydroartemisinin, piperaquine, pyronaridine, artesunate, amodiaquine, mefloquine, sulfadoxine, pyrimethamine, lumefantrine, quinine, chloroquine, atovaquone, and proguanil.

36. The pharmaceutical composition according to claim 35, wherein the one or more additional agent is pyronaridine and/or artesunate.

37. A pharmaceutical composition comprising a compound of claim 27, and a pharmaceutically acceptable carrier.

38. The pharmaceutical composition according to claim 37, further comprising one or more additional agents selected from the anti-malarial agents artemether, lumefantrine, dihydroartemisinin, piperaquine, pyronaridine, artesunate, amodiaquine, mefloquine, sulfadoxine, pyrimethamine, lumefantrine, quinine, chloroquine, atovaquone, and proguanil, and a pharmaceutically acceptable carrier.

39. The pharmaceutical composition according to claim 38, wherein the one or more additional agent is pyronaridine and/or artesunate.

40. A pharmaceutical composition comprising a compound of claim 28, and a pharmaceutically acceptable carrier.

41. The pharmaceutical composition according to claim 40, further comprising one or more additional agents selected from the antimalarial agents artemether, lumefantrine, dihydroartemisinin, piperaquine, pyronaridine, artesunate, amodiaquine, mefloquine, sulfadoxine, pyrimethamine, lumefantrine, quinine, chloroquine, atovaquone, and proguanil, and a pharmaceutically acceptable carrier.

42. The pharmaceutical composition according to claim 41, wherein the one or more additional agent is pyronaridine and/or artesunate.

43. A method for treating a *Plasmodium* infection, or for treating malaria, which comprises administering to a subject in need of such treatment a therapeutically effective amount of a compound of claim 1, or a pharmaceutically acceptable salt thereof.

44. A method for treating malaria, which comprises administering to a subject in need of such treatment a therapeutically effective amount of a compound of claim 1, or a pharmaceutically acceptable salt thereof.

45. A method for dual inhibition of plasmepsin IX and plasmepsin X which comprises administering to a subject in need of such treatment a therapeutically effective amount of a compound of claim 1, or a pharmaceutically acceptable salt thereof.

46. A method for treating a *Plasmodium* infection, or for treating malaria, comprising administration to a subject in need thereof of a an effective amount of compound of claim 1, or a pharmaceutically acceptable salt thereof, and an effective amount of one or more additional anti-malarial agents.

47. The method for treating a *Plasmodium* infection, or for treating malaria, in a subject in need thereof comprising administration of an effective amount of a compound of claim 26 to said subject.

48. A method for treating malaria, in a subject in need thereof comprising administration of an effective amount of a compound of claim 29 to said subject.

49. A method for treating a *Plasmodium* infection, or for treating malaria, in a subject in need thereof comprising administration to said subject an effective amount of the compound of claim 27 and an effective amount of one or more additional agents, wherein the one or more additional agents is an anti-malarial agent.

50. A method for treating malaria, in a subject in need thereof comprising administration to said subject an effective amount of the compound of claim 30 and an effective amount of one or more additional agents, wherein the one or more additional agents is an anti-malarial agent.

51. A method for treating a *Plasmodium* infection, or for treating malaria, in a subject in need threof comprising administration to said subject an effective amount of the compound of claim 28 and an effective amount of one or more additional agents, wherein the one or more additional agents is an anti-malarial agent.

52. A method for treating malaria, in a subject in need threof comprising administration to said subject an effective amount of the compound of claim 31 and an effective amount of one or more additional agents, wherein the one or more additional agents is an anti-malarial agent.

* * * * *